US008236805B2

(12) United States Patent
Gilbert et al.

(10) Patent No.: US 8,236,805 B2
(45) **Date of Patent: *Aug. 7, 2012**

(54) SUBSTITUTED PIPERAZINES AS $CB_1$ ANTAGONISTS

(75) Inventors: Eric J. Gilbert, Scotch Plains, NJ (US); Michael W. Miller, Scotch Plains, NJ (US); Jack D. Scott, Scotch Plains, NJ (US); Andrew W. Stamford, Chatham, NJ (US); William J. Greenlee, Teaneck, NJ (US); Jay Weinstein, Upper Montclair, NJ (US)

(73) Assignees: Intervet Inc., Summit, NJ (US); Intervet International B.V., Boxmeer (NL)

( * ) Notice: Subject to any disclaimer, the term of this patent is extended or adjusted under 35 U.S.C. 154(b) by 0 days.

This patent is subject to a terminal disclaimer.

(21) Appl. No.: 12/564,678

(22) Filed: Sep. 22, 2009

(65) Prior Publication Data

US 2010/0029607 A1 Feb. 4, 2010

Related U.S. Application Data

(62) Division of application No. 11/292,264, filed on Dec. 1, 2005, now Pat. No. 7,700,597.

(60) Provisional application No. 60/633,106, filed on Dec. 3, 2004.

(51) Int. Cl.
*A61K 31/497* (2006.01)
*C07D 403/00* (2006.01)

(52) U.S. Cl. .................................. 514/253.01; 544/359

(58) Field of Classification Search ........................ None
See application file for complete search history.

(56) References Cited

U.S. PATENT DOCUMENTS 3,663,548 A * 5/1972 Nitta et al. .................... 544/403
4,229,207 A 10/1980 Laanio et al.
4,839,360 A 6/1989 Sato et al.
4,917,896 A 4/1990 Peck et al.
4,983,597 A 1/1991 Yang et al.
5,073,544 A 12/1991 Peck et al.
5,185,349 A 2/1993 Augelli-Szafran
5,234,895 A 8/1993 Felix
5,306,817 A 4/1994 Thiruvengadam et al.
5,332,817 A 7/1994 Desai et al.
5,464,788 A 11/1995 Bock et al.
5,508,424 A 4/1996 Carmosin et al.
5,561,227 A 10/1996 Thiruvengadam et al.
5,580,883 A 12/1996 Goto et al.
5,624,920 A 4/1997 McKittrick et al.
5,624,941 A 4/1997 Barth et al.
5,631,365 A 5/1997 Rosenblum et al.
5,633,246 A 5/1997 McKittrick et al.
5,656,624 A 8/1997 Vaccaro et al.
5,688,785 A 11/1997 Vaccaro
5,688,787 A 11/1997 Burnett et al.
5,688,990 A 11/1997 Shankar
5,698,548 A 12/1997 Dugar et al.
5,756,470 A 5/1998 Yumibe et al.
5,756,504 A 5/1998 Bock et al.
5,767,115 A 6/1998 Rosenblum et al.
5,780,480 A 7/1998 Wai et al.
5,846,966 A 12/1998 Rosenblum et al.
6,093,812 A 7/2000 Thiruvengadam et al.
6,121,319 A 9/2000 Somers
6,147,090 A 11/2000 DeNinno et al.
6,147,250 A 11/2000 Somers
6,207,822 B1 3/2001 Thiruvengadam et al.
6,369,077 B1 4/2002 Marquis et al.
RE37,721 E 5/2002 Rosenblum et al.
6,391,865 B1 5/2002 Baroudy et al.
6,432,984 B1 8/2002 Barth et al.
6,441,001 B1 8/2002 Watson et al.
6,498,156 B2 12/2002 Glombik et al.
6,528,529 B1 3/2003 Brann et al.
6,627,757 B2 9/2003 Fu et al.
6,642,258 B1 11/2003 Bourrie et al.
6,703,386 B2 3/2004 Glombik et al.
6,902,902 B2 6/2005 Unett et al.
6,982,267 B2 1/2006 Stamford et al.
7,056,942 B2 * 6/2006 Hildesheim et al. .......... 514/411
7,105,505 B2 9/2006 Zeng et al.
(Continued)

FOREIGN PATENT DOCUMENTS

EP 0230402 4/1993
(Continued)

OTHER PUBLICATIONS

Adam, et al., "Recent Advances in the Cannabinoids", Expert Opin. Ther. Patents; (2002), pp. 1475-1489, vol. 12, Issue 10.
Anderson, et al., "The Preparation of β-Substituted Amines from Mixtures of Epoxide Opening Products via a Common Aziridinium Ion Intermediate", Tetrahedron: *Asymmetry*, (1999), pp. 2655-2663, vol. 10.
Bingham, et al., "Over One Hundred Solvates of Sulfathiazole†", Chem. Commun., (2001), pp. 603-604.
(Continued)

*Primary Examiner* — Noble Jarrell
(74) *Attorney, Agent, or Firm* — David J. Kerwick

(57) ABSTRACT

Compounds of Formula (I):

(I)

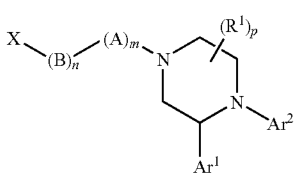

or pharmaceutically acceptable salts, solvates, or esters thereof, are useful in treating diseases or conditions mediated by $CB_1$ receptors, such as metabolic syndrome and obesity, neuroinflammatory disorders, cognitive disorders and psychosis, addiction (e.g., smoking cessation), gastrointestinal disorders, and cardiovascular conditions.

51 Claims, No Drawings

U.S. PATENT DOCUMENTS

| | | | | |
|---|---|---|---|---|
| 7,700,597 | B2 | 4/2010 | Gilbert et al. | |
| 2001/0006972 | A1 | 7/2001 | Williams | |
| 2002/0039774 | A1 | 4/2002 | Kramer et al. | |
| 2002/0128252 | A1 | 9/2002 | Glombik et al. | |
| 2002/0128253 | A1 | 9/2002 | Glombik et al. | |
| 2002/0128476 | A1 | 9/2002 | Marquis, Jr. et al. | |
| 2002/0137689 | A1 | 9/2002 | Glombik et al. | |
| 2003/0087933 | A1 | 5/2003 | Blanchard et al. | |
| 2003/0105028 | A1 | 6/2003 | Ghosal et al. | |
| 2003/0109673 | A1 | 6/2003 | Yonghong | |
| 2003/0139343 | A1 | 7/2003 | Ramakrishnan | |
| 2003/0171588 | A1 | 9/2003 | Kahl et al. | |
| 2003/0186960 | A1 | 10/2003 | Lauffer et al. | |
| 2004/0058820 | A1 | 3/2004 | Hagmann et al. | |
| 2004/0063929 | A1 | 4/2004 | Tomiyama et al. | |
| 2004/0106800 | A1 | 6/2004 | Lange et al. | |
| 2004/0142377 | A1 | 7/2004 | Unett et al. | |
| 2004/0142922 | A1 | 7/2004 | Alanine et al. | |
| 2004/0147572 | A1 | 7/2004 | Guba et al. | |
| 2004/0167129 | A1 | 8/2004 | Mayweg et al. | |
| 2004/0167185 | A1 | 8/2004 | Shankar et al. | |
| 2004/0180927 | A1 | 9/2004 | Marquis, Jr. et al. | |
| 2004/0235854 | A1 | 11/2004 | Kruse et al. | |
| 2004/0254224 | A1 | 12/2004 | Foord et al. | |
| 2005/0004178 | A1 | 1/2005 | Unett et al. | |
| 2005/0154029 | A1 | 7/2005 | Unett et al. | |
| 2005/0187263 | A1 | 8/2005 | Minnich et al. | |
| 2005/0187280 | A1 | 8/2005 | Minnich et al. | |
| 2007/0197628 | A1 | 8/2007 | Chackalamannil et al. | |
| 2007/0203183 | A1 | 8/2007 | Gilbert et al. | |
| 2009/0105208 | A1 | 4/2009 | Gilbert et al. | |
| 2010/0029607 | A1 | 2/2010 | Gilbert et al. | |
| 2010/0249144 | A1* | 9/2010 | Demong et al. | 514/253.01 |
| 2010/0286160 | A1* | 11/2010 | Gilbert et al. | 514/252.11 |

FOREIGN PATENT DOCUMENTS

| | | |
|---|---|---|
| EP | 0612745 | 8/1994 |
| EP | 0268222 | 3/1996 |
| JP | 3-200758 | 9/1991 |
| JP | 4-266830 | 9/1992 |
| JP | 4-364175 | 12/1992 |
| NL | 6603256 | 9/1967 |
| WO | WO 88/01131 | 2/1988 |
| WO | WO 93/02048 | 2/1993 |
| WO | WO 94/17038 | 8/1994 |
| WO | WO 95/03196 | 2/1995 |
| WO | WO 95/08532 | 3/1995 |
| WO | WO 95/25443 | 9/1995 |
| WO | WO 96/01656 | 1/1996 |
| WO | WO 97/22597 | 6/1997 |
| WO | WO 98/56820 | 12/1998 |
| WO | WO 99/38498 | 8/1999 |
| WO | WO 00/38721 | 7/2000 |
| WO | WO 00/38727 | 7/2000 |
| WO | WO 00/66558 | 11/2000 |
| WO | WO 01/02372 | 1/2001 |
| WO | WO 01/58869 | 8/2001 |
| WO | WO 01/77320 | 10/2001 |
| WO | WO 01/94385 | 12/2001 |
| WO | WO 02/066464 | 8/2002 |
| WO | WO 02/098853 | 12/2002 |
| WO | WO 03/008559 | 1/2003 |
| WO | WO 03/027637 | 4/2003 |
| WO | WO 03/042174 | 5/2003 |
| WO | WO 03/051850 | 6/2003 |
| WO | WO 03/062392 | 7/2003 |
| WO | WO 03/082190 | 10/2003 |
| WO | WO 03/084942 | 10/2003 |
| WO | WO 2004/000803 | 12/2003 |
| WO | WO 2004/000804 | 12/2003 |
| WO | WO 2004/000805 | 12/2003 |
| WO | WO 2004/005247 | 1/2004 |
| WO | WO 2004/033431 | 4/2004 |
| WO | WO 2004/058255 | 7/2004 |
| WO | WO 2004/071378 | 8/2004 |
| WO | WO 2004/071394 | 8/2004 |
| WO | WO 2004/083388 | 9/2004 |
| WO | WO 2004/085408 | 10/2004 |
| WO | WO 2004/099157 | 11/2004 |
| WO | WO 2005/000775 | 1/2005 |
| WO | WO 2005/011677 | 2/2005 |
| WO | WO 2005/016867 | 2/2005 |
| WO | WO 2005/016870 | 2/2005 |
| WO | WO 2005/020988 | 3/2005 |
| WO | WO 2005/020992 | 3/2005 |
| WO | WO 2005/051937 | 6/2005 |
| WO | WO 2005/077950 | 8/2005 |
| WO | WO 2005/080386 | 9/2005 |
| WO | WO 2006/060461 | 6/2006 |
| WO | WO 2007/084319 | 7/2007 |
| WO | WO 2007/084450 | 7/2007 |
| WO | WO 2008/130616 | 10/2008 |
| WO | WO 2009/005645 | 1/2009 |
| WO | WO 2009/005671 | 1/2009 |

OTHER PUBLICATIONS

Borisy et al, "Systematic Discovery of Multicomponent Therapeutics", PNAS, vol. 100, No. 13, pp. 7977-7982 (2003).

Brettle, Roger, et al., "The Selective Reduction of αβ-Olefinic Amides", Tetrahedron Letters, 1980, pp. 2915-2916, vol. 21. (XP-002441723).

Caira, et al., "Preparation and Crystal Characterization of a Polymorph, a Monohydrate, and an Ethyl Acetate Solvate of the Antifungal Fluconazole", Journal of Pharmaceutical Sciences, (2004) pp. 601-611, vol. 93, No. 3.

Chemical Abstracts Service, Columbus, Ohio, US; Banciu, Mircea D. et al., (XP002441898); Database accession No. 1996:738817; abstract.

Chemical Abstracts Service, Columbus, Ohio, US; Dhaon, Madhup K. et al., (XP002441901); Database accession No. 1977:106004; abstract.

Chemical Abstracts Service, Columbus, Ohio, US; Dodds, E.C., et al., (XP002441902); Database accession No. 1955:42823; abstract.

Chemical Abstracts Service, Columbus, Ohio, US; Eto, Masashi et al., (XP002441899); Database accession No. 1993:427963; abstract.

Chemical Abstracts Service, Columbus, Ohio, US; Langer, F., et al., (XP002441904);Database accession No. 1956:24005; abstract.

Chemical Abstracts Service, Columbus, Ohio, US; Melles, J.L., (XP002441903);Database accession No. 1953:44564; abstract.

Chemical Abstracts Service, Columbus, Ohio, US; Tokita, Sumio, et al., (XP002441900); Database accession No. 1991:228432; abstract.

Chemical Abstracts Service, Columbus, Ohio, US; Zhang J.-H., et al, (XP002441897); Database accession No. 2004:785021; abstract.

Chong et al., "Current, New and Future Treatments in Dyslipidaemia and Atherosclerosis"—Drugs, (2000), pp. 55-93, vol. 60, Issue 1.

Fancher et al, "4-Alkyl+(or Aralkyl) 1-Aryl-2-piperazinones", Chemical Therapeutics Research Laboratory, Miles Labs, Inc., Indiana, (1963) vol. 7 pp. 154-158.

Gerson, Fabian, et al., "The Radical Anions of 1,2-Diphenylcyclohexene and Structurally Related Compounds. Conformational ESR and ENDOR Studies", Helvetica Chimica Acta, 1987, pp. 1558-1568, vol. 70, No. 6. (XP-002441721).

Gschwend, Heinz W., et al., "Intramolecular [x4-x2]-cycloadditions: Preparative and Kinetic Aspects", Angew. Chem. Internat. Edit. 1972, pp. 294-295, vol. 11, No. 4.(XP-009086254).

Gschwend, Heinz W., et al., "Rates of Intramolecular Diels-Alder Reactions of Pentadienylacrylamides", J. Org. Chem., 1973, pp. 2169-2175, vol. 38, No. 12.(XP-002441724).

Gylling et al., "Serum Sterols During Stanol Ester Feeding in a Mildly Hypercholesterolemic Population"—Journal of Lipid Research, (1999), pp. 593-600, vol. 40.

Huettinger et al., "Hypolipidemic activity of HOE-402 is Mediated by Stimulation of the LDL Receptor Pathway"—Arterioscler. Thromb., (1993), pp. 1005-1012, vol. 13.

Japanese Patent No. 03200758, dated Sep. 2, 1991 (English Abstract).

Japanese Patent No. 04026683, dated Jan. 29, 1992 (English Abstract).

Japanese Patent No. 04364175, dated Dec. 16, 1992 (English Abstract).

Josephsohn, Nathan S. et al., "Efficient and Practical Ag-Catalyzed Cycloadditions between Arylimines and the Danishefsky Diene", J. Am. Chem. Society, 2003, pp. 4018-4019, vol. 125, No. 14.
Kirkham, "Endogenous cannabinoids: a new target in the treatment of obesity", Am. J. Physiol. Regul. Integr. Comp. Physiol., (2002), pp. R343-R344, vol. 284.
Kvaerno et al., "An In Vitro Assay for Evaluation of Small-Molecule Inhibitors of Cholesterol Absorption", Angew. Chem. Int. Ed., (2004), pp. 4653-4656, vol. 43.
Lange et al., "Synthesis, Biological Properties, and Molecular Modeling Investigations of Novel 3,4-Diarylpyrazolines as Potent and Selective CB1 Cannabinoid Receptor Antagonists", J. Med. chem., (2004), pp. 627-643, vol. 47.
Lange, Jos H.M., et al., "Novel 3,4-diarylpyrazolines as potent cannabinoid CB1 receptor antagonists with lower lipophilicity", Bioorganic & Medicinal Chemistry Letters, 2005, pp. 4794-4798, vol. 15, No. 21.
PCT International Search Report mailed Jul. 30, 2007 for counterpart PCT Application No. PCT/US2007/000705.
PCT Written Opinion of the International Searching Authority for PCT/US2007/001024—8 pages.
International Search Report (PCT/US2007/001024), mail date Aug. 21, 2007—8 pages.
International Search Report for PCT/US2005/043281 dated May 19, 2006—5 pages.
Petite et al, The therapeutic applications of annabinoid agonists and antagonists, Ashley Publications, Emerging Drugs (1998) 3:39-53.
Porter et al., "The Endocannabinoid Nervous System: Unique Opportunities for Therapeutic Intervention", Pharmacology and Therapeutics vol. 90, pp. 45-60, 2001.
Ram et al., "Potential Hypolipidemic Agents: Part V†-Synthesis and Biological Activity of New Ethyl 4-(2-oxoazetidin-4-yl) phenoxyalkanoates‡", Indian J. Chem. Sect. B. 29B, (1990), pp. 1134-1137, vol. 12.
Sanofi-Aventis Publication, "A New Approach to Cardiovascular Risk Management"—Bear Stearns Conference, New York (Sep. 2004), pp. 19-24.
Shea, K.J., et al., Kinetic Investigation of the Type 2 Intramolecular Diels-Alder Cycloaddition, American Chemical Society, 1988, pp. 860-864, vol. 110, No. 3.(XP-002441722).
Trillou, C.R. etal., "Anti-obesity effect of SR141716, a CB1 receptor antagonist, in diet-induced obese mice"—Am. J. Physiol. Regul. Integr. Comp., Physiol., (2003), pp. R345-R353, vol. 284.
Van Tonder, et al., "Preparation and Physicochemical Characterization of 5 Niclosamide Solvates and 1 Hemisolvate", *AAPS PharmSciTech*, (2004), pp. 1-10, vol. 5, Issue 1.
Weis, Robert et al., "Synthesis of 2-substituted bamipine derivatives", Tetrahedron, (2003), vol. 9 pp. 1395-1402.
Weis, Robert et al., "Synthesis of new 1,2,7 analogs of diphenylpyraline", Tetrahedron, (2003) vol. 9 pp. 1403-1411.
Wikström et al., "Synthesis and Pharmacological Testing of 1,2,3,4,10,14b-Hexahydro-6-methoxy-2-methyldibenzo[c,f]pyrazino[1,2-a]azepin and Its Enantiomers in Comparison with the Two Antidepressants Mianserin and Mirtazapine", J. Med. Chem., vol. 45, pp. 3280-3285 (2002).
Vippaglinta et al, "Crystalline Solids", Advanced Drug Delivery Reviews 48 (2001) 3-26.
Wilson, et al., "Endocannabinoid Signaling in the Brain", Science 296, 678 (2002).

* cited by examiner

SUBSTITUTED PIPERAZINES AS $CB_1$ ANTAGONISTS

The present application is a divisional of application U.S. Ser. No. 11/292,264, filed Dec. 1, 2005, now U.S. Pat. No. 7,700,597, which claims the benefit of priority to U.S. Provisional Application No. 60/633,106, filed Dec. 3, 2004, each of which is incorporated herein by reference.

BACKGROUND OF THE INVENTION

The $CB_1$ receptor is one of the most abundant neuromodulatory receptors in the brain, and is expressed at high levels in the hippocampus, cortex, cerebellum, and basal ganglia (e.g., Wilson et al., *Science,* 2002, vol. 296, 678-682). Selective $CB_1$ receptor antagonists, for example pyrazole derivatives such as rimonabant (e.g., U.S. Pat. No. 6,432,984), can be used to treat various conditions, such as obesity and metabolic syndrome (e.g., Bensaid et al., *Molecular Pharmacology,* 2003 vol. 63, no. 4, pp. 908-914; Trillou et al., *Am. J. Physiol. Regul. Integr. Comp. Physiol.* 2002 vol. 284, R345-R353; Kirkham, *Am. J. Physiol. Regul. Integr. Comp. Physiol.* 2002 vol. 284, R343-R344), neuroinflammatory disorders (e.g., Adam, et al., *Expert Opin. Ther. Patents,* 2002, vol. 12, no. 10, 1475-1489; U.S. Pat. No. 6,642,258), cognitive disorders and psychosis (e.g., Adam et al., *Expert Opin. Ther. Pat.,* 2002, vol. 12, pp. 1475-1489), addiction (e.g., smoking cessation; U.S. Patent Publ. 2003/0087933), gastrointestinal disorders (e.g., Lange et al., *J. Med. Chem.* 2004, vol. 47, 627-643) and cardiovascular conditions (e.g., Porter et al., *Pharmacology and Therapeutics,* 2001 vol. 90, 45-60; Sanofi-Aventis Publication, Bear Stearns Conference, New York, Sep. 14, 2004, pages 19-24).

However, there is still a need for improved cannabinoid agents, particularly selective $CB_1$ receptor antagonists, with fewer side-effects and improved efficacy. It is therefore an object of the present invention to provide substituted piperazines useful in the treatment of diseases or conditions mediated by $CB_1$ receptors.

WO 95/25443, U.S. Pat. No. 5,464,788, and U.S. Pat. No. 5,756,504 describe N-arylpiperazine compounds useful for treating preterm labor, stopping labor, and dysmenorrhea. However, none of the N-aryl piperazines exemplified therein have an aryl and/or heteroaryl substituent at both the 1- and 2-positions of the piperazine ring.

WO 01/02372 and U.S. Published Application No. 2003/0186960 describe cyclized amino acid derivatives for treating or preventing neuronal damage associated with neurological diseases. However, none of the 3-aryl piperazine 2-ones exemplified therein have an aryl and/or heteroaryl substituent at both the 1- and 2-positions of the piperazine ring.

WO 96/01656 describes radiolabelled substituted piperazines useful in pharmacological screening procedures, including labeled N-aryl piperazines. However, none of the N-aryl piperazines exemplified therein have an aryl and/or heteroaryl substituent at both the 1- and 2-positions of the piperazine ring.

U.S. Pat. No. 5,780,480 describes N-aryl piperazines useful as fibrinogen receptor antagonists for inhibiting the binding of fibrinogen to blood platelets, and for inhibiting the aggregation of blood platelets. However, none of the N-aryl piperazines exemplified therein have an aryl and/or heteroaryl substituent at both the 1- and 2-positions of the piperazine ring.

WO 03/008559 describes choline analogs useful for treating conditions or disorders. However, the only substituted piperazine derivative exemplified is N-(2-hydroxyethyl)-N'-(2-pyridylmethyl)-piperazine.

JP 3-200758, JP 4-26683, and JP 4-364175 describe N,N'-diarylpiperazines (i.e., 1,4-diarylpiperazines) prepared by reacting bis(2-hydroxyethyl)arylamines with an amine such as aniline. However, no 1,2-disubstituted piperazines are exemplified.

WO 97/22597 describes various 1,2,4-trisubstituted piperazine derivatives as tachykinin antagonists for treating tachykinin-mediated diseases such as asthma, bronchitis, rhinitis, cough, expectoration, etc. However, none of the 1,2,4-trisubstituted piperazine derivatives exemplified therein have an aryl and/or heteroaryl substituent at both the 1- and 2-positions of the piperazine ring.

EP 0268222, WO 88/01131, U.S. Pat. No. 4,917,896, and U.S. Pat. No. 5,073,544 describe compositions for enhancing the penetration of active agents through the skin, comprising azacyclohexanes, including N-acyl and N,N'-diacylpiperazines. However, none of the N-acyl or N,N'-diacylpiperazines exemplified therein have an aryl and/or heteroaryl substituent at both the 1- and 2-positions of the piperazine ring.

U.S. Pat. No. 6,528,529 describes compounds, including N,N'-disubstituted piperazines, which are selective for muscarinic acetylcholine receptors and are useful for treating diseases such as Alzheimer's disease. However, none of the N,N'-disubstituted piperazines exemplified therein have an aryl and/or heteroaryl substituent at both the 1- and 2-positions of the piperazine ring.

NL 6603256 describes various biologically active piperazine derivatives. However, none of the piperazine derivatives exemplified therein have a substituted aryl and/or heteroaryl substituent at both the 1- and 2-positions of the piperazine ring.

Wikström et al., *J. Med. Chem.* 2002, 45, 3280-3285, describe the synthesis of 1,2,3,4,10,14b-hexahydro-6-methoxy-2-methyldibnzo[c,f]pyrazine[1,2-a]azepin. However, none of the piperazine intermediates described therein have a substituted aryl and/or heteroaryl substituent at both the 1- and 2-positions of the piperazine ring.

BRIEF SUMMARY OF THE INVENTION

In its many embodiments, the present invention provides a novel class of substituted piperazine compounds as selective $CB_1$ receptor antagonists for treating various conditions including, but not limited to metabolic syndrome (e.g., obesity, waist circumference, lipid profile, and insulin sensitivity), neuroinflammatory disorders, cognitive disorders, psychosis, addictive behavior, gastrointestinal disorders, and cardiovascular conditions.

The selective $CB_1$ receptor antagonists of the present invention are piperazine derivatives having the structure of Formula (I):

(I)

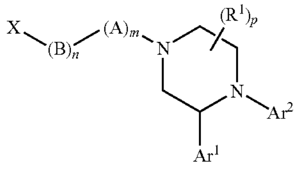

or a pharmaceutically acceptable salt, solvate, or ester thereof, wherein:

$Ar^1$ and $Ar^2$ are independently aryl or heteroaryl, wherein said aryl and heteroaryl are substituted with one or more groups $Y^1$;

n and m are independently 0 or 1;

A is selected from the group consisting of —C(O)—, —$S(O)_2$—, —C(=N—$OR^2$)—, and —$(C(R^2)_2)_q$— wherein q is 1, 2, or 3;

B is selected from the group consisting of —N($R^2$)—, —C(O)—, and —$(C(R^3)_2)_r$— wherein r is 1 or 2, with the proviso that when B is —C(O)—, then A is —C(O)— or —$(C(R^2)_2)_q$—;

X is selected from the group consisting of H, alkyl, —S-alkyl, —$S(O)_2$-alkyl, —$S(O)_2$-cycloalkyl, —$S(O)_2$-aryl, —$S(O)_2$-heteroaryl, cycloalkyl, benzo-fused cycloalkyl, benzo-fused heterocycloalkyl, benzo-fused heterocycloalkenyl, heterocycloalkyl, —C($R^2$)═C($R^2$)-aryl, —C($R^2$)═C($R^2$)-heteroaryl, —$OR^2$, —O-alkylene-O-alkyl, —S-aryl, —N$(R^4)_2$, —$(C(R^2)_2)_s$-heteroaryl, —C(O)—O-alkyl, —C(O)-aryl, —C(O)-heteroaryl, —N═O, —C(S-alkyl)=N—$S(O)_2$-aryl, —C(N$(R^2)_2$)═N—$S(O)_2$-aryl, and —$(C(R^2)_2)_s$-aryl wherein s is 0, 1, or 2, wherein the heteroaryl portion of said —$(C(R^2)_2)_s$-heteroaryl, the aryl portion of said —C($R^2$)═C($R^2$)-aryl, the heteroaryl portion of said —C($R^2$)═C($R^2$)— heteroaryl, the aryl portion of said —S-aryl, the aryl portion of said —$S(O)_2$-aryl, the heteroaryl portion of said —$S(O)_2$-heteroaryl, the aryl portion of said —C(O)-aryl, the heteroaryl portion of said —C(O)-heteroaryl, the aryl portion of said —$(C(R^2)_2)_s$-aryl, the aryl portion of said —C(S-alkyl)=N—$S(O)_2$-aryl, the aryl portion of said —C(N$(R^2)_2$)═N—$S(O)_2$-aryl, the benzo portion of said benzo-fused cycloalkyl, the benzo portion of said benzo-fused heterocycloalkyl, and the benzo portion of said benzo-fused heterocycloalkenyl of X are unsubstituted or substituted with one or more groups $Y^1$, and said cycloalkyl, the cycloalkyl portion of said —$S(O)_2$-cycloalkyl, said heterocycloalkyl, the cycloalkyl portion of said benzo-fused cycloalkyl, the heterocycloalkyl portion of said benzo-fused heterocycloalkyl, and the heterocycloalkenyl portion of said benzo-fused heterocycloalkenyl of X are unsubstituted or substituted with one or more groups $Y^2$;

each $R^1$ is independently selected from the group consisting of alkyl, haloalkyl, -alkylene-N$(R^5)_2$, -alkylene-$OR^2$, alkylene-$N_3$, -alkylene-CN, and alkylene-O—$S(O)_2$-alkyl; or two $R^1$ groups attached to the same ring carbon atom form a carbonyl group;

p is 0, 1, 2, 3, or 4;

each $R^2$ is independently H, alkyl, or aryl, wherein said aryl of $R^2$ is unsubstituted or substituted with one or more groups $Y^1$;

each $R^3$ is selected from the group consisting of H, alkyl, unsubstituted aryl, aryl substituted with one or more $Y^1$ groups, —$OR^2$, -alkylene-O-alkyl, and -alkylene-OH;

each $R^4$ is selected from the group consisting of H, alkyl, aryl, —C(O)—O-alkyl, —C(O)-alkyl, —C(O)-aryl, and —$S(O)_2$aryl, wherein said aryl, the aryl portion of said —C(O)-aryl, and the aryl portion of said —$S(O)_2$aryl of $R^4$ are unsubstituted or substituted with one or more $Y^1$ groups;

each $R^5$ is selected from the group consisting of H, alkyl, aryl, —$S(O)_2$-alkyl, —$S(O)_2$-cycloalkyl, —$S(O)_2$-aryl, —C(O)—N$(R^2)_2$, —C(O)-alkyl, and -alkylene-OH, wherein said aryl and the aryl portion of said —$S(O)_2$-aryl of $R^5$ are unsubstituted or substituted with one or more Z groups;

each $Y^1$ is independently selected from the group consisting of alkyl, cycloalkyl, heterocycloalkyl, heterocycloalkenyl, halo, haloalkyl, benzyl, aryl, heteroaryl, —O-aryl, —S-aryl, —$S(O)_2$-alkyl, —$S(O)_2$-cycloalkyl, —$S(O)_2$-aryl, -alkylene-CN, —CN, —C(O)-alkyl, —C(O)-aryl, —C(O)-haloalkyl, —C(O)O-alkyl, —N($R^2$)C(O)-alkyl, —N($R^2$)C(O)—N$(R^2)_2$, —OH, —O-alkyl, —O-haloalkyl, —O-alkylene-C(O)OH, —S-alkyl, —S-haloalkyl, -alkylene-OH, -alkylene-C(O)—O-alkyl, —O-alkylene-aryl, and —N$(R^5)_2$, wherein said aryl, heteroaryl, the aryl portion of said —O-aryl, the aryl portion of said —S-aryl, the aryl portion of said —$S(O)_2$-aryl, the aryl portion of said benzyl, the aryl portion of said —C(O)-aryl, and the aryl portion of said —O-alkylene-aryl of $Y^1$ are unsubstituted or substituted with one or more groups Z; or two groups $Y^1$ form a —O—$CH_2$—O— group;

each $Y^2$ is independently selected from the group consisting of alkyl, haloalkyl, aryl, -alkylene-aryl, —CN, —C(O)-alkyl, —$S(O)_2$-cycloalkyl, -alkylene-N$(R^2)_2$, —C(O)-alkylene-N$(R^4)_2$, —C(O)—O-alkyl, —C(O)-aryl, and —C(O)-haloalkyl, wherein said aryl and the aryl portion of said —C(O)-aryl of $Y^2$ are unsubstituted or substituted with one or more groups Z; or two groups $Y^2$ form a —O—$CH_2CH_2$—O— group; or two of said $Y^2$ substituents attached to the same ring carbon atom of a cycloalkyl, benzo-fused cycloalkyl, benzo-fused heterocycloalkyl, benzo-fused heterocycloalkenyl, or heterocycloalkyl ring, together with the ring carbon atom to which they are both attached, form a carbonyl group; and each Z is independently selected from the group consisting of alkyl, halo, haloalkyl, —OH, —O-alkyl, and —CN.

In another embodiment, the present invention also provides for compositions comprising at least one selective $CB_1$ receptor antagonist compound of Formula (I), above, or a pharmaceutically acceptable salt, solvate, or ester thereof, and a pharmaceutically acceptable carrier.

In another embodiment, the present invention also provides for compositions comprising at least on selective $CB_1$ receptor antagonist compound of Formula (I), or a pharmaceutically acceptable salt, solvate, or ester thereof, in combination with at least one cholesterol lowering compound.

In yet another embodiment, the present invention also provides for a method of treating, reducing, or ameliorating metabolic syndrome, obesity, waist circumference, lipid profile, insulin sensitivity, neuroinflammatory disorders, cognitive disorders, psychosis, addictive behavior, gastrointestinal disorders, and cardiovascular conditions by administering an effective amount of at least one compound of Formula (I), or a pharmaceutically acceptable salt, solvate, or ester thereof, to a patient in need thereof.

In yet another embodiment, the present invention also provides for a method of treating vascular conditions, hyperlipidaemia, atherosclerosis, hypercholesterolemia, sitosterolemia, vascular inflammation, metabolic syndrome, stroke, diabetes, obesity and/or reducing the level of sterol(s) by administering an effective amount of a composition comprising a combination of at least one compound of Formula (I), or a pharmaceutically acceptable salt, solvate, or ester thereof, and at least one cholesterol lowering compound.

DETAILED DESCRIPTION OF THE INVENTION

The selective $CB_1$ receptor antagonist compounds of the present invention are selective $CB_1$ receptor antagonists of mammalian $CB_1$ receptors, preferably human $CB_1$ receptors, and variants thereof. Mammalian $CB_1$ receptors also include $CB_1$ receptors found in rodents, primates, and other mammalian species.

In one embodiment, the selective $CB_1$ receptor antagonist compounds of the present invention are selective $CB_1$ receptor antagonists that bind to a $CB_1$ receptor with a binding affinity ($K_{i(CB1)}$, measured as described herein) of about 400 nM or less, or about 200 nM or less, or about 100 nM or less, or about 10 nM or less. These ranges are inclusive of all values and subranges therebetween.

In one embodiment, the selective $CB_1$ receptor antagonist compounds of the present invention are selective $CB_1$ receptor antagonists that have a ratio of $CB_1$ receptor affinity to $CB_2$ receptor affinity ($K_{i(CB1)}$:$K_{i(CB2)}$, measured as described herein) of about 1:2 or better, or about 1:10 or better, or about 1:25 or better, or about 1:50 or better, or about 1:75 or better, or about 1:90 or better. These ranges are inclusive of all values and subranges therebetween.

Thus, in one embodiment, a selective $CB_1$ receptor antagonist of the present invention has an affinity for the $CB_1$ receptor, measured as described herein, of at least 400 nM or less, and a ratio of $CB_1$ to $CB_2$ receptor affinity (i.e., $K_{i(CB1)}$:$K_{i(CB2)}$) of at least 1:2 or better. In another embodiment the $CB_1$ receptor affinity is about 200 nM or less, and the $K_{i(CB1)}$:$K_{i(CB2)}$ is about 1:10 or better. In another embodiment the $CB_1$ affinity is about 100 nM or less, and the $K_{i(CB1)}$:$K_{i(CB2)}$ is about 1:25 or better. In another embodiment the $CB_1$ affinity is about 10 nM or less, and the $K_{i(CB1)}$:$K_{i(CB2)}$ is about 1:75 or better. In another embodiment the $CB_1$ affinity is about 10 nM or less, and the $K_{i(CB1)}$:$K_{i(CB2)}$ is about 1:90 or better. These ranges are inclusive of all values and subranges therebetween.

In one embodiment, the present invention provides for a selective $CB_1$ receptor antagonist compound of Formula (I), or a pharmaceutically acceptable salt, solvate, or ester thereof, wherein the various substituent groups (i.e., X, $Ar^1$, $Ar^2$, etc.) are as defined herein.

In another embodiment of the compound of the present invention, or a pharmaceutically acceptable salt, solvate, or ester thereof, $Ar^1$ and $Ar^2$ are independently $(C_6-C_{10})$aryl or $(C_2-C_{10})$heteroaryl, wherein said $(C_6-C_{10})$aryl and $(C_2-C_{10})$heteroaryl are substituted with one or more groups $Y^1$;

n and m are independently 0 or 1;

A is selected from the group consisting of —C(O)—, $—S(O)_2—$, $—C({=}N—OR^2)—$, and $—(C(R^2)_2)_q—$ wherein q is 1, 2, or 3;

B is selected from the group consisting of $—N(R^2)—$, —C(O)—, and $—(C(R^3)_2)_r—$ wherein r is 1 or 2, with the proviso that when B is —C(O)—, then A is —C(O)— or $—(C(R^2)_2)_q—$;

X is selected from the group consisting of H, $(C_1-C_6)$alkyl, $—S—(C_1-C_6)$alkyl, $—S(O)_2—(C_1-C_6)$alkyl, $—S(O)_2—(C_3-C_{10})$cycloalkyl, $—S(O)_2—(C_6-C_{10})$aryl, $—S(O)_2—(C_2-C_{10})$heteroaryl, $(C_3-C_{10})$cycloalkyl, benzo-fused $(C_3-C_{10})$cycloalkyl, benzo-fused $(C_2-C_{10})$heterocycloalkyl, benzo-fused $(C_2-C_{10})$heterocycloalkenyl, $(C_2-C_{10})$heterocycloalkyl, $—C(R^2){=}C(R^2)—(C_6-C_{10})$aryl, $—C(R^2){=}C(R^2)—(C_2-C_{10})$heteroaryl, $—OR^2$, $—O—(C_1-C_6)$alkylene-$O—(C_1-C_6)$alkyl, $—S—(C_6-C_{10})$aryl, $—N(R^4)_2$, $—(C(R^2)_2)_s—(C_2-C_{10})$heteroaryl, $—C(O)—O—(C_1-C_6)$alkyl, $—C(O)—(C_6-C_{10})$aryl, $—C(O)—(C_2-C_{10})$heteroaryl, —N=O, $—C(S—(C_1-C_6)alkyl){=}N—S(O)_2—(C_6-C_{10})$aryl, $—C(N(R^2)_2){=}N—S(O)_2—(C_6-C_{10})$aryl, and $—(C(R^2)_2)_s—(C_6-C_{10})$aryl wherein s is 0, 1, or 2, wherein the $(C_2-C_{10})$heteroaryl portion of said $—(C(R^2)_2)_s—(C_2-C_{10})$heteroaryl, the $(C_6-C_{10})$aryl portion of said $—C(R^2){=}C(R^2)—(C_6-C_{10})$aryl, the $(C_2-C_{10})$heteroaryl portion of said $—C(R^2){=}C(R^2)—(C_2-C_{10})$heteroaryl, the $(C_6-C_{10})$aryl portion of said $—S—(C_6-C_{10})$aryl, the $(C_6-C_{10})$aryl portion of said $—S(O)_2—(C_6-C_{10})$aryl, the $(C_2-C_{10})$heteroaryl portion of said $—S(O)_2—(C_2-C_{10})$heteroaryl, the $(C_6-C_{10})$aryl portion of said $—C(O)—(C_6-C_{10})$aryl, the $(C_2-C_{10})$heteroaryl portion of said $—C(O)—(C_2-C_{10})$heteroaryl, the $(C_6-C_{10})$aryl portion of said $—(C(R^3)_2)_s—(C_6-C_{10})$aryl, the $(C_6-C_{10})$aryl portion of said $—C(S—(C_1-C_6)alkyl){=}N—S(O)_2—(C_6-C_{10})$aryl, the $(C_6-C_{10})$aryl portion of said $—C(N(R^2)_2){=}N—S(O)_2—(C_6-C_{10})$aryl, the benzo portion of said benzo-fused $(C_3-C_{10})$cycloalkyl, the benzo portion of said benzo-fused $(C_2-C_{10})$heterocycloalkyl, and the benzo portion of said benzo-fused $(C_2-C_{10})$heterocycloalkenyl of X are unsubstituted or substituted with one or more groups $Y^1$, and said $(C_3-C_{10})$cycloalkyl, the $(C_3-C_{10})$cycloalkyl portion of said $—S(O)_2—(C_3-C_{10})$cycloalkyl, said $(C_2-C_{10})$heterocycloalkyl, the $(C_3-C_{10})$cycloalkyl portion of said benzo-fused $(C_3-C_{10})$cycloalkyl, the $(C_2-C_{10})$heterocycloalkyl portion of said benzo-fused $(C_2-C_{10})$heterocycloalkyl, and the $(C_2-C_{10})$heterocycloalkenyl portion of said benzo-fused $(C_2-C_{10})$heterocycloalkenyl of X are unsubstituted or substituted with one or more groups $Y^2$;

each $R^1$ is independently selected from the group consisting of $(C_1-C_6)$alkyl, $—(C_1-C_6)$alkylene-$N(R^5)_2$, $—(C_1-C_6)$alkylene-$OR^2$, $(C_1-C_6)$alkylene-$N_3$, and $(C_1-C_6)$alkylene-$O—S(O)_2—(C_1-C_6)$alkyl; or two $R^1$ groups attached to the same ring carbon atom form a carbonyl group;

p is 0, 1, 2, 3, or 4;

each $R^2$ is independently H, $(C_1-C_6)$alkyl, or $(C_6-C_{10})$aryl, wherein said $(C_6-C_{10})$aryl of $R^2$ is unsubstituted or substituted with one or more groups $Y^1$;

each $R^3$ is selected from the group consisting of H, $(C_1-C_6)$alkyl, unsubstituted $(C_6-C_{10})$aryl, $(C_6-C_{10})$aryl substituted with one or more $Y^1$ groups, $—OR^2$, $—(C_1-C_6)$alkylene-$O—(C_1-C_6)$alkyl, and $—(C_1-C_6)$alkylene-OH;

each $R^4$ is selected from the group consisting of H, $(C_1-C_6)$alkyl, $(C_6-C_{10})$aryl, $—C(O)—O—(C_1-C_6)$alkyl, $—C(O)—(C_1-C_6)$alkyl, $—C(O)—(C_6-C_{10})$aryl, and $—S(O)_2—(C_6-C_{10})$aryl, wherein said $(C_6-C_{10})$aryl, the $(C_6-C_{10})$aryl portion of said $—C(O)—(C_6-C_{10})$aryl, and the $(C_6-C_{10})$aryl portion of said $—S(O)_2—(C_6-C_{10})$aryl of $R^4$ are unsubstituted or substituted with one or more $Y^1$ groups;

each $R^5$ is selected from the group consisting of H, $(C_1-C_6)$alkyl, $(C_6-C_{10})$aryl, $—S(O)_2—(C_1-C_6)$alkyl, $—S(O)_2—(C_3-C_{10})$cycloalkyl, $—S(O)_2$-aryl, $—C(O)—N(R^2)_2$, $—C(O)—(C_1-C_6)$alkyl, and $—(C_1-C_6)$alkylene-OH, wherein said $(C_6-C_{10})$aryl and the $(C_6-C_{10})$aryl portion of said $—S(O)_2—(C_6-C_{10})$aryl of $R^5$ are unsubstituted or substituted with one or more Z groups;

each $Y^1$ is independently selected from the group consisting of $(C_1-C_6)$alkyl, $(C_3-C_{10})$cycloalkyl, $(C_2-C_{10})$heterocycloalkyl, $(C_2-C_{10})$heterocycloalkenyl, halo, $(C_1-C_6)$haloalkyl, benzyl, $(C_6-C_{10})$aryl, $(C_2-C_{10})$heteroaryl, $—O—(C_6-C_{10})$aryl, $—S—(C_6-C_{10})$aryl, $—S(O)_2—(C_1-C_6)$alkyl, $—S(O)_2—(C_3-C_{10})$cycloalkyl, $—S(O)_2—(C_6-C_{10})$aryl, $—(C_1-C_6)$alkylene-CN, —CN, $—C(O)—(C_1-C_6)$alkyl, $—C(O)—(C_6-C_{10})$aryl, $—C(O)—(C_1-C_6)$alkyl, $—C(O)—(C_1-C_6)$haloalkyl, $—C(O)O—(C_1-C_6)$alkyl, $—N(R^2)C(O)—(C_1-C_6)$alkyl, $—N(R^2)C(O)—N(R^2)_2$, —OH, $—O—(C_1-C_6)$alkyl, $—O—(C_1-C_6)$haloalkyl, —O—($C_1$-$C_6$)alkylene-C(O)OH, —S—($C_1$-$C_6$)alkyl, —S—($C_1$-$C_6$)haloalkyl, —($C_1$-$C_6$)alkylene-OH, —($C_1$-$C_6$)alkylene-C(O)—O—($C_1$-$C_6$)alkyl, —O—($C_1$-$C_6$)alkylene-($C_6$-$C_{10}$)aryl, and —N($R^5$)$_2$, wherein said ($C_6$-$C_{10}$)aryl, said ($C_2$-$C_{10}$)heteroaryl, the ($C_6$-$C_{10}$)aryl portion of said —O—($C_6$-$C_{10}$)aryl, the ($C_6$-$C_{10}$)aryl portion of said —S—($C_6$-$C_{10}$)aryl, the ($C_6$-$C_{10}$)aryl portion of said —S(O)$_2$—($C_6$-$C_{10}$)aryl, said benzyl, the ($C_6$-$C_{10}$)aryl portion of said —C(O)—($C_6$-$C_{10}$)aryl, and the ($C_6$-$C_{10}$)aryl portion of said —O—($C_1$-$C_6$)alkylene-($C_6$-$C_{10}$)aryl of $Y^1$ are unsubstituted or substituted with one or more groups Z; or two groups $Y^1$ form a —O—$CH_2$—O— group;

each $Y^2$ is independently selected from the group consisting of ($C_1$-$C_6$)alkyl, ($C_1$-$C_6$)haloalkyl, ($C_6$-$C_{10}$)aryl, —($C_1$-$C_6$)alkylene-($C_6$-$C_{10}$)aryl, —CN, —C(O)—($C_1$-$C_6$)alkyl, —S(O)$_2$—($C_3$-$C_{10}$)cycloalkyl, —($C_1$-$C_6$)alkylene-N($R^2$)$_2$, —C(O)—($C_1$-$C_6$)alkylene-N($R^4$)$_2$, —C(O)—O—($C_1$-$C_6$)alkyl, —C(O)— ($C_6$-$C_{10}$)aryl, and —C(O)—($C_1$-$C_6$)haloalkyl, wherein said aryl and the ($C_6$-$C_{10}$)aryl portion of said —C(O)— ($C_6$-$C_{10}$)aryl of $Y^2$ are unsubstituted or substituted with one or more groups Z; or two groups $Y^2$ form a —O—$CH_2CH_2$—O— group; or two of said $Y^2$ substituents attached to the same ring carbon atom of a ($C_3$-$C_{10}$)cycloalkyl, benzo-fused ($C_3$-$C_{10}$)cycloalkyl, benzo-fused ($C_2$-$C_{10}$)heterocycloalkyl, benzo-fused ($C_2$-$C_{10}$)heterocycloalkenyl, or ($C_2$-$C_{10}$)heterocycloalkyl ring, together with the ring carbon atom to which they are both attached, form a carbonyl group; and e and Z is independently selected from the group consisting of ($C_1$-$C_6$)alkyl, halo, ($C_1$-$C_6$)haloalkyl, —OH, —O—($C_1$-$C_6$)alkyl, and —CN.

In another embodiment of the compounds of the present invention, or pharmaceutically acceptable salts, solvates, or esters thereof, $Ar^1$ and $Ar^2$ are independently aryl substituted with one or more groups $Y^1$.

In another embodiment of the compounds of the present invention, or pharmaceutically acceptable salts, solvates, or esters thereof, $Ar^1$ and $Ar^2$ are independently aryl substituted with one or more groups $Y^1$, m is 1; and A is —C(O)—.

In another embodiment of the compounds of the present invention, or pharmaceutically acceptable salts, solvates, or esters thereof, $Ar^1$ and $Ar^2$ are independently aryl substituted with one or more groups $Y^1$, m is 1; n is 0; and A is —C(O)—.

In another embodiment of the compounds of the present invention, or pharmaceutically acceptable salts, solvates, or esters thereof, $Ar^1$ and $Ar^2$ are independently aryl substituted with one or more groups $Y^1$, m is 1; n is 1; B is —NH—; and A is —C(O)—.

In another embodiment of the compounds of the present invention, or pharmaceutically acceptable salts, solvates, or esters thereof, $Ar^1$ and $Ar^2$ are independently aryl substituted with one or more groups $Y^1$, m is 1; n is 1; B is —(C($R^2$)$_2$)$_r$— wherein r is 1 or 2; and A is —C(O)—.

In another embodiment of the compounds of the present invention, or pharmaceutically acceptable salts, solvates, or esters thereof, $Ar^1$ and $Ar^2$ are independently aryl substituted with one or more groups $Y^1$, m is 1; n is 1; B is —N($R^2$)— wherein r is 1 or 2; and A is —C(O)—.

In another embodiment of the compounds of the present invention, or pharmaceutically acceptable salts, solvates, or esters thereof, m is 1; and A is —S(O)$_2$—.

In another embodiment of the compounds of the present invention, or pharmaceutically acceptable salts, solvates, or esters thereof, m is 1; n is 0; and A is —S(O)$_2$—.

In another embodiment of the compounds of the present invention, or pharmaceutically acceptable salts, solvates, or esters thereof, m is 1; n is 1; B is —N($R^2$)—; and A is —S(O)$_2$—.

In another embodiment of the compounds of the present invention, or pharmaceutically acceptable salts, solvates, or esters thereof, m is 1; A is —C(=N—O$R^2$)—; and n is 0.

In another embodiment of the compounds of the present invention, or pharmaceutically acceptable salts, solvates, or esters thereof, m is 1; A is —(C($R^2$)$_2$)$_q$— wherein q is 1, 2, or 3; and n is 0.

In another embodiment of the compounds of the present invention, or pharmaceutically acceptable salts, solvates, or esters thereof, X is aryl or heteroaryl, and said aryl or heteroaryl of X is unsubstituted or substituted with one or more $Y^1$ groups; m is 1; A is —(C($R^2$)$_2$)$_q$— wherein q is 1, 2, or 3; and n is 0.

In another embodiment of the compounds of the present invention, or pharmaceutically acceptable salts, solvates, or esters thereof, X is aryl or heteroaryl, and said aryl or heteroaryl of X is unsubstituted or substituted with one or more $Y^1$ groups; m is 1; A is —(C($R^2$)$_2$)$_q$— wherein q is 1 or 2; and n is 0.

In another embodiment of the compounds of the present invention, or pharmaceutically acceptable salts, solvates, or esters thereof, m is 0; B is (C($R^3$)$_2$)$_r$— wherein r is 1, 2, or 3; and A is —(C($R^2$)$_2$)$_q$— wherein q is 1, 2, or 3.

In another embodiment of the compounds of the present invention, or pharmaceutically acceptable salts, solvates, or esters thereof, m and n are both 1; B is —(C($R^3$)$_2$)$_r$— wherein r is 1, 2, or 3; and n is 1.

In another embodiment of the compounds of the present invention, or pharmaceutically acceptable salts, solvates, or esters thereof, m and n are both 0.

In another embodiment of the compounds of the present invention, or pharmaceutically acceptable salts, solvates, or esters thereof, X is —(C($R^2$)$_2$)$_s$-aryl wherein s is 0, 1, or 2.

In another embodiment of the compounds of the present invention, or pharmaceutically acceptable salts, solvates, or esters thereof, X is heteroaryl.

In another embodiment of the compounds of the present invention, or pharmaceutically acceptable salts, solvates, or esters thereof, X is cycloalkyl.

In another embodiment of the compounds of the present invention, or pharmaceutically acceptable salts, solvates, or esters thereof, X is heterocycloalkyl.

In another embodiment of the compounds of the present invention, or pharmaceutically acceptable salts, solvates, or esters thereof, X is alkyl.

In another embodiment of the compounds of the present invention, or pharmaceutically acceptable salts, solvates, or esters thereof, X is —N($R^4$)$_2$.

In another embodiment of the compounds of the present invention, or pharmaceutically acceptable salts, solvates, or esters thereof, m and n are both 1; B is —(C($R^3$)$_2$)$_r$— wherein r is 1, 2, or 3; and A is —C(O)—.

In another embodiment of the compounds of the present invention, or pharmaceutically acceptable salts, solvates, or esters thereof, m and n are both 1; A is —C(O)—; and B is —NH—.

In yet another embodiment the compounds of the present invention, or pharmaceutically acceptable salts, solvates, or esters thereof, have the following Formula (IA):

(IA)

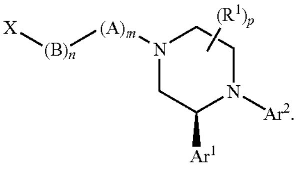

In yet another embodiment the compounds of the present invention, or pharmaceutically acceptable salts, solvates, or esters thereof, have the following Formula (IB):

(IB)

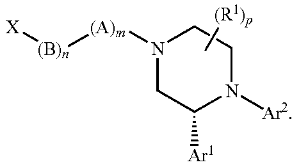

In yet another embodiment the compounds of the present invention, or pharmaceutically acceptable salts, solvates, or esters thereof, have the following Formula (IC):

(IC)

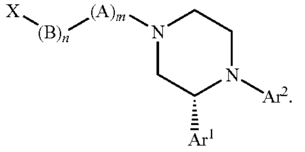

In yet another embodiment, the compounds of the present invention, or pharmaceutically acceptable salts, solvates, or esters thereof, have the Formula (IC) above, wherein m is 1 and A is —C(O)—.

In yet another embodiment, the compounds of the present invention, or pharmaceutically acceptable salts, solvates, or esters thereof, have the Formula (IC) above, wherein m is 1, n is 0, and A is —C(O)—.

In yet another embodiment, the compounds of the present invention, or pharmaceutically acceptable salts, solvates, or esters thereof, have the Formula (IC) above, wherein m is 1, n is 1, A is —C(O)—, and B is —N($R^2$)—.

In yet another embodiment, the compounds of the present invention, or pharmaceutically acceptable salts, solvates, or esters thereof, have the Formula (IC) above, wherein m is 1 and A is —$S(O)_2$—.

In yet another embodiment, the compounds of the present invention, or pharmaceutically acceptable salts, solvates, or esters thereof, have the Formula (IC) above, wherein m is 1, n is 0, and A is —$S(O)_2$—.

In yet another embodiment, the compounds of the present invention, or pharmaceutically acceptable salts, solvates, or esters thereof, have the Formula (IC) above, wherein m is 1, ni 1, B is —N($R^2$)—, and A is —$S(O)_2$—.

In yet another embodiment, the compounds of the present invention, or pharmaceutically acceptable salts, solvates, or esters thereof are selected from the group consisting of:

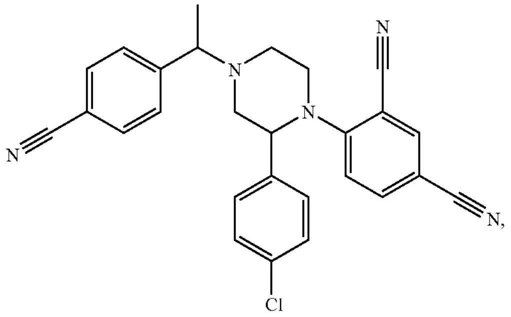

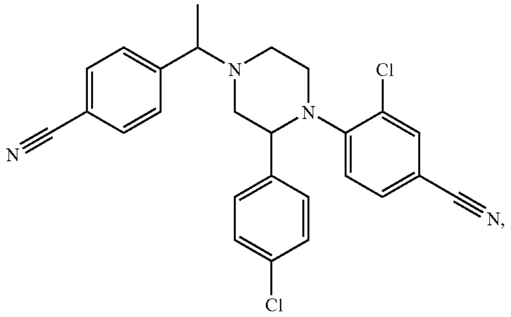

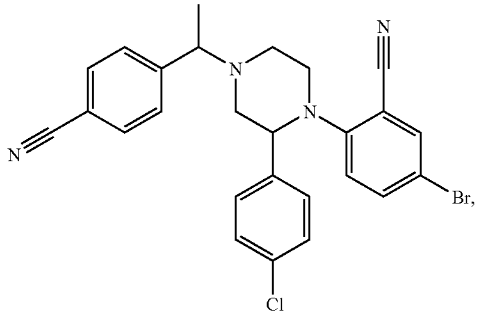

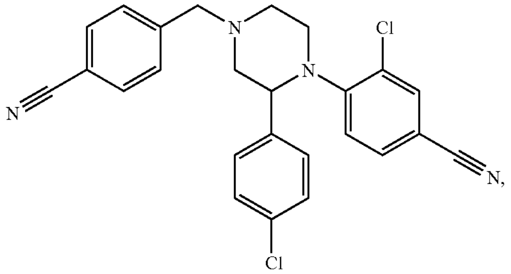

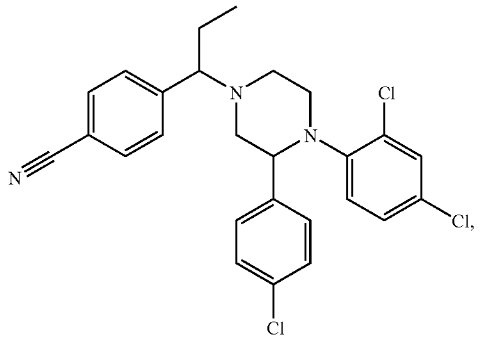

-continued
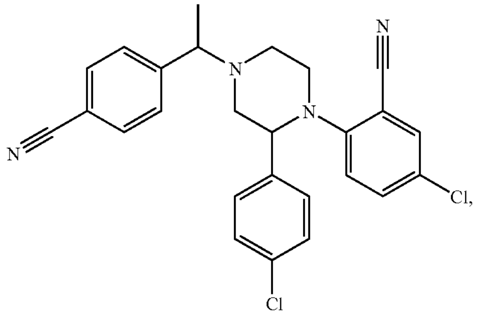
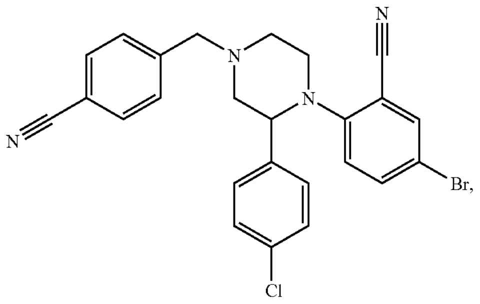
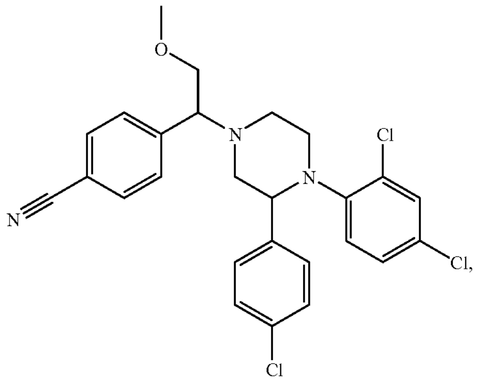
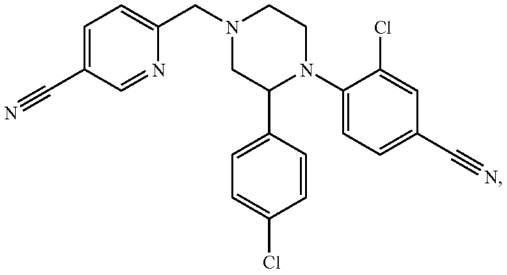
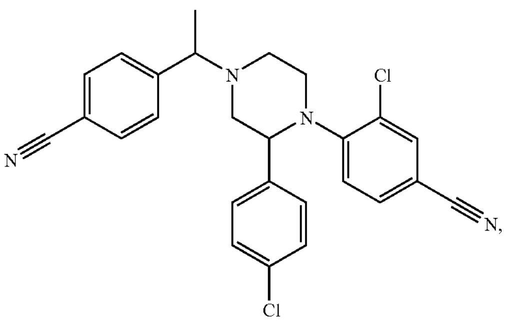
-continued
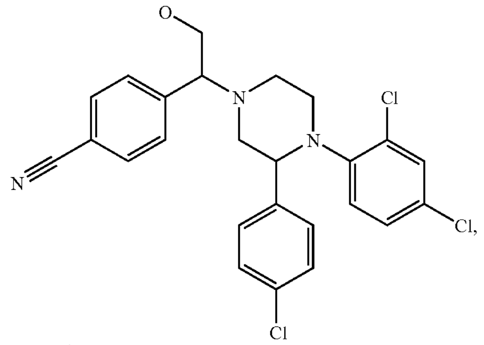
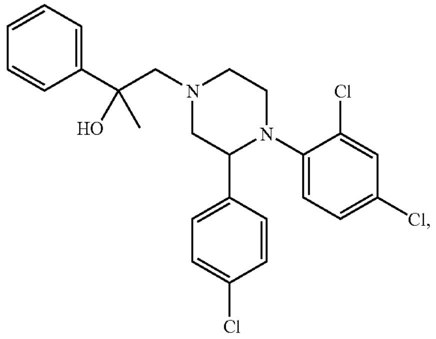
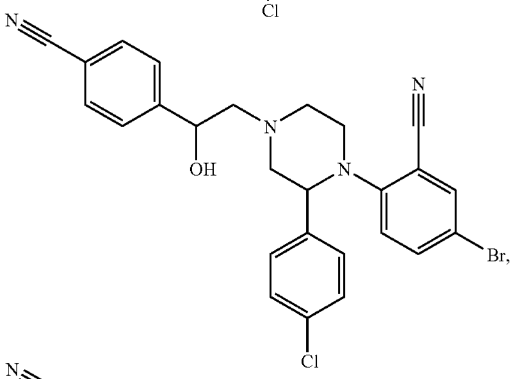
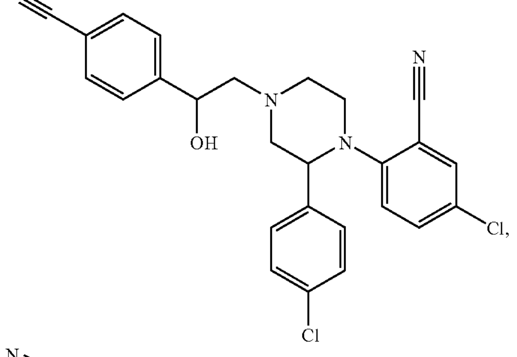
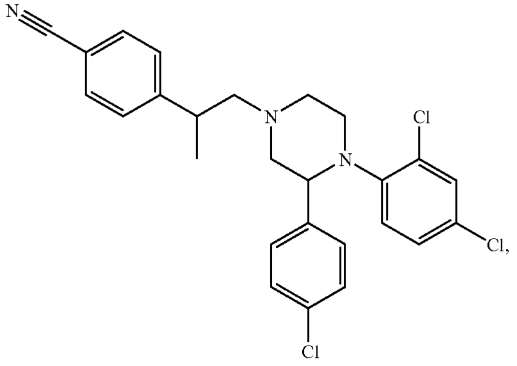

-continued
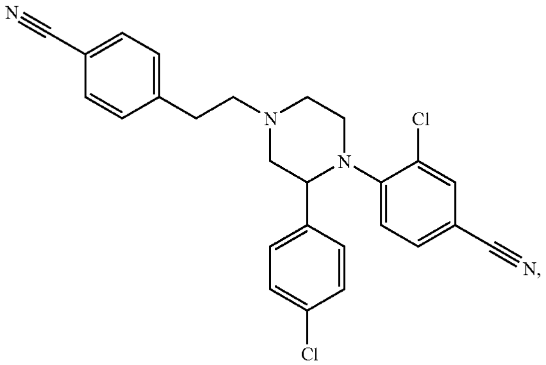
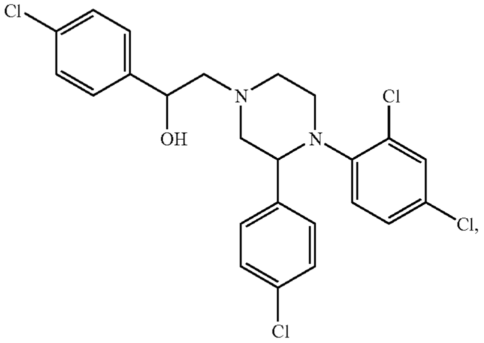
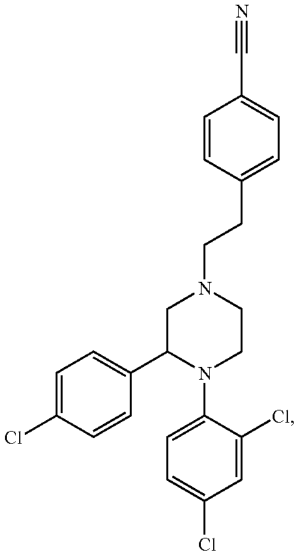
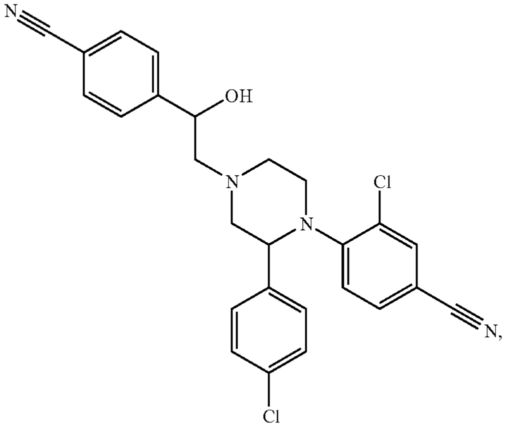
-continued
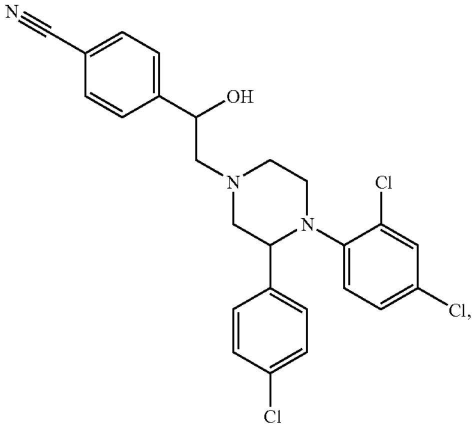
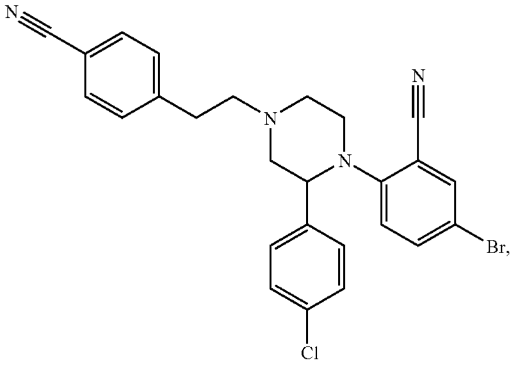
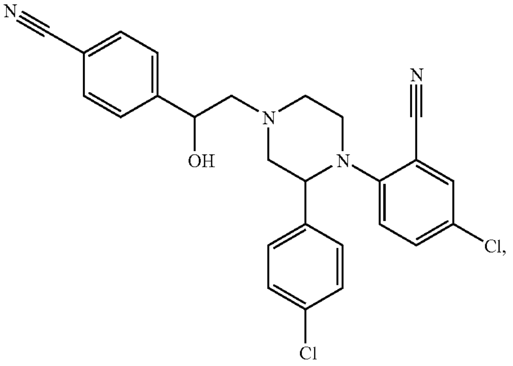
and
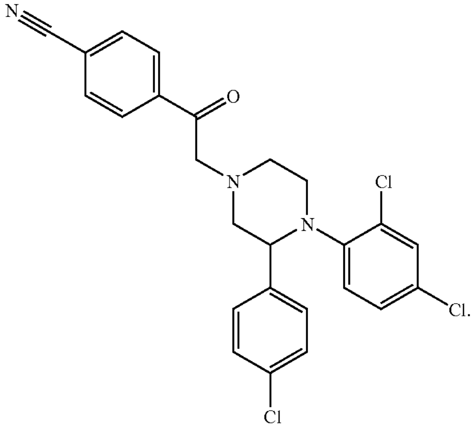
One of ordinary skill will recognize that the compounds shown above have stereogenic centers. Thus, the compounds shown above include all possible stereoisomers.

In yet another embodiment, the compounds of the present invention, or pharmaceutically acceptable salts, solvates, or esters thereof are selected from the group consisting of:

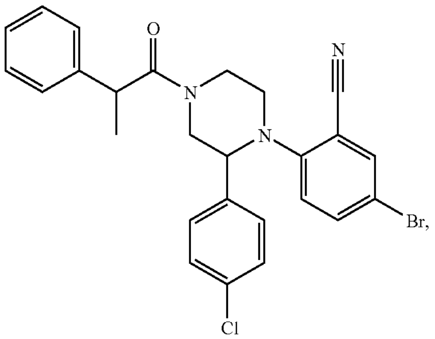
,

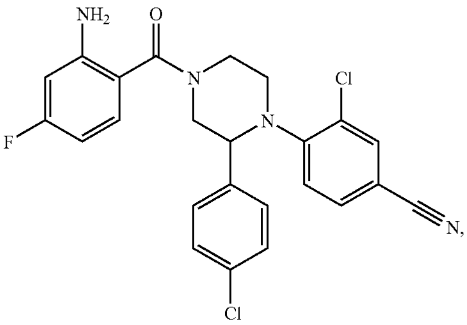
,

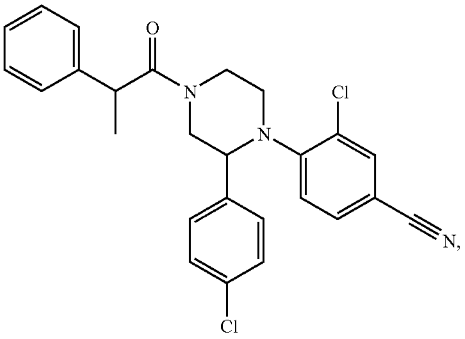
,

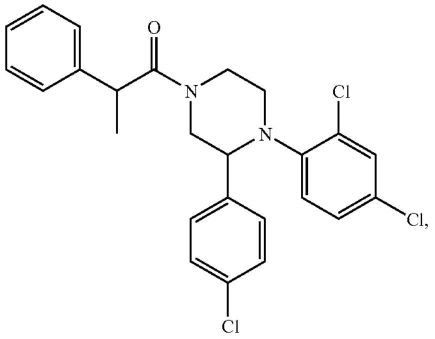
,

-continued

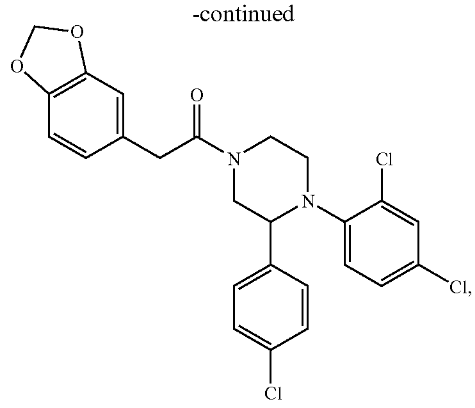
,

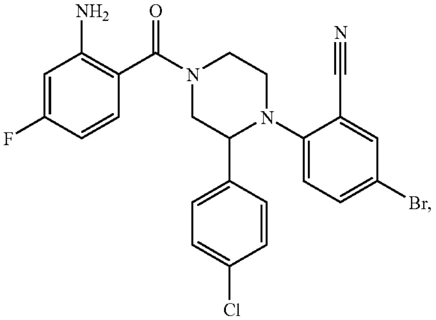
,

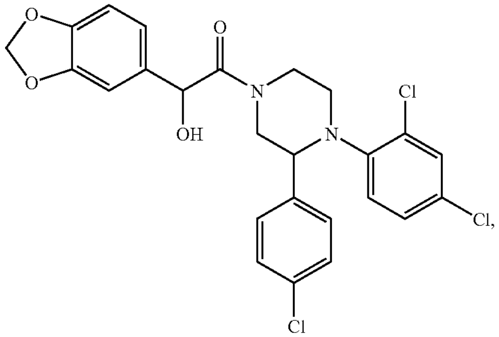
, and

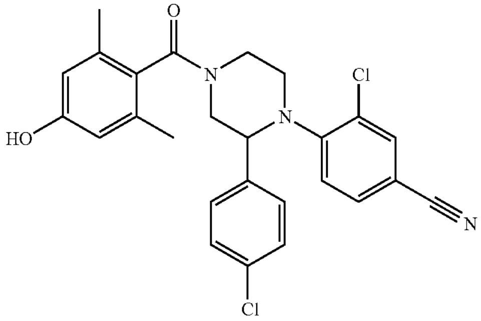

or a pharmaceutically acceptable salt, solvate, or ester thereof. One of ordinary skill will recognize that the compounds shown above have stereogenic centers. Thus, the compounds shown above include all possible stereoisomers.

$Ar^1$ and $Ar^2$ are independently aryl or heteroaryl, wherein said aryl and heteroaryl are substituted with one or more groups $Y^1$ Non-limiting examples of said aryl of $Ar^1$ and/or $Ar^2$ include, for example, phenyl, naphthyl, pyridyl (e.g., 2-, 3-, and 4-pyridyl), quinolyl, etc. substituted with one or more (e.g., 1, 2, 3, or 4) $Y^1$ groups as defined herein.

A is selected from the group consisting of —C(O)—, —$S(O)_2$—, —C(=N—$OR^2$)—, and —$(C(R^2)_2)_q$— wherein q is 1, 2, or 3. Non-limiting examples of A when A is $(C(R^2)_2)_q$— include, for example, —$CH_2$—, —$CH_2CH_2$—, —$CH(CH_3)$—, —$C(CH_3)_2$—, —$CH_2CH_2CH_2$—, —$CH(CH_3)CH_2$—, —$CH_2CH(CH_3)$—, —$CH(CH_3)$—$(CH_2)_2$—, —$(CH_2)_2$—$CH(CH_3)$—, —CH(phenyl)-$CH_2$—, —$CH_2$—CH(phenyl)-, —CH(phenyl)-, etc. Non-limiting examples of A when A is —C(═N—$OR^2$)— include —C(═N—OH)—, —C(═N—$OCH_3$)—, —C(═N—$OCH_2CH_3$)—, —C(═N—$OCH(CH_3)_2$)—, —C(═N—$OC(CH_3)_3$)—, —C(═N—O-phenyl), etc.

B is selected from the group consisting of —$N(R^2)$—, —C(O)—, and —$(C(R^3)_2)_r$— wherein r is 1 or 2. Non-limiting examples of B when B is —$(C(R^3)_2)_r$— include, for example, —$CH_2$—, —$CH_2CH_2$—, —$CH(CH_3)$—, —$C(CH_3)_2$—, —$CH(CH(CH_3)_2)$—, —$CH(CH_2CH(CH_3)_2)$—, —$CH_2CH_2CH_2$—, —$CH(CH_3)CH_2$—, —$CH_2CH(CH_3)$—, —$CH(CH_3)$—$(CH_2)_2$—, —$(CH_2)_2$—$CH(CH_3)$—, —CH(phenyl)-$CH_2$—, —$CH_2$—CH(phenyl)-, —CH(phenyl)-, —CH(OH)—, —$C(CH_3)(OH)$—, —CH(OH)$CH_2$—, —$CH_2$CH(OH)—, —CH(OH)$CH_2CH(CH_3)$—, —$CH(CH(OH)(CH_3))$—, —$CH(CH_3)CH_2CH$(OH)—, —$CH(CH_2OH)$—, —$CH(OCH_3)$—, —$CH(OCH_3)CH_2$—, —$CH_2CH(OCH_3)$—, —$CH(OCH_3)CH_2CH(CH_3)$—, —$CH(CH_3)CH_2CH(OCH_3)$—, —$CH(CH_2OCH_3)$—, —$CH(OCH_3)$—, —$CH(OCH_2CH_3)CH_2$—, —$CH_2CH(OCH_2CH_3)$—, —$CH(OCH_2CH_3)CH_2CH(CH_3)$—, —$CH(CH_3)CH_2CH(OCH_2CH_3)$—, —$CH(CH_2OCH_2CH_3)$—, etc. Non-limiting examples of B when B is —$N(R^2)$— include —NH—, —N(alkyl)-, —N(aryl)-, wherein the terms "alkyl" and "aryl" are as defined above.

X is selected from the group consisting of H, alkyl, —S-alkyl, —$S(O)_2$-alkyl, —$S(O)_2$-cycloalkyl, —$S(O)_2$-aryl, —$S(O)_2$-heteroaryl, cycloalkyl, benzo-fused cycloalkyl, benzo-fused heterocycloalkyl, benzo-fused heterocycloalkenyl, heterocycloalkyl, —$C(R^2)$═$C(R^2)$-aryl, —$C(R^2)$═$C(R^2)$-heteroaryl, —$OR^2$, —O-alkylene-O-alkyl, —S-aryl, —$N(R^4)_2$, —$(C(R^2)_2)_s$-heteroaryl, —C(O)—O-alkyl, —C(O)-aryl, —C(O)-heteroaryl, —N═O, —C(S-alkyl)=N—$S(O)_2$-aryl, —$C(N(R^2)_2)$═N—$S(O)_2$-aryl, and —$(C(R^2)_2)_s$-aryl wherein s is 0, 1, or 2. Non-limiting examples of X when X is alkyl include methyl, ethyl, n-propyl, iso-propyl, n-butyl, iso-butyl, sec-butyl, tert-butyl, n-pentyl, iso-pentyl, neo-pentyl, n-hexyl, iso-hexyl, etc. Non-limiting examples of X when X is —S-alkyl include —S-methyl, —S-ethyl, —S-(n-propyl), —S-(iso-propyl), —S-(n-butyl), —S-(iso-butyl), —S-(sec-butyl), —S-(tert-butyl), —S-(n-pentyl), —S-(iso-pentyl), —S-(neo-pentyl), —S-(n-hexyl), —S-(iso-hexyl), etc. Non-limiting examples of X when X is —$S(O)_2$-alkyl include —$S(O)_2$-methyl, —$S(O)_2$-ethyl, —$S(O)_2$-(n-propyl), —$S(O)_2$-(iso-propyl), —$S(O)_2$-(n-butyl), —$S(O)_2$-(iso-butyl), —$S(O)_2$-(sec-butyl), —$S(O)_2$-(tert-butyl), —$S(O)_2$-(n-pentyl), —$S(O)_2$-(iso-pentyl), —$S(O)_2$-(neo-pentyl), —$S(O)_2$-(n-hexyl), —$S(O)_2$-(iso-hexyl), etc. Non-limiting examples of X when X is —$S(O)_2$-cycloalkyl include —$S(O)_2$-cyclopropyl, —$S(O)_2$-cyclobutyl, —$S(O)_2$-cyclopentyl, —$S(O)_2$-cyclohexyl, —$S(O)_2$-cycloheptyl, —$S(O)_2$-adamantyl, —$S(O)_2$-(bicyclo[2.1.1]hexanyl), —$S(O)_2$-(bicyclo[2.2.1]heptenyl), —$S(O)_2$-(bicyclo[3.1.1]heptenyl), —$S(O)_2$-(bicyclo[2.2.2]octenyl), —$S(O)_2$-(bicyclo[3.2.1]octenyl), etc. Non-limiting examples of X when X is —$S(O)_2$-aryl includes —$S(O)_2$-phenyl, —$S(O)_2$-naphthyl, etc. Non-limiting examples of X when X is —$S(O)_2$-heteroaryl include —$S(O)_2$-pyridyl, —$S(O)_2$-azaindolyl, —$S(O)_2$-benzimidazolyl, —$S(O)_2$-benzofuranyl, —$S(O)_2$-furanyl, —$S(O)_2$-indolyl, etc. Non-limiting examples of X when X is cycloalkyl include cyclopropyl, cyclobutyl, cyclopentyl, cyclohexyl, cycloheptyl, adamantyl, bicyclo[2.1.1]hexanyl, bicyclo[2.2.1]heptenyl, bicyclo[3.1.1]heptenyl, bicyclo[2.2.2]octenyl, bicyclo[3.2.1]octenyl, etc. Non-limiting examples of X when X is benzo-fused cycloalkyl include 1,2,3,4-tetrahydronaphthyl, indanyl, bicyclo[4.2.0]octa-1,3,5-trienyl, etc. Non-limiting examples of X when X is benzo-fused heterocycloalkyl includes 3,4-dihydro-2H-benzo[1,4]oxazinyl, chromanyl, 2,3-dihydro-1H-indolyl, 2,3-dihydro-1H-isoindolyl, 2,3-dihydro-benzofuranyl, 1,3-dihydro-isobenzofuranyl, 2,3-dihydro-benzo[b]thiophenyl, 1,3-dihydro-benzo[c]thiophenyl, etc. Non-limiting examples of X when X is benzo-fused heterocycloalkenyl include 2H-benzo[1,4]oxazinyl, 4H-chromenyl, 4H-chromenyl, 3H-indolyl, 1H-isoindolyl, 4H-benzo[1,4]oxazinyl, etc. Non-limiting examples of X when X is heterocycloalkyl include morpholinyl, piperazinyl, piperidinyl, pyrrolidinyl, tetrahydrofuranyl, tetrahydrothiophenyl, tetrahydropyranyl, azetidinyl, etc. When X is —$C(R^2)$═$C(R^2)$-aryl, non-limiting examples of X include —CH═CH-aryl, —$C(CH_3)$═CH-aryl, —CH═$C(CH_3)$-aryl, —$C(CH_3)$═$C(CH_3)$-aryl, —C(phenyl)=CH-aryl, —C(phenyl)=$C(CH_3)$-aryl, where "aryl" includes, for example, the aryl groups listed above. When X is —$C(R^2)$═$C(R^2)$-heteroaryl, non-limiting examples of X include —CH═CH-heteroaryl, —$C(CH_3)$═CH-heteroaryl, —CH═$C(CH_3)$— heteroaryl, —$C(CH_3)$═$C(CH_3)$— heteroaryl, —C(phenyl)=CH-heteroaryl, —C(phenyl)=$C(CH_3)$— heteroaryl, where "heteroaryl" includes, for example, the heteroaryl groups listed above. When X is —$OR^2$, $R^2$ is defined as described herein. Thus, X includes —OH, —O-alkyl (where the term "alkyl" is defined as described above), and —O-aryl (where the term "aryl" is defined as described above). When X is —O-alkylene-O-alkyl, non-limiting examples of X include —O—$CH_2$—O—$CH_3$, —O—$CH(CH_3)$—O—$CH_3$, —O—$CH_2CH_2$—O—$CH_3$, —O—$CH_2CH_2$—O—$CH_2CH_3$, —O—$CH(OCH_3)CH_2CH(CH_3)_2$, —O—$CH(CH_3)CH_2CH_2$—O—$CH_3$, —O—$CH_2CH_2$—O—$CH_2CH_3$, etc. Non-limiting examples of X when X is —S-aryl includes —S-phenyl, —S-naphthyl, etc. Non-limiting examples of X when X is —$N(R^4)_2$ include —$NH_2$, —NH(alkyl), —$N(alkyl)_2$, —NH(aryl), —N(alkyl)(aryl), —$N(aryl)_2$, —NH—C(O)—O-alkyl, —N(alkyl)-C(O)—O-alkyl, —N(aryl)-C(O)—O-alkyl, —NH—C(O)alkyl, —N(alkyl)-C(O)alkyl, and —N(aryl)-C(O)alkyl where the terms "alkyl" and "aryl" are defined as described above. Non-limiting examples of X when X is —$(C(R^2)_2)_s$-heteroaryl, include heteroaryl, —$C(R^2)_2$-heteroaryl, —$(C(R^2)_2)_2$-heteroaryl, where $R^2$ and the term "heteroaryl" are as defined herein, and "—$(C(R^2)_2)_s$-" includes —$CH_2$—, —$CH_2CH_2$—, —$CH(CH_3)$—, —$C(CH_3)_2$—, —$CH(CH(CH_3)_2)$—, —$CH(CH_2CH(CH_3)_2)$—, —$CH_2CH_2CH_2$—, —$CH(CH_3)CH_2$—, —$CH_2CH(CH_3)$—, —$CH(CH_3)$—$(CH_2)_2$—, —$(CH_2)_2$—$CH(CH_3)$—, —CH(phenyl)-$CH_2$—, —$CH_2$—CH(phenyl)-, —CH(phenyl)-, etc. Non-limiting examples of X when X is —C(O)—O-alkyl include —C(O)—O-(methyl), —C(O)—O-(ethyl), —C(O)—O-(n-propyl), —C(O)—O-(iso-propyl), —C(O)—O-(n-butyl), —C(O)—O-(iso-butyl), —C(O)—O-(sec-butyl), —C(O)—O-(tert-butyl), —C(O)—O-(n-pentyl), —C(O)—O-(iso-pentyl), —C(O)—O-(neo-pentyl), etc. Non-limiting examples of X when X is —C(O)-aryl include —C(O)-phenyl, —C(O)-naphthyl, etc. Non-limiting examples of X when X is —C(O)-heteroaryl include —C(O)-pyridyl, —C(O)-azaindolyl, —C(O)-benzimidazolyl, —C(O)-benzothiophenyl, —C(O)-furanyl, —C(O)-furazanyl, —C(O)-indolyl, —C(O)-isoquinolyl, etc. When X is —C(S-alkyl)=N—$S(O)_2$-aryl, the "alkyl" and "aryl" portions thereof can independently include any of the alkyl and aryl groups described herein. Likewise, when X is —$C(N(R^2)_2)$═N—$S(O)_2$-aryl said $R^2$ groups and the "aryl" portion are as defined herein.

Non-limiting examples of X when X is —$(C(R^2)_2)_s$-aryl, include aryl, —$C(R^2)_2$-aryl, —$(C(R^2)_2)_2$-aryl, where $R^2$ and the term "aryl" are as defined herein, and "—$(C(R^2)_2)_s$-" is as defined above. Said heteroaryl, the heteroaryl portion of said —$(C(R^2)_2)_s$-heteroaryl, the aryl portion of said —$C(R^2)$═C$(R^2)$-aryl, the heteroaryl portion of said —$C(R^2)$═$C(R^2)$—heteroaryl, the aryl portion of said —S-aryl, the aryl portion of said —$S(O)_2$-aryl, the heteroaryl portion of said —$S(O)_2$-heteroaryl, the aryl portion of said —C(O)-aryl, the heteroaryl portion of said —C(O)-heteroaryl, the aryl portion of said —$(C(R^2)_2)_s$-aryl, the benzo portion of said benzo-fused cycloalkyl, the benzo portion of said benzo-fused heterocycloalkyl, and the benzo portion of said benzo-fused heterocycloalkenyl of X are unsubstituted or substituted with one or more groups $Y^1$, where $Y^1$ is defined as described herein, and said cycloalkyl, the cycloalkyl portion of said —$S(O)_2$-cycloalkyl, said heterocycloalkyl, the cycloalkyl portion of said benzo-fused cycloalkyl, the heterocycloalkyl portion of said benzo-fused heterocycloalkyl, and the heterocycloalkenyl portion of said benzo-fused heterocycloalkenyl of X are unsubstituted or substituted with one or more groups $Y^2$ where $Y^2$ is defined as described herein.

Each $R^1$ is independently selected from the group consisting of alkyl, haloalkyl, -alkylene-$N(R^5)_2$, -alkylene-$OR^2$, alkylene-$N_3$, and alkylene-O—$S(O)_2$-alkyl. Non-limiting examples of $R^1$ when $R^1$ is alkyl include methyl, ethyl, n-propyl, iso-propyl, n-butyl, iso-butyl, sec-butyl, tert-butyl, n-pentyl, iso-pentyl, neo-pentyl, n-hexyl, iso-hexyl, etc. Non-limiting examples of $R^1$ when $R^1$ is haloalkyl include —$CF_3$, —$CHF_2$, —$CH_2F$, —$CH_2CF_3$, —$CF_2CF_3$, —$CH_2Br$, —$CH_2Cl$, —$CCl_3$, etc. When $R^1$ is alkylene-$N_3$ or alkylene-O—$S(O)_2$-alkyl, the alkylene portion thereof can include any of the alkylene groups described herein (e.g., —$CH_2$—, —$CH_2CH_2$—, —$CH(CH_3)$—, —$CH_2CH_2CH_2$—, —$CH(CH_3)CH_2CH_2$—, etc. Similarly, the "alkyl" portion of alkylene-O—$S(O)_2$-alkyl can include any alkyl group described herein (e.g., methyl, ethyl, propyl, butyl, pentyl, etc.) Non-limiting examples of $R^1$ when $R^1$ is -alkylene-$N(R^5)_2$ include —$CH_2$—$N(R^5)_2$, —$CH(CH_3)$—$N(R^5)_2$, —$CH_2CH_2$—$N(R^5)_2$, —$CH_2CH_2CH_2$—$N(R^5)_2$, —$CH(CH_3)CH_2CH_2$—$N(R^5)_2$, etc., wherein each $R^5$ is independently defined as described herein. For example, the "—$N(R^5)_2$" portion of -alkylene-$N(R^5)_2$ of $R^1$ can be —$NH_2$, —$N(CH_3)_2$, —$NH(CH_3)$, —NH(phenyl), —$N(phenyl)_2$, —NH—$S(O)_2$—$CH_3$, —NH—$S(O)_2$-cyclopropyl, —NH—C(O)—$NH_2$, —NH—C(O)—$N(CH_3)_2$, —NH—C(O)—$CH_3$, —NH—$CH_2CH_2$—OH, etc. Non-limiting examples of $R^1$ when $R^1$ is -alkylene-$OR^2$ include —$CH_2$—$OR^2$, —$CH(CH_3)$—$OR^2$, —$CH_2CH_2$—$OR^2$, —$CH(OR^2)CH_2CH(CH_3)_2$, —$CH(CH_3)CH_2CH_2$—$OR^2$, wherein $R^2$ is defined as described herein. For example, the "—$OR^2$" portion of said -alkylene-$OR^2$ of $R^1$ can be —OH, —$OCH_3$, —$OCH_2CH_3$, —$OCH(CH_3)_2$, —O-phenyl. Alternatively, two $R^1$ groups attached to the same ring carbon atom can form a carbonyl group, for example as shown below:

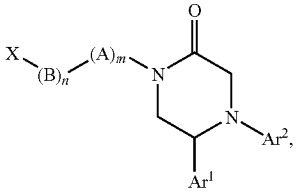

-continued

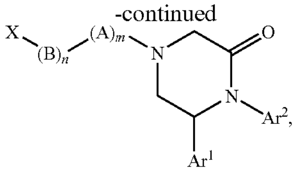

or

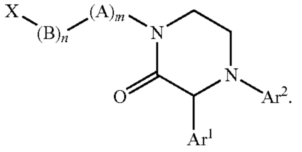

Each $R^2$ is independently H, alkyl, or aryl. Non-limiting examples of $R^2$ when $R^2$ is alkyl include methyl, ethyl, n-propyl, iso-propyl, n-butyl, iso-butyl, sec-butyl, tert-butyl, n-pentyl, iso-pentyl, neo-pentyl, n-hexyl, iso-hexyl, etc. Non-limiting examples of $R^2$ when $R^2$ is aryl include phenyl, naphthyl, etc., wherein said aryl may be unsubstituted or substituted with one or more $Y^1$ groups as defined herein.

Each $R^3$ is selected from the group consisting of H, alkyl, unsubstituted aryl, aryl substituted with one or more $Y^1$ groups, —$OR^2$, -alkylene-O-alkyl, and -alkylene-OH. Non-limiting examples of $R^3$ when $R^3$ is alkyl include methyl, ethyl, n-propyl, iso-propyl, n-butyl, iso-butyl, sec-butyl, tert-butyl, n-pentyl, iso-pentyl, neo-pentyl, n-hexyl, iso-hexyl, etc. Non-limiting examples of $R^3$ when $R^3$ is aryl include phenyl, naphthyl, etc., wherein said aryl may be unsubstituted or substituted with one or more $Y^1$ groups as defined herein. Non-limiting examples of $R^3$ when $R^3$ is —$OR^2$ include —OH, —$OCH_3$, —$OCH_2CH_3$, —$OCH(CH_3)_2$, —O-phenyl, etc. Non-limiting examples of $R^3$ when $R^3$ is -alkylene-O-alkyl include —O—$CH_2$—O—$CH_3$, —O—$CH_2CH_2$—O—$C(CH_3)_3$, —O—$CH(CH_3)$—O—$CH_3$, —O—$CH_2CH_2$—O—$CH_3$, —O—$CH_2CH_2$—O—$CH_2CH_3$, —O—$CH(OCH_3)CH_2CH(CH_3)_2$, —O—$CH(CH_3)CH_2CH_2$—O—$CH_3$, —O—$CH_2CH_2$—O—$CH_2CH_3$, etc. Non-limiting examples of $R^3$ when $R^3$ is -alkylene-OH include —$CH_2$—OH, —$CH_2CH_2$—OH, —$CH_2CH_2CH_2$—OH, —$CH(OH)CH_3$, —$CH_2CH(OH)CH_3$, etc.

Each $R^4$ is selected from the group consisting of H, alkyl, aryl, —C(O)—O-alkyl, —C(O)-alkyl, —C(O)-aryl, and —$S(O)_2$aryl. Non-limiting examples of $R^4$ when $R^4$ is alkyl include methyl, ethyl, n-propyl, iso-propyl, n-butyl, iso-butyl, sec-butyl, tert-butyl, n-pentyl, iso-pentyl, neo-pentyl, n-hexyl, iso-hexyl, etc. Non-limiting examples of $R^4$ when $R^4$ is aryl include phenyl, naphthyl, etc., wherein said aryl may be unsubstituted or substituted with one or more $Y^1$ groups as defined herein. Non-limiting examples of $R^4$ when $R^4$ is —C(O)—O-alkyl include —C(O)—O—$CH_3$, —C(O)—O—$CH_2CH_3$, —C(O)—O—$CH_2CH_2CH_3$, —C(O)—O—$CH(CH_3)_2$, —C(O)—O—$CH_2CH_2CH_2CH_3$, —C(O)—O—$CH_2CH(CH_3)_2$, —C(O)—O—$CH(CH_3)CH_2CH_3$, —C(O)—O—$C(CH_3)_3$, —C(O)—O—$CH_2CH_2CH_2CH_2CH_3$, —C(O)—O—$CH_2CH(CH_3)CH_2CH_3$, —C(O)—O—$CH_2CH_2CH(CH_3)_2$, —C(O)—O—$CH_2CH_2CH_2CH_2CH_2CH_3$, —C(O)—O—$CH(CH_3)CH_2CH_2CH_2CH_3$, —C(O)—O—$CH_2CH(CH_3)CH_2CH_2CH_3$, —C(O)—O—$CH_2CH_2CH(CH_3)CH_2CH_3$, —C(O)—O—$CH_2CH_2CH_2CH(CH_3)_2$, etc. Non-limiting examples of $R^4$ when $R^4$ is —C(O)-alkyl include —C(O)—$CH_3$, —C(O)—$CH_2CH_3$, —C(O)—$CH_2CH_2CH_3$, —C(O)—$CH(CH_3)_2$, —C(O)—$CH_2CH_2CH_2CH_3$, —C(O)—$CH_2CH(CH_3)_2$, —C(O)—$CH(CH_3)CH_2CH_3$, —C(O)—$C(CH_3)_3$, —C(O)—$CH_2CH_2CH_2CH_2CH_3$, —C(O)—$CH_2CH(CH_3)CH_2CH_3$, —C(O)—$CH_2CH_2CH$ $(CH_3)_2$, —C(O)—$CH_2CH_2CH_2CH_2CH_2CH_3$, —C(O)—CH$(CH_3)CH_2CH_2CH_2CH_3$, —C(O)—$CH_2CH(CH_3)CH_2CH_2CH_3$, —C(O)—$CH_2CH_2CH(CH_3)CH_2CH_3$, —C(O)—$CH_2CH_2CH_2CH(CH_3)_2$, etc. Non-limiting examples of $R^4$ when $R^4$ is —C(O)-aryl include —C(O)-phenyl, —C(O)-naphthyl, etc., optionally substituted with one or more $Y^1$ groups. Non-limiting examples of $R^4$ when $R^4$ is —$S(O)_2$aryl include —$S(O)_2$-phenyl, —$S(O)_2$-naphthyl, etc., optionally substituted with one or more $Y^1$ groups.

Each $R^5$ is selected from the group consisting of H, alkyl, aryl, —$S(O)_2$-alkyl, —$S(O)_2$-cycloalkyl, —$S(O)_2$-aryl, —C(O)—$N(R^2)_2$, —C(O)-alkyl, and -alkylene-OH. Non-limiting examples of $R^5$ when $R^5$ is alkyl include methyl, ethyl, n-propyl, iso-propyl, n-butyl, iso-butyl, sec-butyl, tert-butyl, n-pentyl, iso-pentyl, neo-pentyl, n-hexyl, iso-hexyl, etc. Non-limiting examples of $R^5$ when $R^5$ is aryl include phenyl, naphthyl, etc., wherein said aryl may be unsubstituted or substituted with one or more Z groups as defined herein. Non-limiting examples of $R^5$ when $R^5$ is —$S(O)_2$-alkyl include —$S(O)_2$—$CH_3$, —$S(O)_2$—$CH_2CH_3$, —$S(O)_2$—$CH_2CH_2CH_3$, —$S(O)_2$—$CH(CH_3)_2$, —$S(O)_2$—$CH_2CH_2CH_2CH_3$, —$S(O)_2$—$CH_2CH(CH_3)_2$, —$S(O)_2$—CH$(CH_3)CH_2CH_3$, —$S(O)_2$—$C(CH_3)_3$, —$S(O)_2$—$CH_2CH_2CH_2CH_2CH_3$, —$S(O)_2$—$CH_2CH(CH_3)CH_2CH_3$, —$S(O)_2$—$CH_2CH_2CH(CH_3)_2$, —$S(O)_2$—$CH_2CH_2CH_2CH_2CH_2CH_3$, —$S(O)_2$—$CH(CH_3)CH_2CH_2CH_2CH_3$, —$S(O)_2$—$CH_2CH(CH_3)CH_2CH_2CH_3$, —$S(O)_2$—$CH_2CH_2CH(CH_3)CH_2CH_3$, —$S(O)_2$—$CH_2CH_2CH_2CH(CH_3)_2$, etc. Non-limiting examples of $R^5$ when $R^5$ is —$S(O)_2$-cycloalkyl include —$S(O)_2$-cyclopropyl, —$S(O)_2$-cyclobutyl, —$S(O)_2$-cyclopentyl, —$S(O)_2$-cyclohexyl, —$S(O)_2$-adamantyl, —$S(O)_2$-norbornyl, —$S(O)_2$-decalyl, etc. Non-limiting examples of $R^5$ when $R^5$ is —C(O)—$N(R^2)_2$ include —C(O)—$NH_2$, —C(O)—NH(alkyl), —C(O)—N(alkyl)$_2$, —C(O)—NH(aryl), —C(O)—N(alkyl)(aryl), —C(O)—N(aryl)$_2$, wherein the terms “aryl” and “alkyl” are as defined above, and said “aryl” may be unsubstituted or substituted with one or more $Y^1$ groups as defined herein. Non-limiting examples of $R^5$ when $R^5$ is —C(O)-alkyl include —C(O)—$CH_3$, —C(O)—$CH_2CH_3$, —C(O)—$CH_2CH_2CH_3$, —C(O)—$CH(CH_3)_2$, —C(O)—$CH_2CH_2CH_2CH_3$, —C(O)—$CH_2CH(CH_3)_2$, —C(O)—CH$(CH_3)CH_2CH_3$, —C(O)—$C(CH_3)_3$, —C(O)—$CH_2CH_2CH_2CH_2CH_3$, —C(O)—$CH_2CH(CH_3)CH_2CH_3$, —C(O)—$CH_2CH_2CH(CH_3)_2$, —C(O)—$CH_2CH_2CH_2CH_2CH_2CH_3$, —C(O)—$CH(CH_3)CH_2CH_2CH_2CH_3$, —C(O)—$CH_2CH(CH_3)CH_2CH_2CH_3$, —C(O)—$CH_2CH_2CH(CH_3)CH_2CH_3$, —C(O)—$CH_2CH_2CH_2CH(CH_3)_2$, etc. Non-limiting examples of $R^5$ when $R^5$ is -alkylene-OH include —$CH_2$—OH, —$CH_2CH_2$—OH, —$CH_2CH_2CH_2$—OH, —CH(OH)$CH_3$, —$CH_2$CH(OH)$CH_3$, etc. Non-limiting examples of $R^5$ when $R^5$ is —$S(O)_2$aryl include —$S(O)_2$-phenyl, —$S(O)_2$-naphthyl, etc., optionally substituted with one or more $Y^1$ groups.

Each $Y^1$ is independently selected from the group consisting of alkyl, cycloalkyl, heterocycloalkyl, heterocycloalkenyl, halo, haloalkyl, benzyl, aryl, heteroaryl, —O-aryl, —S-aryl, —$S(O)_2$-alkyl, —$S(O)_2$-cycloalkyl, —$S(O)_2$-aryl, -alkylene-CN, —CN, —C(O)-alkyl, —C(O)-aryl, —C(O)-haloalkyl, —C(O)O-alkyl, —$N(R^2)$C(O)-alkyl, —$N(R^2)$C(O)—$N(R^2)_2$, —OH, —O-alkyl, —O-haloalkyl, —O-alkylene-C(O)OH, —S-alkyl, —S-haloalkyl, -alkylene-OH, -alkylene-C(O)—O-alkyl, —O-alkylene-aryl, and —$N(R^5)_2$. Non-limiting examples of $Y^1$ when $Y^1$ is alkyl include methyl, ethyl, n-propyl, iso-propyl, n-butyl, iso-butyl, sec-butyl, tert-butyl, n-pentyl, iso-pentyl, neo-pentyl, n-hexyl, iso-hexyl, etc. Non-limiting examples of $Y^1$ when $Y^1$ is cycloalkyl include cyclopropyl, cyclobutyl, cyclopentyl, cyclohexyl, adamantyl, norbornyl, etc. Non-limiting examples of $Y^1$ when $Y^1$ is heterocycloalkyl include morpholinyl, piperazinyl, piperidinyl, pyrrolidinyl, tetrahydrofuranyl, tetrahydrothiophenyl, tetrahydropyranyl, azetidinyl, etc. Non-limiting examples of $Y^1$ when $Y^1$ is heterocycloalkenyl include 2H-benzo[1,4]oxazinyl, 4H-chromenyl, 4H-chromenyl, 3H-indolyl, 1H-isoindolyl, 4H-benzo[1,4]oxazinyl, etc. Non-limiting examples of $Y^1$ when $Y^1$ is halo include chloro, bromo, and iodo. Non-limiting examples of $Y^1$ when $Y^1$ is haloalkyl include —$CF_3$, —$CHF_2$, —$CH_2F$, —$CH_2CF_3$, —$CF_2CF_3$, —$CH_2Br$, —$CH_2Cl$, —$CCl_3$, etc. Non-limiting examples of $Y^1$ when $Y^1$ is aryl include phenyl, naphthyl, etc. Non-limiting examples of $Y^1$ when $Y^1$ is heteroaryl include azaindolyl, benzimidazolyl, benzofuranyl, furanyl, 2-pyridinyl, 3-pyridinyl, 4-pyridinyl, furazanyl, indolyl, quinolyl, isoquinolyl, phthalazinyl, pyrazinyl, pyridazinyl, pyrimidyl, pyrrolyl, quinoxalinyl, thiophenyl, isoxazolyl, triazolyl, thiazolyl, indazolyl, thiadiazolyl, imidazolyl, benzo[b]thiophenyl, tetrazolyl, pyrazolyl, etc. Non-limiting examples of $Y^1$ when $Y^1$ is —O-aryl include —O-phenyl, —O-naphthyl, etc. Non-limiting examples of $Y^1$ when $Y^1$ is —S-aryl include —S-phenyl, —S-naphthyl, etc. Non-limiting examples of $Y^1$ when $Y^1$ is —$S(O)_2$-alkyl include —$S(O)_2$—$CH_3$, —$S(O)_2$—$CH_2CH_3$, —$S(O)_2$—$CH_2CH_2CH_3$, —$S(O)_2$—$CH(CH_3)_2$, —$S(O)_2$—$CH_2CH_2CH_2CH_3$, —$S(O)_2$—$CH_2CH(CH_3)_2$, —$S(O)_2$—$CH(CH_3)CH_2CH_3$, —$S(O)_2$—$C(CH_3)_3$, —$S(O)_2$—$CH_2CH_2CH_2CH_2CH_3$, —$S(O)_2$—$CH_2CH(CH_3)CH_2CH_3$, —$S(O)_2$—$CH_2CH_2CH(CH_3)_2$, —$S(O)_2$—$CH_2CH_2CH_2CH_2CH_2CH_3$, —$S(O)_2$—$CH(CH_3)CH_2CH_2CH_2CH_3$, —$S(O)_2$—$CH_2CH(CH_3)CH_2CH_2CH_3$, —$S(O)_2$—$CH_2CH_2CH(CH_3)CH_2CH_3$, —$S(O)_2$—$CH_2CH_2CH_2CH(CH_3)_2$, etc. Non-limiting examples of $Y^1$ when $Y^1$ is —$S(O)_2$-cycloalkyl include —$S(O)_2$-cyclopropyl, —$S(O)_2$-cyclobutyl, —$S(O)_2$-cyclopentyl, —$S(O)_2$-cyclohexyl, —$S(O)_2$-adamantyl, —$S(O)_2$-norbornyl, etc. Non-limiting examples of $Y^1$ when $Y^1$ is —$S(O)_2$-aryl include —$S(O)_2$-phenyl, —$S(O)_2$-naphthyl, etc. Non-limiting examples of $Y^1$ when $Y^1$ is -alkylene-CN include —O—$CH_2$—CN, —O—$CH_2CH_2$—CN, —$CH_2CH_2CH_2CN$, —O—$CH(CH_3)$—CN, —O—CH(CN)$CH_2CH(CH_3)_2$, —O—$CH(CH_3)CH_2CH_2$—CN, etc. Non-limiting examples of $Y^1$ when $Y^1$ is —C(O)-alkyl include —C(O)—$CH_3$, —C(O)—$CH_2CH_3$, —C(O)—$CH_2CH_2CH_3$, —C(O)—$CH(CH_3)_2$, —C(O)—$CH_2CH_2CH_2CH_3$, —C(O)—$CH_2CH(CH_3)_2$, —C(O)—$CH(CH_3)CH_2CH_3$, —C(O)—$C(CH_3)_3$, —C(O)—$CH_2CH_2CH_2CH_2CH_3$, —C(O)—$CH_2CH(CH_3)CH_2CH_3$, —C(O)—$CH_2CH_2CH(CH_3)_2$, —C(O)—$CH_2CH_2CH_2CH_2CH_2CH_3$, —C(O)—$CH(CH_3)CH_2CH_2CH_2CH_3$, —C(O)—$CH_2CH(CH_3)CH_2CH_2CH_3$, —C(O)—$CH_2CH_2CH(CH_3)CH_2CH_3$, —C(O)—$CH_2CH_2CH_2CH(CH_3)_2$, etc. Non-limiting examples of $Y^1$ when $Y^1$ is -alkylene-OH include —$CH_2$—OH, —$CH_2CH_2$—OH, —$CH_2CH_2CH_2$—OH, —CH(OH)$CH_3$, —$CH_2$CH(OH)$CH_3$, etc. Non-limiting examples of $Y^1$ when $Y^1$ is —C(O)-aryl include —C(O)-phenyl, —C(O)-naphthyl, etc. Non-limiting examples of $Y^1$ when $Y^1$ is —C(O)-haloalkyl include —C(O)—$CF_3$, —C(O)—$CHF_2$, —C(O)—$CH_2F$, —C(O)—$CH_2CF_3$, —C(O)—$CF_2CF_3$, —C(O)—$CH_2Br$, —C(O)—$CH_2Cl$, —C(O)—$CCl_3$, etc. Non-limiting examples of $Y^1$ when $Y^1$ is —C(O)O-alkyl include —C(O)—O—$CH_3$, —C(O)—O—$CH_2CH_3$, —C(O)—O—$CH_2CH_2CH_3$, —C(O)—O—$CH(CH_3)_2$, —C(O)—O—$CH_2CH_2CH_2CH_3$, —C(O)—O—$CH_2CH(CH_3)_2$, —C(O)—O—$CH(CH_3)CH_2CH_3$, —C(O)—O—$C(CH_3)_3$, —C(O)—O—$CH_2CH_2CH_2CH_2CH_3$, —C(O)—O—$CH_2CH(CH_3)CH_2CH_3$, —C(O)—O—$CH_2CH_2CH$ $(CH_3)_2$, —C(O)—O—$CH_2CH_2CH_2CH_2CH_2CH_3$, —C(O)—O—$CH(CH_3)CH_2CH_2CH_2CH_3$, —C(O)—O—$CH_2CH(CH_3)CH_2CH_2CH_3$, —C(O)—O—$CH_2CH_2CH(CH_3)CH_2CH_3$, —C(O)—O—$CH_2CH_2CH_2CH(CH_3)_2$, etc. Non-limiting examples of $Y^1$ when $Y^1$ is —$N(R^2)$C(O)-alkyl include —NH—C(O)-alkyl, —N(alkyl)-C(O)-alkyl, and —N(aryl)-C(O)-alkyl wherein the terms “alkyl” and “aryl” are as defined above. Non-limiting examples of $Y^1$ when $Y^1$ is —$N(R^2)$C(O)—$N(R^2)_2$ include —NHC(O)—$NH_2$, —NHC(O)—$N(alkyl)_2$, —NHC(O)—$N(aryl)_2$, —NHC(O)—NH-alkyl, —NHC(O)—NH-aryl, —N(alkyl)C(O)—NH-alkyl, —N(alkyl)C(O)—NH-aryl, —N(aryl)C(O)—NH-aryl, —N(aryl)C(O)—NH-aryl, etc. Non-limiting examples of $Y^1$ when $Y^1$ is —O-alkyl include —O—$CH_3$, —O—$CH_2CH_3$, —O—$CH_2CH_2CH_3$, —O—$CH(CH_3)_2$, —O—$CH_2CH_2CH_2CH_3$, —O—$CH_2CH(CH_3)_2$, —O—$CH(CH_3)CH_2CH_3$, —O—$C(CH_3)_3$, —O—$CH_2CH_2CH_2CH_2CH_3$, —O—$CH_2CH(CH_3)CH_2CH_3$, —O—$CH_2CH_2CH(CH_3)_2$, —O—$CH_2CH_2CH_2CH_2CH_2CH_3$, —O—$CH(CH_3)CH_2CH_2CH_2CH_3$, —O—$CH_2CH(CH_3)CH_2CH_2CH_3$, —O—$CH_2CH_2CH(CH_3)CH_2CH_3$, —O—$CH_2CH_2CH_2CH(CH_3)_2$, etc. Non-limiting examples of $Y^1$ when $Y^1$ is —O-haloalkyl include —O—$CF_3$, —O—$CHF_2$, —O—$CH_2F$, —O—$CH_2CF_3$, —O—$CF_2CF_3$, —O—$CH_2Br$, —O—$CH_2Cl$, —O—$CCl_3$, etc. Non-limiting examples of $Y^1$ when $Y^1$ is —O-alkylene-C(O)OH include —O—$CH_2$—C(O)OH, —O—$CH_2CH_2$—C(O)OH, —$CH_2CH_2CH_2$C(O)OH, —O—$CH(CH_3)$—C(O)OH, —O—CH(C(O)OH)$CH_2CH(CH_3)_2$, —O—$CH(CH_3)CH_2CH_2$—C(O)OH, etc. Non-limiting examples of $Y^1$ when $Y^1$ is —S-alkyl include —S—$CH_3$, —S—$CH_2CH_3$, —S—$CH_2CH_2CH_3$, —S—$CH(CH_3)_2$, —S—$CH_2CH_2CH_2CH_3$, —S—$CH_2CH(CH_3)_2$, —S—$CH(CH_3)CH_2CH_3$, —S—$C(CH_3)_3$, —S—$CH_2CH_2CH_2CH_2CH_3$, —S—$CH_2CH(CH_3)CH_2CH_3$, —S—$CH_2CH_2CH(CH_3)_2$, —S—$CH_2CH_2CH_2CH_2CH_2CH_3$, —S—$CH(CH_3)CH_2CH_2CH_2CH_3$, —S—$CH_2CH(CH_3)CH_2CH_2CH_3$, —S—$CH_2CH_2CH(CH_3)CH_2CH_3$, —S—$CH_2CH_2CH_2CH(CH_3)_2$, etc. Non-limiting examples of $Y^1$ when $Y^1$ is —S-haloalkyl include —S—$CF_3$, —S—$CHF_2$, —S—$CH_2F$, —S—$CH_2CF_3$, —S—$CF_2CF_3$, —S—$CH_2Br$, —S—$CH_2Cl$, —S—$CCl_3$, etc. Non-limiting examples of $Y^1$ when $Y^1$ is -alkylene-OH include —$CH_2$—OH, —$CH_2CH_2$—OH, —$CH_2CH_2CH_2$—OH, —$CH(OH)CH_3$, —$CH_2CH(OH)CH_3$, etc. Non-limiting examples of $Y^1$ when $Y^1$ is -alkylene-C(O)—O-alkyl include —O—$CH_2$—C(O)O—$CH_3$, —O—$CH_2$—C(O)O—$CH_2CH_3$, —O—$CH_2CH_2$—C(O)O—$CH_2CH_3$, —O—$CH_2CH_2CH_2$—C(O)O—$CH_3$, —O—$CH_2CH_2$—C(O)O—$C(CH_3)_3$, —O—$CH(CH_3)$—C(O)O—$CH_3$, —O—$CH_2CH_2$—C(O)O—$CH_3$, —O—CH(C(O)$OCH_3$)$CH_2CH(CH_3)_2$, —O—$CH(CH_3)CH_2CH_2$—C(O)O—$CH_3$, etc. Non-limiting examples of $Y^1$ when $Y^1$ is —O-alkylene-aryl include —O—$CH_2$-phenyl, —O—$CH_2CH_2$-phenyl, —O—$CH(CH_3)$-phenyl, —O—$CH_2CH(CH_3)$-phenyl, —O$C(CH_3)_2$-phenyl, —O—$CH(CH_2CH_3)$-phenyl, etc. Non-limiting examples of $Y^1$ when $Y^1$ is —$N(R^5)_2$ include —$NH_2$, —$N(CH_3)_2$, —$NH(CH_3)$, —NH(phenyl), —$N(phenyl)_2$, —NH—$S(O)_2$—$CH_3$, —NH—$S(O)_2$-cyclopropyl, —NH—C(O)—$NH_2$, —NH—C(O)—$N(CH_3)_2$, —NH—C(O)—$CH_3$, —NH—$CH_2CH_2$—OH, etc. The aryl or heteroaryl portions of any of the groups of $Y^1$ may be unsubstituted or substituted with one or more Z groups as defined herein.

Each $Y^2$ is independently selected from the group consisting of alkyl, haloalkyl, aryl, -alkylene-aryl, —CN, —C(O)-alkyl, —$S(O)_2$-cycloalkyl, -alkylene-$N(R^2)_2$, —C(O)-alkylene-$N(R^4)_2$, —C(O)—O-alkyl, —C(O)-aryl, and —C(O)-haloalkyl. Non-limiting examples of $Y^2$ when $Y^2$ is alkyl include —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$(CH_3)_3$, —$CH_2CH_2CH_2CH_2CH_3$, —$CH_2CH(CH_3)CH_2CH_3$, —$CH_2CH_2CH(CH_3)_2$, —$CH_2CH_2CH_2CH_2CH_2CH_3$, —$CH(CH_3)CH_2CH_2CH_2CH_3$, —$CH_2CH(CH_3)CH_2CH_2CH_3$, —$CH_2CH_2CH(CH_3)CH_2CH_3$, —$CH_2CH_2CH_2CH(CH_3)_2$, etc. Non-limiting examples of $Y^2$ when $Y^2$ is aryl include phenyl, naphthyl, etc. Non-limiting examples of $Y^2$ when $Y^2$ is -alkylene-aryl include —$CH_2$-phenyl, —$CH_2CH_2$-phenyl, —$CH(CH_3)$-phenyl, —$CH_2CH(CH_3)$-phenyl, —$C(CH_3)_2$-phenyl, —$CH(CH_2CH_3)$-phenyl, etc. Non-limiting examples of $Y^2$ when $Y^2$ is —C(O)-alkyl include —C(O)—$CH_3$, —C(O)—$CH_2CH_3$, —C(O)—$CH_2CH_2CH_3$, —C(O)—$CH(CH_3)_2$, —C(O)—$CH_2CH_2CH_2CH_3$, —C(O)—$CH_2CH(CH_3)_2$, —C(O)—$CH(CH_3)CH_2CH_3$, —C(O)—$C(CH_3)_3$, —C(O)—$CH_2CH_2CH_2CH_2CH_3$, —C(O)—$CH_2CH(CH_3)CH_2CH_3$, —C(O)—$CH_2CH_2CH(CH_3)_2$, —C(O)—$CH_2CH_2CH_2CH_2CH_2CH_3$, —C(O)—$CH(CH_3)CH_2CH_2CH_2CH_3$, —C(O)—$CH_2CH(CH_3)CH_2CH_2CH_3$, —C(O)—$CH_2CH_2CH(CH_3)CH_2CH_3$, —C(O)—$CH_2CH_2CH_2CH(CH_3)_2$, etc. Non-limiting examples of $Y^2$ when $Y^2$ is —$S(O)_2$-cycloalkyl include —$S(O)_2$-cyclopropyl, —$S(O)_2$-cyclobutyl, —$S(O)_2$-cyclopentyl, —$S(O)_2$-cyclohexyl, —$S(O)_2$-norbornyl, —$S(O)_2$-adamantyl, etc. Non-limiting examples of $Y^2$ when $Y^2$ is -alkylene-$N(R^2)_2$ include -alkylene-$N(R^2)_2$ include —$CH_2$—$N(R^2)_2$, —$CH(CH_3)$—$N(R^2)_2$, —$CH_2CH_2$—$N(R^2)_2$, —$CH_2CH_2CH_2$—$N(R^2)_2$, —$CH(CH_3)CH_2CH_2$—$N(R^2)_2$, etc., wherein each $R^2$ is independently defined as described herein. For example, the “—$N(R^2)_2$” portion of -alkylene-$N(R^2)_2$ of $Y^2$ can be —$NH_2$, —$N(CH_3)_2$, —$NH(CH_3)$, —NH(phenyl), —$N(phenyl)_2$, —$N(CH_2CH_3)_2$, —$NH(CH_2CH_3)$, etc. Non-limiting examples of $Y^2$ when $Y^2$ is —C(O)-alkylene-$N(R^4)_2$ include —C(O)—$CH_2$—$N(R^4)_2$, —C(O)—$CH(CH_3)$—$N(R^4)_2$, —C(O)—$CH_2CH_2$—$N(R^4)_2$, —C(O)—$CH_2CH_2CH_2$—$N(R^4)_2$, —C(O)—$CH(CH_3)CH_2CH_2$—$N(R^4)_2$, etc., wherein each $R^4$ is independently defined as described herein. For example the “—$N(R^4)_2$” portion of —C(O)-alkylene-$N(R^4)_2$ of $Y^2$ can be —$NH_2$, —$N(CH_3)_2$, —$NH(CH_3)$, —NH(phenyl), —$N(phenyl)_2$, —$N(CH_2CH_3)_2$, —$NH(CH_2CH_3)$, —NH—C(O)—O—$CH_3$, —NH—C(O)—O—$CH_2CH_3$, —$N(CH_3)$—C(O)—O—$CH_3$, —$N(CH_3)$—C(O)—O—$CH_2CH_3$, —NH—C(O)—$CH_3$, —NH—C(O)—$CH_2CH_3$, —$N(CH_3)$—C(O)—$CH_3$, —$N(CH_3)$—C(O)—$CH_2CH_3$, etc. Non-limiting examples of $Y^2$ when $Y^2$ is —C(O)—O-alkyl include —C(O)—O—$CH_3$, —C(O)—O—$CH_2CH_3$, —C(O)—O—$CH_2CH_2CH_3$, —C(O)—O—$CH(CH_3)_2$, —C(O)—O—$CH_2CH_2CH_2CH_3$, —C(O)—O—$CH_2CH(CH_3)_2$, —C(O)—O—$CH(CH_3)CH_2CH_3$, —C(O)—O—$C(CH_3)_3$, —C(O)—O—$CH_2CH_2CH_2CH_2CH_3$, —C(O)—O—$CH_2CH(CH_3)CH_2CH_3$, —C(O)—O—$CH_2CH_2CH(CH_3)_2$, —C(O)—O—$CH_2CH_2CH_2CH_2CH_2CH_3$, —C(O)—O—$CH(CH_3)CH_2CH_2CH_2CH_3$, —C(O)—O—$CH_2CH(CH_3)CH_2CH_2CH_3$, —C(O)—O—$CH_2CH_2CH(CH_3)CH_2CH_3$, —C(O)—O—$CH_2CH_2CH_2CH(CH_3)_2$, etc. Non-limiting examples of $Y^2$ when $Y^2$ is —C(O)-aryl include —C(O)-phenyl, —C(O)-naphthyl, etc., optionally substituted with one or more Z groups. Non-limiting examples of $Y^2$ when $Y^2$ is —C(O)-haloalkyl include —C(O)—$CF_3$, —C(O)—$CHF_2$, —C(O)—$CH_2F$, —C(O)—$CH_2CF_3$, —C(O)—$CF_2CF_3$, —C(O)—$CH_2Br$, —C(O)—$CH_2Cl$, —C(O)—$CCl_3$, etc.

Each Z is independently selected from the group consisting of alkyl, halo, haloalkyl, —OH, —O-alkyl, and —CN. The terms "alkyl", "halo", aloalkyl", and "—O-alkyl" are as defined above.

As used throughout the specification, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. In one embodiment alkyl groups contain about 1 to about 12 carbon atoms in the chain.

In another embodiment alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. Non-limiting examples of suitable alkyl groups include methyl, ethyl, n-propyl, isopropyl, n-butyl, t-butyl, n-pentyl, heptyl, nonyl, or decyl.

"Alkylene" means a divalent group obtained by removal of a hydrogen atom from an alkyl group that is defined above. Non-limiting examples of alkylene include methylene, ethylene and propylene. "Lower alkylene" means an alkylene having about 1 to 6 carbon atoms in the chain, which may be straight or branched.

"Alkenyl" means an aliphatic hydrocarbon group containing at least one carbon-carbon double bond and which may be straight or branched and comprising about 2 to about 15 carbon atoms in the chain. In one embodiment alkenyl groups have about 2 to about 12 carbon atoms in the chain. In another embodiment alkenyl groups have about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. The term "substituted alkenyl" means that the alkenyl group may be substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkenylene" means a divalent group obtained by removal of a hydrogen atom from an alkenyl group that is defined above.

"Alkynyl" means an aliphatic hydrocarbon group containing at least one carbon-carbon triple bond and which may be straight or branched and comprising about 2 to about 15 carbon atoms in the chain. In one embodiment alkynyl groups have about 2 to about 12 carbon atoms in the chain. In another embodiment alkynyl groups have about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl, 3-methylbutynyl, n-pentynyl, and decynyl. The term "substituted alkynyl" means that the alkynyl group may be substituted by one or more substituents which may be the same or different, each substituent being independently selected from the group consisting of alkyl, aryl and cycloalkyl.

"Aryl" (sometimes abbreviated "ar" or "Ar") means an aromatic monocyclic or multicyclic ring system comprising about 6 to about 14 carbon atoms, or about 6 to about 10 carbon atoms. The aryl group can be optionally substituted with one or more "ring system substituents" which may be the same or different, and are as defined herein. Non-limiting examples of suitable aryl groups include phenyl, naphthyl, and biphenyl.

"Aryloxy" means a —O-aryl group, wherein aryl is defined as above. the aryloxy group is attached to the parent moiety through the ether oxygen.

"Arylene" means a divalent aryl group obtained by the removal of a hydrogen atom from an aryl group as defined above. Non-limiting examples of arylenes include, for example, 1,2-phenylene, 1,3-phenylene, or 1,4-phenylene.

"Heteroaryl" means an aromatic monocyclic or multicyclic ring system comprising about 5 to about 14 ring atoms, or about 5 to about 10 ring atoms, in which one or more of the ring atoms is an element other than carbon, for example nitrogen, oxygen or sulfur, alone or in combination. In one embodiment heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Cycloalkyl" means a non-aromatic mono- or multicyclic ring system comprising about 3 to about 13 carbon atoms, or about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalin, norbornyl, adamantyl and the like.

"Cycloalkylene" means a divalent cycloalkyl group obtained by the removal of a hydrogen atom from a cycloalkyl group as defined above. Non-limiting examples of cycloalkylenes include:

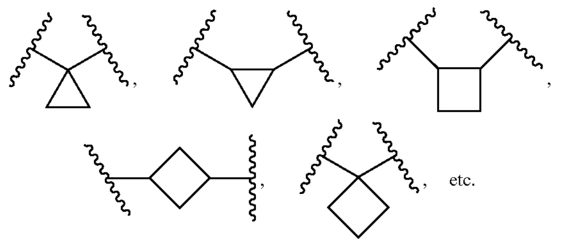

etc.

"Heterocycloalkyl" means a non-aromatic saturated monocyclic or multicyclic ring system comprising about 3 to about 10 ring atoms, or about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. In one embodiment heterocycloalkyls contain about 5 to about 6 ring atoms. The prefix aza, oxa or thia before the heterocycloalkyl root name means that at least a nitrogen, oxygen or sulfur atom respectively is present as a ring atom. The heterocycloalkyl can be optionally substituted by one or more "ring system substituents" which may be the same or different, and are as defined herein. The nitrogen or sulfur atom of the heterocycloalkyl can be optionally oxidized to the corresponding N-oxide, S-oxide or S,S-dioxide. Non-limiting examples of suitable monocyclic heterocycloalkyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Heterocycloalkenyl" means a non-aromatic unsaturated monocyclic or multicyclic ring system comprising about 3 to about 10 ring atoms, or about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Heterocycloalkenyls have at least one double bond, wherein said double bond may be between two ring carbon atoms, between a ring carbon atom and a ring heteroatom (e.g., between a ring carbon atom and a ring nitrogen atom), or between two ring heteroatoms (e.g., between two ring nitrogen atoms). If more than one double bond is present in the ring, each double bond is independently defined as described herein. In another embodiment heterocycloalkenyls contain about 5 to about 6 ring atoms. The prefix aza, oxa or thia before the heterocycloalkenyl root name means that at least a nitrogen, oxygen or sulfur atom respectively is present as a ring atom. The heterocycloalkenyl can be optionally substituted by one or more "ring system substituents" which may be the same or different, and are as defined herein. The nitrogen or sulfur atom of the heterocycloalkenyl can be optionally oxidized to the corresponding N-oxide, S-oxide or S,S-dioxide. Non-limiting examples of suitable monocyclic heterocycloalkenyl rings include thiazolinyl, 2,3-dihydro-1H-pyrrolyl, 2,5-dihydro-1H-pyrrolyl, 3,4-dihydro-2H-pyrrolyl, 2,3-dihydro-furan, 2,5-dihydro-furan, etc.

"Benzo-fused heterocycloalkenyl" means a heterocycloalkenyl, as defined above, to which one or more phenyl rings has been fused, so that each phenyl ring shares two ring carbon atoms with the cycloalkyl ring. Non-limiting examples of benzo-fused cycloalkyls are 4H-chromene, chromene-4-one, 1H-isochromene, etc.

"Benzo-fused cycloalkyl" means a cycloalkyl, as defined above, to which one or more phenyl rings has been fused, so that each phenyl ring shares two ring carbon atoms with the cycloalkyl ring. Non-limiting examples of benzo-fused cycloalkyls are indanyl and tetradehydronaphthyl:

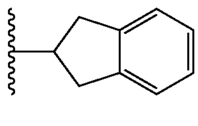

or

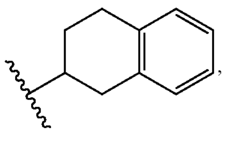

, and non-limiting examples of a dibenzo-fused cycloalkyls are fluorenyl:

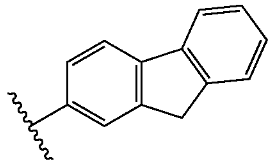

and
acenaphthenyl:

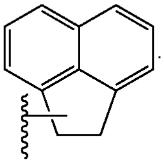

.

"Benzo-fused heterocycloalkyl" means a heterocycloalkyl, as defined above, to which one or more phenyl rings has been fused, so that each phenyl ring shares two ring carbon atoms with the heterocycloalkyl ring. A non-limiting example of a benzo-fused heterocycloalkyls is 2,3-dihydrobenzo[1,4]dioxinyl.

"Cycloalkenyl" means a non-aromatic mono or multicyclic ring system comprising about 3 to about 10 carbon atoms, or about 5 to about 10 carbon atoms, which contains at least one carbon-carbon double bond. In one embodiment cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cycloheptenyl, and the like. Non-limiting example of a suitable multicyclic cycloalkenyl is norbornylenyl.

"Halo" (or "halogeno" or "halogen") means fluoro, chloro, bromo, or iodo groups. Preferred are fluoro, chloro or bromo, and more preferred are fluoro and chloro.

"Haloalkyl" means an alkyl as defined above wherein one or more hydrogen atoms on the alkyl are replaced by a halo group as defined above.

"Ring system substituent" means a substituent attached to an aromatic or non-aromatic ring system which, for example, replaces an available hydrogen on the ring system. Ring system substituents may be the same or different, and are defined as described herein.

"Alkoxy" means an —O-alkyl group in which the alkyl group is as previously described. Non-limiting examples of suitable alkoxy groups include methoxy, ethoxy, n-propoxy, isopropoxy, n-butoxy and heptoxy. The bond to the parent moiety is through the ether oxygen.

With reference to the number of moieties (e.g., substituents, groups or rings) in a compound, unless otherwise defined, the phrases "one or more" and "at least one" mean that there can be as many moieties as chemically permitted, and the determination of the maximum number of such moieties is well within the knowledge of those skilled in the art.

When used herein, the term "independently", in reference to the substitution of a parent moiety with one or more substituents, means that the parent moiety may be substituted with any of the listed substituents, either individually or in combination, and any number of chemically possible substituents may be used. As a non-limiting example, a phenyl independently substituted with one or more alkyl or halo substituents can include, chlorophenyl, dichlorophenyl, trichlorophenyl, tolyl, xylyl, 2-chloro-3-methylphenyl, 2,3-dichloro-4-methylphenyl, etc.

As used herein, the term "composition" is intended to encompass a product comprising the specified ingredients in the specified amounts, as well as any product which results, directly or indirectly, from combination of the specified ingredients in the specified amounts.

The wavy line  as a bond generally indicates a mixture of, or either of, the possible isomers, e.g., containing (R)- and (S)-stereochemistry. For example,

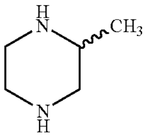

means containing both

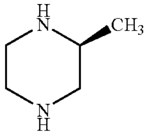 and 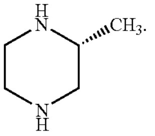

Moreover, when the stereochemistry of a chiral center (or stereogenic center) is not expressly indicated, a mixture of, or any of the individual possible isomers are contemplated. Thus, for example,

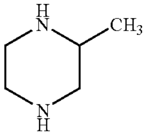

means containing

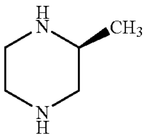 and/or 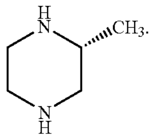

Lines drawn into the ring systems, such as, for example:

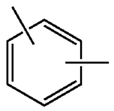

indicate that the indicated line (bond) may be attached to any of the substitutable ring carbon atoms.

As well known in the art, a bond drawn from a particular atom wherein no moiety is depicted at the terminal end of the bond indicates a methyl group bound through that bond to the atom, unless stated otherwise. For example:

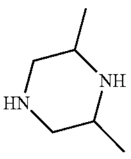 represents 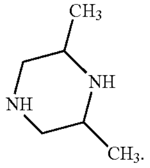

It should also be noted that any carbon or heteroatom with unsatisfied valences in the text, schemes, examples, structural formulae, and any Tables herein is assumed to have the hydrogen atom or atoms to satisfy the valences.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "isolated" or "in isolated form" for a compound refers to the physical state of said compound after being isolated from a synthetic process or natural source or combination thereof. The term "purified" or "in purified form" for a compound refers to the physical state of said compound after being obtained from a purification process or processes described herein or well known to the skilled artisan, in sufficient purity to be characterizable by standard analytical techniques described herein or well known to the skilled artisan.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any variable (e.g., aryl, heterocycle, $R^2$, etc.) occurs more than one time in any constituent or in any Formula (e.g., Formula I), its definition on each occurrence is independent of its definition at every other occurrence.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of formula I or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the present invention may also exist as, or optionally be converted to a solvate. The preparation of solvates is generally known. Thus, for example, M. Caira et al, *J. Pharmaceutical Sci.,* 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.,* 5(1), article 12 (2004); and A. L. Bingham et al, *Chem. Commun.,* 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

The compounds of Formula (I) form salts that are also within the scope of this invention. Reference to a compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) contains both a basic moiety, such as, but not limited to a piperazine, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula (I) may be formed, for example, by reacting a compound of Formula (I) with an amount of acid or base, such as an equivalent amount, in a medium such as one in which the salt precipitates or in an aqueous medium followed by lyophilization. Acids (and bases) which are generally considered suitable for the formation of pharmaceutically useful salts from basic (or acidic) pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; in *The Orange Book* (Food & Drug Administration, Washington, D.C. on their website); and P. Heinrich Stahl, Camille G. Wermuth (Eds.), *Handbook of Pharmaceutical Salts: Properties, Selection, and Use*, (2002) Int'l. Union of Pure and Applied Chemistry, pp. 330-331. These disclosures are incorporated herein by reference thereto.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis (dehydroabietyl)ethylenediamine), N-methyl-D-glucamines, N-methyl-D-glucamides, t-butyl amines, piperazine, phenylcyclohexylamine, choline, tromethamine, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of Formula (I), and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

Polymorphic forms of the compounds of Formula (I), and of the salts, solvates and prodrugs of the compounds of Formula (I), are intended to be included in the present invention.

In still another embodiment, the present invention provides a composition comprising at least one compound of Formula (I), or a pharmaceutically acceptable salt, solvate, or ester thereof, and a pharmaceutically acceptable carrier.

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

Unit dosage forms, without limitation, can include tablets, pills, capsules, sustained release pills, sustained release tablets, sustained release capsules, powders, granules, or in the form of solutions or mixtures (i.e., elixirs, tinctures, syrups, emulsions, suspensions). For example, one or more compounds of Formula (I), or salts or solvates thereof, may be combined, without limitation, with one or more pharmaceutically acceptable liquid carriers such as ethanol, glycerol, or water, and/or one or more solid binders such as, for example, starch, gelatin, natural sugars (e.g., glucose or β-lactose), and/or natural or synthetic gums (e.g., acacia, tragacanth, or sodium alginate), carboxymethylcellulose, polyethylene glycol, waxes and the like, and/or disintegrants, buffers, preservatives, anti-oxidants, lubricants, flavorings, thickeners, coloring agents, emulsifiers and the like. In addition, the unit dosage forms can include, without limitation, pharmaceutically acceptable lubricants (e.g., sodium oleate, sodium stearate, magnesium stearate, sodium benzoate, sodium acetate, and sodium chloride) and disintegrators (e.g., starch, methyl cellulose, agar, bentonite, and xanthan gum).

The amount of excipient or additive can range from about 0.1 to about 90 weight percent of the total weight of the treatment composition or therapeutic combination. One skilled in the art would understand that the amount of carrier(s), excipients and additives (if present) can vary.

In another embodiment, the present invention provides a method of treating, reducing, or ameliorating a disease or condition selected from the group consisting of metabolic syndrome, obesity, waist circumference, lipid profile, insulin sensitivity, neuroinflammatory disorders, cognitive disorders, psychosis, addictive behavior, gastrointestinal disorders, and cardiovascular conditions, in a patient in need thereof, comprising administering to said patient an effective amount of at least one compound of Formula (I), or a pharmaceutically acceptable salt, solvate, or ester thereof.

In yet another embodiment, the present invention provides a method of treating, reducing, or ameliorating obesity, in a patient in need thereof, comprising administering to said patient an effective amount of at least one compound of Formula (I), or a pharmaceutically acceptable salt, solvate, or ester thereof.

In yet another embodiment, the present invention provides a method of treating, reducing, or ameliorating metabolic syndrome, obesity, waist circumference, lipid profile, insulin sensitivity, neuroinflammatory disorders, cognitive disorders, psychosis, addictive behavior, gastrointestinal disorders, and cardiovascular conditions, in a patient in need thereof, comprising administering to said patient an effective amount of a composition comprising at least one compound of Formula (I), or a pharmaceutically acceptable salt, solvate, or ester thereof and a pharmaceutically acceptable carrier.

In yet another embodiment, the present invention provides a method of treating, reducing, or ameliorating obesity, in a patient in need thereof, comprising administering to said patient an effective amount of a composition comprising at least one compound of Formula (I), or a pharmaceutically acceptable salt, solvate, or ester thereof and a pharmaceutically acceptable carrier.

The compounds of Formula (I) can be useful as $CB_1$ receptor antagonists for treating, reducing, or ameliorating metabolic syndrome, obesity, waist circumference, lipid profile, insulin sensitivity, neuroinflammatory disorders, cognitive disorders, psychosis, addictive behavior (e.g., smoking cessation), gastrointestinal disorders, and cardiovascular conditions (e.g., elevated cholesterol and triglyceride levels). It is contemplated that the compounds of Formula (I) of the present invention, or pharmaceutically acceptable salts, solvates, or esters thereof, can be useful in treating one or more the conditions or diseases listed above. In particular, the compounds of Formula (I) of the present invention are useful in treating obesity.

"Effective amount" or "therapeutically effective amount" is meant to describe an amount of compound or a composition of the present invention effective in antagonizing a $CB_1$ receptor and thus producing the desired therapeutic effect in a suitable patient.

The selective $CB_1$ receptor antagonist compound of Formula (I), or a pharmaceutically acceptable salt, solvate, or ester thereof, can be administered in a therapeutically effective amount and manner to treat the specified condition. The daily dose of the selective $CB_1$ receptor antagonist of Formula (I) (or pharmaceutically acceptable salts, solvates, or esters thereof) administered to a mammalian patient or subject can range from about 1 mg/kg to about 50 mg/kg (where the units mg/kg refer to the amount of selective $CB_1$ receptor antagonist compound of Formula (I) per kg body weight of the patient), or about 1 mg/kg to about 25 mg/kg, or about 1 mg/kg to about 10 mg/kg.

Alternatively, the daily dose can range from about 1 mg to about 50 mg, or about 1 mg to about 25 mg, or about 5 mg to about 20 mg. Although a single administration of the selective $CB_1$ receptor antagonist compound of Formula (I), or salts, solvates, or esters thereof, can be efficacious, multiple dosages can also be administered. The exact dose, however, can readily be determined by the attending clinician and will depend on such factors as the potency of the compound administered, the age, weight, condition and response of the patient.

The treatment compositions of the present invention can be administered in any conventional dosage form, preferably an oral dosage form such as a capsule, tablet, powder, cachet, suspension or solution. The formulations and pharmaceutical compositions can be prepared using conventional pharmaceutically acceptable and conventional techniques.

In still yet another embodiment, the present invention provides a composition comprising: (a) at least one compound of Formula (I), or a pharmaceutically acceptable salt, solvate, or ester thereof, and (b) at least one cholesterol lowering compound.

Therapeutic combinations also are provided comprising: (a) a first amount of at least one selective $CB_1$ receptor antagonist, or a pharmaceutically acceptable salt, solvate, or ester thereof; and (b) a second amount of at least one cholesterol lowering compound, wherein the first amount and the second amount together comprise a therapeutically effective amount for the treatment or prevention of a vascular condition, diabetes, obesity, hyperlipidemia, metabolic syndrome, or lowering a concentration of a sterol in the plasma of a subject.

Pharmaceutical compositions for the treatment or prevention of a vascular condition, diabetes, obesity, hyperlipidemia, metabolic syndrome, or lowering a concentration of a sterol in the plasma of a subject comprising a therapeutically effective amount of the above compositions or therapeutic combinations and a pharmaceutically acceptable carrier also are provided.

In still yet another embodiment, the compositions and combinations of the present invention comprise at least one compound of Formula (I), or a pharmaceutically acceptable salt, solvate, or ester thereof, and at least one sterol absorption inhibitor or at least one 5α-stanol absorption inhibitor.

In still yet another embodiment of the present invention, there is provided a therapeutic combination comprising: (a) a first amount of at least one compound of Formula (I), or a pharmaceutically acceptable salt, solvate, or ester thereof; and (b) a second amount of at least one cholesterol lowering compound; wherein the first amount and the second amount together comprise a therapeutically effective amount for the treatment or prevention of one or more of a vascular condition, diabetes, obesity, metabolic syndrome, or lowering a concentration of a sterol in the plasma of a subject.

In still yet another embodiment, the present invention provides for a pharmaceutical composition for the treatment or prevention of one or more of a vascular condition, diabetes, obesity, metabolic syndrome, or lowering a concentration of a sterol in the plasma of a subject, comprising a therapeutically effective amount of a composition or therapeutic combination comprising: (a) at least one compound of Formula (I), or a pharmaceutically acceptable salt, solvate, or ester thereof; (b) a cholesterol lowering compound; and (c) a pharmaceutically acceptable carrier.

As used herein, "therapeutic combination" or "combination therapy" means the administration of two or more therapeutic agents, such as a compound according to Formula (I) of the present invention, and a cholesterol lowering compound such as one or more substituted azetidinone or one or more substituted β-lactam, to prevent or treat a condition, for example a vascular condition, such as hyperlipidaemia (for example atherosclerosis, hypercholesterolemia or sitosterolemia), vascular inflammation, metabolic syndrome, stroke, diabetes, obesity and/or reduce the level of sterol(s) (such as cholesterol) in the plasma or tissue. As used herein, "vascular" comprises cardiovascular, cerebrovascular and combinations thereof. The compositions, combinations and treatments of the present invention can be administered by any suitable means which produce contact of these compounds with the site of action in the body, for example in the plasma, liver, small intestine, or brain (e.g., hippocampus, cortex, cerebellum, and basal ganglia) of a subject (mammal or human or other animal). Such administration includes co-administration of these therapeutic agents in a substantially simultaneous manner, such as in a single tablet or capsule having a fixed ratio of active ingredients or in multiple, separate capsules for each therapeutic agent. Also, such administration includes the administration of each type of therapeutic agent in a sequential manner. In either case, the treatment using the combination therapy will provide beneficial effects in treating the condition. A potential advantage of the combination therapy disclosed herein may be a reduction in the required amount of an individual therapeutic compound or the overall total amount of therapeutic compounds that are effective in treating the condition. By using a combination of therapeutic agents, the side effects of the individual compounds can be reduced as compared to a monotherapy, which can improve patient compliance. Also, therapeutic agents can be selected to provide a broader range of complimentary effects or complimentary modes of action.

As discussed above, the compositions, pharmaceutical compositions and therapeutic combinations of the present invention comprise: (a) one or more compounds according to Formula (I) of the present invention, or pharmaceutically acceptable salts, solvates, or esters thereof; and (b) one or more cholesterol lowering agents. A non-limiting list of cholesterol lowering agents useful in the present invention include HMG CoA reductase inhibitor compounds such as lovastatin (for example MEVACOR® which is available from Merck & Co.), simvastatin (for example ZOCOR® which is available from Merck & Co.), pravastatin (for example PRAVACHOL® which is available from Bristol Meyers Squibb), atorvastatin, fluvastatin, cerivastatin, CI-981, rivastatin (sodium 7-(4-fluorophenyl)-2,6-diisopropyl-5-methoxymethylpyridin-3-yl)-3,5-dihydroxy-6-heptanoate), rosuvastatin calcium (CRESTOR® from AstraZeneca Pharmaceuticals), pitavastatin (such as NK-104 of Negma Kowa of Japan); HMG CoA synthetase inhibitors, for example L-659,699 ((E,E)-11-[3'R-(hydroxy-methyl)-4'-oxo-2'R-oxetanyl]-3,5,7R-trimethyl-2,4-undecadienoic acid); squalene synthesis inhibitors, for example squalestatin 1; squalene epoxidase inhibitors, for example, NB-598 ((E)-N-ethyl-N-(6,6-dimethyl-2-hepten-4-ynyl)-3-[(3,3'-bithiophen-5-yl)methoxy] benzene-methanamine hydrochloride); sterol (e.g., cholesterol) biosynthesis inhibitors such as DMP-565; nicotinic acid derivatives (e.g., compounds comprising a pyridine-3-carboxylate structure or a pyrazine-2-carboxylate structure, including acid forms, salts, esters, zwitterions and tautomers) such as niceritrol, nicofuranose and acipimox (5-methylpyrazine-2-carboxylic acid 4-oxide); clofibrate; gemfibrazol; bile acid sequestrants such as cholestyramine (a styrene-divinylbenzene copolymer containing quaternary ammonium cationic groups capable of binding bile acids, such as QUESTRAN® or QUESTRAN LIGHT® cholestyramine which are available from Bristol-Myers Squibb), colestipol (a copolymer of diethylenetriamine and 1-chloro-2,3-epoxypropane, such as COLESTID® tablets which are available from Pharmacia), colesevelam hydrochloride (such as WelChol® Tablets (poly(allylamine hydrochloride) cross-linked with epichlorohydrin and alkylated with 1-bromodecane and (6-bromohexyl)-trimethylammonium bromide) which are available from Sankyo), water soluble derivatives such as 3,3-ioene, N-(cycloalkyl) alkylamines and poliglusam, insoluble quaternized polystyrenes, saponins and mixtures thereof; inorganic cholesterol sequestrants such as bismuth salicylate plus montmorillonite clay, aluminum hydroxide and calcium carbonate antacids; ileal bile acid transport ("IBAT") inhibitors (or apical sodium co-dependent bile acid transport ("ASBT") inhibitors) such as benzothiepines, for example the therapeutic compounds comprising a 2,3,4,5-tetrahydro-1-benzothiepine 1,1-dioxide structure such as are disclosed in PCT Patent Application WO 00/38727 which is incorporated herein by reference; Acyl-CoA:Cholesterol O-acyltransferase ("ACAT") Inhibitors such as avasimibe ([[2,4,6-tris(1-methylethyl)phenyl]acetyl] sulfamic acid, 2,6-bis(1-methylethyl)phenyl ester, formerly known as CI-1011), HL-004, lecimibide (DuP-128) and CL-277082 (N-(2,4-difluorophenyl)-N-[[4-(2,2-dimethylpropyl)phenyl]methyl]-N-heptylurea), and the compounds described in P. Chang et al., "Current, New and Future Treatments in Dyslipidaemia and Atherosclerosis", *Drugs* 2000 July; 60(1); 55-93, which is incorporated by reference herein; Cholesteryl Ester Transfer Protein ("CETP") Inhibitors such as those disclosed in PCT Patent Application No. WO 00/38721 and U.S. Pat. No. 6,147,090, which are incorporated herein by reference; probucol or derivatives thereof, such as AGI-1067 and other derivatives disclosed in U.S. Pat. Nos. 6,121,319 and 6,147,250, herein incorporated by reference; low-density lipoprotein (LDL) receptor activators such as HOE-402, an imidazolidinyl-pyrimidine derivative that directly stimulates LDL receptor activity, described in M. Huettinger et al., "Hypolipidemic activity of HOE-402 is Mediated by Stimulation of the LDL Receptor Pathway", Arterioscler. Thromb. 1993; 13:1005-12, herein incorporated by reference; fish oils containing Omega 3 fatty acids (3-PUFA); natural water soluble fibers, such as psyllium, guar, oat and pectin; plant stanols and/or fatty acid esters of plant stanols, such as sitostanol ester used in BENECOL® margarine; nicotinic acid receptor agonists (e.g., agonists of the HM74 and HM74A receptor which receptor is described in US 2004/0142377, US 2005/0004178, US 2005/0154029, U.S. Pat. No. 6,902,902, WO 2004/071378, WO 2004/071394, WO 01/77320, US 2003/0139343, WO 01/94385, WO 2004/083388, US 2004/254224, US 2004/0254224, US 2003/0109673 and WO 98/56820) for example those described in WO 2004/033431, WO 2005/011677, WO 2005/051937, US 2005/0187280, US 2005/0187263, WO 2005/077950, WO 2005/016867, and WO 2005/016870; and the substituted azetidinone or substituted β-lactam sterol absorption inhibitors discussed in detail below.

As used herein, "sterol absorption inhibitor" means a compound capable of inhibiting the absorption of one or more sterols, including but not limited to cholesterol, phytosterols (such as sitosterol, campesterol, stigmasterol and avenosterol), 5α-stanols (such as cholestanol, 5α-campestanol, 5α-sitostanol), and/or mixtures thereof, when administered in a therapeutically effective (sterol and/or 5α-stanol absorption inhibiting) amount to a mammal or human.

Substituted Azetidinones of Formula (II)

In one embodiment, substituted azetidinones useful in the compositions, therapeutic combinations and methods of the present invention are represented by Formula (II) below:

(II)

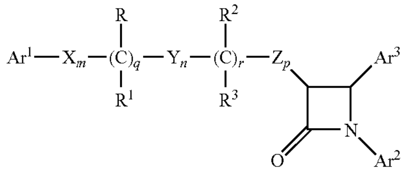

or pharmaceutically acceptable salts, solvates, or esters of the compounds of Formula (II), wherein, in Formula (II) above:

$Ar^1$ and $Ar^2$ are independently selected from the group consisting of aryl and $R^4$-substituted aryl;

$Ar^3$ is aryl or $R^5$-substituted aryl;

X, Y and Z are independently selected from the group consisting of $—CH_2—$, —CH(lower alkyl)- and —C(lower alkyl)$_2$-;

R and $R^2$ are independently selected from the group consisting of $—OR^6$, $—OC(O)R^6$, $—OC(O)OR^9$ and $—OC(O)NR^6R^7$;

$R^1$ and $R^3$ are independently selected from the group consisting of hydrogen, lower alkyl and aryl;

q is 0 or 1; r is 0 or 1; m, n and p are independently selected from 0, 1, 2, 3 or 4; provided that at least one of q and r is 1, and the sum of m, n, p, q and r is 1, 2, 3, 4, 5 or 6; and provided that when p is 0 and r is 1, the sum of m, q and n is 1, 2, 3, 4 or 5;

$R^4$ is 1-5 substituents independently selected from the group consisting of lower alkyl, $—OR^6$, $—OC(O)R^6$, $—OC(O)OR^9$, $—O(CH_2)_{1-5}OR^6$, $—OC(O)NR^6R^7$, $—NR^6R^7$, $—NR^6C(O)R^7$, $—NR^6C(O)OR^9$, $—NR^6C(O)NR^7R^8$, $—NR^6SO_2R^9$, $—C(O)OR^6$, $—C(O)NR^6R^7$, $—C(O)R^6$, $—S(O)_2NR^6R^7$, $S(O)_{0-2}R^9$, $—O(CH_2)_{1-10}—C(O)OR^6$, $—O(CH_2)_{1-10}CONR^6R^7$, -(lower alkylene)$COOR^6$, $—CH{=}CH—C(O)OR^6$, $—CF_3$, —CN, $—NO_2$ and halogen;

$R^5$ is 1-5 substituents independently selected from the group consisting of $—OR^6$, $—OC(O)R^6$, $—OC(O)OR^9$, $—O(CH_2)_{1-5}OR^6$, $—OC(O)NR^6R^7$, $—NR^6R^7$, $—NR^6C(O)R^7$, $—NR^6C(O)OR^9$, $—NR^6C(O)NR^7R^8$, $—NR^6S(O)_2R^9$, $—C(O)OR^6$, $—C(O)NR^6R^7$, $—C(O)R^6$, $—SO_2NR^6R^7$, $S(O)_{0-2}R^9$, $—O(CH_2)_{1-10}—C(O)OR^6$, $—O(CH_2)_{1-10}C(O)NR^6R^7$, -(lower alkylene)$C(O)OR^6$ and $—CH{=}CH—C(O)OR^6$;

$R^6$, $R^7$ and $R^8$ are independently selected from the group consisting of hydrogen, lower alkyl, aryl and aryl-substituted lower alkyl; and $R^9$ is lower alkyl, aryl or aryl-substituted lower alkyl.

Preferably, $R^4$ is 1-3 independently selected substituents, and $R^5$ is preferably 1-3 independently selected substituents.

Certain compounds useful in the therapeutic compositions or combinations of the invention may have at least one asymmetrical carbon atom and therefore all isomers, including enantiomers, diastereomers, stereoisomers, rotamers, tautomers and racemates of the compounds of Formula II-XIII (where they exist) are contemplated as being part of this invention. The invention includes d and l isomers in both pure form and in admixture, including racemic mixtures. Isomers can be prepared using conventional techniques, either by reacting optically pure or optically enriched starting materials or by separating isomers of a compound of the Formulae II-XIII. Isomers may also include geometric isomers, e.g., when a double bond is present.

Those skilled in the art will appreciate that for some of the compounds of the Formulae II-XIII, one isomer may show greater pharmacological activity than other isomers.

Preferred compounds of Formula (II) are those in which $Ar^1$ is phenyl or $R^4$-substituted phenyl, more preferably (4-$R^4$)-substituted phenyl. $Ar^2$ is preferably phenyl or $R^4$-substituted phenyl, more preferably (4-$R^4$)-substituted phenyl. $Ar^3$ is preferably $R^5$-substituted phenyl, more preferably (4-$R^5$)-substituted phenyl. When $Ar^1$ is (4-$R^4$)-substituted phenyl, $R^4$ is preferably a halogen. When $Ar^2$ and $Ar^3$ are $R^4$— and $R^5$-substituted phenyl, respectively, $R^4$ is preferably halogen or $—OR^6$ and $R^5$ is preferably $—OR^6$, wherein $R^6$ is lower alkyl or hydrogen. Especially preferred are compounds wherein each of $Ar^1$ and $Ar^2$ is 4-fluorophenyl and $Ar^3$ is 4-hydroxyphenyl or 4-methoxyphenyl.

X, Y and Z are each preferably $—CH_2—$. $R^1$ and $R^3$ are each preferably hydrogen. R and $R^2$ are preferably $—OR^6$ wherein $R^6$ is hydrogen, or a group readily metabolizable to a hydroxyl (such as $—OC(O)R^6$, $—OC(O)OR^9$ and $—OC(O)NR^6R^7$, defined above).

The sum of m, n, p, q and r is preferably 2, 3 or 4, more preferably 3. Preferred are compounds OF Formula (II) wherein m, n and r are each zero, q is 1 and p is 2.

Also preferred are compounds of Formula (II) in which p, q and n are each zero, r is 1 and m is 2 or 3. More preferred are compounds wherein m, n and r are each zero, q is 1, p is 2, Z is $—CH_2—$ and $R^2$ is $—OR^6$, especially when $R^6$ is hydrogen.

Also more preferred are compounds of Formula (II) wherein p, q and n are each zero, r is 1, m is 2, X is $—CH_2—$ and $R^2$ is $—OR^6$, especially when $R^6$ is hydrogen.

Another group of preferred compounds of Formula (II) is that in which $Ar^1$ is phenyl or $R^4$-substituted phenyl, $Ar^2$ is phenyl or $R^4$-substituted phenyl and $Ar^3$ is $R^5$-substituted phenyl. Also preferred are compounds in which $Ar^1$ is phenyl or $R^4$-substituted phenyl, $Ar^2$ is phenyl or $R^4$-substituted phenyl, $Ar^3$ is $R^5$-substituted phenyl, and the sum of m, n, p, q and r is 2, 3 or 4, more preferably 3. More preferred are compounds wherein $Ar^1$ is phenyl or $R^4$-substituted phenyl, $Ar^2$ is phenyl or $R^4$-substituted phenyl, $Ar^3$ is $R^5$-substituted phenyl, and wherein m, n and r are each zero, q is 1 and p is 2, or wherein p, q and n are each zero, r is 1 and m is 2 or 3.

Substituted Azetidinones of Formula (III)

In a preferred embodiment, a substituted azetidinone of Formula (II) useful in the compositions, therapeutic combinations and methods of the present invention is represented by Formula (III) (ezetimibe) below:

(III)

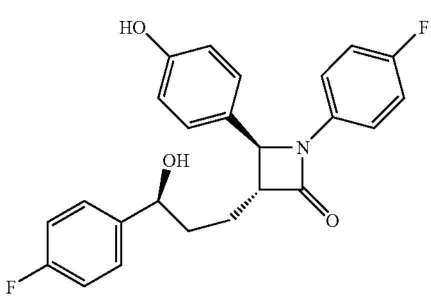

or pharmaceutically acceptable salts, solvates, or esters of the compound of Formula (III). The compound of Formula (III) can be in anhydrous or hydrated form. A product containing ezetimibe compound is commercially available as ZETIA® ezetimibe formulation from MSP Pharmaceuticals.

Compounds of Formula (II) can be prepared by a variety of methods well known to those skilled in the art, for example such as are disclosed in U.S. Pat. Nos. 5,631,365, 5,767,115, 5,846,966, 6,207,822, 6,627,757, 6,093,812, 5,306,817, 5,561,227, 5,688,785, and 5,688,787, each of which is incorporated herein by reference.

Substituted Azetidinones of Formula (IV)

Alternative substituted azetidinones useful in the compositions, therapeutic combinations and methods of the present invention are represented by Formula (IV) below:

(IV)

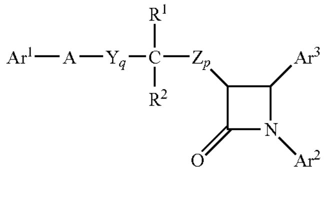

or a pharmaceutically acceptable salt thereof or a solvate thereof, or an ester thereof, wherein, in Formula (IV) above:

$Ar^1$ is $R^3$-substituted aryl;

$Ar^2$ is $R^4$-substituted aryl;

$Ar^3$ is $R^5$-substituted aryl;

Y and Z are independently selected from the group consisting of —$CH_2$—, —CH(lower alkyl)- and —C(lower alkyl)$_2$-;

A is selected from —O—, —S—, —S(O)— or —$S(O)_2$—;

$R^1$ is selected from the group consisting of —$OR^6$, —OC(O)$R^6$, —OC(O)$OR^9$ and —OC(O)$NR^6R^7$;

$R^2$ is selected from the group consisting of hydrogen, lower alkyl and aryl; or $R^1$ and $R^2$ together are ═O;

q is 1, 2 or 3;

p is 0, 1, 2, 3 or 4;

$R^5$ is 1-3 substituents independently selected from the group consisting of —$OR^6$, —OC(O)$R^6$, —OC(O)$OR^9$, —O$(CH_2)_{1-5}OR^9$, —OC(O)$NR^5R^7$, —$NR^6R^7$, —$NR^6$C(O)$R^7$, —$NR^6$C(O)$OR^9$, —$NR^6$C(O)$NR^7R^8$, —$NR^6S(O)_2$-lower alkyl, —$NR^6S(O)_2$-aryl, —C(O)$NR^6R^7$, —$COR^6$, —$SO_2NR^6R^7$, $S(O)_{0-2}$-alkyl, $S(O)_{0-2}$-aryl, —O$(CH_2)_{1-10}$—C(O)$OR^6$, —O$(CH_2)_{1-10}$C(O)$NR^6R^7$, o-halogeno, m-halogeno, o-lower alkyl, m-lower alkyl, -(lower alkylene)-C(O)$OR^6$, and —CH═CH—C(O)$OR^6$;

$R^3$ and $R^4$ are independently 1-3 substituents independently selected from the group consisting of $R^5$, hydrogen, p-lower alkyl, aryl, —$NO_2$, —$CF_3$ and p-halogeno;

$R^6$, $R^7$ and $R^8$ are independently selected from the group consisting of hydrogen, lower alkyl, aryl and aryl-substituted lower alkyl; and $R^9$ is lower alkyl, aryl or aryl-substituted lower alkyl.

Methods for making compounds of Formula (IV) are well known to those skilled in the art. Non-limiting examples of suitable methods are disclosed in U.S. Pat. No. 5,688,990, which is incorporated herein by reference.

Substituted Azetidinones of Formula (V)

In another embodiment, substituted azetidinones useful in the compositions, therapeutic combinations and methods of the present invention are represented by Formula (V):

(V)

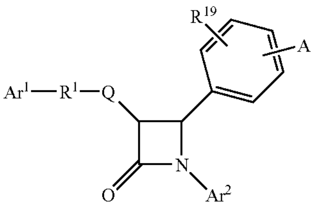

or a pharmaceutically acceptable salt thereof or a solvate thereof, or an ester thereof, wherein, in Formula (V) above:

A is selected from the group consisting of $R^2$-substituted heterocycloalkyl, $R^2$-substituted heteroaryl, $R^2$-substituted benzo-fused heterocycloalkyl, and $R^2$-substituted benzo-fused heteroaryl;

$Ar^1$ is aryl or $R^3$-substituted aryl;

$Ar^2$ is aryl or $R^4$-substituted aryl;

Q is a bond or, with the 3-position ring carbon of the azetidinone, forms the spiro group

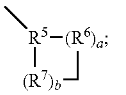

and $R^1$ is selected from the group consisting of:

—$(CH_2)_q$—, wherein q is 2-6, provided that when Q forms a spiro ring, q can also be zero or 1;

—$(CH_2)_e$-G-$(CH_2)_r$—, wherein G is —O—, —C(O)—, phenylene, —$NR^8$— or —$S(O)_{0-2}$—, e is 0-5 and r is 0-5, provided that the sum of e and r is 1-6;

—($C_2$-$C_6$ alkenylene)-; and

—$(CH_2)_f$—V—$(CH_2)_g$—, wherein V is $C_3$-$C_6$ cycloalkylene, f is 1-5 and g is 0-5, provided that the sum of f and g is 1-6;

$R^5$ is selected from:

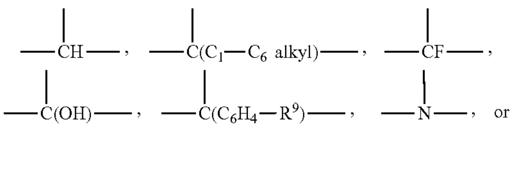

or

-continued

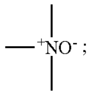

$R^6$ and $R^7$ are independently selected from the group consisting of —$CH_2$—, —$CH(C_1$-$C_6$ alkyl)-, —C(di-($C_1$-$C_6$) alkyl), —CH═CH— and —C($C_1$-$C_6$ alkyl)═CH—; or $R^5$ together with an adjacent $R^6$, or $R^5$ together with an adjacent $R^7$, form a —CH═CH— or a —CH═C($C_1$-$C_6$ alkyl)-group;

a and b are independently 0, 1, 2 or 3, provided both are not zero; provided that when $R^6$ is —CH═CH— or —C($C_1$-$C_6$ alkyl)═CH—, a is 1; provided that when $R^7$ is —CH═CH— or —C($C_0$-$C_6$ alkyl)═CH—, b is 1; provided that when a is 2 or 3, the $R^6$'s can be the same or different; and provided that when b is 2 or 3, the $R^7$'s can be the same or different;

and when Q is a bond, $R^1$ also can be selected from:

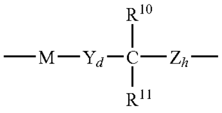

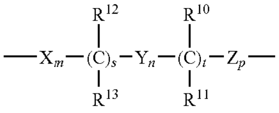

or

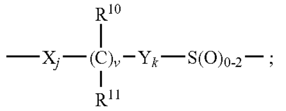

where M is —O—, —S—, —S(O)— or —$S(O)_2$—;

X, Y and Z are independently selected from the group consisting of —$CH_2$—, —$CH(C_1$-$C_6$ alkyl)- and —C(di-($C_1$-$C_6$) alkyl);

$R^{10}$ and $R^{12}$ are independently selected from the group consisting of —$OR^{14}$, —OC(O)$R^{14}$, —OC(O)$OR^{16}$ and —OC(O)$NR^{14}R^{15}$;

$R^{11}$ and $R^{13}$ are independently selected from the group consisting of hydrogen, ($C_1$-$C_6$)alkyl and aryl; or $R^{10}$ and $R^{11}$ together are ═O, or $R^{12}$ and $R^{13}$ together are ═O;

d is 1, 2 or 3;

h is 0, 1, 2, 3 or 4;

s is 0 or 1; t is 0 or 1; m, n and p are independently 0-4; provided that at least one of s and t is 1, and the sum of m, n, p, s and t is 1-6; provided that when p is 0 and t is 1, the sum of m, s and n is 1-5; and provided that when p is 0 and s is 1, the sum of m, t and n is 1-5;

v is 0 or 1;

j and k are independently 1-5, provided that the sum of j, k and v is 1-5;

$R^2$ is 1-3 substituents on the ring carbon atoms selected from the group consisting of hydrogen, ($C_1$-$C_{10}$)alkyl, ($C_2$-$C_{10}$)alkenyl, ($C_2$-$C_{10}$)alkynyl, ($C_3$-$C_6$)cycloalkyl, ($C_3$-$C_6$)cycloalkenyl, $R^{17}$-substituted aryl, $R^{17}$-substituted benzyl, $R^{17}$-substituted benzyloxy, $R^{17}$-substituted aryloxy, halogeno, —$NR^{14}R^{15}$, $NR^{14}R^{15}$($C_1$-$C_6$ alkylene)-, $NR^{14}R^{15}$C(O)($C_1$-$C_6$ alkylene)-, —NHC(O)$R^{16}$, OH, $C_1$-$C_6$ alkoxy, —OC(O)$R^{16}$, —C(O)$R^{14}$, hydroxy($C_1$-$C_6$)alkyl, ($C_1$-$C_6$)alkoxy($C_1$-$C_6$)alkyl, $NO_2$, —$S(O)_{0-2}R^{16}$, —$S(O)_2NR^{14}R^{15}$ and —($C_1$-$C_6$ alkylene)C(O)$OR^{14}$; when $R^2$ is a substituent on a heterocycloalkyl ring, $R^2$ is as defined, or $R^2$ is ═O or

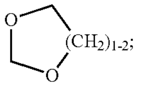

and, where $R^2$ is a substituent on a substitutable ring nitrogen, $R^2$ is hydrogen, ($C_1$-$C_6$)alkyl, aryl, ($C_1$-$C_6$)alkoxy, aryloxy, ($C_1$-$C_6$)alkylcarbonyl, arylcarbonyl, hydroxy, —$(CH_2)_{1-6}CONR^{18}R^{18}$,

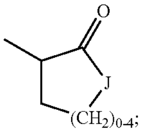

or

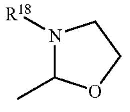

wherein J is —O—, —NH—, —$NR^{18}$— or —$CH_2$—;

$R^3$ and $R^4$ are independently selected from the group consisting of 1-3 substituents independently selected from the group consisting of ($C_1$-$C_6$)alkyl, —$OR^{14}$—OC(O)$R^{14}$—OC(O)$OR^{16}$, —$O(CH_2)_{1-5}OR^{14}$—OC(O)$NR^{14}R^{15}$, —$NR^{14}R^{15}$, —$NR^{14}$C(O)$R^{15}$, —$NR^{14}$C(O)$OR^{16}$, —$NR^{14}$C(O)$NR^{15}R^{19}$, —$NR^{14}S(O)_2R^{16}$, —C(O)$OR^{14}$, —C(O)$NR^{14}R^{15}$, —C(O)$R^{14}$—$S(O)_2NR^{14}R^{15}$, $S(O)_{0-2}R^{16}$, —$O(CH_2)_{1-10}$—C(O)$OR^{14}$, —$O(CH_2)_{1-10}$C(O)$NR^{14}R^{15}$, —($C_1$-$C_6$ alkylene)-C(O)$OR^{14}$, —CH═CH—C(O)$OR^{14}$, —$CF_3$, —CN, —$NO_2$ and halogen;

$R^8$ is hydrogen, ($C_1$-$C_6$)alkyl, aryl ($C_1$-$C_6$)alkyl, —C(O)$R^{14}$ or —C(O)$OR^{14}$;

$R^9$ and $R^{17}$ are independently 1-3 groups independently selected from the group consisting of hydrogen, ($C_1$-$C_6$)alkyl, ($C_1$-$C_6$)alkoxy, —C(O)OH, $NO_2$, —$NR^{14}R^{15}$, OH and halogeno;

$R^{14}$ and $R^{15}$ are independently selected from the group consisting of hydrogen, ($C_1$-$C_6$)alkyl, aryl and aryl-substituted ($C_1$-$C_6$)alkyl;

$R^{16}$ is ($C_1$-$C_6$)alkyl, aryl or $R^{17}$-substituted aryl;

$R^{18}$ is hydrogen or ($C_1$-$C_6$)alkyl; and $R^{19}$ is hydrogen, hydroxy or ($C_1$-$C_6$)alkoxy.

Methods for making compounds of Formula (V) are well known to those skilled in the art. Non-limiting examples of suitable methods are disclosed in U.S. Pat. No. 5,656,624, which is incorporated herein by reference.

Substituted Azetidinones of Formula (VI)

In another embodiment, substituted azetidinones useful in the compositions, therapeutic combinations and methods of the present invention are represented by Formula (VI):

(VI)

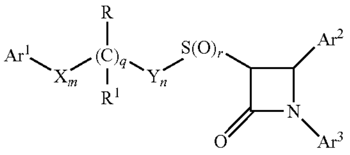

or a pharmaceutically acceptable salt thereof or a solvate thereof, or an ester thereof, wherein, in Formula (VI) above:

$Ar^1$ is aryl, $R^{10}$-substituted aryl or heteroaryl;

$Ar^2$ is aryl or $R^4$-substituted aryl;

$Ar^3$ is aryl or $R^5$-substituted aryl;

X and Y are independently selected from the group consisting of —$CH_2$—, —CH(lower alkyl)- and —C(lower alkyl)$_2$-;

R is $-OR^6$, $-OC(O)R^6$, $-OC(O)OR^9$ or $-OC(O)NR^6R^7$; $R^1$ is hydrogen, lower alkyl or aryl; or R and $R^1$ together are $=O$;

q is 0 or 1;

r is 0, 1 or 2;

m and n are independently 0, 1, 2, 3, 4 or 5; provided that the sum of m, n and q is 1, 2, 3, 4 or 5;

$R^4$ is 1-5 substituents independently selected from the group consisting of lower alkyl, $-OR^6$, $-OC(O)R^6$, $-OC(O)OR^9$, $-O(CH_2)_{1-5}OR^6$, $-OC(O)NR^6R^7$, $-NR^6R^7$, $-NR^6C(O)R^7$, $-NR^6C(O)OR^9$, $-NR^6C(O)NR^7R^8$, $-NR^6S(O)_2R^9$, $-C(O)OR^6$, $-C(O)NR^6R^7$, $-C(O)R^6$, $-S(O)_2NR^6R^7$, $S(O)_{0-2}R^9$, $-O(CH_2)_{1-10}-C(O)OR^6$, $-O(CH_2)_{1-10}C(O)NR^6R^7$, -(lower alkylene)$C(O)OR^6$ and $-CH=CH-C(O)OR^6$;

$R^5$ is 1-5 substituents independently selected from the group consisting of $-OR^6$, $-OC(O)R^6$, $-OC(O)OR^9$, $-O(CH_2)_{1-5}OR^6$, $-OC(O)NR^6R^7$, $-NR^6R^7$, $-NR^6C(O)R^7$, $-NR^6C(O)OR^9$, $-NR^6C(O)NR^7R^8$, $-NR^6S(O)_2R^9$, $-C(O)OR^6$, $-C(O)NR^6R^7$, $-C(O)R^6$, $-S(O)_2NR^6R^7$, $S(O)O\text{-}2R^9$, $-O(CH_2)_{1-10}-C(O)OR^6$, $-O(CH_2)_{1-10}C(O)NR^6R^7$, $-CF_3$, $-CN$, $-NO_2$, halogen, -(lower alkylene)$C(O)OR^6$ and $-CH=CH-C(O)OR^6$;

$R^6$, $R^7$ and $R^8$ are independently selected from the group consisting of hydrogen, lower alkyl, aryl and aryl-substituted lower alkyl;

$R^9$ is lower alkyl, aryl or aryl-substituted lower alkyl; and $R^{10}$ is 1-5 substituents independently selected from the group consisting of lower alkyl, $-OR^6$, $-OC(O)R^6$, $-OC(O)OR^9$, $-O(CH_2)_{1-5}OR^6$, $-OC(O)NR^6R^7$, $-NR^6R^7$, $-NR^6C(O)R^7$, $-NR^6C(O)OR^9$, $-NR^6C(O)NR^7R^8$, $-NR^6S(O)_2R^9$, $-C(O)OR^6$, $-C(O)NR^6R^7$, $-C(O)R^6$, $-S(O)_2NR^6R^7$, $-S(O)_{0-2}R^9$, $-O(CH_2)_{1-10}-C(O)OR^6$, $-O(CH_2)_{1-10}C(O)NR^6R^7$, $-CF_3$, $-CN$, $-NO_2$ and halogen.

Methods for making compounds of Formula (VI) are well known to those skilled in the art. Non-limiting examples of suitable methods are disclosed in U.S. Pat. No. 5,624,920, which is incorporated herein by reference.

Substituted Azetidinones of Formula (VII)

In another embodiment, substituted azetidinones useful in the compositions, therapeutic combinations and methods of the present invention are represented by Formula (VII):

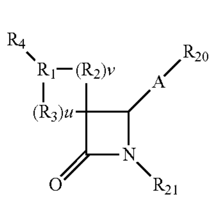

(VII)

or a pharmaceutically acceptable salt thereof or a solvate thereof, or an ester thereof, wherein:

$R^1$ is:

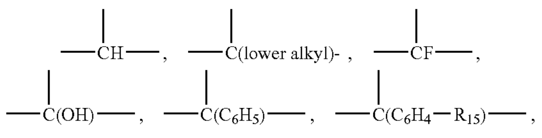

-continued

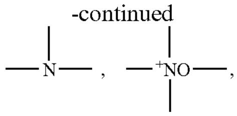

$R^2$ and $R^3$ are independently selected from the group consisting of: $-CH_2-$, $-CH$(lower alkyl)-, $-C$(lower alkyl)$_2$-, $-CH=CH-$ and $-C$(lower alkyl)$=CH-$; or $R^1$ together with an adjacent $R^2$, or $R^1$ together with an adjacent $R^3$, form a $-CH=CH-$ or a $-CH=C$(lower alkyl)- group;

u and v are independently 0, 1, 2 or 3, provided both are not zero; provided that when $R^2$ is $-CH=CH-$ or $-C$(lower alkyl)$=CH-$, v is 1; provided that when $R^3$ is $-CH=CH-$ or $-C$(lower alkyl)$=CH-$, u is 1; provided that when v is 2 or 3, each $R^2$ can be the same or different; and provided that when u is 2 or 3, each $R^3$ can be the same or different;

$R^4$ is selected from $B-(CH_2)_mC(O)-$, wherein m is 0, 1, 2, 3, 4 or 5; $B-(CH_2)_q-$, wherein q is 0, 1, 2, 3, 4, 5 or 6; $B-(CH_2)_e-Z-(CH_2)_r-$, wherein Z is $-O-$, $-C(O)-$, phenylene, $-N(R^8)-$ or $-S(O)_{0-2}-$, e is 0, 1, 2, 3, 4 or 5 and r is 0, 1, 2, 3, 4 or 5, provided that the sum of e and r is 0, 1, 2, 3, 4, 5 or 6; $B-(C_2\text{-}C_6$ alkenylene)-; $B-(C_4\text{-}C_6$ alkadienylene)-; $B-(CH_2)_t-Z-(C_2\text{-}C_6$ alkenylene)-, wherein Z is as defined above, and wherein t is 0, 1, 2 or 3, provided that the sum of t and the number of carbon atoms in the alkenylene chain is 2, 3, 4, 5 or 6; $B-(CH_2)_f-V-(CH_2)_g-$, wherein V is $C_3\text{-}C_6$ cycloalkylene, f is 1, 2, 3, 4 or 5 and g is 0, 1, 2, 3, 4 or 5, provided that the sum of f and g is 1, 2, 3, 4, 5 or 6; $B-(CH_2)_t-V-(C_2\text{-}C_6$ alkenylene)- or $B-(C_2\text{-}C_6$ alkenylene)-$V-(CH_2)_t-$, wherein V and t are as defined above, provided that the sum of t and the number of carbon atoms in the alkenylene chain is 2, 3, 4, 5 or 6; $B-(CH_2)_a-Z-(CH_2)_b-V-(CH_2)_d-$, wherein Z and V are as defined above and a, b and d are independently 0, 1, 2, 3, 4, 5 or 6, provided that the sum of a, b and d is 0, 1, 2, 3, 4, 5 or 6; or $T\text{-}(CH_2)_n-$, wherein T is a $C_3\text{-}C_6$ cycloalkyl and s is 0, 1, 2, 3, 4, 5 or 6; or $R^1$ and $R^4$ together form the group

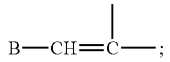

B is selected from indanyl, indenyl, naphthyl, tetrahydronaphthyl, heteroaryl or W-substituted heteroaryl, wherein heteroaryl is selected from the group consisting of pyrrolyl, pyridinyl, pyrimidinyl, pyrazinyl, triazinyl, imidazolyl, thiazolyl, pyrazolyl, thienyl, oxazolyl and furanyl, and for nitrogen-containing heteroaryls, the N-oxides thereof, or

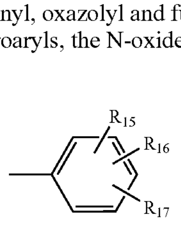

W is 1 to 3 substituents independently selected from the group consisting of lower alkyl, hydroxy lower alkyl, lower alkoxy, alkoxyalkyl, alkoxyalkoxy, alkoxycarbonylalkoxy, (lower alkoxyimino)-lower alkyl, lower alkanedioyl, lower alkyl lower alkanedioyl, allyloxy, $-CF_3$, $-OCF_3$, benzyl, $R^7$-benzyl, benzyloxy, $R^7$-benzyloxy, phenoxy, $R^7$-phenoxy, dioxolanyl, $NO_2$, $-N(R^8)(R^9)$, $N(R^8)(R^9)$-lower alkylene-, $N(R^8)(R^9)$-lower alkylenyloxy-, OH, halogeno, $-CN$, $-N_3$, —$NHC(O)OR^{10}$, —$NHC(O)R^{10}$, $R^{11}(O)_2SNH$—, $(R^{11}(O)_2S)_2N$—, —$S(O)_2NH_2$, —$S(O)_{0-2}R^8$, tert-butyldimethyl-silyloxymethyl, —$C(O)R^{12}$, —$C(O)OR^{19}$, —$C(O)N(R^8)(R^9)$, —$CH{=}CHC(O)R^{12}$, -lower alkylene-$C(O)R^{12}$, $R^{10}C(O)$(lower alkylenyloxy)-, $N(R^8)(R^9)C(O)$(lower alkylenyloxy)- and

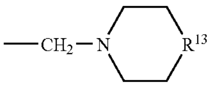

for substitution on ring carbon atoms, and the substituents on the substituted heteroaryl ring nitrogen atoms, when present, are selected from the group consisting of lower alkyl, lower alkoxy, —$C(O)OR^{10}$, —$C(O)R^{10}$, OH, $N(R^8)(R^9)$-lower alkylene-, $N(R^8)(R^9)$-lower alkylenyloxy-, —$S(O)_2NH_2$ and 2-(trimethylsilyl)-ethoxymethyl;

$R^7$ is 1-3 groups independently selected from the group consisting of lower alkyl, lower alkoxy, —C(O)OH, $NO_2$, —$N(R^8)(R^9)$, OH, and halogeno;

$R^8$ and $R^9$ are independently selected from H or lower alkyl;

$R^{10}$ is selected from lower alkyl, phenyl, $R^7$-phenyl, benzyl or $R^7$-benzyl;

$R^{11}$ is selected from OH, lower alkyl, phenyl, benzyl, $R^7$-phenyl or $R^7$-benzyl;

$R^{12}$ is selected from H, OH, alkoxy, phenoxy, benzyloxy,

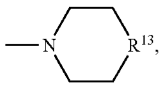

—$N(R^8)(R^9)$, lower alkyl, phenyl or $R^7$-phenyl;

$R^{13}$ is selected from —O—, —$CH_2$—, —NH—, —N(lower alkyl)- or —$NC(O)R^{19}$;

$R^{15}$, $R^{16}$ and $R^{17}$ are independently selected from the group consisting of H and the groups defined for W; or $R^{15}$ is hydrogen and $R^{15}$ and $R^{17}$, together with adjacent carbon atoms to which they are attached, form a dioxolanyl ring;

$R^{19}$ is H, lower alkyl, phenyl or phenyl lower alkyl; and $R^{20}$ and $R^{21}$ are independently selected from the group consisting of phenyl, W-substituted phenyl, naphthyl, W-substituted naphthyl, indanyl, indenyl, tetrahydronaphthyl, benzodioxolyl, heteroaryl, W-substituted heteroaryl, benzo-fused heteroaryl, W-substituted benzo-fused heteroaryl and cyclopropyl, wherein heteroaryl is as defined above.

Methods for making compounds of Formula (VII) are well known to those skilled in the art. Non-limiting examples of suitable methods are disclosed in U.S. Pat. No. 5,698,548, which is incorporated herein by reference.

Substituted Azetidinones of Formula (VIII)

In another embodiment, substituted azetidinones useful in the compositions, therapeutic combinations and methods of the present invention are represented by Formulas (VIIIA) and (VIIIB):

(VIIIA)

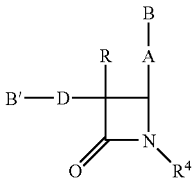

and (VIIIB)

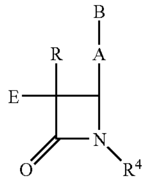

or a pharmaceutically acceptable salt, solvate, or ester thereof, wherein:

A is —CH═CH—, —C≡C— or —$(CH_2)_p$— wherein p is 0, 1 or 2;

B is

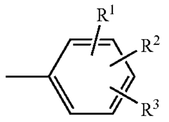

B' is

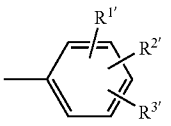

D is —$(CH_2)_mC(O)$— or —$(CH_2)_q$— wherein m is 1, 2, 3 or 4 and q is 2, 3 or 4;

E is $C_{10}$ to $C_{20}$ alkyl or —C(O)—($C_9$ to $C_{19}$)-alkyl, wherein the alkyl is straight or branched, saturated or containing one or more double bonds;

R is hydrogen, $C_1$-$C_{15}$ alkyl, straight or branched, saturated or containing one or more double bonds, or B—$(CH_2)_r$—, wherein r is 0, 1, 2, or 3;

$R^1$, $R^2$, $R^3$, $R^{1'}$, $R^{2'}$, and $R^{3'}$ are independently selected from the group consisting of hydrogen, lower alkyl, lower alkoxy, carboxy, $NO_2$, $NH_2$, OH, halogeno, lower alkylamino, dilower alkylamino, —$NHC(O)OR^5$, $R^6(O)_2SNH$— and —$S(O)_2NH_2$;

$R^4$ is

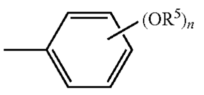

wherein n is 0, 1, 2 or 3;

$R^5$ is lower alkyl; and $R^6$ is OH, lower alkyl, phenyl, benzyl or substituted phenyl wherein the substituents are 1-3 groups independently selected from the group consisting of lower alkyl, lower alkoxy, carboxy, $NO_2$, $NH_2$, OH, halogeno, lower alkylamino and dilower alkylamino; or a pharmaceutically acceptable salt, solvate, or ester thereof.

Sterol Absorption Inhibitors of Formula (IX)

In another embodiment, sterol absorption inhibitors useful in the compositions and methods of the present invention are represented by Formula (IX):

(IX)

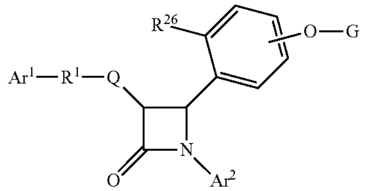

or a pharmaceutically acceptable salt, solvate, or ester thereof, wherein, in Formula (IX) above, $R^{26}$ is H or $OG^1$;

G and $G^1$ are independently selected from the group consisting of H,

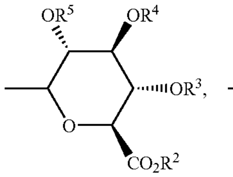

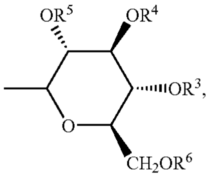

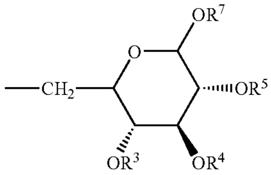

and

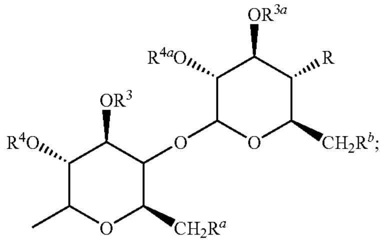

provided that when $R^{26}$ is H or OH, G is not H;

R, $R^a$ and $R^b$ are independently selected from the group consisting of H, —OH, halogeno, —$NH_2$, azido, $(C_1$-$C_6)$alkoxy$(C_1$-$C_6)$-alkoxy or —W—$R^{30}$;

W is independently selected from the group consisting of —NH—C(O)—, —O—C(O)—, —O—C(O)—N($R^{31}$)—, —NH—C(O)—N($R^{31}$)— and —O—C(S)—N($R^{31}$)—;

$R^2$ and $R^6$ are independently selected from the group consisting of H, $(C_1$-$C_6)$alkyl, aryl and aryl$(C_1$-$C_6)$alkyl;

$R^3$, $R^4$, $R^5$, $R^7$, $R^{3a}$ and $R^{4a}$ are independently selected from the group consisting of H, $(C_1$-$C_6)$alkyl, aryl$(C_1$-$C_6)$alkyl, —C(O)$(C_1$-$C_6)$alkyl and —C(O)aryl;

$R^{30}$ is selected from the group consisting of $R^{32}$-substituted T, $R^{32}$-substituted-T-$(C_1$-$C_6)$alkyl, $R^{32}$-substituted-$(C_2$-$C_4)$alkenyl, $R^{32}$-substituted-$(C_1$-$C_6)$alkyl, $R^{32}$-substituted-$(C_3$-$C_7)$cycloalkyl and $R^{32}$-substituted-$(C_3$-$C_7)$cycloalkyl$(C_1$-$C_6)$alkyl;

$R^{31}$ is selected from the group consisting of H and $(C_1$-$C_4)$alkyl;

T is selected from the group consisting of phenyl, furyl, thienyl, pyrrolyl, oxazolyl, isoxazolyl, thiazolyl, iosthiazolyl, benzothiazolyl, thiadiazolyl, pyrazolyl, imidazolyl and pyridyl;

$R^{32}$ is independently selected from 1-3 substituents independently selected from the group consisting of halogeno, $(C_1$-$C_4)$alkyl, —OH, phenoxy, —$CF_3$, —$NO_2$, $(C_1$-$C_4)$alkoxy, methylenedioxy, oxo, $(C_1$-$C_4)$alkylsulfanyl, $(C_1$-$C_4)$alkylsulfinyl, $(C_1$-$C_4)$alkylsulfonyl, —N$(CH_3)_2$, —C(O)—NH$(C_1$-$C_4)$alkyl, —C(O)—N($(C_1$-$C_4)$alkyl$)_2$, —C(O)—$(C_1$-$C_4)$alkyl, —C(O)—$(C_1$-$C_4)$alkoxy and pyrrolidinylcarbonyl; or $R^{32}$ is a covalent bond and $R^{31}$, the nitrogen to which it is attached and $R^{32}$ form a pyrrolidinyl, piperidinyl, N-methylpiperazinyl, indolinyl or morpholinyl group, or a $(C_1$-$C_4)$alkoxycarbonyl-substituted pyrrolidinyl, piperidinyl, N-methylpiperazinyl, indolinyl or morpholinyl group;

$Ar^1$ is aryl or $R^{10}$-substituted aryl;

$Ar^2$ is aryl or $R^{11}$-substituted aryl;

Q is a bond or, with the 3-position ring carbon of the azetidinone, forms the spiro group

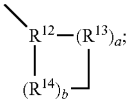

and $R^1$ is selected from the group consisting of

—$(CH_2)_q$—, wherein q is 2-6, provided that when Q forms a spiro ring, q can also be zero or 1;

—$(CH_2)_e$-E-$(CH_2)_r$—, wherein E is —O—, —C(O)—, phenylene, —$NR^{22}$— or —$S(O)_{0\text{-}2}$—, e is 0-5 and r is 0-5, provided that the sum of e and r is 1-6;

—$(C_2$-$C_6)$alkenylene-; and

—$(CH_2)_f$—V—$(CH_2)_g$—, wherein V is $C_3$-$C_6$ cycloalkylene, f is 1-5 and g is 0-5, provided that the sum of f and g is 1-6;

$R^{12}$ is:

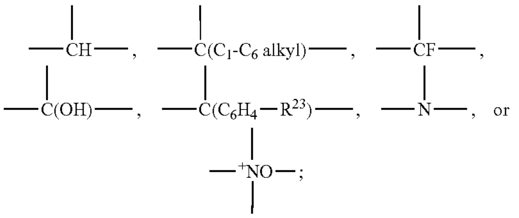

$R^{13}$ and $R^{14}$ are independently selected from the group consisting of —$CH_2$—, —CH($(C_1$-$C_6)$ alkyl)-, —C($(C_1$-$C_6)$ alkyl$)_2$, —CH=CH— and —C($(C_1$-$C_6)$ alkyl)=CH—; or $R^{12}$ together with an adjacent $R^{13}$, or $R^{12}$ together with an adjacent $R^{14}$, form a —CH=CH— or a —CH=C($C_1$-$C_6$ alkyl)- group;

a and b are independently 0, 1, 2 or 3, provided both are not zero;

provided that when $R^{13}$ is —CH=CH— or —C($C_1$-$C_6$ alkyl)=CH—, a is 1;

provided that when $R^{14}$ is —CH=CH— or —C($C_1$-$C_6$ alkyl)=CH—, b is 1;

provided that when a is 2 or 3, each $R^{13}$ can be the same or different; and provided that when b is 2 or 3, each $R^{14}$ can be the same or different;

and when Q is a bond, $R^1$ also can be:

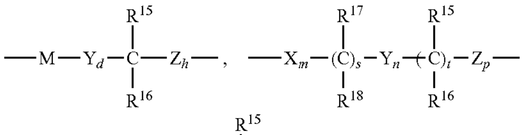

or

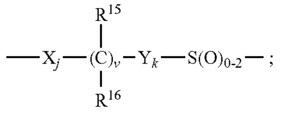

M is —O—, —S—, —S(O)— or —$S(O)_2$—;

X, Y and Z are independently selected from the group consisting of —$CH_2$—, —$CH(C_1$-$C_6)$alkyl- and —$C((C_1$-$C_6)$alkyl$)_2$;

$R^{10}$ and $R^{11}$ are independently selected from the group consisting of 1-3 substituents independently selected from the group consisting of $(C_1$-$C_6)$alkyl, —$OR^{19}$, —$OC(O)R^{19}$, —$OC(O)OR^{21}$, —$O(CH_2)_{1-5}OR^{19}$, —$OC(O)NR^{19}R^{20}$, —$NR^{19}R^{20}$, —$NR_{19}C(O)R^{20}$, —$NR^{19}C(O)OR^{21}$, —$NR^{19}C(O)NR^{20}R^{25}$, —$NR^{19}S(O)_2R^{21}C(O)OR^{19}$, —$C(O)NR^{19}R^{20}$, —$C(O)R^{19}$, —$S(O)_2NR^{19}R^{20}$, $S(O)_{0-2}R^{21}$, —$O(CH_2)_{1-10}$—$C(O)OR^{19}$, —$O(CH_2)_{1-10}C(O)NR^{19}R^{20}$, —$(C_1$-$C_6$ alkylene)-$C(O)OR^{19}$, —CH═CH—$C(O)OR^{19}$, —$CF_3$, —CN, —$NO_2$ and halogen;

$R^{15}$ and $R^{17}$ are independently selected from the group consisting of —$OR^{19}$, —$OC(O)R^{19}$, —$OC(O)OR^{21}$ and —$OC(O)NR^{19}R^{20}$;

$R^{16}$ and $R^{18}$ are independently selected from the group consisting of H, $(C_1$-$C_6)$alkyl and aryl; or $R^{15}$ and $R^{16}$ together are ═O, or $R^{17}$ and $R^{18}$ together are ═O;

d is 1, 2 or 3;

h is 0, 1, 2, 3 or 4;

s is 0 or 1; t is 0 or 1; m, n and p are independently 0-4;

provided that at least one of s and t is 1, and the sum of m, n, p, s and t is 1-6;

provided that when p is 0 and t is 1, the sum of m, s and n is 1-5; and provided that when p is 0 and s is 1, the sum of m, t and n is 1-5;

v is 0 or 1;

j and k are independently 1-5, provided that the sum of j, k and v is 1-5;

and when Q is a bond and $R^1$ is

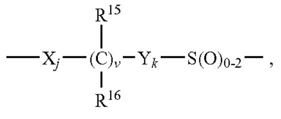

$Ar^1$ can also be pyridyl, isoxazolyl, furanyl, pyrrolyl, thienyl, imidazolyl, pyrazolyl, thiazolyl, pyrazinyl, pyrimidinyl or pyridazinyl;

$R^{19}$ and $R^{20}$ are independently selected from the group consisting of H, $(C_1$-$C_6)$alkyl, aryl and aryl-substituted $(C_1$-$C_6)$alkyl;

$R^{21}$ is $(C_1$-$C_6)$alkyl, aryl or $R^{24}$-substituted aryl;

$R^{22}$ is H, $(C_1$-$C_6)$alkyl, aryl $(C_1$-$C_6)$alkyl, —$C(O)R^{19}$ or —$C(O)OR^{19}$;

$R^{23}$ and $R^{24}$ are independently 1-3 groups independently selected from the group consisting of H, $(C_1$-$C_6)$alkyl, $(C_1$-$C_6)$alkoxy, —C(O)OH, $NO_2$, —$NR^{19}R^{20}$, —OH and halogeno; and $R^{25}$ is H, —OH or $(C_1$-$C_6)$alkoxy.

Methods for making compounds of Formula (IX) are well known to those skilled in the art. Non-limiting examples of suitable methods are disclosed in U.S. Pat. No. 5,756,470, which is incorporated herein by reference.

Substituted Azetidinones of Formula (X)

In another embodiment, substituted azetidinones useful in the compositions and methods of the present invention are represented by Formula (X) below:

(X)

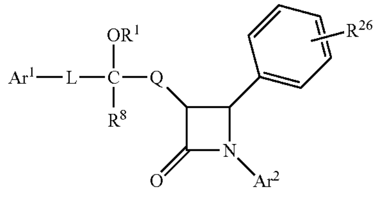

or a pharmaceutically acceptable salt, solvate, or ester thereof, wherein in Formula (X):

$R^1$ is selected from the group consisting of H, G, $G^1$, $G^2$, —$SO_3H$ and —$PO_3H$;

G is selected from the group consisting of: H,

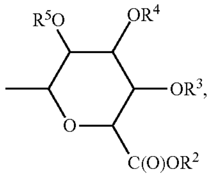

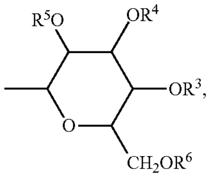

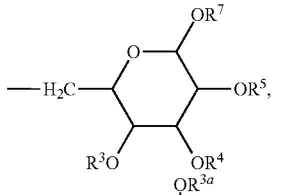

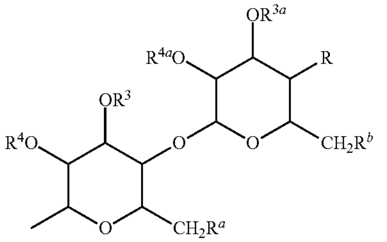

and

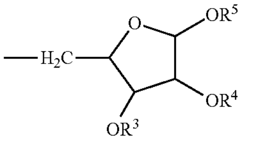

(Sugar Derivatives)

wherein R, $R^a$ and $R^b$ are each independently selected from the group consisting of H, —OH, halo, —$NH_2$, azido, $(C_1$-$C_6)$alkoxy$(C_1$-$C_6)$alkoxy or —W—$R^{30}$;

W is independently selected from the group consisting of —NH—C(O)—, —O—C(O)—, —O—C(O)—$N(R^{31})$—, —NH—C(O)—$N(R^{31})$— and —O—C(S)—$N(R^{31})$—;

$R^2$ and $R^6$ are each independently selected from the group consisting of H, $(C_1\text{-}C_6)$alkyl, acetyl, aryl and aryl$(C_1\text{-}C_6)$alkyl;

$R^3$, $R^4$, $R^5$, $R^7$, $R^{3a}$ and $R^{4a}$ are each independently selected from the group consisting of H, $(C_1\text{-}C_6)$alkyl, acetyl, aryl$(C_1\text{-}C_6)$alkyl, —$C(O)(C_1\text{-}C_6)$alkyl and —C(O)aryl;

$R^{30}$ is independently selected from the group consisting of $R^{32}$-substituted T, $R^{32}$-substituted-T-$(C_1\text{-}C_6)$alkyl, $R^{32}$-substituted-$(C_2\text{-}C_4)$alkenyl, $R^{32}$-substituted-$(C_1\text{-}C_6)$alkyl, $R^{32}$-substituted-$(C_3\text{-}C_7)$cycloalkyl and $R^{32}$-substituted-$(C_3\text{-}C_7)$cycloalkyl$(C_1\text{-}C_6)$alkyl;

$R^{31}$ is independently selected from the group consisting of H and $(C_1\text{-}C_4)$alkyl;

T is independently selected from the group consisting of phenyl, furyl, thienyl, pyrrolyl, oxazolyl, isoxazolyl, thiazolyl, isothiazolyl, benzothiazolyl, thiadiazolyl, pyrazolyl, imidazolyl and pyridyl;

$R^{32}$ is independently selected from 1-3 substituents which are each independently selected from the group consisting of H, halo, $(C_1\text{-}C_4)$alkyl, —OH, phenoxy, —$CF_3$, —$NO_2$, $(C_1\text{-}C_4)$alkoxy, methylenedioxy, oxo, $(C_1\text{-}C_4)$alkylsulfanyl, $(C_1\text{-}C_4)$alkylsulfinyl, $(C_1\text{-}C_4)$alkylsulfonyl, —$N(CH_3)_2$, —C(O)—$NH(C_1\text{-}C_4)$alkyl, —C(O)—$N(C_1\text{-}C_4\text{alkyl})_2$, —C(O)—$(C_1\text{-}C_4)$alkyl, —C(O)—$(C_1\text{-}C_4)$alkoxy and pyrrolidinylcarbonyl; or $R^{32}$ is a covalent bond and $R^{31}$, the nitrogen to which it is attached and $R^{32}$ form a pyrrolidinyl, piperidinyl, N-methylpiperazinyl, indolinyl or morpholinyl group, or a $(C_1\text{-}C_4)$alkoxycarbonyl-substituted pyrrolidinyl, piperidinyl, N-methylpiperazinyl, indolinyl or morpholinyl group;

$G^1$ is represented by the structure:

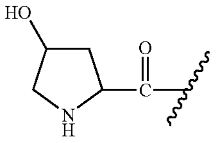,
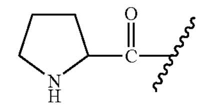
or
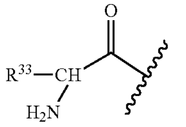

wherein $R^{33}$ is independently selected from the group consisting of unsubstituted alkyl $R^{34}$-substituted alkyl $(R^{35})(R^{36})$alkyl-,

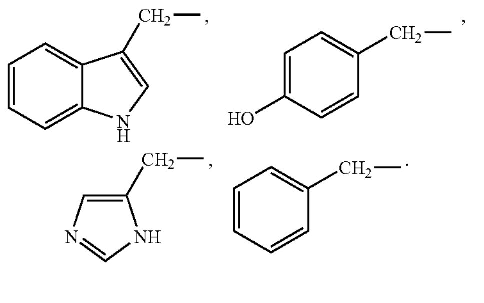

$R^{34}$ is one to three substituents, each $R^{34}$ being independently selected from the group consisting of HO(O)C—, HO—, HS—, $(CH_3)S$—, $H_2N$—, $(NH_2)(NH)C(NH)$—, $(NH_2)C(O)$— and $HO(O)CCH(NH_3^+)CH_2SS$—;

$R^{35}$ is independently selected from the group consisting of H and $NH_2$—;

$R^{36}$ is independently selected from the group consisting of H, unsubstituted alkyl, $R^{34}$-substituted alkyl, unsubstituted cycloalkyl and $R^{34}$-substituted cycloalkyl;

$G^2$ is represented by the structure:

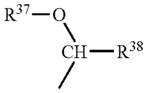

wherein $R^{37}$ and $R^{38}$ are each independently selected from the group consisting of $(C_1\text{-}C_6)$alkyl and aryl;

$R^{26}$ is one to five substituents, each $R^{26}$ being independently selected from the group consisting of:

a) H;
b) —OH;
c) —$OCH_3$;
d) fluorine;
e) chlorine;
f) —O-G;
g) —O-$G^1$;
h) —O-$G^2$;
i) —$SO_3H$; and
j) —$PO_3H$;

provided that when $R^1$ is H, $R^{26}$ is not H, —OH, —$OCH_3$ or —O-G;

$Ar^1$ is aryl, $R^{10}$-substituted aryl, heteroaryl or $R^{10}$-substituted heteroaryl;

$Ar^2$ is aryl, $R^{11}$-substituted aryl, heteroaryl or $R^{11}$-substituted heteroaryl;

L is selected from the group consisting of:

a) a covalent bond;
b) —$(CH_2)_q$—, wherein q is 1-6;
c) —$(CH_2)_e$-E-$(CH_2)_r$—, wherein E is —O—, —C(O)—, phenylene, —$NR^{22}$— or —$S(O)_{0\text{-}2}$—, e is 0-5 and r is 0-5, provided that the sum of e and r is 1-6;
d) —$(C_2\text{-}C_6)$alkenylene-;
e) —$(CH_2)_f$—V—$(CH_2)_g$—, wherein V is $C_3\text{-}C_6$cycloalkylene, f is 1-5 and g is 0-5, provided that the sum of f and g is 1-6; and
f)

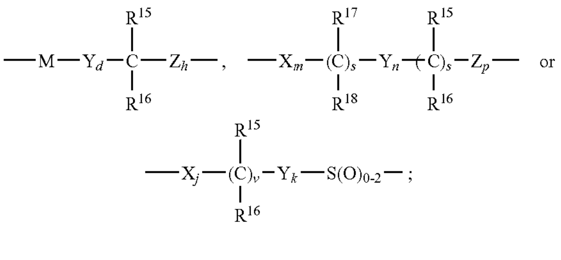

wherein M is —O—, —S—, —S(O)— or —$S(O)_2$—;

X, Y and Z are each independently selected from the group consisting of —$CH_2$—, —$CH(C_1\text{-}C_6)$alkyl- and —$C((C_1\text{-}C_6)\text{alkyl})_2$-;

$R^8$ is selected from the group consisting of H and alkyl;

$R^{10}$ and $R^{11}$ are each independently selected from the group consisting of 1-3 substituents which are each independently selected from the group consisting of $(C_1\text{-}C_6)$alkyl, —$OR^{19}$, —$OC(O)R^{19}$, —$OC(O)OR^2$, —$O(CH_2)_{1\text{-}5}OR^{19}$, —$OC(O)NR^{19}R^{20}$, —$NR^{19}R^{20}$, —$NR^{19}C(O)R^{20}$, —$NR^{19}C(O)OR^{21}$, —$NR^{19}C(O)NR^{20}R^{25}$, —$NR^{19}S(O)_2R^{21}$, —$C(O)OR^{19}$, —$C(O)NR^{19}R^{20}$, —$C(O)R^{19}$, —$S(O)_2NR^{19}R^{20}$, $S(O)_{0\text{-}2}$—$R^{21}$, —$O(CH_2)_{1\text{-}10}$—$C(O)OR^{19}$, —$O(CH_2)_{1\text{-}10}C$ (O)$NR^{19}R^{20}$, —($C_1$-$C_6$ alkylene)-C(O)$OR^{19}$, —CH═CH—C(O)$OR^{19}$, —$CF_3$, —CN, —$NO_2$ and halo;

$R^{15}$ and $R^{17}$ are each independently selected from the group consisting of —$OR^{19}$, —OC(O)$R^{19}$, —OC(O)$OR^{21}$, —OC(O)$NR^{19}R^{20}$;

$R^{16}$ and $R^{18}$ are each independently selected from the group consisting of H, ($C_1$-$C_6$)alkyl and aryl; or $R^{15}$ and $R^{16}$ together are ═O, or $R^{17}$ and $R^{18}$ together are ═O;

d is 1, 2 or 3;

h is 0, 1, 2, 3 or 4;

s is 0 or 1;

t is 0 or 1;

m, n and p are each independently selected from 0-4;

provided that at least one of s and t is 1, and the sum of m, n, p, s and t is 1-6; provided that when p is 0 and t is 1, the sum of m, n and p is 1-5; and provided that when p is 0 and s is 1, the sum of m, t and n is 1-5;

v is 0 or 1;

j and k are each independently 1-5, provided that the sum of j, k and v is 1-5;

Q is a bond, —$(CH_2)_q$—, wherein q is 1-6, or, with the 3-position ring carbon of the azetidinone, forms the spiro group

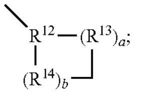

wherein $R^{12}$ is

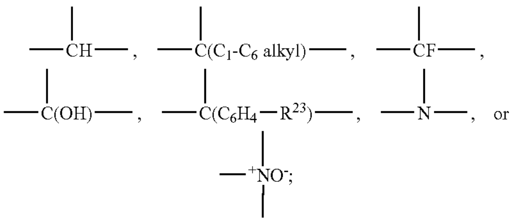

$R^{13}$ and $R^{14}$ are each independently selected from the group consisting of —$CH_2$—, —CH($C_1$-$C_6$ alkyl)-, —C(($C_1$-$C_6$) alkyl)$_2$, —CH═CH— and —C($C_1$-$C_6$ alkyl)═CH—; or $R^{12}$ together with an adjacent $R^{13}$, or $R^{12}$ together with an adjacent $R^{14}$, form a —CH═CH— or a —CH═C($C_1$-$C_6$ alkyl)- group;

a and b are each independently 0, 1, 2 or 3, provided both are not zero; provided that when $R^{13}$ is —CH═CH— or —C($C_1$-$C_6$ alkyl)═CH—, a is 1; provided that when $R^{14}$ is —CH═CH— or —C($C_1$-$C_6$ alkyl)═CH—, b is 1; provided that when a is 2 or 3, each $R^{13}$ can be the same or different; and provided that when b is 2 or 3, each $R^{14}$ can be the same or different;

and when Q is a bond and L is

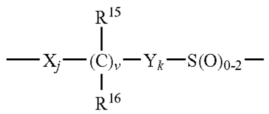

then $Ar^1$ can also be pyridyl, isoxazolyl, furanyl, pyrrolyl, thienyl, imidazolyl, pyrazolyl, thiazolyl, pyrazinyl, pyrimidinyl or pyridazinyl;

$R^{19}$ and $R^{20}$ are each independently selected from the group consisting of H, ($C_1$-$C_6$)alkyl, aryl and aryl-substituted ($C_1$-$C_6$)alkyl;

$R^{21}$ is ($C_1$-$C_6$)alkyl, aryl or $R^{24}$-substituted aryl;

$R^{22}$ is H, ($C_1$-$C_6$)alkyl, aryl ($C_1$-$C_6$)alkyl, —C(O)$R^{19}$ or —C(O)$OR^{19}$;

$R^{23}$ and $R^{24}$ are each independently selected from the group consisting of 1-3 substituents which are each independently selected from the group consisting of H, ($C_1$-$C_6$)alkyl, ($C_1$-$C_6$)alkoxy, —C(O)OH, $NO_2$, —$NR^{19}R^{20}$, —OH and halo; and $R^{25}$ is H, —OH or ($C_1$-$C_6$)alkoxy.

Examples of compounds of Formula (X) which are useful in the methods and combinations of the present invention and methods for making such compounds are disclosed in U.S. patent application Ser. No. 10/166,942, filed Jun. 11, 2002, incorporated herein by reference. Substituted Azetidinones of Formulae (XI)-(XIII)

An example of a useful substituted azetidinone is one represented by the Formula (XI):

(XI)

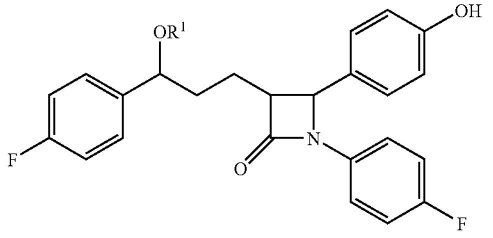

wherein $R^1$ is defined as above.

A more preferred compound is one represented by Formula (XII):

(XII)

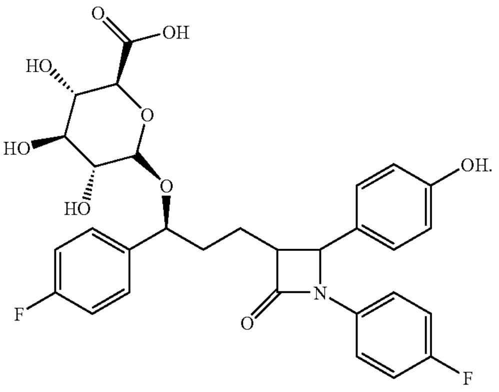

Another useful compound is represented by Formula (XIII):

(XIII)

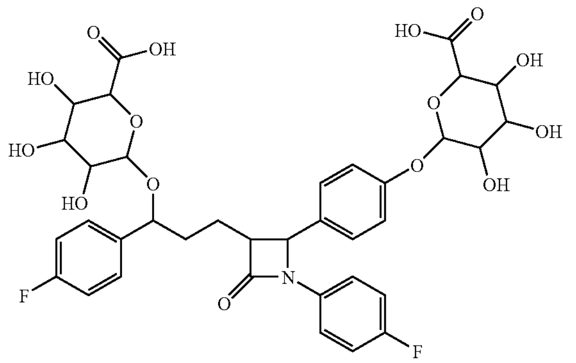

Other useful substituted azetidinone compounds include N-sulfonyl-2-azetidinones such as are disclosed in U.S. Pat. No. 4,983,597, ethyl 4-(2-oxoazetidin-4-yl)phenoxy-alkanoates such as are disclosed in Ram et al., Indian J. Chem. Sect. B. 29B, 12 (1990), p. 1134-7, diphenyl azetidinones and derivatives disclosed in U.S. Patent Publication Nos. 2002/0039774, 2002/0128252, 2002/0128253 and 2002/0137689, 2004/063929, WO 2002/066464, U.S. Pat. Nos. 6,498,156 and 6,703,386, each of which is incorporated by reference herein.

Other sterol absorption inhibitors useful in the compositions, therapeutic combinations and methods of the present invention are described in WO 2004/005247, WO 2004/000803, WO 2004/000804, WO 2004/000805, WO 0250027, U.S. published application 2002/0137689, and the compounds described in L. Kværnø et al., Angew. Chem. Int. Ed., 2004, vol. 43, pp. 4653-4656, all of which are incorporated herein by reference. An illustrative compound of Kværnø et al. is:

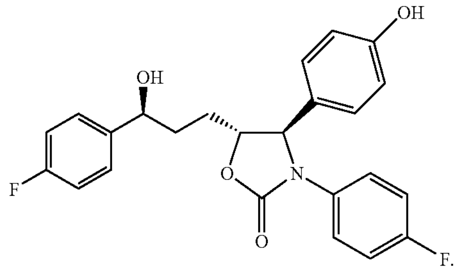

The compounds of Formulae II-XIII can be prepared by known methods, including the methods discussed above and, for example, in WO 93/02048, U.S. Pat. Nos. 5,306,817 and 5,561,227, herein incorporated by reference, which describe the preparation of compounds wherein —$R^1$-Q- is alkylene, alkenylene or alkylene interrupted by a hetero atom, phenylene or cycloalkylene; WO 94/17038 and U.S. Pat. No. 5,698,548, herein incorporated by reference, describe the preparation of compounds wherein Q is a spirocyclic group; WO 95/08532, U.S. Pat. No. 5,631,365, U.S. Pat. No. 5,767,115, U.S. Pat. No. 5,846,966, and U.S. Pat. No. R.E. 37,721, herein incorporated by reference, describe the preparation of compounds wherein —$R^1$-Q- is a hydroxy-substituted alkylene group; PCT/US95/03196, herein incorporated by reference, describes compounds wherein —$R^1$-Q- is a hydroxy-substituted alkylene attached to the $Ar^1$ moiety through an —O— or $S(O)_{0-2}$— group; and U.S. Ser. No. 08/463,619, filed Jun. 5, 1995, herein incorporated by reference, describes the preparation of compounds wherein —$R^1$-Q- is a hydroxy-substituted alkylene group attached to the azetidinone ring by a —$S(O)_{0-2}$— group. Each of the above patents or publications are herein incorporated by reference in their entirety.

The daily dose of the sterol absorption inhibitor(s) administered to the subject can range from about 0.1 to about 1000 mg per day, preferably about 0.25 to about 50 mg/day, and more preferably about 10 mg per day, given in a single dose or 2-4 divided doses. The exact dose, however, is determined by the attending clinician and is dependent on the potency of the compound administered, the age, weight, condition and response of the patient.

For administration of pharmaceutically acceptable salts of the above compounds, the weights indicated above refer to the weight of the acid equivalent or the base equivalent of the therapeutic compound derived from the salt.

In another embodiment of the present invention, the compositions or therapeutic combinations described above comprise one or more selective $CB_1$ receptor antagonist compounds of Formula (I) in combination with one or more cholesterol biosynthesis inhibitors and/or lipid-lowering compounds discussed below.

Generally, a total daily dosage of cholesterol biosynthesis inhibitor(s) can range from about 0.1 to about 160 mg per day, and preferably about 0.2 to about 80 mg/day in single or 2-3 divided doses.

In another alternative embodiment, the compositions, therapeutic combinations or methods of the present invention can comprise at least one compound of Formula (I), or pharmaceutically acceptable salts, solvates, or esters thereof, and one or more bile acid sequestrants (insoluble anion exchange resins), co-administered with or in combination with the compound of Formula (I), or a pharmaceutically acceptable salt, solvate, or ester thereof, and a substituted azetidinone or a substituted β-lactam discussed above.

Bile acid sequestrants bind bile acids in the intestine, interrupting the enterohepatic circulation of bile acids and causing an increase in the faecal excretion of steroids. Use of bile acid sequestrants is desirable because of their non-systemic mode of action. Bile acid sequestrants can lower intrahepatic cholesterol and promote the synthesis of apo B/E (LDL) receptors that bind LDL from plasma to further reduce cholesterol levels in the blood.

Generally, a total daily dosage of bile acid sequestrant(s) can range from about 1 to about 50 grams per day, and preferably about 2 to about 16 grams per day in single or 2-4 divided doses.

In an alternative embodiment, the compositions or treatments of the present invention can comprise at least one compound of Formula (I), or pharmaceutically acceptable salts, solvates, or esters thereof, and one or more IBAT inhibitors. The IBAT inhibitors can inhibit bile acid transport to reduce LDL cholesterol levels. Generally, a total daily dosage of IBAT inhibitor(s) can range from about 0.01 to about 1000 mg/day, and preferably about 0.1 to about 50 mg/day in single or 2-4 divided doses.

In another alternative embodiment, the compositions or treatments of the present invention can comprise at least one compound of Formula (I), or pharmaceutically acceptable salts, solvates, or esters thereof, and nicotinic acid (niacin) and/or derivatives thereof. Nicotinic acid and its derivatives inhibit hepatic production of VLDL and its metabolite LDL and increases HDL and apo A-1 levels. An example of a suitable nicotinic acid product is NIASPAN® (niacin extended-release tablets) which are available from Kos.

Generally, a total daily dosage of nicotinic acid or a derivative thereof can range from about 500 to about 10,000 mg/day, preferably about 1000 to about 8000 mg/day, and more preferably about 3000 to about 6000 mg/day in single or divided doses.

In another alternative embodiment, the compositions or treatments of the present invention can comprise at least one compound of Formula (I), or pharmaceutically acceptable salts, solvates, or estes thereof, and one or more AcylCoA: Cholesterol O-acyltransferase ("ACAT") Inhibitors, which can reduce LDL and VLDL levels. ACAT is an enzyme responsible for esterifying excess intracellular cholesterol and may reduce the synthesis of VLDL, which is a product of cholesterol esterification, and overproduction of apo B-100-containing lipoproteins. Generally, a total daily dosage of ACAT inhibitor(s) can range from about 0.1 to about 1000 mg/day in single or 2-4 divided doses.

In another alternative embodiment, the compositions or treatments of the present invention can comprise at least one compound of Formula (I), or pharmaceutically acceptable salts, solvates, or esters thereof, and one or more Cholesteryl Ester Transfer Protein ("CETP") Inhibitors. CETP is responsible for the exchange or transfer of cholesteryl ester carrying HDL and triglycerides in VLDL. Pancreatic cholesteryl ester hydrolase (pCEH) inhibitors such as WAY-121898 also can be co-administered with or in combination.

Generally, a total daily dosage of CETP inhibitor(s) can range from about 0.01 to about 1000 mg/day, and preferably about 0.5 to about 20 mg/kg body weight/day in single or divided doses.

In another alternative embodiment, the compositions or treatments of the present invention can comprise at least one compound of Formula (I), or pharmaceutically acceptable salts, solvates, or esters thereof, and probucol or derivatives thereof, which can reduce LDL levels.

Generally, a total daily dosage of probucol or derivatives thereof can range from about 10 to about 2000 mg/day, and preferably about 500 to about 1500 mg/day in single or 2-4 divided doses.

In another alternative embodiment, the compositions or treatments of the present invention can comprise at least one compound of Formula (I), or pharmaceutically acceptable salts, solvates, or esters thereof, and low-density lipoprotein (LDL) receptor activators.

Generally, a total daily dosage of LDL receptor activator(s) can range from about 1 to about 1000 mg/day in single or 2-4 divided doses.

In another alternative embodiment, the compositions or treatments of the present invention can comprise at least one compound of Formula (I), or pharmaceutically acceptable salts, solvates, or esters thereof, and fish oil. Generally, a total daily dosage of fish oil or Omega 3 fatty acids can range from about 1 to about 30 grams per day in single or 2-4 divided doses.

In another alternative embodiment, the compositions or treatments of the present invention can further comprise at least one compound of Formula (I), or pharmaceutically acceptable salts, solvates, or esters thereof, and natural water soluble fibers, such as psyllium, guar, oat and pectin, which can reduce cholesterol levels. Generally, a total daily dosage of natural water soluble fibers can range from about 0.1 to about 10 grams per day in single or 2-4 divided doses.

In another alternative embodiment, the compositions or treatments of the present invention can comprise at least one compound of Formula (I), or pharmaceutically acceptable salts, solvates, or esters thereof, and plant sterols, plant stanols and/or fatty acid esters of plant stanols, such as sitostanol ester used in BENECOL® margarine, which can reduce cholesterol levels. Generally, a total daily dosage of plant sterols, plant stanols and/or fatty acid esters of plant stanols can range from about 0.5 to about 20 grams per day in single or 2-4 divided doses.

In another alternative embodiment, the compositions or treatments of the present invention can comprise at least one compound of Formula (I), or pharmaceutically acceptable salts, solvates, or esters thereof, and antioxidants, such as probucol, tocopherol, ascorbic acid, β-carotene and selenium, or vitamins such as vitamin $B_6$ or vitamin $B_{12}$. Generally, a total daily dosage of antioxidants or vitamins can range from about 0.05 to about 10 grams per day in single or 2-4 divided doses.

In another alternative embodiment, the compositions or treatments of the present invention can comprise at least one compound of Formula (I), or pharmaceutically acceptable salts, solvates, or esters thereof, and monocyte and macrophage inhibitors such as polyunsaturated fatty acids (PUFA), thyroid hormones including throxine analogues such as CGS-26214 (a thyroxine compound with a fluorinated ring), gene therapy and use of recombinant proteins such as recombinant apo E. Generally, a total daily dosage of these agents can range from about 0.01 to about 1000 mg/day in single or 2-4 divided doses.

Also useful with the present invention are compositions or therapeutic combinations that further comprise hormone replacement agents and compositions. Useful hormone agents and compositions for hormone replacement therapy of the present invention include androgens, estrogens, progestins, their pharmaceutically acceptable salts and derivatives thereof. Combinations of these agents and compositions are also useful.

The dosage of androgen and estrogen combinations vary, desirably from about 1 mg to about 4 mg androgen and from about 1 mg to about 3 mg estrogen. Examples include, but are not limited to, androgen and estrogen combinations such as the combination of esterified estrogens (sodium estrone sulfate and sodium equilin sulfate) and methyltestosterone (17-hydroxy-17-methyl-, (17B)-androst-4-en-3-one) available from Solvay Pharmaceuticals, Inc., Marietta, Ga., under the tradename Estratest.

Estrogens and estrogen combinations may vary in dosage from about 0.01 mg up to 8 mg, desirably from about 0.3 mg to about 3.0 mg. Examples of useful estrogens and estrogen combinations include:

(a) the blend of nine (9) synthetic estrogenic substances including sodium estrone sulfate, sodium equilin sulfate, sodium 17α-dihydroequilin sulfate, sodium 17α-estradiol sulfate, sodium 17β-dihydroequilin sulfate, sodium 17α-dihydroequilenin sulfate, sodium 17β-dihydroequilenin sulfate, sodium equilenin sulfate and sodium 17β-estradiol sulfate; available from Duramed Pharmaceuticals, Inc., Cincinnati, Ohio, under the tradename Cenestin;

(b) ethinyl estradiol (19-nor-17α-pregna-1,3,5(10)-trien-20-yne-3,17-diol; available by Schering Plough Corporation, Kenilworth, N.J., under the tradename Estinyl;

(c) esterified estrogen combinations such as sodium estrone sulfate and sodium equilin sulfate; available from Solvay under the tradename Estratab and from Monarch Pharmaceuticals, Bristol, Tenn., under the tradename Menest;

(d) estropipate (piperazine estra-1,3,5(10)-trien-17-one, 3-(sulfooxy)-estrone sulfate); available from Pharmacia & Upjohn, Peapack, N.J., under the tradename Ogen and from Women First Health Care, Inc., San Diego, Calif., under the tradename Ortho-Est; and (e) conjugated estrogens (17α-dihydroequilin, 17α-estradiol, and 17β-dihydroequilin); available from Wyeth-Ayerst Pharmaceuticals, Philadelphia, Pa., under the tradename Premarin.

Progestins and estrogens may also be administered with a variety of dosages, generally from about 0.05 to about 2.0 mg progestin and about 0.001 mg to about 2 mg estrogen, desirably from about 0.1 mg to about 1 mg progestin and about 0.01 mg to about 0.5 mg estrogen. Examples of progestin and estrogen combinations that may vary in dosage and regimen include:

(a) the combination of estradiol (estra-1,3,5(10)-triene-3, 17β-diol hemihydrate) and norethindrone (17β-acetoxy-19-nor-17α-pregn-4-en-20-yn-3-one); which is available from Pharmacia & Upjohn, Peapack, N.J., under the tradename Activella;

(b) the combination of levonorgestrel (d(−)-13β-ethyl-17α-ethinyl-17β-hydroxygon-4-en-3-one) and ethinyl estradial; available from Wyeth-Ayerst under the tradename Alesse, from Watson Laboratories, Inc., Corona, Calif., under the tradenames Levora and Trivora, Monarch Pharmaceuticals, under the tradename Nordette, and from Wyeth-Ayerst under the tradename Triphasil;

(c) the combination of ethynodiol diacetate (19-nor-17α-pregn-4-en-20-yne-3β,17-diol diacetate) and ethinyl estradiol; available from G.D. Searle & Co., Chicago, Ill., under the tradename Demulen and from Watson under the tradename Zovia;

(d) the combination of desogestrel (13-ethyl-11-methylene-18,19-dinor-17α-pregn-4-en-20-yn-17-ol) and ethinyl estradiol; available from Organon under the tradenames Desogen and Mircette, and from Ortho-McNeil Pharmaceutical, Raritan, N.J., under the tradename Ortho-Cept;

(e) the combination of norethindrone and ethinyl estradiol; available from Parke-Davis, Morris Plains, N.J., under the tradenames Estrostep and FemHRT, from Watson under the tradenames Microgestin, Necon, and Tri-Norinyl, from Ortho-McNeil under the tradenames Modicon and Ortho-Novum, and from Warner Chilcott Laboratories, Rockaway, N.J., under the tradename Ovcon;

(f) the combination of norgestrel ((±)-13-ethyl-17-hydroxy-18,19-dinor-17α-preg-4-en-20-yn-3-one) and ethinyl estradiol; available from Wyeth-Ayerst under the tradenames Ovral and Lo/Ovral, and from Watson under the tradenames Ogestrel and Low-Ogestrel;

(g) the combination of norethindrone, ethinyl estradiol, and mestranol (3-methoxy-19-nor-17α-pregna-1,3,5(10)-trien-20-yn-17-ol); available from Watson under the tradenames Brevicon and Norinyl;

(h) the combination of 17β-estradiol (estra-1,3,5(10)-triene-3,17β-diol) and micronized norgestimate (17α-17-(Acetyloxyl)-1,3-ethyl-18,19-dinorpregn-4-en-20-yn-3-one3-oxime); available from Ortho-McNeil under the tradename Ortho-Prefest;

(i) the combination of norgestimate (18,19-dinor-17-pregn-4-en-20-yn-3-one, 17-(acetyloxy)-13-ethyl-, oxime, (17(α)-(+)-) and ethinyl estradiol; available from Ortho-McNeil under the tradenames Ortho Cyclen and Ortho Tri-Cyclen; and (j) the combination of conjugated estrogens (sodium estrone sulfate and sodium equilin sulfate) and medroxyprogesterone acetate (20-dione, 17-(acetyloxy)-6-methyl-, (6(α))-pregn-4-ene-3); available from Wyeth-Ayerst under the tradenames Premphase and Prempro.

In general, a dosage of progestins may vary from about 0.05 mg to about 10 mg or up to about 200 mg if microsized progesterone is administered. Examples of progestins include norethindrone; available from ESI Lederle, Inc., Philadelphia, Pa., under the tradename Aygestin, from Ortho-McNeil under the tradename Micronor, and from Watson under the tradename Nor-QD; norgestrel; available from Wyeth-Ayerst under the tradename Ovrette; micronized progesterone (pregn-4-ene-3,20-dione); available from Solvay under the tradename Prometrium; and medroxyprogesterone acetate; available from Pharmacia & Upjohn under the tradename Provera.

In another alternative embodiment, the compositions, therapeutic combinations or methods of the present invention can comprise at least one compound of Formula (I), or pharmaceutically acceptable salts, solvates, or esters thereof, and one or more obesity control medications. Useful obesity control medications include, but are not limited to, drugs that reduce energy intake or suppress appetite, drugs that increase energy expenditure and nutrient-partitioning agents. Suitable obesity control medications include, but are not limited to, noradrenergic agents (such as diethylpropion, mazindol, phenylpropanolamine, phentermine, phendimetrazine, phendamine tartrate, methamphetamine, phendimetrazine and tartrate); serotonergic agents (such as sibutramine, fenfluramine, dexfenfluramine, fluoxetine, fluvoxamine and paroxtine); thermogenic agents (such as ephedrine, caffeine, theophylline, and selective β3-adrenergic agonists); alpha-blocking agents; kainite or AMPA receptor antagonists; leptin-lipolysis stimulated receptors; phosphodiesterase enzyme inhibitors; compounds having nucleotide sequences of the mahogany gene; fibroblast growth factor-10 polypeptides; monoamine oxidase inhibitors (such as befloxatone, moclobemide, brofaromine, phenoxathine, esuprone, befol, toloxatone, pirlindol, amiflamine, sercloremine, bazinaprine, lazabemide, milacemide and caroxazone); compounds for increasing lipid metabolism (such as evodiamine compounds); and lipase inhibitors (such as orlistat). Generally, a total dosage of the above-described obesity control medications can range from 1 to 3,000 mg/day, desirably from about 1 to 1,000 mg/day and more desirably from about 1 to 200 mg/day in single or 2-4 divided doses.

The compositions, therapeutic combinations or methods of the present invention can comprise at least one compound of Formula (I), or pharmaceutically acceptable salts, solvates, or esters thereof, and one or more blood modifiers which are chemically different from the substituted azetidinone and substituted β-lactam compounds (such as compounds II-XIII above) and the lipid modulating agents discussed above, for example, they contain one or more different atoms, have a different arrangement of atoms or a different number of one or more atoms than the sterol absorption inhibitor(s) or lipid modulating agents discussed above. Useful blood modifiers include but are not limited to anti-coagulants (argatroban, bivalirudin, dalteparin sodium, desirudin, dicumarol, lyapolate sodium, nafamostat mesylate, phenprocoumon, tinzaparin sodium, warfarin sodium); antithrombotic (anagrelide hydrochloride, bivalirudin, cilostazol, dalteparin sodium, danaparoid sodium, dazoxiben hydrochloride, efegatran sulfate, enoxaparin sodium, fluretofen, ifetroban, ifetroban sodium, lamifiban, lotrafiban hydrochloride, napsagatran, orbofiban acetate, roxifiban acetate, sibrafiban, tinzaparin sodium, trifenagrel, abciximab, zolimomab aritox); fibrinogen receptor antagonists (roxifiban acetate, fradafiban, orbofiban, lotrafiban hydrochloride, tirofiban, xemilofiban, monoclonal antibody 7E3, sibrafiban); platelet inhibitors (cilostazol, clopidogrel bisulfate, epoprostenol, epoprostenol sodium, ticlopidine hydrochloride, aspirin, ibuprofen, naproxen, sulindae, idomethacin, mefenamate, droxicam, diclofenac, sulfinpyrazone, piroxicam, dipyridamole); platelet aggregation inhibitors (acadesine, beraprost, beraprost sodium, ciprostene calcium, itazigrel, lifarizine, lotrafiban hydrochloride, orbofiban acetate, oxagrelate, fradafiban, orbofiban, tirofiban, xemilofiban); hemorrheologic agents (pentoxifylline); lipoprotein associated coagulation inhibitors; Factor VIIa inhibitors (4H-31-benzoxazin-4-ones, 4H-3,1-benzoxazin-4-thiones, quinazolin-4-ones, quinazolin-4-thiones, benzothiazin-4-ones, imidazolyl-boronic acid-derived peptide analogues TFPI-derived peptides, naphthalene-2-sulfonic acid {1-[3-(aminoiminomethyl)-benzyl]-2-oxo-pyrrolidin-3-(S)-yl} amide trifluoroacetate, dibenzofuran-2-sulfonic acid {1-[3-(aminomethyl)-benzyl]-5-oxo-pyrrolidin-3-yl}-amide, tolulene-4-sulfonic acid {1-[3-(aminoiminomethyl)-benzyl]-2-oxo-pyrrolidin-3-(S)-yl}-amide trifluoroacetate, 3,4-dihydro-1H-isoquinoline-2-sulfonic acid {1-[3-(aminoiminomethyl)-benzyl]-2-oxo-pyrrolin-3-(S)-yl}-amide trifluoroacetate); Factor Xa inhibitors (disubstituted pyrazolines, disubstituted triazolines, substituted n-[(aminoiminomethyl)phenyl] propylamides, substituted n-[(aminomethyl)phenyl] propylamides, tissue factor pathway inhibitor (TFPI), low molecular weight heparins, heparinoids, benzimidazolines, benzoxazolinones, benzopiperazinones, indanones, dibasic (amidinoaryl) propanoic acid derivatives, amidinophenyl-pyrrolidines, amidinophenyl-pyrrolines, amidinophenyl-isoxazolidines, amidinoindoles, amidinoazoles, bis-arlysulfonylaminobenzamide derivatives, peptidic Factor Xa inhibitors).

The compositions, therapeutic combinations or methods of the present invention can comprise at least one compound of Formula (I), or pharmaceutically acceptable salts, solvates, or esters thereof, and one or more cardiovascular agents which are chemically different from the substituted azetidinone and substituted β-lactam compounds (such as compounds II-XIII above) and the lipid modulating agents discussed above, for example, they contain one or more different atoms, have a different arrangement of atoms or a different number of one or more atoms than the sterol absorption inhibitor(s) or PPAR receptor activators discussed above. Useful cardiovascular agents include but are not limited to calcium channel blockers (clentiazem maleate, amlodipine besylate, isradipine, nimodipine, felodipine, nilvadipine, nifedipine, teludipine hydrochloride, diltiazem hydrochloride, belfosdil, verapamil hydrochloride, fostedil); adrenergic blockers (fenspiride hydrochloride, labetalol hydrochloride, proroxan, alfuzosin hydrochloride, acebutolol, acebutolol hydrochloride, alprenolol hydrochloride, atenolol, bunolol hydrochloride, carteolol hydrochloride, celiprolol hydrochloride, cetamolol hydrochloride, cicloprolol hydrochloride, dexpropranolol hydrochloride, diacetolol hydrochloride, dilevalol hydrochloride, esmolol hydrochloride, exaprolol hydrochloride, flestolol sulfate, labetalol hydrochloride, levobetaxolol hydrochloride, levobunolol hydrochloride, metalol hydrochloride, metoprolol, metoprolol tartrate, nadolol, pamatolol sulfate, penbutolol sulfate, practolol, propranolol hydrochloride, sotalol hydrochloride, timolol, timolol maleate, tiprenolol hydrochloride, tolamolol, bisoprolol, bisoprolol fumarate, nebivolol); adrenergic stimulants; angiotensin converting enzyme (ACE) inhibitors (benazepril hydrochloride, benazeprilat, captopril, delapril hydrochloride, fosinopril sodium, libenzapril, moexipril hydrochloride, pentopril, perindopril, quinapril hydrochloride, quinaprilat, ramipril, spirapril hydrochloride, spiraprilat, teprotide, enalapril maleate, lisinopril, zofenopril calcium, perindopril erbumine); antihypertensive agents (althiazide, benzthiazide, captopril, carvedilol, chlorothiazide sodium, clonidine hydrochloride, cyclothiazide, delapril hydrochloride, dilevalol hydrochloride, doxazosin mesylate, fosinopril sodium, guanfacine hydrochloride, methyldopa, metoprolol succinate, moexipril hydrochloride, monatepil maleate, pelanserin hydrochloride, phenoxybenzamine hydrochloride, prazosin hydrochloride, primidolol, quinapril hydrochloride, quinaprilat, ramipril, terazosin hydrochloride, candesartan, candesartan cilexetil, telmisartan, amlodipine besylate, amlodipine maleate, bevantolol hydrochloride); angiotensin II receptor antagonists (candesartan, irbesartan, losartan potassium, candesartan cilexetil, telmisartan); anti-anginal agents (amlodipine besylate, amlodipine maleate, betaxolol hydrochloride, bevantolol hydrochloride, butoprozine hydrochloride, carvedilol, cinepazet maleate, metoprolol succinate, molsidomine, monatepil maleate, primidolol, ranolazine hydrochloride, tosifen, verapamil hydrochloride); coronary vasodilators (fostedil, azaclorzine hydrochloride, chromonar hydrochloride, clonitrate, diltiazem hydrochloride, dipyridamole, droprenilamine, erythrityl tetranitrate, isosorbide dinitrate, isosorbide mononitrate, lidoflazine, mioflazine hydrochloride, mixidine, molsidomine, nicorandil, nifedipine, nisoldipine, nitroglycerine, oxprenolol hydrochloride, pentrinitrol, perhexyline maleate, prenylamine, propatyl nitrate, terodiline hydrochloride, tolamolol, verapamil); diuretics (the combination product of hydrochlorothiazide and spironolactone and the combination product of hydrochlorothiazide and triamterene).

The compositions, therapeutic combinations or methods of the present invention can comprise at least one compound of Formula (I), or pharmaceutically acceptable salts, solvates, or esters thereof, and one or more antidiabetic medications for reducing blood glucose levels in a human. Useful antidiabetic medications include, but are not limited to, drugs that reduce energy intake or suppress appetite, drugs that increase energy expenditure and nutrient-partitioning agents. Suitable antidiabetic medications include, but are not limited to, sulfonylurea (such as acetohexamide, chlorpropamide, gliamilide, gliclazide, glimepiride, glipizide, glyburide, glibenclamide, tolazamide, and tolbutamide), meglitinide (such as repaglinide and nateglinide), biguanide (such as metformin and buformin), alpha-glucosidase inhibitor (such as acarbose, miglitol, camiglibose, and voglibose), certain peptides (such as amlintide, pramlintide, exendin, and GLP-1 agonistic peptides), and orally administrable insulin or insulin composition for intestinal delivery thereof. Generally, a total dosage of the above-described antidiabetic medications can range from 0.1 to 1,000 mg/day in single or 2-4 divided doses.

Mixtures of two, three, four or more of any of the pharmacological or therapeutic agents described above can be used in the compositions and therapeutic combinations of the present invention.

Since the present invention relates to treating conditions as discussed above, by treatment with a combination of active ingredients wherein the active ingredients may be administered separately, the invention also relates to combining separate pharmaceutical compositions in kit form. That is, a kit is contemplated wherein two separate units are combined: a pharmaceutical composition comprising at least one selective $CB_1$ receptor antagonist of Formula (I), or a pharmaceutically acceptable salt, solvate, or ester thereof, and a separate pharmaceutical composition comprising at least one cholesterol lowering compound as described above. The kit will preferably include directions for the administration of the separate components. The kit form is particularly advantageous when the separate components must be administered in different dosage forms (e.g., oral and parenteral) or are administered at different dosage intervals.

In yet another embodiment, the present invention provides a method of treating, reducing, or ameliorating a disease or condition selected from the group consisting of metabolic syndrome, obesity, waist circumference, lipid profile, insulin sensitivity, neuroinflammatory disorders, cognitive disorders, psychosis, addictive behavior, gastrointestinal disorders, vascular conditions, hyperlipidaemia, atherosclerosis, hypercholesterolemia, sitosterolemia, vascular inflammation, stroke, diabetes, and cardiovascular conditions, and/or reduce the level of sterol(s) in a patient in need thereof, comprising administering to said patient an effective amount of at least one compound of Formula (I), or a pharmaceutically acceptable salt, solvate, or ester thereof, and one or more cholesterol lowering compound.

The treatment compositions and therapeutic combinations comprising at least one compound of Formula (I) and at least one cholesterol lowering agent can inhibit the intestinal absorption of cholesterol in mammals can be useful in the treatment and/or prevention of conditions, for example vascular conditions, such as atherosclerosis, hypercholesterolemia and sitosterolemia, stroke, obesity and lowering of plasma levels of cholesterol in mammals, in particular in mammals.

In another embodiment of the present invention, the compositions and therapeutic combinations of the present invention can inhibit sterol or 5α-stanol absorption or reduce plasma concentration of at least one sterol selected from the group consisting of phytosterols (such as sitosterol, campesterol, stigmasterol and avenosterol) and/or 5α-stanol (such as cholestanol, 5α-campestanol, 5α-sitostanol), cholesterol and mixtures thereof. The plasma concentration can be reduced by administering to a mammal in need of such treatment an effective amount of at least one treatment composition or therapeutic combination comprising at least one selective $CB_1$ receptor antagonist and at least one cholesterol lowering compound, for example a sterol absorption inhibitor described above. The reduction in plasma concentration of sterols or 50α-stanols can range from about 1 to about 70 percent, and preferably about 10 to about 50 percent. Methods of measuring serum total blood cholesterol and total LDL cholesterol are well known to those skilled in the art and for example include those disclosed in PCT WO 99/38498 at page 11, incorporated by reference herein. Methods of determining levels of other sterols in serum are disclosed in H. Gylling et al., "Serum Sterols During Stanol Ester Feeding in a Mildly Hypercholesterolemic Population", J. Lipid Res. 40: 593-600 (1999), incorporated by reference herein.

The treatments of the present invention can also reduce the size or presence of plaque deposits in vascular vessels. The plaque volume can be measured using (IVUS), in which a tiny ultrasound probe is inserted into an artery to directly image and measure the size of atherosclerotic plaques, in a manner well know to those skilled in the art.

EXAMPLES

Preparation of Examples 1, 2, 4, 6, 7, 9, 19, and 10

Scheme 1

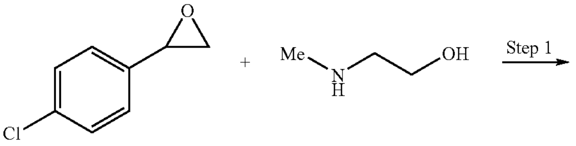

i

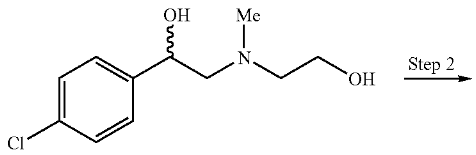

ii

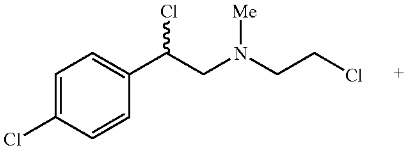

iii

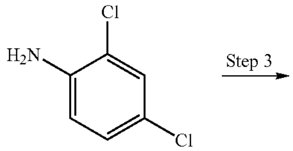

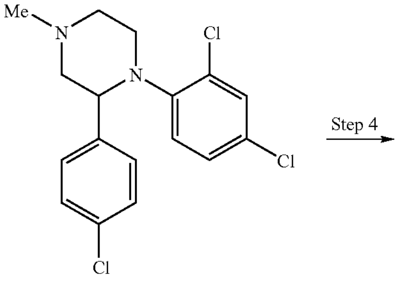

Ex. 2

Scheme 2

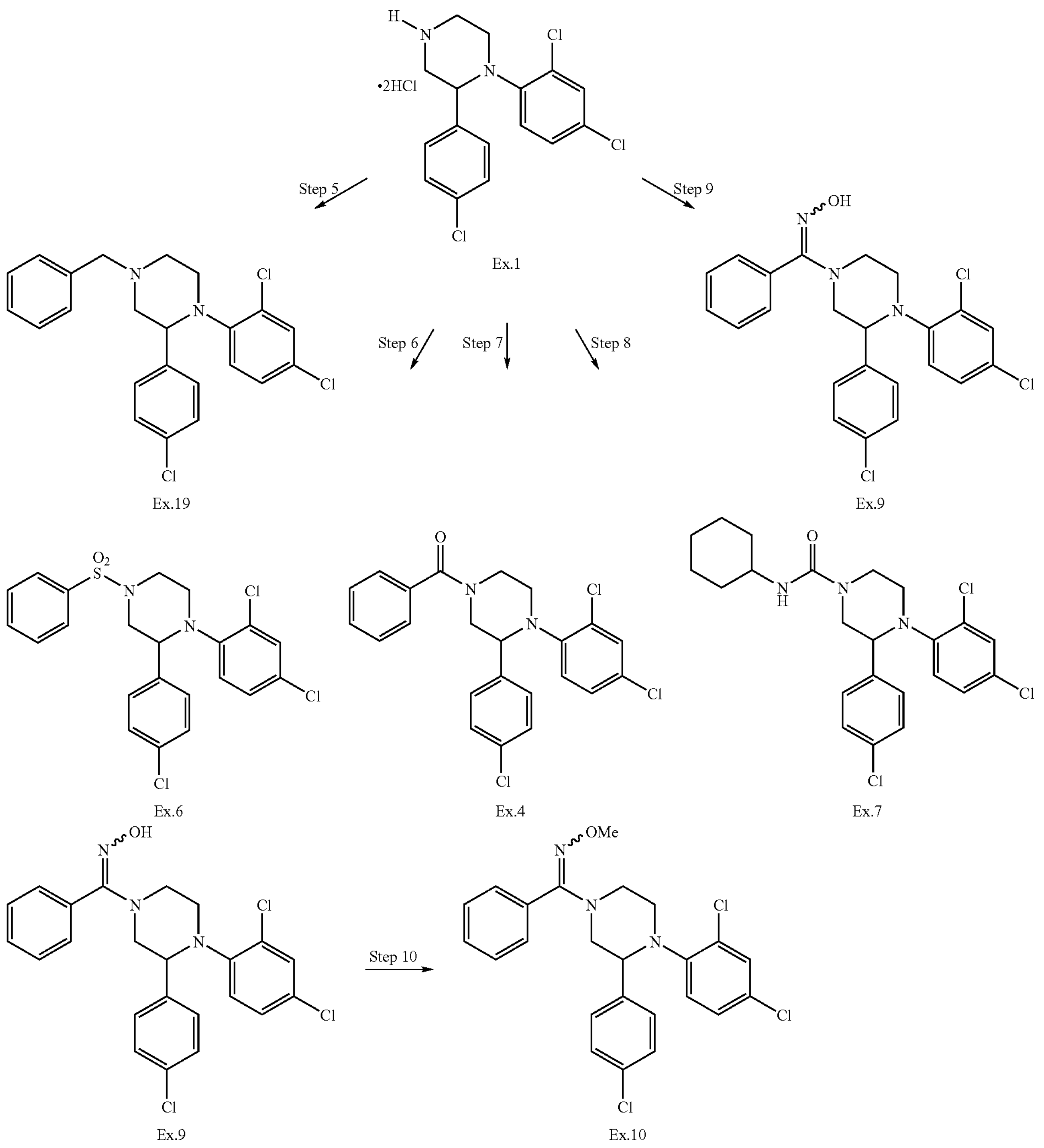

Step 1:

To neat 2-(4-chlorophenyl)oxirane i (10.1 g, 65.4 mmol) was added N-methylethanolamine (7.36 g, 98.1 mmol). The reaction mixture was warmed to 130° C. and stirred for 15 h. The reaction mixture was then cooled to room temperature (approximately 21° C.) and purified directly by silica gel chromatography (8% MeOH/$CH_2Cl_2$) to provide the diol ii (13.1 g, 57.2 mmol).

Step 2:

To a solution of the diol ii (13.1 g, 57.2 mmol) in $CHCl_3$ (110 mL) at 0° C. was added a solution of $SOCl_2$ (57 mL) in $CHCl_3$ (100 mL), dropwise, over 20 minutes. After the addition of the $SOCl_2$ solution was complete, the reaction mixture was warmed to reflux and stirred for 3.5 h. The reaction was cooled to room temperature and then concentrated in vacuo. The resulting oil was taken up into $CH_2Cl_2$ and stirred vigorously with saturated aqueous $NaHCO_3$. The mixture was extracted with $CH_2Cl_2$ and the combined $CH_2Cl_2$ layers were washed with water and brine, then dried ($MgSO_4$), filtered, and concentrated in vacuo to provide iii (14.2 g, 53.2 mmol). The chloride iii was used directly, or converted to its HCl salt. The HCl salt of chloride iii was prepared by dissolving chloride iii in $CH_2Cl_2$ and adding excess 2N HCl/diethyl ether.

After stirring the mixture for 5 minutes, the solvent was removed in vacuo to provide the HCl salt of chloride iii as a solid.

Step 3:

To a solution of iii (3.27 g, 12.3 mmol) in propionitrile (40 mL) was added 2,4-dichloroaniline (5.97 g, 36.9 mmol). The reaction mixture was warmed to reflux and stirred for 18 h. The reaction mixture was then cooled to room temperature and concentrated in vacuo. Purification of the residue by silica gel chromatography (5% MeOH/$CH_2Cl_2$) provided the piperazine Example 2 (2.92 g, 8.21 mmol).

Step 4:

To a solution of the piperazine Example 2 (2.92 g, 8.21 mmol) in dichloroethane (27 mL) at room temperature was added Proton-Sponge® (1,8-bis(dimethylamino)naphthalene; available from Aldrich) (0.52 g, 2.46 mmol) and 1-chloroethylchloroformate (2.35 g, 16.4 mmol). The reaction mixture was warmed to reflux and stirred for 21 h. The dichloroethane was removed in vacuo and MeOH (30 mL) was then added. The reaction mixture was then warmed to reflux and stirred for 7 h. The reaction mixture was concentrated in vacuo and the resulting oil was taken up into $CH_2Cl_2$. Saturated aqueous $NaHCO_3$ was added, and the mixture was stirred vigorously, then extracted with $CH_2Cl_2$. The organic layers were combined and washed with water and brine, dried ($MgSO_4$), filtered, and concentrated in vacuo to provide the piperazine Example 1 (2.11 g, 6.19 mmol).

Step 5:

To a solution of piperazine Example 1 (0.135 g, 0.33 mmol) in dichloroethane (1.3 mL) was added triethylamine (0.07 g, 0.66 mmol), benzaldehyde (0.052 g, 0.49 mmol), and sodium triacetoxyborohydride (0.14 g, 0.66 mmol). The reaction was stirred for 18 h at room temperature. $CH_2Cl_2$ was added, and the solution was then washed with saturated aqueous $NaHCO_3$, water, and brine, dried ($MgSO_4$), filtered, and concentrated in vacuo to provide a residue that was adsorbed on excess PS-TsOH resin in $CH_2Cl_2$. After 2 h, the resin was filtered and washed with $CH_2Cl_2$ and MeOH. The resin was then stirred with 7N $NH_3$/MeOH for 1 h, filtered, and washed with $CH_2Cl_2$. The filtrate was concentrated in vacuo to provide Example 19 (0.086 g, 0.20 mmol).

Step 6:

To a solution of the piperazine Example 1 (0.10 g, 0.24 mmol) in dichloroethane (1 mL) was added TEA (i.e., triethylamine) (0.09 g, 0.96 mmol) and benzenesulfonyl chloride (0.05 g, 0.3 mmol) at room temperature. The reaction mixture was stirred for 12 h and concentrated in vacuo. The resulting residue was purified by silica gel preparative plate TLC (i.e., thin layer chromatography) (2000 μm, 20% EtOAc/hexane) to provide the sulfonamide Example 6 (0.11 g, 0.22 mmol).

Step 7:

To a solution of the piperazine Example 1 (0.14 g, 0.33 mmol) in $CH_2Cl_2$ (1.7 mL) at 0° C. was added TEA (0.10 g, 0.10 mmol) followed by benzoyl chloride (0.05 g, 0.37 mmol). The cold bath was allowed to warm slowly to room temperature, and the reaction mixture was stirred for 20 h. $CH_2Cl_2$ was added and the mixture washed with water and brine, dried ($MgSO_4$), filtered, and concentrated in vacuo. The resulting residue was purified by silica gel chromatography to provide the amide Example 4 (0.13 g, 0.29 g).

Step 8:

To a solution of the piperazine Example 1 (0.18 g, 0.45 mmol) in dichloroethane (2 mL) was added TEA (0.14 g, 1.3 mmol) followed by cyclohexylisocyanate (0.08 g, 0.67 mmol). The reaction mixture was warmed to reflux and stirred for 17 h, then cooled to room temperature. $CH_2Cl_2$ was added, and the solution was washed with water and brine, dried ($MgSO_4$), filtered and concentrated in vacuo. The resulting residue was purified by silica gel prep plate TLC (2000 μm, 30% EtOAc/hexane) to provide the urea Example 7 (0.19 g, 0.41 mmol).

Step 9:

To a solution of benzaldehyde (2.00 g, 18.8 mmol) in ethanol (13 mL) was added hydroxylamine hydrochloride (2.61 g, 37.6 mmol) and pyridine (3.8 mmol). The solution was warmed to reflux and stirred for 18 h. The reaction mixture was concentrated in vacuo and the resulting residue was taken up into $CH_2Cl_2$, washed with water and brine, dried ($MgSO_4$), filtered, and concentrated in vacuo to provide the phenyloxime (2.0 g, 16.5 mmol). The phenyloxime was taken up into DMF (i.e., dimethylformamide) (55 mL), and N-chlorosuccinimide (2.43 g, 18.2 mmol) was added at room temperature. The reaction mixture was stirred for 23 h and then water was added. The mixture was extracted with EtOAc. The organic layers were combined and washed with water and brine, dried ($MgSO_4$), filtered and concentrated in vacuo to provide the benzohydroximoyl chloride that was used directly.

To the piperazine Example 1 (0.50 g, 1.21 mmol) in $CH_2Cl_2$ (4 mL) was added diisopropylethylamine (0.55 g, 4.23 mmol) and the benzohydroximoyl chloride prepared as described above (0.28 g, 1.81 mmol), at room temperature. The reaction mixture was stirred for 15 h and $CH_2Cl_2$ was then added. The solution was then washed with water and brine, dried ($MgSO_4$), filtered and concentrated in vacuo. The residue was purified by silica gel chromatography (30% EtOAc/hexane) to provide the amidoxime Example 9 (0.44 g, 0.95 mmol).

Step 10:

To a solution of the amidoxime Example 9 (0.074 g, 0.15 mmol) in toluene (0.5 mL) was added 50% aqueous NaOH (0.5 mL), methyl iodide (0.04 g, 0.30 mmol), and tetrabutylammonium iodide (0.003 g, 0.007 mmol). The resulting reaction mixture was stirred at room temperature for 18 h, then water was added and the mixture was extracted with EtOAc. The combined organic layers were washed with water and brine, dried ($MgSO_4$), filtered, and concentrated in vacuo. The resulting residue was purified by silica gel preparative plate TLC (2000 μm, 10% EtOAc/hexane) to provide the O-methylamidoxime Example 10 (0.05 g, 0.10 mmol).

Preparation of Example 3

Ex. 3

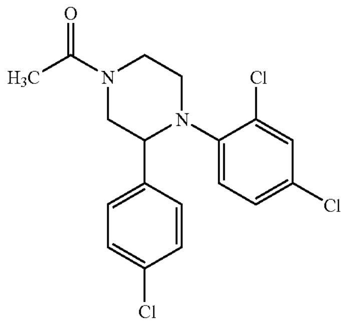

Example 3 was prepared from Example 1 using procedures similar to those used to prepare Example 4, except that acetyl chloride was used in Step 7 (above) instead of benzoyl chloride.

Preparation of Example 5

Ex. 5

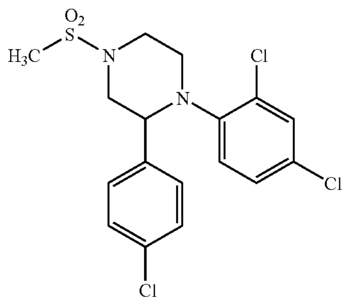

Example 5 was prepared from Example 1 using procedures similar to those used to prepare Example 6, except that methanesulfonyl chloride was used in Step 6 (above) instead of benzenesulfonyl chloride.

Preparation of Example 8

Ex. 8

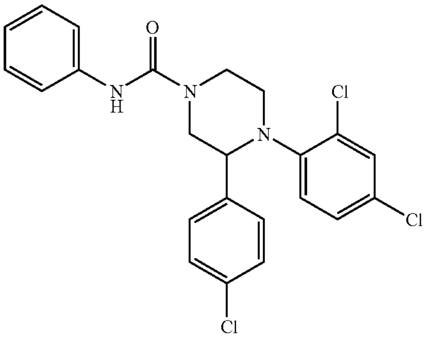

Example 8 was prepared from Example 1 using procedures similar to those used to prepare Example 7, except that phenylisocyanate was used in Step 8 (above) instead of cyclohexylisocyanate.

Preparation of Example 11

Ex. 11

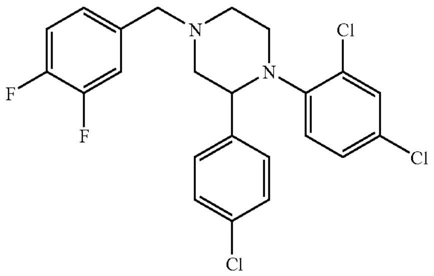

Example 11 was prepared from Example 1 using procedures similar to those used to prepare Example 19, except that 3,4-difluorobenzaldehyde was used in Scheme 2, Step 5 (above) instead of benzaldehyde.

Preparation of Example 12

Ex. 12

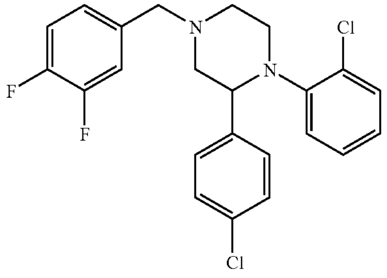

Example 12 was prepared using procedures similar to those used to prepare Example 19, except that in Scheme 1, Step 3 (above), the HCl salt of iii was used instead of iii, 2-chloroaniline was used instead of 2,4-dichloroaniline, acetonitrile was used instead of propionitrile, NaI (1 equiv.) and diisopropylethylamine (3 equiv.) was added, and in Scheme 2, Step 5 (above), 3,4-difluorobenzaldehyde was used instead of benzaldehyde.

Preparation of Example 13

Ex. 13

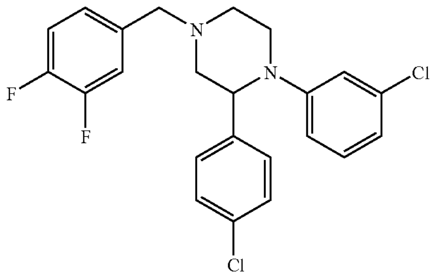

Example 13 was prepared using procedures similar to those used to prepare Example 19, except that in Scheme 1, Step 3 (above), the HCl salt of iii was used instead of iii, 3-chloroaniline was used instead of 2,4-dichloroaniline, acetonitrile was used instead of propionitrile, NaI (1 equiv.) and diisopropylethylamine (3 equiv.) was added, and in Scheme 2, Step 5 (above), 3,4-difluorobenzaldehyde was used instead of benzaldehyde.

Preparation of Example 14

Ex. 14

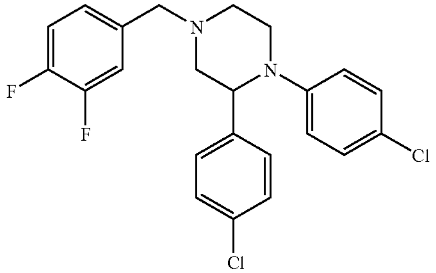

Example 14 was prepared using procedures similar to those used to prepare Example 19, except that in Scheme 1, Step 3 (above), 4-chloroaniline was used instead of 2,4-dichloroaniline, acetonitrile was used instead of propionitrile, and NaI was added, and in Scheme 2, Step 5 (above), 3,4-difluorobenzaldehyde was used instead of benzaldehyde.

Preparation of Example 15

Ex. 15

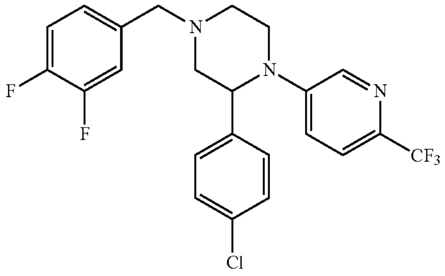

Example 15 was prepared using procedures similar to those used to prepare Example 19, except that in Scheme 1, Step 3 (above), 6-trifluoromethyl-pyridin-3-ylamine was used instead of 2,4-dichloroaniline, acetonitrile was used instead of propionitrile, NaI (1 equiv.) and diisopropylethylamine (3 equiv.) was added, and in Scheme 2, Step 5 (above), 3,4-difluorobenzaldehyde was used instead of benzaldehyde.

Preparation of Example 16

Ex. 16

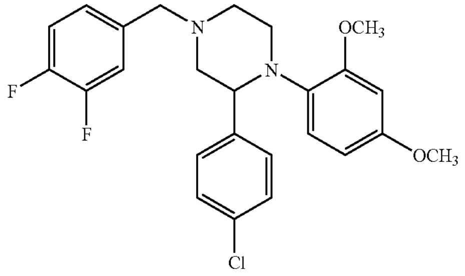

Example 16 was prepared using procedures similar to those used to prepare Example 19, except that in Scheme 1, Step 3 (above), 2,4-dimethoxyaniline was used instead of 2,4-dichloroaniline, acetonitrile was used instead of propionitrile, NaI (1 equiv.) and diisopropylethylamine (3 equiv.) was added, and in Scheme 2, Step 5 (above), 3,4-difluorobenzaldehyde was used instead of benzaldehyde.

Preparation of Example 17

Ex. 17

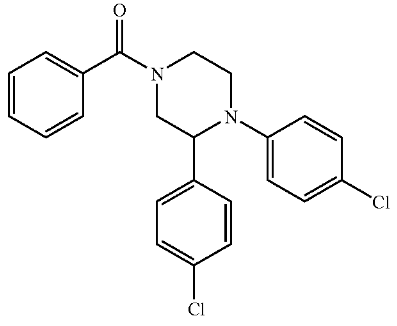

Example 17 was prepared using procedures similar to those used to prepare Example 4, except that in Scheme 1, Step 3 (above), the HCl salt of iii was used instead of iii, 4-chloroaniline was used instead of 2,4-dichloroaniline, acetonitrile was used instead of propionitrile, and NaI (1 equiv.) and diisopropylethylamine (3 equiv.) was added.

Preparation of Example 18

Ex. 18

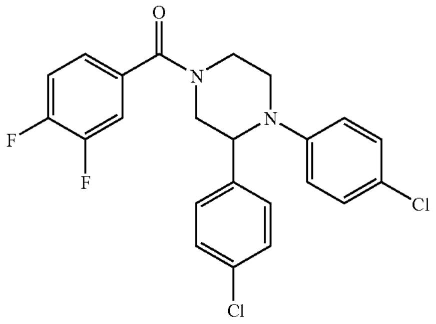

Example 18 was prepared using procedures similar to those used to prepare Example 4, except that in Scheme 1, Step 3 (above), the HCl salt of iii was used instead of iii, 4-chloroaniline was used instead of 2,4-dichloroaniline, acetonitrile was used instead of propionitrile, NaI (1 equiv.) and diisopropylethylamine (3 equiv.) was added, and in Step 7 (above), 3,4-difluorobenzoyl chloride was used instead of benzoyl chloride.

Preparation of Examples 20-110

Ex. 20

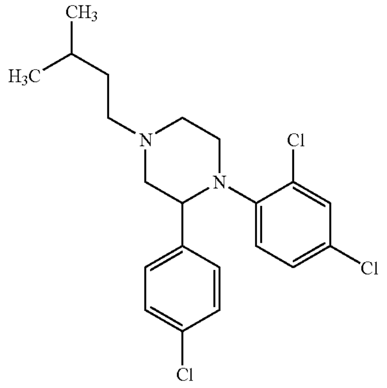

Ex. 21

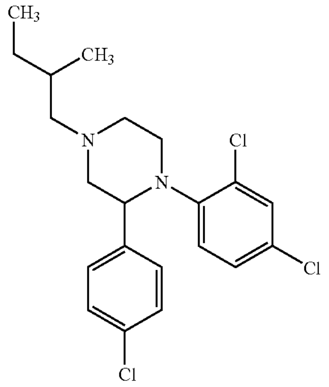

-continued
Ex. 22
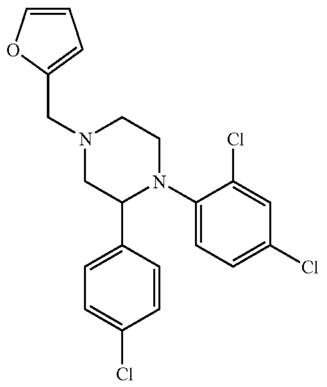
Ex. 23
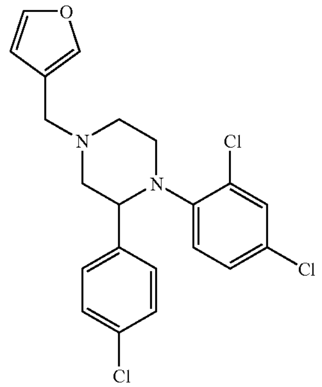
Ex. 24
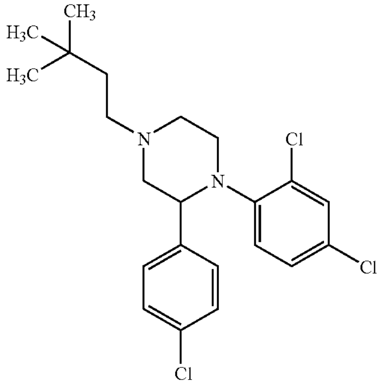
Ex. 25
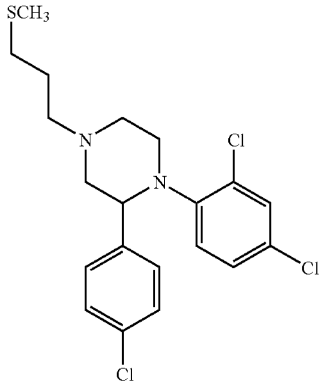
-continued
Ex. 26
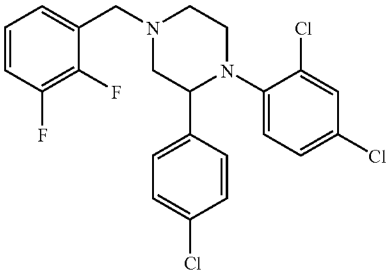
Ex. 27
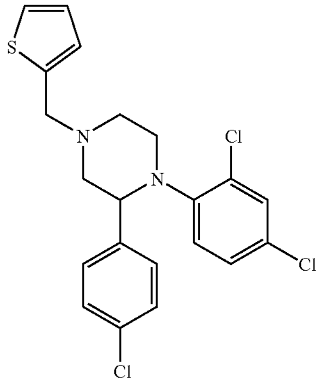
Ex. 28
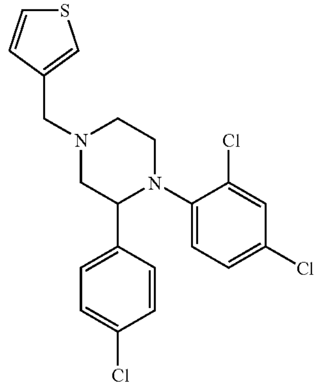
Ex. 29
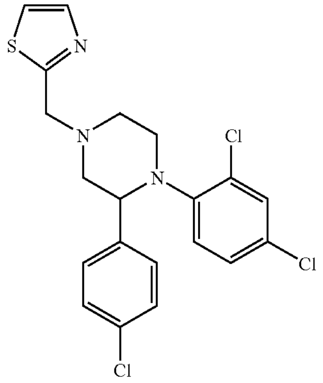

-continued
Ex. 30
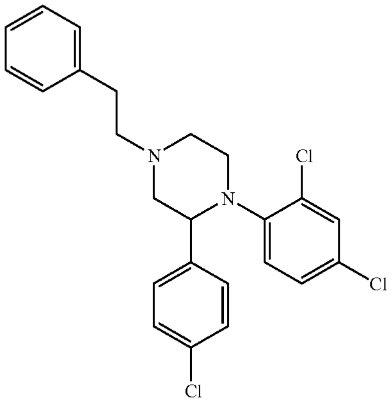
Ex. 31
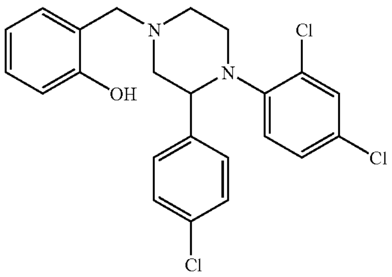
Ex. 32
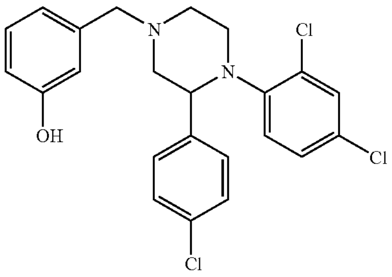
Ex. 33
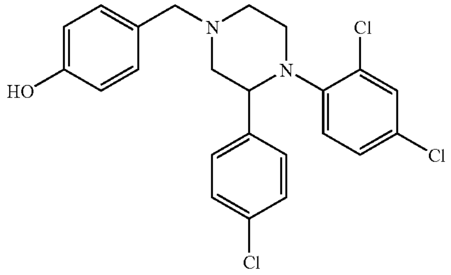
Ex. 34
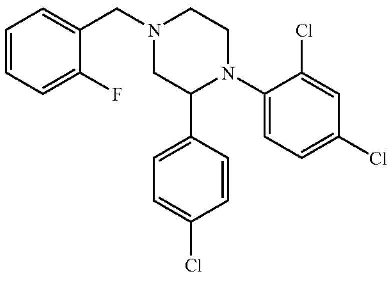
-continued
Ex. 35
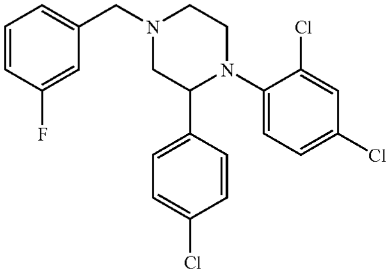
Ex. 36
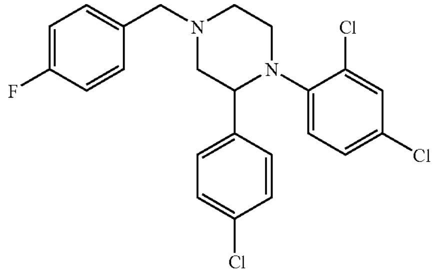
Ex. 37
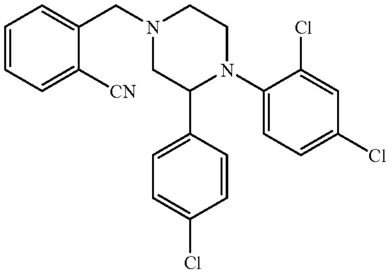
Ex. 38
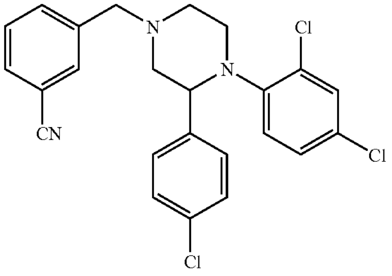
Ex. 39
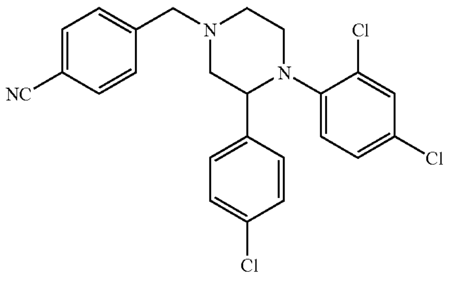

-continued
Ex. 40
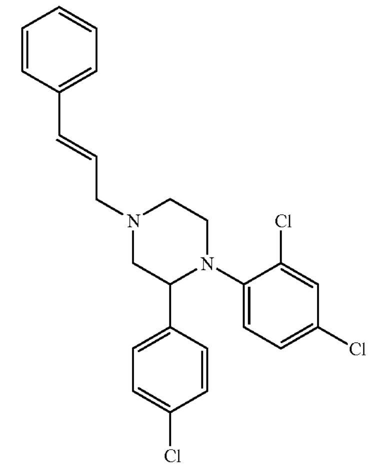
Ex. 41
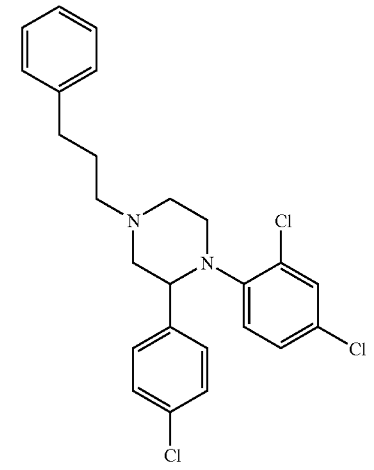
Ex. 42
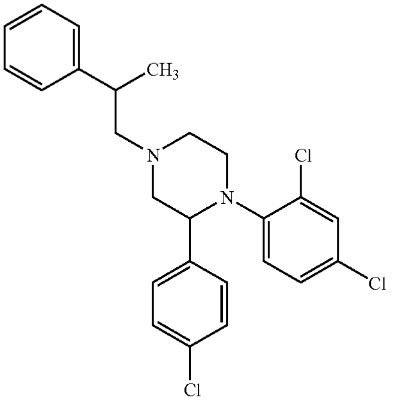
Ex. 43
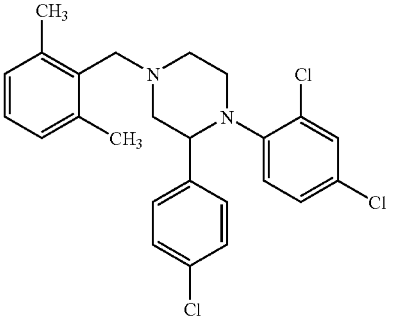
-continued
Ex. 44
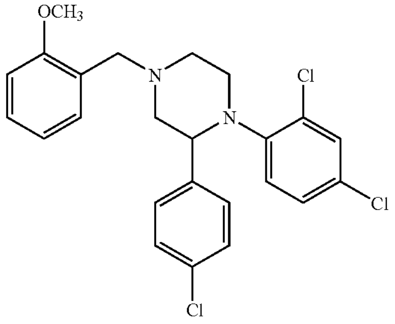
Ex. 45
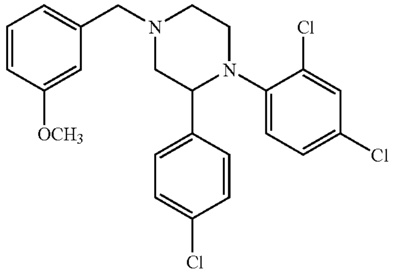
Ex. 46
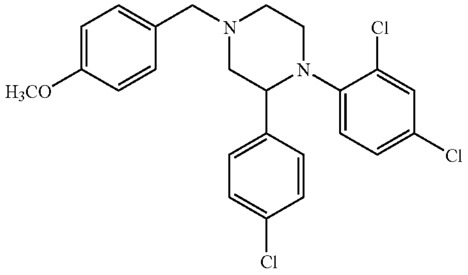
Ex. 47
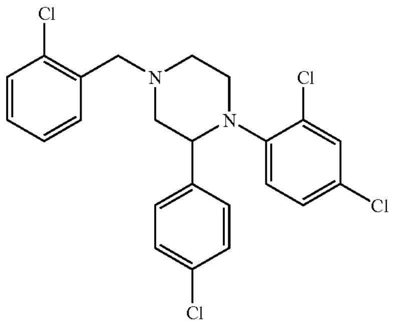
Ex. 48
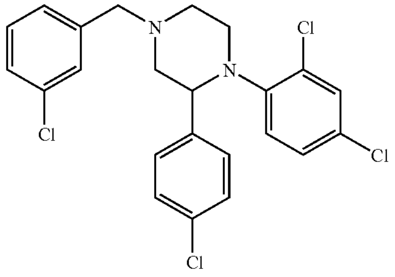

-continued
Ex. 49
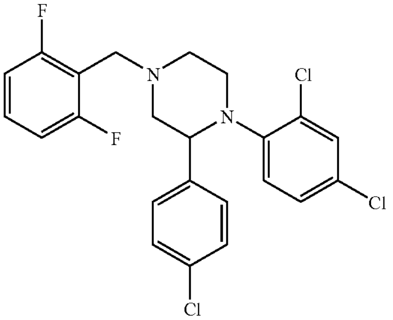
Ex. 50
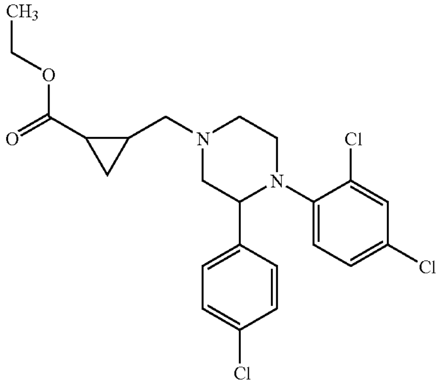
Ex. 51
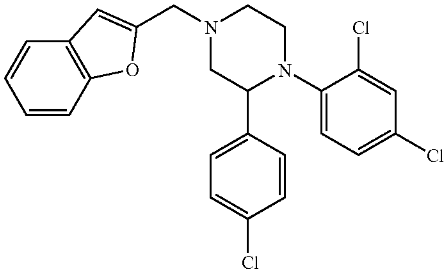
Ex. 52
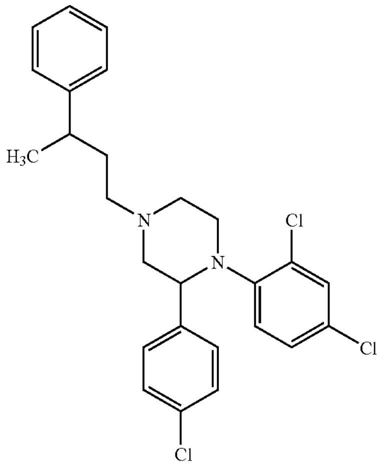
-continued
Ex. 53
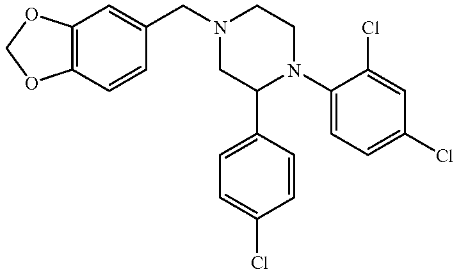
Ex. 54
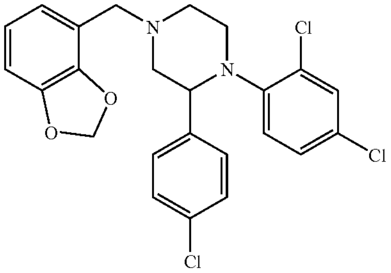
Ex. 55
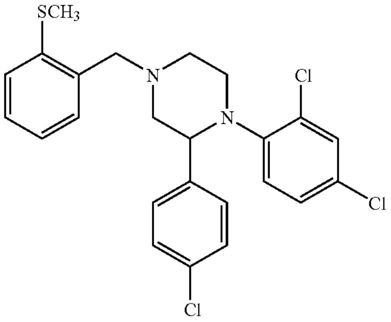
Ex. 56
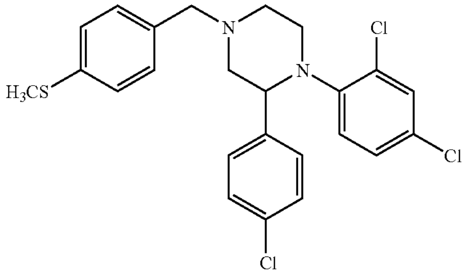
Ex. 57
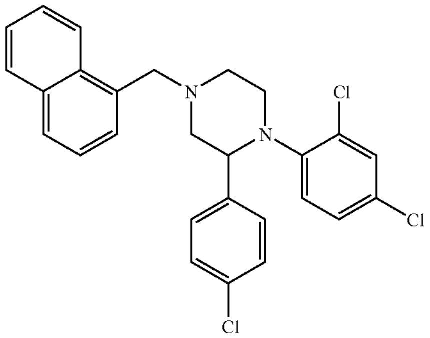

-continued
Ex. 58
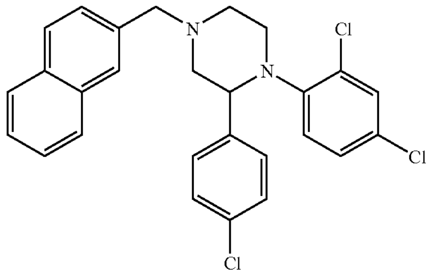
Ex. 59
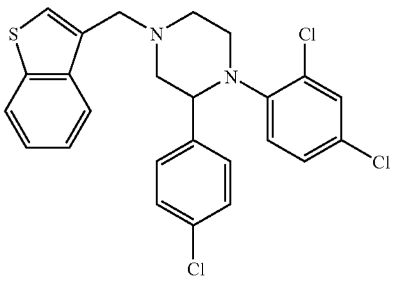
Ex. 60
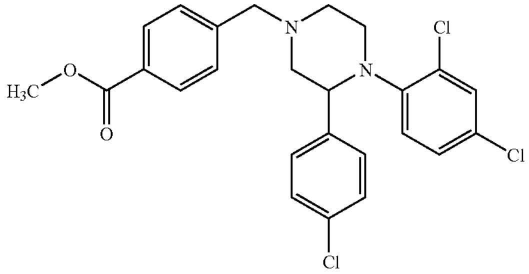
Ex. 61
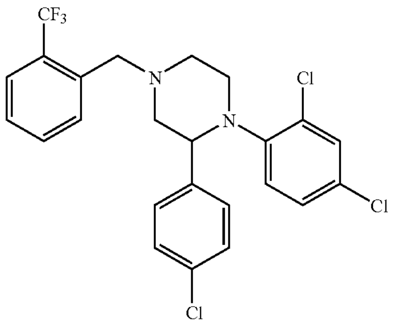
Ex. 62
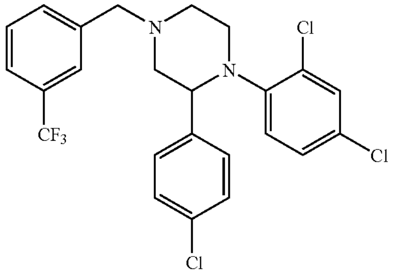
-continued
Ex. 63
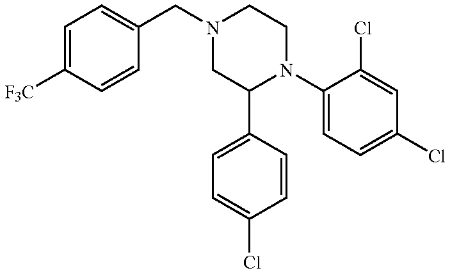
Ex. 64
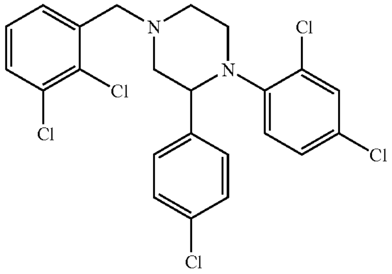
Ex. 65
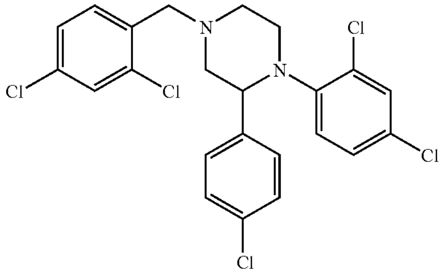
Ex. 66
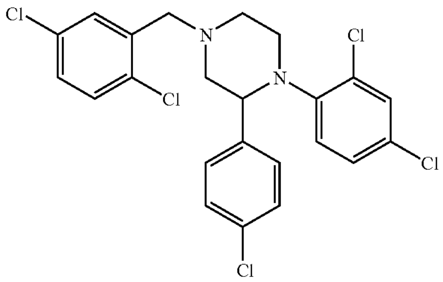
Ex. 67
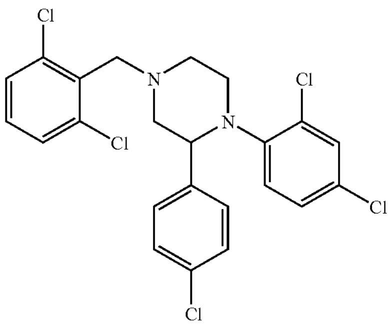

-continued
Ex. 68
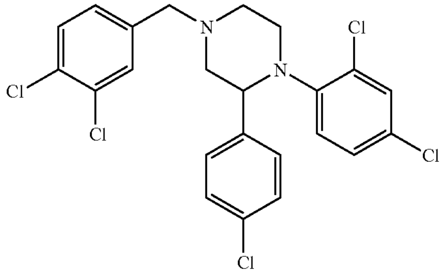
Ex. 69
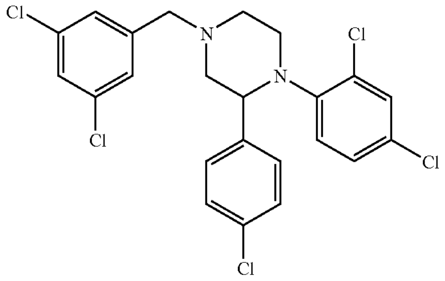
Ex. 70
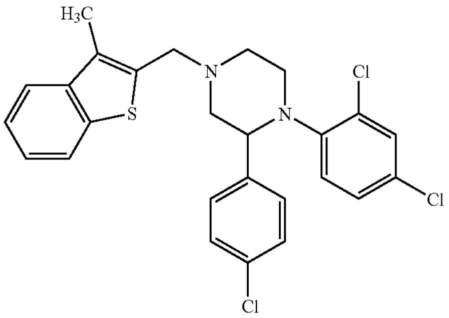
Ex. 71
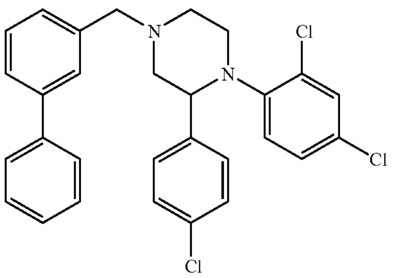
Ex. 72
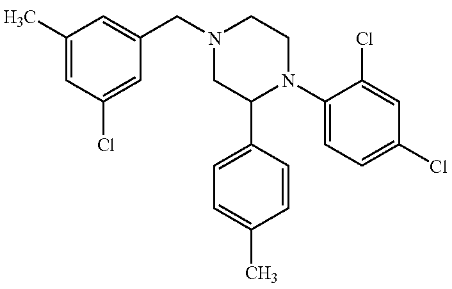
-continued
Ex. 73
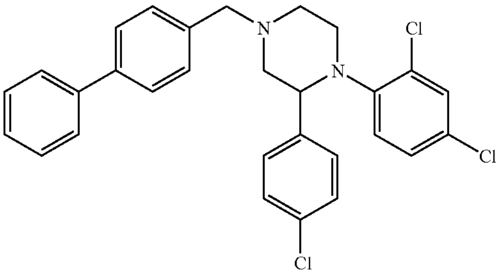
Ex. 74
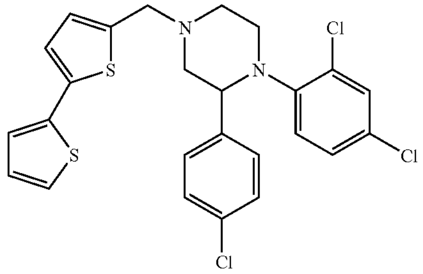
Ex. 75
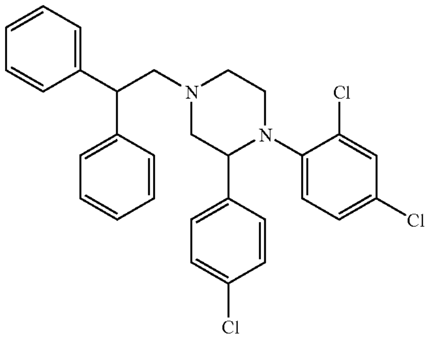
Ex. 76
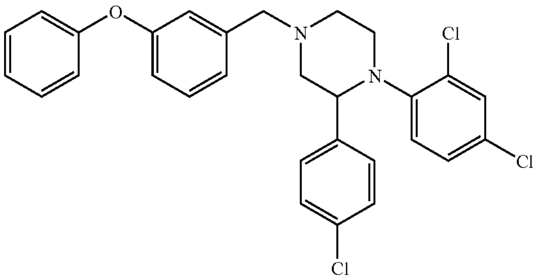
Ex. 77
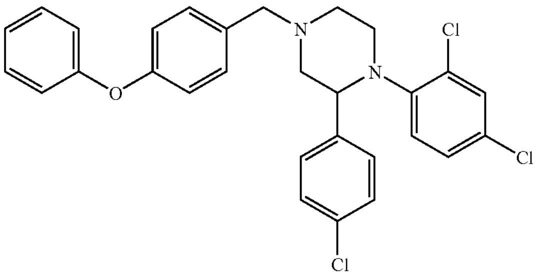

-continued
Ex. 78
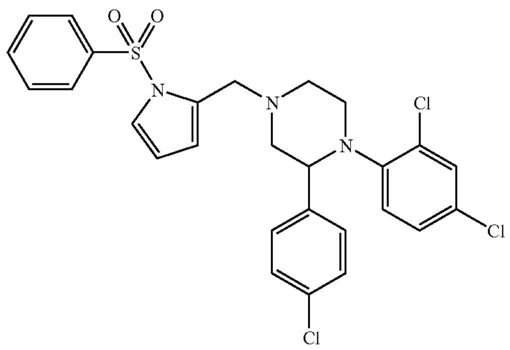
Ex. 79
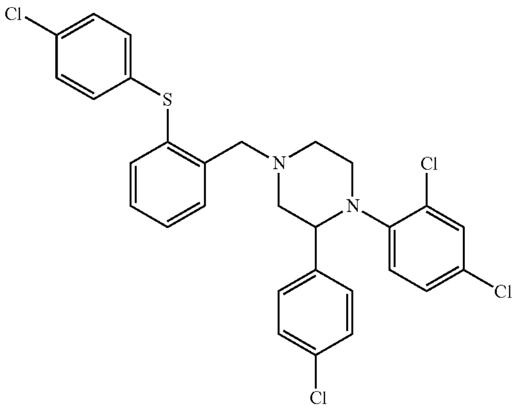
Ex. 80
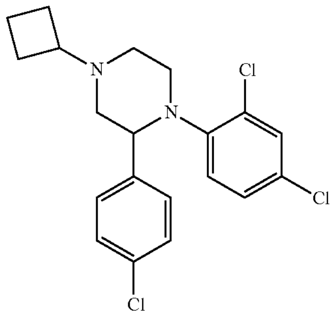
Ex. 81
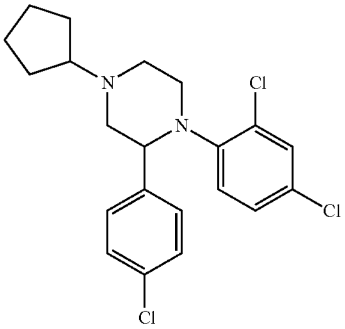
-continued
Ex. 82
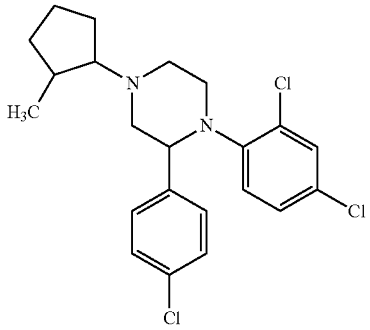
Ex. 83
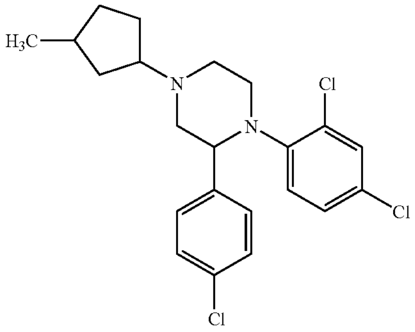
Ex. 84
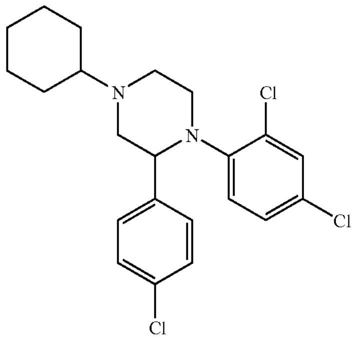
Ex. 85
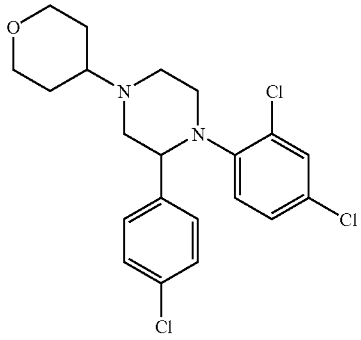
Ex. 86
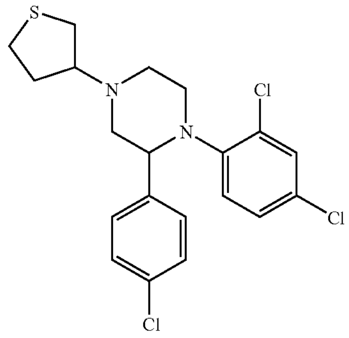

-continued
Ex. 87
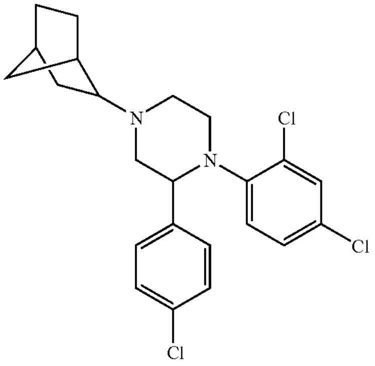
Ex. 88
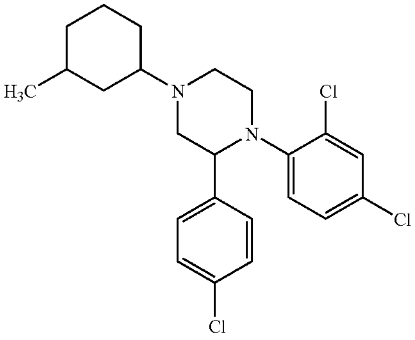
Ex. 89
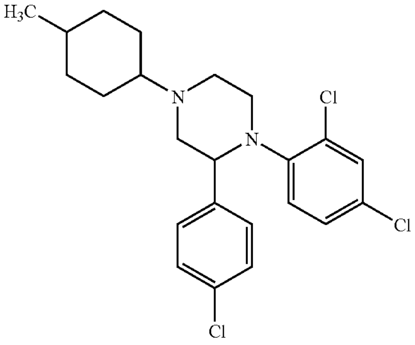
Ex. 90
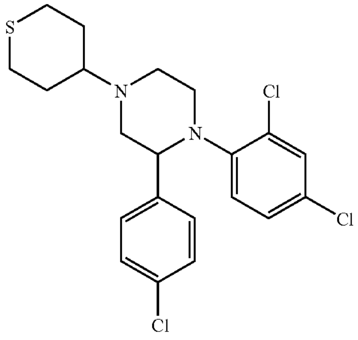
-continued
Ex. 91
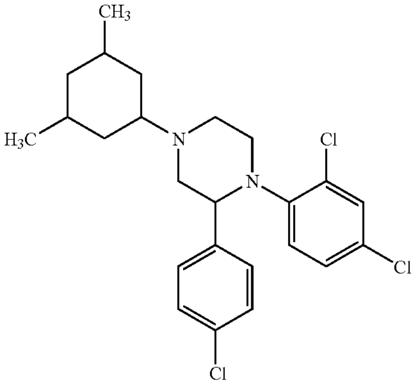
Ex. 92
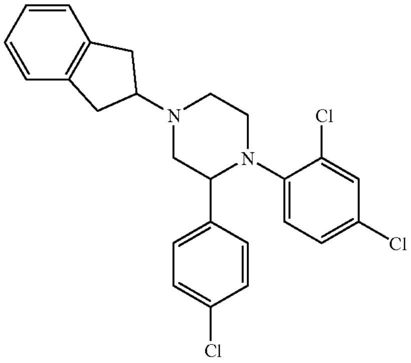
Ex. 93
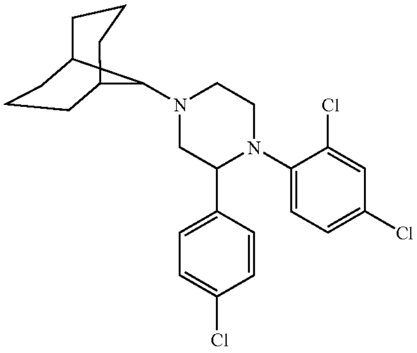
Ex. 94
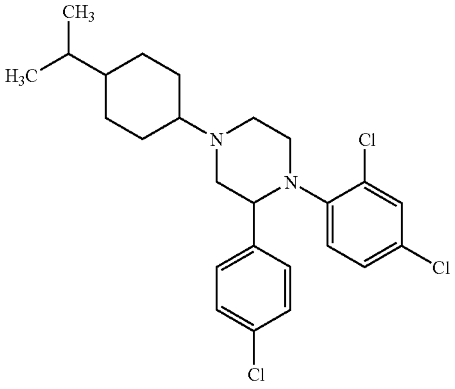

-continued
Ex. 95
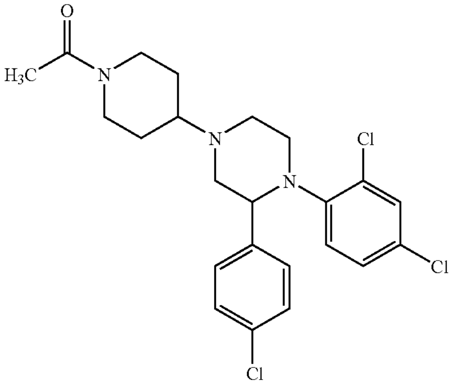
Ex. 96
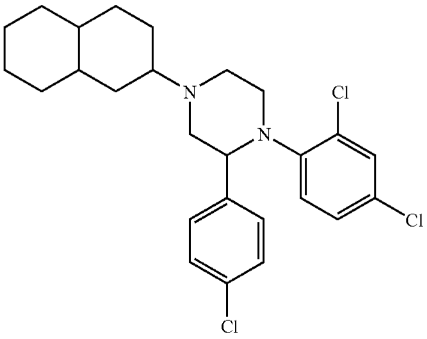
Ex. 97
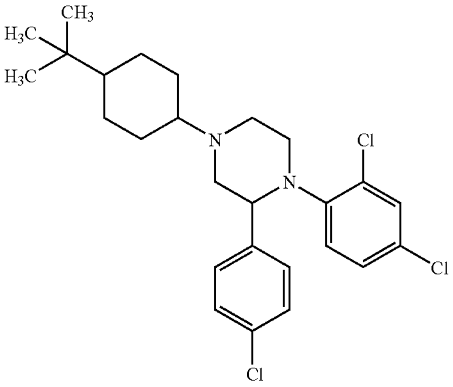
Ex. 98
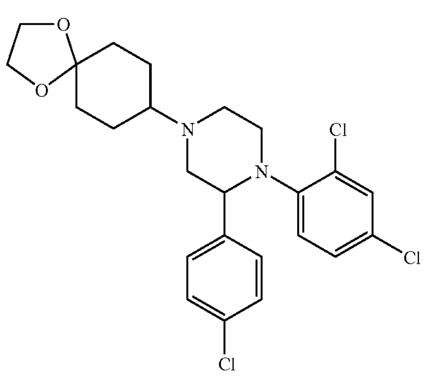
-continued
Ex. 99
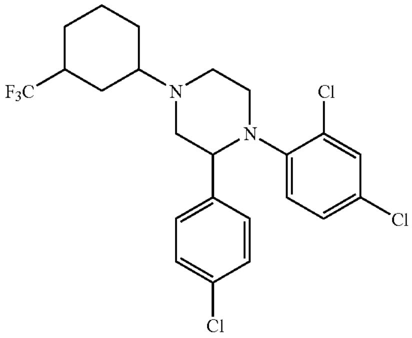
Ex. 100
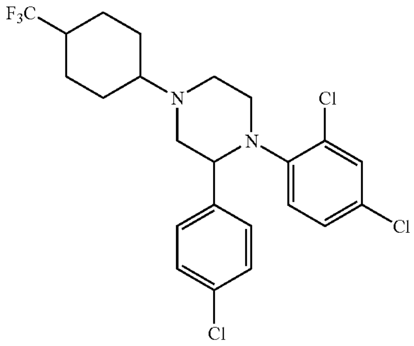
Ex. 101
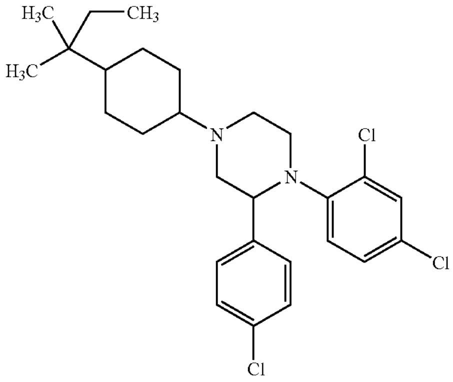
Ex. 102
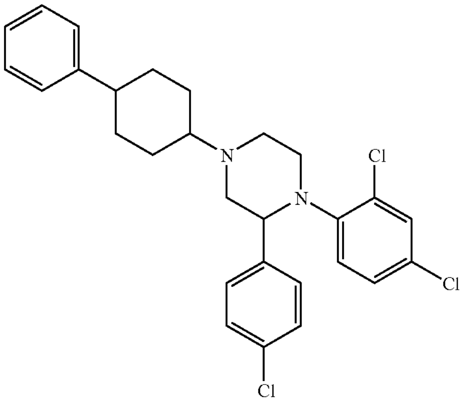

-continued
Ex. 103
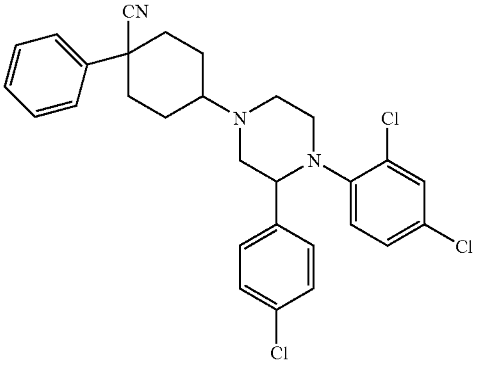
Ex. 104
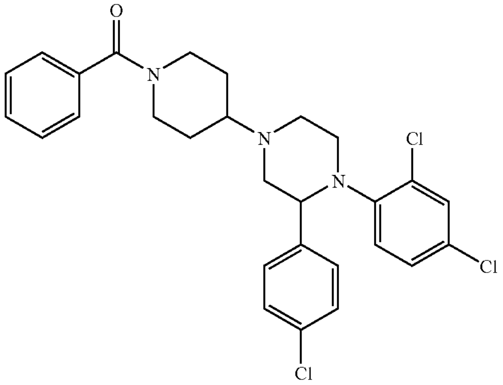
Ex. 105
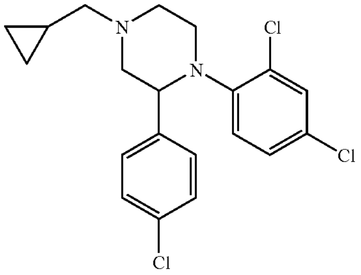
Ex. 106
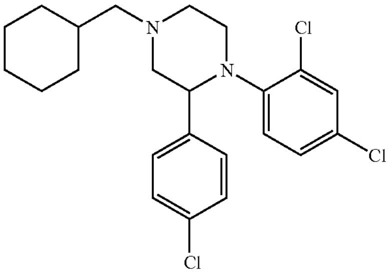
Ex. 107
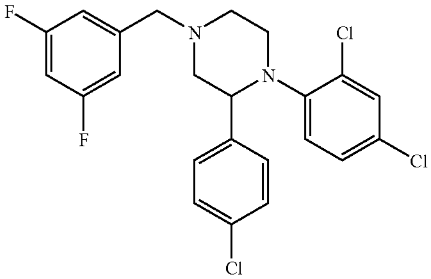
-continued
Ex. 108
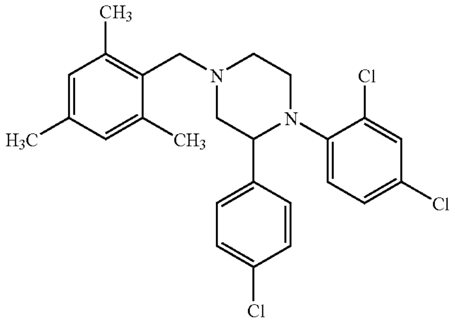
Ex. 109
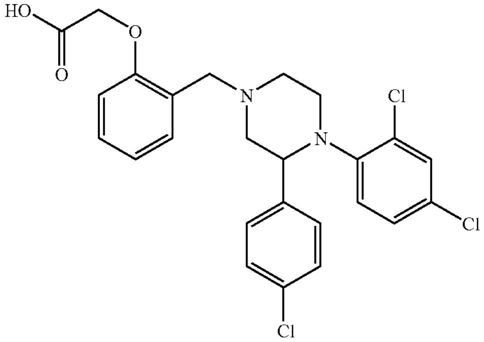
Ex. 110
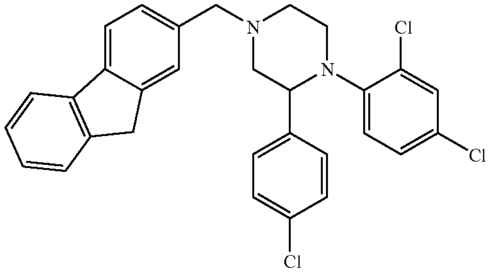
Examples 20-110 were prepared by the following method, using a parallel synthesis approach.
Scheme 3
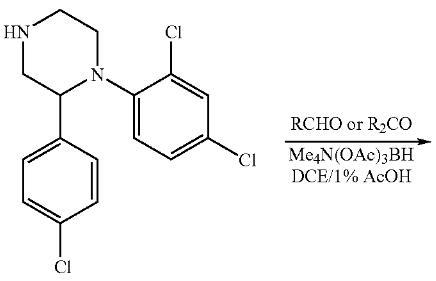
Ex. 1

-continued

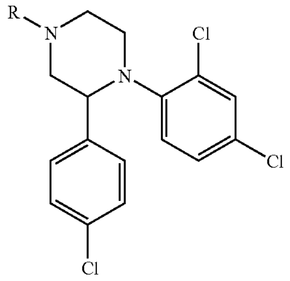

The piperazine Example 1, prepared as described above (0.72 g, 2.1 mmol) and $Me_4N(OAc)_3BH$ (1.11 g, 4.2 mmol) was dissolved in a 1% acetic acid/dichloroethane (DCE) solution (100 mL). Aliquots (1 mL) of the resulting mixture were added to 96 wells of a deep well polypropylene microtiter plate. To each of the wells was then added one of 96 different aldehydes or ketones (shown in Table I, below) (1.0 M solution in MeCN, 150 μL) via a TECAN liquid handler.

TABLE I

| Aldehydes/Ketones Used | |
|---|---|
| Example | Ketone/Aldehyde |
| 20 | 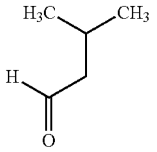 |
| 21 | 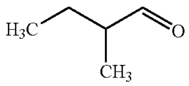 |
| 22 | 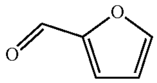 |
| 23 | 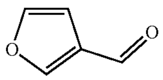 |
| 24 | 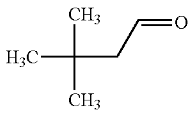 |
| 25 | 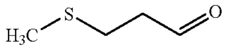 |
| 26 | 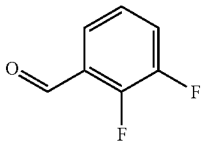 |
| 27 | 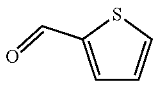 |
| 28 | 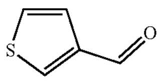 |

TABLE I-continued

| Aldehydes/Ketones Used | |
|---|---|
| Example | Ketone/Aldehyde |
| 29 | 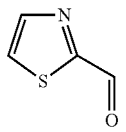 |
| 30 | 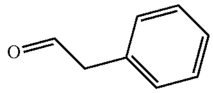 |
| 31 | 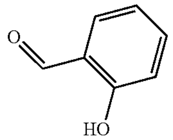 |
| 32 | 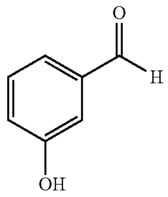 |
| 33 | 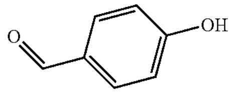 |
| 34 | 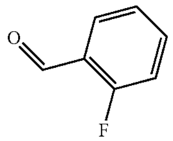 |
| 35 | 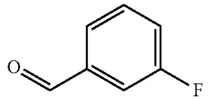 |
| 36 | 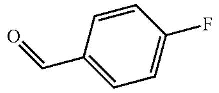 |
| 37 | 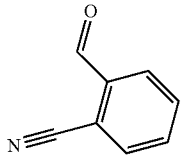 |
| 38 | 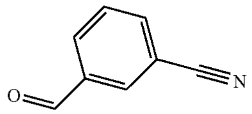 |
| 39 | 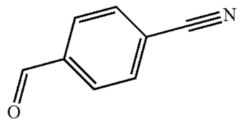 |

TABLE I-continued
| Aldehydes/Ketones Used | |
|---|---|
| Example | Ketone/Aldehyde |
| 40 | 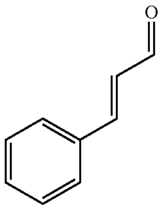 |
| 41 | 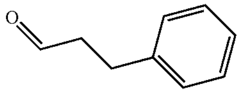 |
| 42 | 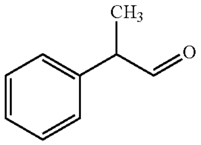 |
| 43 | 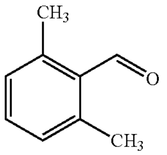 |
| 44 | 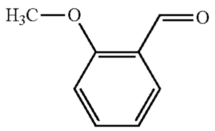 |
| 45 | 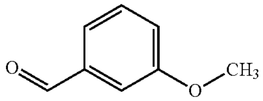 |
| 46 | 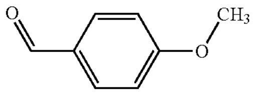 |
| 47 | 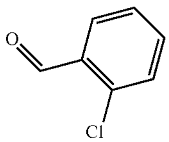 |
| 48 | 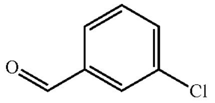 |
| 49 | 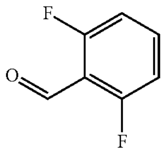 |
| 50 | 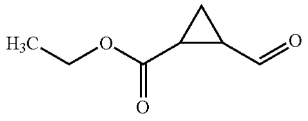 |
| 51 | 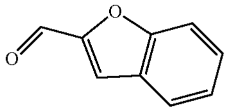 |
| 52 | 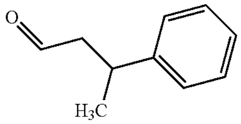 |
| 53 | 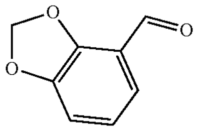 |
| 54 | 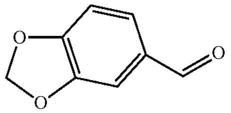 |
| 55 | 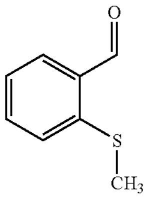 |
| 56 | 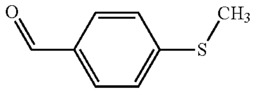 |
| 57 | 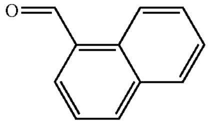 |
| 58 | 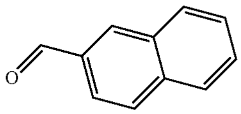 |
| 59 | 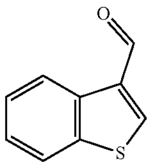 |
| 60 | 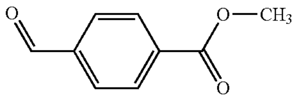 |

TABLE I-continued
| Aldehydes/Ketones Used | |
|---|---|
| Example | Ketone/Aldehyde |
| 61 | 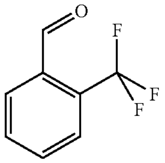 |
| 62 | 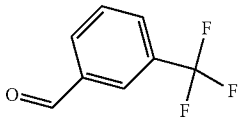 |
| 63 | 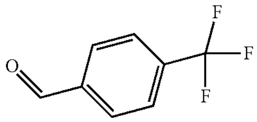 |
| 64 | 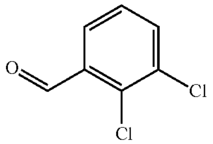 |
| 65 | 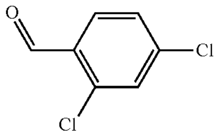 |
| 66 | 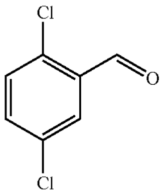 |
| 67 | 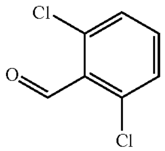 |
| 68 | 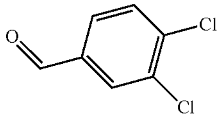 |
| 69 | 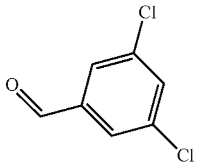 |
TABLE I-continued
| Aldehydes/Ketones Used | |
|---|---|
| Example | Ketone/Aldehyde |
| 70 | 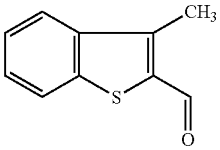 |
| 71 | 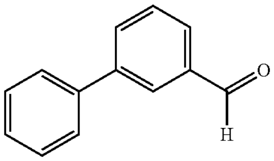 |
| 72 | 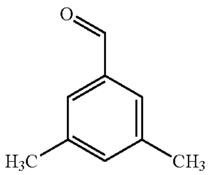 |
| 73 | 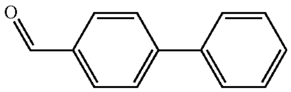 |
| 74 | 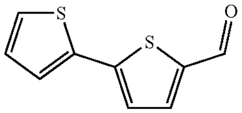 |
| 75 | 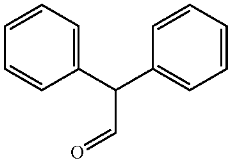 |
| 76 | 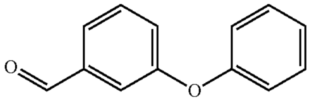 |
| 77 | 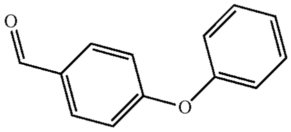 |
| 78 | 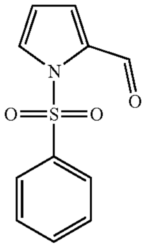 |

TABLE I-continued
| Aldehydes/Ketones Used | |
|---|---|
| Example | Ketone/Aldehyde |
| 79 | 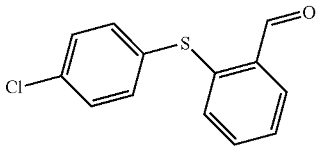 |
| 80 | 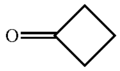 |
| 81 | 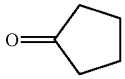 |
| 82 | 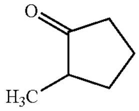 |
| 83 | 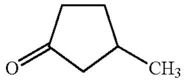 |
| 84 | 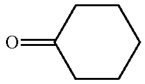 |
| 85 | 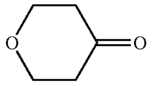 |
| 86 | 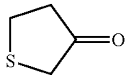 |
| 87 | 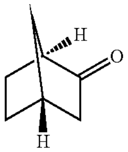 |
| 88 | 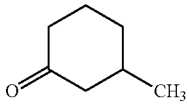 |
| 89 | 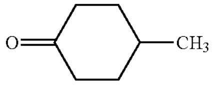 |
| 90 | 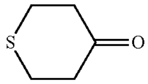 |
| 91 | 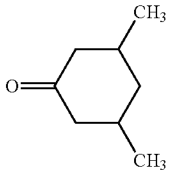 |
TABLE I-continued
| Aldehydes/Ketones Used | |
|---|---|
| Example | Ketone/Aldehyde |
| 92 | 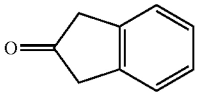 |
| 93 | 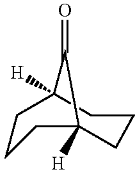 |
| 94 | 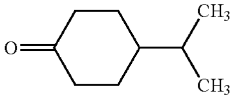 |
| 95 | 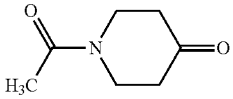 |
| 96 | 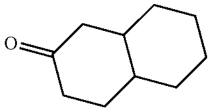 |
| 97 | 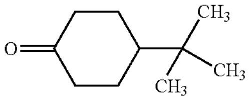 |
| 98 | 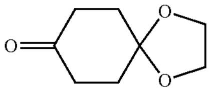 |
| 99 | 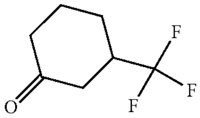 |
| 100 | 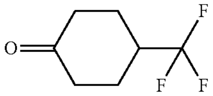 |
| 101 | 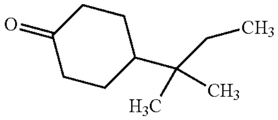 |
| 102 | 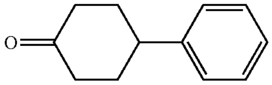 |

TABLE I-continued

| Aldehydes/Ketones Used | |
|---|---|
| Example | Ketone/Aldehyde |
| 103 | 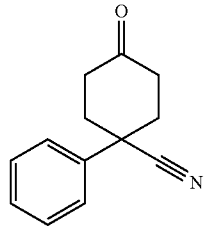 |
| 104 | 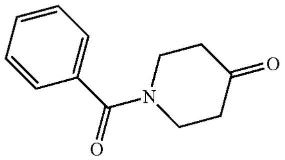 |
| 105 | 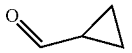 |
| 106 | 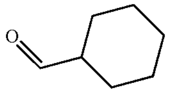 |
| 107 | 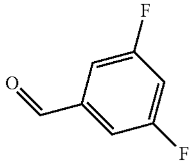 |
| 108 | 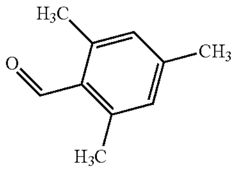 |
| 109 | 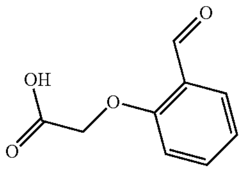 |
| 110 | 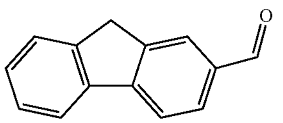 |

The plate was then sealed and shaken at room temperature for 3 days. MP-TsOH resin (i.e., macroporous resin functionalized with toluenesulfonic acid groups; available from Argonaut Technologies, Inc.) (100 mg) was then added to each well of the plate. The plate was then resealed and shaken for 2 h. The bottom of the plate was opened and the filtrate from each well was collected in the corresponding 2 mL well of a 96-well plate. The resin in each well was washed with $CH_2Cl_2$ (4×) followed by MeOH (3×). The bottom of the plate was then resealed and an aliquot of 2 N $NH_3$/MeOH (1.5 mL) was added to each well to remove crude product bound to the MP-TsOH resin. The plate was sealed and shaken for 2 h. The bottom of the plate was opened and the filtrate from each well was collected in the corresponding 2 mL well of a 96-well plate. The resin in each well was washed with MeOH (1×). An aliquot from each well was removed for LC/MS analysis. The remaining solution from each well was transferred to 96 corresponding 2-dram bar-coded vials using a TECAN liquid handler. The solvent was then removed from each of the vials using a SPEEDVAC concentrator, to provide crude Products I.

LC/MS analysis showed that most crude Products I contained 10-40% of starting piperazine Example 1. The desired product was also determined to be present in the filtrate by TLC (i.e., thin layer chromatography) analysis. The filtrates were then transferred by a TECAN liquid handler to 96 corresponding BOHDAN MINIBLOCK cartridges containing approximately 100 mg of MP-TsOH resin. The cartridges were sealed and shaken for 20 h. The solvent was then removed from each cartridge in vacuo and the resin was washed in each cartridge with $CH_2Cl_2$ (3×) and MeOH (3×, 1.5 mL). A 3.5 N $NH_3$/MeOH-THF (1:1) solution (1.5 mL) was then added to the resin in each cartridge to remove crude product bound to the MP-TsOH resin. The cartridges were sealed and shaken for 20 h. The solvent from each cartridge was collected by filtration and the resin in each cartridge was treated with 7 N $NH_3$/MeOH (1.5 mL) for 8 h. The solvent was removed by filtration and the filtrates were combined in 96 corresponding 2-dram bar-coded vials. An aliquot form each vial was analyzed by LC/MS, and the remaining solvent from each vial was removed in vacuo to provide crude Products II.

The MP-TsOH resin from Product I was manually transferred with MeOH from the plate to 96 corresponding cartridges of a BOHDAN MINIBLOCK. The solution from each cartridge was then removed by filtration and the resin in each cartridge was treated with 3.5 N $NH_3$ in MeOH/THF (1:1, 18 h, 1.5 mL). The filtrate from each cartridge was collected and the resin in each cartridge was again treated with 3.5 N $NH_3$ in MeOH/THF (1:1, 8 h, 1.5 mL). The filtrates were combined with the corresponding Product I and an aliquot from each combined filtrate was submitted for LC/MS analysis. The solvent from each sample was removed in vacuo to provide Product III.

Products II were added to Products III if it was determined by LC/MS analysis that a sufficient quantity of desired product was present in Product II. The combined products were transferred with DCE/MeCN (i.e. dichloroethane/acetonitrile, 1:1, 3 mL) to 96 corresponding BOHDAN MINIBLOCK cartridges containing PS-NCO resin (polystyrene functionalized with isocyanate groups; available from Argonaut Technologies, Inc.) (6 equiv.). The cartridges were capped and shaken for 3 days. The products were filtered into individual vials and the resin was washed with DCE/MeCN (1:1, 2x, 0.5 mL). An aliquot from each vial was removed for LC/MS analysis, and the remaining solvent was removed using a SPEEDVAC concentrator to provide desired products, Examples 20-110.

Preparation of Examples 111-154 and 171
Ex. 111
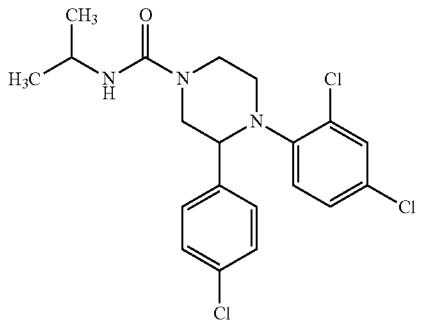
Ex. 112
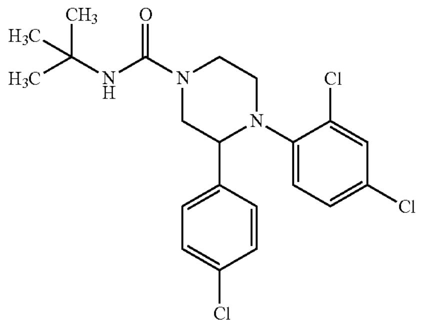
Ex. 113
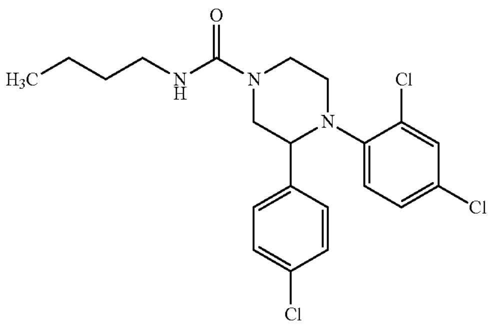
Ex. 114
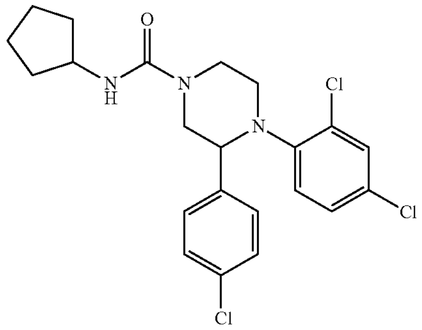
-continued
Ex. 115
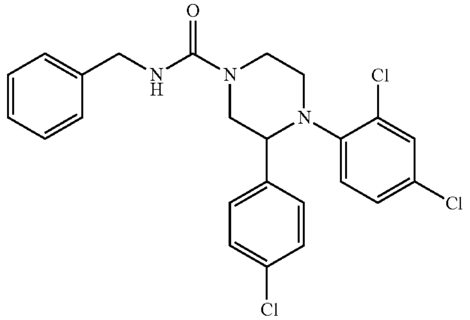
Ex. 116
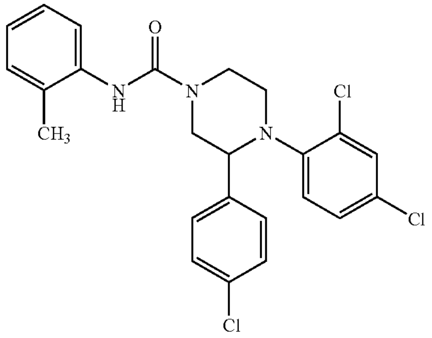
Ex. 117
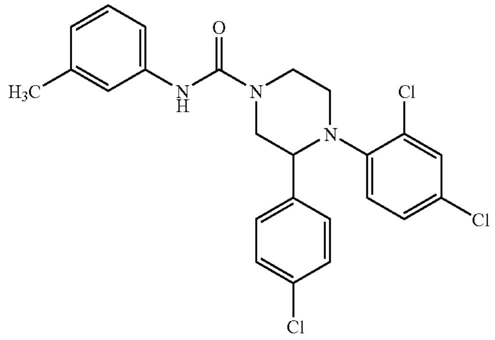
Ex. 118
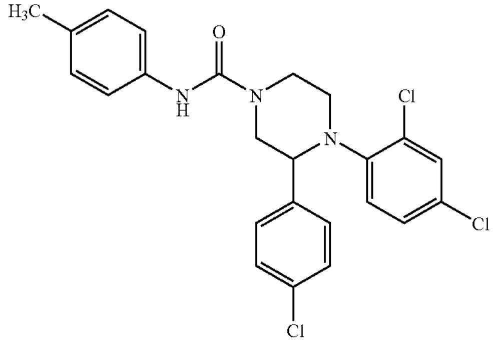

-continued
Ex. 119
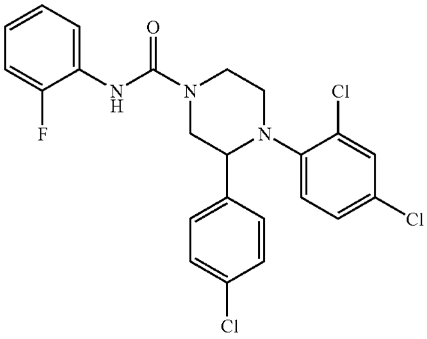
Ex. 120
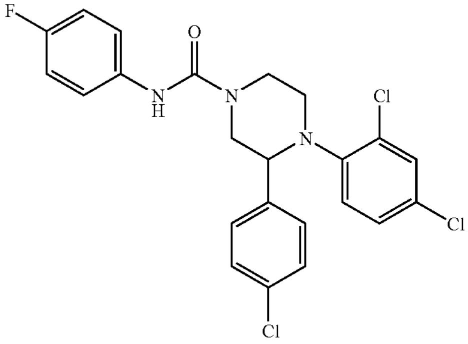
Ex. 121
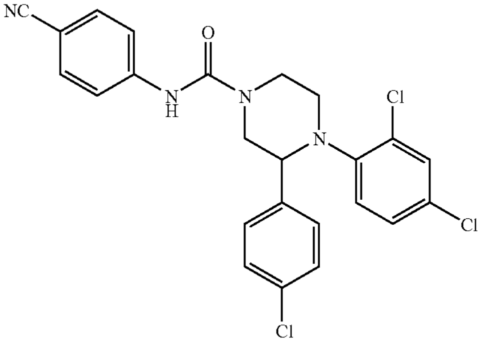
Ex. 122
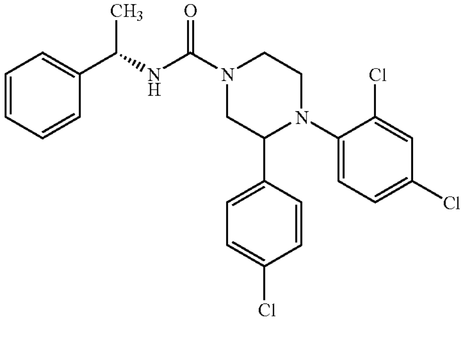
-continued
Ex. 123
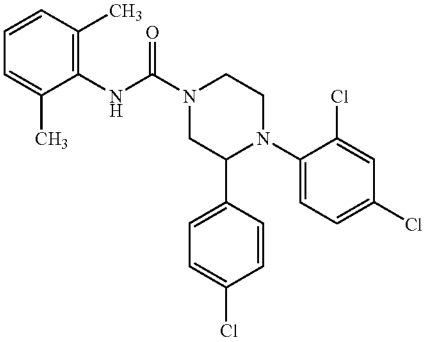
Ex. 124
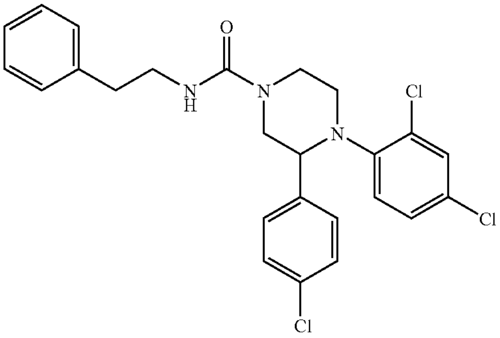
Ex. 125
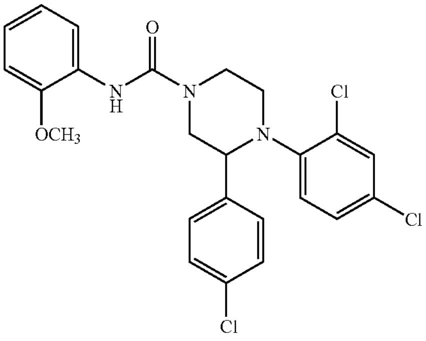
Ex. 126
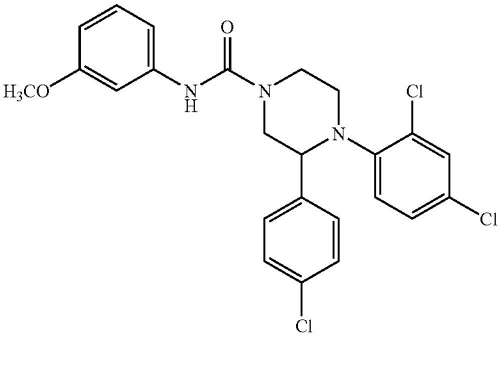

-continued
Ex. 127
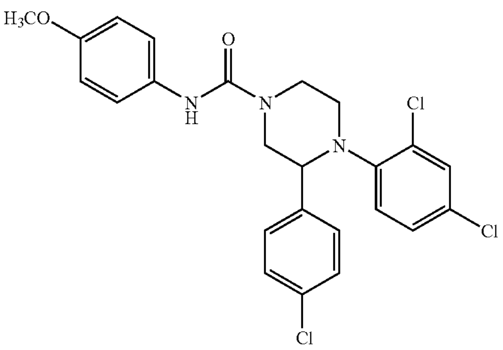
Ex. 128
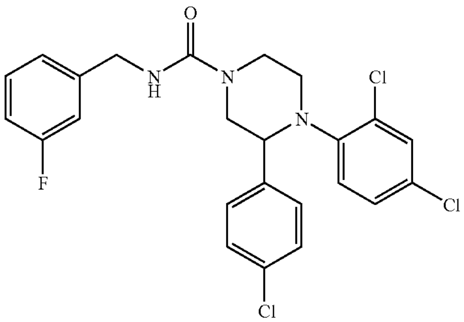
Ex. 129
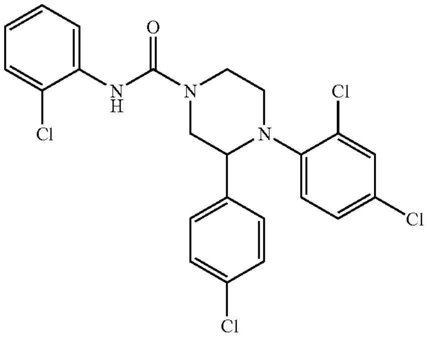
Ex. 130
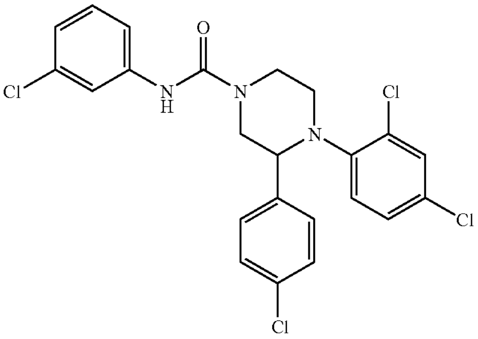
-continued
Ex. 131
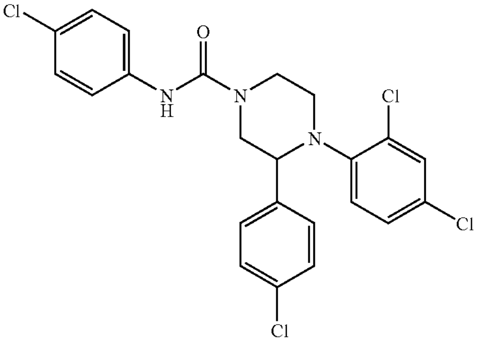
Ex. 132
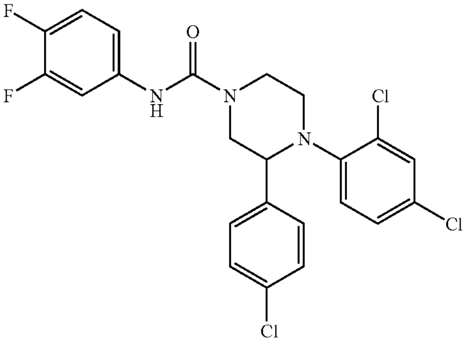
Ex. 133
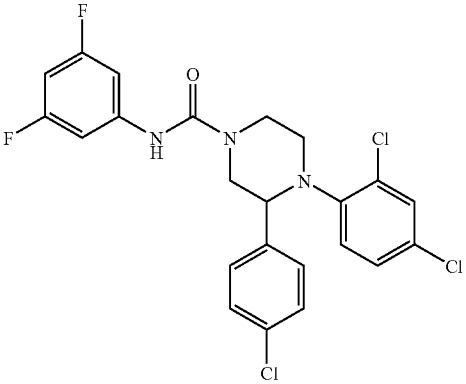
Ex. 134
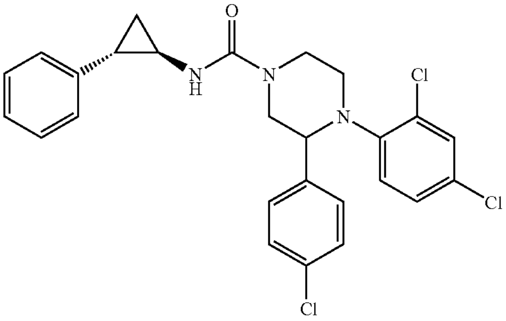

-continued
Ex. 135
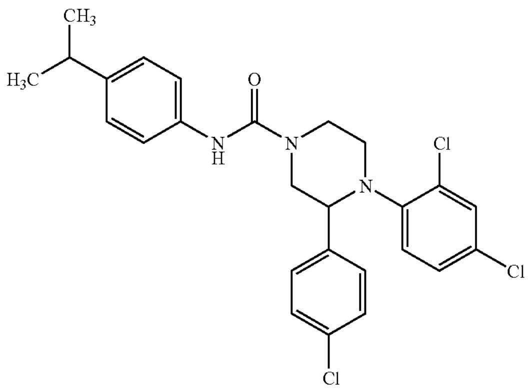
Ex. 136
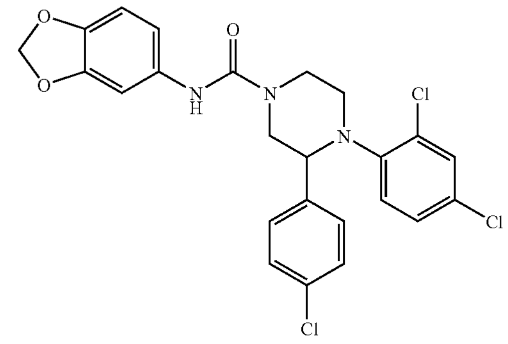
Ex. 137
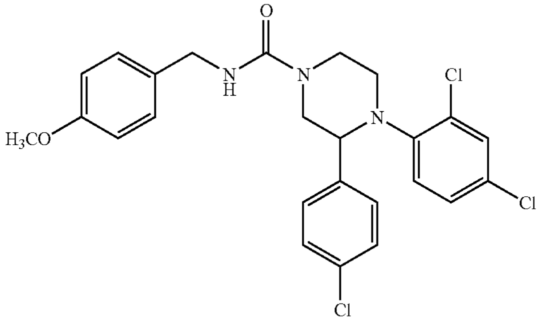
Ex. 138
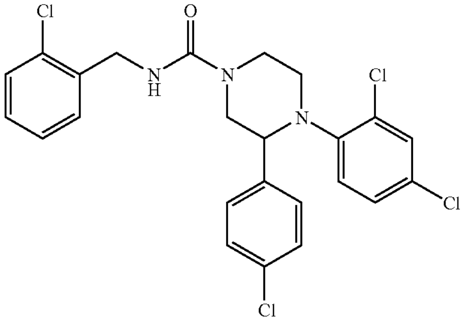
-continued
Ex. 139
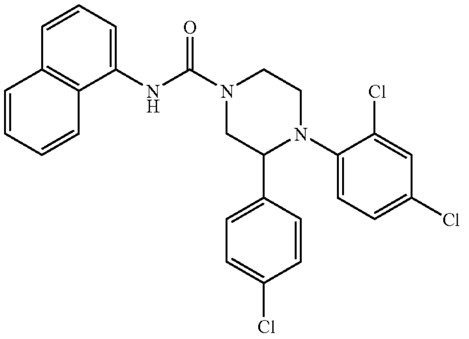
Ex. 140
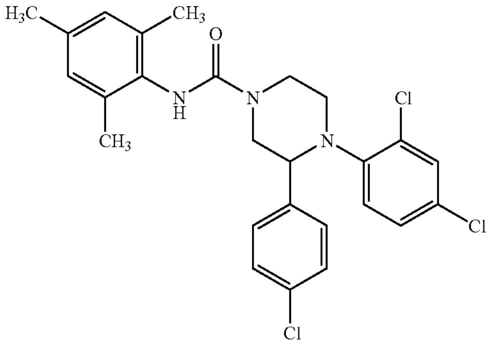
Ex. 141
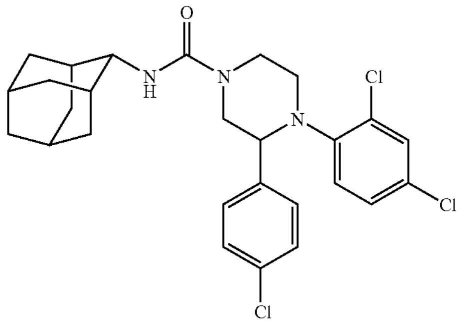
Ex. 142
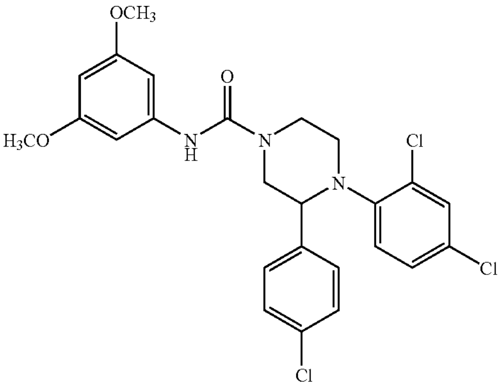

-continued
Ex. 143
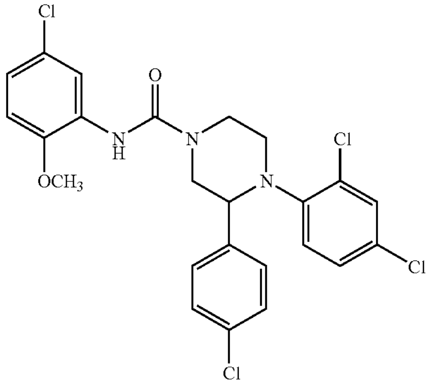
Ex. 144
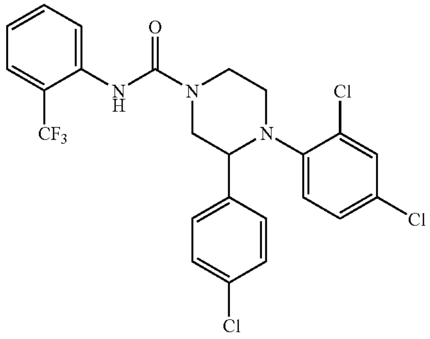
Ex. 145
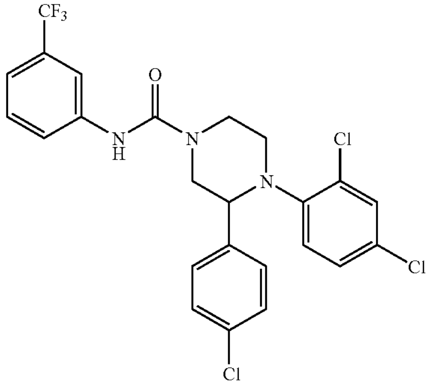
Ex. 146
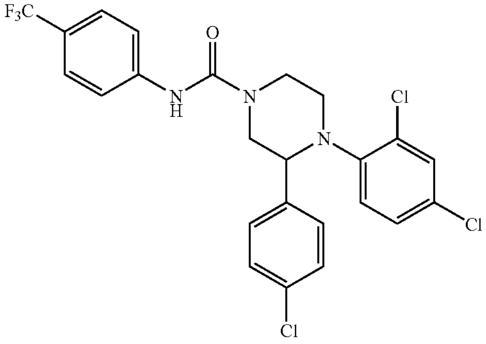
-continued
Ex. 147
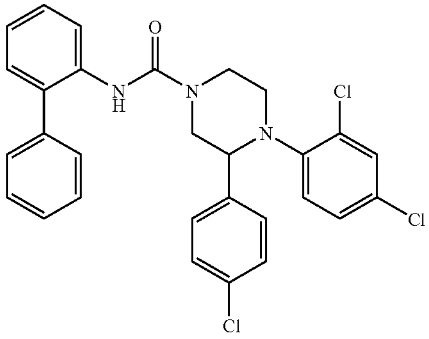
Ex. 148
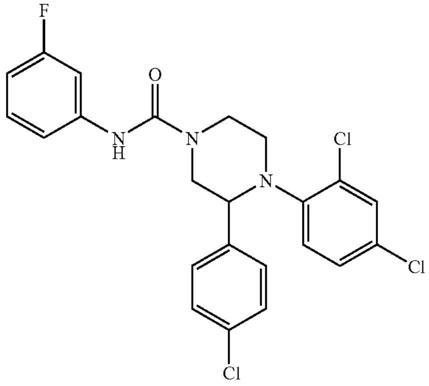
Ex. 149
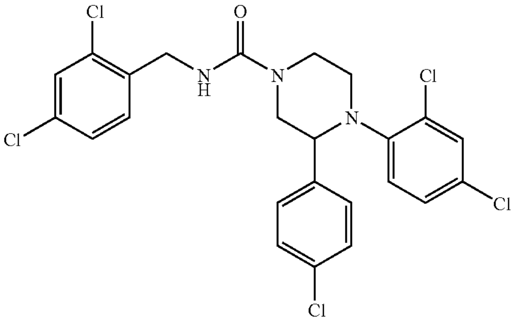
Ex. 150
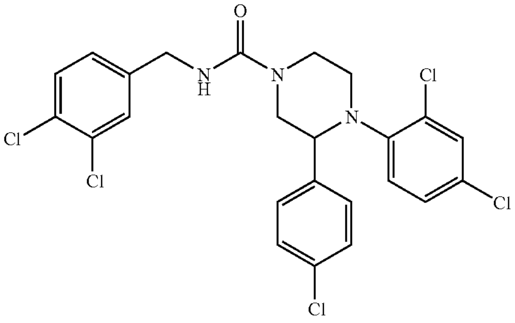

-continued

Ex. 151

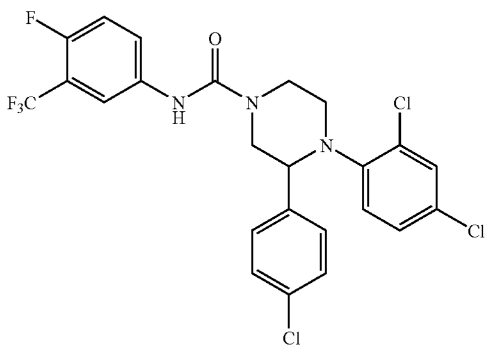

Ex. 152

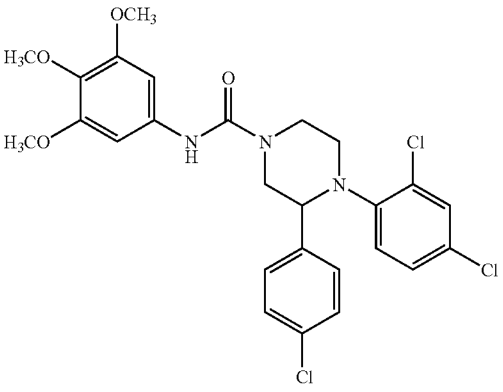

Ex. 153

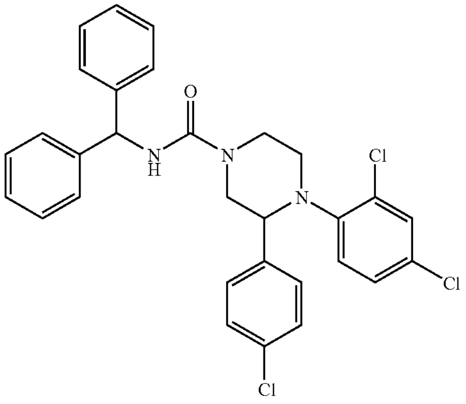

Ex. 154

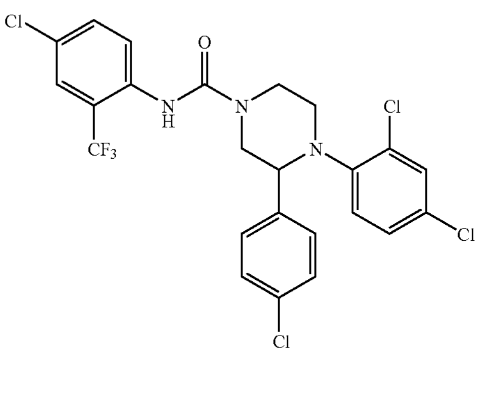

-continued

Ex. 171

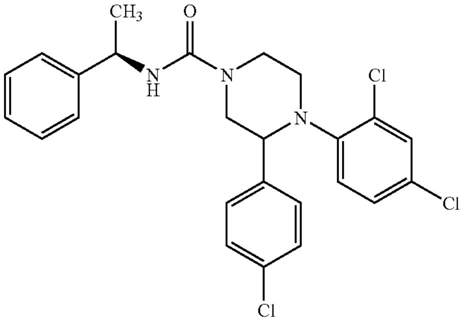

Examples 111-154 and 171 were prepared using the following parallel synthetic method.

Scheme 4

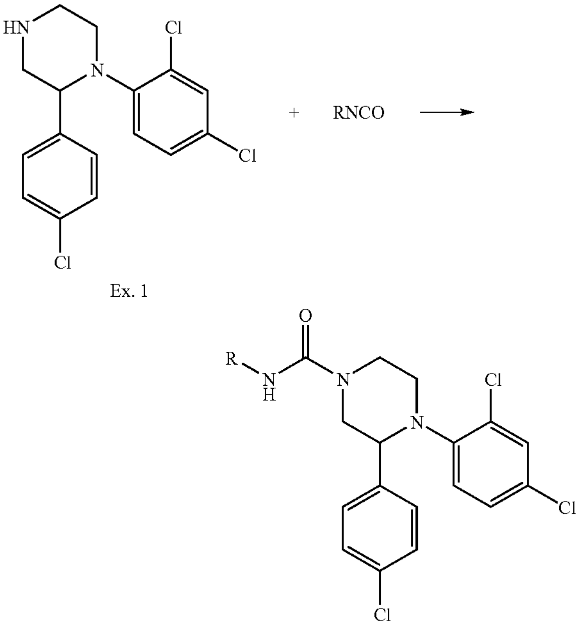

A dichloroethane:acetonitrile (1:1) stock solution of piperazine Example 1 (1 mL, 0.023 mmol) was added to 48 wells of a deep well polypropylene microtiter plate. 0.5 M stock solutions of each individual isocyanates (RNCO) (Table II, below) in dichloromethane (0.14 mL, 0.07 mmol) were added to the plate, which was then sealed and shaken at 25° C. for 20 h. The solutions were then filtered through a polypropylene frit into a second microtiter plate containing PS-Isocyanate resin (i.e., polystyrene resin functionalized with isocyanate groups, available from Argonaut Technologies, Inc.) (0.046 g, 0.07 mmol) and PS-Trisamine resin (i.e., polystyrene resin functionalized with the tris-(2-aminoethyl)amine group, available from Argonaut Technologies, Inc.) (0.042 g, 0.18 mmol). After the top plate was washed with MeCN (acetonitrile) (0.5 mL/well), the plate was removed, the bottom plate sealed, and then shaken for 16 h at 25° C. The solutions were then filtered through a polypropylene frit into a 96-well collection plate. The wells of the top plate were washed with MeCN (0.5 mL/well) and the top plate removed. The resultant solutions in the collection plate were transferred into vials and the solvent removed in vacuo using a SPEEDVAC. The resulting samples were evaluated by LC/MS and those that were >70% pure are listed above.
TABLE II
| Isocyanates Used | |
|---|---|
| Example | Isocyanate |
| 111 | 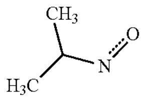 |
| 112 | 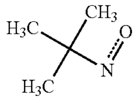 |
| 113 | 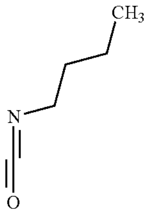 |
| 114 | 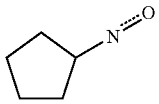 |
| 115 | 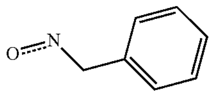 |
| 116 | 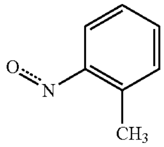 |
| 117 | 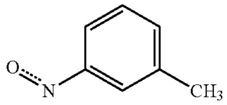 |
| 118 | 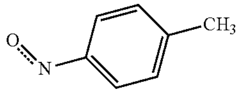 |
| 119 | 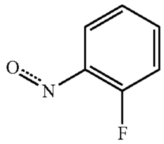 |
| 120 | 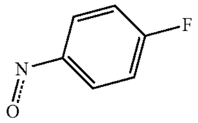 |
| 121 | 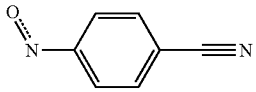 |
TABLE II-continued
| Isocyanates Used | |
|---|---|
| Example | Isocyanate |
| 122 | 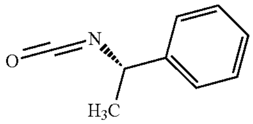 |
| 123 | 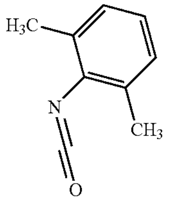 |
| 124 | 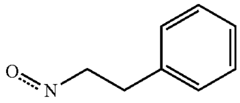 |
| 125 | 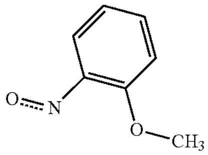 |
| 126 | 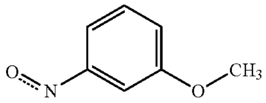 |
| 127 | 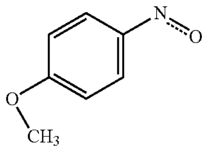 |
| 128 | 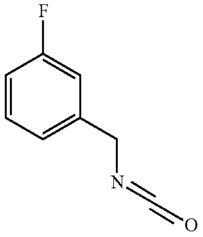 |
| 129 | 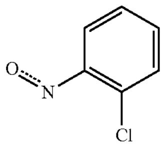 |
| 130 | 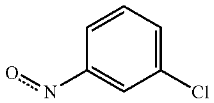 |

TABLE II-continued
| Isocyanates Used | |
|---|---|
| Example | Isocyanate |
| 131 | 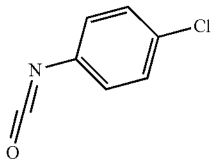 |
| 132 | 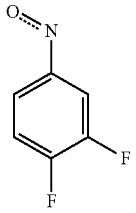 |
| 133 | 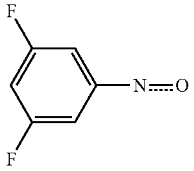 |
| 134 | 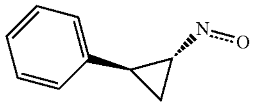 |
| 135 | 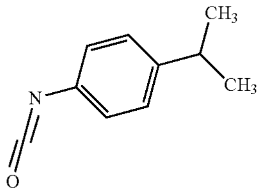 |
| 136 | 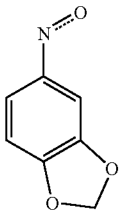 |
| 137 | 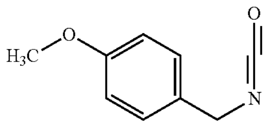 |
| 138 | 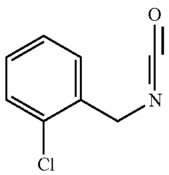 |
TABLE II-continued
| Isocyanates Used | |
|---|---|
| Example | Isocyanate |
| 139 | 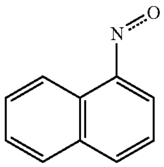 |
| 140 | 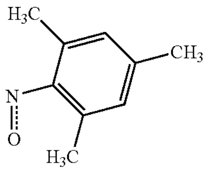 |
| 141 | 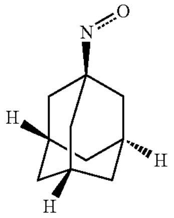 |
| 142 | 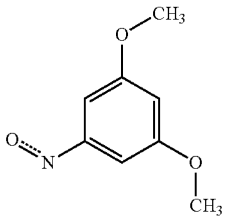 |
| 143 | 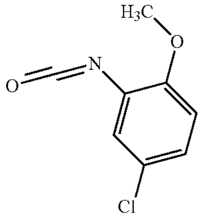 |
| 144 | 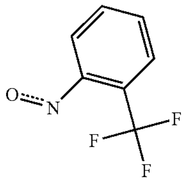 |
| 145 | 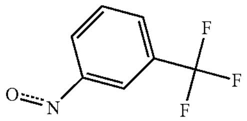 |
| 146 | 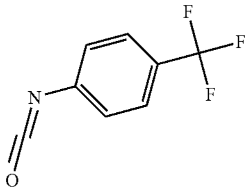 |

TABLE II-continued
| Isocyanates Used | |
|---|---|
| Example | Isocyanate |
| 147 | 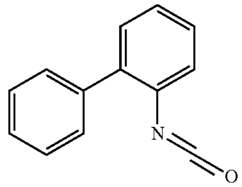 |
| 148 | 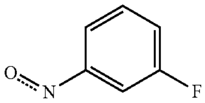 |
| 149 | 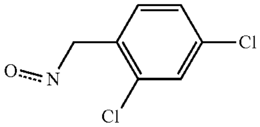 |
| 150 | 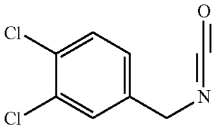 |
| 151 | 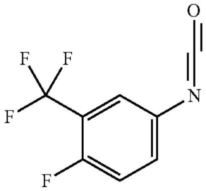 |
| 152 | 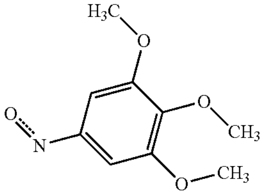 |
| 153 | 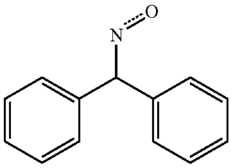 |
| 154 | 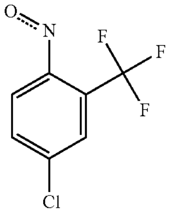 |
TABLE II-continued
| Isocyanates Used | |
|---|---|
| Example | Isocyanate |
| 171 | 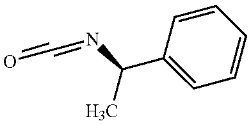 |
Preparation of Examples 155-170 and 172-233
Ex. 155
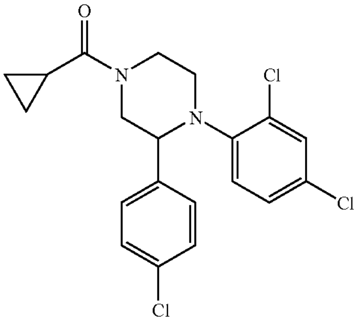
Ex. 156
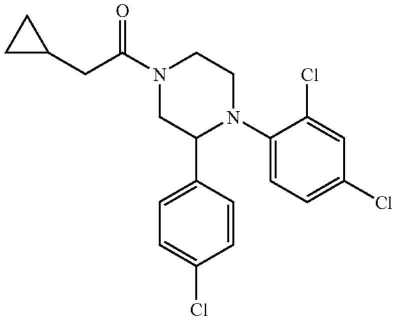
Ex. 157
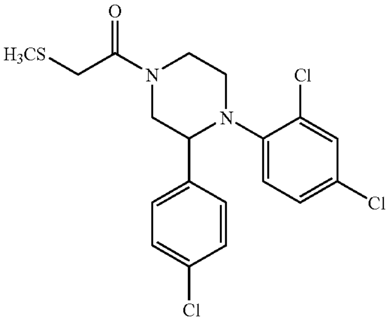

Ex. 158
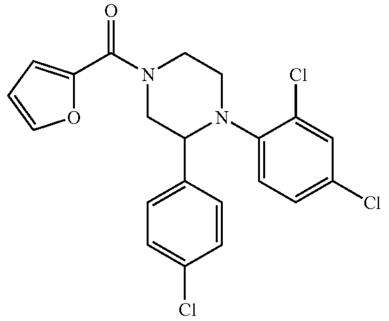
Ex. 159
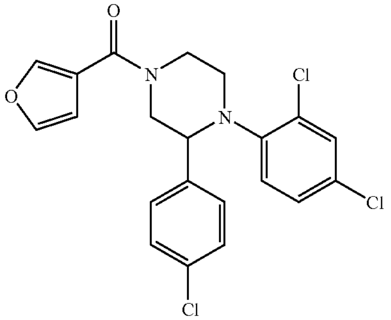
Ex. 160
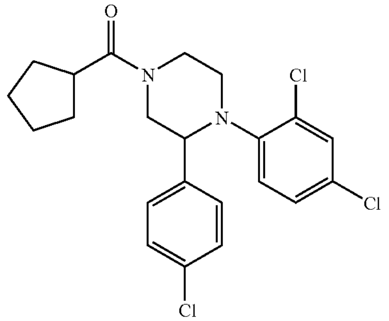
Ex. 161
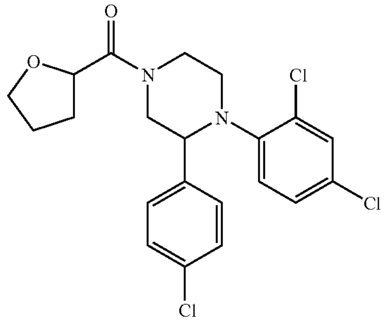
Ex. 162
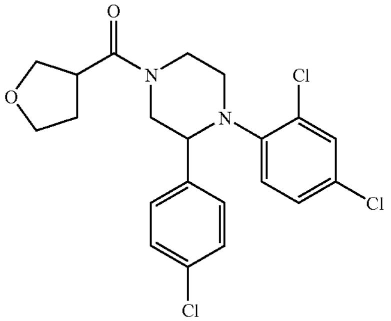
Ex. 163
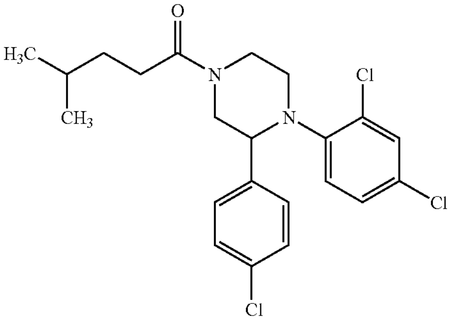
Ex. 164
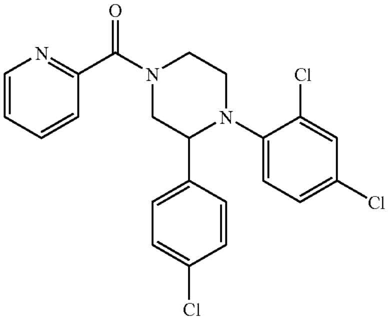
Ex. 165
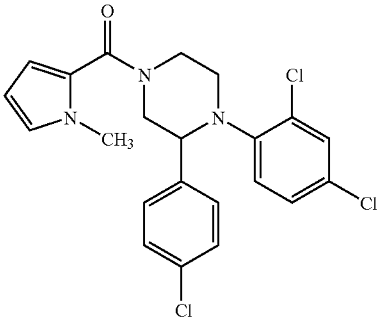
Ex. 166
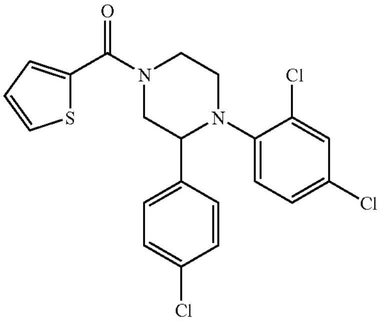
Ex. 167
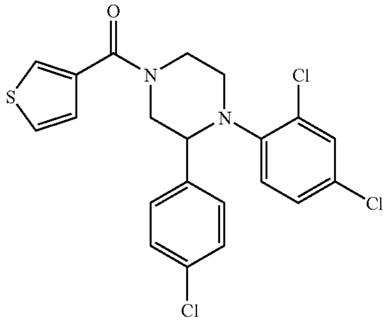

-continued
Ex. 168
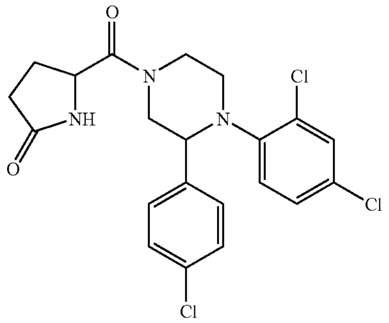
Ex. 169
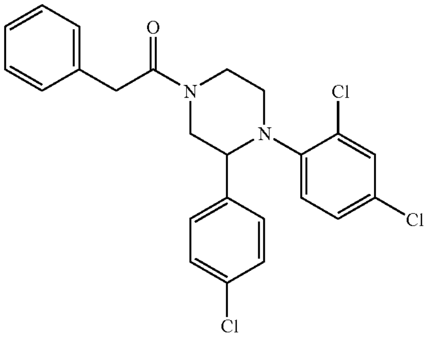
Ex. 170
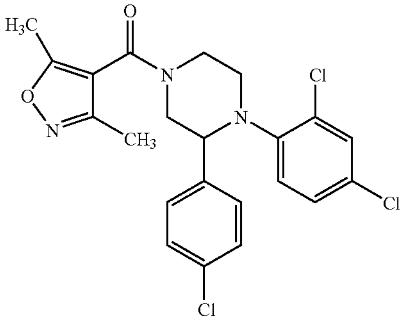
Ex. 172
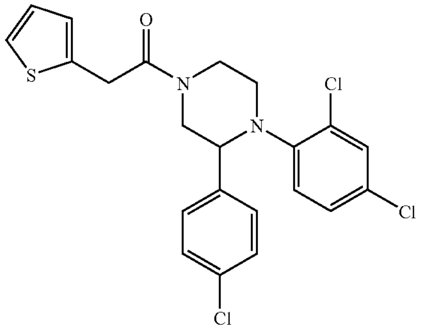
Ex. 173
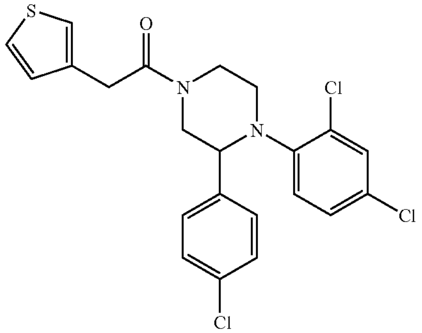
-continued
Ex. 174
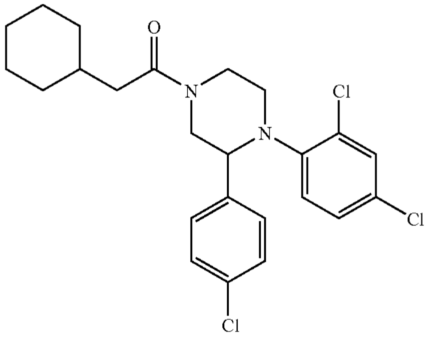
Ex. 175
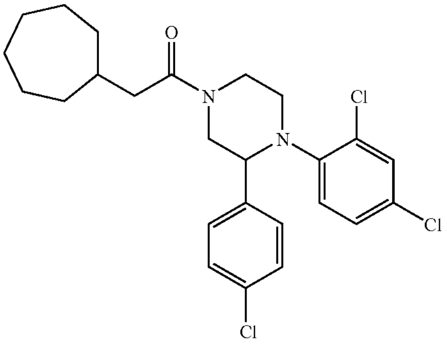
Ex. 176
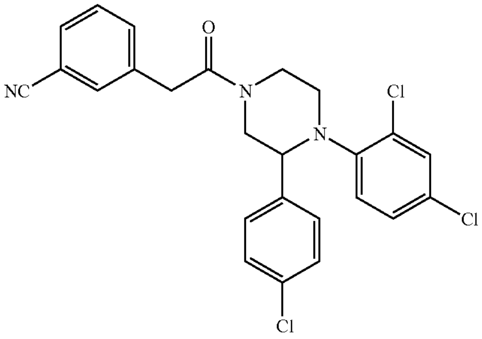
Ex. 177
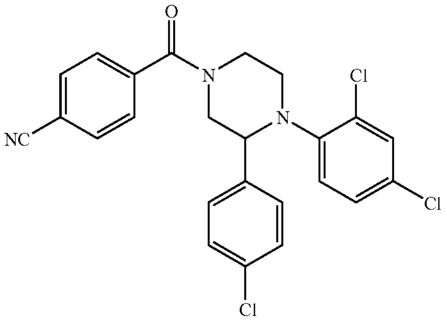

-continued
Ex. 178
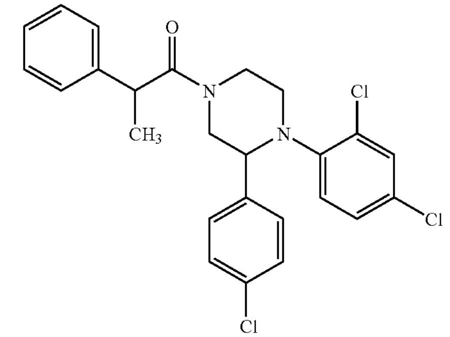
Ex. 179
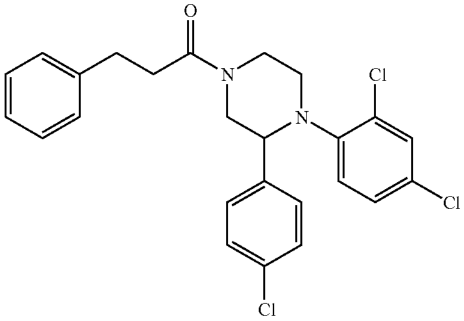
Ex. 180
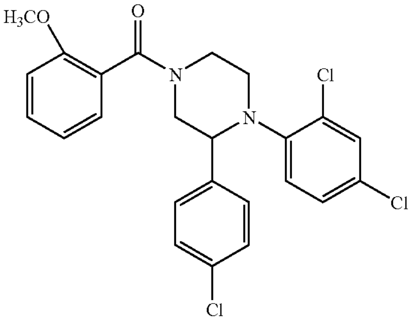
Ex. 181
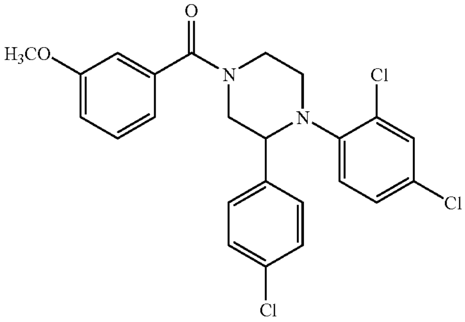
Ex. 182
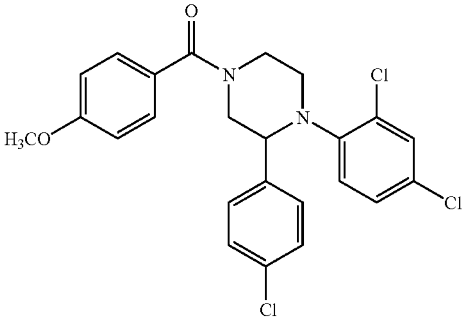
-continued
Ex. 183
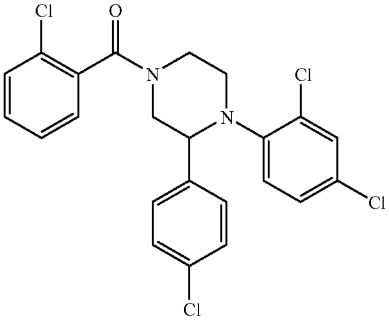
Ex. 184
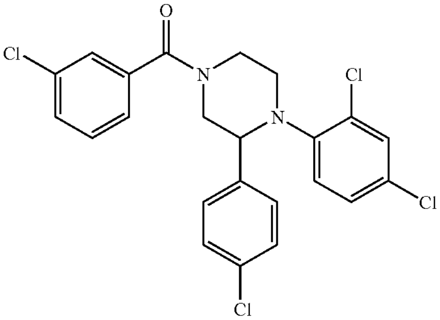
Ex. 185
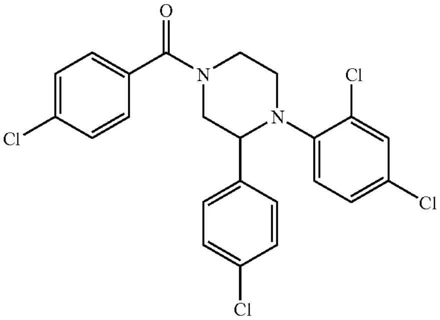
Ex. 186
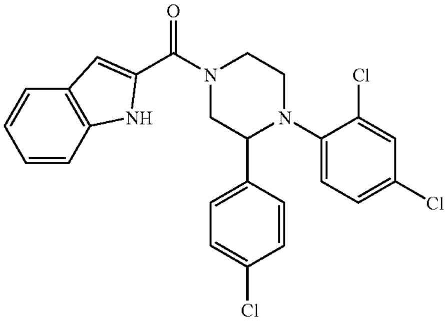
Ex. 187
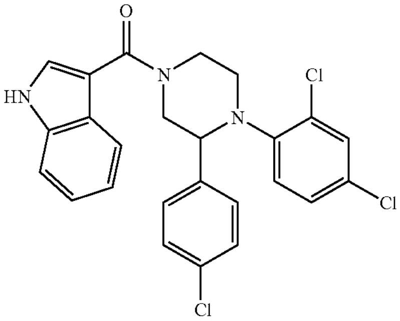

-continued
Ex. 188
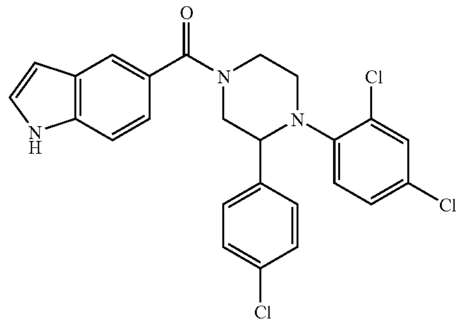
Ex. 189
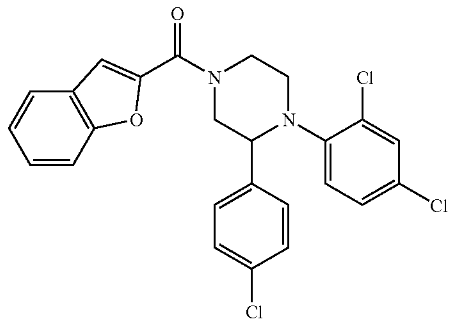
Ex. 190
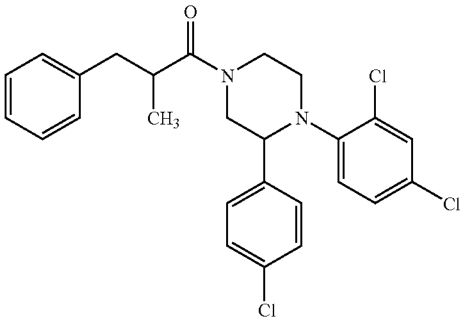
Ex. 191
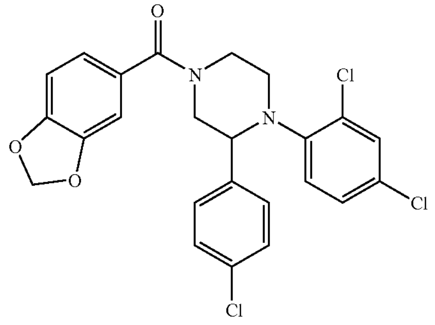
-continued
Ex. 192
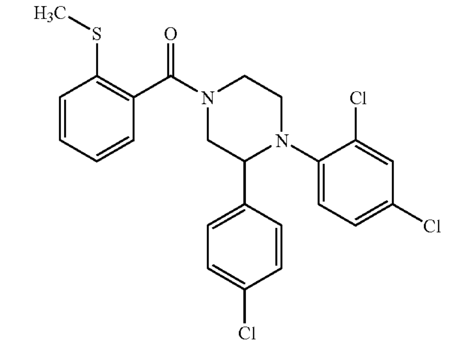
Ex. 193
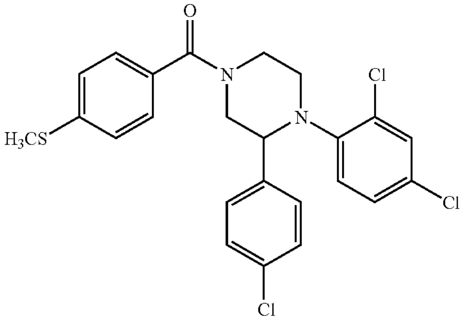
Ex. 194
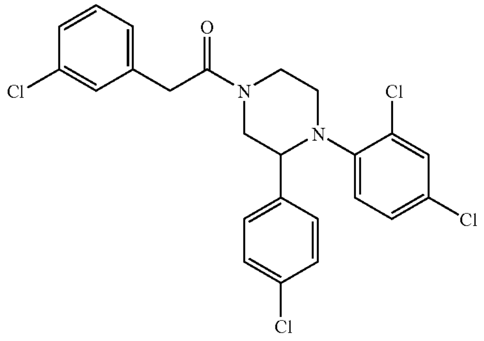
Ex. 195
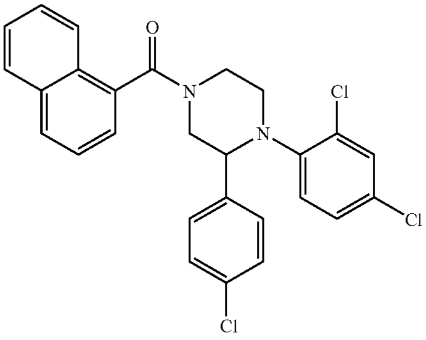

-continued
Ex. 196
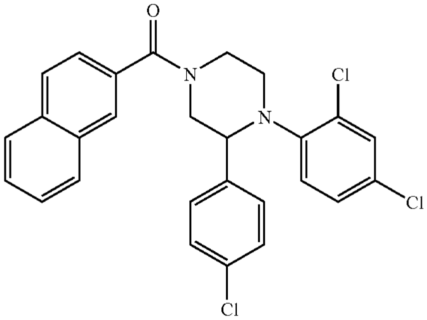
Ex. 197
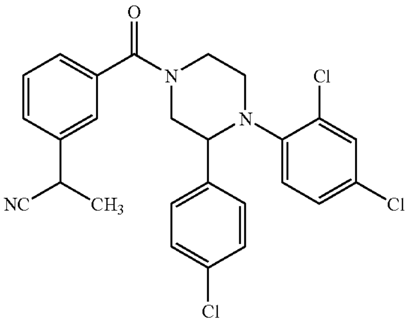
Ex. 198
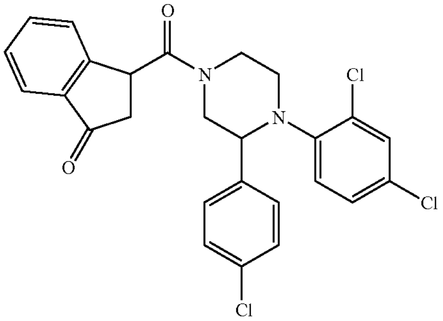
Ex. 199
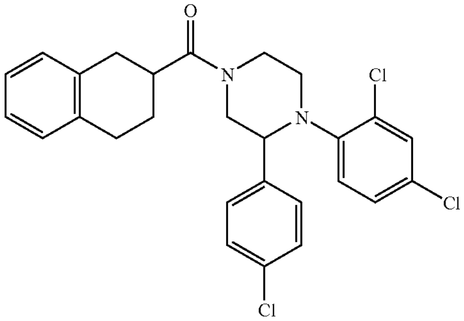
Ex. 200
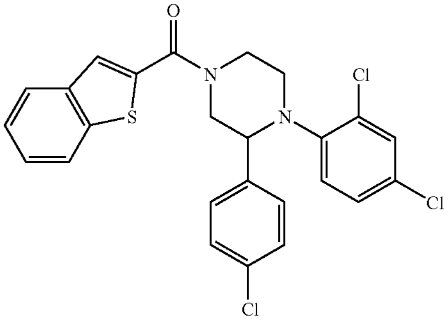
-continued
Ex. 201
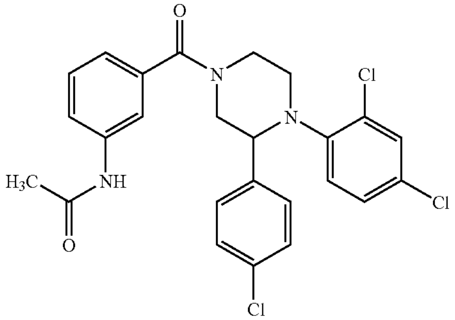
Ex. 202
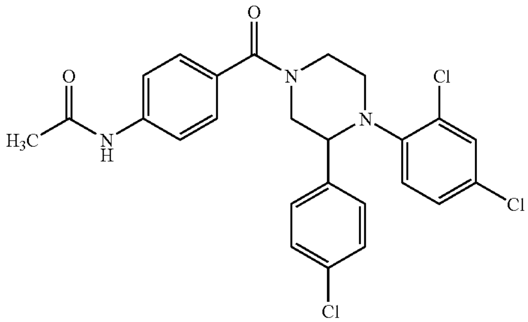
Ex. 203
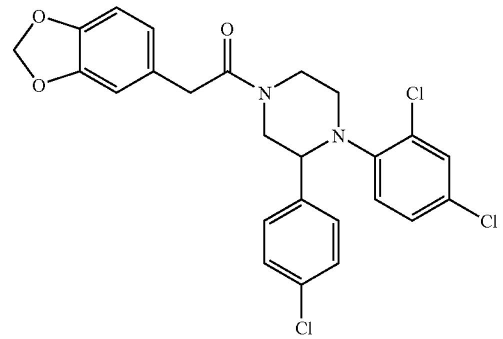
Ex. 204
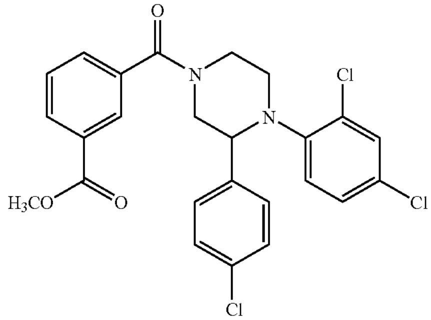

Ex. 205
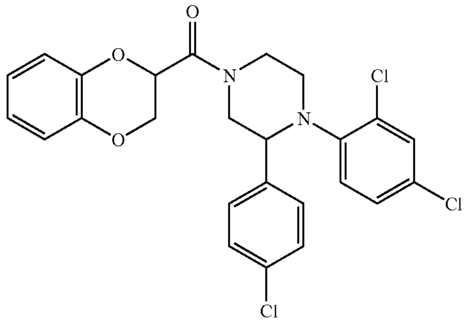
Ex. 206
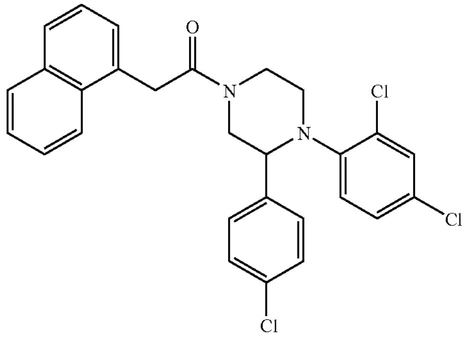
Ex. 207
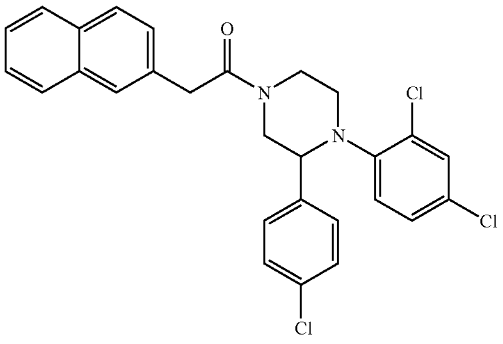
Ex. 208
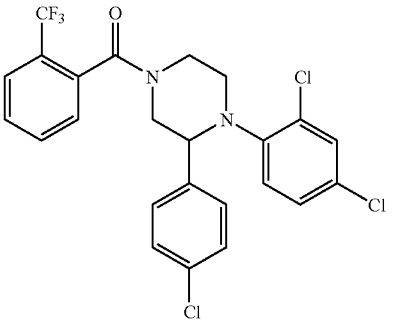
Ex. 209
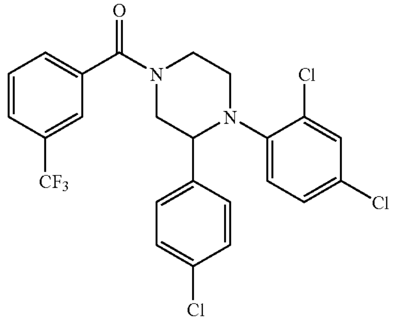
Ex. 210
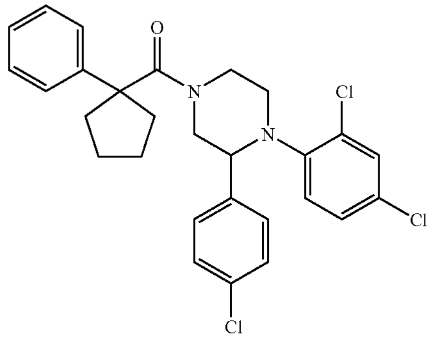
Ex. 211
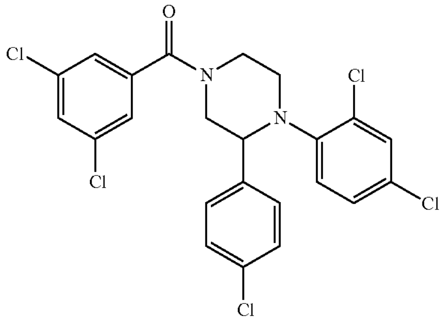
Ex. 212
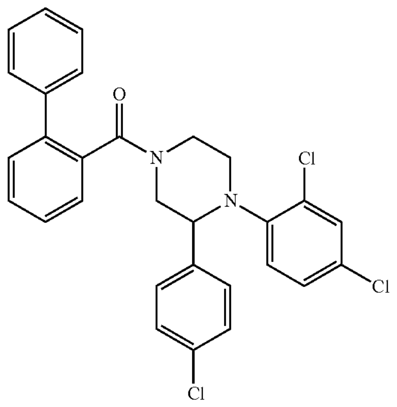

-continued
Ex. 213
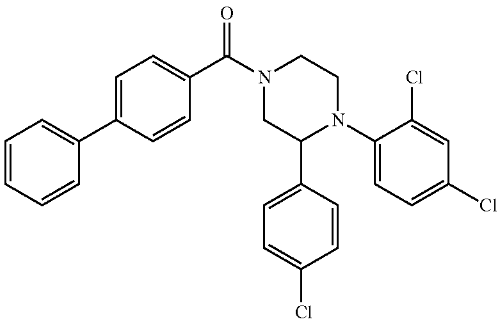
Ex. 214
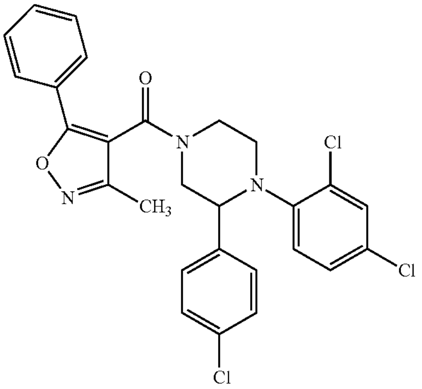
Ex. 215
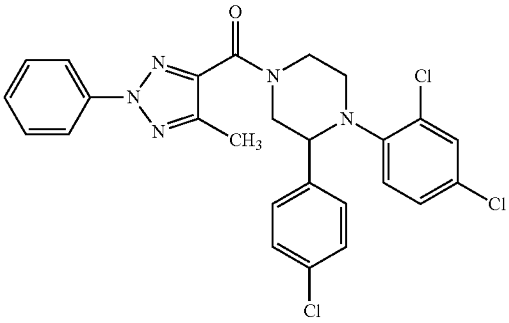
Ex. 216
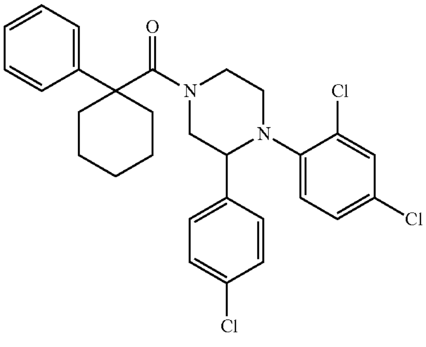
-continued
Ex. 217
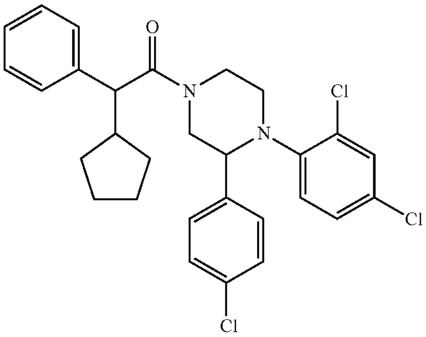
Ex. 218
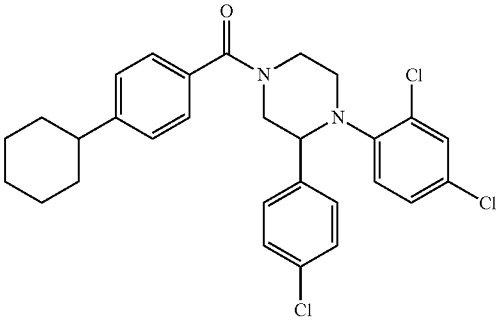
Ex. 219
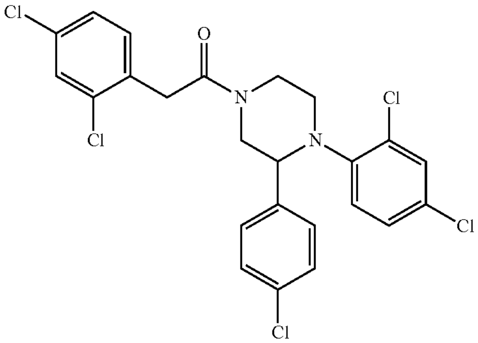
Ex. 220
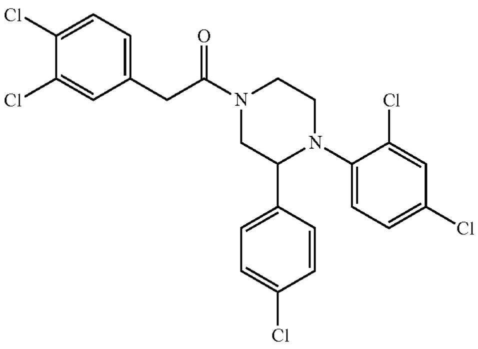

-continued
Ex. 221
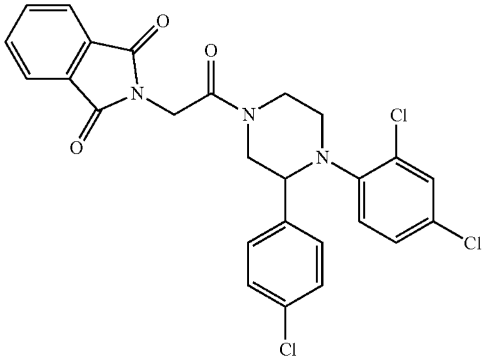
Ex. 222
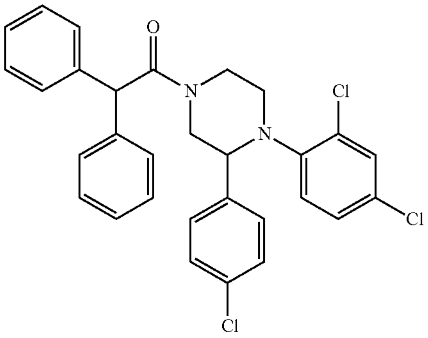
Ex. 223
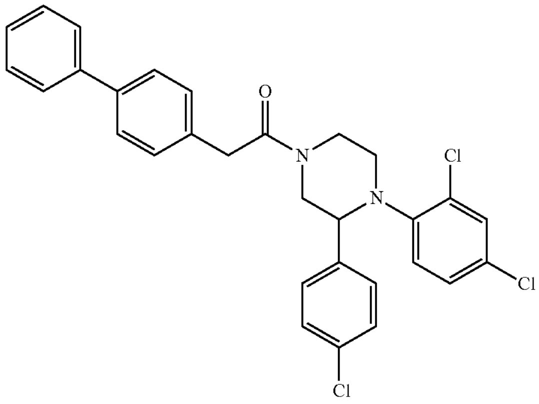
Ex. 224
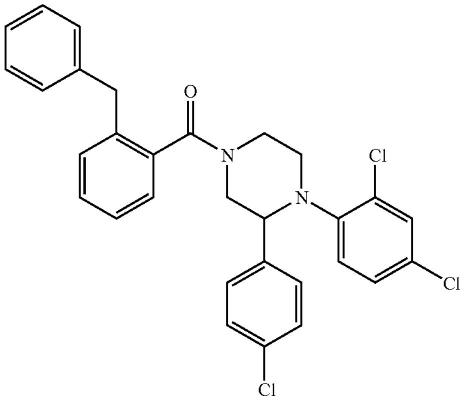
-continued
Ex. 225
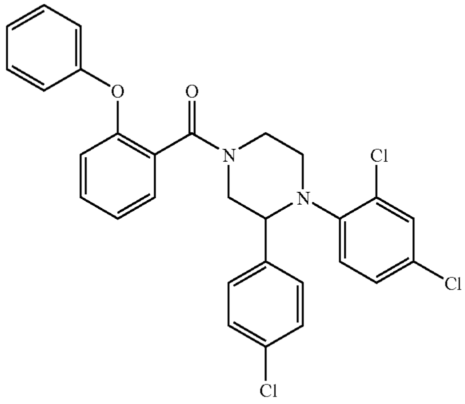
Ex. 226
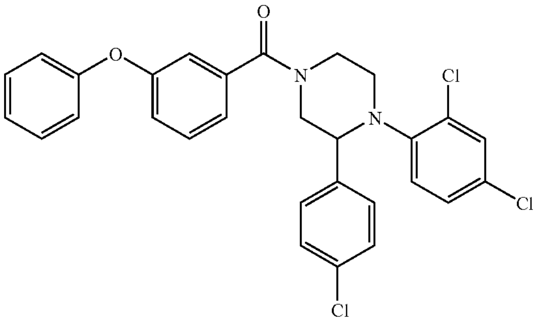
Ex. 227
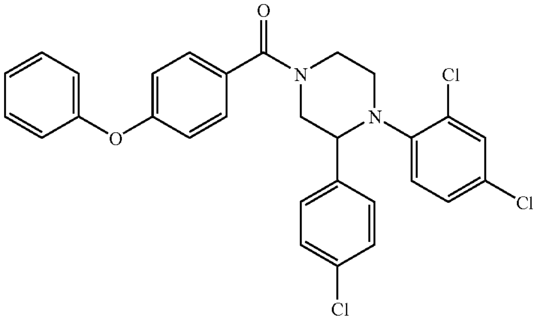
Ex. 228
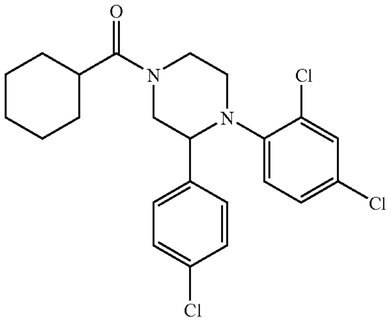

-continued

Ex. 229

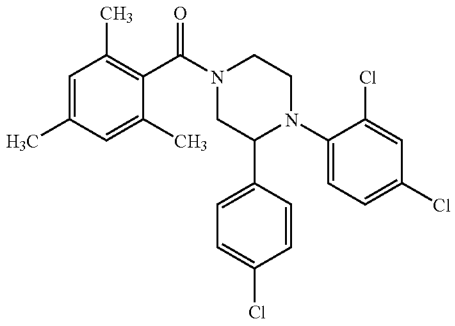

Ex. 230

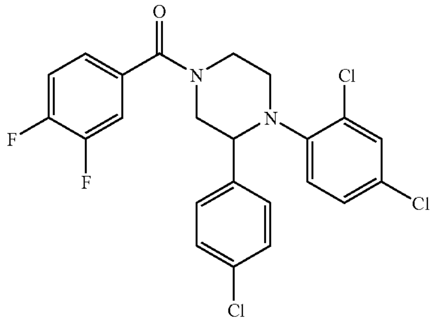

Ex. 231

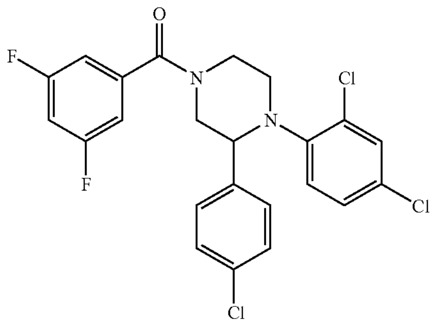

Ex. 232

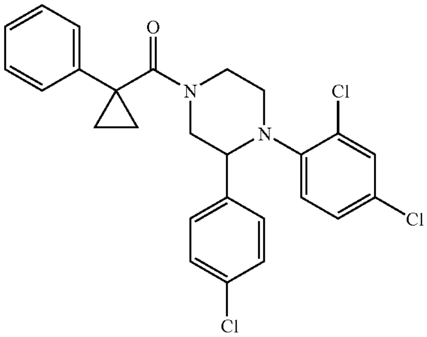

-continued

Ex. 233

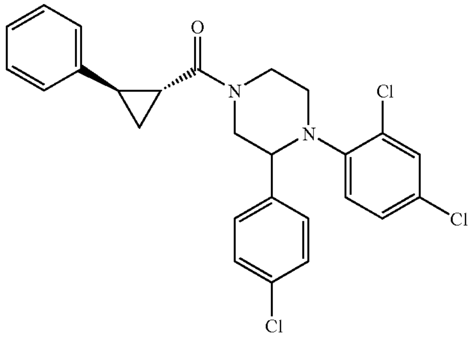

Examples 155-170 and 172-233 were prepared using the following parallel synthetic method.

Scheme 5

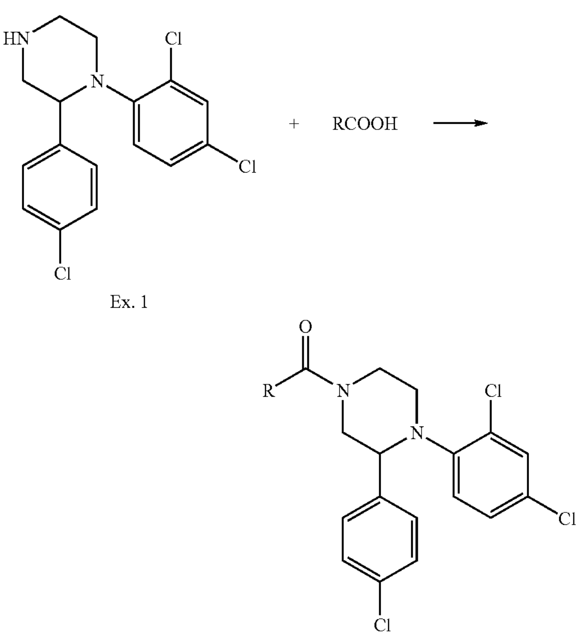

PS-EDC resin (i.e., polystyrene functionalized with EDC-1-(dimethylaminopropyl)-3-ethylcarbodiimide—available from Polymer Laboratories) (0.082 g, 1.42 mmol) was added to 96 wells of a deep well polypropylene microtiter plate followed by a MeCN/THF (3:2) stock solution (1 mL) of piperazine Example 1 (0.021 mmol) and HOBt (i.e., 1-hydroxybenzotriazole hydrate) (0.031 mmol). 1 M stock solutions of each of the individual acids (RCOOH) (Table III, below) (0.042 mL, 0.042 mmol) were added to the wells, which were then sealed and shaken at 25° C. for 18 h. The solutions were filtered through a polypropylene frit into a second microtiter plate containing PS-Isocyanate resin (3 equiv., 0.07 mmol) and PS-Trisamine resin (8 equiv., 0.17 mmol). After the top plate was washed with MeCN (0.5 mL/well), the plate was removed, the bottom microtiter plate was sealed and then shaken at 25° C. for 16 h. The solutions were filtered through a polypropylene frit into a 96-well collection plate. The wells of the top plate were then washed with MeCN (0.5 mL/well), and the plate removed. The resultant solutions in the collection plate were transferred into vials and the solvent removed in vacuo using a SPEEDVAC. The resulting samples were evaluated by LCMS and those that were >70% pure are shown above.
TABLE III
Carboxylic Acids Used to Prepare Examples 155-170 and 172-233
| Example | Carboxylic Acid Structure |
|---|---|
| 155 | 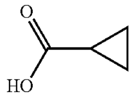 |
| 156 | 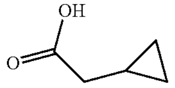 |
| 157 | 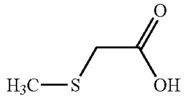 |
| 158 | 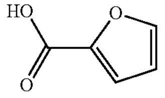 |
| 159 | 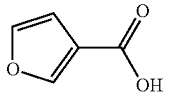 |
| 160 | 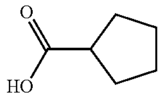 |
| 161 | 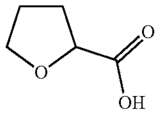 |
| 162 | 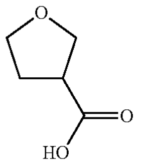 |
| 163 | 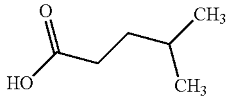 |
| 164 | 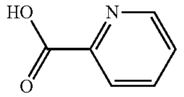 |
| 165 | 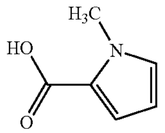 |
| 166 | 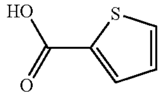 |
TABLE III-continued
Carboxylic Acids Used to Prepare Examples 155-170 and 172-233
| Example | Carboxylic Acid Structure |
|---|---|
| 167 | 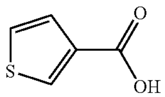 |
| 168 | 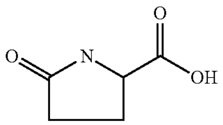 |
| 169 | 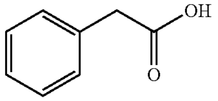 |
| 170 | 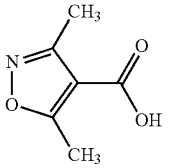 |
| 171 | 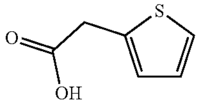 |
| 173 | 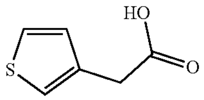 |
| 174 | 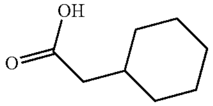 |
| 175 | 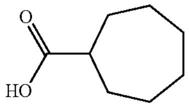 |
| 176 | 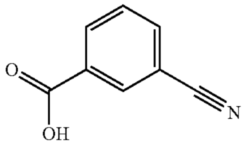 |
| 177 | 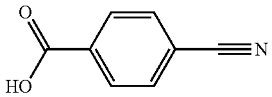 |
| 178 | 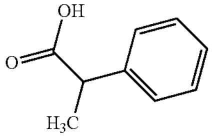 |
| 179 | 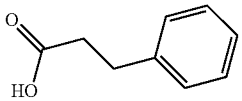 |

TABLE III-continued
| Carboxylic Acids Used to Prepare Examples 155-170 and 172-233 | |
|---|---|
| Example | Carboxylic Acid Structure |
| 180 | 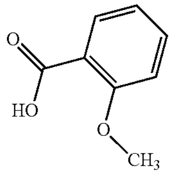 |
| 181 | 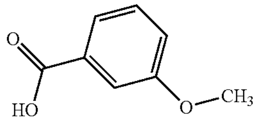 |
| 182 | 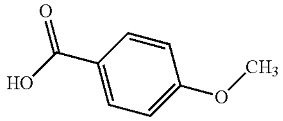 |
| 183 | 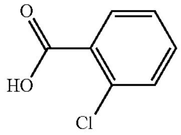 |
| 184 | 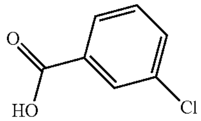 |
| 185 | 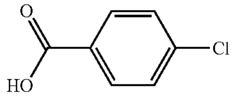 |
| 186 | 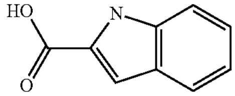 |
| 187 | 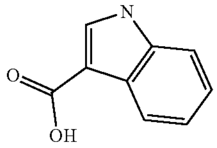 |
| 188 | 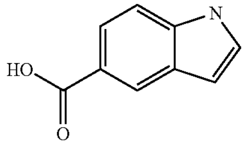 |
| 189 | 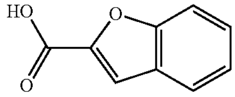 |
| 190 | 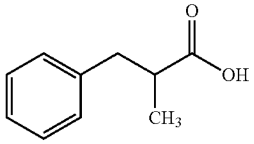 |
TABLE III-continued
| Carboxylic Acids Used to Prepare Examples 155-170 and 172-233 | |
|---|---|
| Example | Carboxylic Acid Structure |
| 191 | 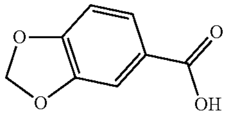 |
| 192 | 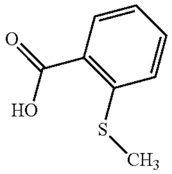 |
| 193 | 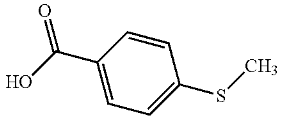 |
| 194 | 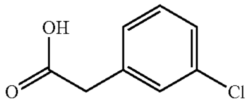 |
| 195 | 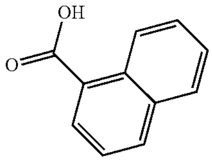 |
| 196 | 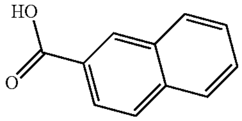 |
| 197 | 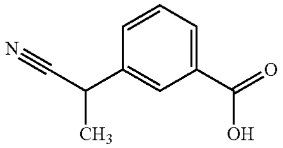 |
| 198 | 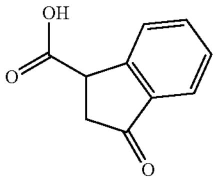 |
| 199 | 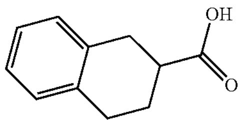 |
| 200 | 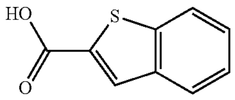 |

TABLE III-continued
Carboxylic Acids Used to Prepare Examples 155-170 and 172-233
| Example | Carboxylic Acid Structure |
|---|---|
| 201 | 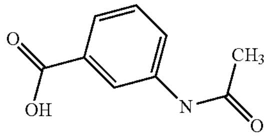 |
| 202 | 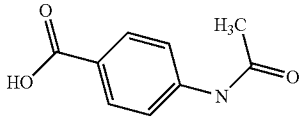 |
| 203 | 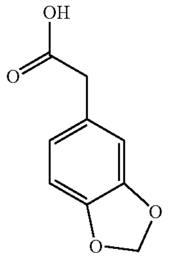 |
| 204 | 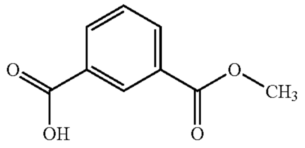 |
| 205 | 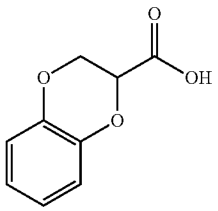 |
| 206 | 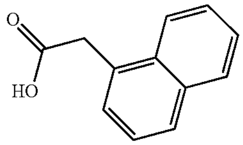 |
| 207 | 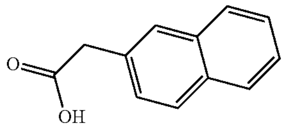 |
| 208 | 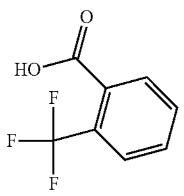 |
TABLE III-continued
Carboxylic Acids Used to Prepare Examples 155-170 and 172-233
| Example | Carboxylic Acid Structure |
|---|---|
| 209 | 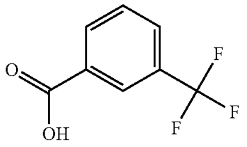 |
| 210 | 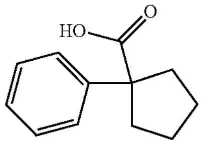 |
| 211 | 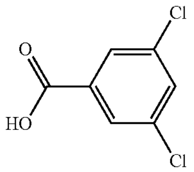 |
| 212 | 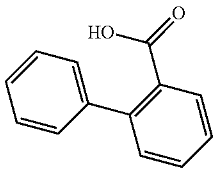 |
| 213 | 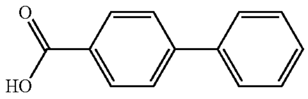 |
| 214 | 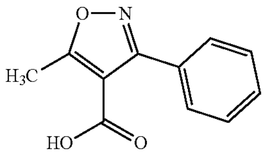 |
| 215 | 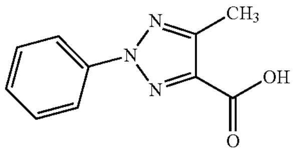 |
| 216 | 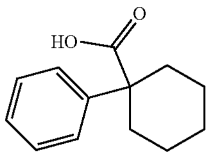 |
| 217 | 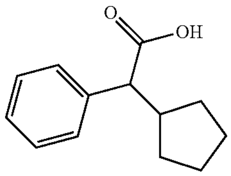 |
| 218 | 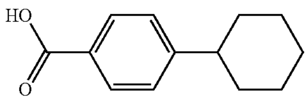 |

TABLE III-continued
| Carboxylic Acids Used to Prepare Examples 155-170 and 172-233 | |
|---|---|
| Example | Carboxylic Acid Structure |
| 219 | 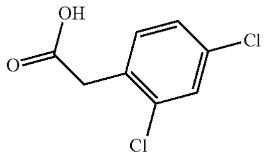 |
| 220 | 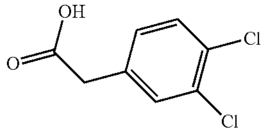 |
| 221 | 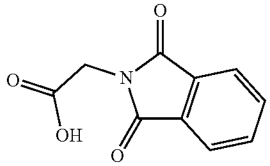 |
| 222 | 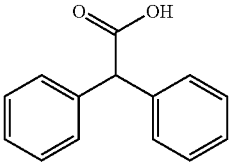 |
| 223 | 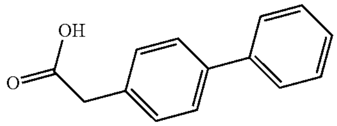 |
| 224 | 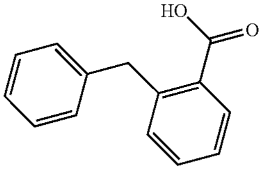 |
| 225 | 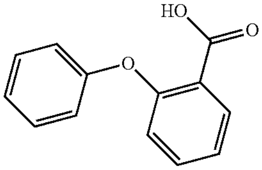 |
| 226 | 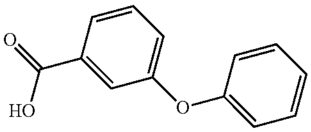 |
| 227 | 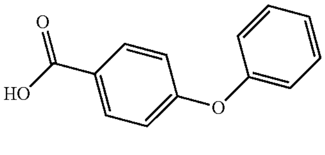 |
TABLE III-continued
| Carboxylic Acids Used to Prepare Examples 155-170 and 172-233 | |
|---|---|
| Example | Carboxylic Acid Structure |
| 228 | 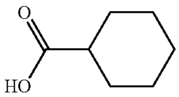 |
| 229 | 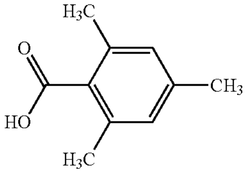 |
| 230 | 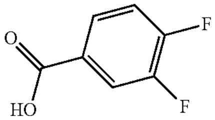 |
| 231 | 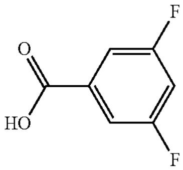 |
| 232 | 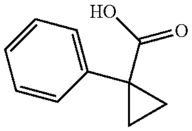 |
| 233 | 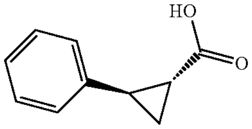 |
Preparation of Examples 234-246
Scheme 6
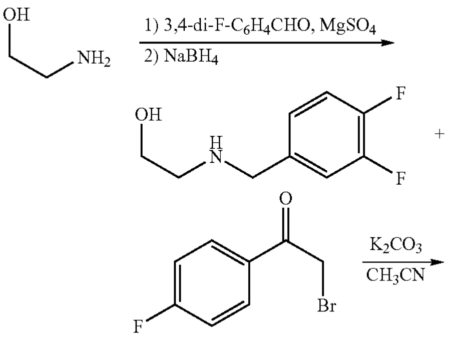

-continued

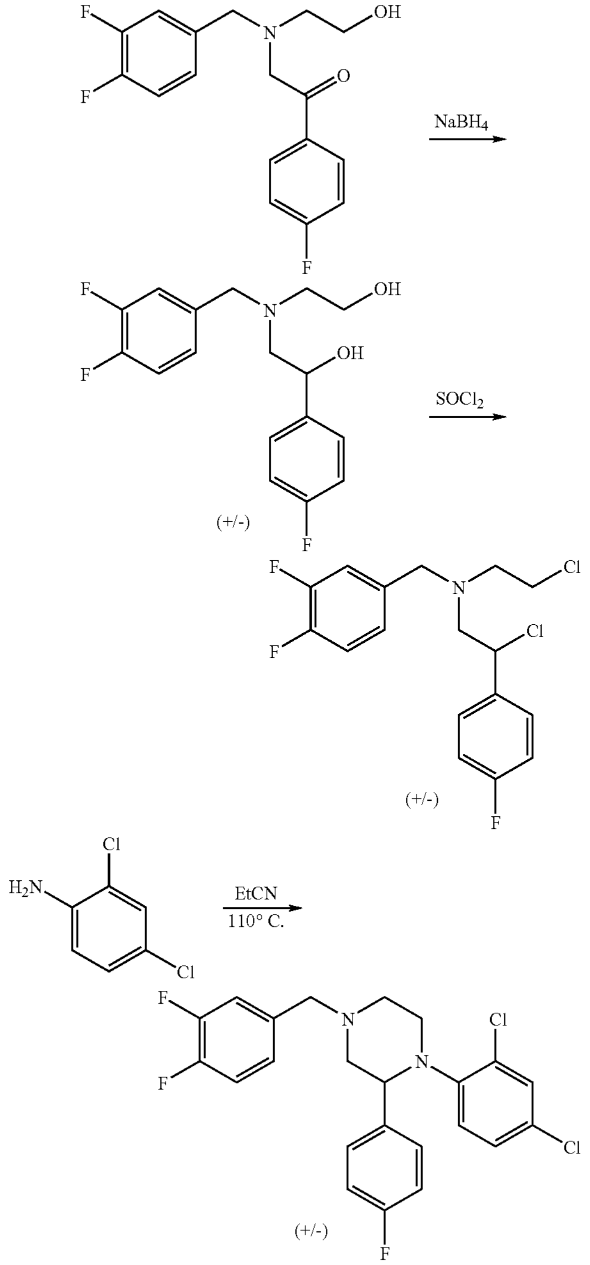

Example 234

Step 1:

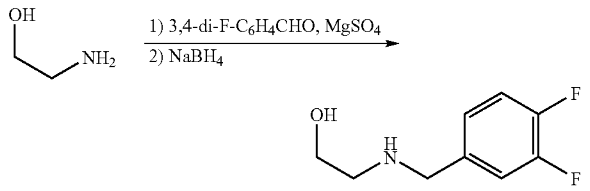

Ethanolamine (3 g), 3,4-difluorobenzaldehyde (7 g), and $MgSO_4$ (15 g) were taken up in $CH_2Cl_2$ and stirred at 25° C. (4 h). The solution was filtered and concentrated, thereby providing the imine as a thick oil. The imine was taken up MeOH and cooled to 0° C. Sodium borohydride (1.9 g) was added in portions at 0° C. After the addition of $NaBH_4$, the reaction was warmed to 25° C. and stirred for 0.5 h. The reaction mixture was quenched with 1 N $HCl_{(aq.)}$. The mixture was concentrated to remove MeOH. The residue was extracted with $Et_2O$. The aqueous layer was cooled to 0° C. and made basic via addition of NaOH pellets (pH=11-12). The aqueous layer was extracted with $CH_2Cl_2$. The combined $CH_2Cl_2$ layers were dried ($MgSO_4$), filtered, and concentrated to furnish the amino-alcohol (6.5 g, 70%) as a thick oil.

Step 2:

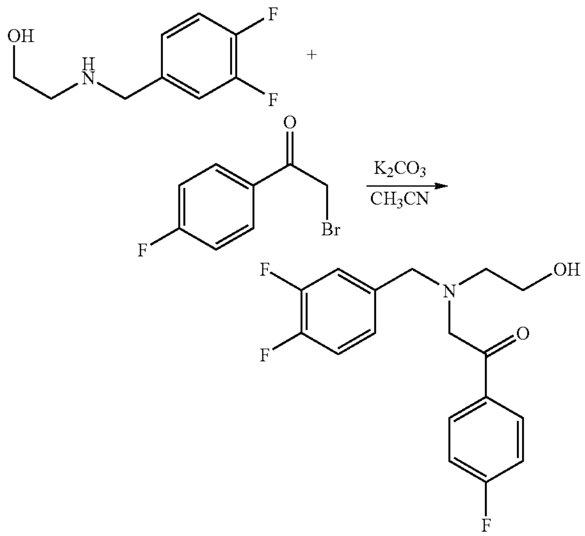

The amino-alcohol (390 mg), bromo-ketone (500 mg), and $K_2CO_3$ (380 mg) were taken up in $CH_3CN$ and stirred at 25° C. (19 h). The solution was concentrated. The residue was partitioned between EtOAc and water. The aqueous layer was extracted with EtOAc. The combined EtOAc layers were washed with brine, dried ($MgSO_4$), and filtered. Concentration gave a yellow oil. Purification via thin-layer preparative chromatography (10% EtOAc in $CH_2Cl_2$, $SiO_2$) gave 610 mg (90%) of the keto-alcohol as an oil.

Step 3:

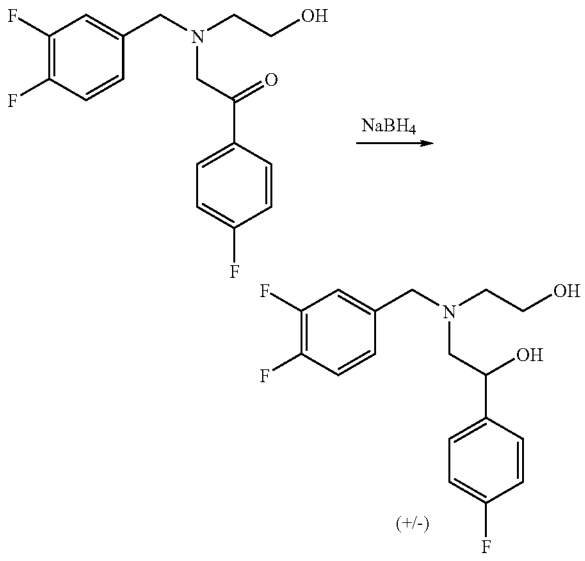

The keto-alcohol (610 mg) was taken up in MeOH. Sodium borohydride (90 mg) was added, and the solution was stirred at 25° C. (20 h). The solution was quenched with $NaHCO_{3(aq.)}$ and concentrated to remove MeOH. The mixture was partitioned between EtOAc and water. The aqueous layer was extracted with EtOAc. The combined organic layers were washed with brine, dried ($MgSO_4$), filtered, and concentrated to afford 540 mg (88%) of the diol as a colorless oil.

Step 4:

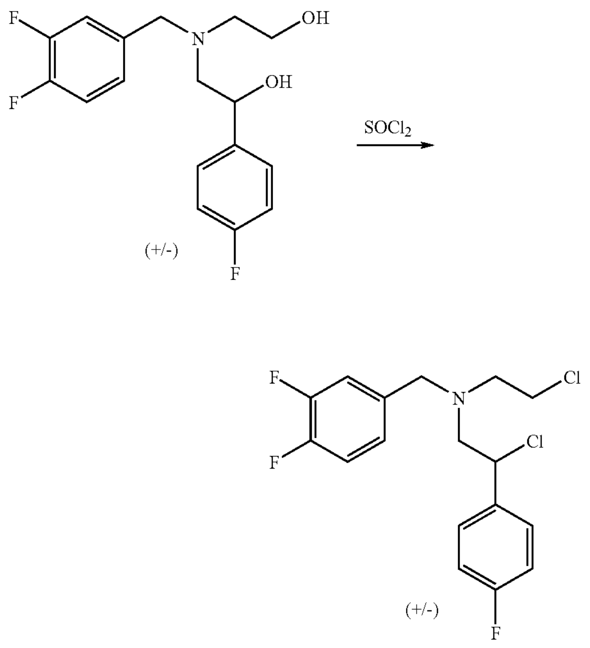

The diol (540 mg) and $SOCl_2$ (493 mg) were taken up in DCE and refluxed for 4 h (85° C.). The solution was diluted with $CH_2Cl_2$ and washed with saturated $NaHCO_{3(aq.)}$. The aqueous layer was extracted with $CH_2Cl_2$. The combined organic layers were dried ($MgSO_4$), filtered, and concentrated to give the di-chloro-amine as a yellow oil. This material was used without any further purification.

Step 5:

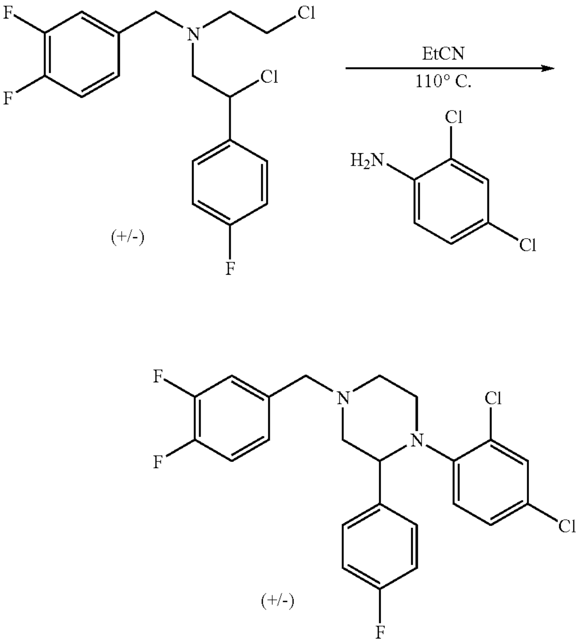

Example 234

The dichloro-amine (200 mg) and 2,4-dichloroaniline (269 mg) were taken up in EtCN (i.e., propionitrile) and heated at 110° C. (18 h). The solution was concentrated. The residue was partitioned between EtOAc and saturated $NaHCO_{3(aq.)}$. The aqueous layer was extracted with EtOAc. The combined organic layers were washed with brine and dried ($MgSO_4$). Filtration and concentration gave a yellow oil. Purification via thin-layer preparative chromatography (15% EtOAc in hexanes, $SiO_2$) gave 24 mg (10%) of Example 234 as a colorless oil.

The following Examples were prepared following the same procedures described in Scheme 6 using the appropriate reagents outlined in Table IV. The bromoketones of Table IV are commercially available, e.g. from Aldrich or Acros.

TABLE IV

| Example | Bromo-Ketone Step 2 | Aniline Step 5 | Structure |
|---|---|---|---|
| 235 | 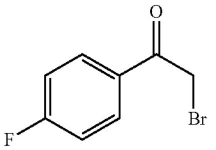 | 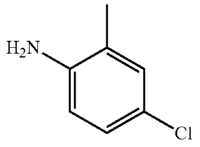 | 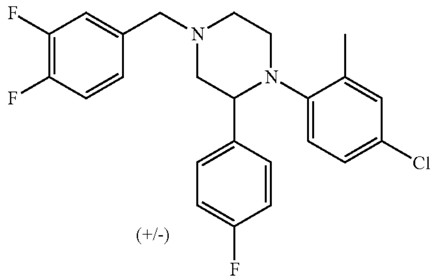 |

TABLE IV-continued
| Example | Bromo-Ketone Step 2 | Aniline Step 5 | Structure |
|---|---|---|---|
| 236 | 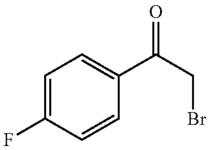 | 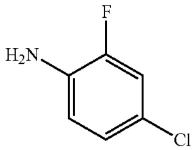 | 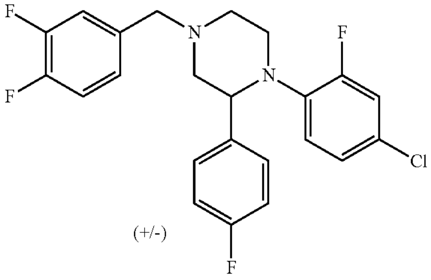 (+/-) |
| 237 | 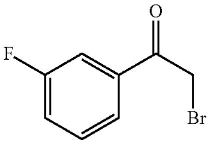 | 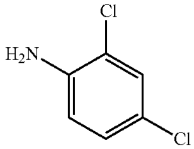 | 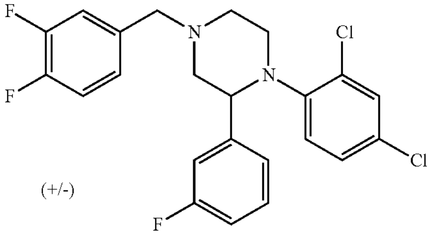 (+/-) |
| 238 | 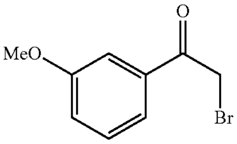 | 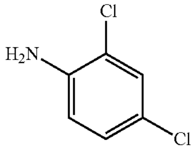 | 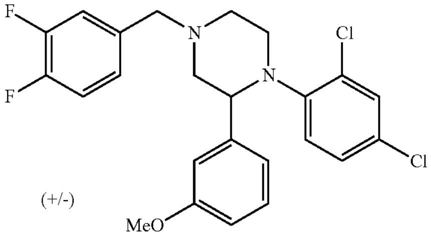 (+/-) |
| 239 | 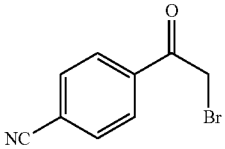 | 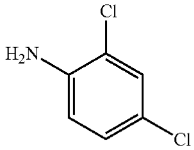 | 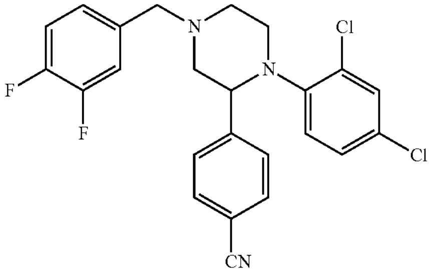 |
| 240 | 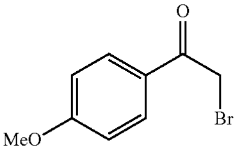 | 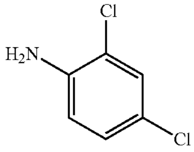 | 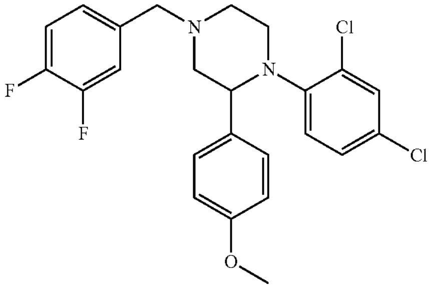 |

TABLE IV-continued
| Example | Bromo-Ketone Step 2 | Aniline Step 5 | Structure |
|---|---|---|---|
| 241 | 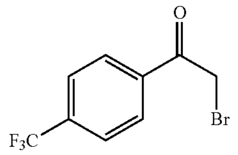 | 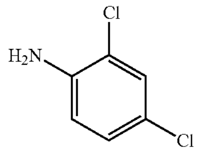 | 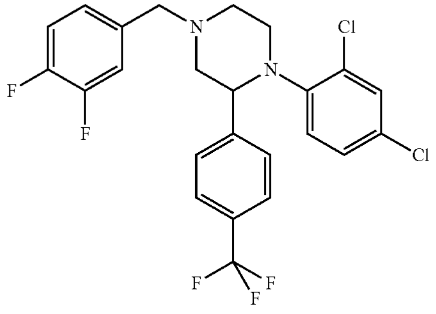 |
| 242 | 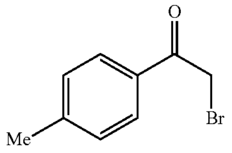 | 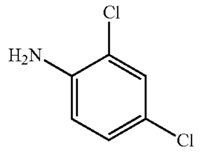 | 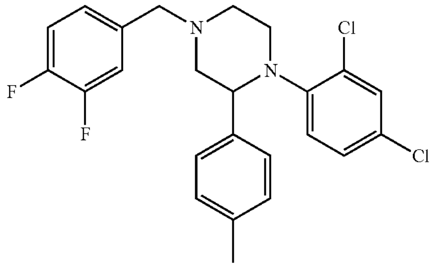 |
| 243 | 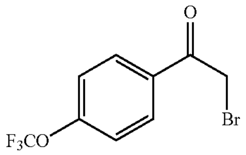 | 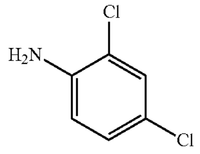 | 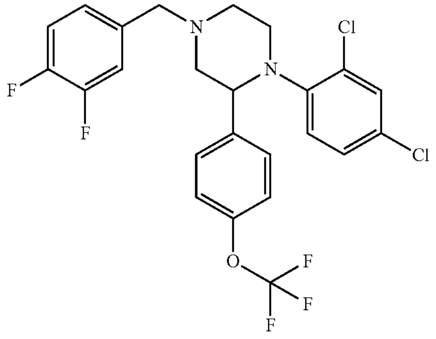 |
| 244 | 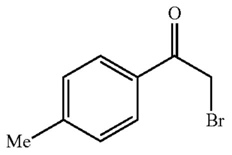 | 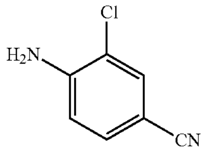 | 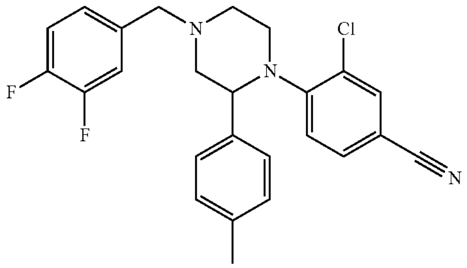 |
| 245 | 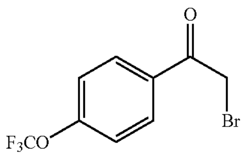 | 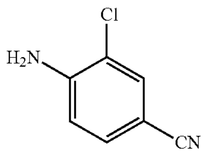 | 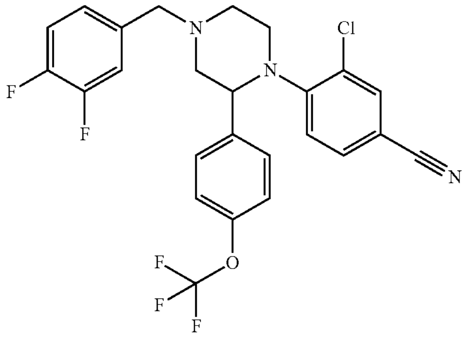 |

TABLE IV-continued
| Example | Bromo-Ketone Step 2 | Aniline Step 5 | Structure |
| --- | --- | --- | --- |
| 246 | 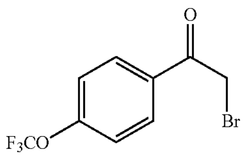 | 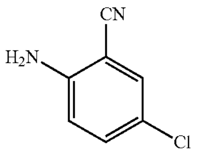 | 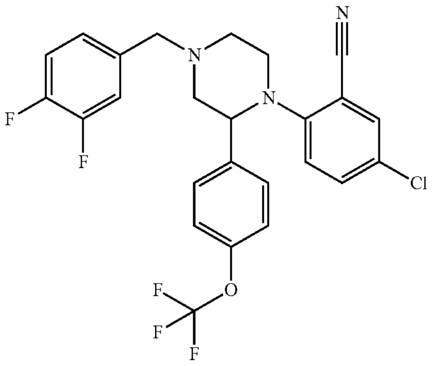 |
Preparation of Example 247
Scheme 7
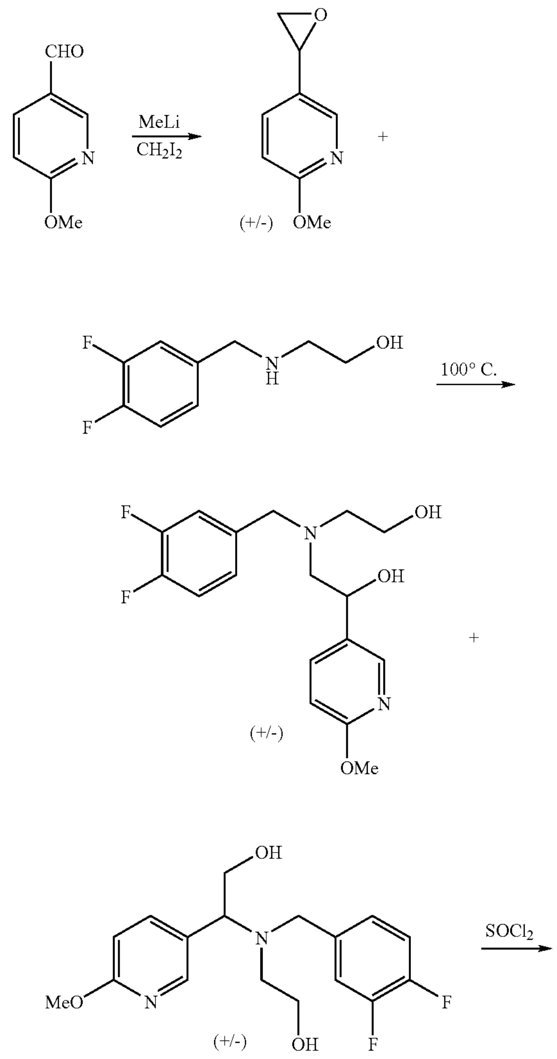
-continued
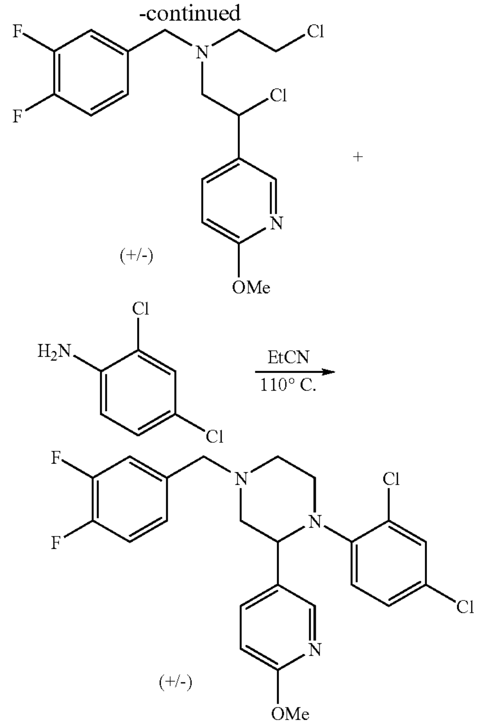
Example 247
Step 1:
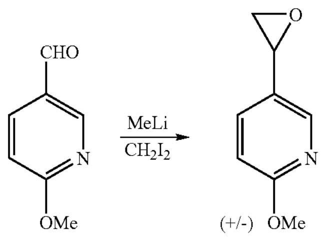
The aldehyde (2 g) and $CH_2I_2$ (1.8 mL) were taken up in THF (40 mL) and cooled to 0° C. Methyllithium-LiBr complex (20 mL of a 1.5 M solution in $Et_2O$) was added dropwise to the reaction. The mixture was stirred at 0° C. for 1 h and then at 25° C. for 1 h. The mixture was poured into ice. The mixture was extracted with EtOAc. The combined organic layers were washed with brine and dried ($MgSO_4$). Filtration and concentration gave the epoxide (2.2 g, 100%) as a yellow oil.

Step 2:

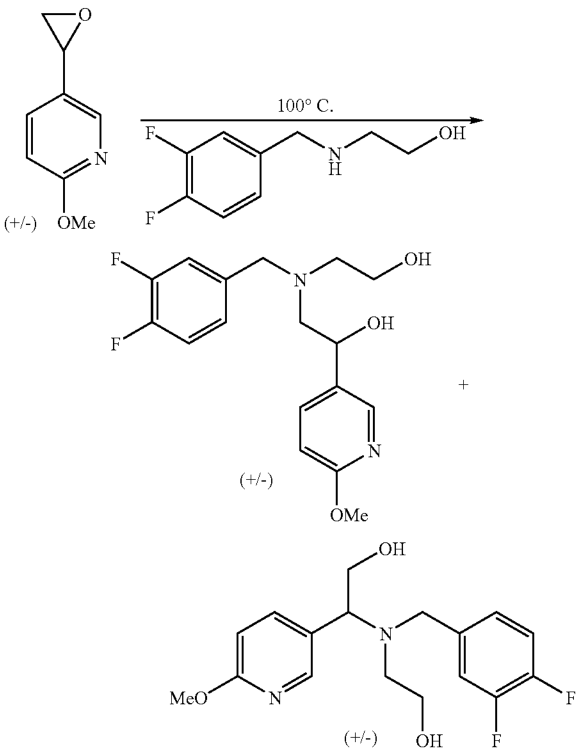

The epoxide (2.4 g) and amino-alcohol (2.97 g) were heated neat at 100° C. (18 h). The residue was purified via flash chromatography (3/1 $CH_2Cl_2$/acetone, $SiO_2$) to give 3 g (58%) of the diols as a mixture of isomers.

Step 3:

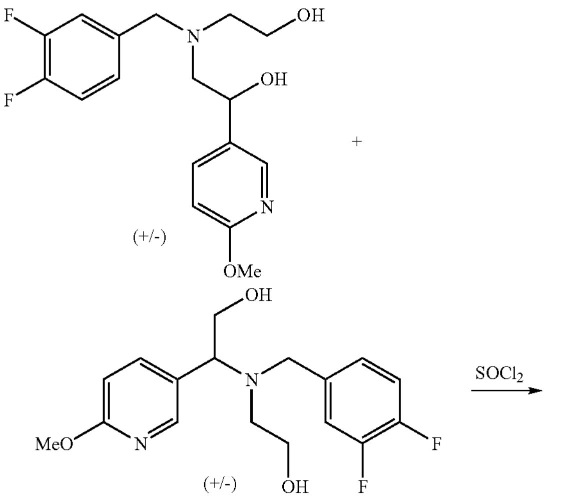

-continued

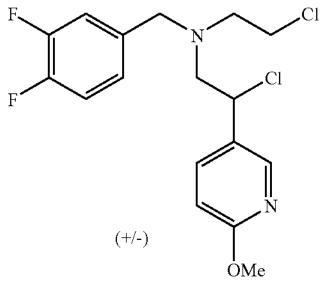

The mixture of diols (250 mg) and $SOCl_2$ (0.2 mL) were taken up in DCE and heated at 70° C. (45 min). The solution was cooled and partitioned between $CH_2Cl_2$ and 1 N $NaOH_{(aq.)}$. The aqueous layer was extracted with $CH_2Cl_2$. The combined organic layers were dried ($MgSO_4$), filtered, and concentrated to give 187 mg (67%) of the dichloro-amine as a yellow oil. This material was used without any further purification.

Step 4:

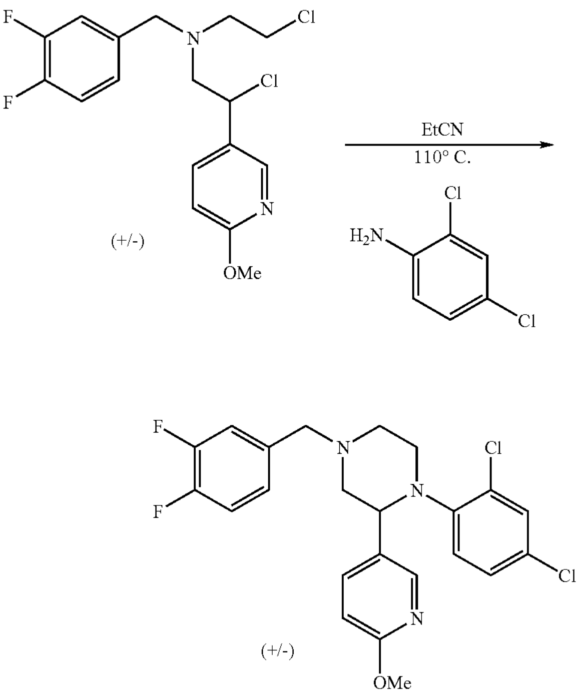

Example 247

The dichloro-amine (187 mg), 2,4-dichloroaniline (242 mg), and NaI (50 mg) were taken up in EtCN and heated at 100° C. (19 h). The solution was concentrated. The residue was partitioned between $CH_2Cl_2$ and 1 N $NaOH_{(aq.)}$. The aqueous layer was extracted with $CH_2Cl_2$. The combined organic layers were dried ($MgSO_4$), filtered, and concentrated. The material contained the desired product and the uncyclized intermediate. The residue was taken up in EtCN and NaI (50 mg) was added. The solution was heated at 10° C. (18 h). The solution was worked up as before. Purification via thin-layer preparative chromatography (9/1 hexanes/acetone, $SiO_2$) gave 47 mg (20%) of Example 247 as a yellow oil.

Preparation of Example 248

Example 248

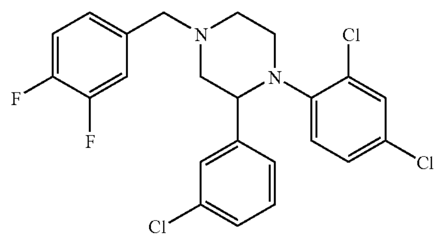

The piperazine Example 248 was prepared in a manner similar to the method used to prepare Example 247 except that 3-chlorostyrene oxide (prepared as in step 1, Scheme 7) was used instead of the pyridyl epoxide in step 2 of Scheme 7, above.

Preparation of Example 249

Scheme 8

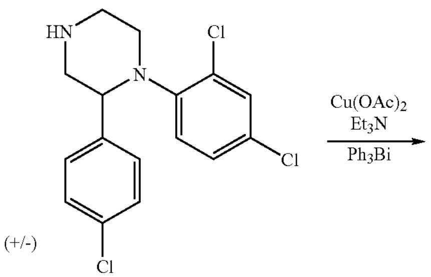

Example 1

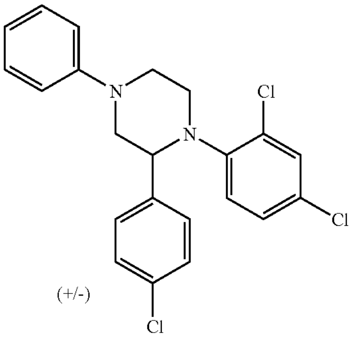

Example 249

The NH piperazine Example 1 (100 mg), $Ph_3Bi$ (385 mg), $Cu(OAc)_2$ (106 mg), and $Et_3N$ (0.12 mL) were taken up in toluene and heated at 115° C. (18 h). The solution was filtered and concentrated. Purification via thin-layer preparative chromatography (10/1 hexanes/$Et_2O$, $SiO_2$) gave 78 mg (64%) of Example 249 as a white solid.

Preparation of Example 250

Scheme 9

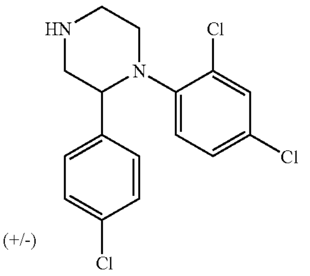

Example 1

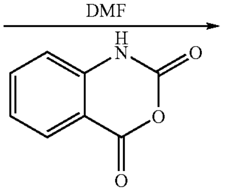

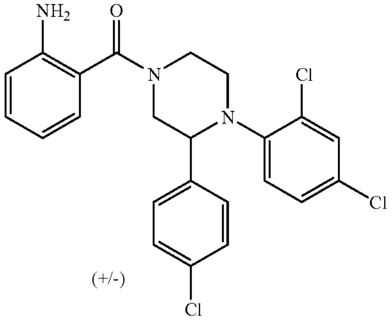

Example 250

The NH piperazine Example 1 (540 mg) and isatoic anhydride (410 mg) were stirred at 25° C. (18 h). More isatoic anhydride was added (400 mg), and the mixture was stirred at 60° C. (18 h). The solution was partitioned between EtOAc and water. The aqueous layer was extracted with EtOAc. The combined organic layers were washed with brine and dried ($MgSO_4$). Filtration and concentration gave a yellow oil. Purification via flash chromatography (1/1 EtOAc/hexanes, $SiO_2$) gave 268 mg (37%) of Example 250 as a white solid.

Preparation of Examples 251-253

Scheme 10

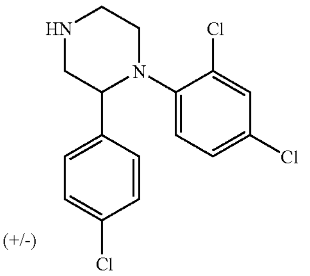

Example 1

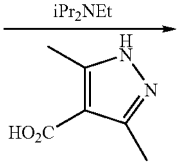

-continued

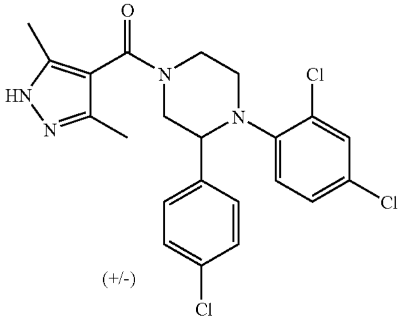

Example 251

The NH piperazine Example 1 (220 mg), EDC (i.e., 1-(3-dimethylaminopropyl)-3-ethylcarbodiimide hydrochloride) (245 mg), HOBT (i.e., 1-hydroxybenzotriazole) (172 mg), acid (108 mg), and $iPr_2NEt$ (206 mg) were taken up in $CH_3CN$ and stirred at 25° C. (18 h). The solution was partitioned between EtOAc and 1 N $NaOH_{(aq.)}$. The aqueous layer was extracted with EtOAc. The combined organic layers were washed with brine and dried ($MgSO_4$). Filtration and concentration gave a solid. The solid was triturated with $Et_2O$. The white solid was collected and dried to give 125 mg (42%) of Example 251.

The following examples were prepared according to the procedure described in Scheme 10 using the appropriate reagents. The carboxylic acids in Table V were prepared by methods described in WO 00/66558 or U.S. Pat. No. 6,391,865, both of which are herein incorporated by reference in their entirety.

TABLE V

| Example | Carboxylic Acid | Structure |
|---|---|---|
| 252 | 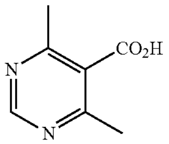 | 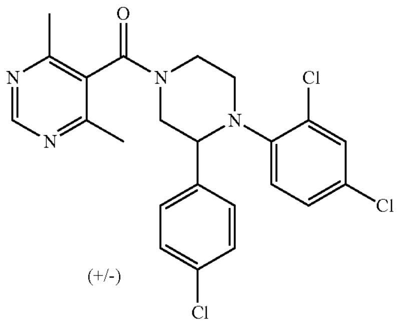 |
| 253 | 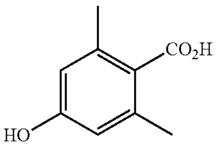 | 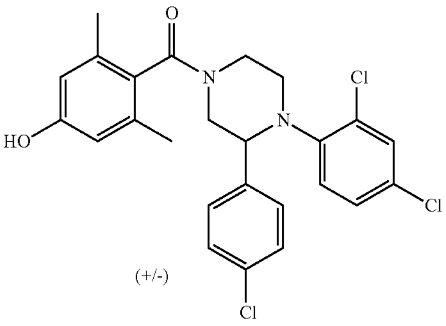 |

Preparation of Example 254

Scheme 11

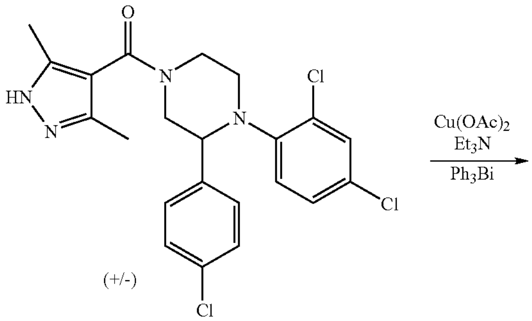

Example 251

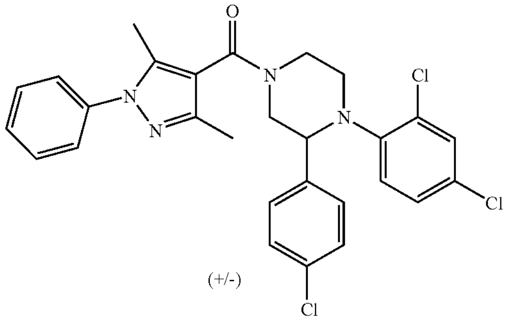

Example 254

Example 254 was prepared from Example 251 using the procedure described above in Scheme 8.

Preparation of Example 255

Scheme 12

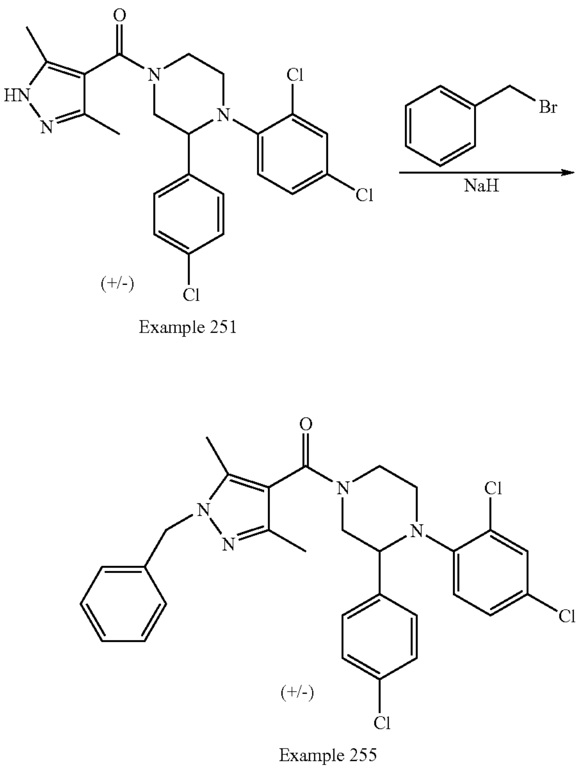

Example 251

Example 255

Example 251 (40 mg) was taken up in THF at 25° C. NaH (15 mg of a 60 wt % dispersion in oil) was added. After 10-15 minutes, benzyl bromide (30 mg) was added, and the solution was stirred at 25° C. (18 h). The solution was concentrated, and the residue was partitioned between EtOAc and water. The aqueous layer was extracted with EtOAc. The combined organic layers were washed with brine and dried ($MgSO_4$). Filtration and concentration gave a yellow oil. Purification via thin-layer preparative chromatography (5% MeOH in $CH_2Cl_2$, $SiO_2$) gave 14 mg (29%) of the N-benzyl analog Example 255 as an oil.

Preparation of Example 256

Scheme 13

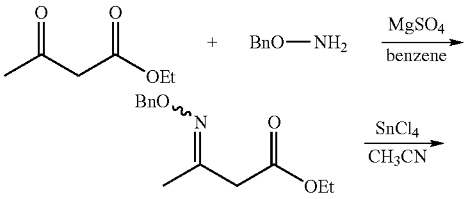

-continued

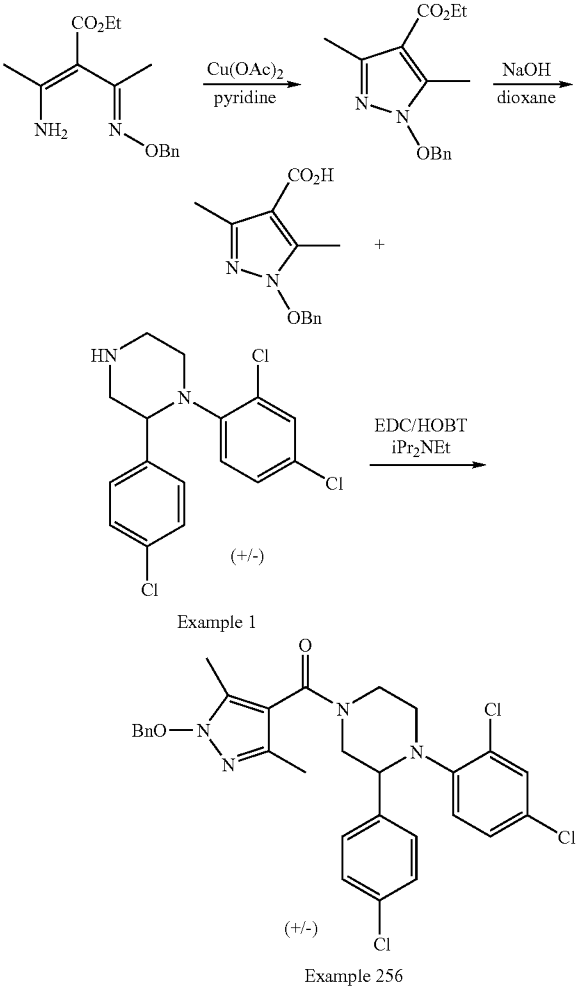

Example 1

Example 256

Step 1:

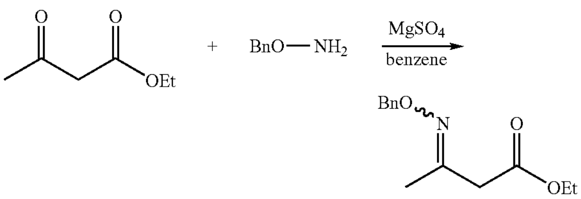

Ethyl acetoacetate (7.5 g, 58 mmol) and O-Benzyl hydroxylamine (7.1 g, 58 mmol), and $MgSO_4$ (5 g) were taken up in benzene and stirred at 25° C. for 24 hours. Filtration and concentration gave the oxime.

Step 2:

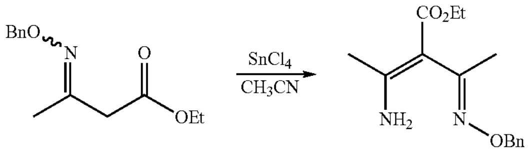

The oxime (1.0 g, 4.25 mmol) was taken up in $CH_3CN$ (8 mL) and cooled to 0° C. $SnCl_4$ (4.3 ml, 1.0 M in $CH_2Cl_2$) was added dropwise to the solution at 0° C. The solution was stirred at 0° C. for one hour. The solution was quenched with saturated $Na_2CO_3$ (aq.). The mixture was extracted with EtOAc. The combined organic layers were washed with brine and dried ($MgSO_4$). Filtration and concentration gave a colorless oil. Purification via flash chromatography (3/1 hexanes/EtOAc, $SiO_2$) gave 415 mg (35%) of the enamide as a colorless oil.

Step 3:

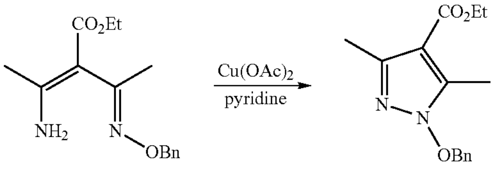

The enamide (415 mg, 1.5 mmol) and $Cu(OAc)_2$ (400 mg) were taken up in pyridine. The mixture was heated at 100° C. for 4 hours. The solution was cooled and concentrated. The residue was partitioned between EtOAc and 10% $NH_4OH_{(aq.)}$. The aqueous layer was extracted with EtOAc. The combined organic layers were washed with brine and dried ($MgSO_4$). Filtration and concentration gave a brown oil. Purification via flash chromatography (9/1 hexanes/EtOAc, $SiO_2$) gave 330 mg (80%) of the pyrazole as a colorless oil.

Step 4:

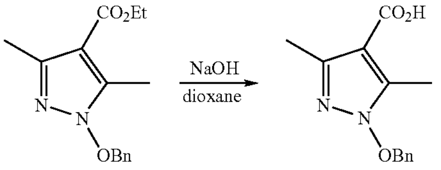

The ester (545 mg, 1.99 mmol) and 1 N $NaOH_{(aq.)}$ was taken up in dioxane/EtOH. The solution was heated at 75° C. for 24 hours. The solution was concentrated. The solution was acidified with 1 M $HCl_{(aq.)}$ (pH=2-3). The resulting white precipitate was collected and dried under high vacuum. The acid was obtained as a white powder (314 mg, 64%). $^1H$ NMR ($CDCl_3$, 400 MHz) δ 2.07 (s, 3H), 2.46 (s, 3H), 5.26 (s, 2H), 7.25-7.37 (m, 5H). HRMS calc'd for $C_{13}H_{15}O_3N$ ($MH^+$) 247.1083; Found: 247.1089.

Step 5:

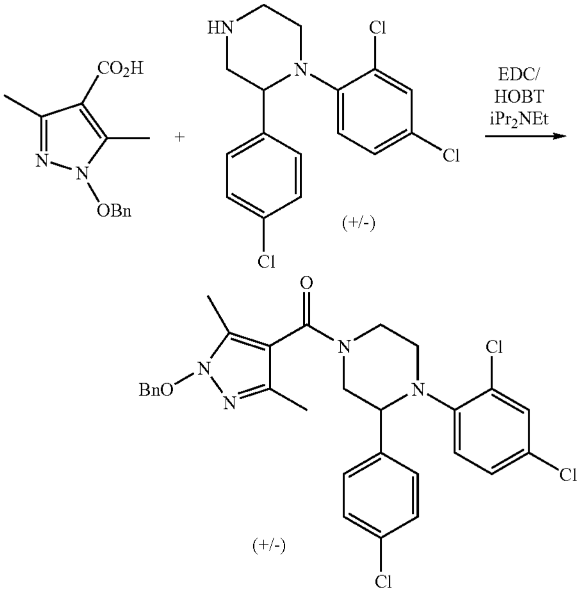

Example 256

Preparation of Examples 257-262

Scheme 14

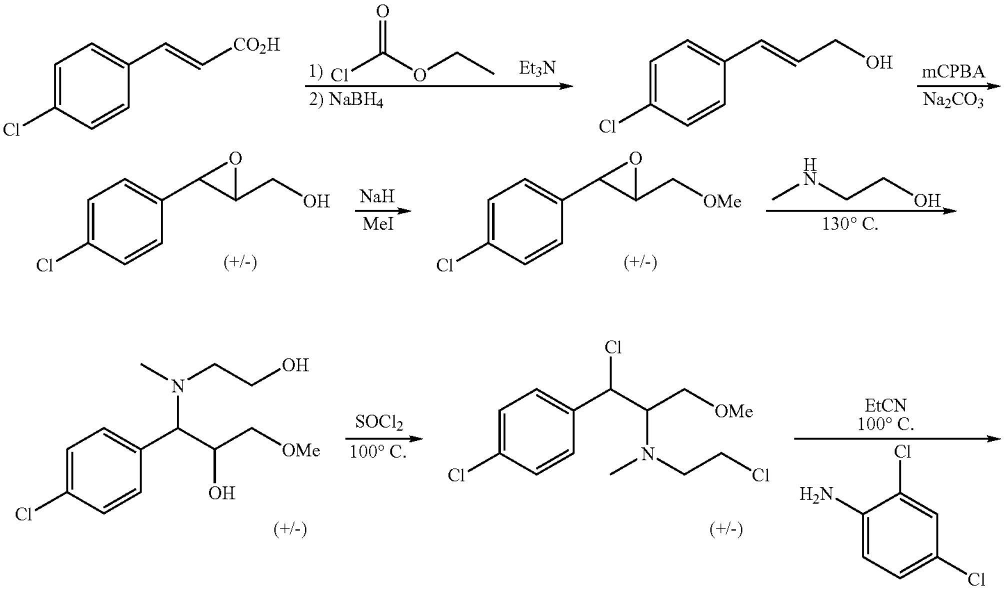

-continued

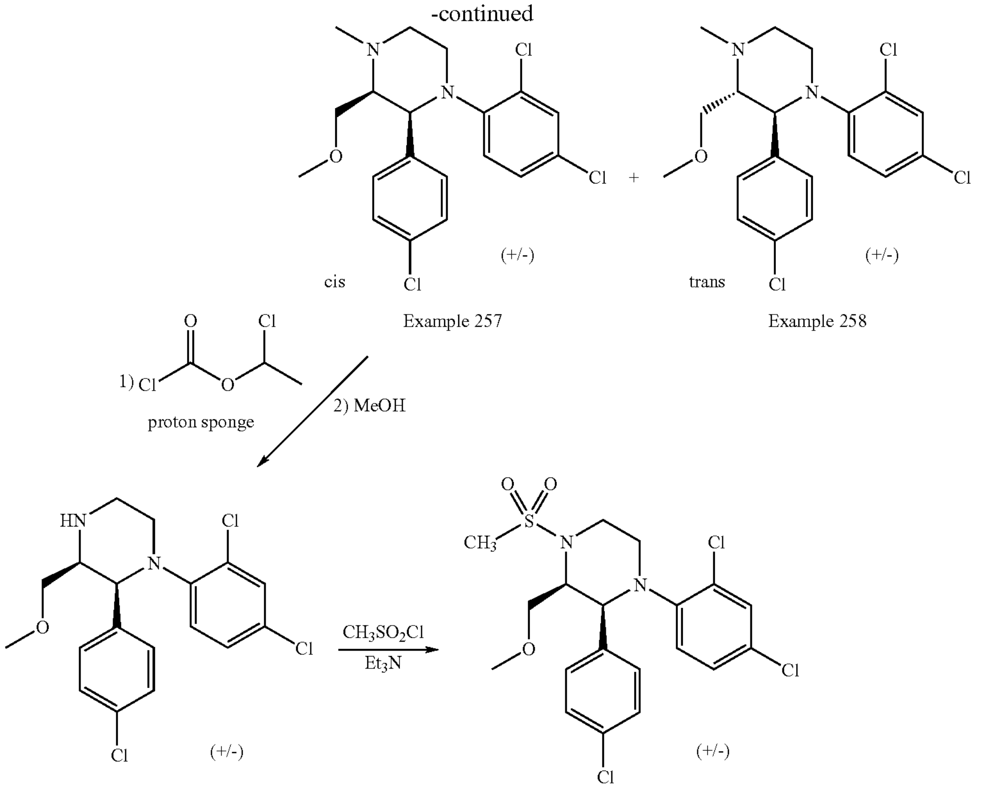

Example 257

Example 258

Example 259

Example 260

Step 1:

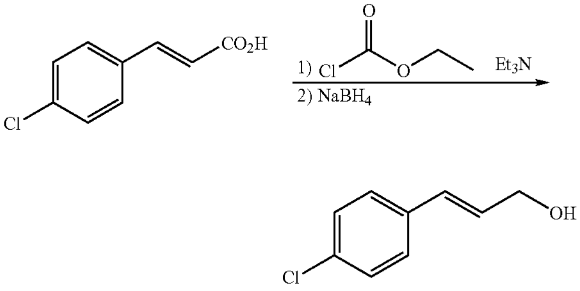

4-Chloro-cinnamic acid (30 g) and $Et_3N$ (18.3 g) were taken up in THF (300 mL) at 0° C. Ethyl chloroformate (17.3 mL) was added dropwise at 0° C. The slurry was stirred at 0° C. for one hour. The $Et_3NHCl$ was removed by filtration, and the filtrate was filtered directly into cold water. The filtrate was washed with cold THF. The solution was placed into an ice-bath, and $NaBH_4$ (13.2 g) was added in portions (with gas evolution). The ice bath was removed, and the resulting solution was stirred at 25° C. (16 h). The reaction was quenched with 2 M $HCl_{(aq.)}$. Diethyl ether was added, and the mixture was allowed to stir at 25° C. for 3 hours. The aqueous layer was extracted with $Et_2O$. The combined organic layers were washed with brine and dried ($MgSO_4$). Filtration and concentration gave a yellow oil. Purification via flash chromatography (15% EtOAc in $CH_2Cl_2$, $SiO_2$) gave 23.5 grams (85% yield) of the alcohol as an oil that slowly solidified.

Step 2:

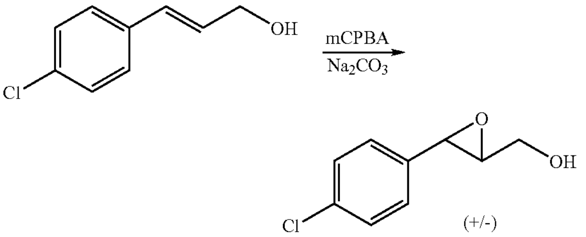

The alcohol (23.5 g) and $Na_2CO_3$ (17.8 g) were taken up in $CH_2Cl_2$ (300 mL) and cooled to 0° C. (mechanical stirrer). m-CPBA (i.e. m-chloroperoxybenzoic acid) (38 grams) was added in portions at 0° C. The mixture was warmed to 25° C. and stirred at that temp for 16 hours. The solution was washed with 10% $Na_2S_2O_{3(aq.)}$ and saturated $NaHCO_{3(aq.)}$. The organic layers were dried ($MgSO_4$), filtered, and concentrated. Purification via flash chromatography (15% EtOAc in $CH_2Cl_2$, $SiO_2$) gave 16.5 grams (64%) of the racemic epoxide as an oil.

Step 3:

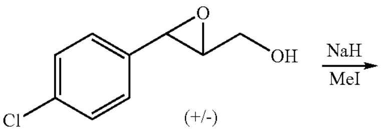

-continued

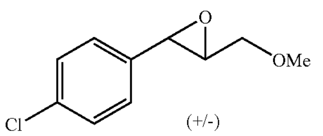

Sodium hydride (4.3 g) was suspended in DMF (100 mL) at −20° C. The epoxy-alcohol (16.5 g) was added, and the reaction mixture was stirred at −20° C. for 0.5 h. Iodomethane (19 g) was added at −20° C., and the resulting reaction mixture was stirred at that temperature for 40 minutes. The reaction mixture was allowed to warm to 25° C. and stir at that temperature for 3 hours. The reaction mixture was poured into a mixture of EtOAc and water. The aqueous layer was extracted with EtOAc. The combined organic layers were washed with brine, dried ($MgSO_4$), and filtered which furnished the methyl ether (14.6 g, 82%). This material was used without any further purification.

Step 4:

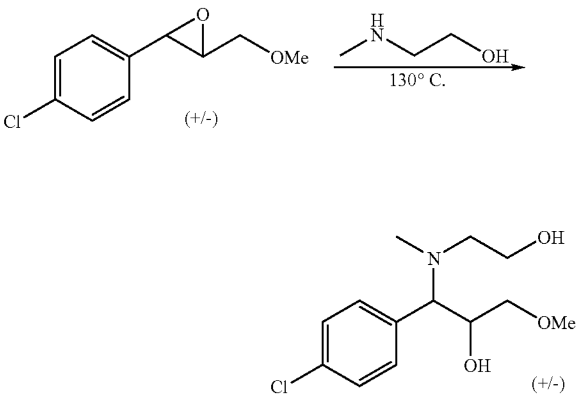

The methyl ether (14.6 g) and N-methyl-ethanolamine (5.5 g) were heated neat (130° C., 24 hours). Purification via flash chromatography ($CH_2Cl_2$, EtOAc, then 20% MeOH in EtOAc, $SiO_2$) furnished the diol (15 g, 75%) as a viscous oil.

Step 5:

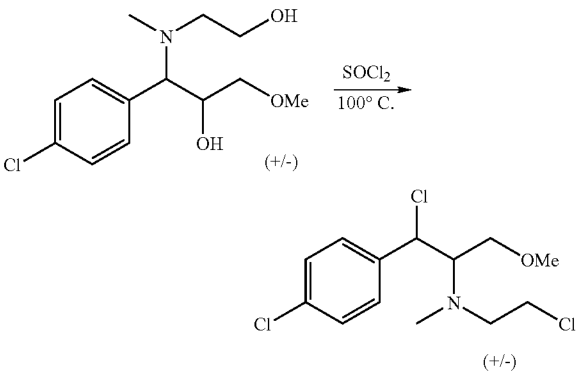

The diol (7 g) and $SOCl_2$ (4.7 mL) were taken up in DCE (50 mL) and the solution was heated to 100° C. (3 h). The solution was diluted with $CH_2Cl_2$ and slowly quenched with saturated $NaHCO_{3(aq.)}$. The aqueous layer was extracted with $CH_2Cl_2$. The combined organic layers were dried ($MgSO_4$), filtered, and concentrated to furnish the di-chloro amine (7.2 g, 91%). This material was used without any further purification.

Step 6:

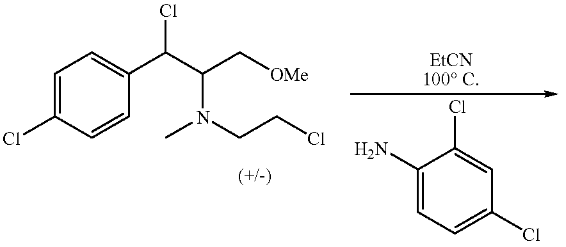

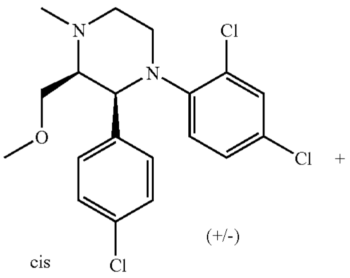

cis

Example 257

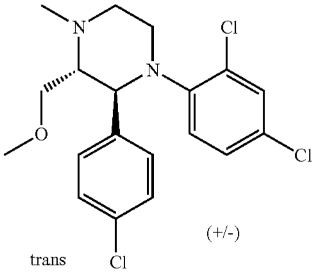

trans

Example 258

The dichloro-amine (7.2 g) and 2,4-dichloroaniline (11.5 g) were heated in propionitrile (100° C., 24 h). Solution was evaporated. The residue was partitioned between EtOAc and 2 N $NaOH_{(aq.)}$. The aqueous layer was extracted with EtOAc. The combined organic layers were washed with brine, dried ($MgSO_4$), and filtered. Purification via flash chromatography twice (2% MeOH in $CH_2Cl_2$ then 10% acetone in $CH_2Cl_2$, $SiO_2$) furnished the cis and trans piperazines, Examples 257 and 258, (8.05 grams, 85% 10/1 cis/trans ratio) as thick oils that solidified on standing.

Step 7:

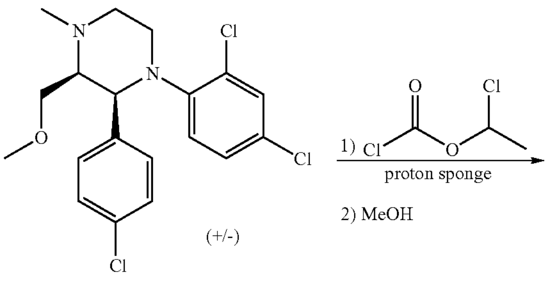

Example 257

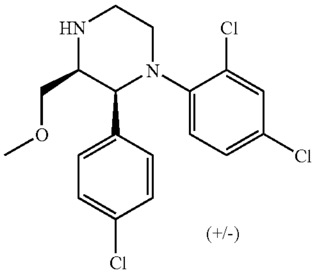

Example 259

The cis-N-methyl piperazine Example 257 (2 g), proton sponge (i.e., N,N,N',N'-tetramethylnaphthalene-1,8-diamine) (0.32 g), and 1-chloroethyl-chloroformate (1.4 g) were heated in DCE (90° C., 20 h). The solution was concentrated. The residue was taken up in MeOH and heated at reflux for 7 hours. The solution was evaporated. The residue was partitioned between EtOAc and saturated $NaHCO_{3(aq.)}$. The aqueous layer was extracted with EtOAc. The combined organic layers were washed with brine and dried ($MgSO_4$). Filtration and concentration gave a yellow oil. Purification via flash chromatography (5% MeOH in $CH_2Cl_2$, $SiO_2$) gave the NH piperazine Example 259 (1.3 g, 67%) as a yellow oil.

Step 8:

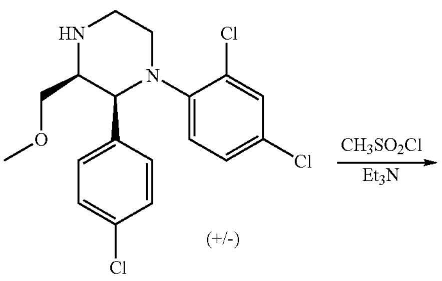

Example 259

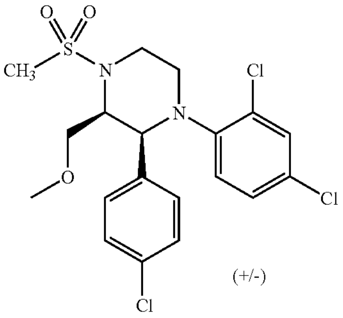

Example 260

The NH-piperazine Example 259 (100 mg) and $Et_3N$ (34 mg) were taken up in $CH_2Cl_2$. $MeSO_2Cl$ (35 mg) was added, and the solution was stirred at 25° C. (16 h). The solution was diluted with $CH_2Cl_2$ and washed with 1 N $NaOH_{(aq.)}$. The aqueous layer was extracted with $CH_2Cl_2$. The combined organic layers were dried ($MgSO_4$), filtered, and concentrated. Purification via thin-layer preparative chromatography (2% EtOAc in $CH_2Cl_2$, $SiO_2$) furnished the sulfonamide Example 260 (77 mg, 64%) as a yellow oil.

The following examples were prepared according to Step 8 in Scheme 14 using the appropriate reagent (Table VI).

TABLE VI

| Example | Sulfonyl Chloride | Structure |
|---|---|---|
| 261 | 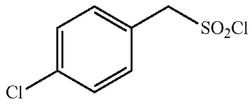 | 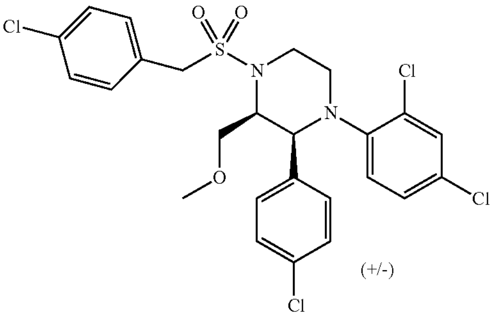 |

TABLE VI-continued

| Example | Sulfonyl Chloride | Structure |
|---|---|---|
| 262 | 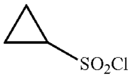 | 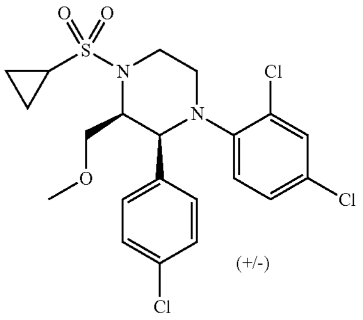 |

Preparation of Examples 263-266

Examples 263-266 were prepared using procedures similar to those described in Scheme 14, as shown in Scheme 15.

Scheme 15

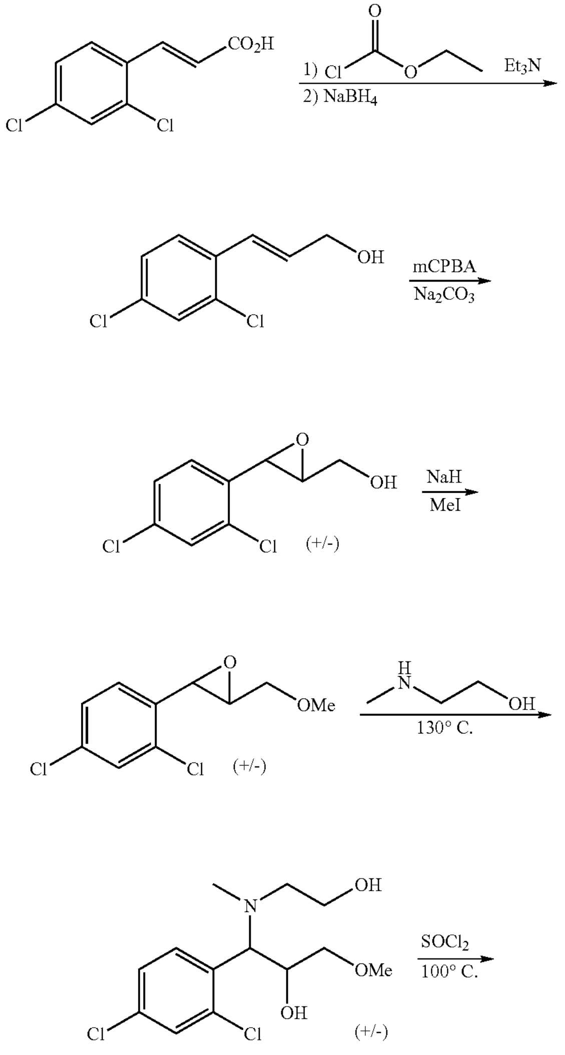

-continued

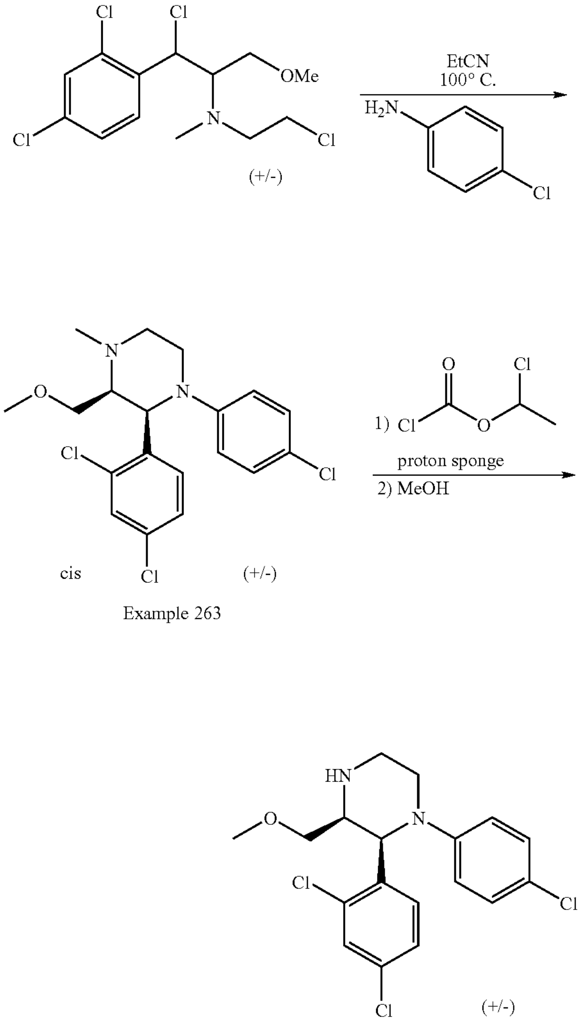

Example 263

Example 264

The Examples shown in Table VII were prepared from the appropriate sulfonyl chlorides and the piperazine Example 264 shown in Scheme 15 according to the procedure outlined in Step 8 of Scheme 14.

TABLE VII

| Example | Sulfonyl Chloride Step 7 | Structure |
|---|---|---|
| 265 | 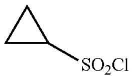 | 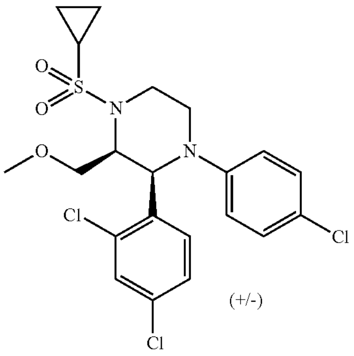 |
| 266 | $CH_3SO_2Cl$ | 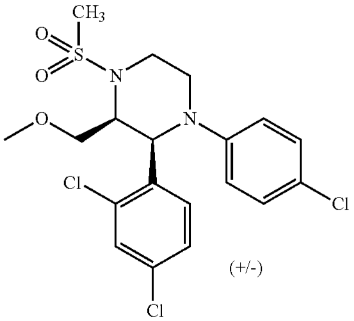 |

Preparation of Examples 267-270

Scheme 16

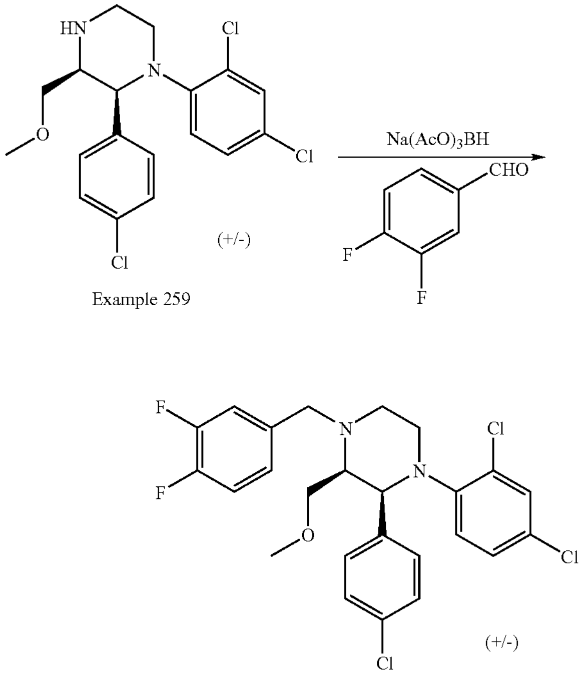

Example 267

The NH-piperazine Example 259 (100 mg), 3,4-difluorobenzaldehyde (40 mg), and $Na(AcO)_3BH$ (110 mg) were stirred in $CH_2Cl_2$ at 25° C. (16 h). The solution was diluted with $CH_2Cl_2$ and washed with 1 N $NaOH_{(aq.)}$. The aqueous layer was extracted with $CH_2Cl_2$. The combined organic layers were dried ($MgSO_4$). Filtration and concentration gave a yellow oil. Purification via preparative thin-layer chromatography (2% EtOAc in $CH_2Cl_2$, $SiO_2$) furnished 44 mg (33%) of Example 267 as a colorless oil.

Following the same procedure as described in Scheme 16 the following Example was prepared from the appropriate aldehyde.

TABLE VIII

| Example | Aldehyde | Structure |
|---|---|---|
| 268 | 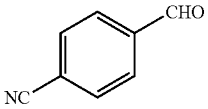 | 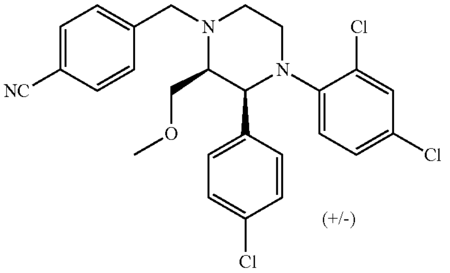 |

The following Examples were prepared using the piperazine Example 264 of Scheme 15 and the procedure of Scheme 16. The appropriate reagents are listed below (Table IX).

TABLE IX

| Example | Aldehyde | Structure |
| --- | --- | --- |
| 269 | 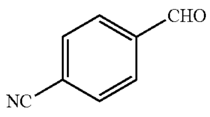 | 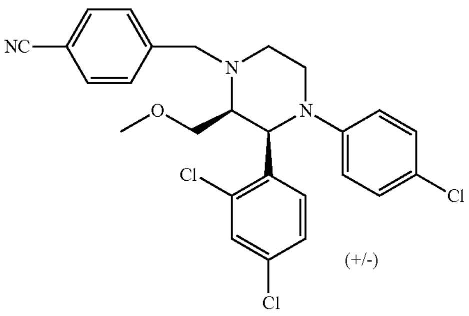 |
| 270 | 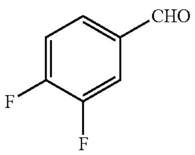 | 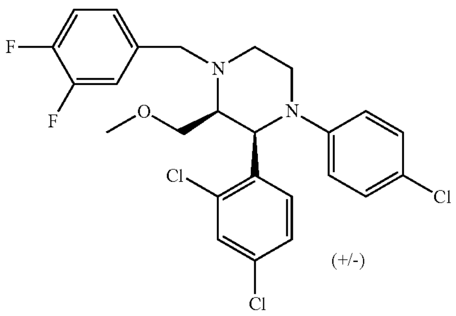 |

Preparation of Examples 271-272

Scheme 17

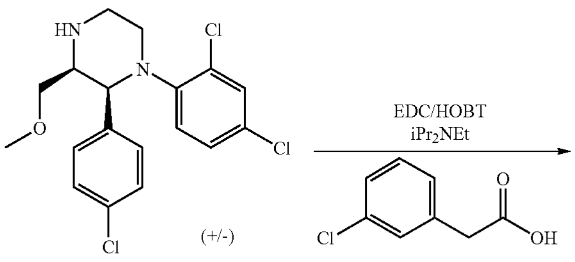

Example 259

-continued

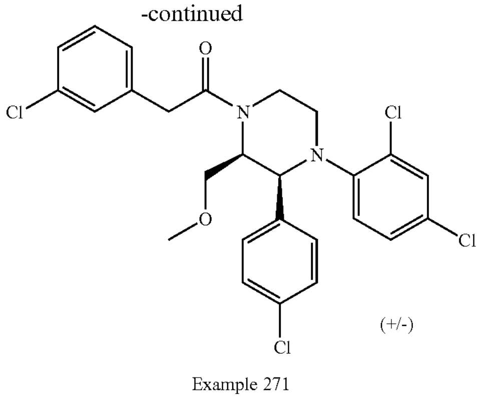

Example 271

The NH-piperazine Example 259 (100 mg), EDC (99 mg), HOBT (69 mg), iPrNEt (67 mg), and the acid (48 mg) were taken up in $CH_2Cl_2$. The solution was stirred at 25° C. (16 h). The solution was diluted with $CH_2Cl_2$ and washed with 1 N $NaOH_{(aq.)}$. The aqueous layer was extracted with $CH_2Cl_2$. The combined organic layers were dried ($MgSO_4$), filtered, and concentrated. Purification via thin-layer preparative chromatography (5% EtOAc in $CH_2Cl_2$, $SiO_2$) furnished the amide Example 271 (20 mg, 14%) as a colorless oil.

The following Example was prepared according to the procedures described in Scheme 17 using the piperazine Example 264 shown in Scheme 15. The appropriate reagent is listed below (Table X).

TABLE X

| Example | Aldehyde Scheme 2 | Structure |
|---|---|---|
| 272 | 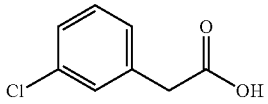 | 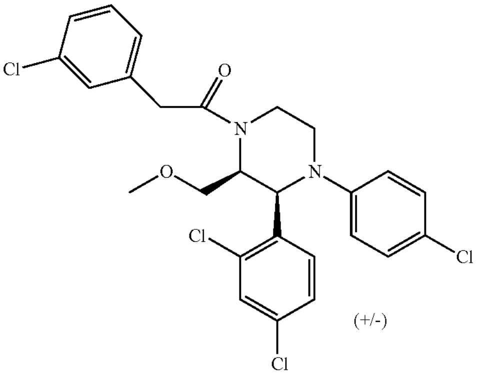  |

Preparation of Examples 273-274

Scheme 18

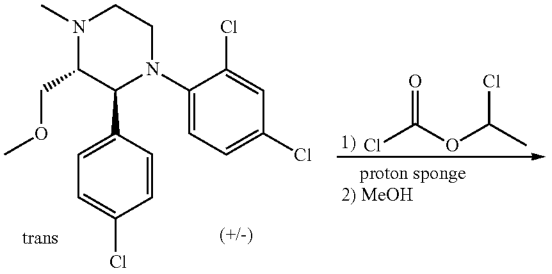

Example 258

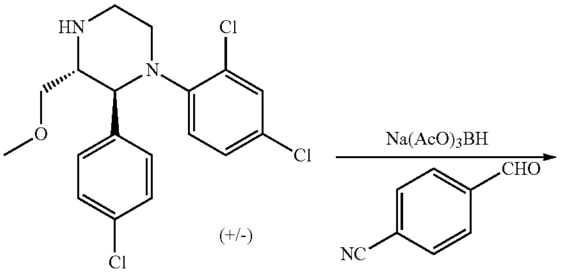

Example 273

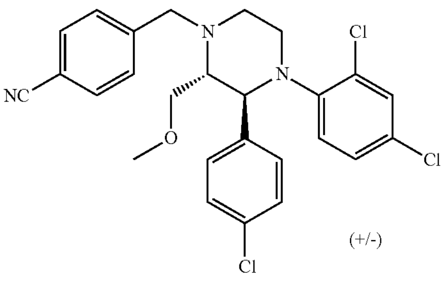

Example 274

Step 1:

The trans-piperazine Example 258 was converted into the NH piperazine Example 273 as described previously in Scheme 14, Step 7.

Step 2:

The NH piperazine Example 273 and 4-cyanobenzaldehyde were reacted following the procedure described in Scheme 16 to provide Example 274.

Preparation of Example 275

Scheme 19

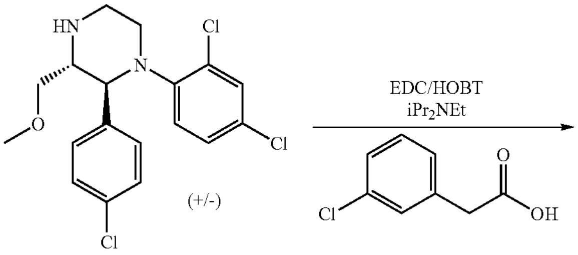

Example 273

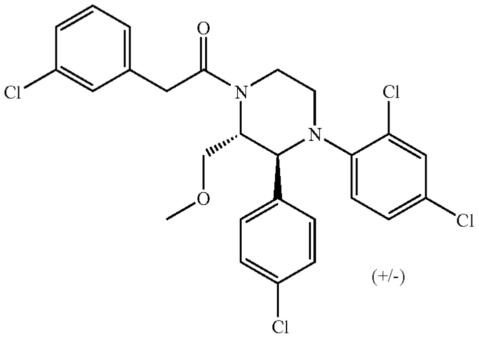

Example 275

Example 275 was prepared using the procedure described for the corresponding cis isomer (Scheme 17).

Preparation of Examples 276-277

Scheme 20

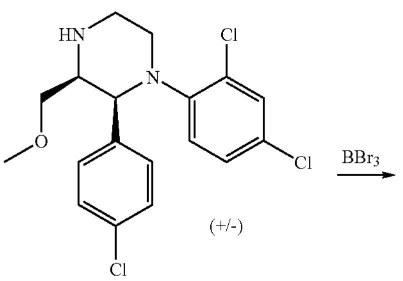

Example 264

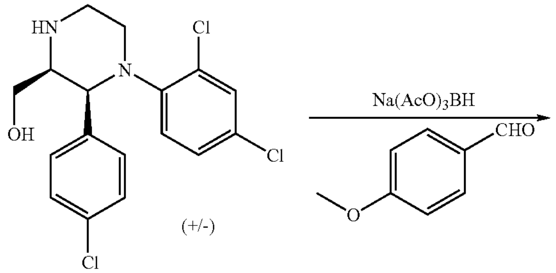

Example 276

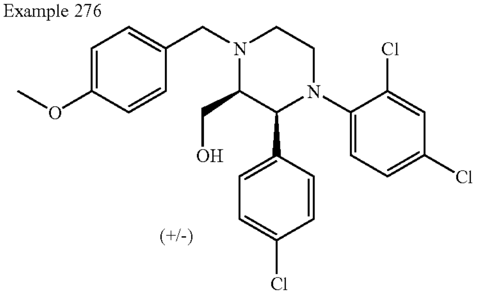

Example 277

Step 1:

The NH-piperazine Example 264 (108 mg) was taken up in $CH_2Cl_2$. Boron tribromide (0.13 mL) was added, and the resulting solution was stirred at 25° C. (16 h). The solution was quenched with saturated $NaHCO_{3(aq.)}$. The aqueous layer was extracted with $CH_2Cl_2$. The combined organic layers were dried ($MgSO_4$), filtered, and concentrated. The crude product Example 276 was used without any further purification.

Step 2:

The amino-alcohol Example 276 (460 mg) and 4-methoxybenzaldehyde were reacted according to the procedure described above (Scheme 18) to furnish Example 277.

Preparation of Example 278

Scheme 21

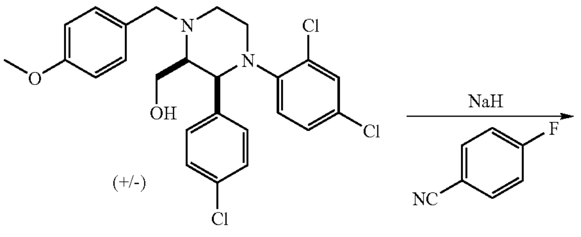

Example 277

-continued

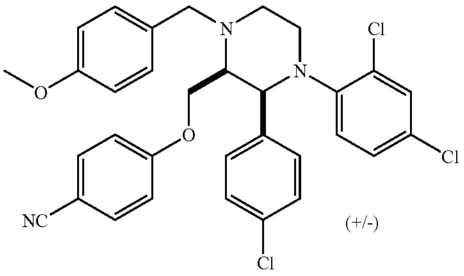

Example 278

The N-benzyl piperazine Example 277 (160 mg) and NaH (46 mg, 60 wt % oil dispersion) were taken up in DMF. Then 4-fluoro-cyanobenzene (100 mg) was added, and the resulting solution was stirred at 25° C. (4 h). The reaction was partitioned between EtOAc and water. The aqueous layers were extracted with EtOAc. The combined organic layers were washed with brine and dried ($MgSO_4$). Filtration and concentration gave a yellow oil. Purification via thin-layer preparative chromatography (5/1 hexanes/EtOAc, $SiO_2$) furnished 4 mg (2%) of the ether Example 278 as an oil.

Preparation of Examples 279-280

Scheme 22

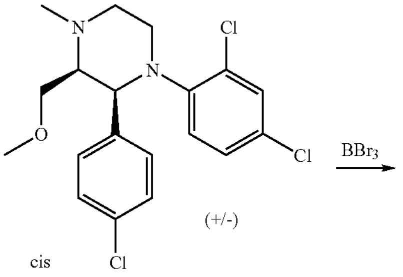

Example 257

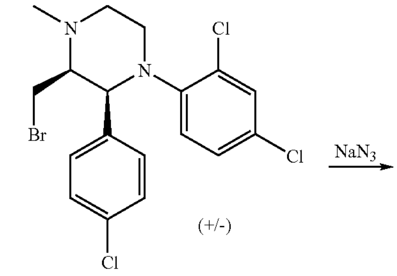

Example 279

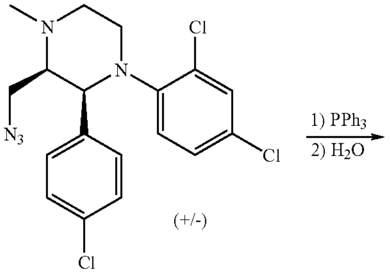

-continued

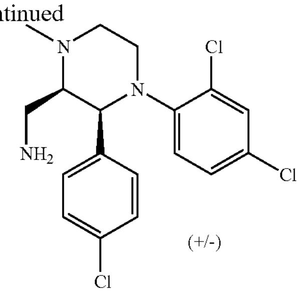

Example 280

Step 1:

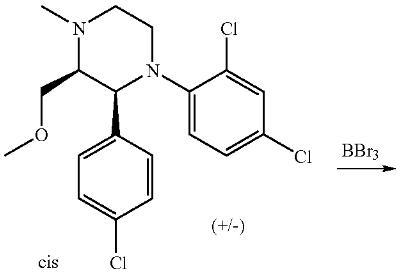

Example 257

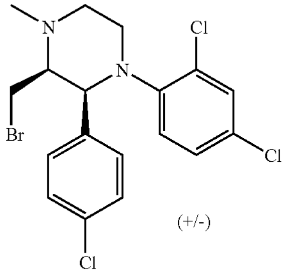

Example 279

The piperazine Example 257 (1.3 g) was taken up in $CH_2Cl_2$. Boron tribromide (17 mL of a 1.0 M solution in $CH_2Cl_2$) was added, and the solution was stirred at 25° C. (16 h). The solution was diluted with $CH_2Cl_2$ and washed with saturated $NaHCO_{3(aq.)}$. The aqueous layers were extracted with $CH_2Cl_2$. The combined organic layers were dried ($MgSO_4$), filtered, and concentrated. Purification via flash chromatography ($CH_2Cl_2$ then 10% EtOAc in $CH_2Cl_2$) furnished the bromide (1.1 g, 70%).

Step 2:

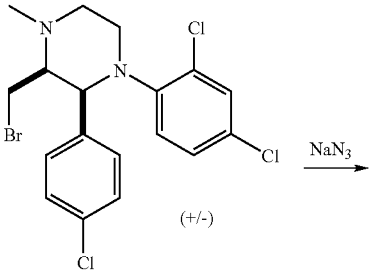

Example 279

-continued

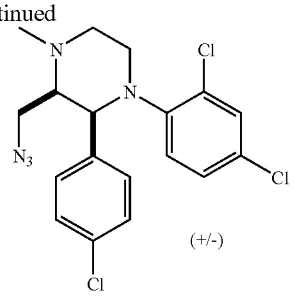

The bromide (1.2 g) and $NaN_3$ (340 mg) were taken up in DMSO and stirred at 25° C. (72 h). The solution was partitioned between $Et_2O$ and water. The aqueous layers were extracted with $Et_2O$. The combined organic layers were washed with brine, dried ($MgSO_4$), filtered, and concentrated to furnish the azide (1 g, 94%).

Step 3:

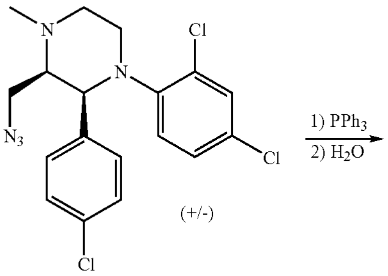

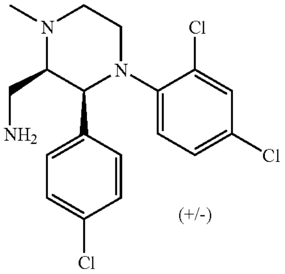

Example 280

The azide (500 mg) and $PPh_3$ (640 mg) were taken up in THF (4 mL) and heated at reflux (65° C.) for 2 hours. Water (4 mL) was added, and the mixture was stirred at 40° C. (16 h). The mixture was concentrated. The residue was partitioned between EtOAc and water. The aqueous layer was extracted with EtOAc. The combined organic layers were washed with brine, dried ($MgSO_4$), filtered, and concentrated. Purification via thin-layer preparative chromatography (4% 7 N $NH_3$ in MeOH in $CH_2Cl_2$, $SiO_2$) furnished the amine (340 mg, 88%) Example 280.

Preparation of Example 281-282

Scheme 23

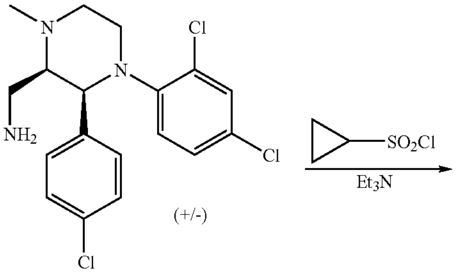

Example 280

-continued

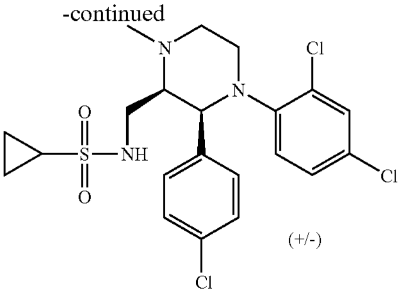

Example 281

The amine Example 280 (160 mg) and $Et_3N$ (95 mg) were taken up in $CH_2Cl_2$. Cyclopropylsulfonyl chloride (88 mg) was added, and the solution was stirred at 25° C. (16 h). The solution was diluted with $CH_2Cl_2$ and washed with 1 N $NaOH_{(aq.)}$. The aqueous layer was extracted with $CH_2Cl_2$. The combined organic layers were dried ($MgSO_4$), filtered, and concentrated. Purification via thin-layer preparative chromatography (8% MeOH in $CH_2Cl_2$, $SiO_2$) furnished 138 mg (68%) of Example 281.

Example 282

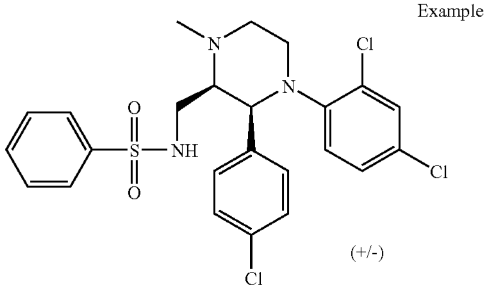

Example 282 was prepared according to the procedure described previously (Scheme 23) using benzenesulfonyl chloride.

Preparation of Examples 283-288

Scheme 24

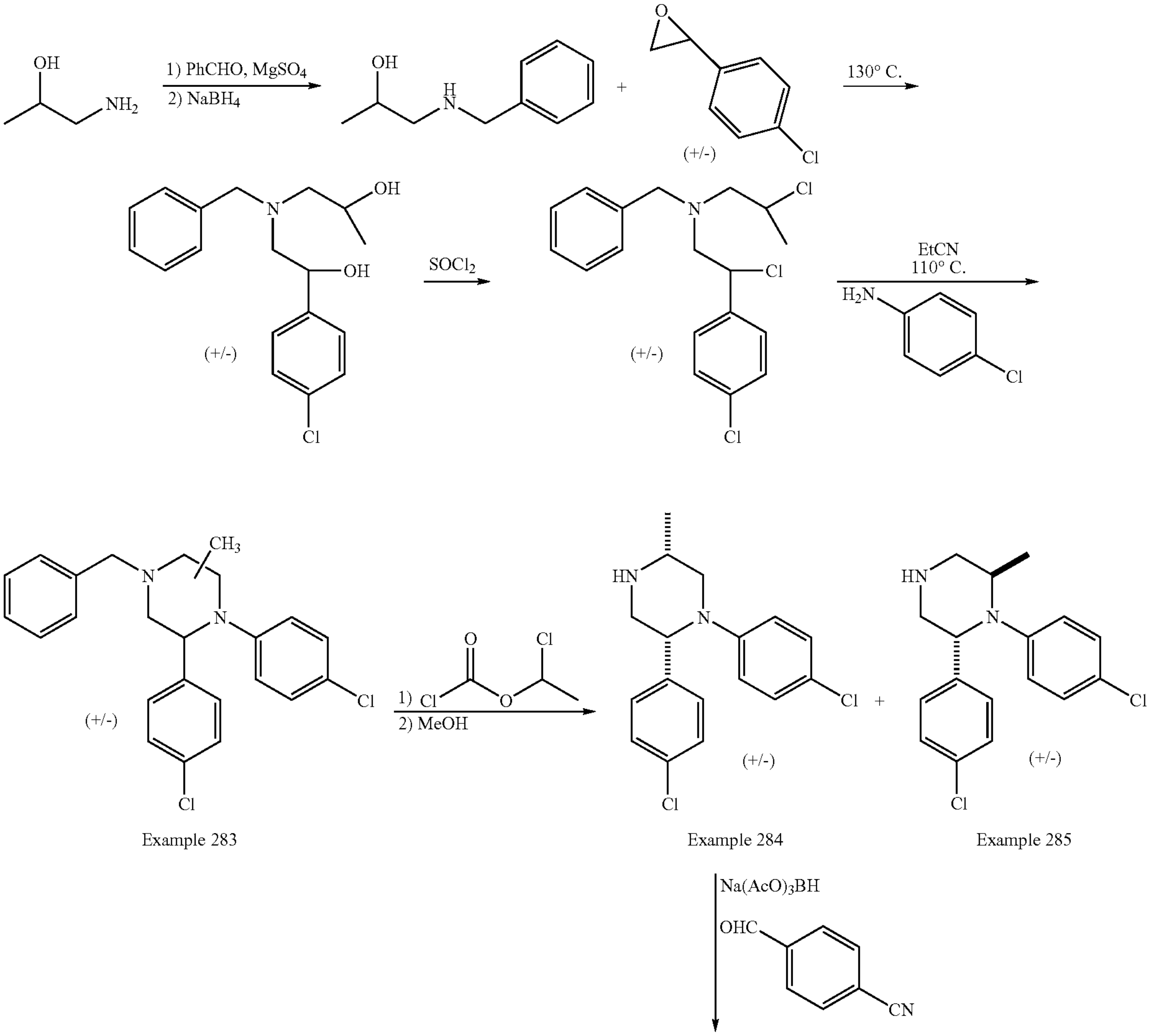

Example 283

Example 284

Example 285

-continued

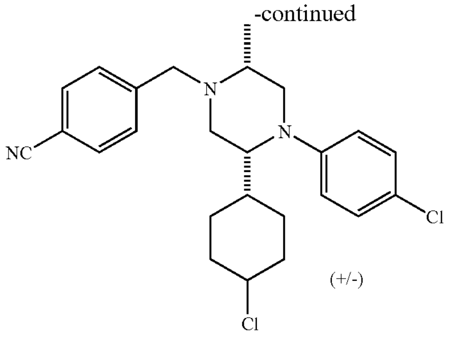

Example 286

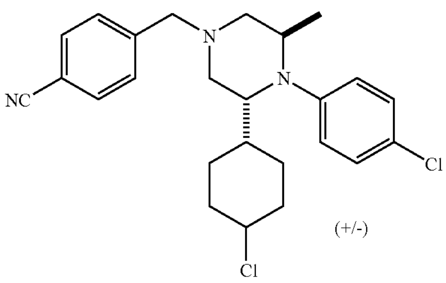

Example 287

Step 1

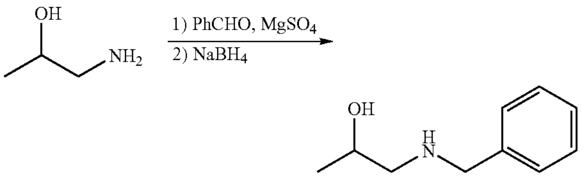

1-Amino-2-isopropanol (2 g), benzaldehyde (2.7 ml), and $MgSO_4$ (8 g) were taken up in $CH_2Cl_2$ and stirred at 25° C. (16 h). The mixture was filtered and concentrated which furnished an imine as a solid. The imine was taken up in MeOH and $NaBH_4$ (1 g) was added in portions. The solution was stirred at 25° C. (3 h). The solution was concentrated. The residue was partitioned between $Et_2O$ and 1 M $HCl_{(aq.)}$. The aqueous acidic layer was extracted with $Et_2O$. The aqueous layer was cooled (0° C.) and rendered basic via addition of NaOH pellets (pH=11-12). The mixture was extracted with $CH_2Cl_2$. The combined organic layers were dried ($MgSO_4$), filtered, and concentrated which furnished the amino-alcohol as a thick oil (3.84 g, 87%).

Step 2:

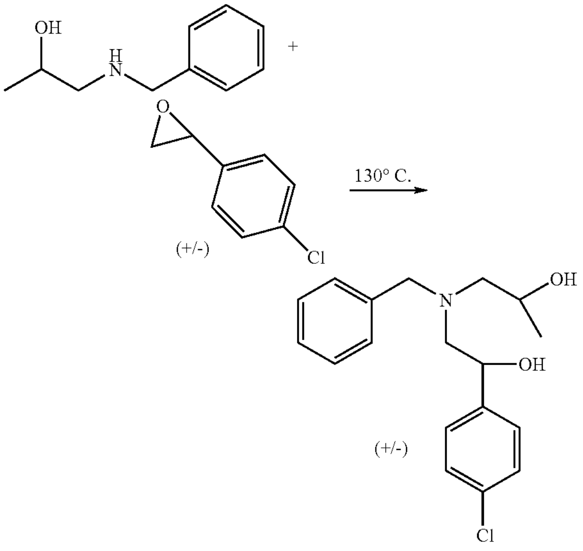

(+/−)-4-chloro-styrene oxide (2.8 mL) and the amino-alcohol (3.8 g) were heated neat at 130° C. (18 h) which furnished the diol as a thick gum. The diol was used in Step 3 without any further purification.

Step 3:

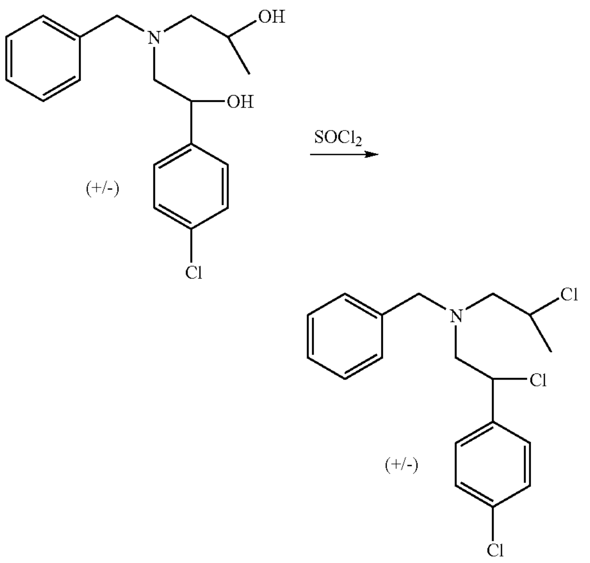

The crude diol from Step 2 (23 mmol) was taken up in DCE (i.e., dichloroethane). Thionyl chloride (4.3 mL) was added, and the solution was heated at reflux (85° C., 3.5 h). The solution was cooled and washed with 1 N $NaOH_{(aq.)}$. The aqueous layer was extracted with $CH_2Cl_2$. The combined organic layers were dried ($MgSO_4$), filtered, and concentrated which furnished the dichloro-amine as a thick gum. This material was used without any further purification in Step 4.

Step 4:

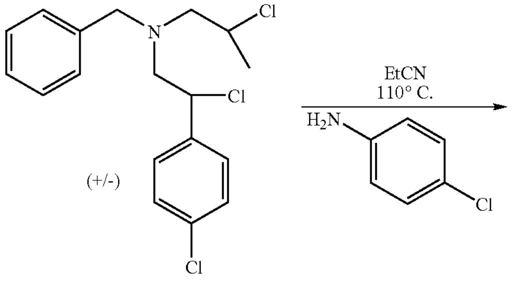

-continued

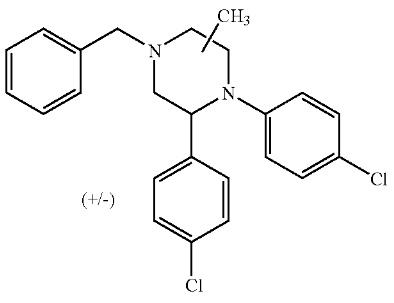

Example 283

The dichloro-amine (7.9 g) and 4-chloroaniline (1.2 g) were taken up in EtCN and heated at 110° C. (19 h). The solution was concentrated and partitioned between $CH_2Cl_2$ and 1 N $NaOH_{(aq.)}$. The aqueous layer was extracted with $CH_2Cl_2$. The combined organic layers were dried ($MgSO_4$), filtered, and concentrated. Purification via flash chromatography (9/1 hexanes/$Et_2O$, $SiO_2$) gave 1.2 g (35%) of the piperazine Example 283 as a mixture of isomers.

Step 5:

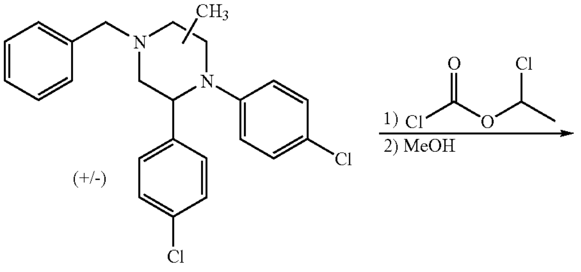

Example 283

-continued

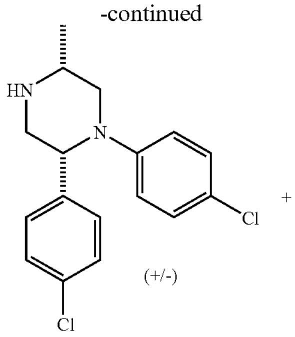

Example 284

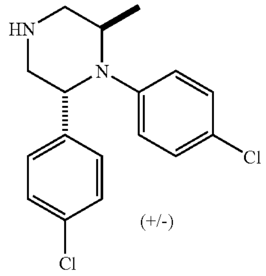

Example 285

The piperazine Example 283 (1 g) and 1-chloroethyl-chloroformate ((0.3 mL) were taken up in DCE and heated (85° C., 18 h). The solution was concentrated. The residue was taken up in MeOH and heated at reflux (80° C., 3.5 h). The solution was concentrated. The residue was partitioned between $CH_2Cl_2$ and 1 N $NaOH_{(aq.)}$. The aqueous layer was extracted with $CH_2Cl_2$. The combined organic layers were dried ($MgSO_4$). Filtration and concentration gave a yellow oil. Purification via thin-layer preparative chromatography (9/1 $CH_2Cl_2$/MeOH, $SiO_2$) gave 100 mg of the 2,5-cis isomer Example 284 and 50 mg of the 2,6-trans isomer Example 285.

Step 6:

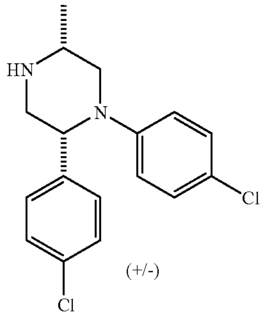

Example 284

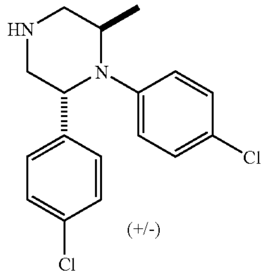

Example 285

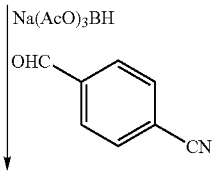

-continued

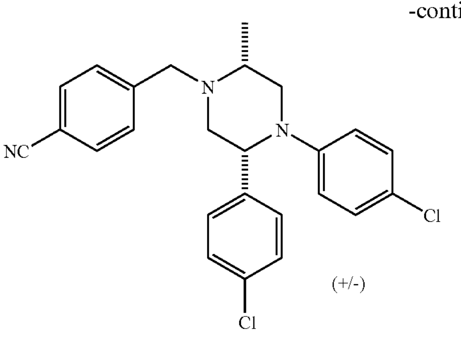

Example 286

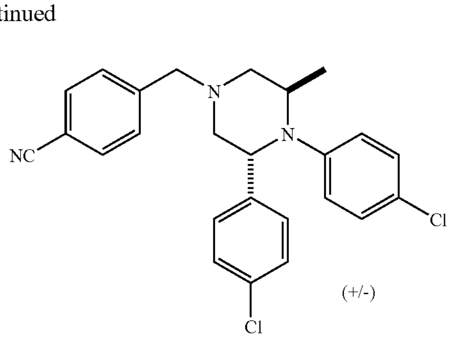

Example 287

The 2,5-cis-NH piperazine Example 284 (100 mg), 4-cyanobenzaldehyde (48 mg), and $Na(AcO)_3BH$ (127 mg) were taken up in $CH_2Cl_2$ and stirred at 25° C. (19 h). The solution was diluted with $CH_2Cl_2$ and washed with 1 N $NaOH_{(aq.)}$. The aqueous layer was extracted with $CH_2Cl_2$. The combined organic layers were dried ($MgSO_4$), filtered, and concentrated. Purification via thin-layer preparative chromatography (4/1 hexanes/EtOAc, $SiO_2$) gave 49 mg (37%) of Example 286 as a colorless oil. Following the same procedure, the 2,6-trans-NH piperazine Example 285 was converted into Example 287.

Example 288

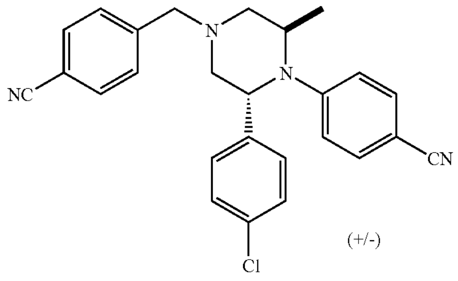

Example 288 was prepared according to conditions described for Example 287 using 4-cyano-aniline in Step 4 of Scheme 24.

Preparation of Examples 289-294

Scheme 25

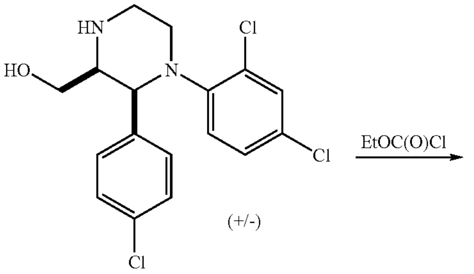

Example 276

-continued

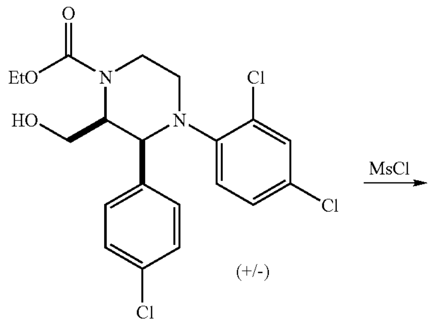

Example 289

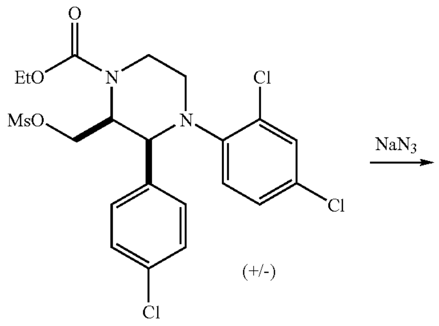

Example 290

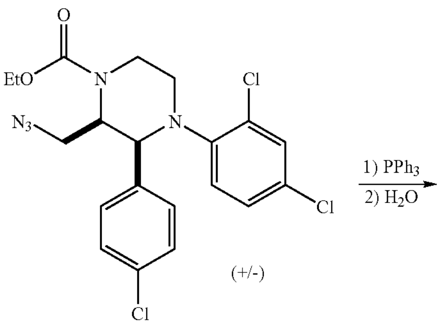

Example 291

-continued

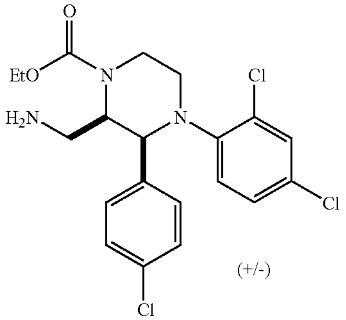

Example 292

Step 1:

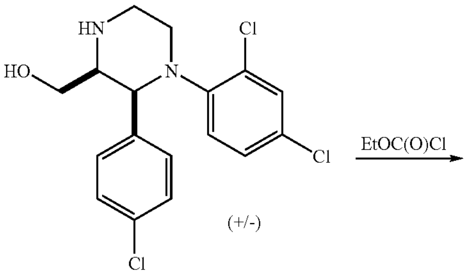

Example 276

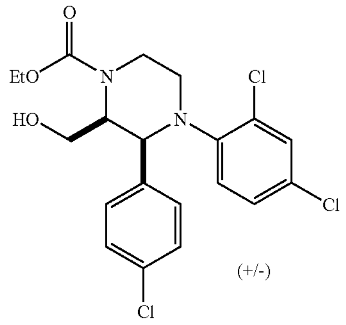

Example 289

The amino-alcohol Example 276 from Scheme 20 (400 mg) and $iPr_2NEt$ (170 mg) were taken up in $CH_2Cl_2$. Ethyl chloroformate (130 mg) was added, and the solution was stirred at 25° C. for 30 minutes. The solution was diluted with $CH_2Cl_2$ and washed with saturated $NaHCO_3$ (aq.). The aqueous layer was extracted with $CH_2Cl_2$. The combined organic layers were dried ($MgSO_4$), filtered, and concentrated. Purification via thin-layer preparative chromatography (15% EtOAc in $CH_2Cl_2$, $SiO_2$) furnished the carbamate Example 289.

Step 2:

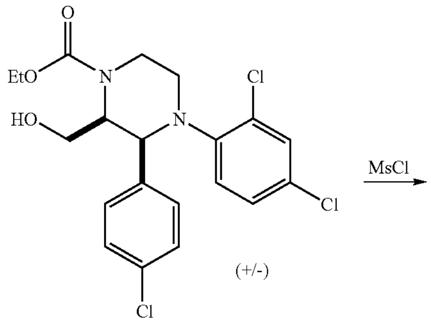

Example 289

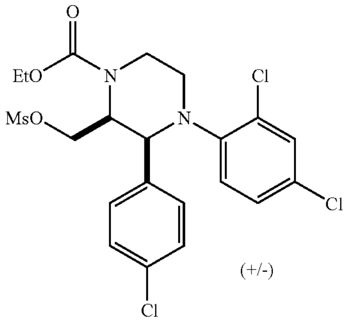

Example 290

The carbamate Example 289 and $Et_3N$ (4 eq.) were taken up in $CH_2Cl_2$. Methanesulfonyl chloride (4 eq.) was added at 25° C. The solution was stirred at 25° C. for 15 minutes. The solution was diluted with $CH_2Cl_2$ and washed with saturated $NaHCO_3$ (aq.). The aqueous layer was extracted with $CH_2Cl_2$. The combined organic layers were dried ($MgSO_4$). Filtration and concentration gave the mesylate Example 290, which was used without further purification in Step 3.

Step 3:

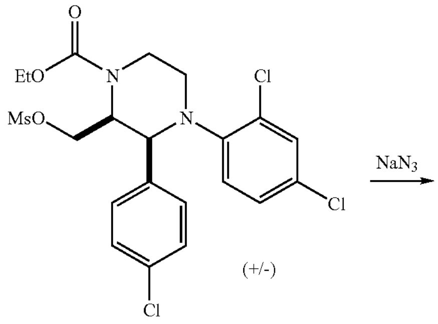

Example 290

-continued

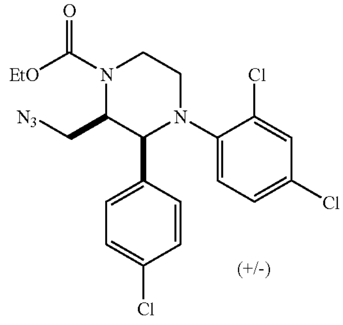

Example 291

The mesylate Example 290 from above and sodium azide (130 mg) were taken up in acetone and heated at reflux (60° C., 18 h). More sodium azide was added (500 mg), and the reaction was heated for an additional 18 h (60° C.). The solution was concentrated, and the residue was partitioned between EtOAc and water. The aqueous layer was extracted with EtOAc. The combined organic layers were washed with brine and dried ($MgSO_4$). Filtration and concentration gave the azide Example 291 as a yellow oil (320 mg. 64% from the amino-alcohol).

Step 4:

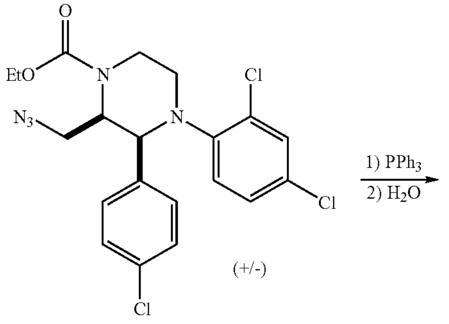

Example 291

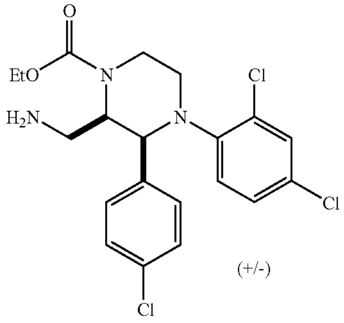

Example 292

The azide Example 291 (320 mg) and $PPh_3$ (220 mg) were taken up in THF and heated at 65° C. (5 h). Water (2 mL) was added, and the solution was heated at reflux (65° C., 18 h). The solution was concentrated, and the residue was partitioned between EtOAc and water. The aqueous layer was extracted with EtOAc. The combined organic layers were washed with brine and dried ($MgSO_4$). Filtration and concentration gave the crude amine. Purification via thin-layer preparative chromatography (10% MeOH in $CH_2Cl_2$, $SiO_2$) gave 210 mg (70%) of the amine Example 292.

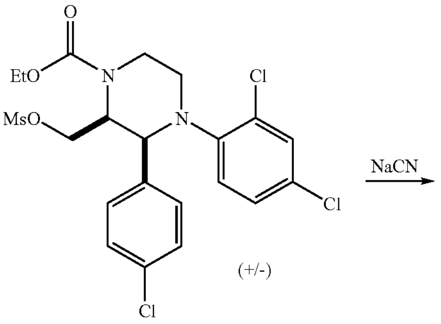

Example 290

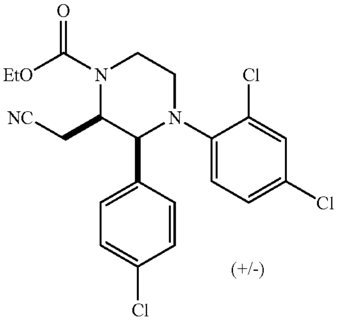

Example 293

The mesylate Example 290 from Scheme 25 (300 mg) and NaCN (43 mg) were taken up in DMF and heated at 90° C. (18 h). The solution was partitioned between EtOAc and water. The aqueous layer was extracted with EtOAc. The combined organic layers were washed with brine and dried ($MgSO_4$). Filtration and concentration gave a yellow oil. Purification via thin-layer preparative chromatography (5% EtOAc in $CH_2Cl_2$, $SiO_2$) gave the cyano-carbamate Example 293 (130 mg, 50%) as a white solid.

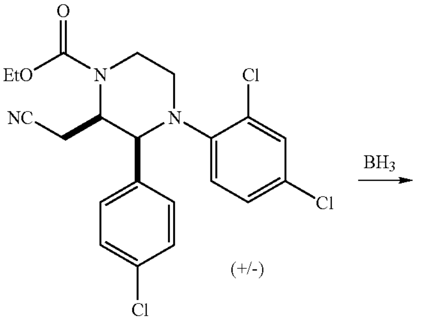

Example 293

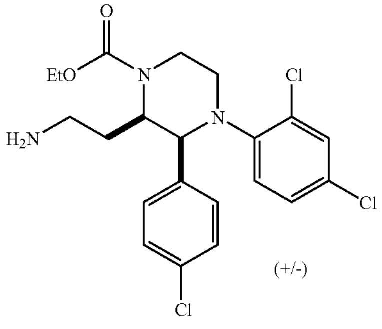

Example 294

The cyano-carbamate Example 293 (120 mg) was taken up in THF. Borane-THF (0.5 mL of a 1.0 M solution in THF) was added, and the solution was heated to reflux (70° C., 5 h). Additional $BH_3$ (2.2 mL of a 1.0 M solution in THF) was added to the reaction, and the reaction was heated at ref lux (70° C., 18 h). The solution was cooled and quenched with 1 M $HCl_{(aq.)}$. The solution was stirred at 25° C. (20 minutes) and then rendered basic with 1 N $NaOH_{(aq.)}$. The mixture was extracted with EtOAc. The combined organic layers were washed with brine and dried ($MgSO_4$). Filtration and concentration gave a yellow oil. Purification via thin-layer preparative chromatography (15% MeOH in $CH_2Cl_2$, $SiO_2$) gave 100 mg (83%) of the amine as a yellow oil.

Preparation of Examples 295-301

Scheme 26

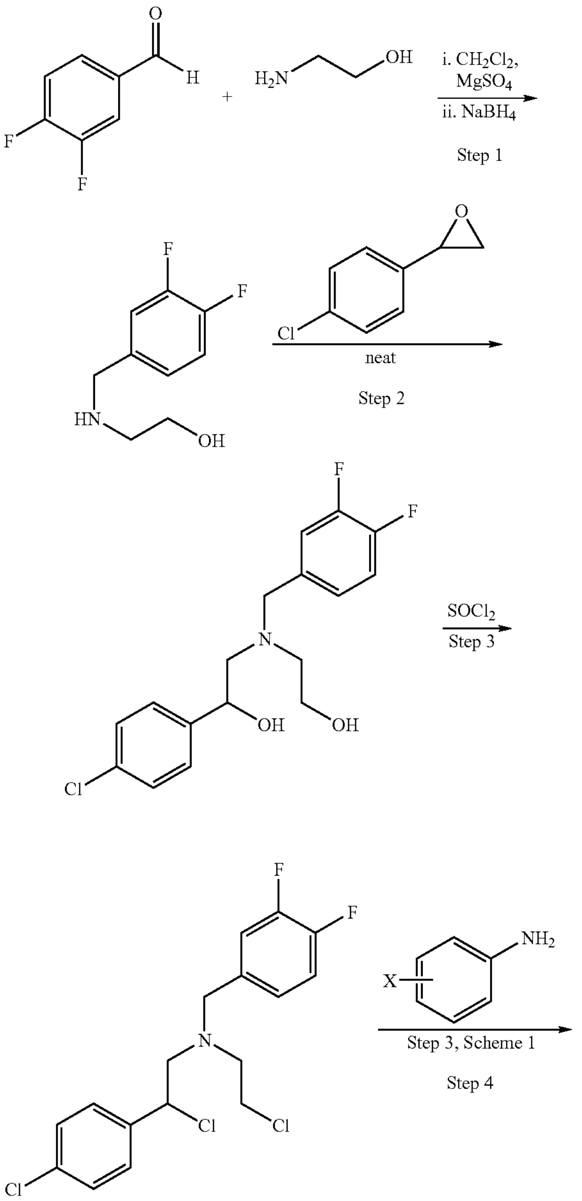

-continued

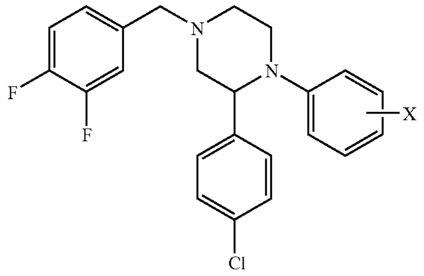

Step 1:

To 3,4-difluorobenzaldehyde (15.0 g, 105 mmol) in $CH_2Cl_2$ (100 mL) was added ethanolamine (6.4 g, 105 mmol) and $MgSO_4$ (32 g). The reaction mixture was stirred for 20 h at room temperature. The reaction was filtered and concentrated in vacuo. The residue was taken up into MeOH (100 mL), cooled to 0° C., and $NaBH_4$ was added. The reaction mixture was stirred for 2 h allowing the cold bath to warm to room temperature. The reaction was then concentrated in vacuo and 3N HCl was added. The mixture was extracted with ether. The aqueous layer was then rendered basic with 3N NaOH and then extracted with EtOAc. The EtOAc extractions were combined and washed with water and brine. The organic layer was dried ($MgSO_4$), filtered, and concentrated in vacuo to provide the corresponding amino-alcohol (14.0 g, 75 mmol).

Step 2:

To the amino-alcohol from step 1 (7.0 g, 37 mmol) was added 4-chlorostryrene oxide (5.0 mL, 41.5 mmol). The neat reaction mixture was warmed to 130° C. and stirred for 20 h, cooled to room temperature and purified by silica gel chromatography (3-5% $MeOH/CH_2Cl_2$) to provide the corresponding amino-diol (12.6 g, 36.8 mmol).

Step 3:

To the amino-diol prepared in step 2 (12.6 g, 37 mmol) in $CHCl_3$ (122 mL) at 0° C. was added $SOCl_2$ (61 mL) dropwise. After addition, the reaction mixture was warmed to reflux and stirred for 2 h. The reaction was concentrated in vacuo. The residue was taken up into $CH_2Cl_2$ and stirred vigorously with saturated $NaHCO_3$. The organic layer was washed with brine and dried ($MgSO_4$). The organic layer was filtered and concentrated in vacuo. The residue was purified by silica gel chromatography (10% EtOAc/hexane) to provide the corresponding amino-dichloride (10.0 g, 26 mmol).

Step 4:

Following the procedure of step 3 in Scheme 1, the anilines listed in Table XI were used in place of 2,4-dichloroaniline to provide the desired diarylpiperazine compound.

TABLE XI
| Example # | Example Structure | aniline |
|---|---|---|
| 295 | 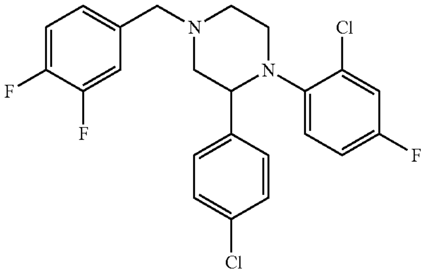 | 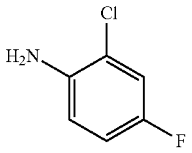 |
| 296 | 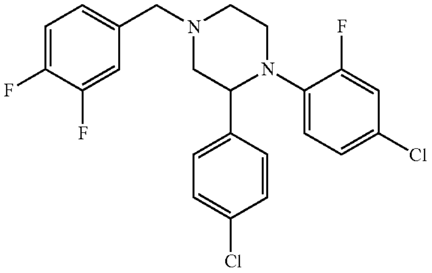 | 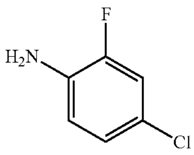 |
| 297 | 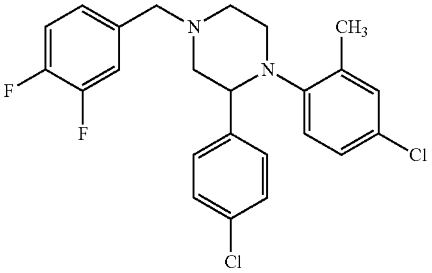 | 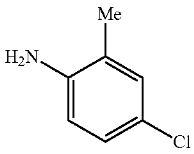 |
| 298 | 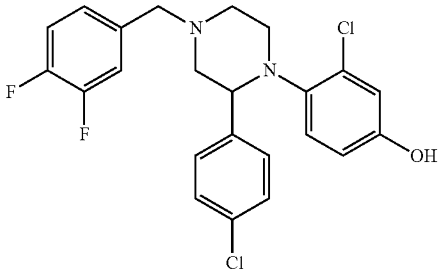 | 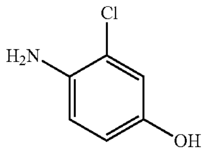 |
| 299 | 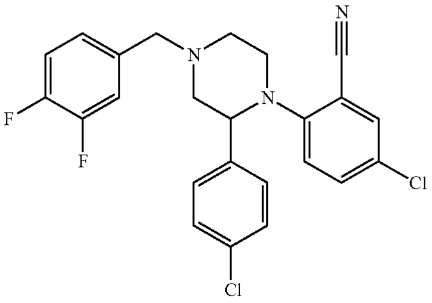 | 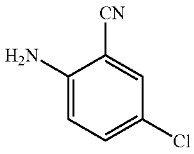 |

TABLE XI-continued
| Example # | Example Structure | aniline |
|---|---|---|
| 300 | 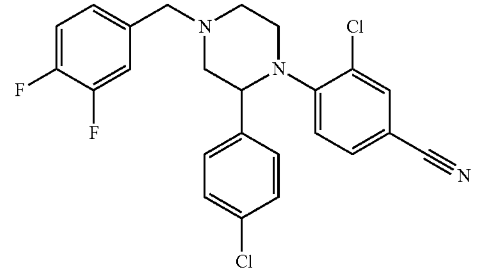 | 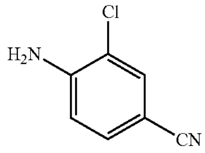 |
| 301 | 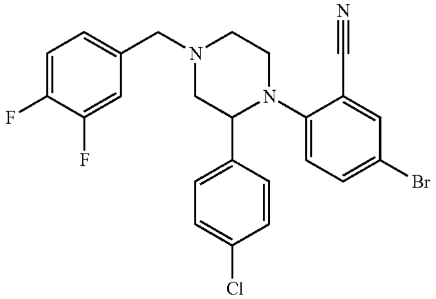 | 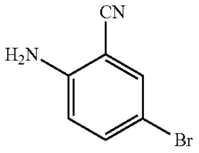 |
Preparation of Example 302
Scheme 27
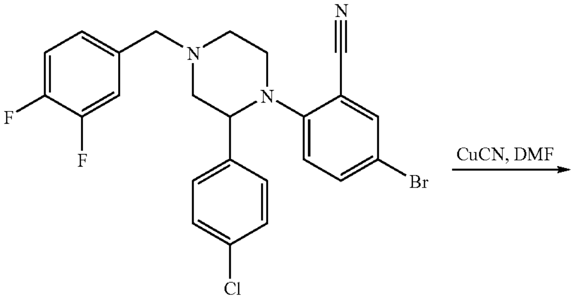
Example 301
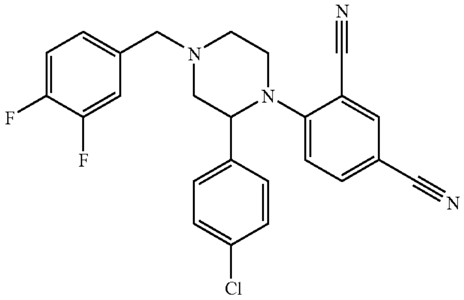
Example 302
Example 302 was prepared using the procedure of step 1, Scheme 29 used to prepare Example 308.
Preparation of Examples 303-304
Scheme 28
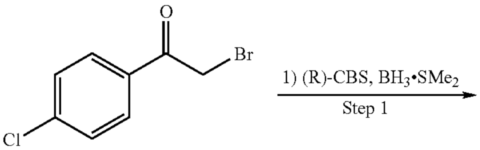
i
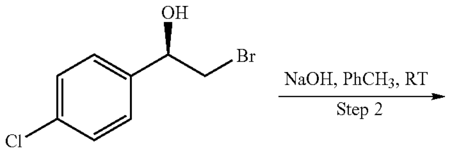
ii
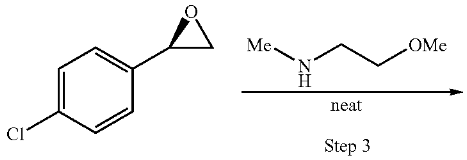
iii -continued

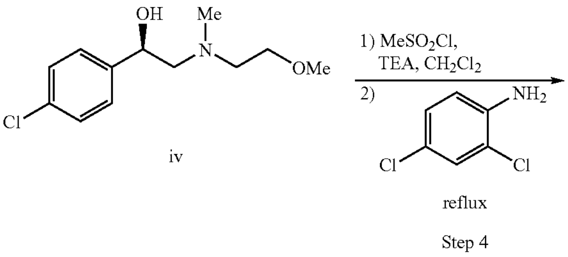

iv

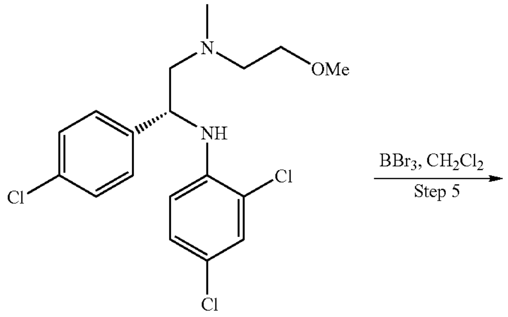

v

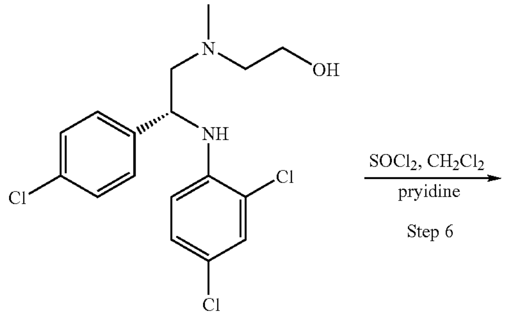

vi

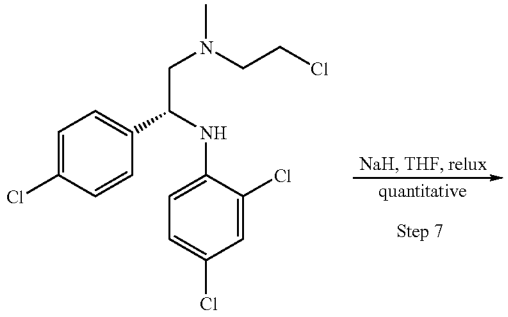

vii

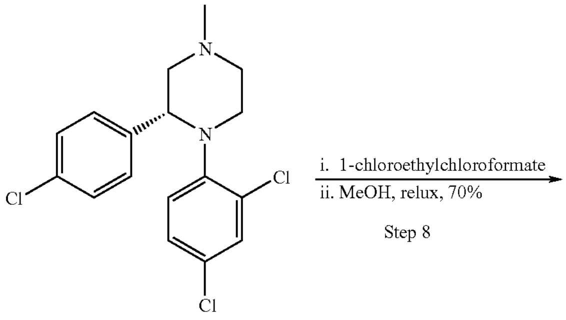

Example 303

-continued

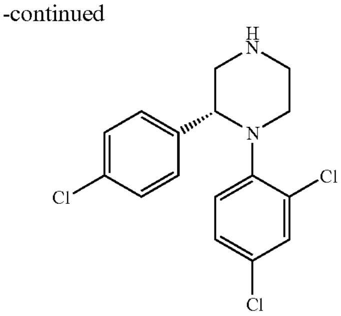

Example 304 ii

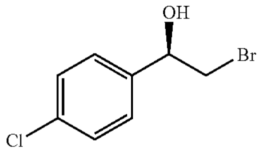

Step 1:

To 2-bromo-4'-chloroacetophenone (233 g, 1000 mmol) in THF (1 L) at 0° C. was added (R)-2-methyl-CBS-oxazaborolidine (available from Aldrich) (1.0 M in THF, 200 mL, 200 mmol) through an addition funnel. $BH_3.SMe_2$ (2.0 M in THF, 300 mL, 600 mL) was added slowly over 25 min. The reaction was stirred at room temperature for 2 h. The reaction was cooled to 0° C., and MeOH (200 mL) was added slowly (with gas evolution). The resulting solution was concentrated in vacuo and then diluted with $CH_2CO_2$ (3.5 L). The organic layer was washed with 1N HCl, water, and brine, then dried ($MgSO_4$), filtered, and concentrated in vacuo to provide bromo-alcohol ii as an oil that solidified on standing (237 g).

iii

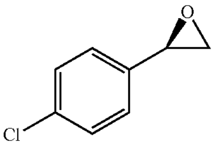

Step 2:

The bromo-alcohol ii from step 2 (237 g, 1000 mmol) was dissolved in toluene (3.5 L) and 3N NaOH (3.5 L) was added. The reaction was stirred vigorously at room temperature for 3 h. The organic layer was washed with water and brine and dried ($MgSO_4$), then filtered and concentrated in vacuo to provide the epoxide iii (154 g, 1000 mmol). The ee (i.e., enantiomeric excess) of the epoxide was found to be >96% ee by HPLC [R,R-Whelko-O-1, 99.75:0.25 hexane/IPA, 1 mL/min, 220 nm. Isomer A retention time 10.5 min, isomer B (major) 14.1 min)].

iv

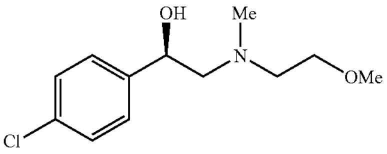

Step 3:

To the epoxide iii prepared in step 2 (102 g, 662 mmol) was added N-(2-methoxyethyl)methyl amine (83 g, 930 mmol). The reaction mixture was heated neat (i.e., without solvent) to 100° C. and stirred for 18 h. The reaction mixture was cooled to room temperature and then concentrated in vacuo to remove the excess amine, thereby providing amino-alcohol iv as a mixture of regiosomeric ring opening products (~12:1) (154 g, 96%).

v

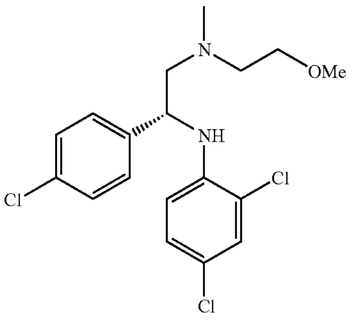

Step 4:

To the amino-alcohol iv prepared in step 3 (101 g, 416 mmol) in $CH_2Cl_2$ (2 L) at 0° C. was added TEA (i.e., triethylamine) (145 mL, 1040 mmol) followed by methanesulfonyl chloride (52.4 g, 460 mmol). The reaction mixture was stirred at room temperature for 2 h and then methanesulfonyl chloride (4 mL, 6 mmol) was added. The reaction mixture was stirred for an additional 1 h, then 2,4-dichloroaniline (67.5 g, 416 mmol) was added and the mixture was warmed to reflux. The refluxing mixture was stirred for 20 h and cooled to room temperature. $CH_2Cl_2$ (2 L) was added, and the reaction mixture was washed with saturated $NaHCO_3$, water, and brine, then dried ($Mg_2SO_4$), filtered, and concentrated in vacuo to provide v (167 g) as a pale oil that was used directly in the following synthetic step. This process is expected to go with retention of configuration as described in *Tetrahedron: Asymmetry* 10 (1999) 2655-2663 (herein incorporated by reference).

vi

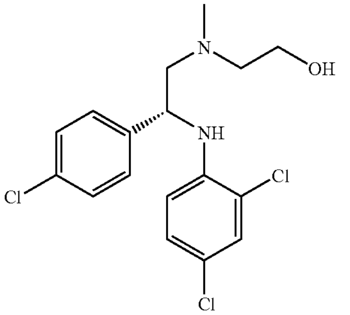

Step 5:

To v (167 g, 433 mmol) in $CH_2CO_2$ (1.5 L) at 0° C. was added $BBr_3$ (164 g, 433 mmol) over 30 minutes. The reaction was stirred at 0° C. for 1 h and then for additional 3.5 h at room temperature. Saturated $NaHCO_3$ (3.5 L) was added slowly with gas evolution from the reaction mixture. The reaction mixture was extracted with $CH_2Cl_2$. The organic extracts were combined and washed with water (2 L), and brine (2 L), dried ($MgSO_4$), filtered, and concentrated in vacuo to provide a brown oil that was purified by silica gel chromatography (30% EtOAc/hexane) to yield amino-alcohol vi (90 g, 241 mmol).

vii

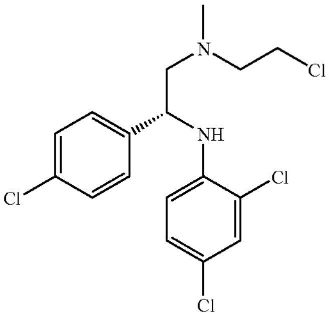

Step 6:

To the amino-alcohol vi prepared in step 5 (90 g, 240 mmol) in $CH_2Cl_2$ (1 L) at 0° C. was added pyridine (40 mL, 480 mmol) followed by thionyl chloride (53 mL, 720 mmol). The cold bath was removed and the reaction was stirred at room temperature for 4 h and then concentrated in vacuo without heating. The sample was taken up into EtOAc, (2 L) and cooled to 0° C. Saturated $NaHCO_3$ (1 L) was cautiously added (with gas evolution). The EtOAc layer was washed with water (1 L), brine (1 L), dried ($MgSO_4$/$NaSO_4$), filtered and concentrated in vacuo to provide a brown oil that was purified by silica gel chromatography (10% EtOAc/hexane) to give chloro-amine vii as a pale brown oil (84 g, 89%).

Example 303

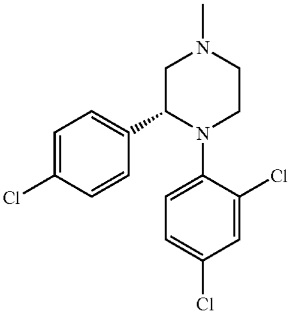

Step 7:

To chloro-amine vii prepared in step 6 (84 g, 214 mmol) in THF (1 L) was added NaH (60% dispersion in mineral oil) (21.14 g, 535 mmol) in one portion. The reaction mixture was warmed to reflux and stirred for 4 h, then cooled to 0° C. 1 L of an ice/water mixture was then added (gas evolution). $CH_2Cl_2$ (2 L) was added and the reaction mixture was stirred. The aqueous phase was washed with $CH_2Cl_2$, and the $CH_2Cl_2$ layers were then combined and washed with water (1 L), and brine (1 L). The reaction mixture was dried ($MgSO_4$), filtered, and concentrated in vacuo to provide Example 303 as a brown oil (83 g) contaminated with mineral oil. The material was used in the following step directly, without further purification.

Example 304

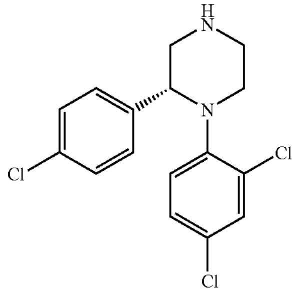

Step 8:

To N-methylpiperazine Example 303 (83 g) in DCE (0.8 L) at room temperature was added proton sponge (9.2 g, 43 mmol) followed by 1-chloroethylchloroformate (46.3 mL, 429 mmol). The reaction was warmed to reflux and stirred for 3 h. The reaction mixture was cooled to room temperature and concentrated in vacuo. MeOH (1 L) was added and the reaction mixture was warmed to reflux. The reaction mixture was stirred at reflux for 1.5 h and cooled to room temperature, then concentrated in vacuo. $CH_2Cl_2$ (1.5 L) was added and the reaction mixture was washed with saturated $NaHCO_3$, water, and brine. The reaction mixture was then dried ($MgSO_4$), filtered, and concentrated in vacuo. The concentrated residue was purified by silica gel chromatography ($CH_2Cl_2$ then 5% MeOH/$CH_2Cl_2$) to provide the piperazine Example 304 (60 g, 214 mmol). The ee was determined to be 98% ee by HPLC analysis (Chiralcel OD column, 94:6 hexane/isopropyl alcohol, 1 mL/min, 254 nm-isomer A retention time 8.4 min, isomer B 10.9 min).

Preparation of Example 305

Example 305

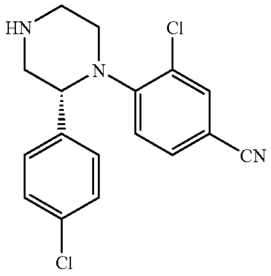

The piperazine Example 305 was prepared using a procedure similar to the procedure used to prepare Example 304, except that 4-amino-3-chlorobenzonitrile was used in place of 2,4-dichloroaniline in Step 4.

Preparation of Example 306

Example 306

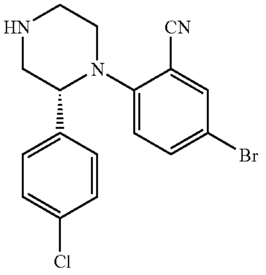

The piperazine Example 306 was prepared using a procedure similar to the procedure used to prepare Example 304 except that 2-amino-5-bromobenzonitrile was used in place of 2,4-dichloroaniline in Step 4.

Preparation of Examples 307-309

Scheme 29

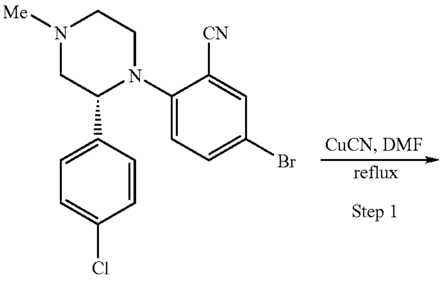

Example 307

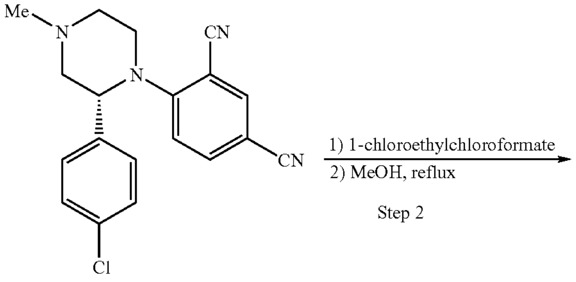

Example 308

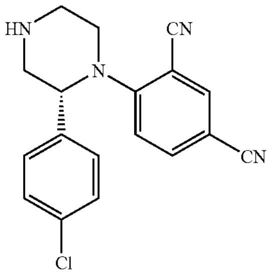

Example 309

Step 1:

The N-methylpiperazine Example 307 was prepared using a procedure similar to the procedure used to prepare Example 303 except that 2-amino-5-bromobenzonitrile was used in place of 2,4-dichloroaniline in Step 4. The N-methylpiperazine Example 307 (2.70 g, 7 mmol) in DMF (14 mL) was treated with CuCN (1.88 g, 21 mmol). The reaction mixture was warmed to reflux and stirred for 48 h. The reaction mixture was cooled to room temperature and EtOAc was added followed by saturated $NH_4Cl/NH_4OH$ 9:1 solution. The mixture was stirred vigorously for 15 minutes and then extracted with EtOAc. The organic layers were combined and washed with water, and brine. The organic layer ($MgSO_4$) was dried, filtered, and concentrated in vacuo. The residue was then purified by silica gel chromatography (4% MeOH/$CH_2Cl_2$) to provide the N-methylpiperazine Example 308 (1.0 g, 3.0 mmol).

Step 2:

The N-methylpiperazine Example 308 was demethylated to form Example 309 as in Step 8 of Scheme 28.

Preparation of Example 310

Example 310

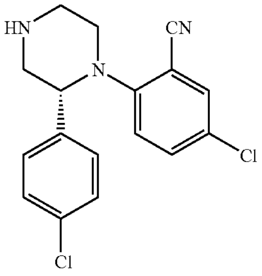

The 4-chloro-2-cyanopiperazine Example 310 was prepared using a procedure similar to the procedure used to prepare Example 304 of Scheme 28 except that 2-amino-5-chlorobenzonitrile was used in place of 2,4-dichloroaniline in step 4.

Preparation of Example 311

Scheme 30

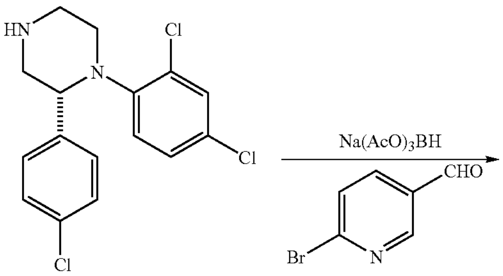

Example 304

-continued

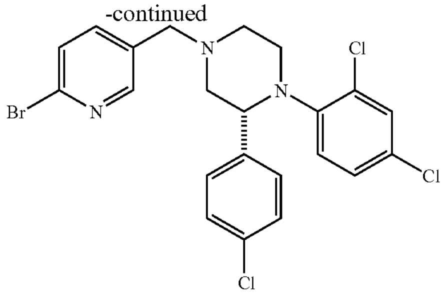

Example 311

The enantio-enriched piperazine Example 304 (500 mg), 6-bromo-pyridine-3-carbaldehyde (326 mg), and $Na(AcO)_3BH$ (371 mg) were taken up in $CH_2Cl_2$ and stirred at 25° C. (18 h). The reaction mixture was diluted with $CH_2Cl_2$ and washed with 1 N $NaOH_{(aq.)}$. The aqueous layer was extracted with $CH_2Cl_2$. The combined organic layers were dried ($MgSO_4$), filtered, and concentrated. Purification via flash chromatography (4/1 hexanes/EtOAc, $SiO_2$) gave 376 mg (50%) of the bromo-pyridine Example 311 as an oil.

Preparation of Examples 312-313

Scheme 31

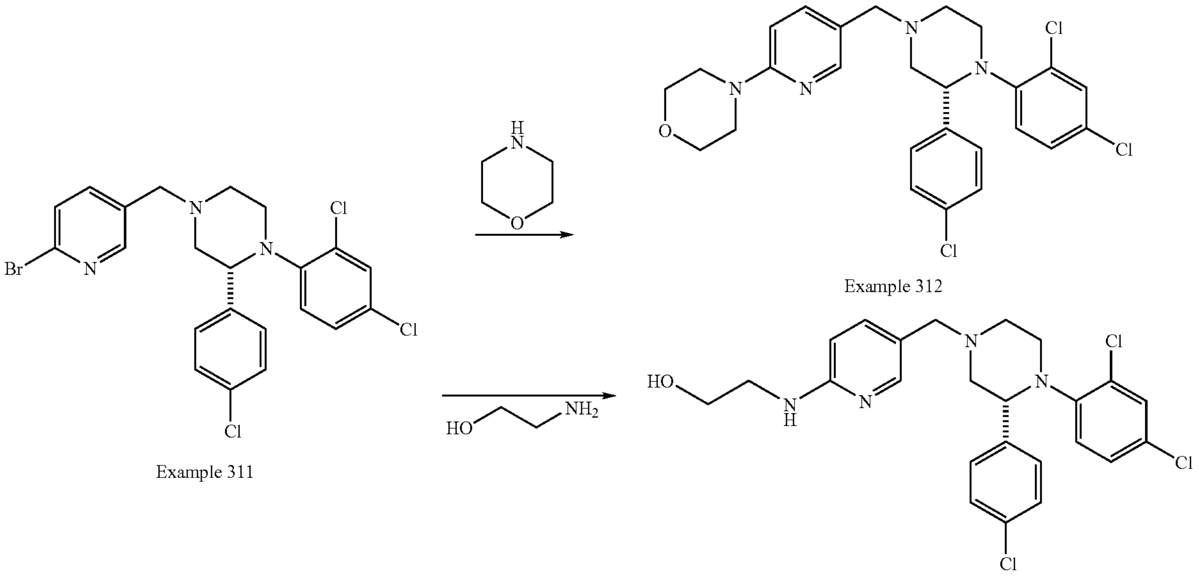

Example 311

Example 312

Example 313

The bromo-pyridine Example 311 (80 mg) and morpholine (0.3 mL) were heated at 10° C. (18 h). The solution was cooled and partitioned between $CH_2Cl_2$ and 1 N $NaOH_{(aq.)}$. The aqueous solution was extracted with $CH_2Cl_2$. The combined organic layers were dried ($MgSO_4$), filtered, and concentrated. Purification via thin-layer preparative chromatography (1/1 hexanes/EtOAc, $SiO_2$) gave 54 mg (65%) of Example 312 as a colorless oil.

In a similar manner, the reaction of Example 311 with ethanol-amine furnished Example 313 as a colorless oil.

Preparation of Examples 314 and 315

Scheme 32

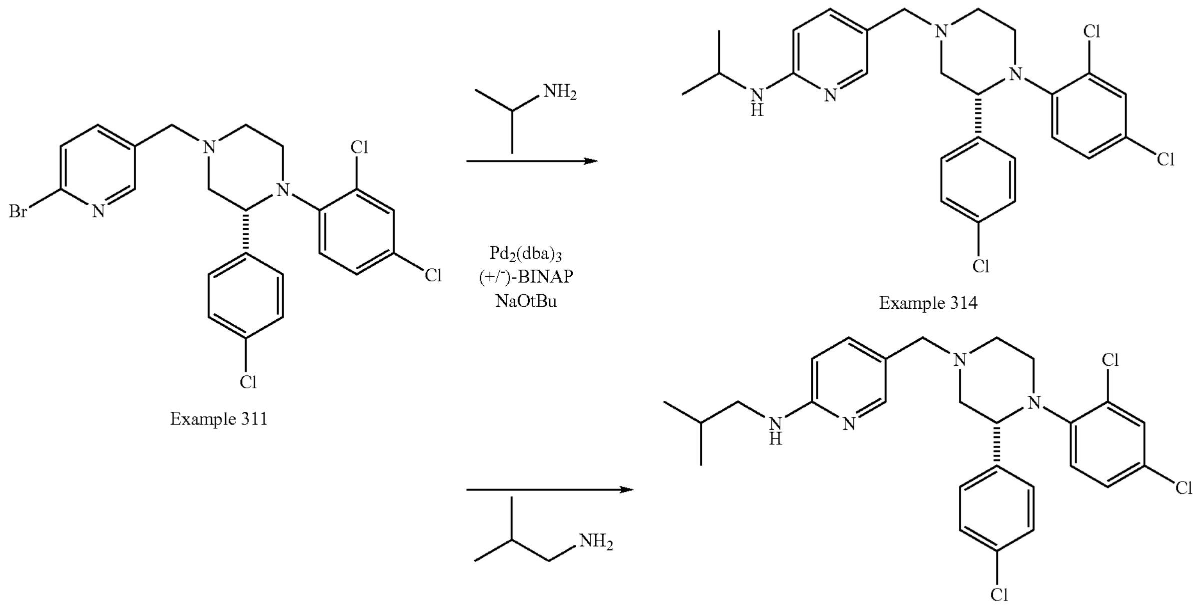

Example 311

Example 314

Example 315

The bromo-pyridine (85 mg) Example 311, racemic-BINAP (i.e., 2,2'-bis-diphenylphosphanyl-[1,1']binaphthalenyl; 40 mg), $Pd_2(dba)_3$ (15 mg), and NaOtBu (100 mg) were taken up in iso-propyl amine and heated at 10° C. in a sealed tube (18 h). The solution was diluted with $Et_2O$ and filtered through Celite. Concentration gave the crude product. Purification via thin-layer preparative chromatography (2/1 hexanes/EtOAc, $SiO_2$) gave 40 mg (48%) of Example 314 as an oil.

In a similar manner, the reaction of Example 311 and iso-butyl amine furnished Example 315 as an oil.

Preparation of Example 316

Scheme 33

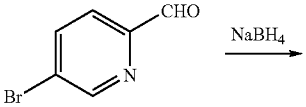

-continued

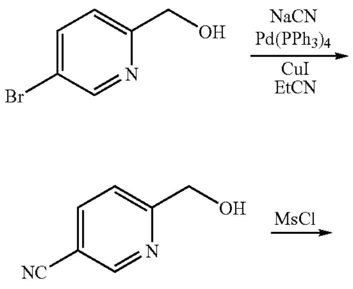

-continued

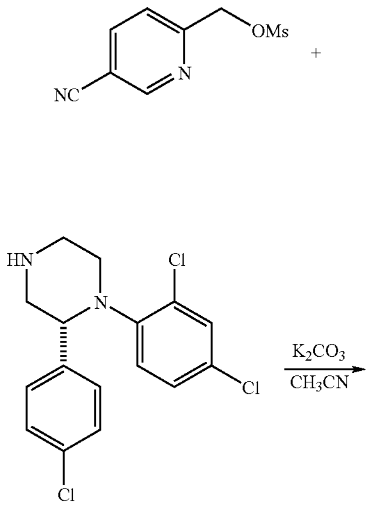

Example 304

-continued

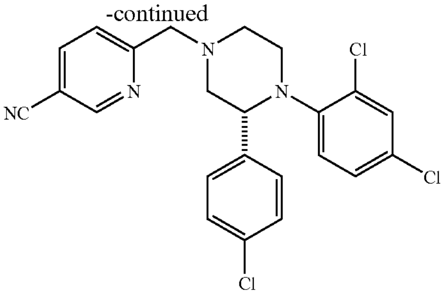

Example 316

Step 1:

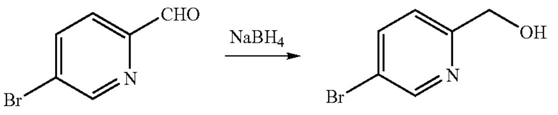

The 5-bromo-pyridine-2-carbaldehyde (2.0 g) was taken up in MeOH and cooled to 0° C. Sodium borohydride (450 mg) was added in portions at 0° C. The solution was warmed to 25° C. and stirred at that temperature for 1.5 h. The solution was concentrated, and the residue was quenched with 1 M $HCl_{(aq.)}$. The solution was stirred at 25° C. for 0.5 h. The solution was rendered basic via addition of solid $K_2CO_3$. The mixture was extracted with $CH_2Cl_2$. The combined organic layers were dried ($MgSO_4$), filtered, and concentrated to give (5-bromo-pyridin-2-yl)-methanol as a white solid.

Step 2:

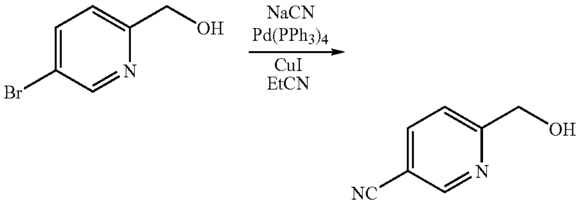

(5-Bromo-pyridin-2-yl)-methanol (1.0 g), NaCN (521 mg), $Pd(PPh_3)_4$ (612 mg), and CuI (200 mg) were taken up in degassed EtCN and heated at 110° C. (4 h). The solution was partitioned between EtOAc and 10% $NH_4OH$ (aq.). The aqueous layer was extracted with EtOAc. The combined organic layers were washed with brine and dried ($MgSO_4$). Filtration and concentration gave a yellow solid. Purification via flash chromatography (1/2 hexanes/EtOAc, $SiO_2$) gave 341 mg (48%) of (5-cyano-pyridin-2-yl)-methanol as a white solid.

Step 3:

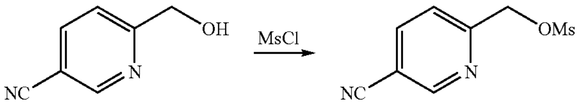

(5-Cyano-pyridin-2-yl)-methanol (100 mg) and $Et_3N$ (0.14 m) were taken up in $CH_2Cl_2$ and cooled to 0° C. Methansulfonyl chloride (0.1 mL) was added and the solution was stirred at 0° C. for 2 h. The solution was diluted with $CH_2Cl_2$ and washed with saturated $NaHCO_3$ (aq.). The aqueous layer was extracted with $CH_2Cl_2$. The combined organic layers were dried ($MgSO_4$). Filtration and concentration gave the mesylate as a yellow oil. The mesylate was used in step 4 without further purification.

Step 4:

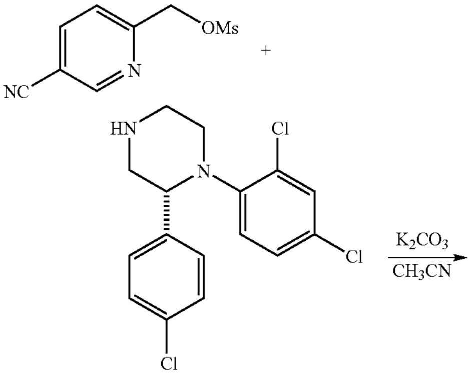

Example 304

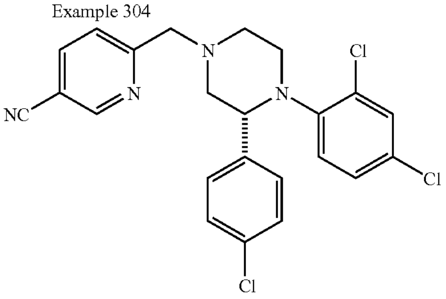

Example 316

The mesylate (0.75 mmol), enantio-enriched piperazine Example 304 (150 mg), and $K_2CO_3$ (152 mg) were taken up in $CH_3CN$ and heated at reflux (95° C., 1.5 h). The solution was cooled and partitioned between EtOAc and 1 N $NaOH_{(aq.)}$. The aqueous layer was extracted with EtOAc. The combined organic layers were washed with brine and dried ($MgSO_4$). Filtration and concentration gave a yellow oil. Purification via thin-layer preparative chromatography (2/1 hexanes/EtOAc, $SiO_2$) gave 155 mg (77%) of Example 316 as a white solid.

Preparation of Example 317

Scheme 34

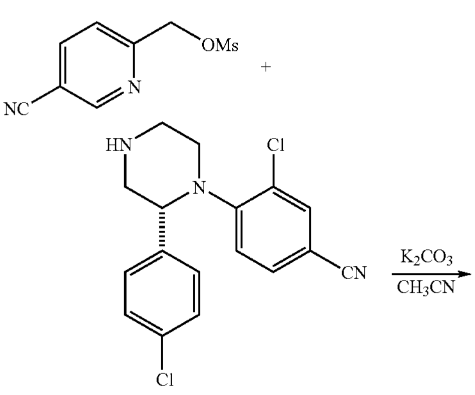

Example 305

-continued

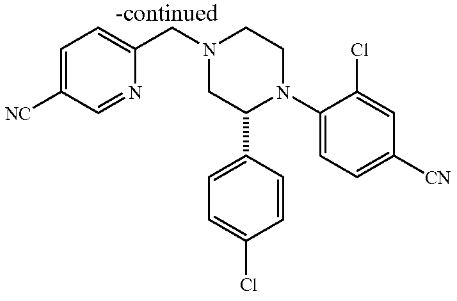

Example 317

Example 317 was prepared according to the procedures described in Scheme 33, Step 4, above, except that cyano-piperazine Example 305 was used instead of Example 304.

Preparation of Example 318

Scheme 35

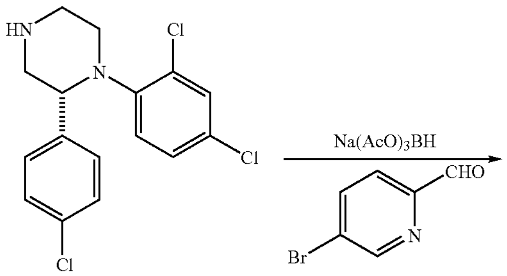

Example 304

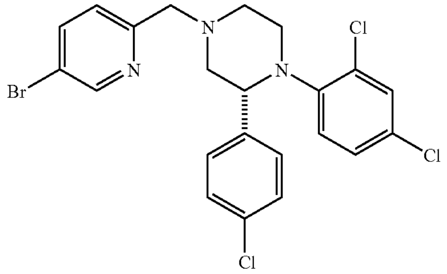

Example 318

Example 318 was prepared according to the procedure described in Scheme 30 except that 5-bromo-pyridine-2-carbaldehyde was used instead of 6-bromo-pyridine-3-carbaldehyde.

Preparation of Examples 319 and 320

Scheme 36

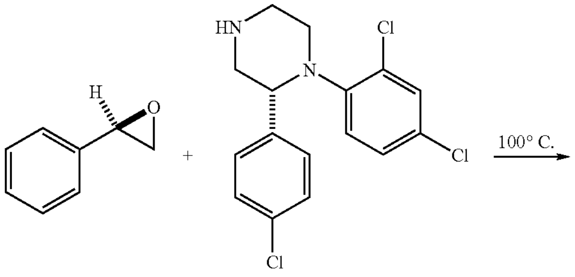

Example 304

-continued

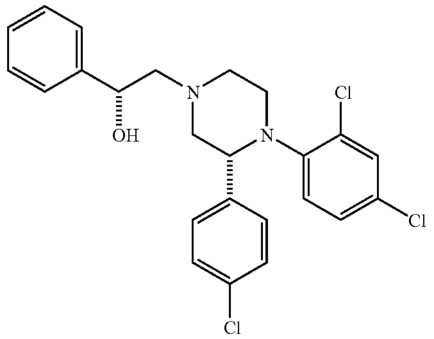

Example 319

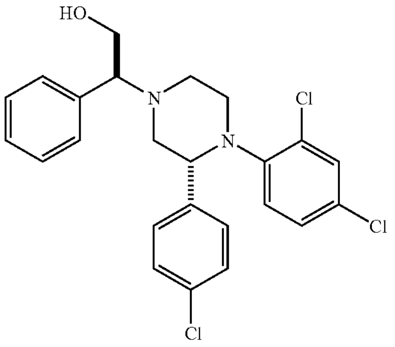

Example 320

(R)-Styrene oxide (0.1 mL) and the enantio-enriched piperazine Example 304 (200 mg) were heated neat at 95° C. (4 h). The residue was purified via thin-layer preparative chromatography (3/1 hexanes/EtOAc, $SiO_2$) to furnish 141 mg (48%) of Example 319 and 47 mg (16%) of Example 320 as colorless oils.

Preparation of Examples 321 and 322

Scheme 37

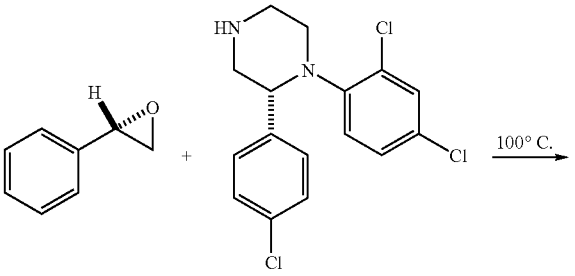

Example 304

-continued

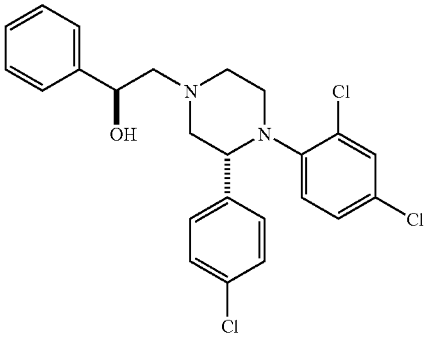

Example 321

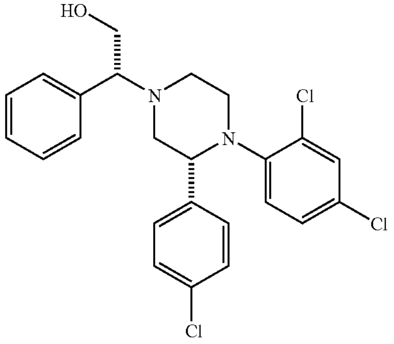

Example 322

Following the procedure in Scheme 36, (S)-styrene oxide and the piperazine Example 304 gave Example 321 and Example 322.

Preparation of Examples 323-335

Scheme 38

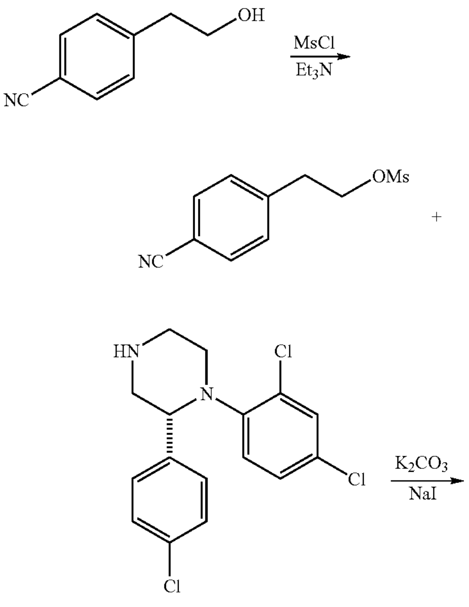

Example 304

-continued

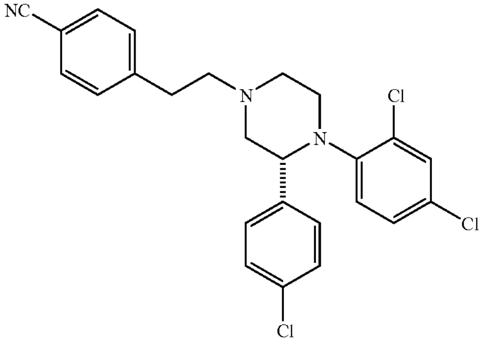

Example 323

Step 1:

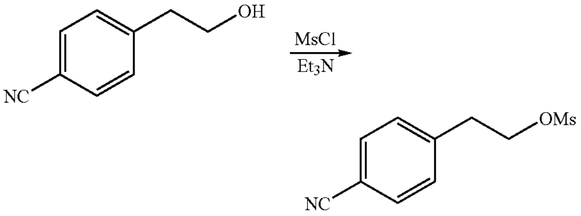

The 4-(2-hydroxyethyl)-benzonitrile (500 mg) and $Et_3N$ (480 mg) were taken up in $CH_2Cl_2$ at 25° C. Methanesulfonyl chloride (470 mg) was added and the solution was stirred at 25° C. (0.5 h). The solution was diluted with $CH_2Cl_2$ and washed with saturated $NaHCO_3$ (aq.). The aqueous layer was extracted with $CH_2Cl_2$. The combined organic layers were dried ($MgSO_4$), filtered, and concentrated. The resulting mesylate was used in step 2 without further purification.

Step 2:

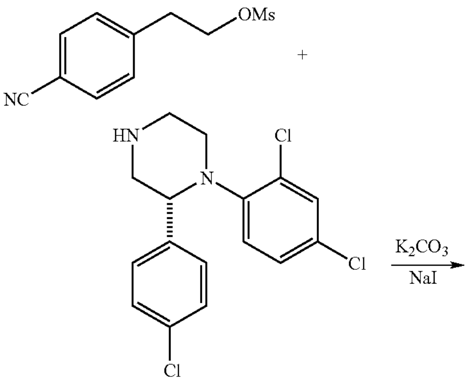

Example 304

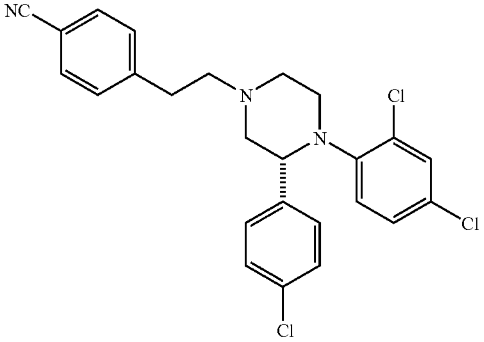

Example 323

The mesylate prepared in step 1 (63 mg), piperazine Example 304 (80 mg), $K_2CO_3$ (97 mg), and NaI (40 mg) were taken up in $CH_3CN$ and heated at reflux (90° C., 18 h). The solution was partitioned between EtOAc and water. The aqueous layer was extracted with EtOAc. The combined organic layers were washed with brine and dried ($MgSO_4$). Filtration and concentration gave a yellow oil. Purification via thin-layer preparative chromatography (7% EtOAc in $CH_2Cl_2$, $SiO_2$) gave 100 mg (90%) of Example 323 as a colorless oil.

The following examples were prepared in a similar manner using the appropriate alcohol and piperazine (Table XII).

TABLE XII

| Example # | Piperazine | Alcohol | Example Structure |
|---|---|---|---|
| 324 | 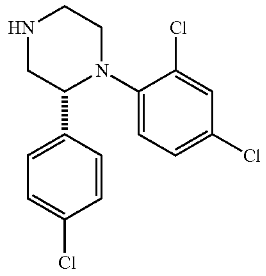 | 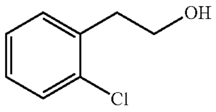 | 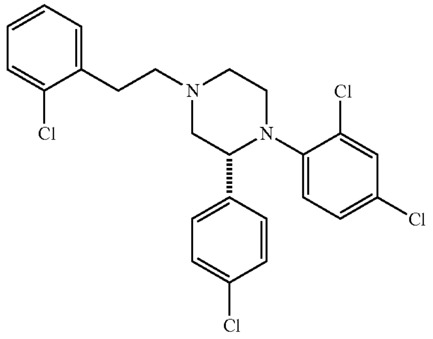 |
| 325 | 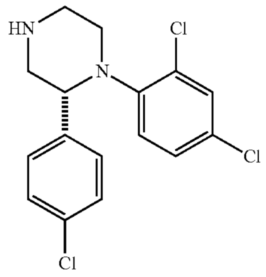 | 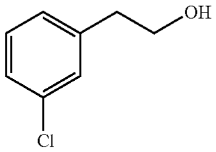 | 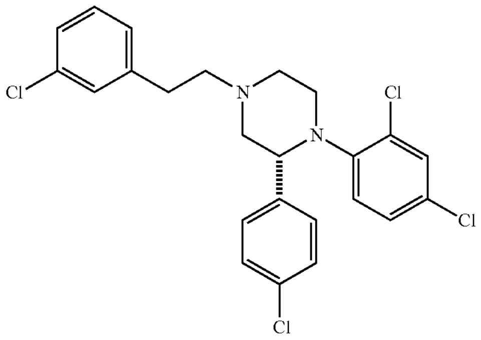 |
| 326 | 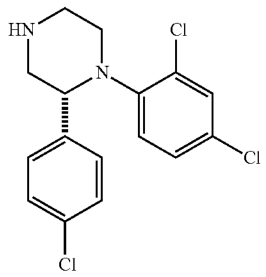 | 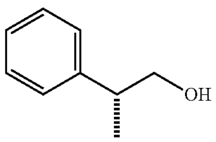 | 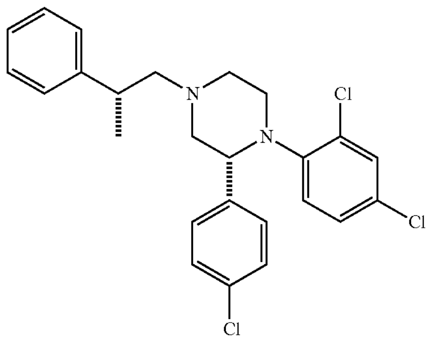 |
| 327 | 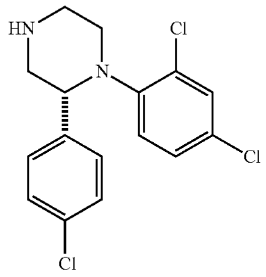 | 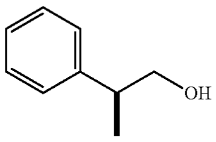 | 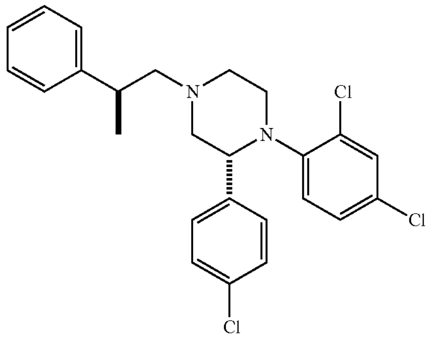 |

TABLE XII-continued
| Example # | Piperazine | Alcohol | Example Structure |
|---|---|---|---|
| 328 | 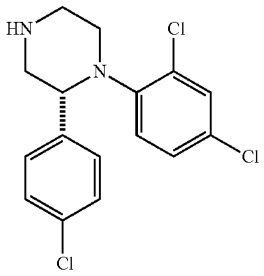 | 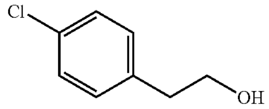 | 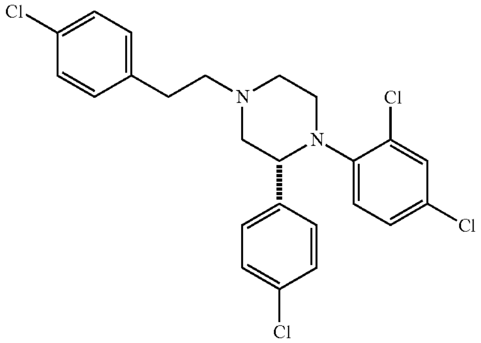 |
| 329 | 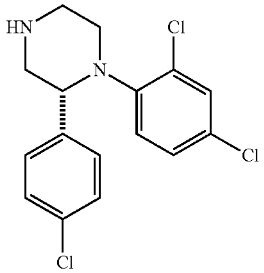 | 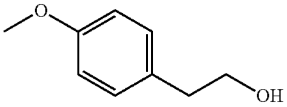 | 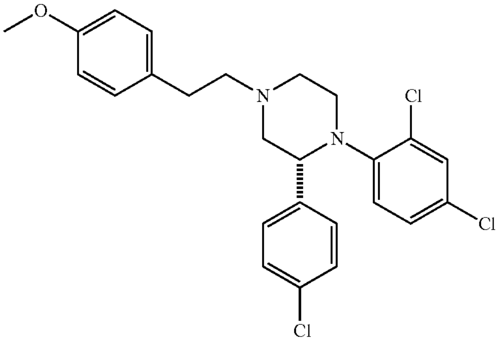 |
| 330 | 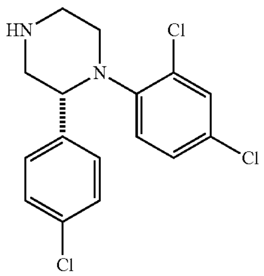 | 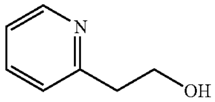 | 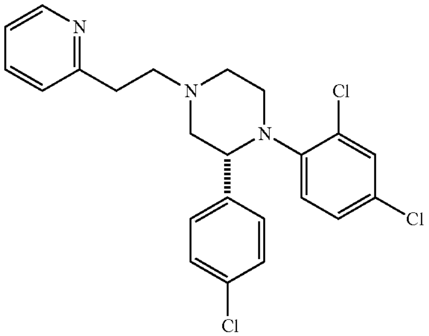 |
| 331 | 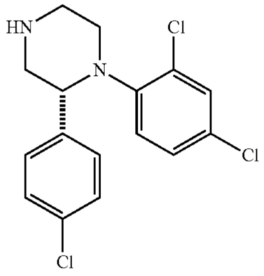 | 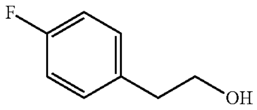 | 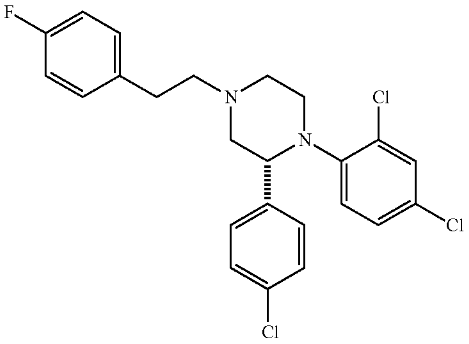 |

TABLE XII-continued
| Example # | Piperazine | Alcohol | Example Structure |
|---|---|---|---|
| 332 | 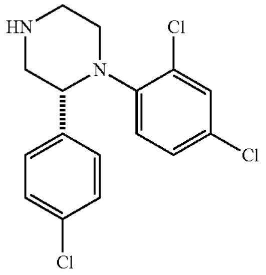 | 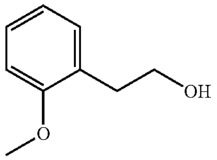 | 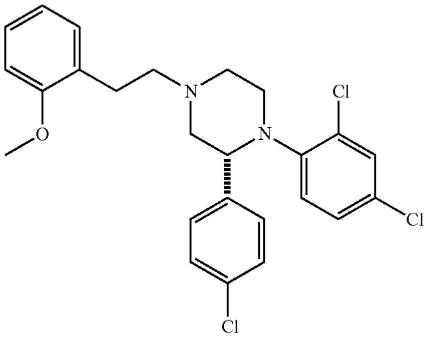 |
| 333 | 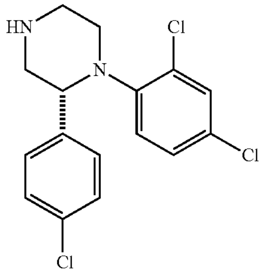 | 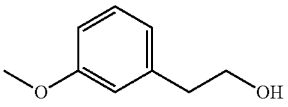 | 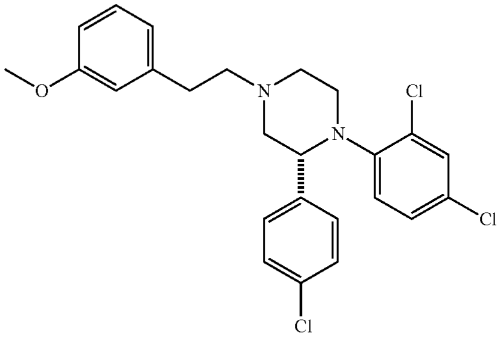 |
| 334 | 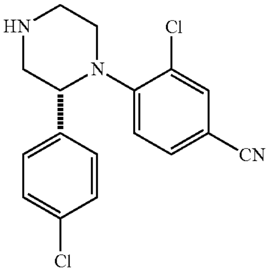 | 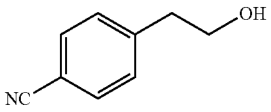 | 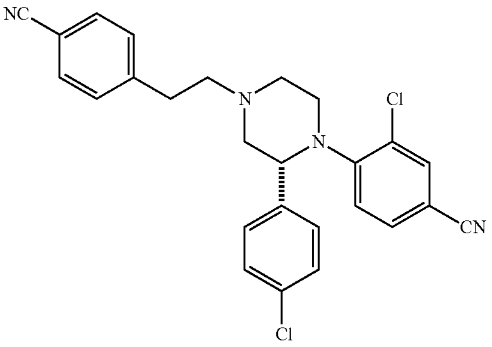 |
| 335 | 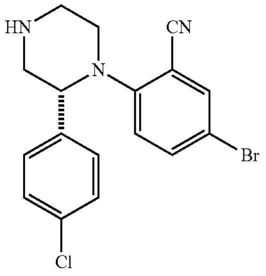 | 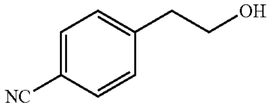 | 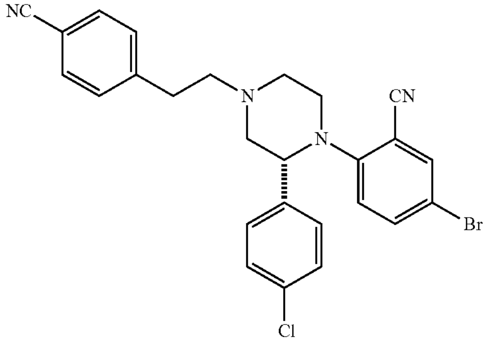 |

Preparation of Example 336

Scheme 39

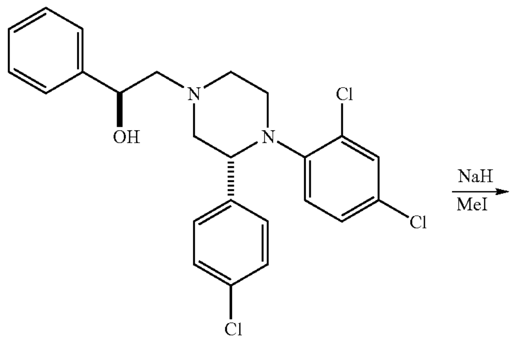

Example 321

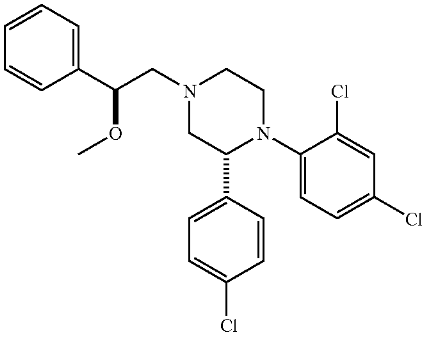

Example 336

The alcohol Example 321 (90 mg) was taken up in THF. Sodium hydride (100 mg of a 60 wt % dispersion in oil) was added. After stirring at 25° C. for 10-15 minutes, iodomethane (0.05 mL) was added. The mixture was stirred at 25° C. (2 h). The solution was partitioned between EtOAc and $H_2O$. The aqueous layer was extracted with EtOAc. The combined organic layers were washed with brine and dried ($MgSO_4$). Filtration and concentration gave a yellow oil. Purification via thin-layer preparative chromatography (3/1 hexanes/EtOAc, $SiO_2$) gave 89 mg (98%) of Example 336 as a colorless oil.

Preparation of Example 337

Scheme 40

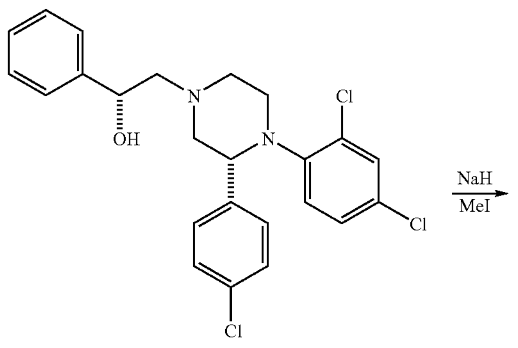

Example 319

-continued

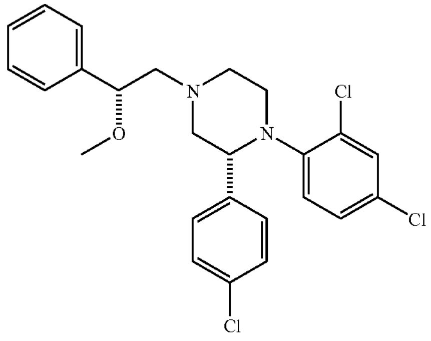

Example 337

Using a procedure similar to the procedure described in Scheme 39, Example 319 was converted into Example 337.

Preparation of Examples 338-339

Scheme 41

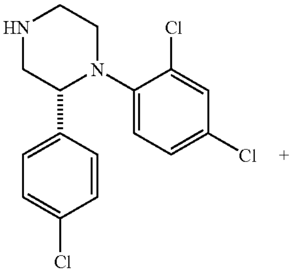

Example 304

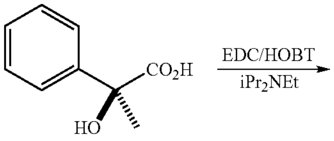

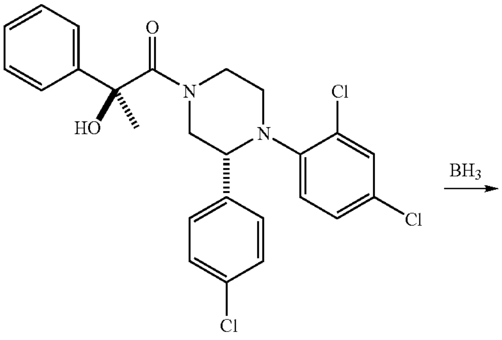

Example 338

-continued

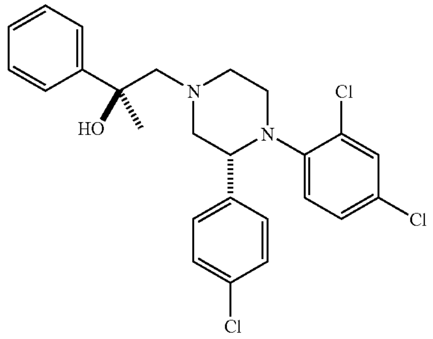

Example 339

Step 1:

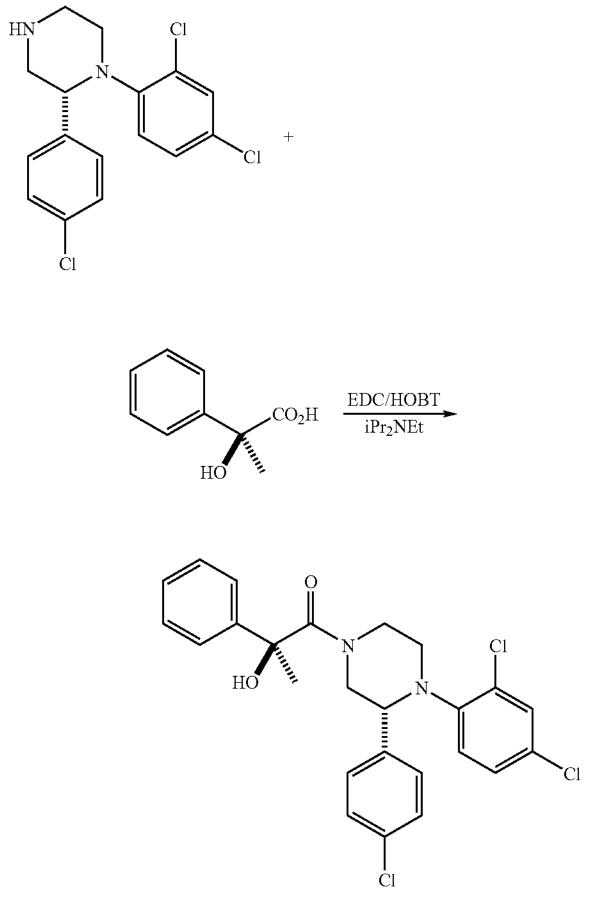

The piperazine Example 304 (300 mg), carboxylic acid (160 mg), EDC (211 mg), HOBT (149 mg), and $iPr_2NEt$ (0.2 mL) were taken up in $CH_3CN$ and heated at 65° C. (18 h). The solution was concentrated. The residue was partitioned between EtOAc and 1 N $NaOH_{(aq.)}$. The aqueous layer was extracted with EtOAc. The combined organic layers were washed with brine and dried ($MgSO_4$). Filtration and concentration gave a yellow oil. Purification via flash chromatography (2/1 hexanes/EtOAc, $SiO_2$) gave 223 mg (52%) of amide Example 338 as a colorless oil.

Step 2:

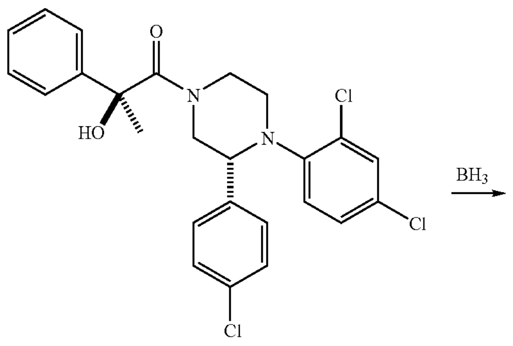

Example 338

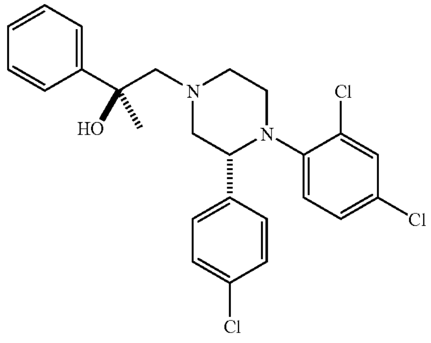

Example 339

The amide Example 338 (223 mg) and $BH_3$-THF complex (1.0 M $BH_3$ in THF, 3 mL) were taken up in THF and heated at reflux (65-70° C., 18 h). The solution was cooled and quenched with MeOH (2-3 mL) and 1 M $HCl_{(aq.)}$ (30-40 mL). The solution was stirred at 25° C. for 2 h. The solution was cooled and rendered basic with NaOH pellets (pH=10-12). The mixture was extracted with EtOAc. The combined organic layers were washed with brine and dried ($MgSO_4$). Filtration and concentration gave a yellow oil. Purification via thin-layer preparative chromatography (6/1 hexanes/EtOAc, $SiO_2$) gave 133 mg (61%) of Example 339 as a colorless oil.

Preparation of Examples 340-341

Scheme 42

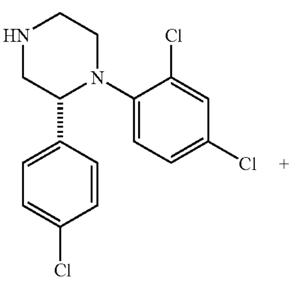

Example 304

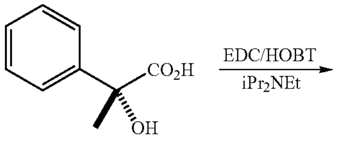

-continued

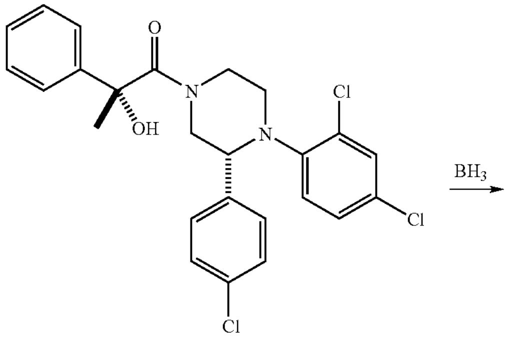

Example 340

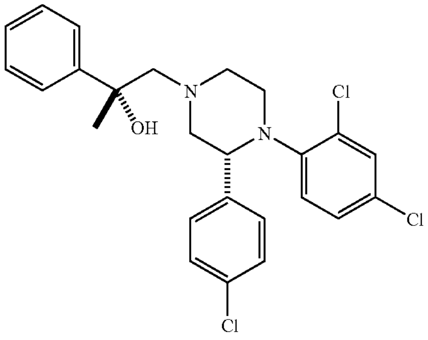

Example 341

Using the procedures outlined in Scheme 41, Examples 340 and 341 were prepared from the appropriate piperazine and acid as shown in Scheme 42.

Preparation of Examples 342-343

Scheme 43

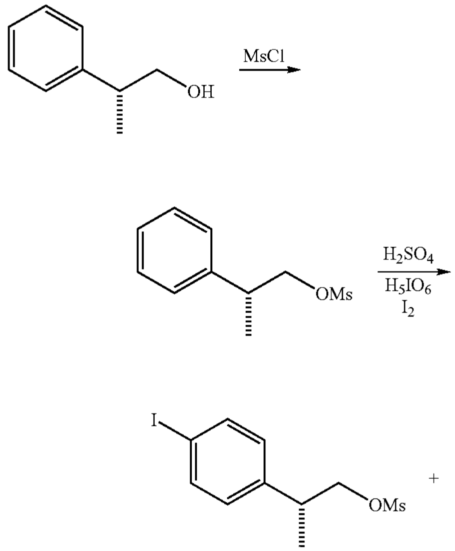

-continued

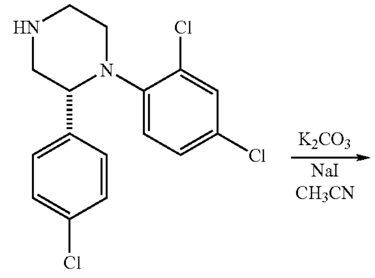

Example 304

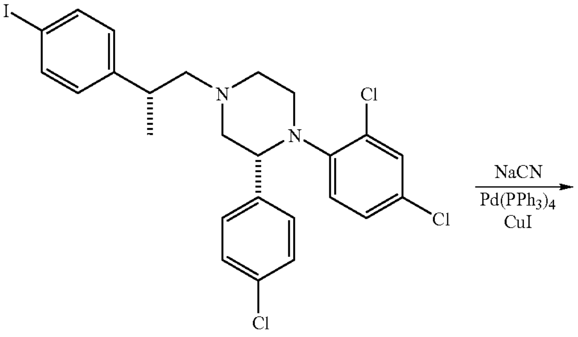

Example 342

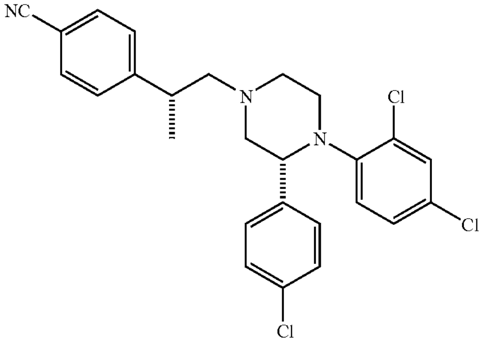

Example 343

Step 1:

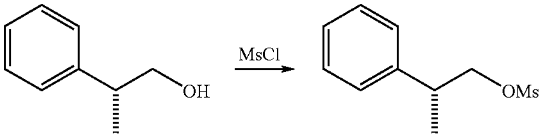

The 2-phenyl-propan-1-ol (500 mg) and $Et_3N$ (0.6 mL) were taken up in $CH_2Cl_2$ and cooled to 0° C. Methanesulfonyl sulfonyl chloride (0.3 mL) was added at 0° C., and the reaction was warmed to 25° C. (3 h). The solution was diluted with $CH_2Cl_2$ and washed with 1 N $NaOH_{(aq.)}$. The aqueous layer was extracted with $CH_2Cl_2$. The combined organic layers were dried ($MgSO_4$). Filtration and concentration gave the corresponding mesylate as a yellow oil, which was used without further purification in step 2.

Step 2:

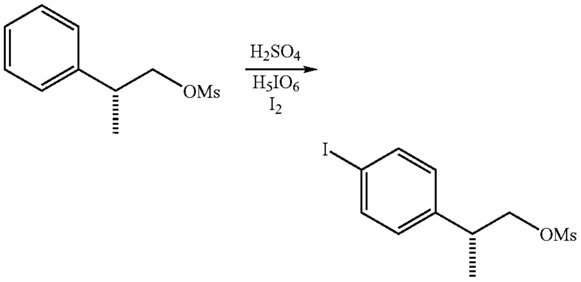

The mesylate prepared in step 1 (798 mg), $H_2SO_4$ (0.2 mL), $H_5IO_6$ (212 mg), and 12 (436 mg) were taken up in glacial acetic acid and stirred at 25° C. (18 h). The reaction mixture was heated at 70° C. for 3 h. The solution was cooled and rendered basic with 3 N NaOH (aq.). The mixture was treated with 10% $Na_2S_2O_3$ (aq.) to decolorize the $I_2$ color. The mixture was extracted with $CH_2Cl_2$. The combined organic layers were dried ($MgSO_4$), filtered, and concentrated. Purification via flash chromatography (4/1 hexanes/EtOAc, $SiO_2$) gave 800 mg (63%) of the iodide as a yellow oil.

Step 3:

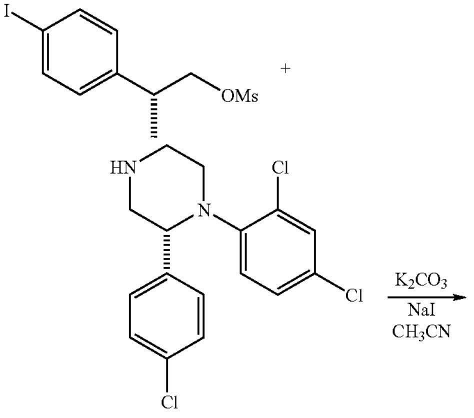

Example 304

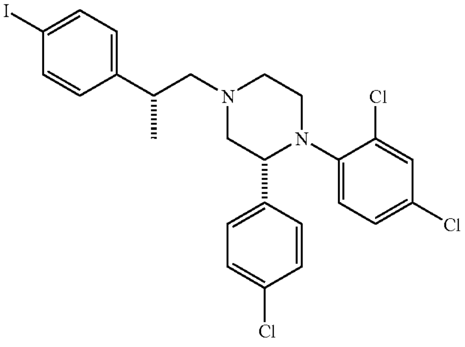

Example 342

The iodide prepared in step 2 (394 mg), piperazine Example 304 (200 mg), $K_2CO_3$ (240 mg), and NaI (44 mg) were taken up in $CH_3CN$ and heated (85-90° C., 18 h). The reaction mixture was partitioned between EtOAc and 1 N $NaOH_{(aq.)}$. The aqueous layer was extracted with EtOAc. The combined organic layers were washed with brine and dried ($MgSO_4$). Filtration and concentration gave a yellow oil. Purification via thin-layer preparative chromatography (8/1 hexanes/EtOAc, $SiO_2$) gave 118 mg (17%) of the iodo-piperazine Example 342 as a colorless foam.

Step 4:

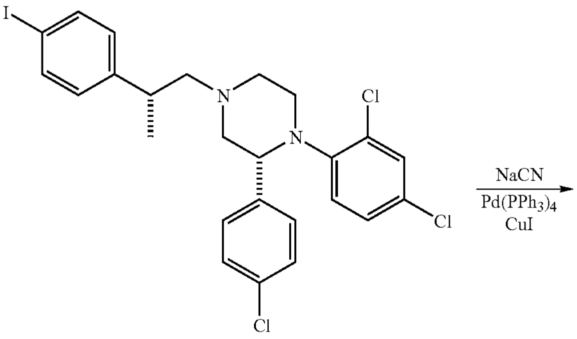

Example 342

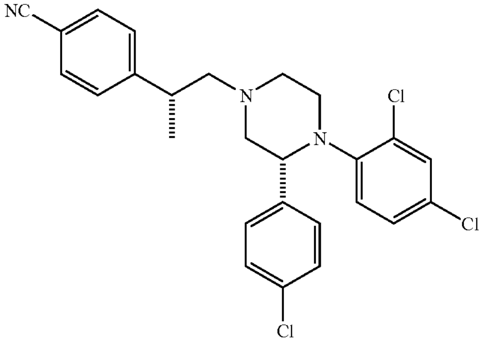

Example 343

The iodo-piperazine Example 342 prepared in step 3 (118 mg), NaCN (20 mg), $Pd(PPh_3)_4$ (23 mg), and CuI (8 mg) were taken up in degassed EtCN and heated at 105° C. for 1 h. The solution was partitioned between EtOAc and 1 N $NaOH_{(aq.)}$. The aqueous layer was extracted with EtOAc. The combined organic layers were washed with brine and dried ($MgSO_4$). Filtration and concentration gave a yellow oil. Purification via preparative thin-layer chromatography (6/1/hexanes/EtOAc, $SiO_2$) gave 58 mg (59%) of Example 343.

Preparation of Examples 344-346

Scheme 44

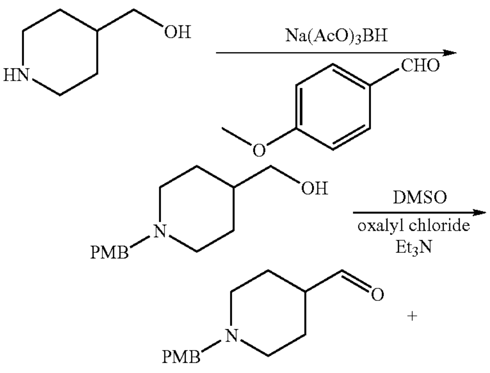

-continued

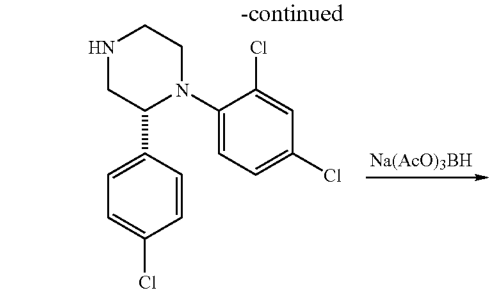

Example 304

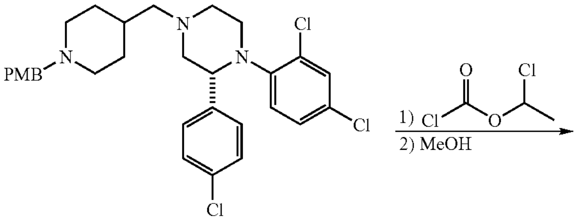

Example 344

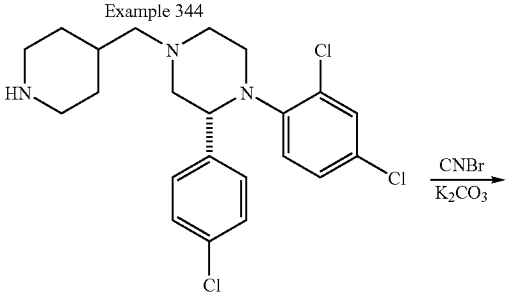

Example 345

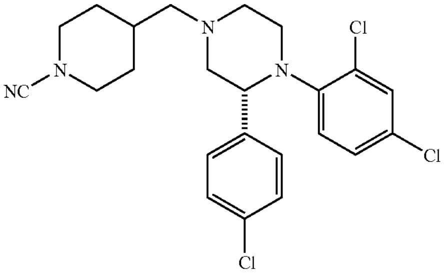

Example 346

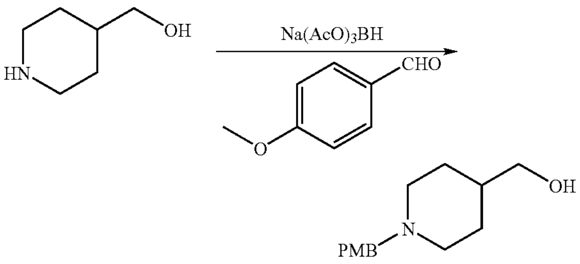

Step 1:

Piperidine-4-yl-methanol (5 g), p-anisaldehyde (6.3 mL), and $Na(AcO)_3BH$ (11 g) were taken up in $CH_2Cl_2$ and stirred at 25° C. (18 h). The solution was diluted with $CH_2Cl_2$ and washed with 1 N $NaOH_{(aq.)}$. The aqueous layer was extracted with $CH_2Cl_2$. The combined organic layers were dried ($MgSO_4$), filtered, and concentrated. The residue was partitioned between $Et_2O$ and 1 M $HCl_{(aq.)}$. The aqueous layer was extracted with $Et_2O$. The aqueous layer was cooled to 0° C. and rendered basic via addition of NaOH pellets (pH=10-12). The mixture was extracted with $CH_2Cl_2$. The combined organic layers were dried ($MgSO_4$), filtered, and concentrated which furnished the PMB alcohol (6.35 g, 62%) as a yellow oil.

Step 2:

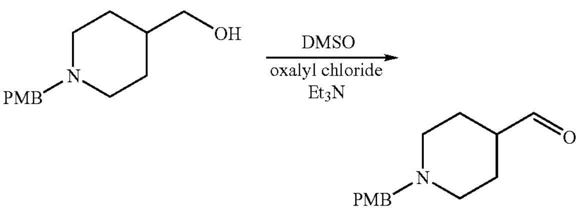

DMSO (2.5 mL) was taken up in $CH_2Cl_2$ (150 mL) and cooled to −40° C. ($CH_3CN/CO_2$). Oxalyl chloride (3.1 mL) in $CH_2Cl_2$ (15 mL) was added dropwise to the solution at −40° C. The solution was stirred at −40° C. for 30 minutes. The PMB alcohol prepared in step 1 (6.35 g) in $CH_2Cl_2$ (15 mL) was added to the solution at −40° C. The resulting solution was stirred at −40° C. for 30 minutes. Triethylamine (11.3 mL) was added to the solution at −40° C., and the resulting slurry was warmed to 25° C. and stirred at that temperature for 1.5 h. The solution was diluted with $CH_2Cl_2$ and washed with 1 N $NaOH_{(aq.)}$. The aqueous layer was extracted with $CH_2Cl_2$. The combined organic layers were dried ($MgSO_4$), filtered, and concentrated to furnish the aldehyde, which was used without further purification in step 3.

Step 3:

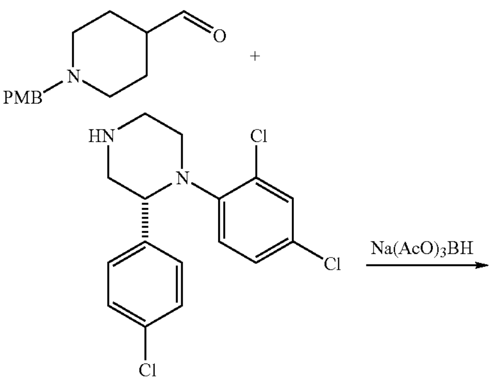

Example 304

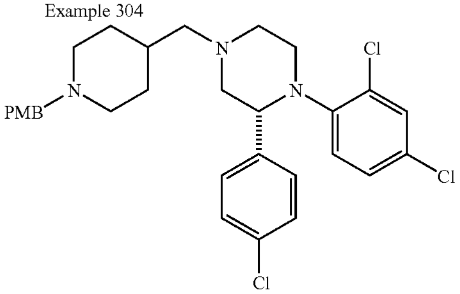

Example 344

The piperazine Example 304 (500 mg), the aldehyde prepared in step 2 (440 mg), and $Na(AcO)_3BH$ (400 mg) were taken up in $CH_2Cl_2$ and stirred at 25° C. (18 h). The solution was diluted with $CH_2Cl_2$ and washed with 1 N $NaOH_{(aq.)}$. The aqueous layer was extracted with $CH_2Cl_2$. The combined organic layers were dried ($MgSO_4$), filtered, and concentrated. Purification via flash chromatography (3/1 hexanes/EtOAc, $SiO_2$) gave 640 mg (78%) of Example 344 as a colorless oil.

Step 4:

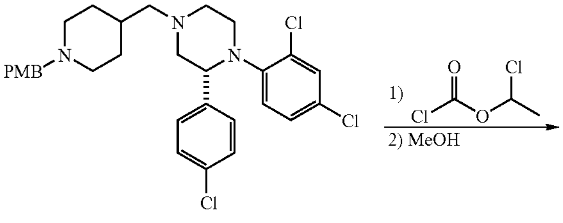

Example 344

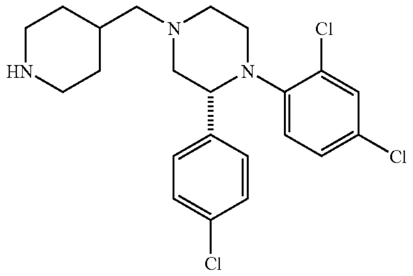

Example 345

Example 344 (640 mg) and the chloro-formate shown above in step 4 (0.2 mL) were taken up in $CH_2Cl_2$ and stirred at 25° C. (18 h). The solution was concentrated. The residue was taken up in MeOH and heated at reflux (65° C., 2.5 h). The solution was concentrated, and the residue was partitioned between 1 M $HCl_{(aq.)}$ and $Et_2O$. The aqueous layer was extracted with $Et_2O$. The aqueous layer was cooled (0° C.) and made basic via addition of NaOH pellets (pH=10-12). The solution was extracted with $CH_2Cl_2$. The combined organic layers were dried ($MgSO_4$), filtered, and concentrated to give Example 345 (367 mg, 74%) as a yellow oil.

Step 5

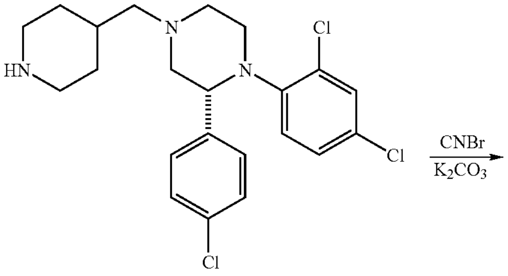

Example 345

-continued

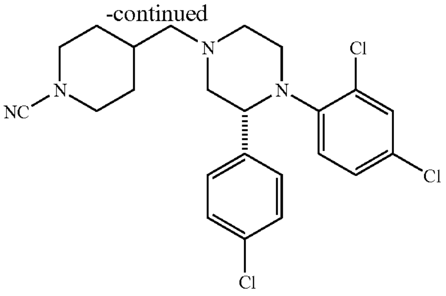

Example 346

Example 345 (70 mg), CNBr (0.2 mL of a 3.0 M solution in $CH_2Cl_2$), and $K_2CO_3$ (66 mg) were taken up in $CH_3CN$ and stirred at 25° C. (4 h). The solution was partitioned between EtOAc and saturated $NaHCO_3$ (aq.). The aqueous layer was extracted with EtOAc. The combined organic layers were washed with brine and dried ($MgSO_4$). Filtration and concentration gave a yellow oil. Purification via thin-layer preparative chromatography (3/1 hexanes/EtOAc, $SiO_2$) gave Example 346 (25 mg, 34%) as a colorless oil.

Preparation of Example 347

Scheme 45

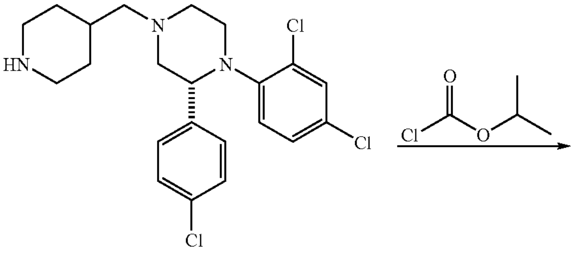

Example 345

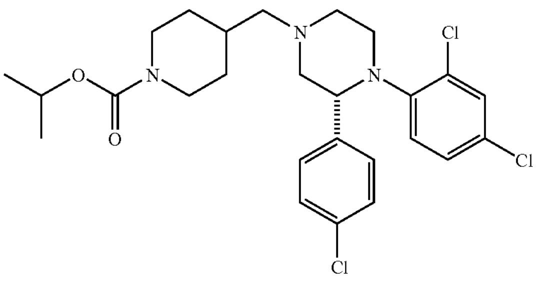

Example 347

Example 345 (70 mg) and the chloro-formate shown above in scheme 16 (0.3 mL) were partitioned between $CH_2Cl_2$ and 1 N $NaOH_{(aq.)}$. The mixture was stirred at 25° C. (4 h). The mixture was diluted with water and $CH_2Cl_2$. The aqueous layer was extracted with $CH_2Cl_2$. The combined organic layers were dried (MgSO4), filtered, and concentrated. Purification via thin-layer preparative chromatography (3/1 hexanes/EtOAc, $SiO_2$) gave Example 347 (63 mg, 75%) as a colorless oil.

Preparation of Example 348

Scheme 46

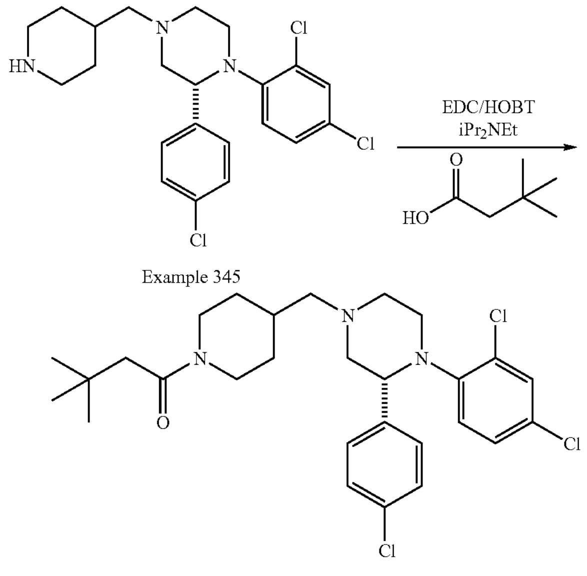

Example 345

Example 348

Example 345 was converted into Example 348 following the procedure outlined in Step 1 of Scheme 41 using the appropriate piperidine and acid shown in Scheme 46.

Preparation of Example 349

Scheme 47

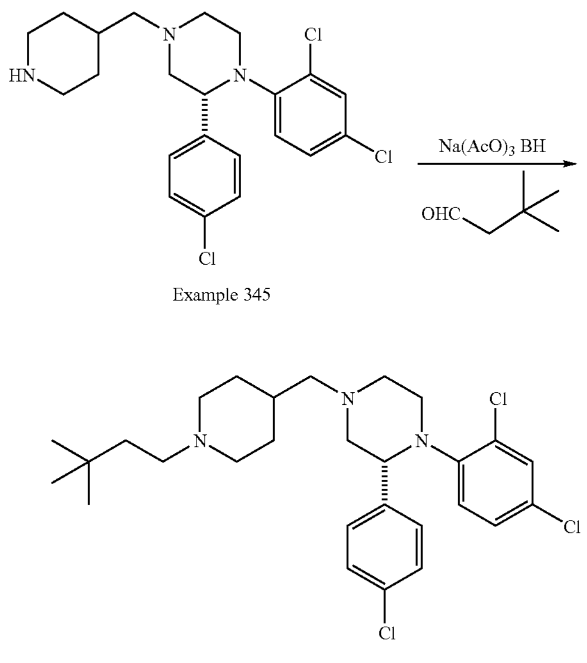

Example 345

Example 349

Example 345 was converted into Example 349 following the procedure outlined in Step 3 of Scheme 44 using the appropriate piperidine and aldehyde shown in Scheme 47.

Preparation of Example 350

Scheme 48

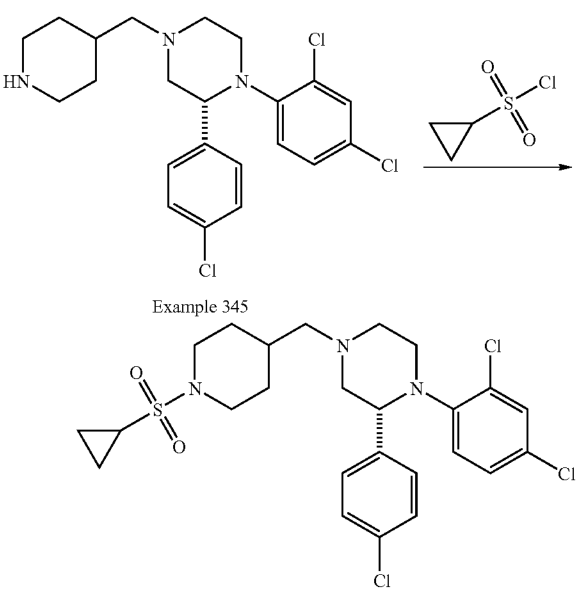

Example 345

Example 350

Example 345 was converted into Example 350 following the procedure outlined in Step 8 of Scheme 14 using the appropriate piperidine and sulfonyl chloride shown in Scheme 48.

Preparation of Example 351

Scheme 49

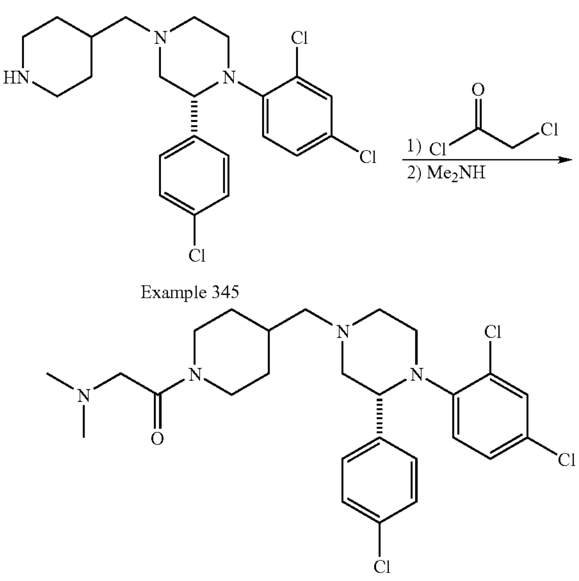

Example 345

Example 351

Example 345 (45 mg) and the acid chloride (0.05 mL) were partitioned between $CH_2Cl_2$ and saturated $NaHCO_3$ (aq.). The mixture was stirred at 25° C. (3 h). The layers were separated, and the aqueous layer was extracted with $CH_2Cl_2$. The organic layers were combined, dried ($MgSO_4$), filtered, and concentrated to furnish the chloro-amide. The chloro-amide was taken up in DMF and 20 mL of a 2.0 M $Me_2NH$ in THF solution was added. The solution was heated in a sealed tube (75° C., 66 h). The solution was concentrated. The residue was partitioned between $CH_2Cl_2$ and 1 N $NaOH_{(aq.)}$. The aqueous layer was extracted with $CH_2Cl_2$. The combined organic layers were dried ($MgSO_4$), filtered, and concentrated. Purification via thin-layer preparative chromatography (20/1 $CH_2Cl_2$/MeOH, $SiO_2$) gave 18 mg (34%) of Example 351 as a colorless oil.

Preparation of Examples 352-354

Scheme 50

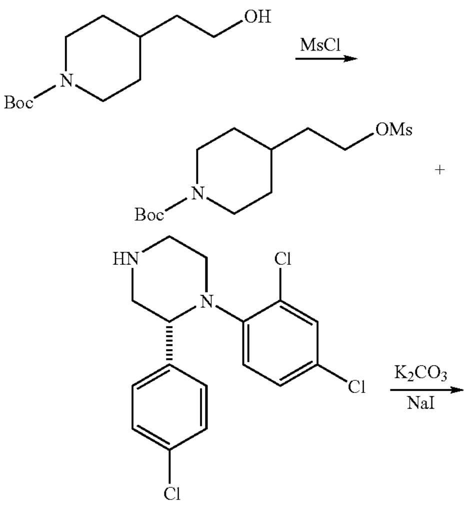

Example 304

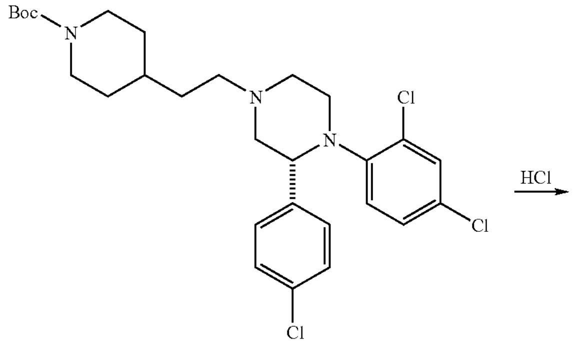

Example 352

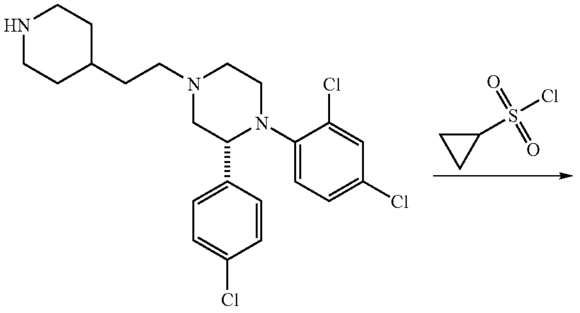

Example 353

-continued

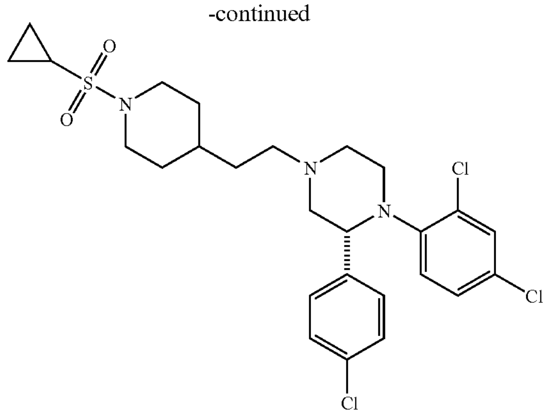

Example 354

Step 1:

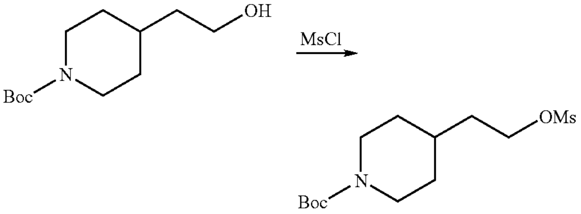

The N-Boc alcohol shown above in Scheme 50 was converted into the mesylate according to the procedure outlined in Step 1 of Scheme 43.

Step 2:

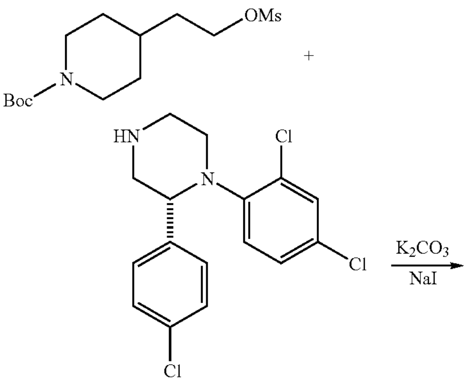

Example 304

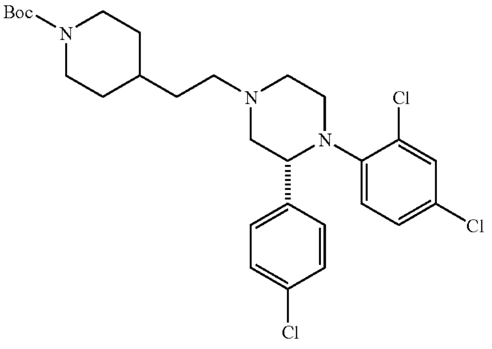

Example 352

Example 352 was prepared according to the procedure outlined in Step 3 of Scheme 43 using the appropriate reagents.

Step 3:

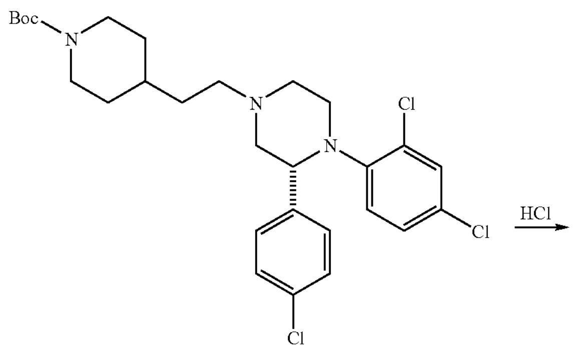

Example 352

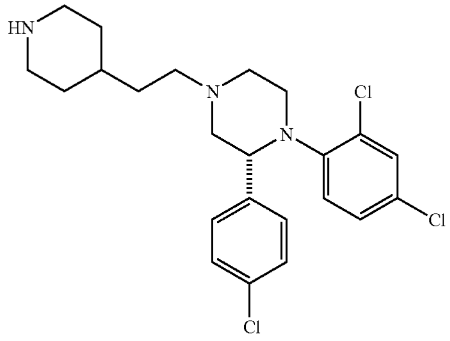

Example 353

Example 352 (750 mg) and 4 M $HCl_{(aq.)}$ were taken up in MeOH and stirred at 25° C. (18 h). The solution was concentrated. The residue was taken up in EtOAc and washed with 1 N $NaOH_{(aq.)}$. The aqueous layer was extracted with EtOAc. The combined organic layers were washed with brine and dried ($MgSO_4$). Filtration and concentration gave Example 353 as a yellow oil.

Step 4:

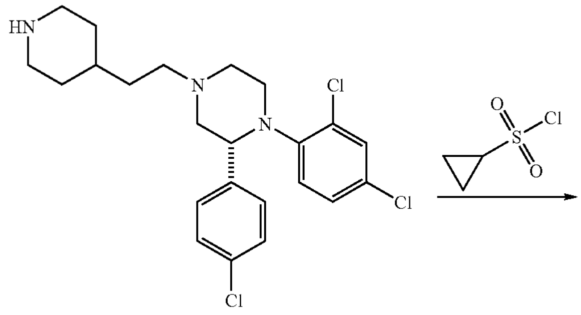

Example 353

-continued

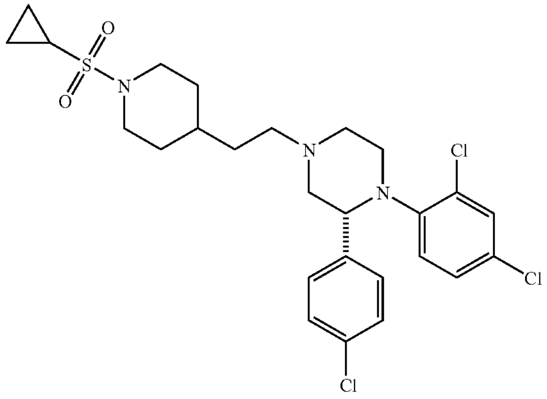

Example 354

Example 353 was converted into Example 354 using the procedures outlined in Step 1 of Scheme 43 using the appropriate reagents.

Preparation of Example 355

Scheme 51

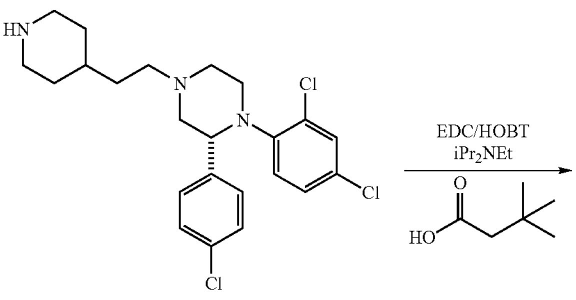

Example 353

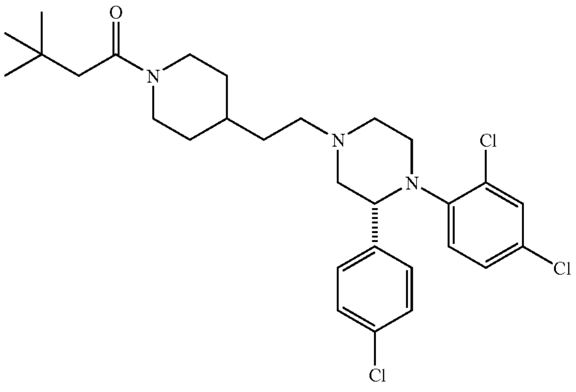

Example 355

Example 353 was converted into Example 355 using the procedure outlined in Scheme 46 using the appropriate reagents.

Preparation of Example 356

Scheme 52

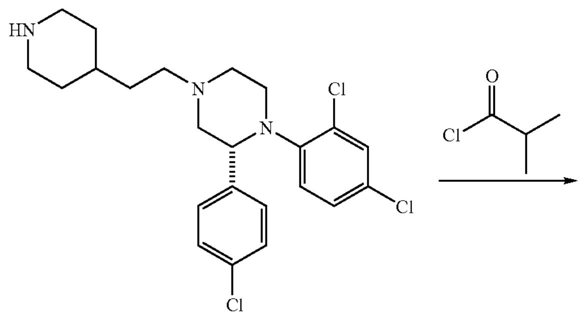

Example 353

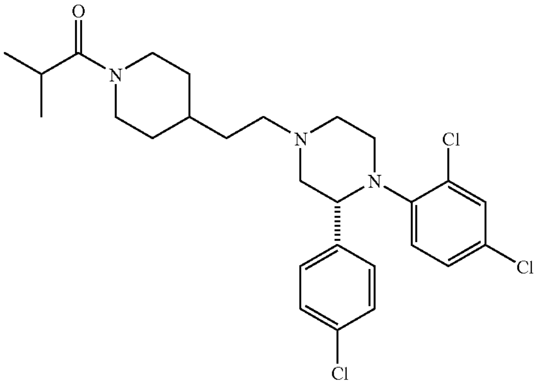

Example 356

Example 353 was converted into Example 356 using the procedure outlined in Scheme 45 using the appropriate reagents.

Preparation of Example 357

Scheme 53

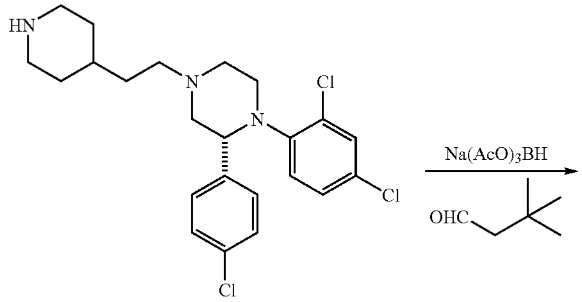

Example 353

-continued

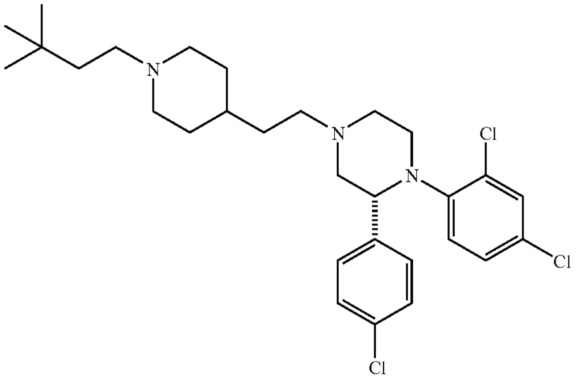

Example 357

Example 353 was converted into Example 357 using the procedure outlined in Step 1 of Scheme 44 using the appropriate reagents.

Preparation of Example 358

Scheme 54

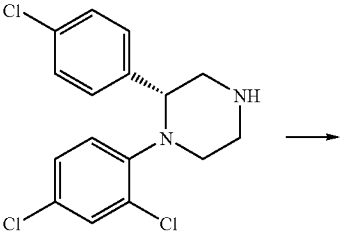

Example 304

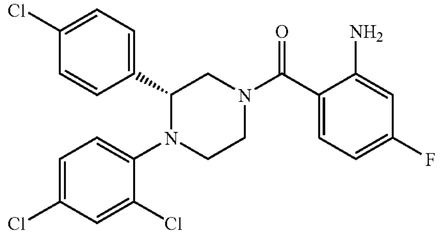

Example 358

To a solution of the piperazine Example 304 in MeCN (3 mL) was added 2-amino-4-fluorobenzoic acid (54 mg, 0.35 mmol), EDCl (67 mg, 0.35 mmol), HOBt (47 mg, 0.35 mmol) and $iPr_2NEt$ (160 uL, 0.92 mmol). The solution was allowed to stir at room temperature overnight. The solution was then concentrated. The crude product was partitioned between EtOAc and 1M NaOH. The aqueous layer was extracted with EtOAc (3×). The combined organic layers were washed with brine, dried over $Na_2SO_4$, filtered and concentrated. The crude product was purified by preparative TLC ($SiO_2$, 2:1 hexanes:EtOAc) to afford Example 358 (99 mg). The product was converted to its HCl salt by dissolving in $CH_2Cl_2$ followed by the addition of 2N HCl (in ether). The solvent was then removed to provide the salt.

Preparation of Example 359

Example 359

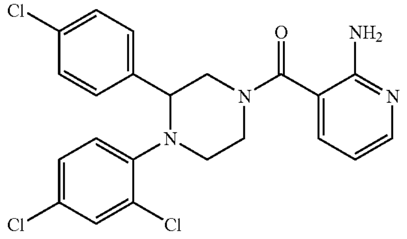

Example 359 was prepared using a procedure similar to that used to prepare Example 358 except that 2-aminonicotinic acid was coupled with Example 1 instead of 2-amino-4-fluorobenzoic acid.

Preparation of Example 360

Example 360

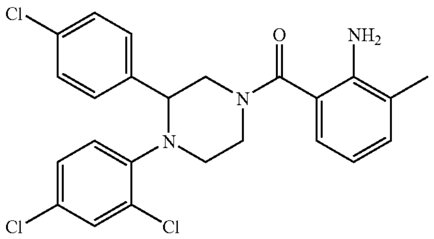

Example 360 was prepared using a procedure similar to that used to prepare Example 359 except that 2-amino-3-methylbenzoic acid was coupled with Example 1 instead of 2-amino-4-fluorobenzoic acid.

Preparation of Example 361

Example 361

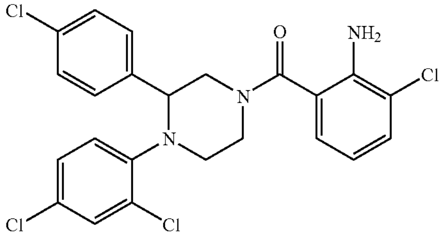

Example 361 was prepared using a procedure similar to that used to prepare Example 359 except that 2-amino-3-chlorobenzoic acid was coupled with Example 1 instead of 2-amino-4-fluorobenzoic acid.

Preparation of Example 362

Example 362

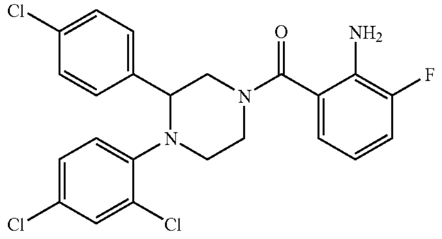

Example 362 was prepared using a procedure similar to that used to prepare Example 359 except that 2-amino-3-fluorobenzoic acid was coupled with Example 1 instead of 2-amino-4-fluorobenzoic acid.

Preparation of Example 363

Example 363

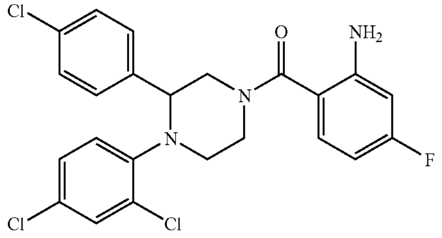

Example 363 was prepared using a procedure similar to that used to prepare Example 359 except that 2-amino-4-fluorobenzoic acid was coupled with Example 1 instead of 2-amino-4-fluorobenzoic acid.

Preparation of Example 364

Scheme 55

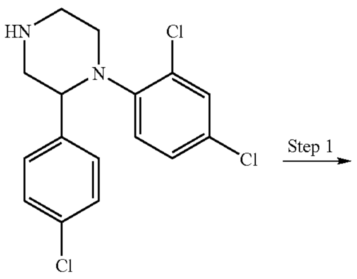

Example 1

-continued

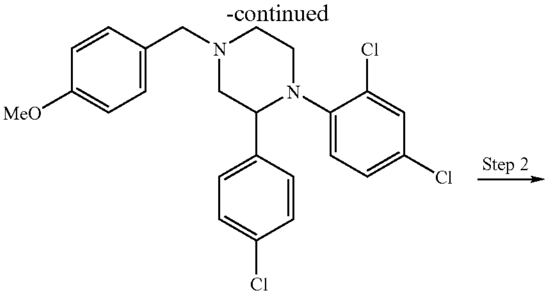

Example 46

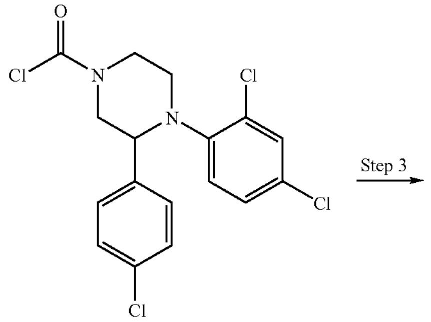

i

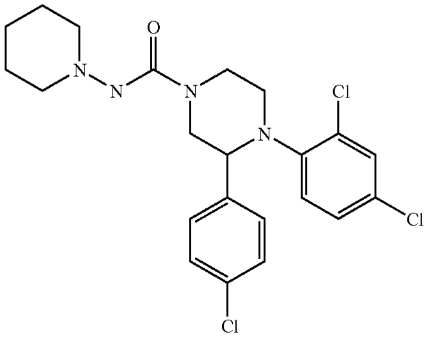

Example 364

Step 1:

To a solution of Example 1 (305 mg, 0.89 mmol) in DCE (5 mL) was added p-anisaldehyde (134 mg, 0.98 mmol), sodium triacetoxyborohydride (208 mg, 0.98 mmol) and acetic acid (59 mg, 0.98 mmol). The solution was stirred at room temperature overnight. The mixture was diluted with $CH_2Cl_2$ and washed with 1 M NaOH (aq.). The aqueous layer was extracted with $CH_2Cl_2$ (3×). The combined organic layers were dried over $Na_2SO_4$, filtered and concentrated. The crude product purified by flash chromatography ($SiO_2$, gradient 100:0 to 60:40 hexanes:EtOAc) to afford Example 46 (180 mg).

Step 2:

To a solution of Example 46 (165 mg, 0.36 mmol) in $CH_2Cl_2$ (5 mL) at 0° C. was added triphosgene (33 mg, 0.125 mmol) in $CH_2Cl_2$ (2 mL). The solution was stirred at 0° C. for 2 h. The solution was then concentrated in vacuo to afford the crude carbamoyl chloride which was used without purification in step 3.

Step 3:

To a solution of the carbamoyl chloride prepared in step 2 (0.36 mmol) in $CH_2Cl_2$ (5 mL) was added 1-amino piperidine (40 mg, 0.40 mmol) and $iPr_2NEt$ (52 mg, 0.40 mmol). The solution was stirred at room temperature overnight. The solution was diluted with $CH_2Cl_2$ and washed with $NaHCO_3$ (aq.). The aqueous layer was extracted with $CH_2Cl_2$ (3×). The combined organic layers were dried over $Na_2SO_4$, filtered and concentrated. The crude product was purified by preparative TLC ($SiO_2$; 2:1 EtOAc:hexanes) to afford Example 364 (38 mg). The product was converted to the HCl salt by dissolving it in $CH_2Cl_2$ followed by the addition of 2N HCl (in ether). The solvent was then removed to provide the salt.

Preparation of Example 365

Example 365

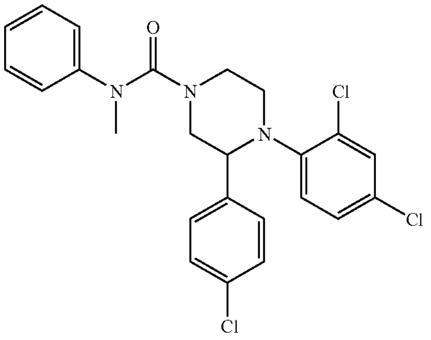

Example 365 was prepared from carbamoyl chloride i (Scheme 55, step 2) using a procedure similar to that used to prepare Example 364, except that N-methylaniline was used in Step 3 (above) instead of 1-aminopiperidine.

Preparation of Example 366

Example 366

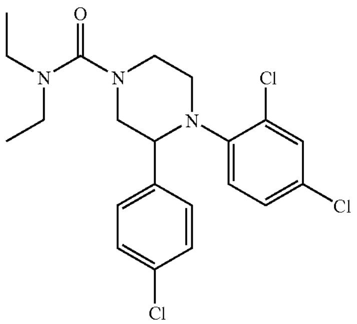

Example 366 was prepared from carbamoyl chloride i (Scheme 55, Step 2) using a procedure similar to that used to prepare Example 364, except that diethylamine was used in Step 3 (above) instead of 1-aminopiperidine.

Preparation of Example 367

Example 367

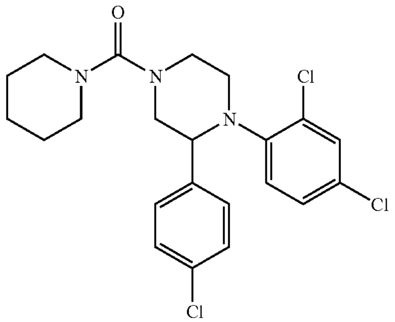

Example 367 was prepared from carbamoyl chloride i (Scheme 55, Step 2) using a procedure similar to that used to prepare Example 364, except that piperidine was used in Step 3 (above) instead of 1-aminopiperidine.

Preparation of Example 368

Scheme 56

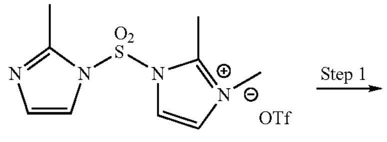

i

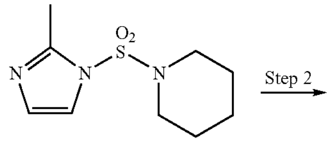

ii

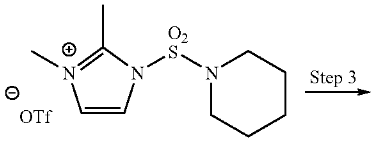

iii

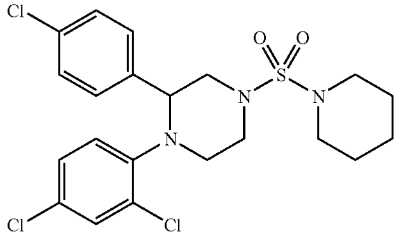

Example 368

Step 1:

To a solution of salt i (method of J. Organic Chem 68, (2003) 115-119; herein incorporated by reference) (233 mg, 0.64 mmol) in MeCN (5 mL) was added piperidine (37 mg, 0.43 mmol). The solution was allowed to stir overnight at room temperature. The solution was then concentrated and the crude product was purified by filtration through a $SiO_2$ plug using EtOAc to wash the plug. The filtrate was concentrated to afford ii (88 mg) as a white crystalline solid.

Step 2:

To a solution of ii (88 mg, 0.38 mmol) in $CH_2Cl_2$ (5 mL) at 0° C. was added methyl triflate (69 mg, 0.42 mmol). The solution was stirred at 0° C. for 2 h. The solution was concentrated to afford iii as a white solid.

Step 3:

To a solution of iii (0.38 mmol) in MeCN (2 mL) was added Example 1 (100 mg, 0.29 mmol). The solution was heated to reflux for 16 h. The solution was then concentrated and purified by flash chromatography ($SiO_2$; gradient elution 100:0 to 80:20 hexanes:EtOAc) to afford Example 368 (150 mg) as a clear oil. The product was converted to the HCl salt by dissolving in $CH_2Cl_2$ followed by the addition of 2N HCl (in ether). The solvent was then removed to provide the salt.

Preparation of Example 369

Example 369

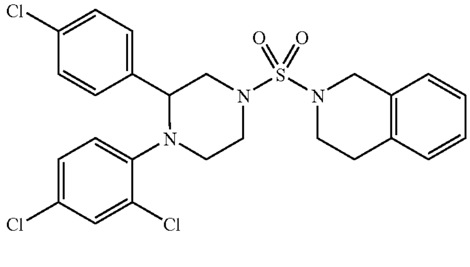

Example 369 was prepared from i (Scheme 56, above) using a procedure similar to that used to prepare Example 368, except that tetrahydroquinoline was used in Step 1 (above) instead of piperidine.

Preparation of Examples 370-371

Scheme 57

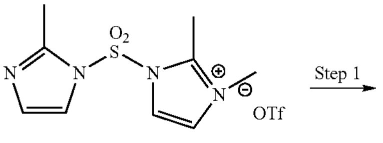

i

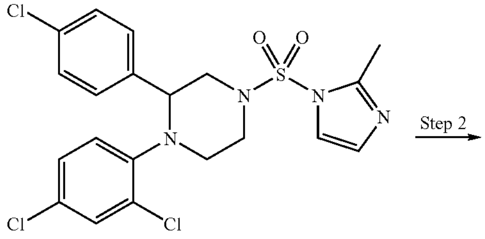

Example 370

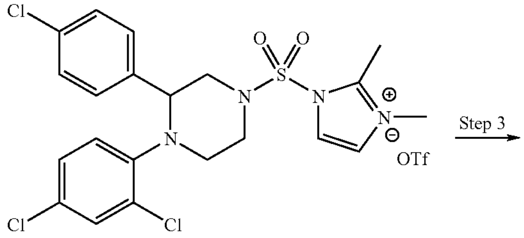

ii

-continued

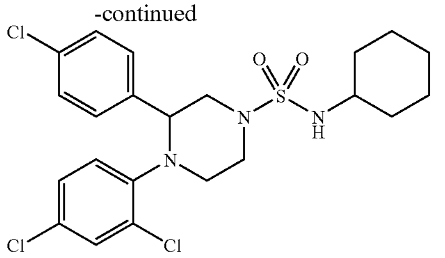

Example 371

Step 1:

To a solution of salt i (555 mg, 1.53 mmol) in MeCN (10 mL) was added Example 1 (349 mg, 1.02 mmol). The solution was allowed to stir overnight at room temperature. The solution was concentrated and the crude product was purified via flash chromatography ($SiO_2$; gradient elution 100:0 to 1:1 hexanes:EtOAc) to afford Example 370 (252 mg) as a white crystalline solid.

Step 2:

To a solution of Example 370 (252 mg, 0.52 mmol) in $CH_2Cl_2$ (15 mL) at 0° C. was added methyl triflate (89 mg, 0.54 mmol). The solution was stirred at 0° C. for 2 h. The solution was concentrated to afford ii as a white solid.

Step 3:

To a solution of ii (0.17 mmol) in MeCN (2 mL) was added aminocyclohexane (17 mg, 0.17 mmol). The solution was heated to reflux for 16 h. The solution was then concentrated and purified by preparative TLC ($SiO_2$ 2:1 hexanes:EtOAc) to afford Example 371 (45 mg) as a clear oil. The product was converted to the HCl salt by dissolving in $CH_2Cl_2$ followed by the addition of 2N HCl (in ether). The solvent was then removed to provide the salt.

Preparation of Example 372

Example 372

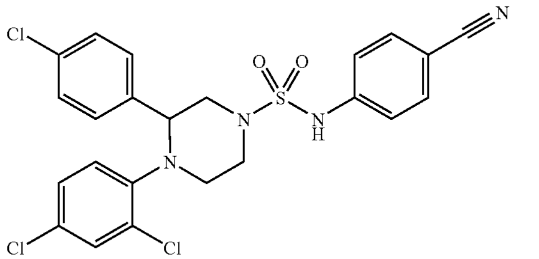

Example 372 was prepared using a procedure similar to that used to prepare Example 371, except 4-cyanoaniline was used instead of aminocyclohexane in Step 3 (above).

Preparation of Example 373

Scheme 57

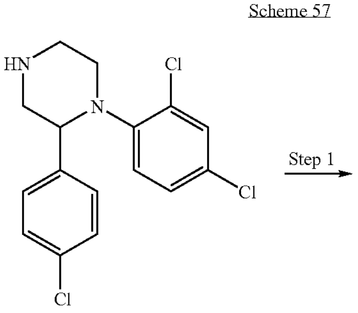

Example 1

-continued

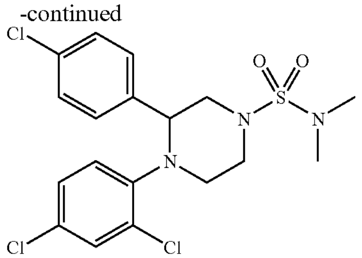

Example 373

To a solution of Example 1 (70 mg, 0.20 mmol) in $CH_2Cl_2$ (2 mL) was added N,N-dimethyl amino sulfonyl chloride (32 mg, 0.23 mol) and $iPr_2NEt$ (31 mg, 0.24 mmol). The solution was stirred at room temperature overnight. The solution was then diluted with $CH_2Cl_2$ The solution was diluted with $CH_2Cl_2$ and washed with $NaHCO_3$ (aq.). The aqueous layer was extracted with $CH_2Cl_2$ (3×). The combined organic layers were dried over $Na_2SO_4$, filtered and concentrated. The crude product was purified by preparative TLC ($SiO_2$; 2:1 EtOAc:hexanes) to afford Example 373 (66 mg). The product was converted to the HCl salt by dissolving in $CH_2Cl_2$ followed by the addition of 2N HCl (in ether). The solvent was then removed to provide the salt.

Preparation of Examples 374-375

Scheme 59

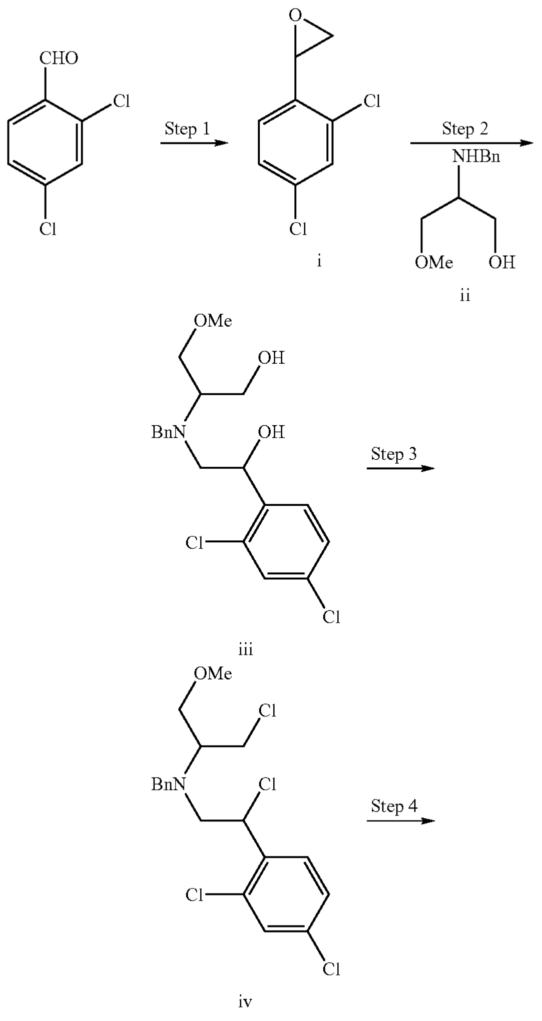

-continued

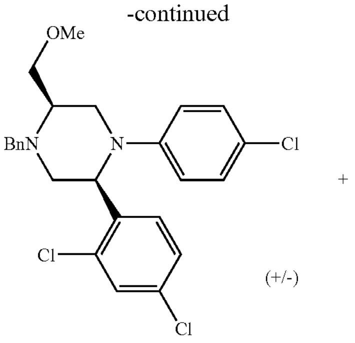

Example 374

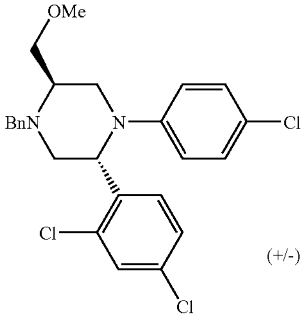

Example 375

Step 1:

To a solution of 2,4-dichlorobenzaldehyde (2.0 g, 11.4 mmol) in anhydrous THF (20 mL) was added diiodomethane (4.59 g, 17.1 mmol). The solution was cooled to 0° C. and butyl lithium-lithium bromide complex (1.5 M in $Et_2O$, 22.8 mmol) was added. The solution was stirred at 0° C. for 1 h and the solution was warmed to room temperature and allowed to stir an additional 1 h. To this reaction was slowly added ice. The mixture was then extracted with EtOAc (3×). The combined organic layers were dried over $Na_2SO_4$, filtered and concentrated to afford i (2.1 g) as an orange oil that was used without purification in Step 2.

Step 2:

To a flask containing ii (prepared by the method of Synthesis (1992) 288-292; herein incorporated by reference) (1.55 g, 7.94 mmol) was added i (1.5 g, 7.94 mmol). The neat mixture was heated to 130° C. for 16 h to afford iii (3.0 g), which was used without purification in Step 3.

Step 3:

To a solution of iii (1.5 g, 3.9 mmol) in DCE (10 mL) was added thionyl chloride (1.16 g, 9.8 mmol). The resultant solution was heated to reflux for 2 h. The reaction was slowly quenched with $NaHCO_3$ (aq.). The mixture was then extracted with $CH_2Cl_2$ (3×). The combined organic layers were dried over $Na_2SO_4$, filtered and concentrated to afford iv (1.64 g), which was used without purification in Step 4.

Step 4:

To a solution of iv (1.64 g, 3.9 mmol) propylnitrile (20 mL) was added 4-chloroaniline (1.49 g, 11.7 mmol). The solution was heated to reflux overnight. The solution was partitioned between $NaHCO_3$ (aq.) and $CH_2Cl_2$. The aqueous layer was extracted with $CH_2Cl_2$ (3×). The combined organic layers were dried over $Na_2SO_4$, filtered, and concentrated. The crude product was purified by flash chromatography ($SiO_2$; gradient elution 100:0 to 9:1 hexanes:EtOAc) to afford Example 374 (265 mg) and after further purification by preparative TLC ($SiO_2$; 9:1 hexanes:EtOAc) Example 375 (60 mg). The products were converted to their HCl salts by dissolving in $CH_2Cl_2$ followed by the addition of 2N HCl (in ether). The solvent was then removed to provide the salts.

Preparation of Examples 376-377

Scheme 60

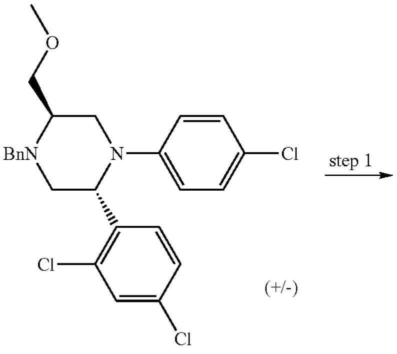

Example 375

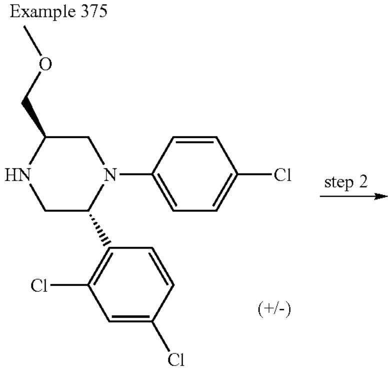

Example 376

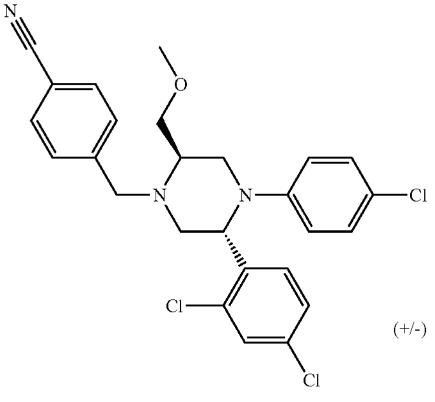

Example 377

Step 1:

To a solution of Example 375 (30 mg, 0.064 mmol) in DCE (2 mL) was added 1-chloroethyl chloroformate (10 mg, 0.07 mmol). The solution was heated to reflux for 1 h. Additional 1-chloroethyl chloroformate (8 mg, 0.056 mmol) was added and the solution was heated to reflux for an additional 8 h. The solution was concentrated. To the crude product was added MeOH (1 mL). The resultant solution was heated to reflux for 1.5 h. The solution was concentrated. The material was partitioned between $CH_2Cl_2$ and $NaHCO_3$ (aq.). The aqueous layer was extracted with $CH_2Cl_2$ (3×). The combined organic layers were dried over $Na_2SO_4$, filtered and concentrated. The crude product was purified by preparative TLC ($SiO_2$ 1:1 hexanes:EtOAc) to afford Example 376 (17 mg).

Step 2:

To a solution of Example 376 (17 mg, 0.05 mmol) in $CH_2Cl_2$ (1 mL) was added 4-cyanobenzaldehyde (7 mg, 0.05 mmol) and sodium triacetoxyborohydride (16 mg, 0.075 mmol). The mixture was stirred at room temperature for 16 h. The mixture was partitioned between EtOAc and $NaHCO_3$ (aq.). The aqueous layer was extracted with EtOAc (3×). The combined organic layers were dried over $Na_2SO_4$, filtered and concentrated. The crude product was purified by preparative TLC ($SiO_2$ 4:1 hexanes:EtOAc) to afford Example 377. The product was converted to the HCl salt by dissolving in $CH_2Cl_2$ followed by the addition of 2N HCl (in ether). The solvent was then removed to provide the salt.

Preparation of Example 378

Example 378

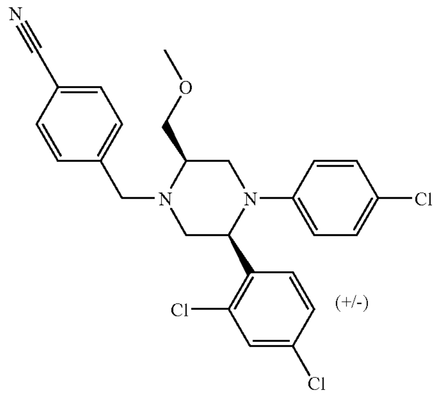

Example 378 was prepared using the same procedure used to prepare Example 377, except Example 374 was used as the starting material instead of Example 375.

Preparation of Example 379

Scheme 61

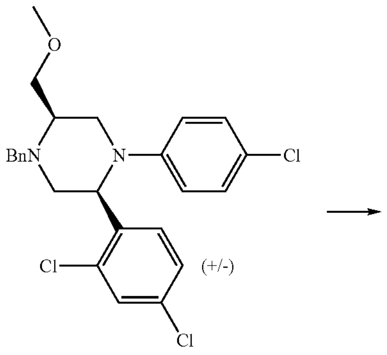

Example 374

-continued

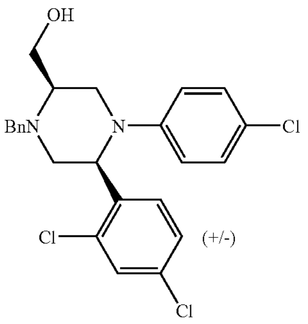

Example 379

To a solution of Example 374 (50 mg, 0.1 mmol) in $CH_2Cl_2$ (5 mL) at 0° C. was added $BBr_3$ (26 mg, 0.15 mmol). The solution was allowed to warm to room temperature and stirred for 3 h. To the solution was added $NaHCO_3$. The mixture was extracted with $CH_2Cl_2$ (3×). The combined organic layers were dried over $Na_2SO_4$, filtered and concentrated. The crude product was purified by preparative TLC ($SiO_2$ 4:1 hexanes: EtOAc) to afford Example 379. The product was converted to the HCl salt by dissolving in $CH_2Cl_2$ followed by the addition of 2N HCl (in ether). The solvent was then removed to provide the salt (9 mg).

Preparation of Example 380

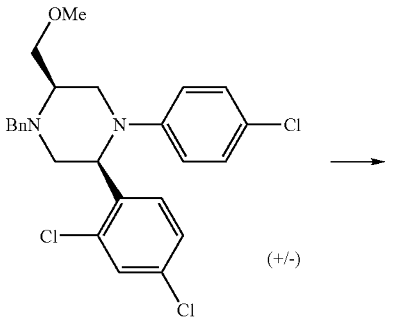

Example 374

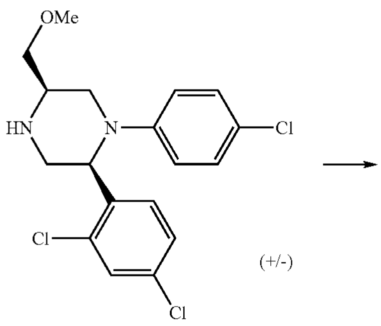

-continued

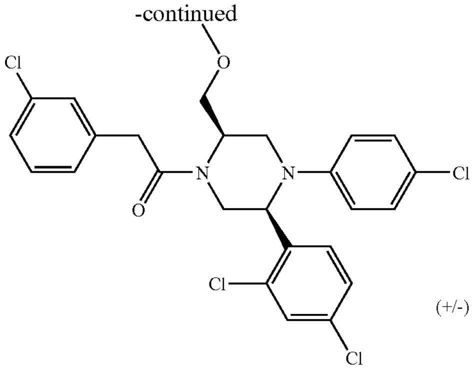

Example 380

Step 1:

Example 374 was converted to the secondary amine using conditions similar to those used to prepare Example 376 in Scheme 60.

Step 2:

The secondary amine prepared in step 1 was reacted with 3-chlorophenylacetic acid using conditions similar to those used to prepare Example 358 in Scheme 54.

Preparation of Example 381

Example 381

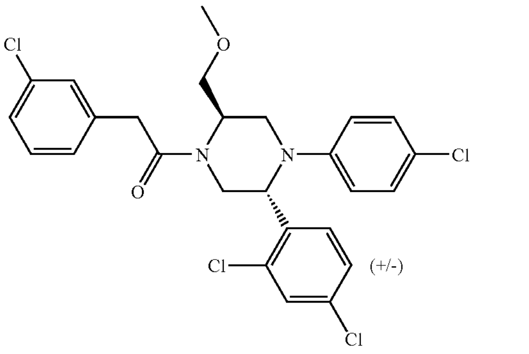

Example 381 was prepared using conditions similar to those used to prepare Example 380, except that Example 376 was used instead of Example 374.

Preparation of Example 382

Scheme 62

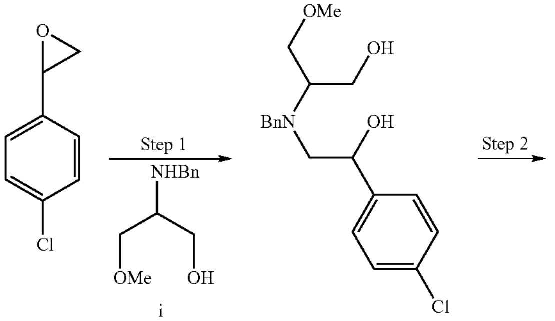

i ii

-continued

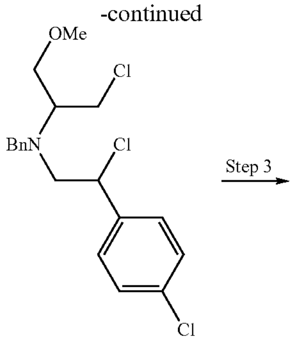

iv

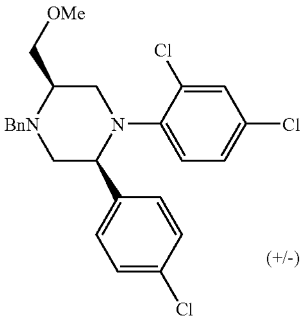

Example 382

Step 1:

To a flask containing i (1.0 g, 5.1 mmol) was added 4-chlorostyrene epoxide. The neat mixture was heated to 130° C. for 18 h to afford the diol ii which was used without purification.

Step 2:

To a solution of ii (710 mg, 2.02 mmol) in $CHCl_3$ (15 mL) was added thionyl chloride (603 mg, 5.07 mmol). The resultant solution was heated to reflux for 3 h. The solution was cooled to room temperature and concentrated. The crude mixture was partitioned between $CH_2Cl_2$ and $NaHCO_3$ (aq.). The mixture was stirred vigorously for 10 min. The layers were separated and the aqueous layer was extracted with $CH_2Cl_2$ (3×). The combined organic layers were dried over $Na_2SO_4$, filtered and concentrated to afford iv, which was used without purification in Step 3.

Step 3:

To a solution of the dichloride iv (3.0 mmol) in propionitrile (20 mL) was added 2,4-dichloroaniline (486 mg, 3.0 mmol) and $iPr_2NEt$ (387 mg, 3.0 mmol). The mixture was heated to 100° C. for 16 h. Cooled solution to room temperature and concentrated.

The crude material was dissolved in anhydrous THF (10 mL). To this solution was added NaH (60 mg, 60% in oil). The mixture was heated to reflux for 16 h. Additional NaH (60 mg, 60% in oil) was added and the mixture was heated to reflux for an additional 24 h. Water was slowly added and the mixture was extracted with EtOAc (3×). The combined organic layers were washed with brine, dried over $Na_2SO_4$, filtered and concentrated. The crude product was purified by preparative TLC ($SiO_2$, 4.1 hexanes:EtOAc) to afford Example 382 (365 mg). The product was converted to the HCl salt by dissolving in $CH_2Cl_2$ followed by the addition of 2N HCl (in ether). The solvent was then removed to provide the salt.

Preparation of Example 383

Example 383

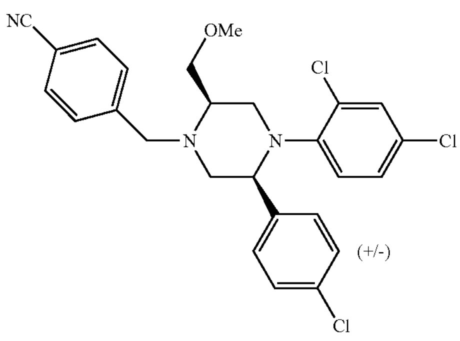

Example 383 was prepared using conditions similar to those used to prepare Example 377, except Example 374 was used as the starting material instead of Example 375.

Preparation of Example 385

Example 385

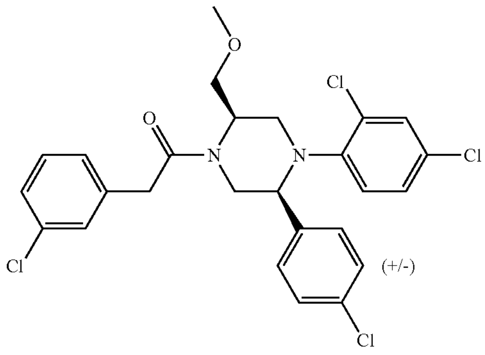

Example 385 was prepared using conditions similar to those used to prepare Example 380.

Preparation of Examples 386-388

Scheme 63

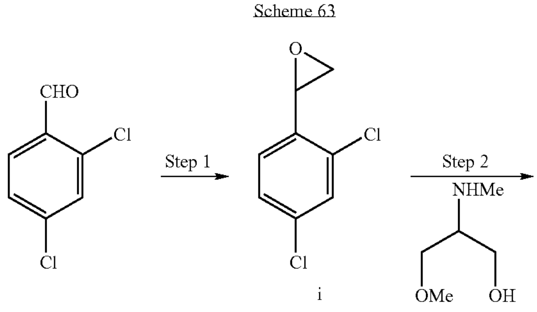

i ii

-continued

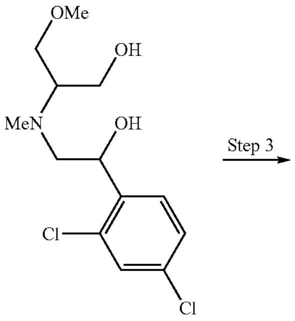

iii

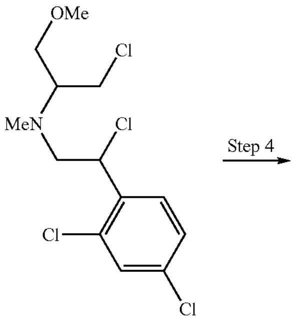

iv

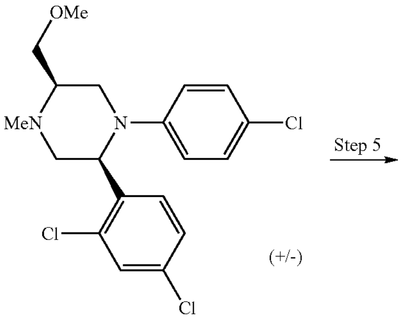

Example 386

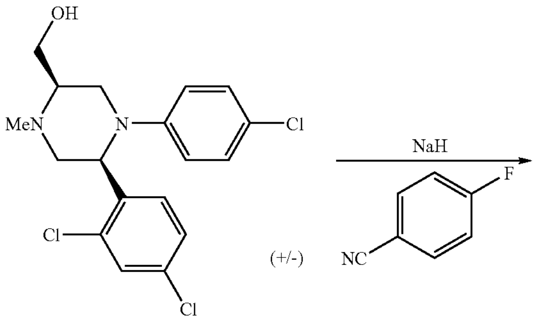

Example 387

-continued

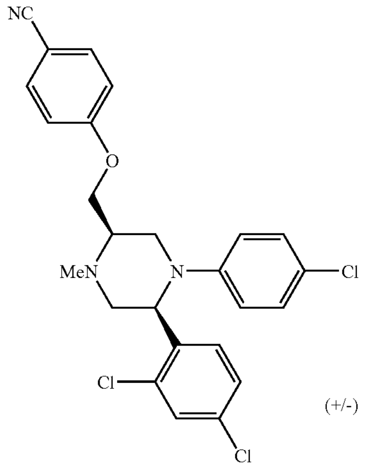

(+/-)

Example 388

The N-methyl piperazine Example 386 was prepared using procedures similar to those described above for Example 374 (Steps 1, 2, 3, and 4). The alcohol Example 387 was prepared from the N-methyl piperazine Example 386 using a procedure similar to that used to prepare Example 379.

The alcohol Example 387 (30 mg) was taken up in DMF. Sodium hydride (12 mg of a 60 wt % dispersion in oil) was added. 4-Fluorobenzonitrile (35 mg) was added, and the solution was stirred at 25° C. (18 h). The solution was partitioned between EtOAc and water. The aqueous layer was extracted with EtOAc. The combined organic layers were washed with brine and dried ($MgSO_4$). Filtration and concentration gave a yellow oil. Purification via thin-layer preparative chromatography (2/1 hexanes/EtOAc, $SiO_2$) gave 21 mg (45%) of Example 388 as an oil.

Preparation of Example 389

Scheme 64

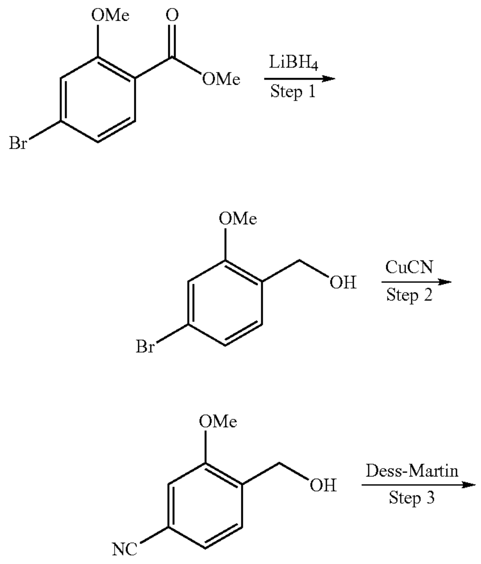

-continued

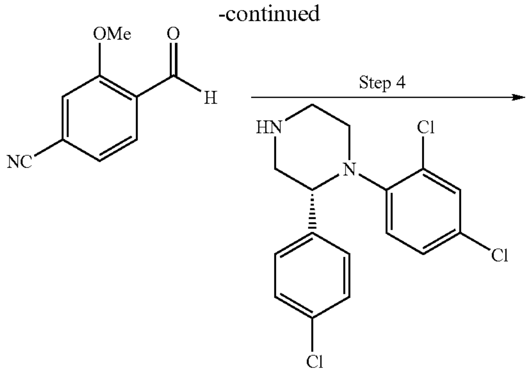

Example 304

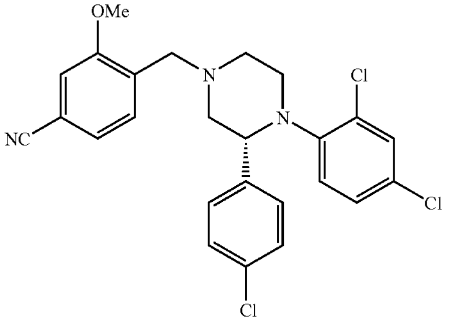

Example 389

Step 1:

To methyl-4-bromo-2-methoxybenzoate (Aldrich) (1.0 g, 4.1 mmol) in THF (10 mL), was added $LiBH_4$ (0.13 g, 6.1 mmol). Ethanol (2 mL) was added dropwise. The resulting reaction mixture was stirred at room temperature for 20 h. 1 N NaOH was added, and the mixture was extracted with EtOAc. The organic layers were combined and washed with water and brine, then dried ($MgSO_4$), filtered, and concentrated in vacuo to provide the corresponding benzyl alcohol (0.86 g, 4.0 mmol).

Step 2:

To the benzyl alcohol prepared in step 1 (0.86 g, 4.0 mmol) in DMF (8 mL) was added CuCN (1.1 g, 12 mmol). The mixture was warmed to 150° C. and stirred for 20 h. The mixture was then cooled to room temperature and EtOAc was added, followed by a saturated $NH_4Cl/NH_4OH$ solution. The mixture was stirred vigorously for 10 minutes and extracted with EtOAc, then the organic layer was dried ($MgSO_4$), filtered, and concentrated in vacuo. Purification by silica gel chromatography provided 4-hydroxymethyl-3-methoxy-benzonitrile (0.38 g, 2.3 mmol).

Step 3:

To 4-hydroxymethyl-3-methoxy-benzonitrile prepared in step 2 (0.38 g, 2.3 mmol) in $CH_2Cl_2$ (8 mL) at room temperature was added Dess-Martin periodinane (1.2 g, 2.8 mmol). The mixture was stirred at room temperature for 20 h. The resulting white precipitate was filtered off and the filtrate concentrated in vacuo. The residue was purified by silica gel chromatography (20% EtOAc/Hex) to provide the corresponding aldehyde (0.32 g, 2.0 mmol).

Step 4:

To the aldehyde prepared in step 3 (0.07 g, 0.44 mmol) in DCE (1 mL) was added the piperazine Example 304 (0.15 g, 0.44 mmol) followed by $Na(OAc)_3BH$ (0.19 g, 0.88 mmol). The mixture was stirred at room temperature for 20 h. $CH_2Cl_2$ was added and the mixture was washed with 1 N NaOH, water and brine. The organic layer was dried ($MgSO_4$), filtered, and concentrated in vacuo. The residue was purified by silica gel chromatography (35% EtOAc/hexane) to provide Example 389 (0.21 g, 0.44 mmol).

Preparation of Example 390

Example 390

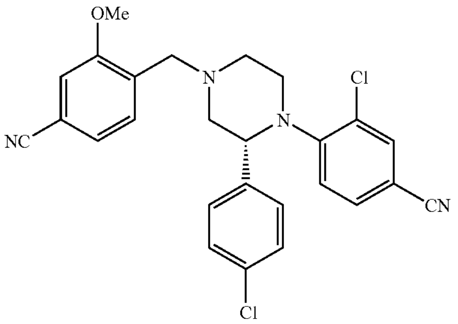

Example 390 was prepared in a manner similar to that used to prepare Example 389 in Scheme 64, except that piperazine Example 305 was used instead of piperazine Example 304 in step 4.

Preparation of Examples 391, 391a, and 391b

Scheme 65

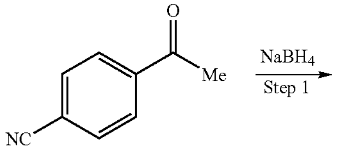

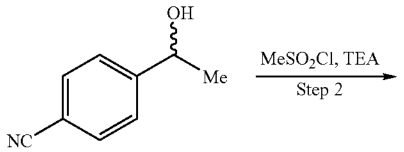

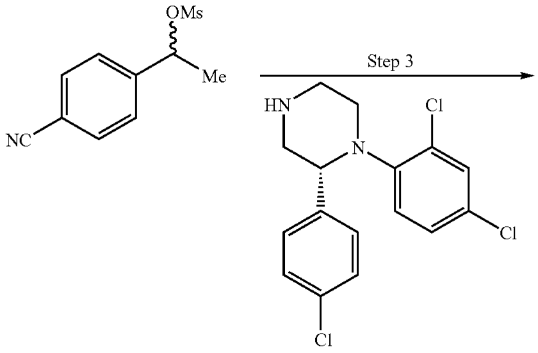

Example 304

-continued

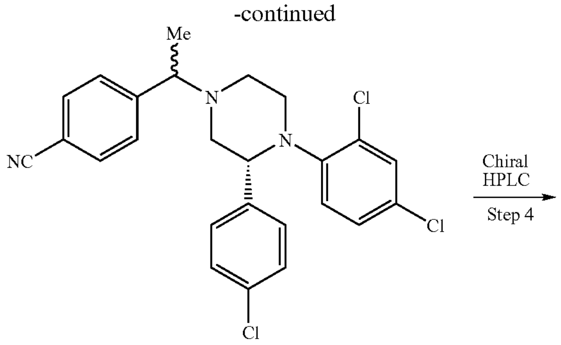

Example 391

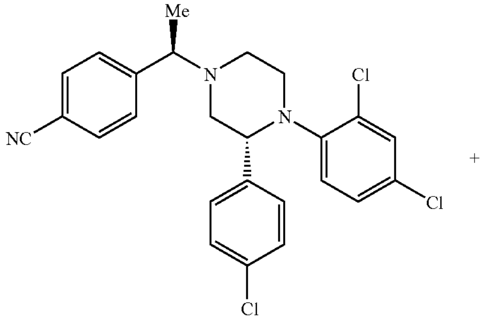

+

Example 391a

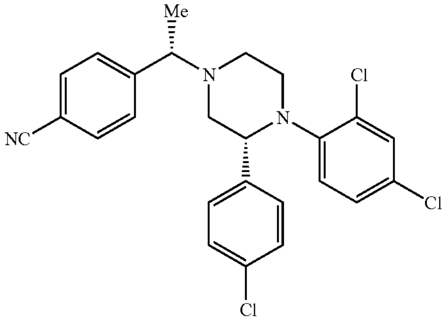

Example 391b

Step 1:

To 4-acetylcyanobenzene (2.0 g, 13.8 mmol) in MeOH (55 mL) was added $NaBH_4$ (0.52 g, 13.0 mmol) in one portion. The reaction was stirred for 3 h, allowing the cold bath to warm. The reaction mixture was concentrated in vacuo. Water was added and the mixture was extracted with ether. The combined organic layers were washed with water and brine, dried ($MgSO_4$), filtered, and concentrated in vacuo to provide the corresponding alcohol (2.0 g, 13.6 mmol).

Step 2:

To the alcohol prepared in step 1 (2.0 g, 13.6 mmol) in $CH_2Cl_2$ (45 mL) at 0° C. was added TEA (2.1 g, 20.4 mmol) followed by $MeSO_2Cl$ (1.87 g, 16.3 mmol). The mixture was stirred for 20 h, allowing the cold bath to warm. $CH_2Cl_2$ was added and the combined organic layers were washed with saturated $NaHCO_3$, water, and brine, then dried ($MgSO_4$), filtered, and concentrated in vacuo to provide the corresponding mesylate (2.88 g, 12.8 mmol).

Step 3:

To the mesylate prepared in step 2 (1.1 g, 4.8 mmol) in acetonitrile (13 mL) was added the piperazine Example 304 (1.3 g, 3.84 mmol) followed by $K_2CO_3$ (1.33 g, 9.6 mmol). The mixture was warmed to reflux and stirred for 20 h, cooled to room temperature, followed by the addition of water. The mixture was extracted with ethyl acetate, and the combined organic layers were washed with water and brine, dried ($MgSO_4$), filtered, and concentrated in vacuo. The concentrate was purified by silica gel chromatography (30% EtOAc/hexane) to provide Example 391 (1.44 g, 3.1 mmol) as a 1:1 mixture of diastereomers.

Step 4:

The mixture of diastereomers of Example 391 were separated by preparative chiral HPLC (Chiraicel OD, 5×50 cm, 3% IPA/hexane, 48 ml/min, 254 nm) to provide a faster eluting and slower eluting stereoisomer.

Preparation of Examples 392a and 392b

Example 392a

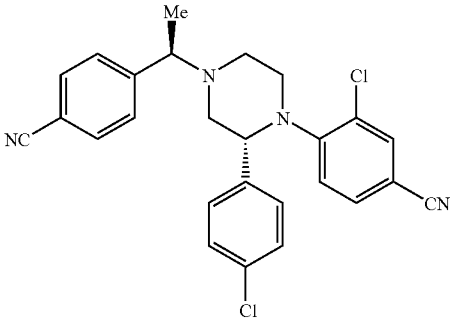

Example 392b

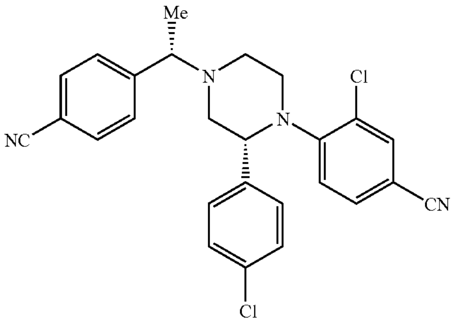

Examples 392a and 392b were prepared using procedures similar to those used to prepare Examples 391a and 391b in Scheme 65, above, except that the piperazine Example 305 was used in step 3 instead of Example 304. Examples 392a and 392b were separated by chiral preparative HPLC (Chiralcel OD, 5×50 cm, 10% IPA/hexane, 48 mL/min, 254 nm).

Alternatively, Example 392a was prepared by the following method:

Scheme 66

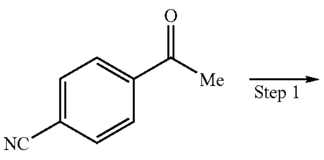

-continued

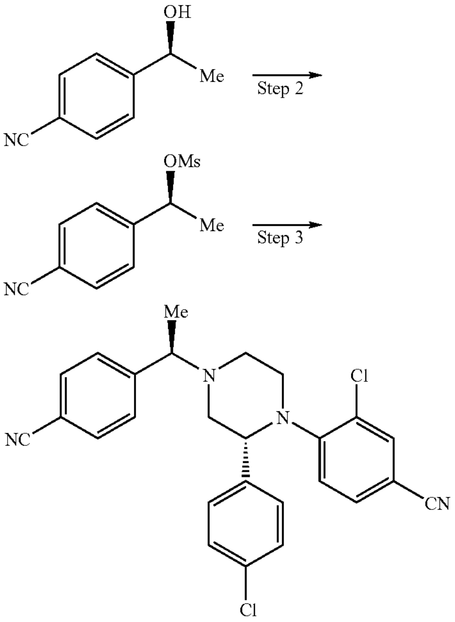

Example 392a

Step 1:

To 4-acetylbenzonitrile (3.0 g, 20.7 mmol) in THF (21 mL) at −18° C. ($CO_2$/ethylene glycol bath) was added (R)-2-methyl-CBS-oxazaborolidine (1M in toluene, 2.1 mL) followed by $BH_3$.$SMe_2$ (2.0M in THF, 7.2 mL) (following the chiral reduction procedure described in Chem. Rev., 1993, 93, 763-784). The cold bath was allowed to expire while stirring for 18 h. MeOH (~10 mL) was added (with gas evolution) and stirred for 15 minutes. The reaction mixture was concentrated in vacuo and taken up into EtOAc. The reaction mixture was then washed with 1N HCL, water, and brine. The organic layer was dried ($MgSO_4$), filtered, and concentrated in vacuo. The residue was purified by silica gel chromatography (5-40% EtOAc/hexanes) to provide the corresponding chiral alcohol (1.85 g, 12.6 mmol).

Step 2:

To the alcohol prepared in step 1 (0.70 g, 4.8 mmol) in $CH_2Cl_2$ (16 mL) at 0° C. was added TEA (triethylamine; 0.72 g, 7.1 mmol) followed by methanesulfonyl chloride (0.60 g, 5.2 mmol). The reaction mixture was stirred at 0° C. for 1 h. $CH_2Cl_2$ was added and the mixture was washed with 1N HCL, water, and brine. The organic layer was dried ($MgSO_4$), filtered, and concentrated in vacuo to provide the corresponding chiral mesylate (1.1 g, 4.7 mmol) that was used directly in the next step without further purification.

Step 3:

To the piperazine Example 305 (1.3 g, 4.0 mmol) in acetonitrile (13 mL) was added the mesylate prepared in step 2 (1.0 g, 4.6 mmol) followed by potassium carbonate (1.4 g, 10.1 mmol). The mixture was warmed to reflux and stirred for 36 h. The mixture was cooled to room temperature and water was added. The mixture was extracted with EtOAc. The organic layers were combined and washed with water and brine, dried ($MgSO_4$), filtered, and concentrated in vacuo. The resulting residue was purified by silica gel chromatography (0-10% MeOH/$CH_2Cl_2$) to provide a mixture of Example 392a and Example 392b (1.0 g) in ~10:1 ratio as determined by chiral HPLC (Chiralcel OD, 10% IPA/hexanes, 1 mL/min, 254 nm-Example 392a retention time=12.0 min; Example 392b retention time 13.8 min). Example 392b was separated from Example 392a by preparative chiral HPLC (Chiralcel OD, 10% IPA/hexanes, 50 mL/min, 254 nm) to provide Example 392a (0.68 g, 1.48 mmol).

Preparation of Examples 393a and 393b

Example 393a

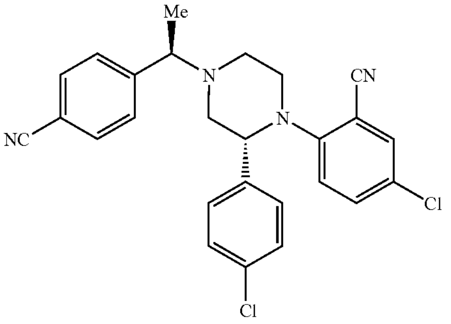

Example 393b

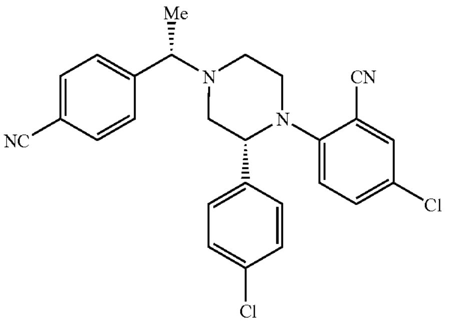

Examples 393a and 393b were prepared using procedures similar to those used to prepare Examples 391a and 391b in Scheme 65, above, except that piperazine Example 310 was used in step 3 instead of Example 304. Examples 393a and 393b were separated by chiral preparative HPLC (Chiralcel OD, 5×50 cm, 25% IPA/hexane, 50 mL/min., 254 nm).

Preparation of Examples 394a and 394b

Example 394a

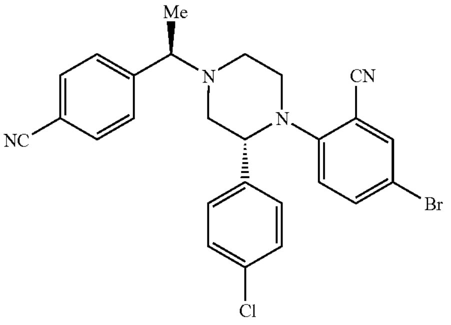

-continued

Example 394b

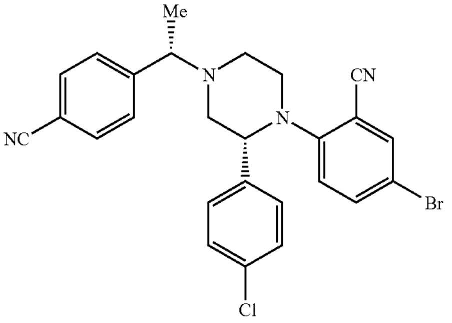

Examples 394a and 394b were prepared using procedures similar to those used to prepare Examples 391a and 391b in Scheme 65, above, except that piperazine Examples 306 was used in step 3 instead of Example 304. Examples 394a and 394b were separated by chiral preparative HPLC (Chiralcel OD, 5×50 cm, 5% IPA/hexane, 50 mL/min, 254 nm).

Preparation of Example 395

Scheme 67

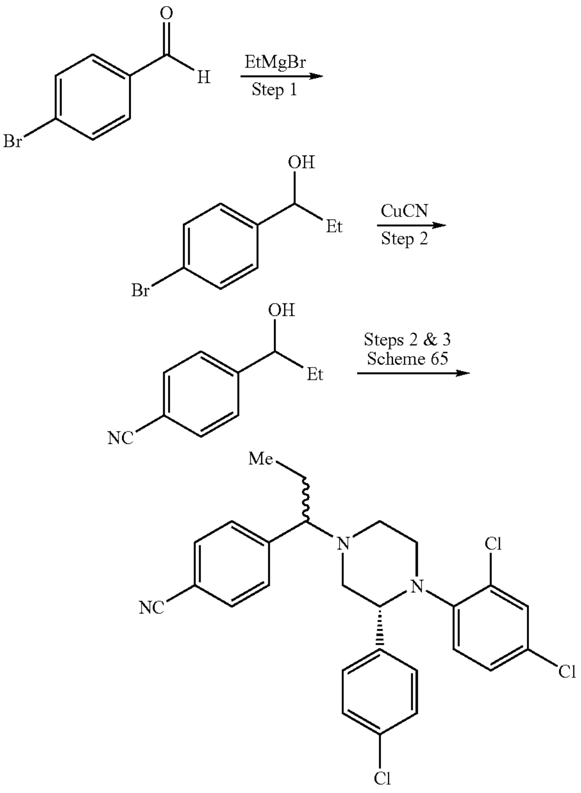

Example 395

Step 1:

To 4-bromobenzaldehyde (1.0 g, 5.4 mmol) in THF (18 mL) at 0° C. was added ethylmagnesium bromide (1.0 M in THF, 5.9 mL). The reaction mixture was stirred for 40 minutes. Water was added, then 25% aqueous sodium citrate solution. The mixture was extracted with EtOAc. The organic layers were combined and washed with water and brine. The organic layer was dried ($MgSO_4$), filtered, and concentrated in vacuo. Purification by silica gel chromatography (20% EtOAc/hexane) provided the corresponding alcohol (0.81 g, 3.8 mmol).

Step 2:

To the alcohol prepared in step 1 (0.8 g, 3.8 mmol) in DMF (14 mL) was added CuCN (1.16 g, 12.9 mmol). The reaction mixture was warmed the to 150° C., stirred for 18 h and then cooled to room temperature. A $NH_4Cl$/saturated $NH_4OH$ (9:1) solution was then added and the mixture was extracted with EtOAc. The organic layers were combined and dried ($MgSO_4$), filtered, and concentrated in vacuo. Purification by silica gel chromatography (30% EtOAc/hexane) provided the corresponding nitrile (0.34 g, 2.1 mmol). The nitrile was converted to Example 395 the procedures described above in steps 2 and 3 of Scheme 65.

Preparation of Example 396

Example 396

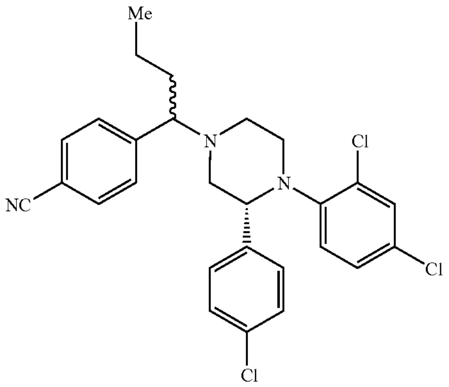

The propyl piperazine Example 396 was prepared using the procedures of Scheme 67 except that propylmagnesium chloride was used instead of ethylmagnesium bromide in step 1.

Preparation of Example 397

Scheme 68

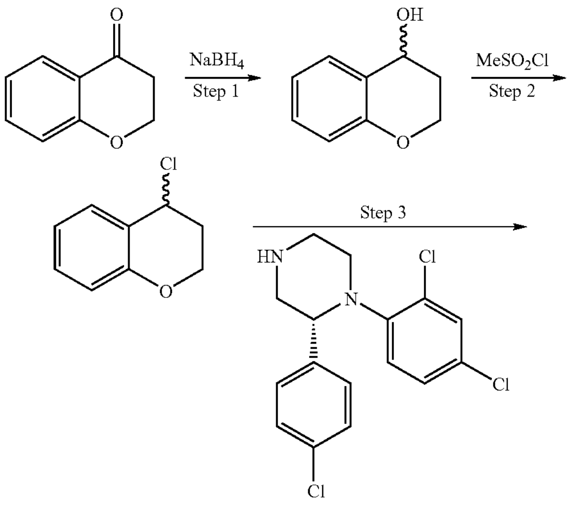

Example 304

-continued

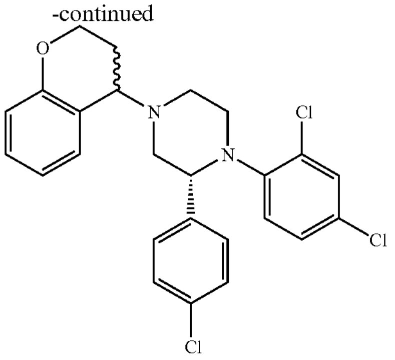

Example 397

Step 1:

To 4-chromanone (1.0 g, 6.75 mmol) in MeOH (20 mL) was added $NaBH_4$ (0.51 g, 13.5 mmol). The reaction mixture was stirred for 2 h and then concentrated in vacuo. 1N HCl was added and the mixture was extracted with EtOAc. The organic layers were combined and washed with water and brine. The organic layer was dried ($MgSO_4$), filtered, and concentrated in vacuo to provide the corresponding alcohol (1.01 g, 6.75 mmol).

Step 2:

To the alcohol prepared in step 1 (1.1 g, 7.3 mmol) in $CH_2Cl_2$ (20 mL) at 0° C. was added TEA (1.53 mL, 11 mmol) followed by methanesulfonyl chloride (0.68 mL, 8.8 mmol). The reaction mixture was stirred for 1 h and $CH_2Cl_2$ was added. The mixture was washed with water and brine. The organic layer was dried ($MgSO_4$), filtered, and concentrated in vacuo to provide the corresponding chloride (1.23 g, 5.38 mmol).

Step 3:

To the piperazine Example 304 (0.10 g, 0.29 mmol) in acetonitrile (1 mL) was added the chloride prepared in step 2 (0.06 g, 0.37 mmol) followed by $K_2CO_3$ (0.10 g, 0.73 mmol). The mixture was warmed to reflux and stirred for 20 h. The reaction mixture was concentrated in vacuo and EtOAc was added. The mixture was washed with water and brine, dried ($MgSO_4$), filtered, and concentrated in vacuo. The residue was purified by silica gel preparative TLC (2000 μm, 10% EtOAc/hexane) to provide Example 397 (0.80 g, 0.17 mmol).

Preparation of Example 398

Scheme 69

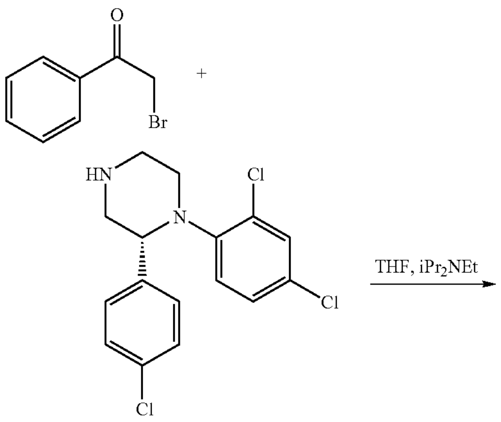

Example 304

-continued

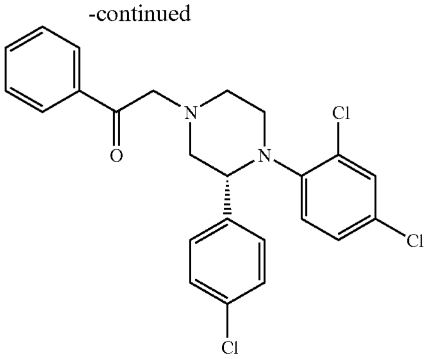

Example 398

To the piperazine Example 304 (1.0 g, 2.9 mmol) in THF (10 mL) was added diisopropylethyl amine (1.1 g, 8.7 mmol) followed by 2-bromoacetophenone (1.1 g, 5.8 mmol). The mixture was stirred for 75 minutes at room temperature and water was added. The mixture was extracted with ethyl acetate, then the combined organic layers were washed with water and brine, dried ($MgSO_4$), filtered, and concentrated in vacuo. Purification by silica gel chromatography (30% EtOAc/hexane) provided Example 398 (1.1 g, 2.4 mmol).

Preparation of Example 399

Example 399

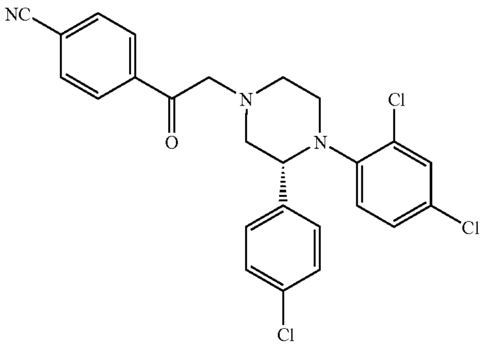

Example 399 was prepared using procedures similar to those used to prepare Example 398 in Scheme 69 except that 2-bromo-4'-cyanoacetophenone was used instead of 2-bromoacetophenone.

Preparation of Example 400

Example 400

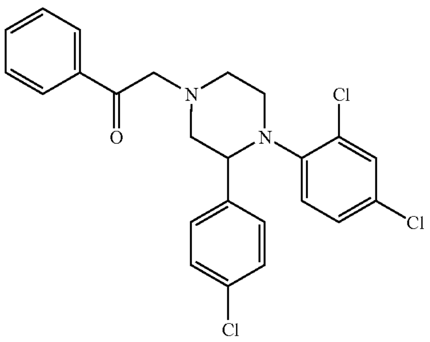

Example 400 was prepared using procedures similar to those used to prepare Example 398 in Scheme 69 except that the racemic piperazine Example 1 was used instead of chiral piperazine Example 304.

Preparation of Examples 401-410

Scheme 70

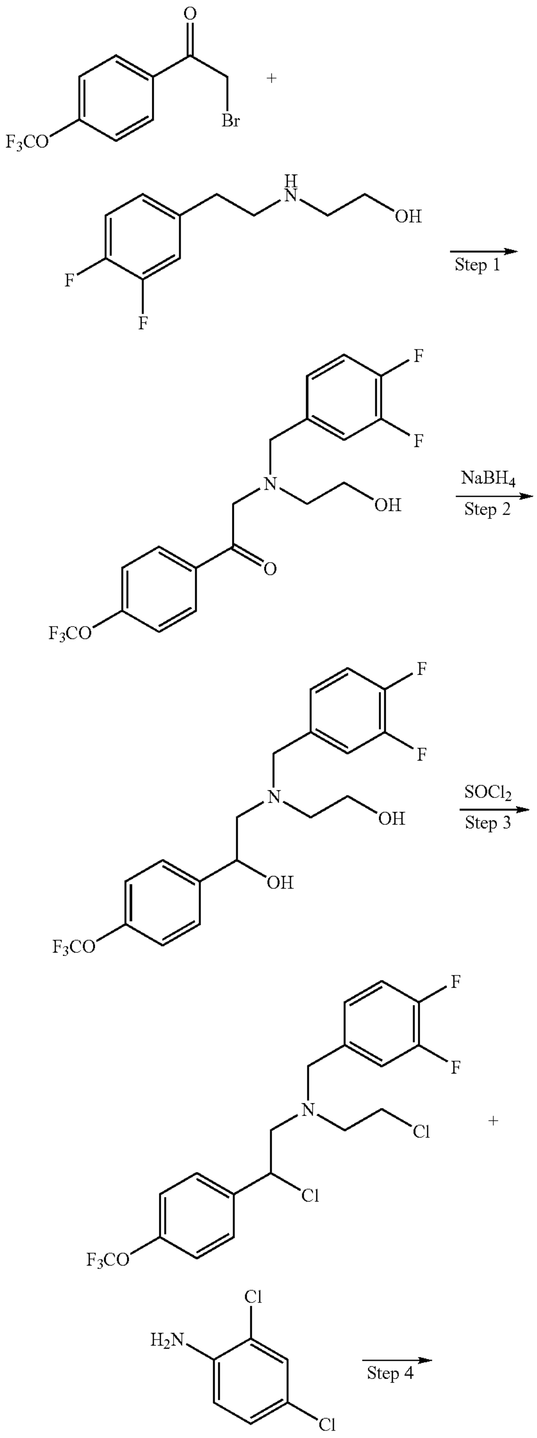

-continued

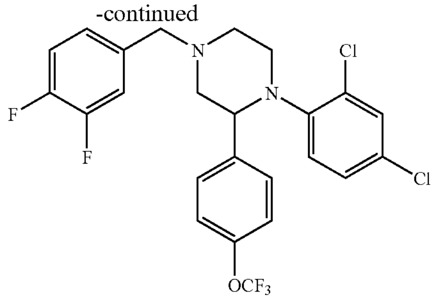

Example 401

Step 1:

To the 2-[2-(3,4-difluorophenyl)-ethylamino]-ethanol (0.5 g, 2.7 mmol) in acetonitrile (5 mL) was added 2-bromo-1-(4-trifluoromethoxyphenyl)-ethanone (0.76 g, 2.7 mmol) and $K_2CO_3$ (0.44 g, 3.2 mmol). The reaction mixture was stirred at room temperature for 20 h, and concentrated in vacuo. Water was added to the concentrate, which was then extracted with EtOAc. The combined organic layers were washed with water and brine, dried ($MgSO_4$), filtered, and concentrated in vacuo. Purification by silica gel chromatography (40% EtOAc/hexane) provided 2-[(3,4-difluorobenzyl)-(2-hydroxyethyl)-amino]-1-(4-trifluoromethoxyphenyl)-ethanone (0.8 g, 2.1 mmol).

Step 2:

To 2-[(3,4-difluorobenzyl)-(2-hydroxyethyl)-amino]-1-(4-trifluoromethoxyphenyl)-ethanone (0.8 g, 2.1 mmol) in MeOH (10 mL) at 0° C. was added $NaBH_4$ (0.12 g, 3.1 mmol) in one portion. The mixture was allowed to warm to room temperature and stirred for 20 h. The reaction mixture was concentrated in vacuo, and the residue was taken up into $CH_2Cl_2$ and washed with 1N NaOH, water, and brine. The organic layer was dried ($MgSO_4$), filtered, and concentrated in vacuo to provide a diol (0.8 g, 2.1 mmol).

Step 3:

To the diol prepared in step 2 (0.8 g, 2.1 mmol) in $CHCl_3$ (16 mL) at 0° C. was added thionyl chloride (4 mL). The reaction mixture was allowed to warm to room temperature and then warmed to reflux and stirred for 2 h. The reaction was cooled to room temperature and concentrated in vacuo. The residue was taked up into $CH_2Cl_2$ and stirred vigorously with saturated $NaHCO_{3(aq)}$. The organic layer was washed with water and brine, then dried ($MgSO_4$), filtered, and concentrated in vacuo to provide the corresponding dichloride (0.74 g).

Step 4:

To the dichloride prepared in step 3 (0.15 g, 0.35 mmol) in propionitrile (1.5 mL) was added the aniline (0.17 g, 1.1 mmol). The reaction mixture was warmed to reflux and stirred for 20 h. The reaction was then concentrated in vacuo. The residue was taken up into $CH_2Cl_2$ and washed with saturated $NaHCO_{3(aq)}$, water, and brine. The organic layer was dried ($MgSO_4$), filtered, and concentrated in vacuo. The residue was purified by preparative silica TLC (25% EtOAc/hexane) to provide Example 401 (0.5 g).

Examples 402-410 listed below in Table XIII were prepared from the appropriate bromoketone and substituted aniline using the general procedure described in Scheme 70.

TABLE XIII

| Example # | Bromoketone | Aniline | Example Structure |
| --- | --- | --- | --- |
| 402 | 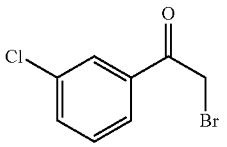 | 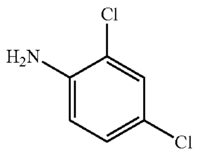 | 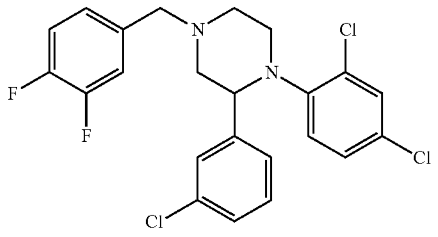 |
| 403 | 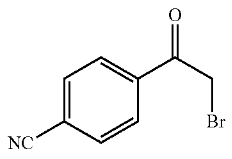 | 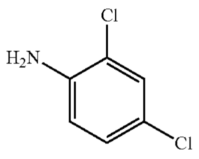 | 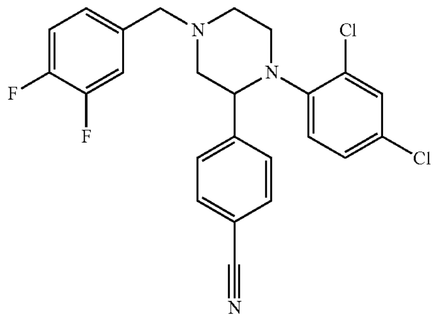 |

TABLE XIII-continued
| Example # | Bromoketone | Aniline | Example Structure |
| --- | --- | --- | --- |
| 404 | 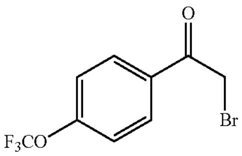 | 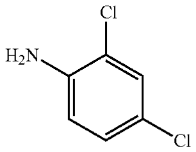 | 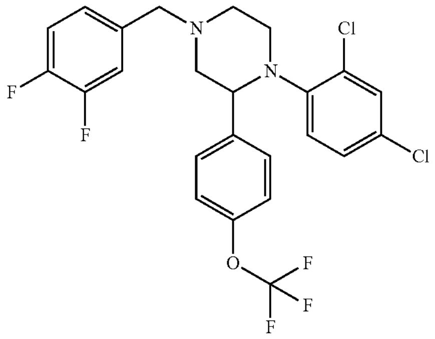 |
| 405 | 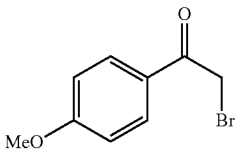 | 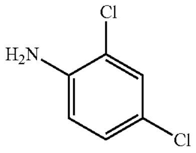 | 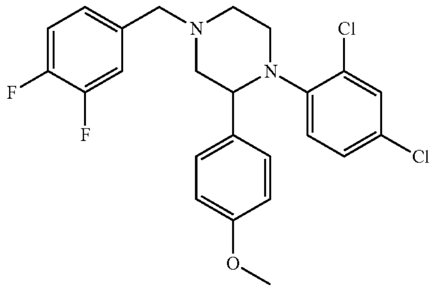 |
| 406 | 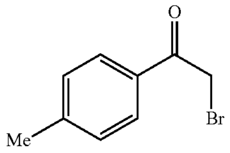 | 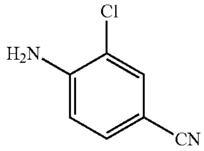 | 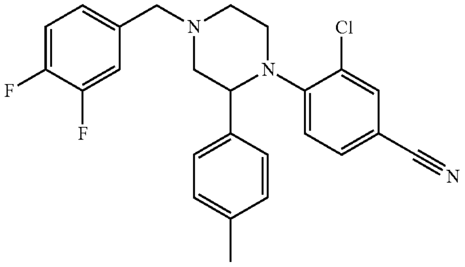 |
| 407 | 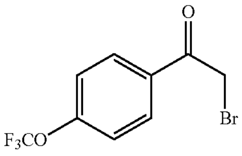 | 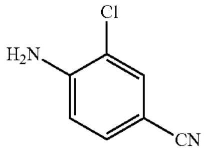 | 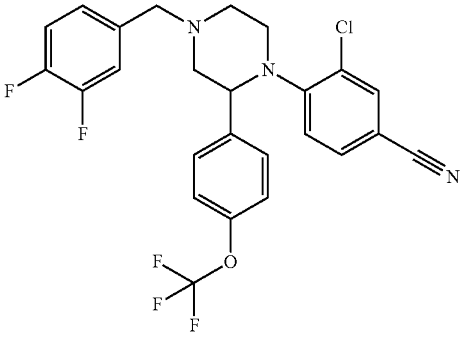 |

TABLE XIII-continued
| Example # | Bromoketone | Aniline | Example Structure |
|---|---|---|---|
| 408 | 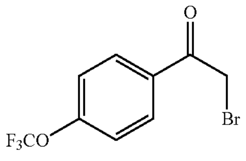 | 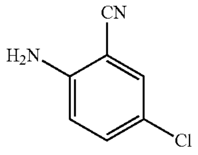 | 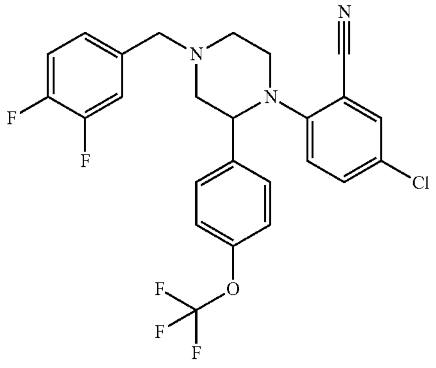 |
| 409 | 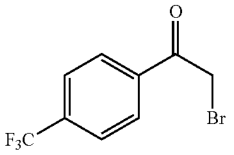 | 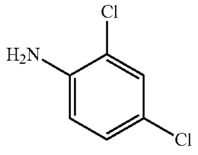 | 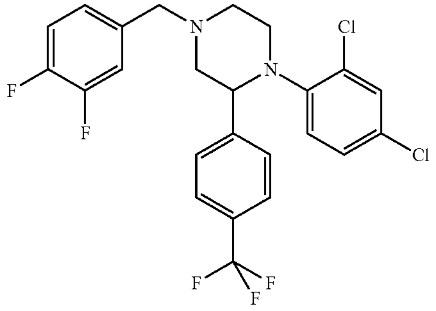 |
| 410 | 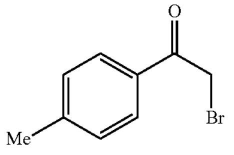 | 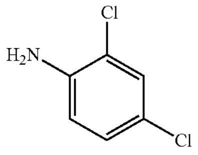 | 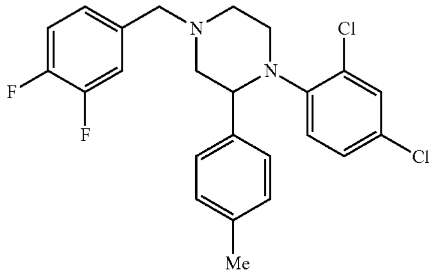 |
Preparation of Example 411
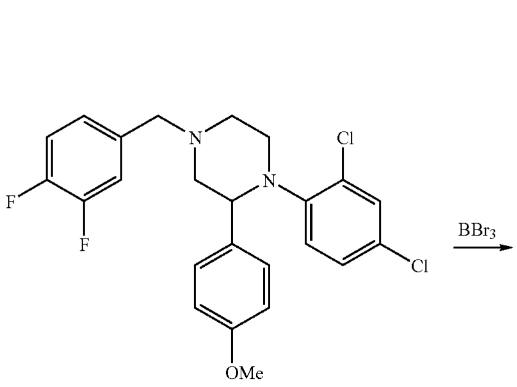
Example 405
-continued
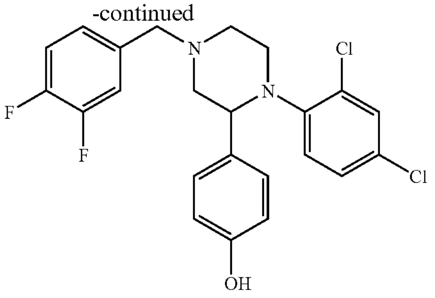
Example 411
To the piperazine Example 405 (0.125 g, 0.27 mmol) in $CH_2Cl_2$ (1 mL) at −78° C. was added boron tribromide (1.0 M in $CH_2Cl_2$, 0.3 mL). The cold bath was removed from the reaction vessel and the reaction mixture was stirred for 30 minutes. Additional boron tribromide (0.6 mL) was added and the reaction was stirred at room temperature for 20 h. The reaction mixture was diluted with $CH_2Cl_2$ and poured into cold saturated $NaHCO_3$ (aq). The mixture was extracted with $CH_2Cl_2$. The organic layers were combined and washed with water and brine. The organic layer was then dried ($MgSO_4$), filtered, and concentrated in vacuo. The residue was triturated with ether to provide Example 411 (0.036 g).

Preparation of Examples 412-415

Scheme 71

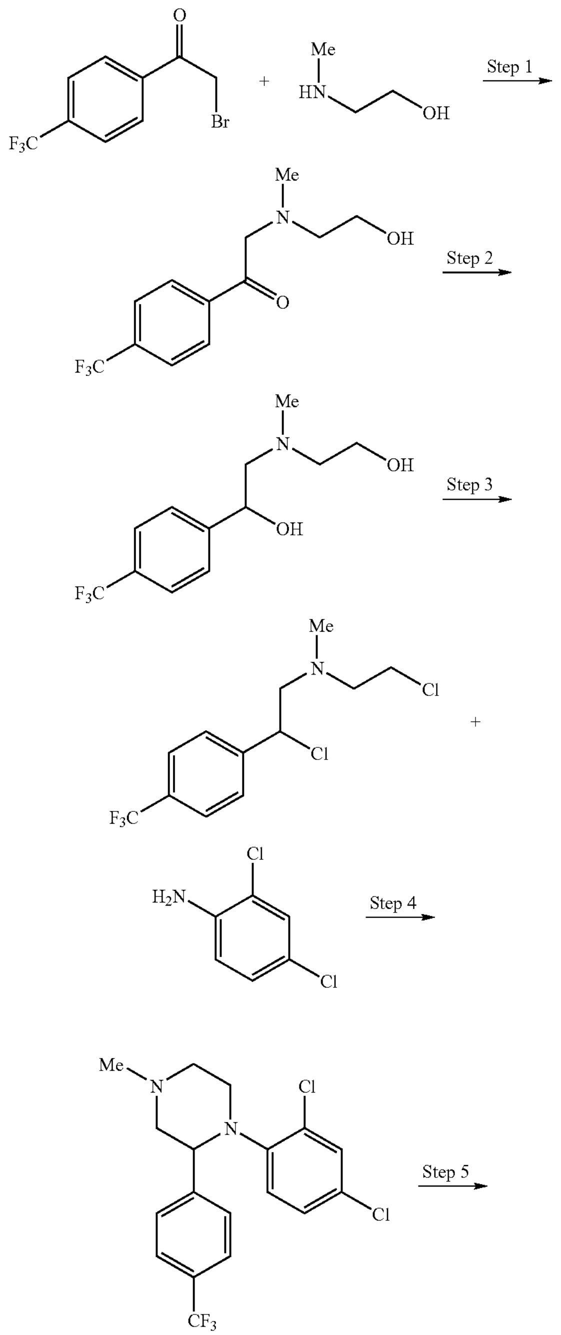

Example 412

-continued

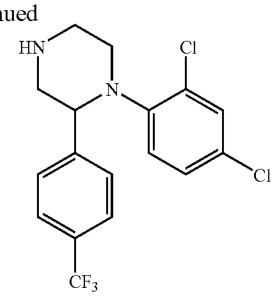

Example 413

Step 1:

To the bromoketone (1.0 g, 3.6 mmol) in acetonitrile (7 mL) was added 2-(methylamino)ethanol (0.3 mL) and $K_2CO_3$ (0.6 g, 4.35 mmol). The reaction mixture was stirred at room temperature for 2 h. The reaction mixture was concentrated in vacuo. The resulting residue was taken up into EtOAc and then washed with water and brine. The organic layer was dried ($MgSO_4$), filtered, and concentrated in vacuo to provide an amino alcohol (0.85 g) which was used in step 2 without further purification.

Step 2:

To the amino alcohol prepared in step 1 (0.83 g, 3.2 mmol) in MeOH (10 mL) at 0° C. was added $NaBH_4$ (0.18 g, 4.8 mmol) in one portion. The reaction mixture was allowed to warm to room temperature while stirring for 20 h. The reaction was concentrated in vacuo and taken up into $CH_2Cl_2$ and washed with 1N NaOH, water, and brine. The organic layer was dried ($MgSO_4$), filtered, and concentrated in vacuo to provide the corresponding diol (0.8 g).

Step 3:

To the diol prepared in step 2 (0.8 g, 3.0 mmol) in dichloroethane (24 mL) at 0° C. was added thionyl chloride (6 mL). The reaction mixture was allowed to warm to room temperature and then heated to reflux for 2 h. The reaction mixture was concentrated in vacuo, taken up into $CH_2Cl_2$ and stirred vigorously with saturated $NaHCO_{3(aq)}$. The organic layer was washed with water and brine and dried ($MgSO_4$). The organic layer was filtered and concentrated in vacuo to provide the corresponding dichloride (0.74 g).

Step 4:

To the dichloride prepared in step 3 (0.2 g, 0.67 mmol) in propionitrile (2 mL) was added 2,4-dichloroaniline (0.32 g). The reaction mixture was warmed to reflux and stirred for 20 h. The reaction was concentrated in vacuo and the residue taken up into $CH_2Cl_2$. The reaction mixture was then washed with 1N NaOH, water, and brine. The organic layer was dried ($MgSO_4$), filtered, and concentrated in vacuo to provide a residue that was purified by silica gel chromatography (0-8% MeOH/EtOAc) to provide Example 412 (0.24 g).

Step 5:

To the piperazine Example 412 (0.24 g) in dichloroethane (2 mL) was added proton sponge (0.04 g) and 1-chloroethylchloroformate (0.13 mL). The reaction mixture was warmed to reflux and stirred for 20 h. The reaction mixture was concentrated in vacuo and the residue taken up into MeOH (2 mL). The solution was warmed to reflux and stirred for 3 h. The reaction mixture was concentrated in vacuo, the resulting residue taken up into $CH_2Cl_2$, and then washed with 1N NaOH, water, and brine. The organic layer was dried ($MgSO_4$), filtered, and concentrated in vacuo. The residue was purified by silica gel chromatography (8% MeOH/$CH_2Cl_2$) to provide the piperazine Example 413 (0.2 g).

The following piperazines were prepared as in Scheme 71 above using the α-bromoketone listed in Table XIV in step 1.

TABLE XIV

| Example # | α-Bromoketone | Example Structure |
|---|---|---|
| 414 | 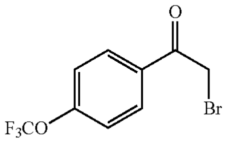 | 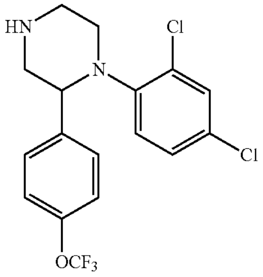 |
| 415 | 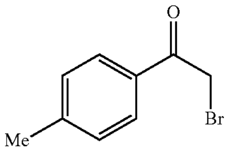 | 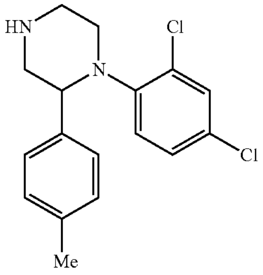 |

Preparation of Example 416

Example 416

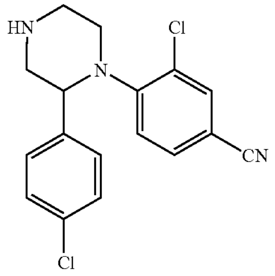

The piperazine Example 416 was prepared in a manner similar to that used to prepare Example 1 in Scheme 1 except that 4-amino-3-chlorobenzonitrile was used instead of 2,4-dichloroaniline in step 3.

Preparation of Example 417

Example 417

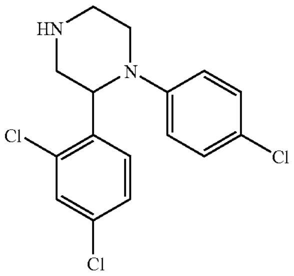

Piperazine Example 417 was prepared in the same manner as Example 1 in Scheme 1 except that 2-(2,4-dichlorophenyl) oxirane (prepared from 2,4-dichlorobenzaldehyde as in step 1 of scheme 7) was used instead of 2-(4-chlorophenyl)oxirane in step 1 and 4-chloroaniline was used instead of 2,4-dichloroaniline in step 3.

Preparation of Example 418

Example 418

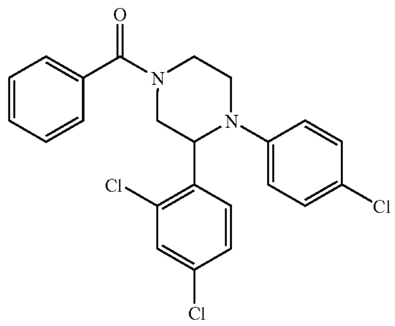

Example 418 was prepared in the same manner as Example 4 in Scheme 2 except that the piperazine Example 417 was used instead of Example 1.

Preparation of Example 419

Example 419

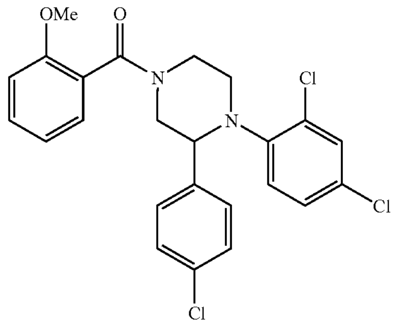

Example 419 was prepared in the same manner as Example 4 in Scheme 2 except that 2-methoxybenzoyl chloride was used instead of benzoyl chloride.

Preparation of Example 420

Example 420

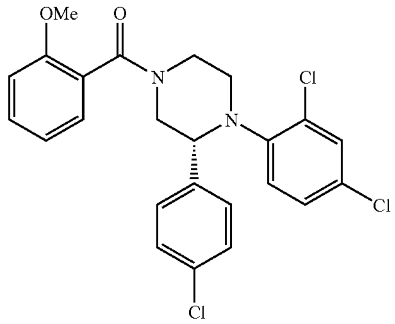

Example 420 was prepared in the same manner as Example 4 in Scheme 2 except that the piperazine Example 304 was used instead of Example 1 and 2-methoxybenzoyl chloride was used instead of benzoyl chloride.

Preparation of Examples 421-424

Scheme 72

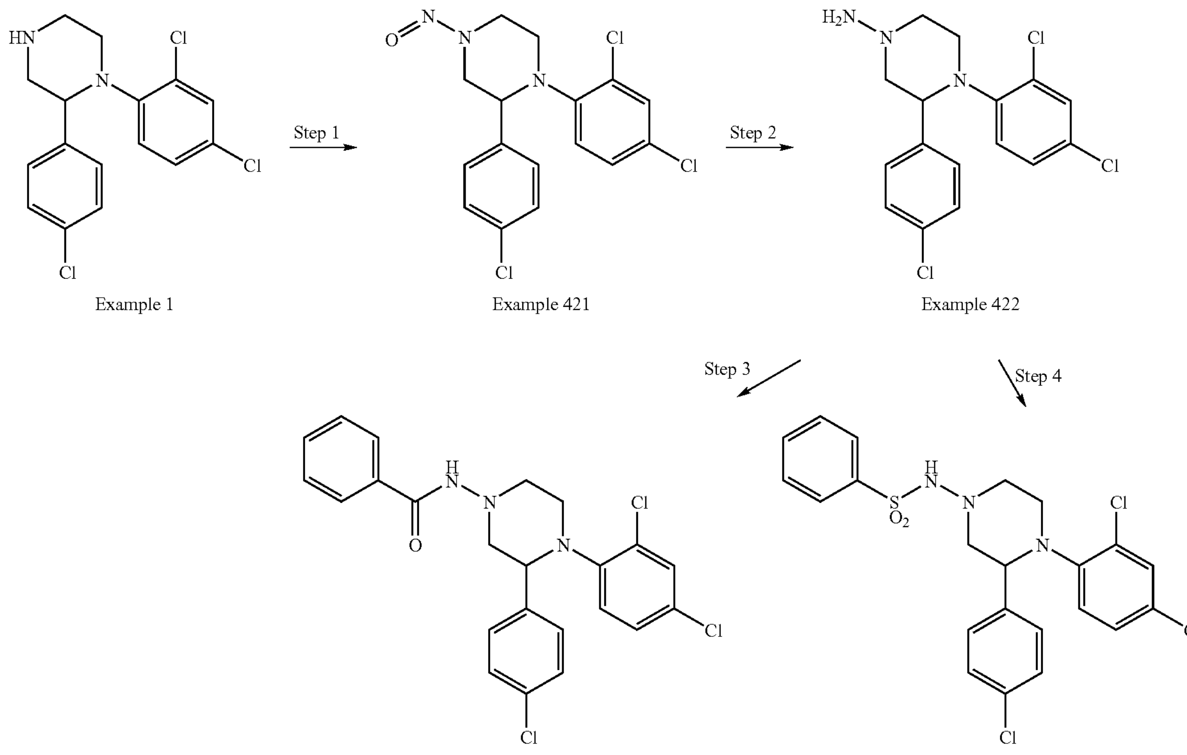

Example 1

Example 421

Example 422

Example 423

Example 424

Step 1:

To the piperazine Example 1 (0.31 g, 0.89 mmol) in THF (3 mL) at 0° C. was added 3N $HCl_{(aq)}$ (1.5 mL). $NaNO_2$ (0.14 g, 2.1 mmol) in water (0.9 mL) was then added and the cold bath was removed from the reaction vessel. The reaction mixture was stirred for 15 h. The reaction mixture was then made basic with 3N NaOH, extracted with EtOAc, and the organic layer was washed with water and brine. The organic layer was then dried ($MgSO_4$), filtered, and concentrated in vacuo to provide Example 421 (0.31 g, 085 mmol).

Step 2:

To the piperazine Example 421 (0.31 g, 0.85 mmol) in AcOH (3 mL) was added water (1.4 mL). Zinc dust was added (0.062 g) in one portion. THF (1 mL) was then added, and the reaction mixture was warmed to 50° C. After 1 h, additional zinc dust (0.3 g) was added. The reaction mixture was stirred at reflux for an additional 1 h. The reaction mixture was cooled to room temperature and filtered. EtOAc was added and the mixture was washed with 3N NaOH, water, and brine. The organic layer was dried ($MgSO_4$), filtered, and concentrated in vacuo. The residue was purified by silica gel chromatography (6% $MeOH/CH_2Cl_2$) to provide Example 422 (0.17 g).

Step 3:

To the aminopiperazine Example 422 (0.07 g, 0.16 mmol) in dichloroethane (1 mL) was added TEA (0.05 g, 0.48 mmol) and benzoyl chloride (0.03 g, 0.2 mmol). The reaction mixture was stirred at room temperature for 1 h. $CH_2Cl_2$ was added to the reaction mixture, which was then washed with saturated $NaHCO_3$, water, and brine. The mixture was then dried ($MgSO_4$), filtered, and the organic layer was concentrated in vacuo. The concentrate was purified by preparative TLC ($SiO_2$) (50% EtOAc/hexane) to provide Example 423 (0.07 g).

Step 4:

To the piperazine Example 422 (0.074 g, 0.17 mmol) in dichloroethane (1 mL) was added TEA (0.05 g, 0.5 mmol) followed by benzene sulfonyl chloride (0.04 g). The mixture was stirred at room temperature for 2 h and $CH_2Cl_2$ was added. The mixture was washed with saturated $NaHCO_3$, water, and brine, dried ($MgSO_4$), filtered, and the organic layer was concentrated in vacuo. Purification by preparative TLC ($SiO_2$) (20% EtOAc/hexane) provided Example 424 (0.05 g).

Preparation of Example 425

Scheme 73

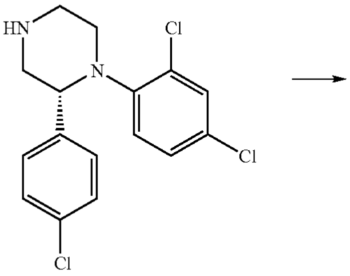

Example 304

-continued

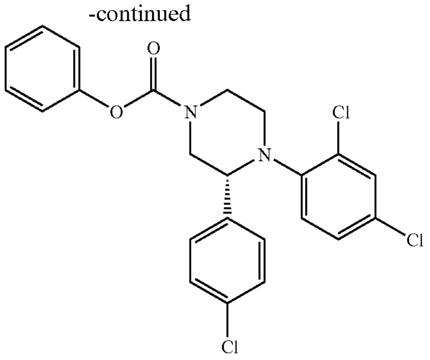

Example 425

The carbamate Example 425 was prepared in the same manner as Example 4 in Scheme 2 except that Example 304 was used as a starting material instead of Example 1 and phenylchloroformate was used instead of benzoyl chloride.

Preparation of Example 426

Example 426

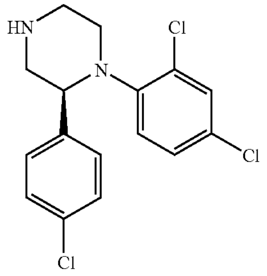

The piperazine Example 426 was prepared in the same manner as the chiral piperazine Example 304 in Scheme 28 except that (S)-2-methyl-CBS-oxazaborolidine was used instead of (R)-2-methyl-CBS-oxazaborolidine in step 1.

Preparation of Examples 427-428

Scheme 74

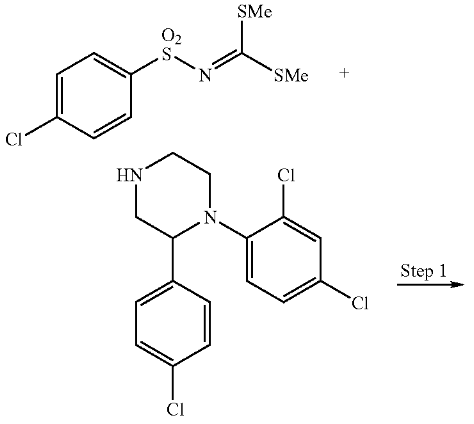

Example 1

-continued

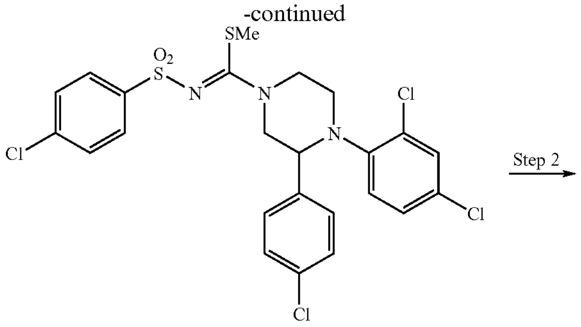

Example 427

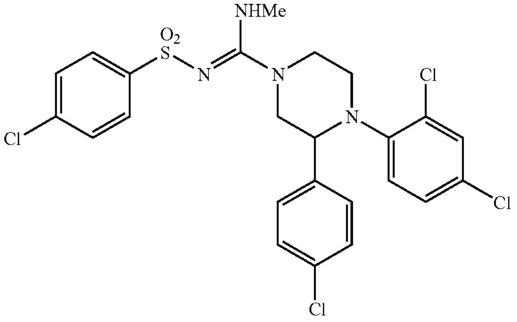

Example 428

Step 1:

The arylsulfonyldithioimide carbonic acid methyl ester was prepared according to the method of Lange et. al. J. Med. Chem. 2004, 47, 627-643 (herein incorporated by reference). To the dithioimide (0.39 g, 1.3 mmol) in propionitrile (4 mL) was added the $Et_3N$ (0.43 mL, 3.1 mmol) and the piperazine Example 1 (0.3 g, 1.3 mmol). The reaction mixture was warmed to reflux and stirred for 20 h, then cooled to room temperature and concentrated in vacuo. The residue, Example 427, was used in step 2 without further purification.

Step 2:

Example 427 was taken up into MeOH (7 mL) and $MeNH_2$ (40% solution in water, 1.5 mL, 18 mmol) was added. The reaction mixture was stirred at room temperature for 20 h, then concentrated in vacuo. The resulting residue was taken up into $CH_2Cl_2$ and the insoluble precipitate was filtered off. The filtrate was concentrated in vacuo and purified by silica gel chromatography (55% EtOAc/hexane) to provide Example 428 (0.35 g, 0.61 mmol).

Preparation of Examples 429-494

Scheme 75

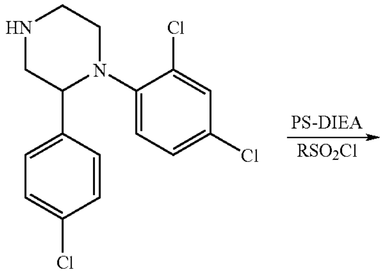

-continued

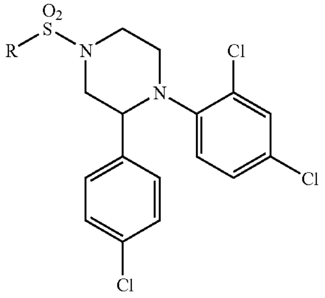

Polystyrene DIEA resin (47 mg, 0.045 mmol) was added to 72-wells of a deep well polypropylene microtiter plate followed by a MeCN/THF (3:2) stock solution (1 mL) of piperazine Example 1 (0.033 mmol). Then 0.5 M stock solutions of each of the individual sulfonyl chlorides ($R_{1-66}SO_2Cl$) (0.135 mL, 0.067 mmol) were added to the wells, which was then sealed and shaken at 25° C. for 20 h. The solutions were filtered thru a polypropylene frit into a second microtiter plate containing polystyrene isocyanate resin (3 equivalents, 0.135 mmol) and polystyrene trisamine resin (6 equivalents, 0.27 mmol). After the top plate was washed with MeCN (0.5 mL), the plate was removed, the bottom microtiter plate sealed and shaken at 25° C. for 16 h. Then the solutions were filtered thru a polypropylene frit into a 96-well collection plate. The wells of the top plate were then washed with MeCN (0.5 mL), and the plate removed. Then the resultant solutions in the collection plate were transferred into vials and the solvents removed in vacuo via a SpeedVac to provide the sulfonamides shown below in Table XV.

TABLE XV

| Example # | Sulfonyl Chloride | Example Structure |
|---|---|---|
| 429 | 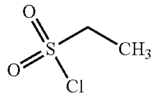 | 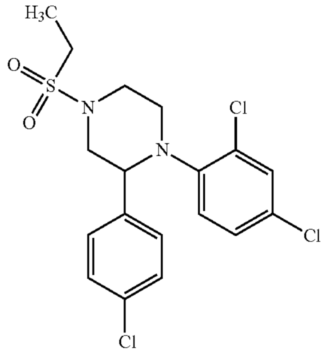 |
| 430 | 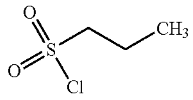 | 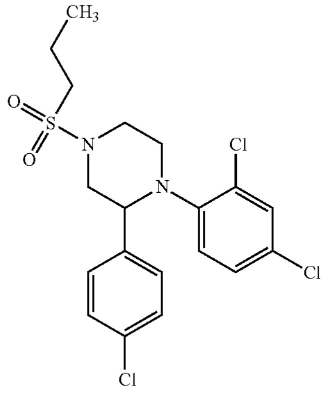 |
| 431 | 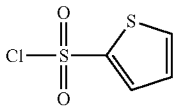 | 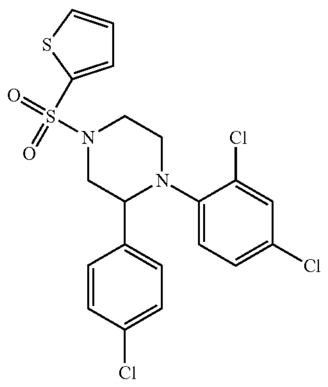 |

TABLE XV-continued
| Example # | Sulfonyl Chloride | Example Structure |
|---|---|---|
| 432 | 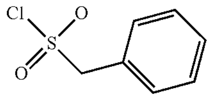 | 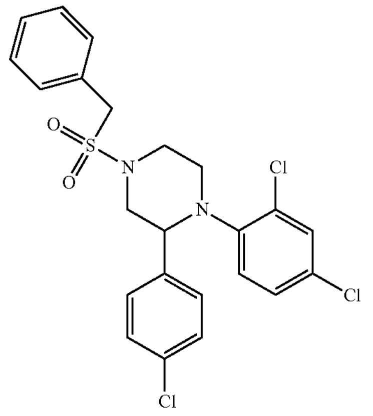 |
| 433 | 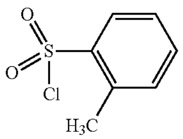 | 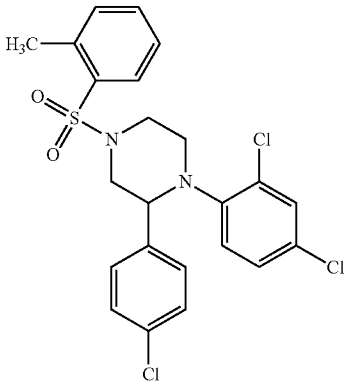 |
| 434 | 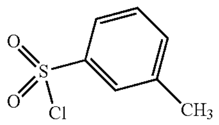 | 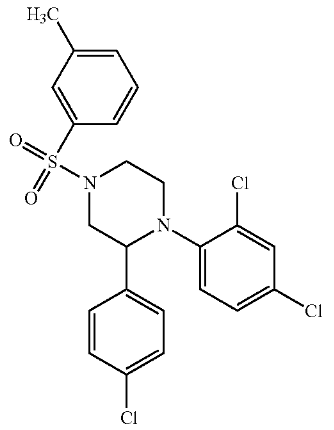 |
| 435 | 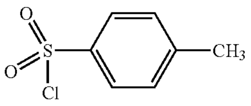 | 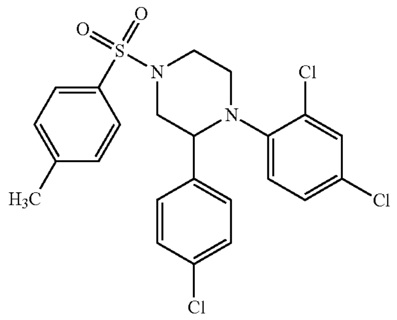 |

TABLE XV-continued
| Example # | Sulfonyl Chloride | Example Structure |
|---|---|---|
| 436 | 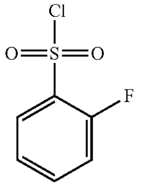 | 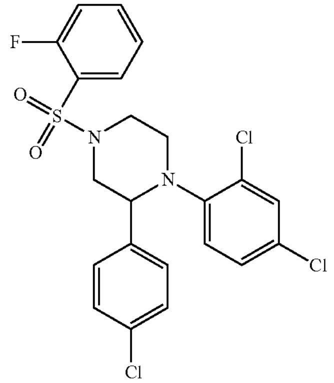 |
| 437 | 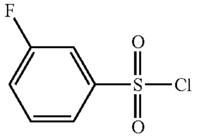 | 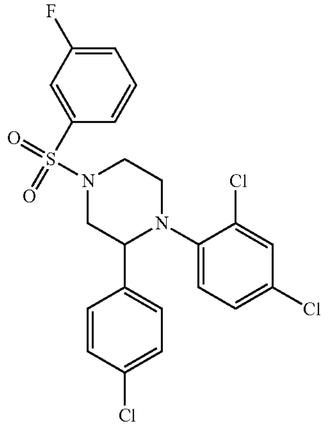 |
| 438 | 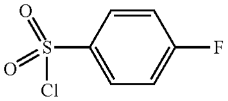 | 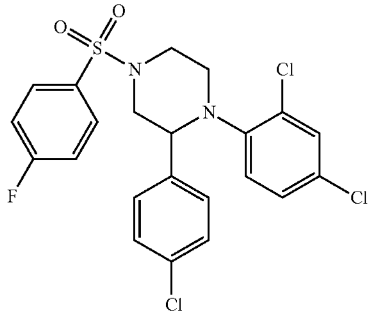 |
| 439 | 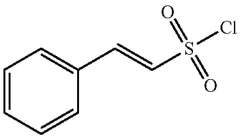 | 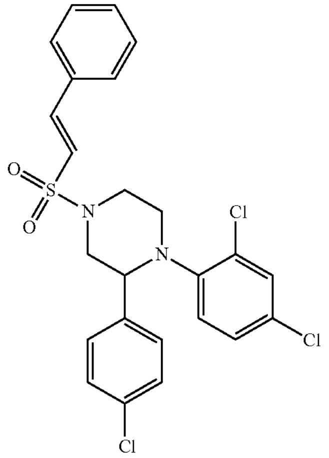 |

TABLE XV-continued
| Example # | Sulfonyl Chloride | Example Structure |
|---|---|---|
| 440 | 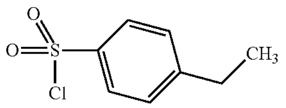 | 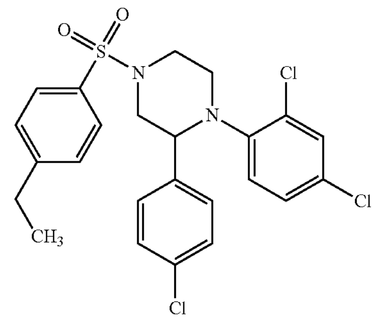 |
| 441 | 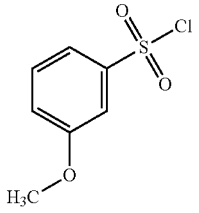 | 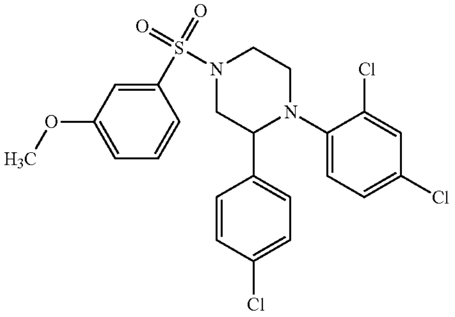 |
| 442 | 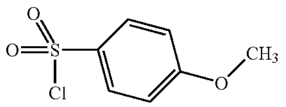 | 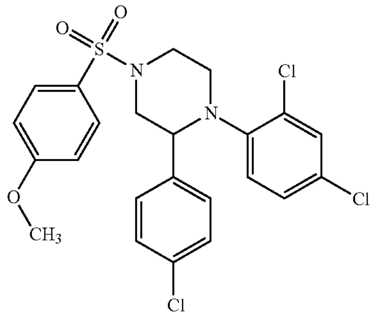 |
| 443 | 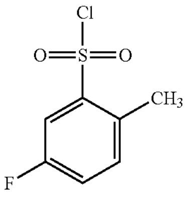 | 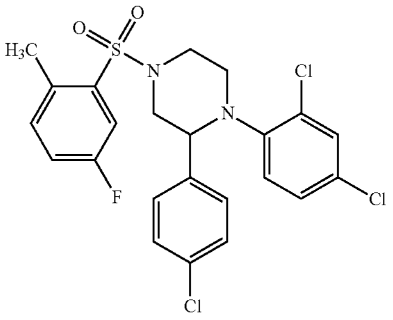 |

TABLE XV-continued
| Example # | Sulfonyl Chloride | Example Structure |
|---|---|---|
| 444 | 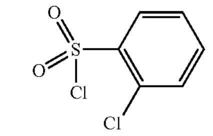 | 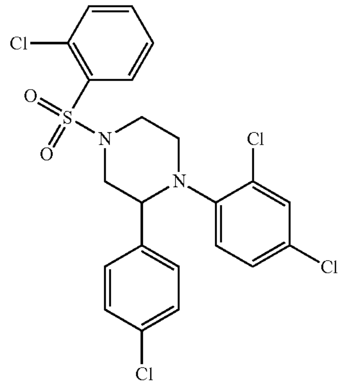 |
| 445 | 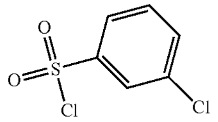 | 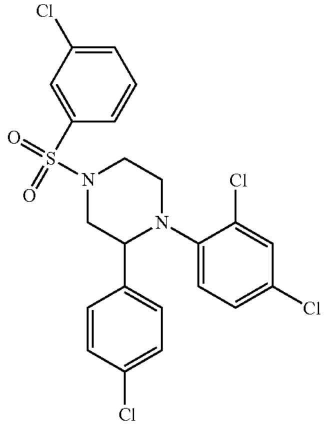 |
| 446 | 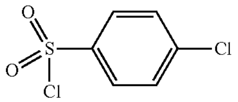 | 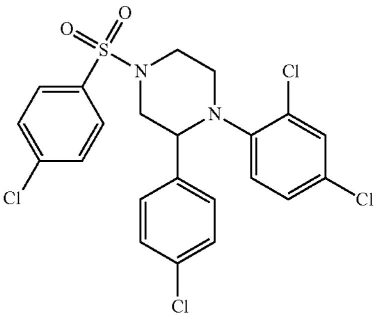 |
| 447 | 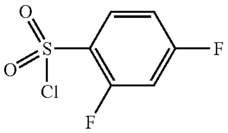 | 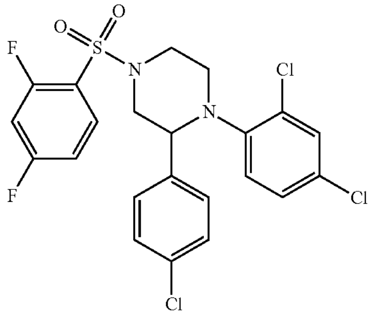 |

TABLE XV-continued
| Example # | Sulfonyl Chloride | Example Structure |
|---|---|---|
| 448 | 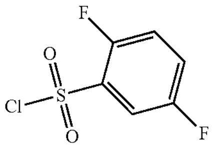 | 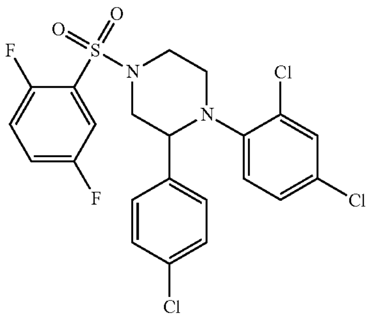 |
| 449 | 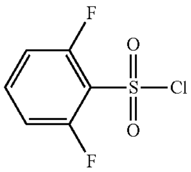 | 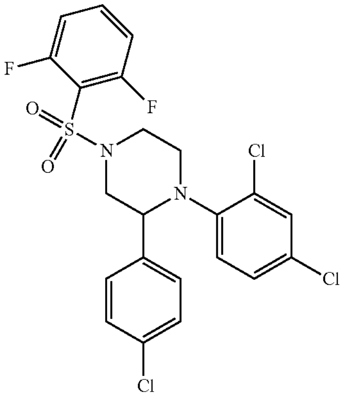 |
| 450 | 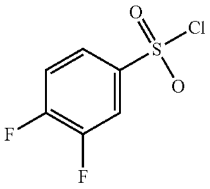 | 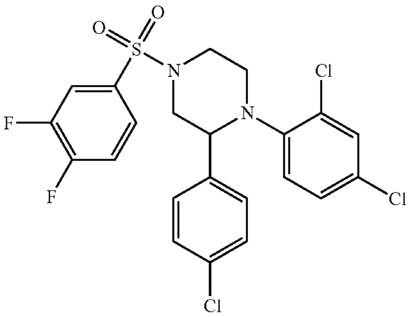 |
| 451 | 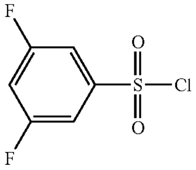 | 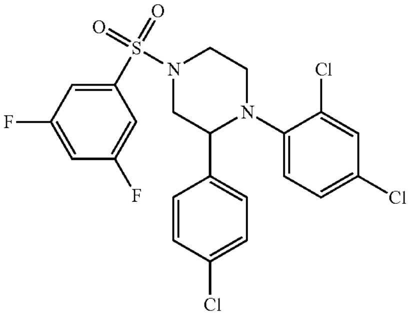 |

TABLE XV-continued
| Example # | Sulfonyl Chloride | Example Structure |
|---|---|---|
| 452 | 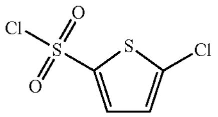 | 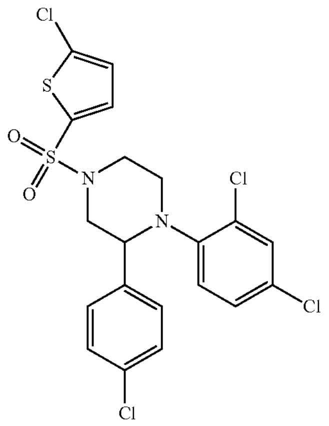 |
| 453 | 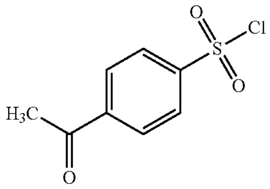 | 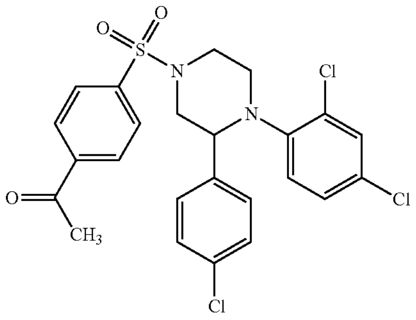 |
| 454 | 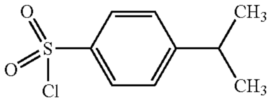 | 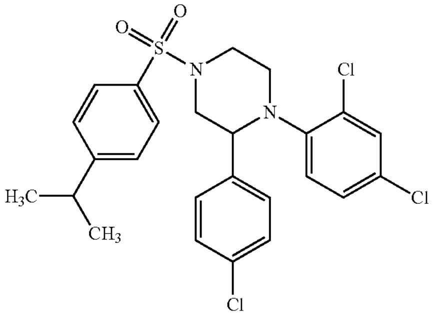 |
| 455 | 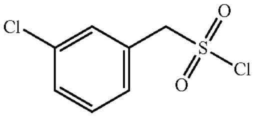 | 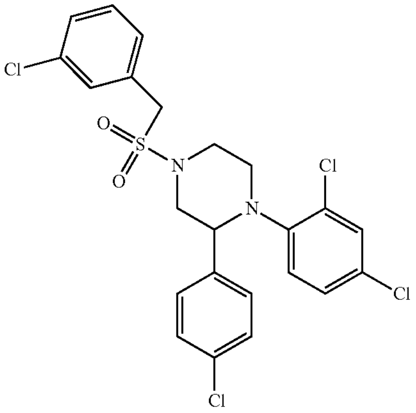 |

TABLE XV-continued
| Example # | Sulfonyl Chloride | Example Structure |
| --- | --- | --- |
| 456 | 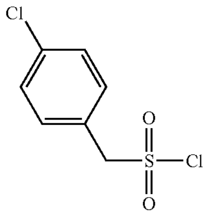 | 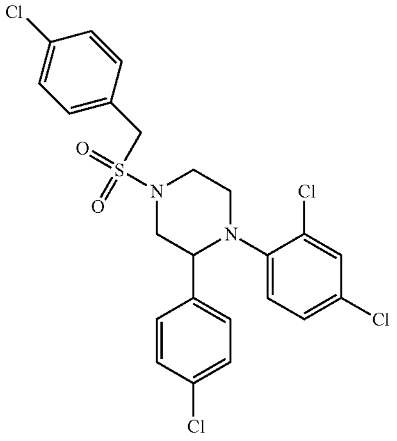 |
| 457 | 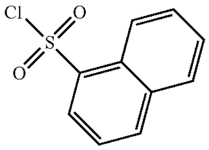 | 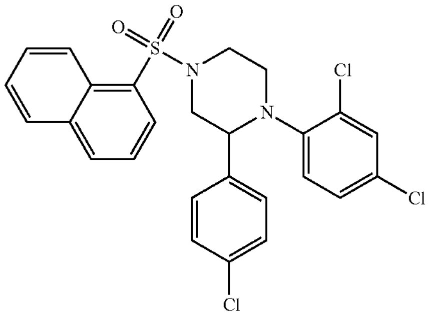 |
| 458 | 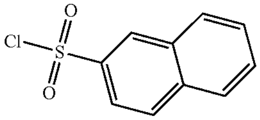 | 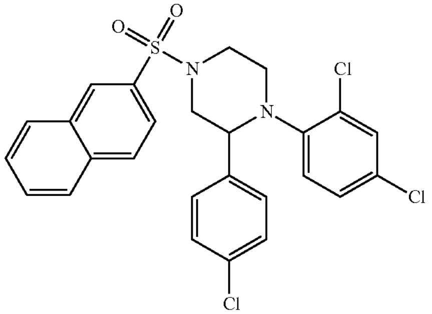 |
| 459 | 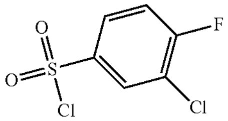 | 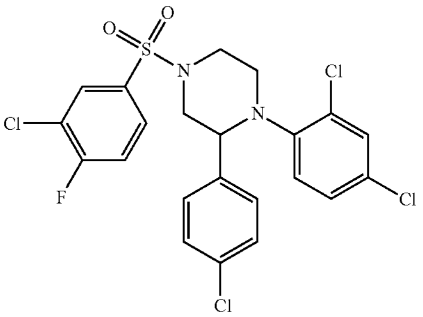 |

TABLE XV-continued
| Example # | Sulfonyl Chloride | Example Structure |
|---|---|---|
| 460 | 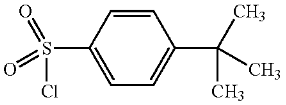 | 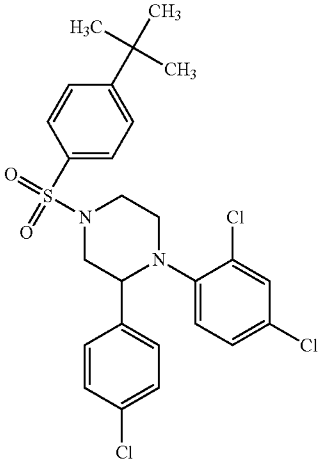 |
| 461 | 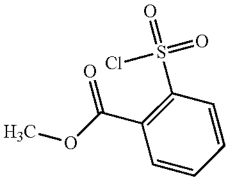 | 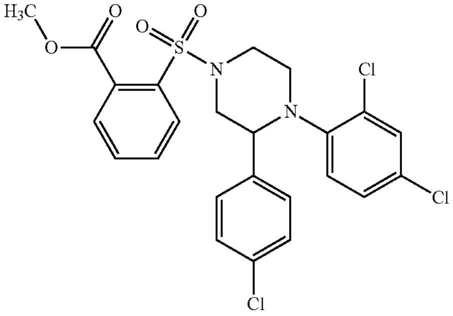 |
| 462 | 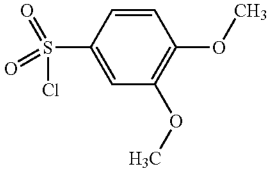 | 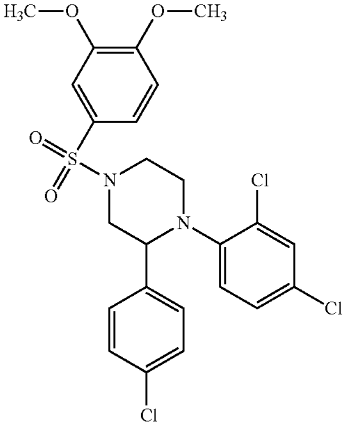 |
| 463 | 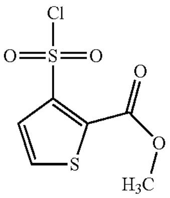 | 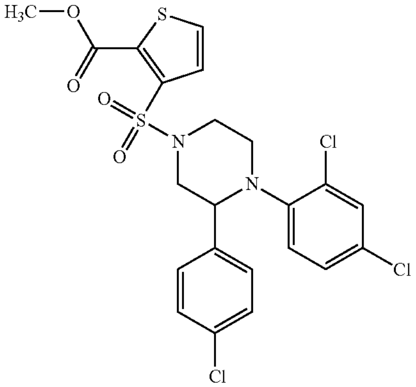 |

TABLE XV-continued
| Example # | Sulfonyl Chloride | Example Structure |
|---|---|---|
| 464 | 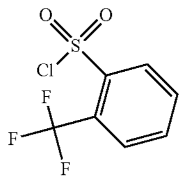 | 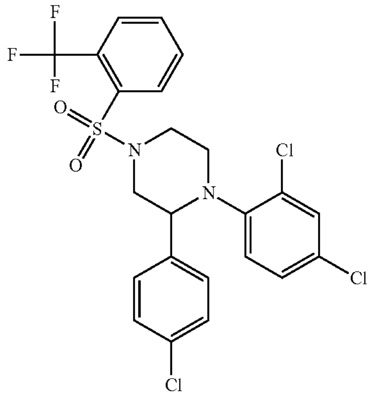 |
| 465 | 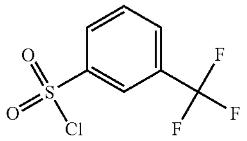 | 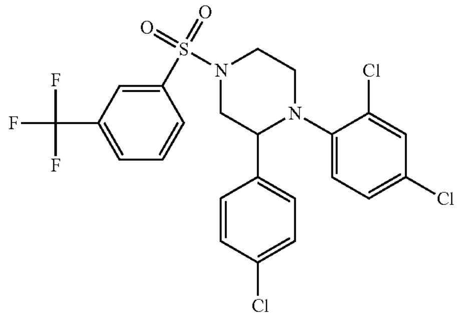 |
| 466 | 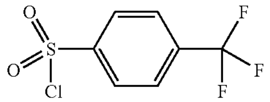 | 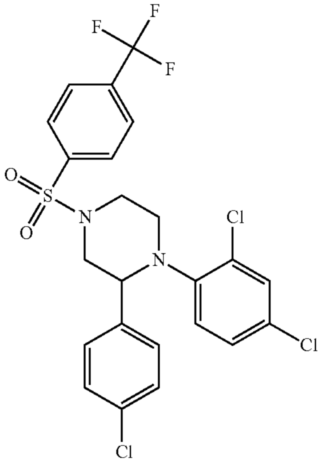 |

TABLE XV-continued
| Example # | Sulfonyl Chloride | Example Structure |
|---|---|---|
| 467 | 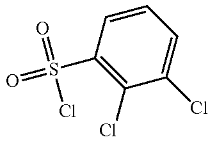 | 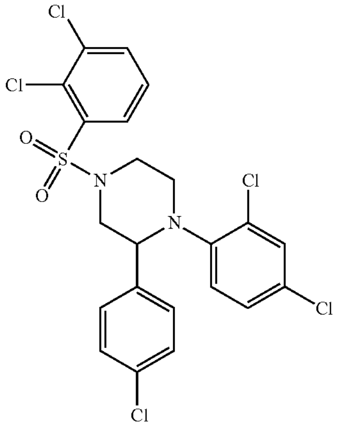 |
| 468 | 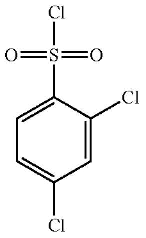 | 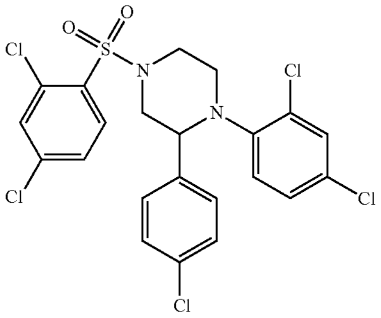 |
| 469 | 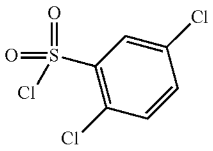 | 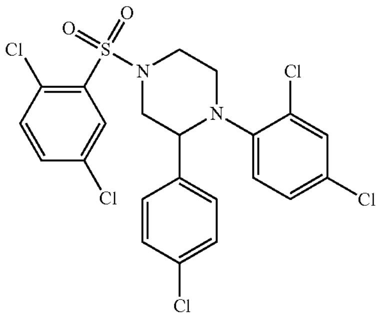 |
| 470 | 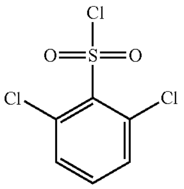 | 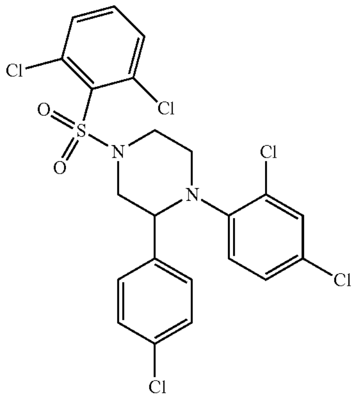 |

TABLE XV-continued
| Example # | Sulfonyl Chloride | Example Structure |
|---|---|---|
| 471 | 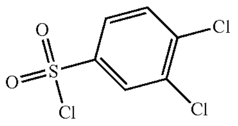 | 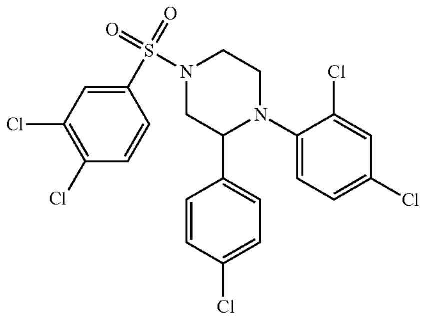 |
| 472 | 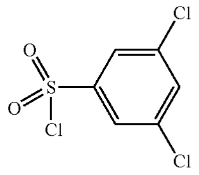 | 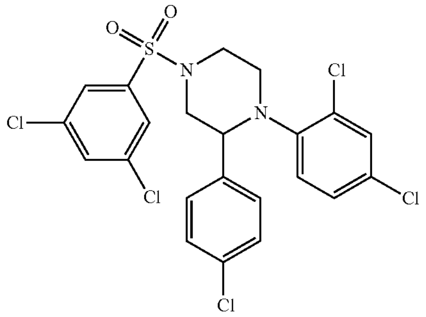 |
| 473 | 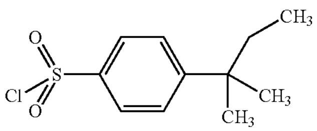 | 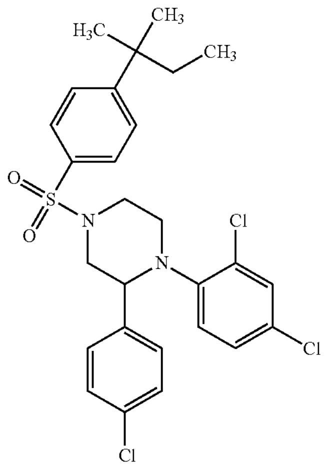 |
| 474 | 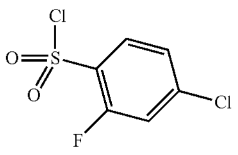 | 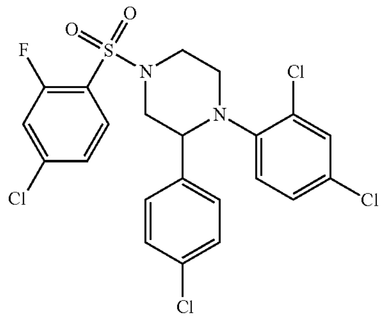 |

TABLE XV-continued
| Example # | Sulfonyl Chloride | Example Structure |
|---|---|---|
| 475 | 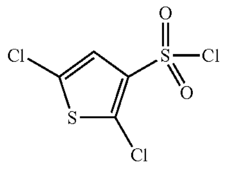 | 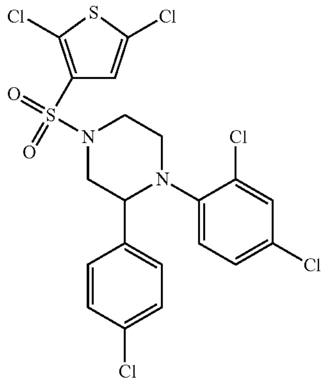 |
| 476 | 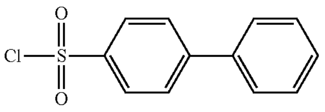 | 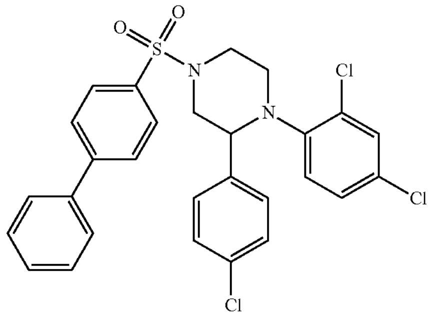 |
| 477 | 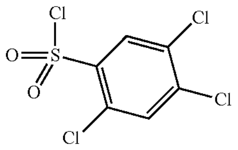 | 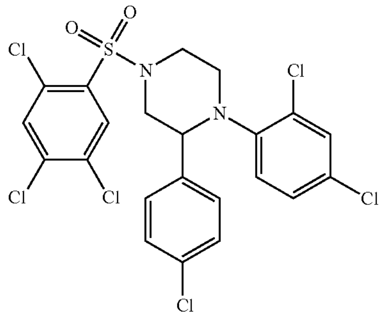 |
| 478 | 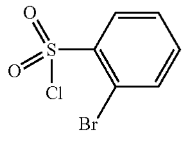 | 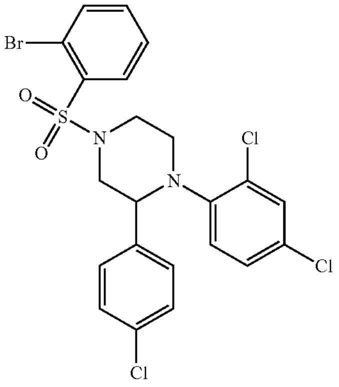 |

TABLE XV-continued
| Example # | Sulfonyl Chloride | Example Structure |
| --- | --- | --- |
| 479 | 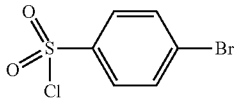 | 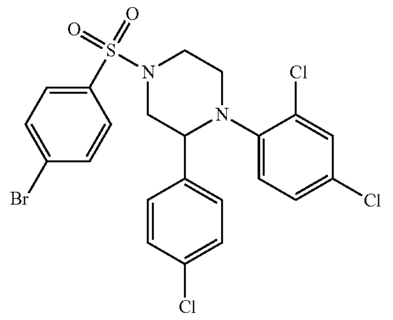 |
| 480 | 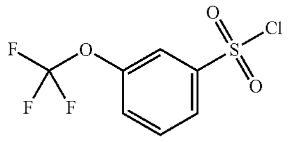 | 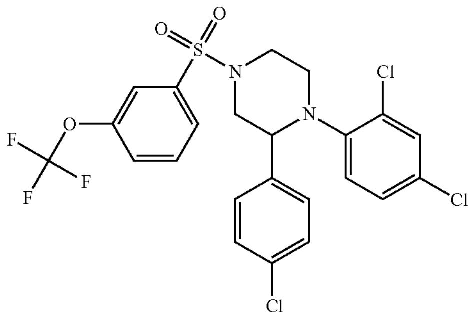 |
| 481 | 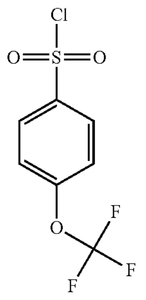 | 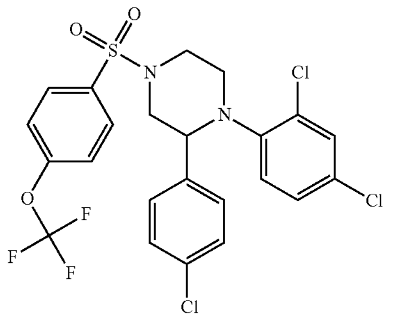 |
| 482 | 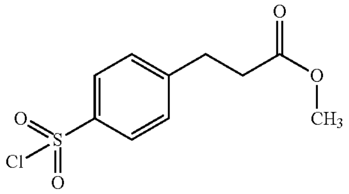 | 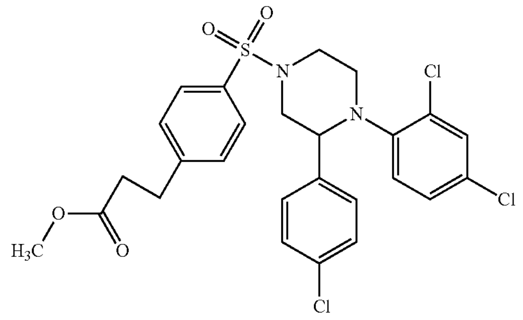 |
| 483 | 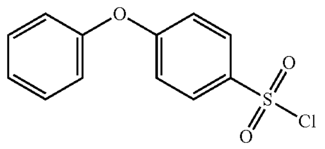 | 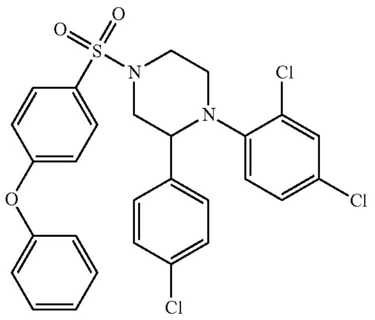 |

TABLE XV-continued
| Example # | Sulfonyl Chloride | Example Structure |
| --- | --- | --- |
| 484 | 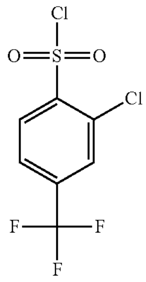 | 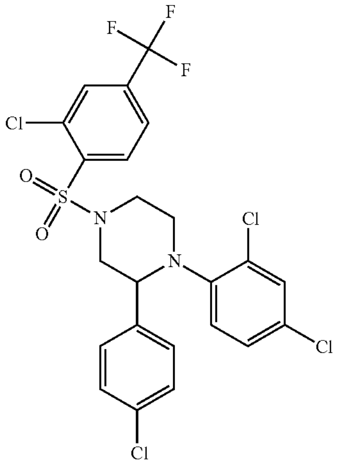 |
| 485 | 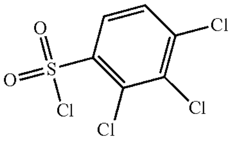 | 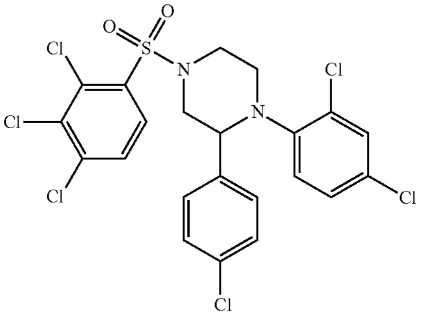 |
| 486 | 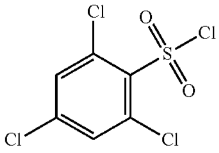 | 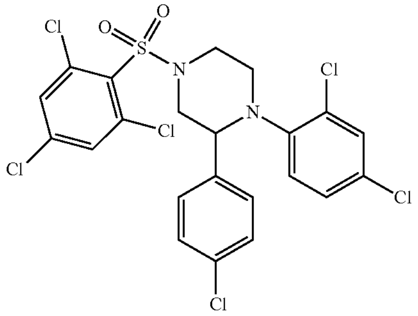 |
| 487 | 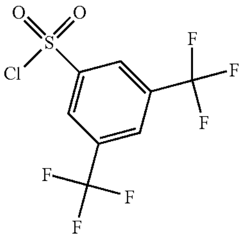 | 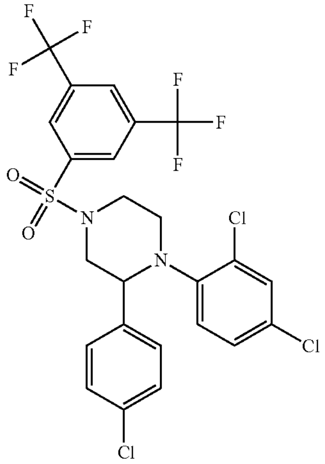 |

TABLE XV-continued
| Example # | Sulfonyl Chloride | Example Structure |
|---|---|---|
| 488 | 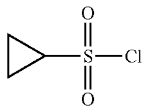 | 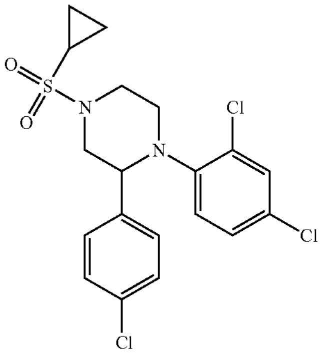 |
| 489 | 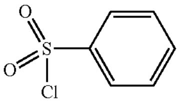 | 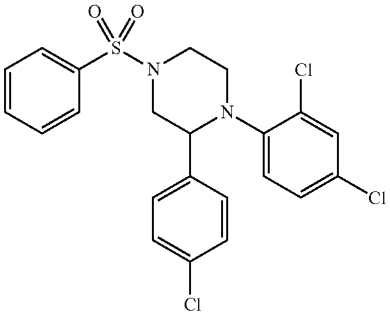 |
| 490 | 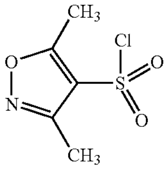 | 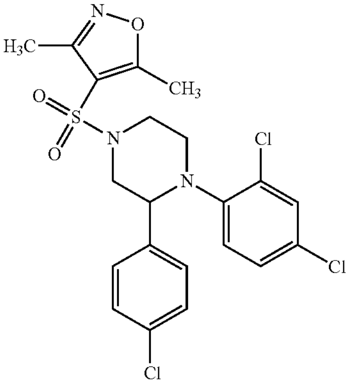 |
| 491 | 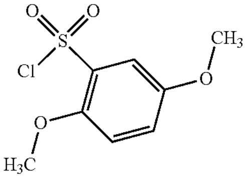 | 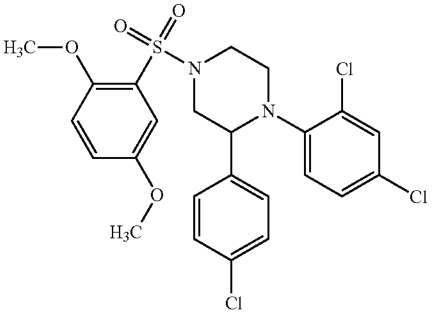 |

TABLE XV-continued
| Example # | Sulfonyl Chloride | Example Structure |
|---|---|---|
| 492 | 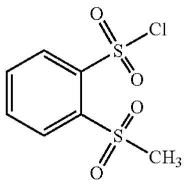 | 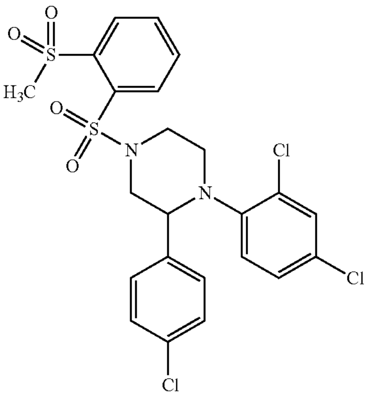 |
| 493 | 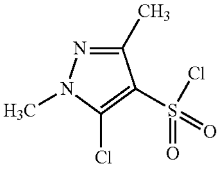 | 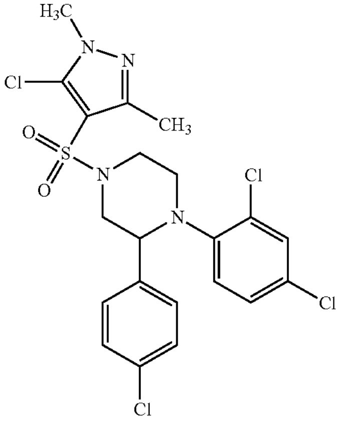 |
| 494 | 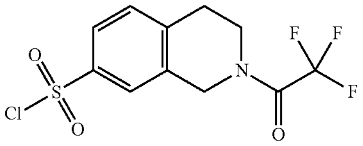 | 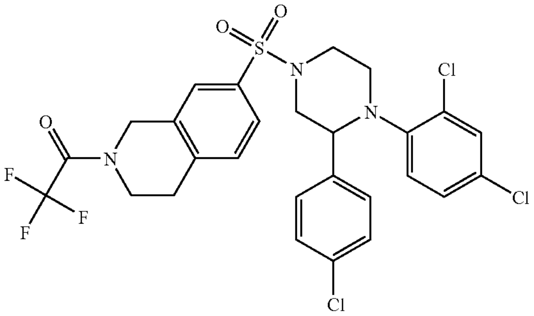 |

Preparation of Examples 495-497
Examples 495-497 were prepared by the reaction of the appropriate piperazine and aldehyde (e.g., by the method of step 4 of Scheme 64), shown in Table XVI, below. The piperazines were prepared, e.g., by the methods described in Scheme 71.
TABLE XVI
| Example # | Piperazine | Aldehyde | Example Structure |
|---|---|---|---|
| 495 | 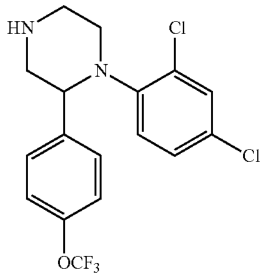 | 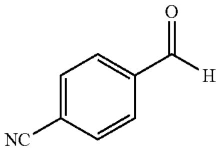 | 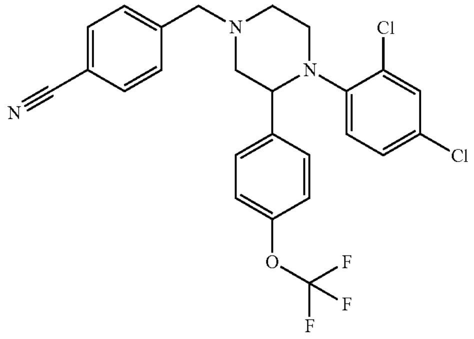 |
| 496 | 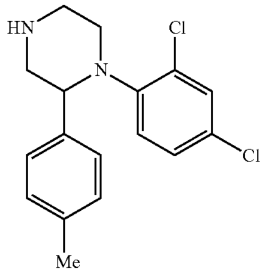 | 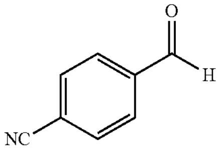 | 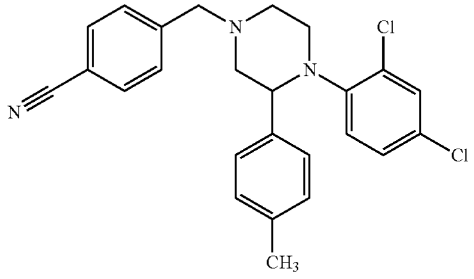 |
| 497 | 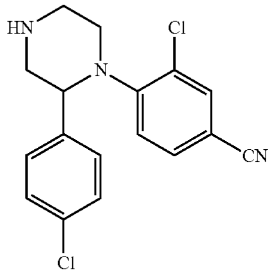 | 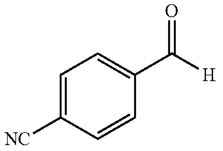 | 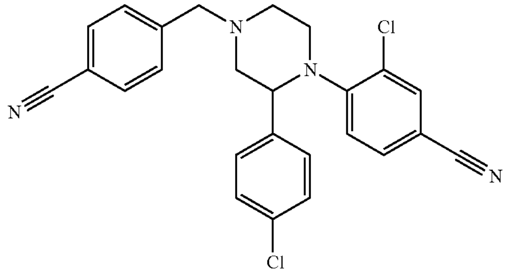 |

Preparation of Examples 498-513
Examples 498-513 were prepared by the reaction of the appropriate piperazine and aldehyde (e.g., by the method of Scheme 64, step 4) shown in Table XVII, below. The piperazines were prepared, e.g, by the method of Scheme 28.
TABLE XVII
| Example # | Piperazine | Aldehyde | Example Structure |
|---|---|---|---|
| 498 | 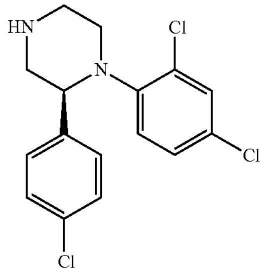 | 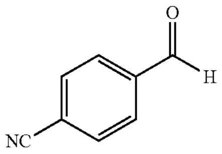 | 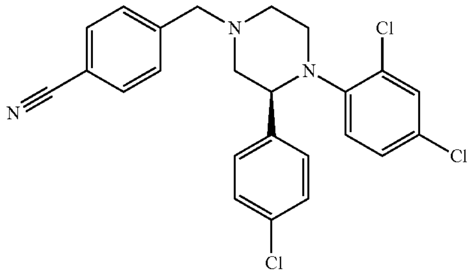 |
| 499 | 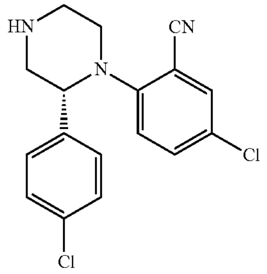 | 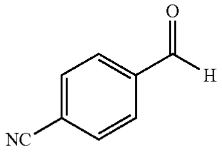 | 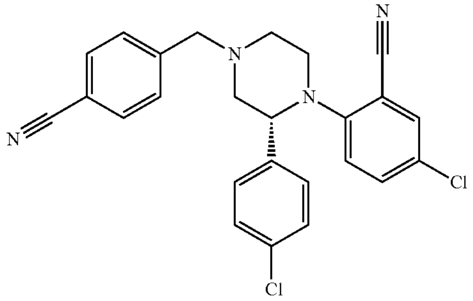 |
| 500 | 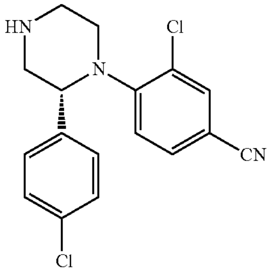 | 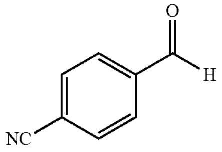 | 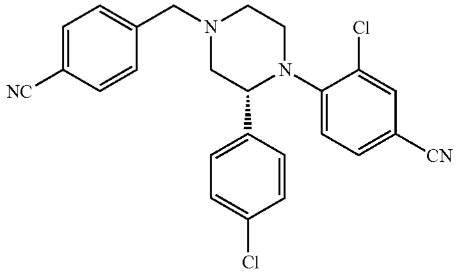 |
| 501 | 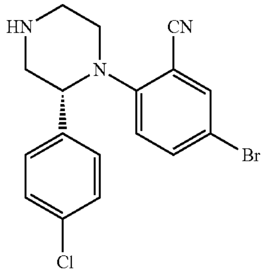 | 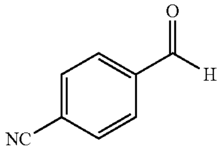 | 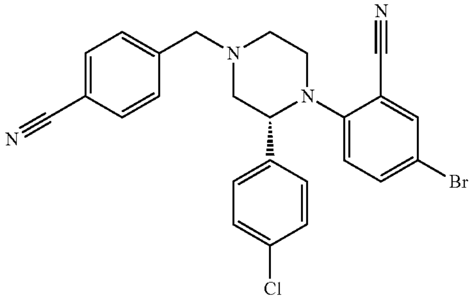 |
| 502 | 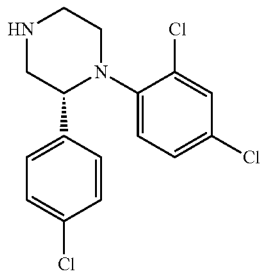 | 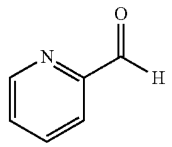 | 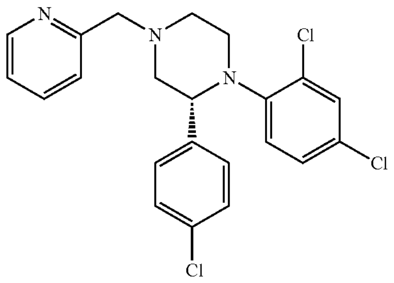 |

TABLE XVII-continued
| Example # | Piperazine | Aldehyde | Example Structure |
|---|---|---|---|
| 503 | 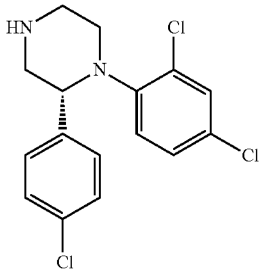 | 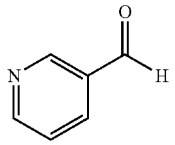 | 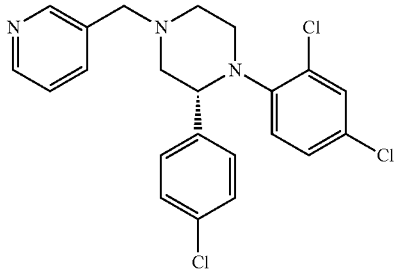 |
| 504 | 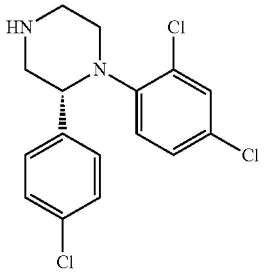 | 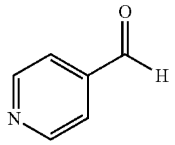 | 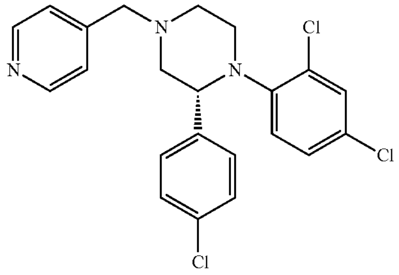 |
| 505 | 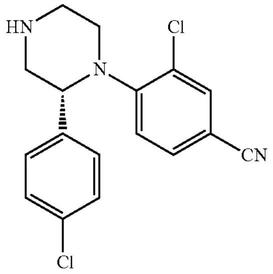 | 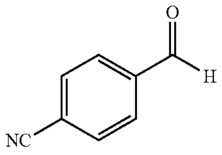 | 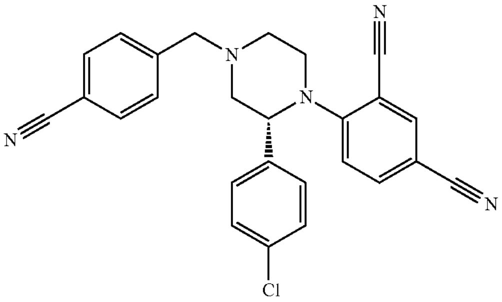 |
| 506 | 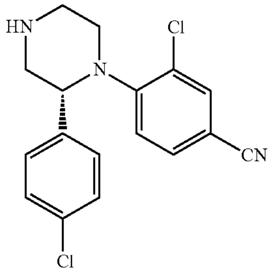 | 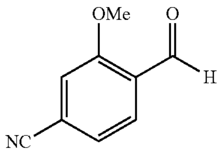 | 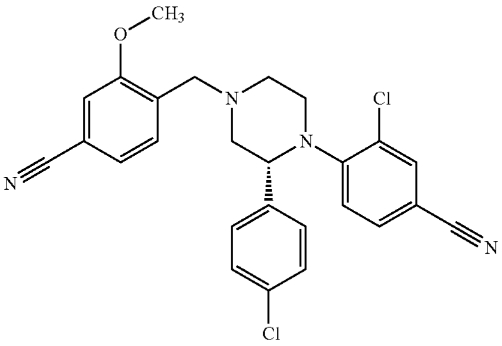 |
| 507 | 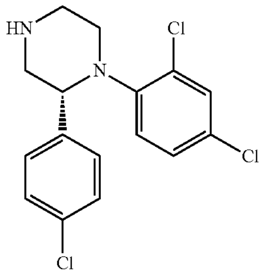 | 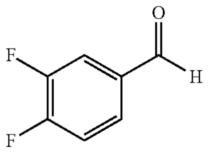 | 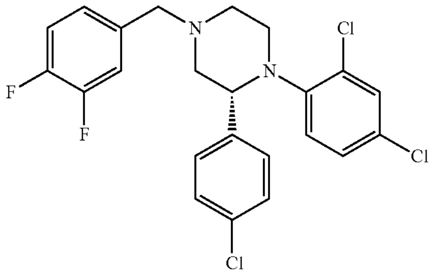 |

TABLE XVII-continued
| Example # | Piperazine | Aldehyde | Example Structure |
| --- | --- | --- | --- |
| 508 | 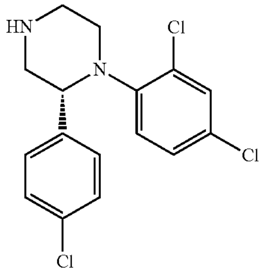 | 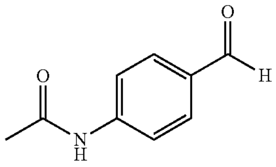 | 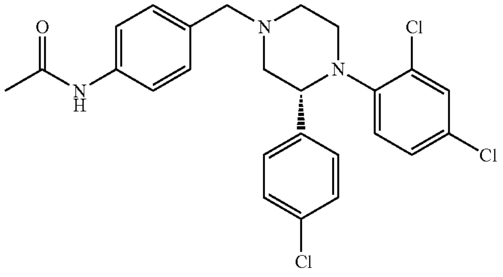 |
| 509 | 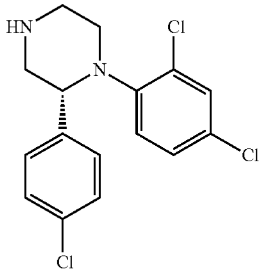 | 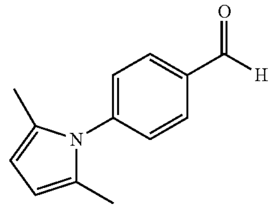 | 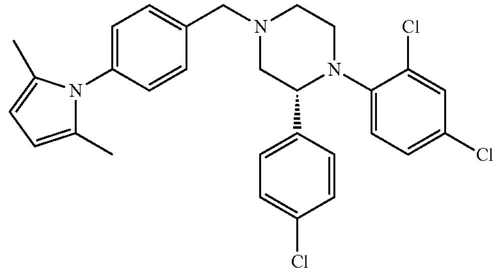 |
| 510 | 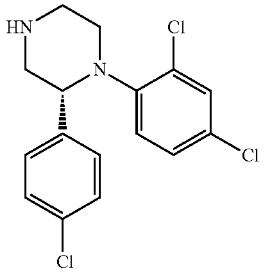 | 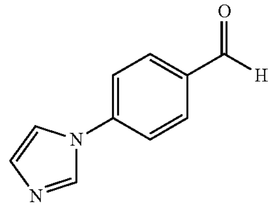 | 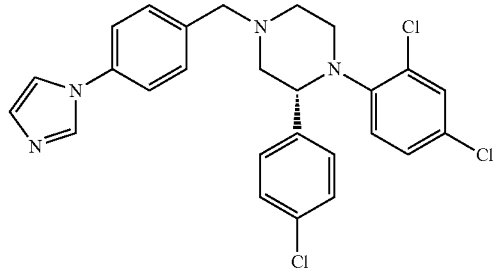 |
| 511 | 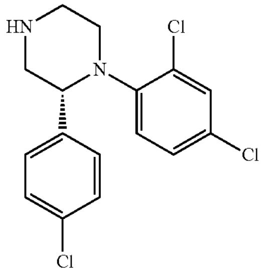 | 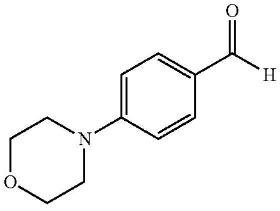 | 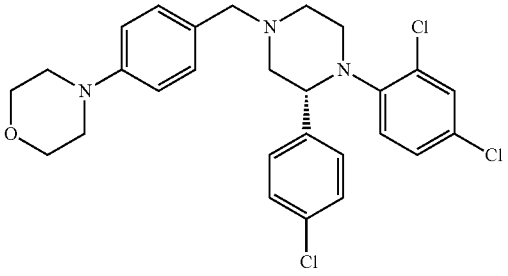 |
| 512 | 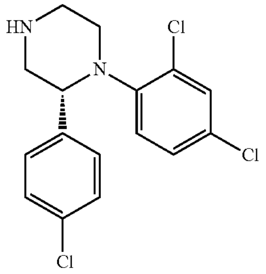 | 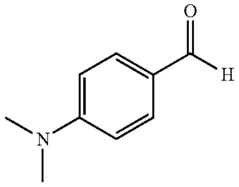 | 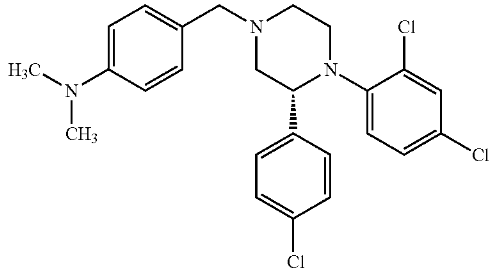 |

TABLE XVII-continued
| Example # | Piperazine | Aldehyde | Example Structure |
|---|---|---|---|
| 513 | 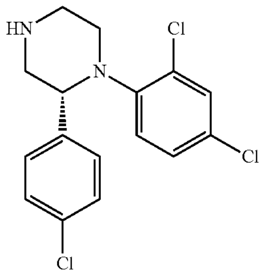 | 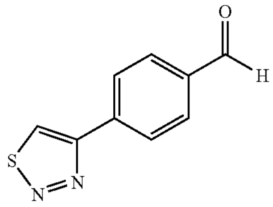 | 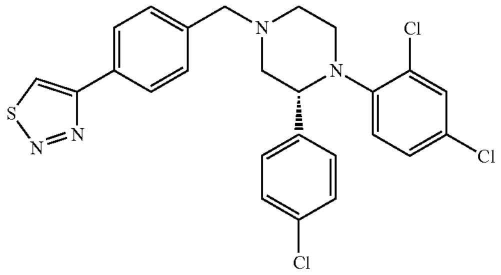 |
Preparation of Examples 514-530
Examples 514-530 were prepared by the reaction of the appropriate piperazine and carboxylic acid (e.g., the method of Scheme 17) shown in Table XVIII, below.
TABLE XVIII
| Example # | Piperazine | Carboxylic Acid | Example Structure |
|---|---|---|---|
| 514 | 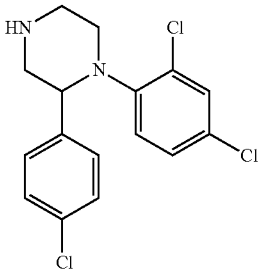 | 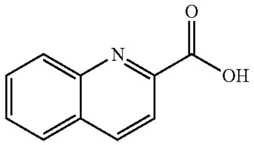 | 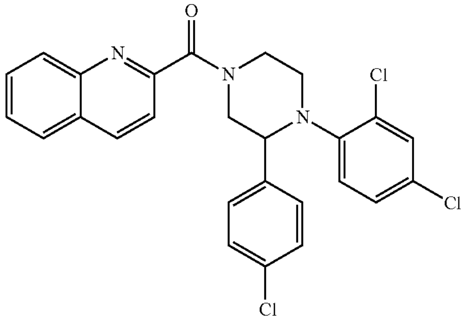 |
| 515 | 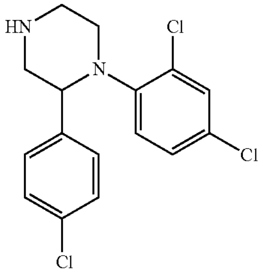 | 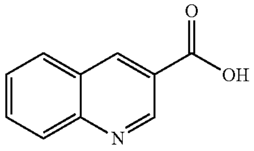 | 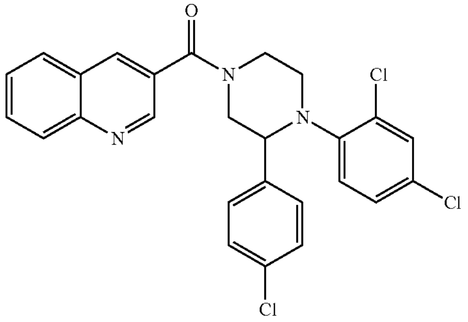 |
| 516 | 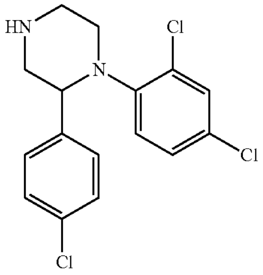 | 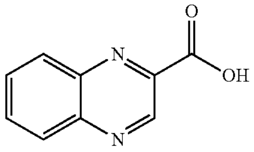 | 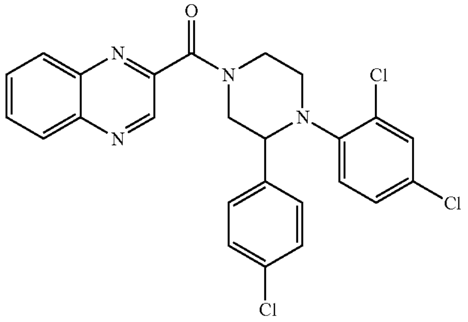 |

TABLE XVIII-continued
| Example # | Piperazine | Carboxylic Acid | Example Structure |
| --- | --- | --- | --- |
| 517 | 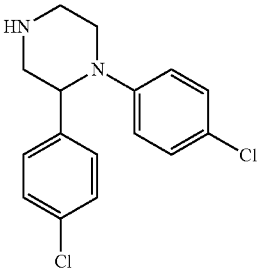 | 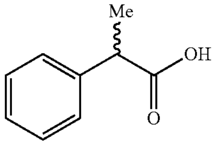 | 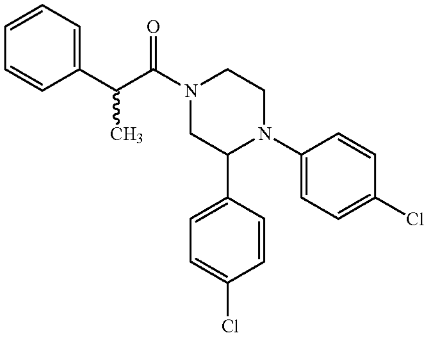 |
| 518 | 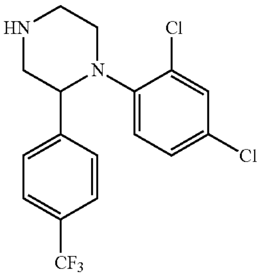 | 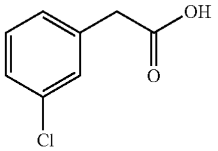 | 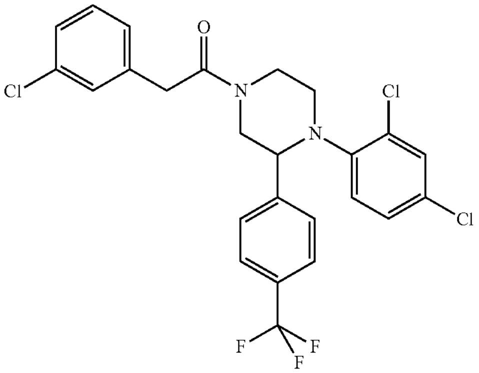 |
| 519 | 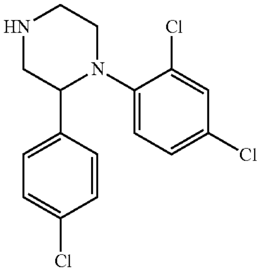 | 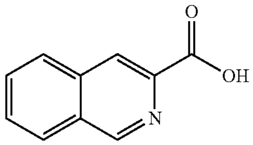 | 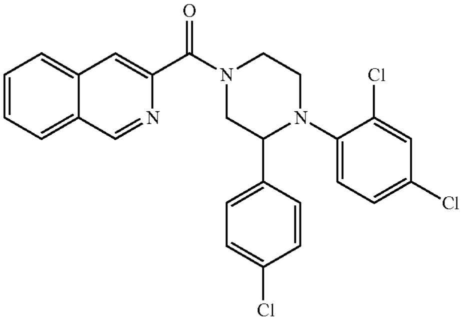 |
| 520 | 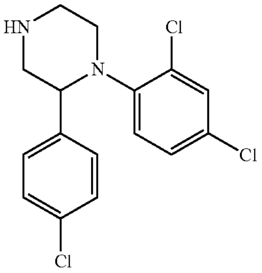 | 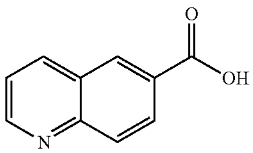 | 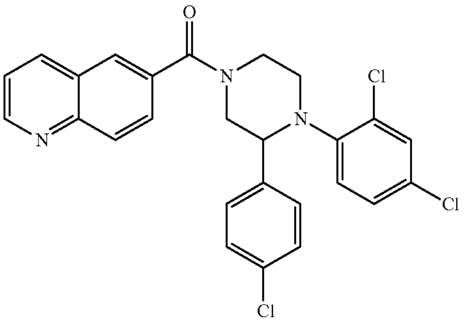 |

TABLE XVIII-continued
| Example # | Piperazine | Carboxylic Acid | Example Structure |
| --- | --- | --- | --- |
| 521 | 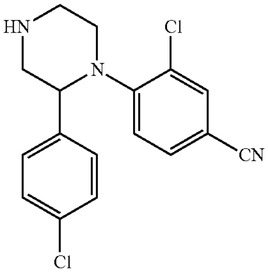 | 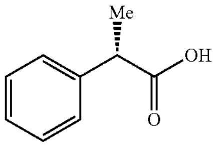 | 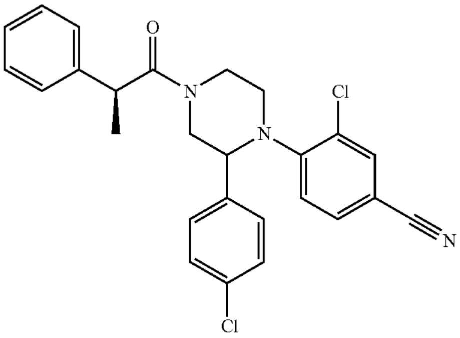 |
| 522 | 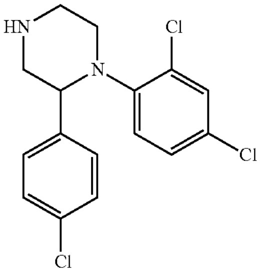 | 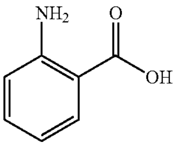 | 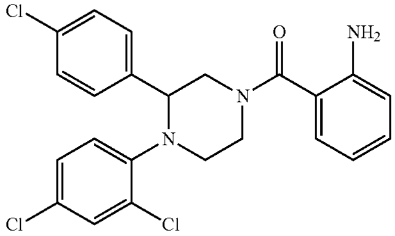 |
| 523 | 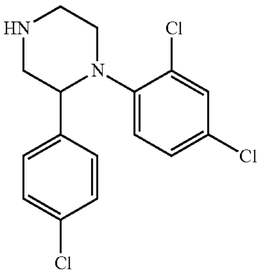 | 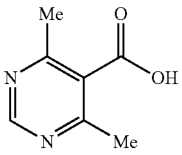 | 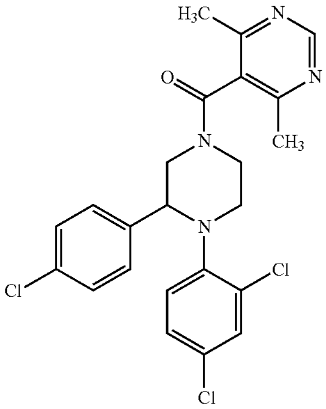 |
| 524 | 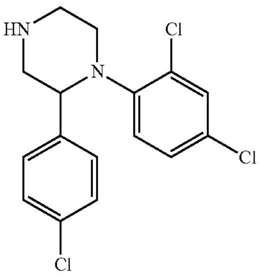 | 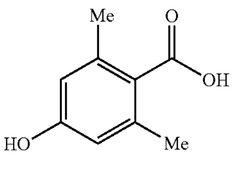 | 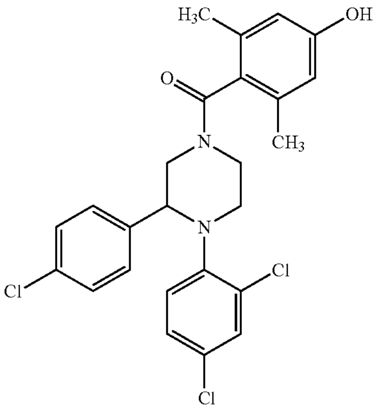 |

TABLE XVIII-continued
| Example # | Piperazine | Carboxylic Acid | Example Structure |
| --- | --- | --- | --- |
| 525 | 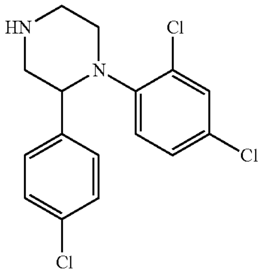 | 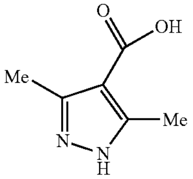 | 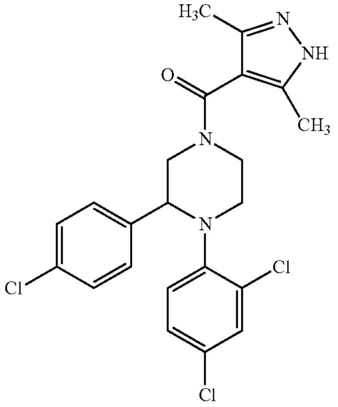 |
| 526 | 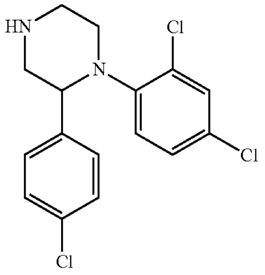 | 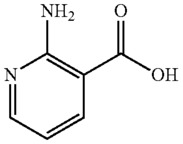 | 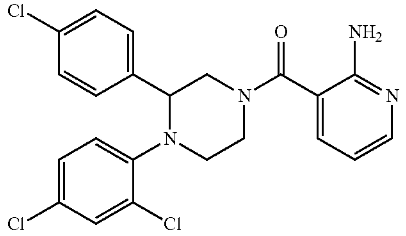 |
| 527 | 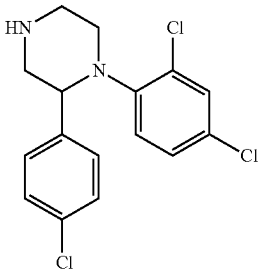 | 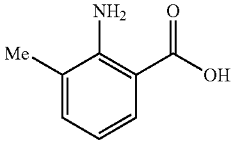 | 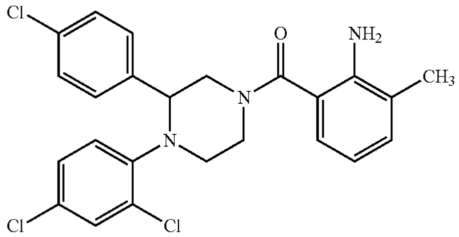 |
| 528 | 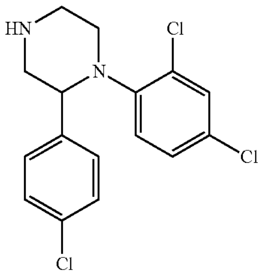 | 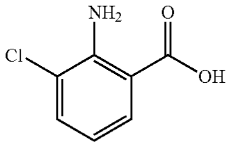 | 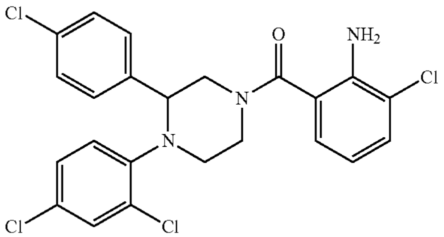 |
| 529 | 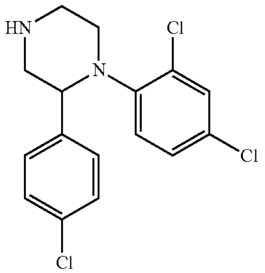 | 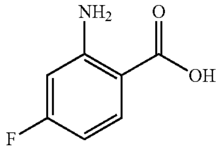 | 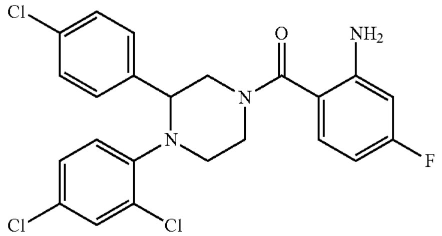 |

TABLE XVIII-continued
| Example # | Piperazine | Carboxylic Acid | Example Structure |
|---|---|---|---|
| 530 | 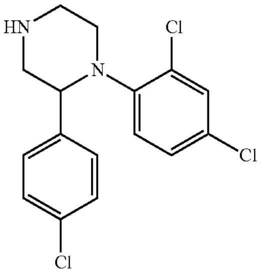 | 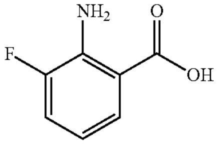 | 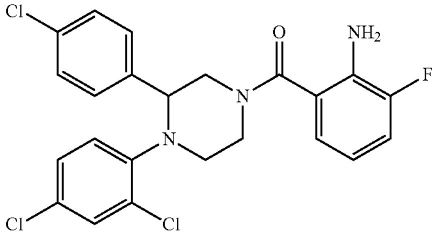 |
Preparation of Examples 531-570
Examples 531-570 were prepared by the reaction of the appropriate piperazine (e.g., Examples 304 or 426) and carboxylic acid shown in Table XIX, below (e.g., by the method of Scheme 17)
TABLE XIX
| Example # | Piperazine | Carboxylic Acid | Example Structure |
|---|---|---|---|
| 531 | 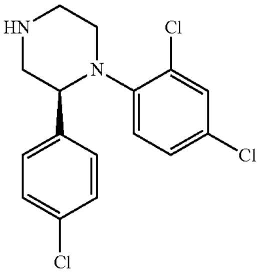 | 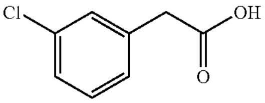 | 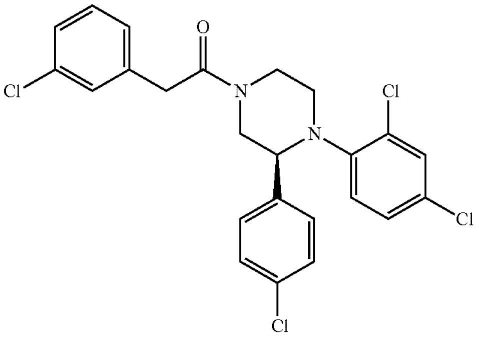 |
| 532 | 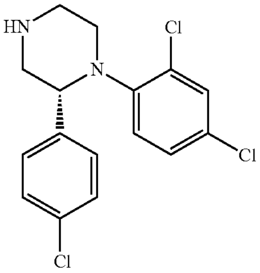 | 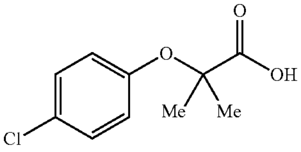 | 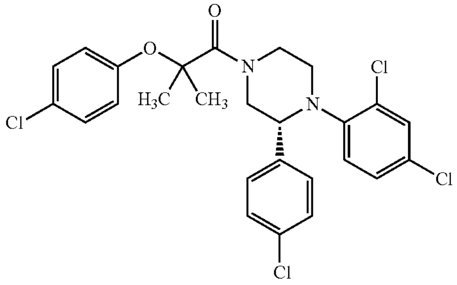 |

TABLE XIX-continued
| Example # | Piperazine | Carboxylic Acid | Example Structure |
|---|---|---|---|
| 533 | 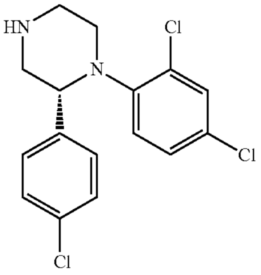 | 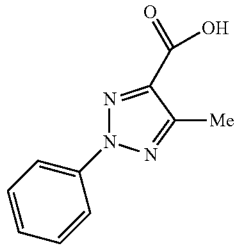 | 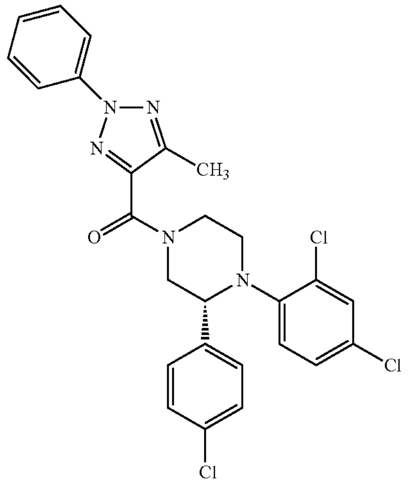 |
| 534 | 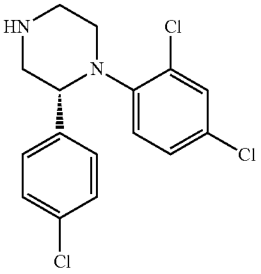 | 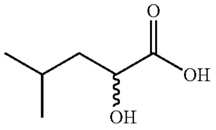 | 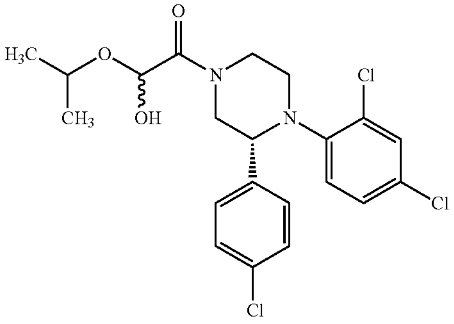 |
| 535 | 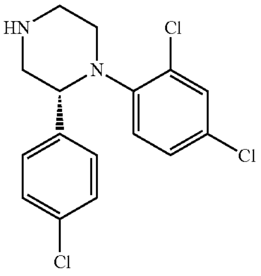 | 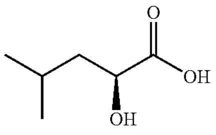 | 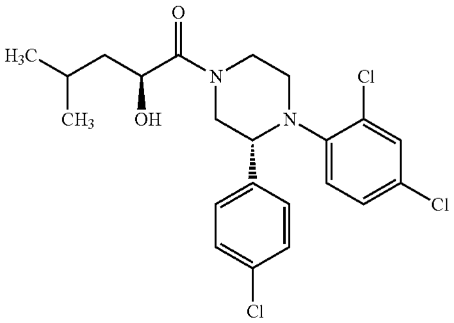 |
| 536 | 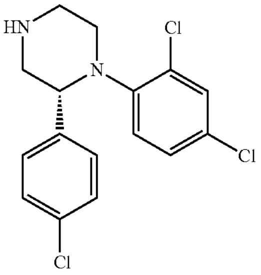 | 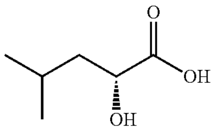 | 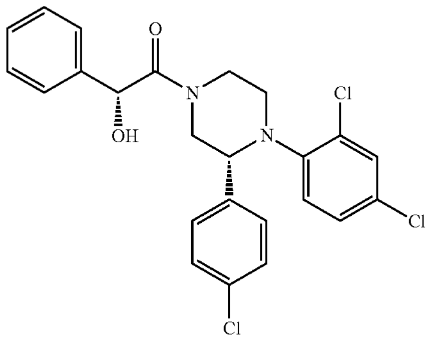 |

TABLE XIX-continued
| Example # | Piperazine | Carboxylic Acid | Example Structure |
|---|---|---|---|
| 537 | 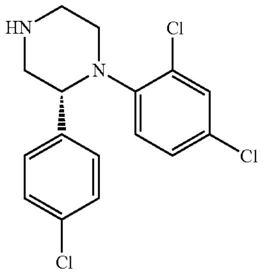 | 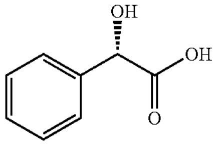 | 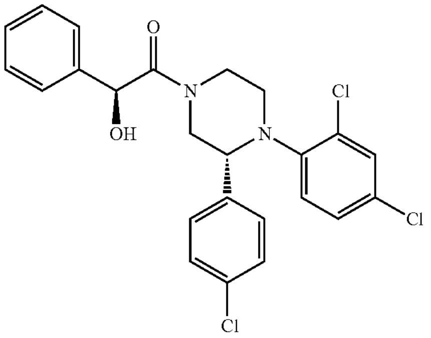 |
| 538 | 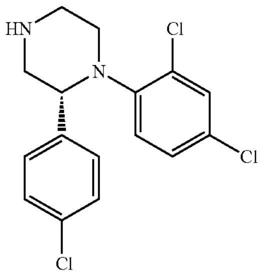 | 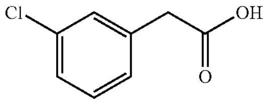 | 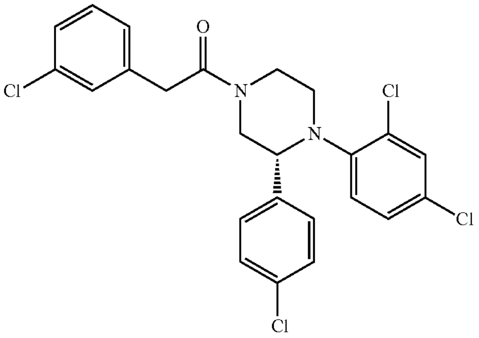 |
| 539 | 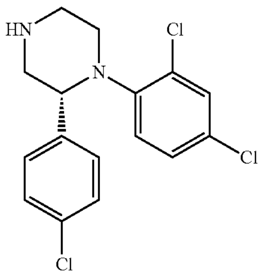 | 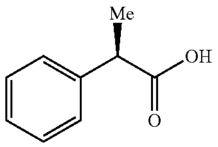 | 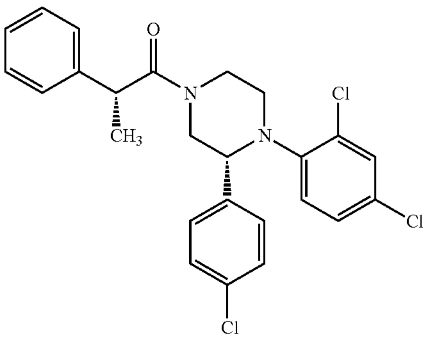 |
| 540 | 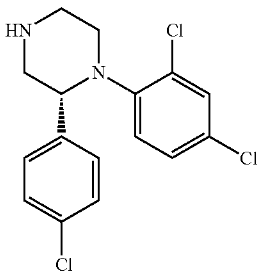 | 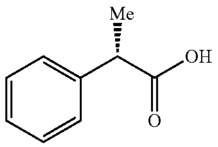 | 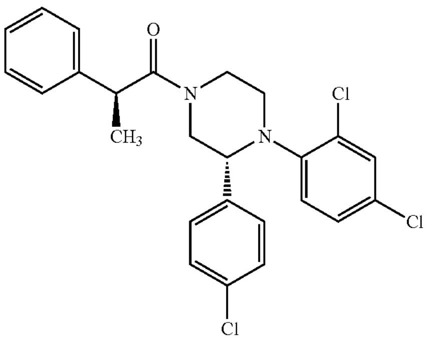 |

TABLE XIX-continued
| Example # | Piperazine | Carboxylic Acid | Example Structure |
| --- | --- | --- | --- |
| 541 | 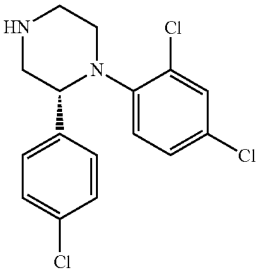 | 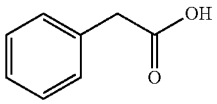 | 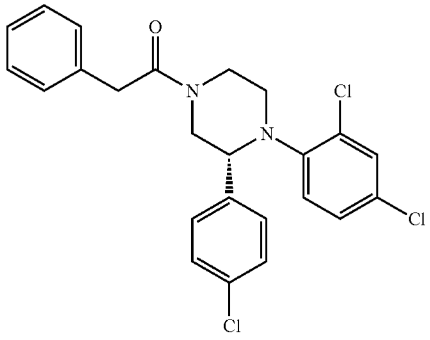 |
| 542 | 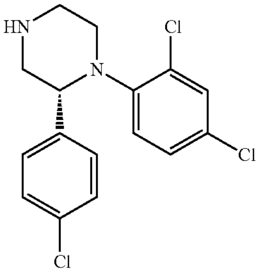 | 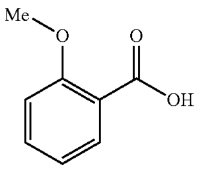 | 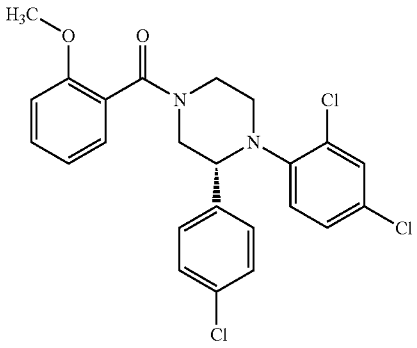 |
| 543 | 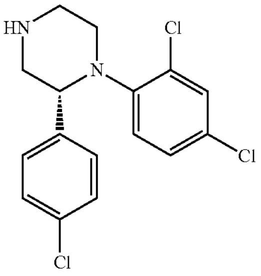 | 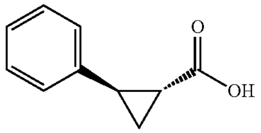 | 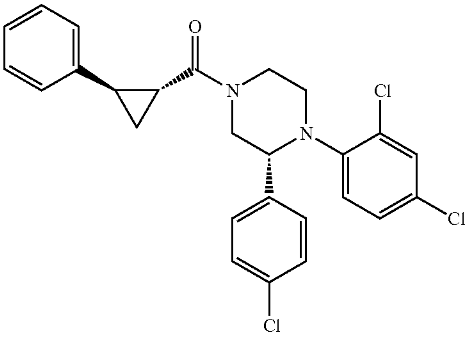 |
| 544 | 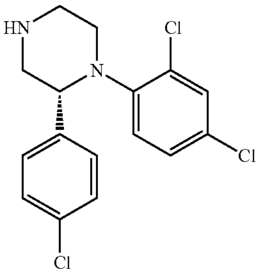 | 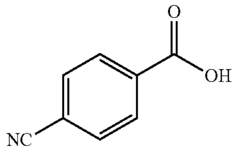 | 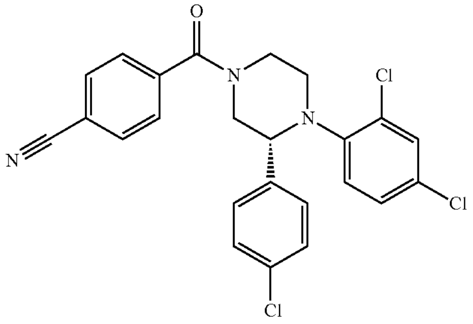 |

TABLE XIX-continued
| Example # | Piperazine | Carboxylic Acid | Example Structure |
| --- | --- | --- | --- |
| 545 | 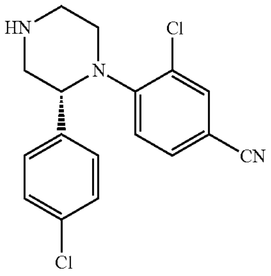 | 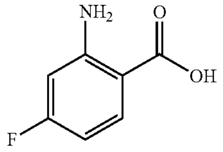 | 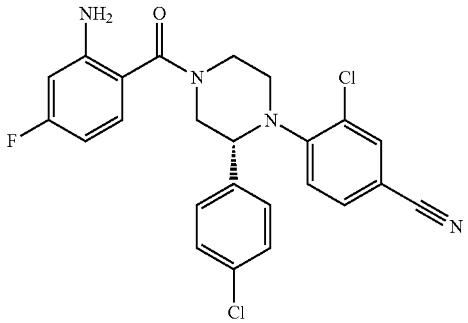 |
| 546 | 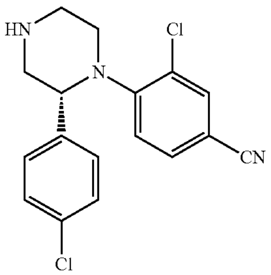 | 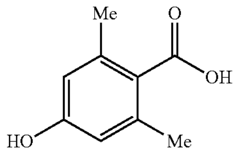 | 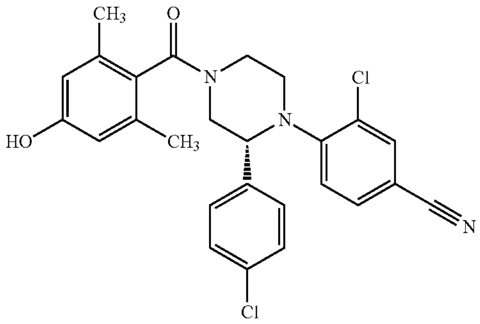 |
| 547 | 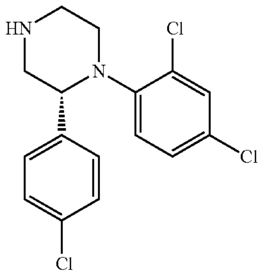 | 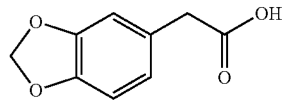 | 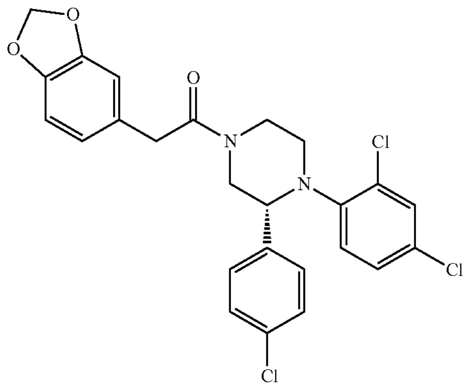 |
| 548 | 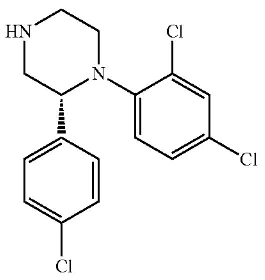 | 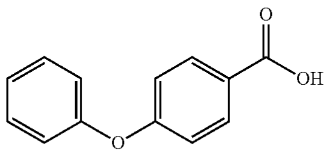 | 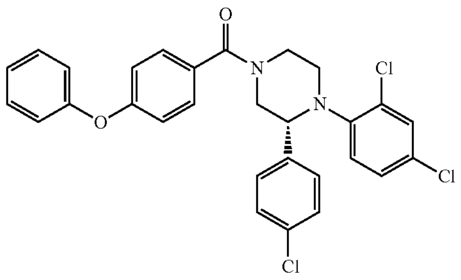 |

TABLE XIX-continued
| Example # | Piperazine | Carboxylic Acid | Example Structure |
| --- | --- | --- | --- |
| 549 | 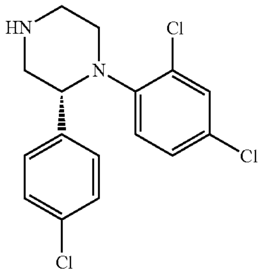 | 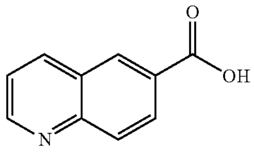 | 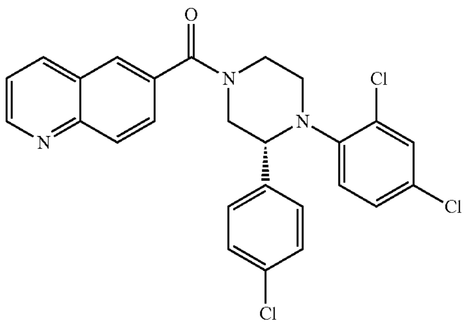 |
| 550 | 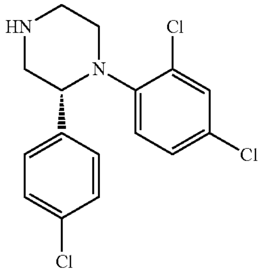 | 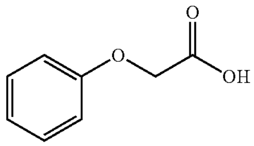 | 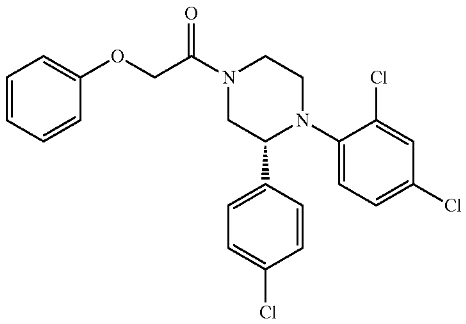 |
| 551 | 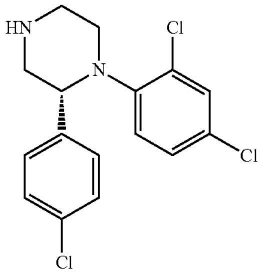 | 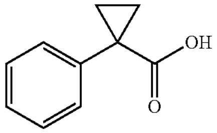 | 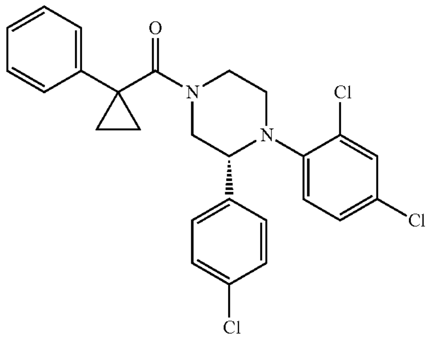 |
| 552 | 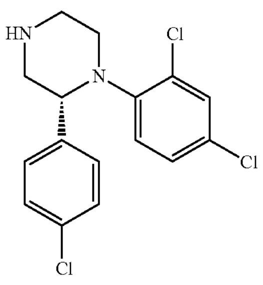 | 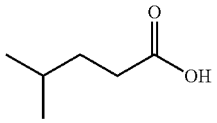 | 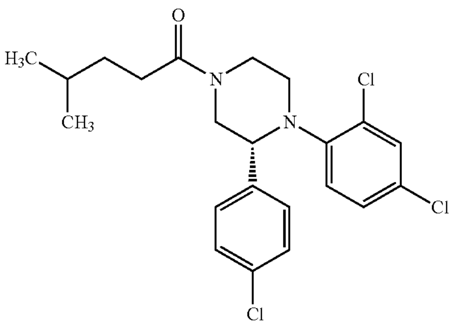 |

TABLE XIX-continued
| Example # | Piperazine | Carboxylic Acid | Example Structure |
|---|---|---|---|
| 553 | 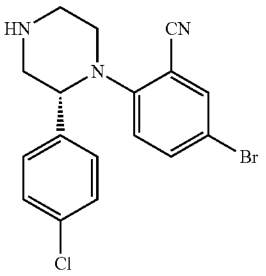 | 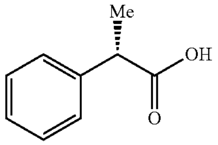 | 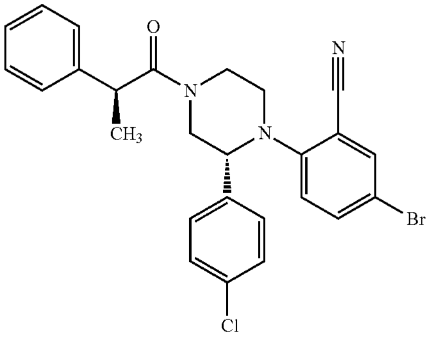 |
| 554 | 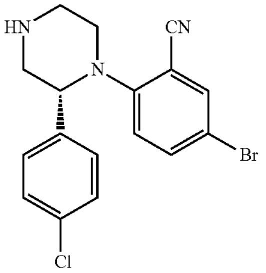 | 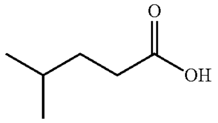 | 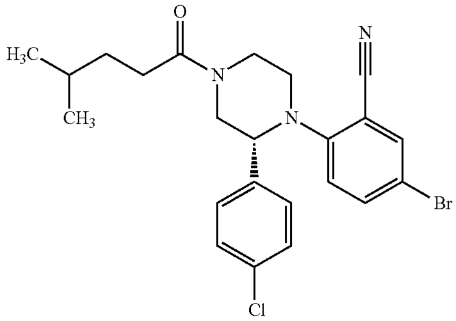 |
| 555 | 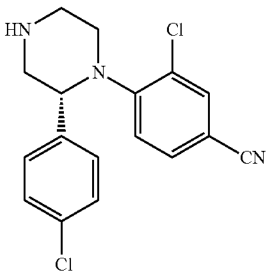 | 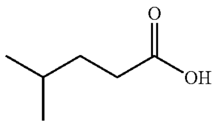 | 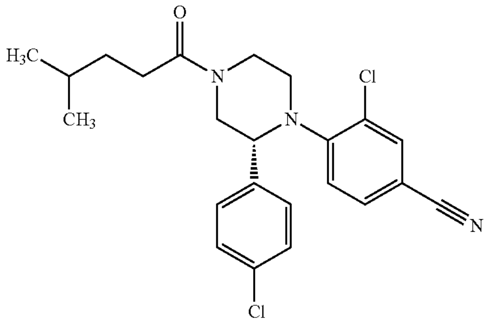 |
| 556 | 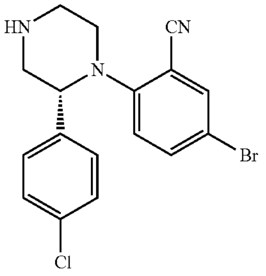 | 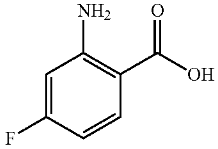 | 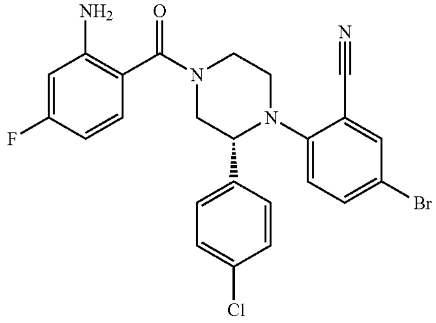 |

TABLE XIX-continued
| Example # | Piperazine | Carboxylic Acid | Example Structure |
|---|---|---|---|
| 557 | 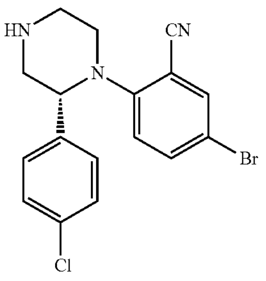 | 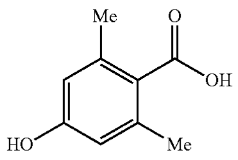 | 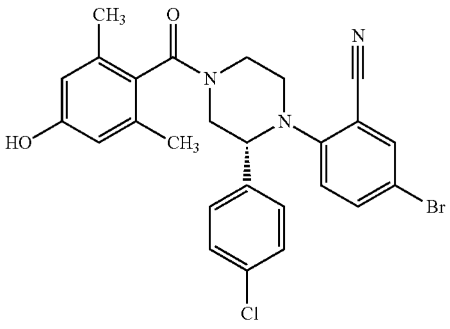 |
| 558 | 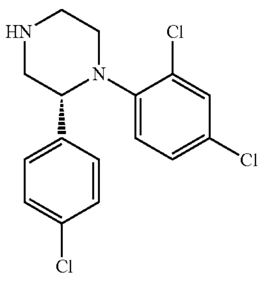 | 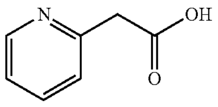 | 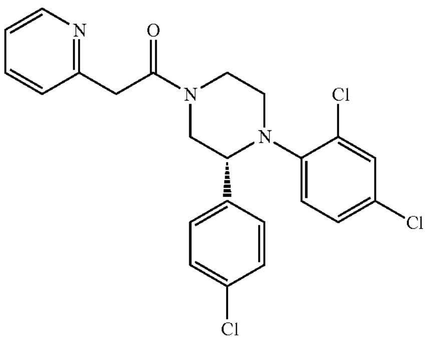 |
| 559 | 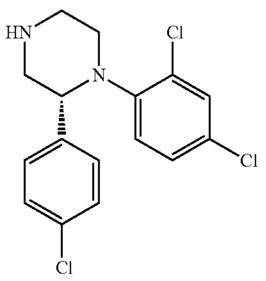 | 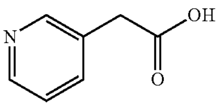 | 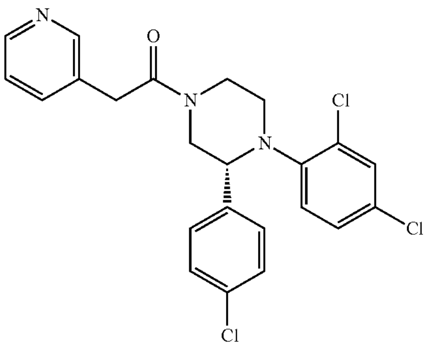 |
| 560 | 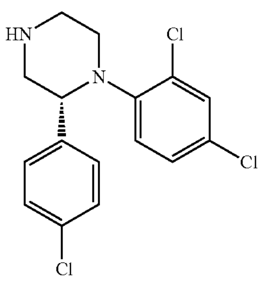 | 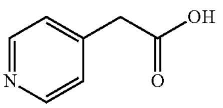 | 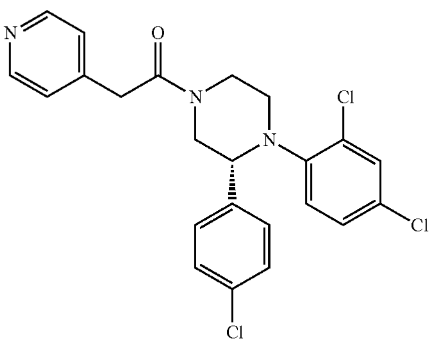 |

TABLE XIX-continued
| Example # | Piperazine | Carboxylic Acid | Example Structure |
|---|---|---|---|
| 561 | 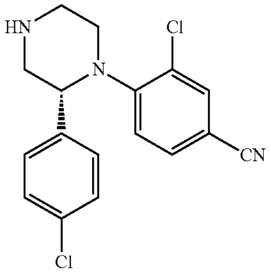 | 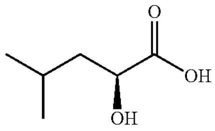 | 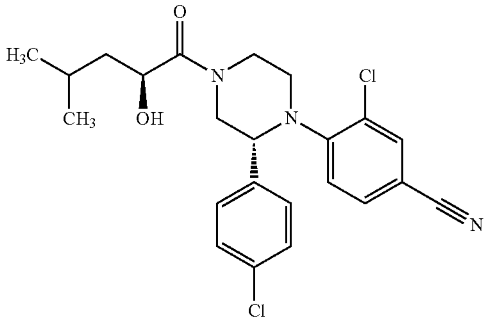 |
| 562 | 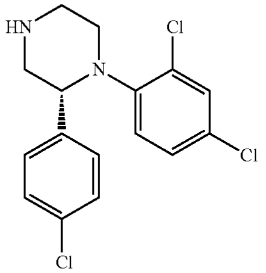 | 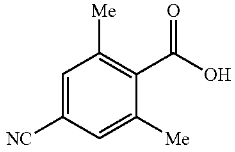 | 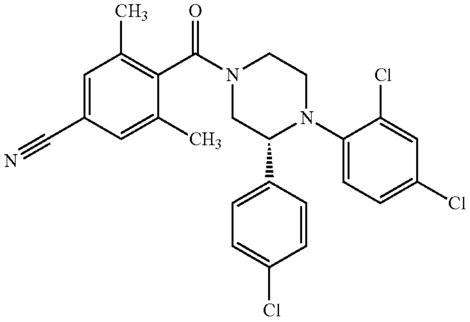 |
| 563 | 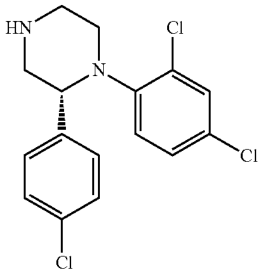 | 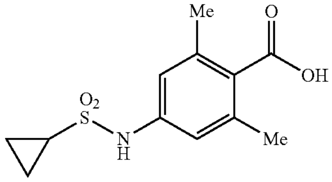 | 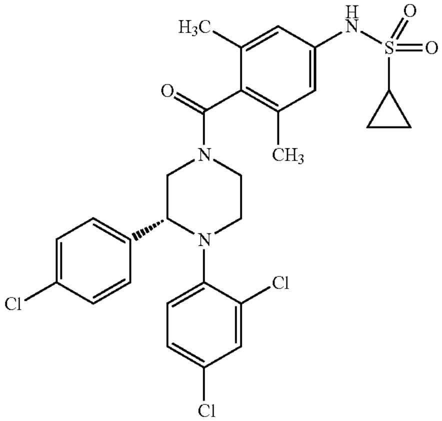 |
| 564 | 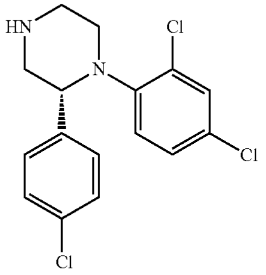 | 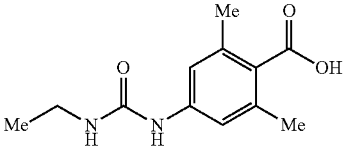 | 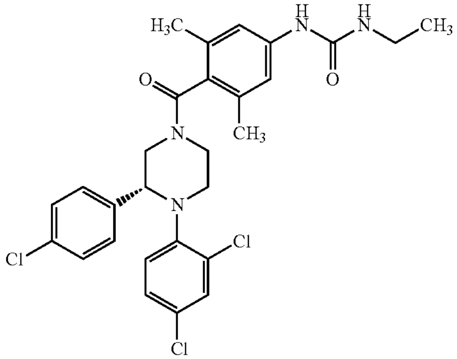 |

TABLE XIX-continued
| Example # | Piperazine | Carboxylic Acid | Example Structure |
|---|---|---|---|
| 565 | 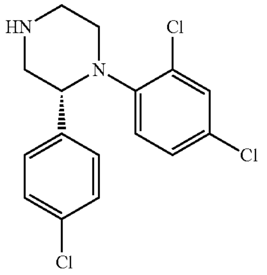 | 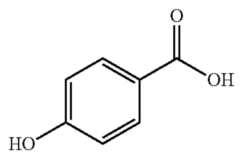 | 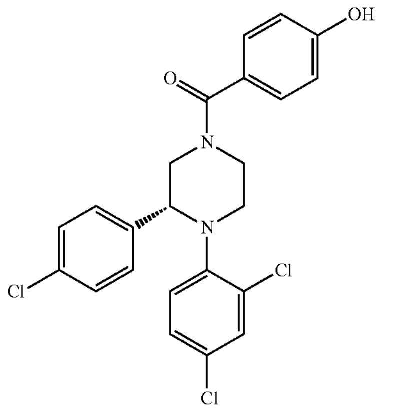 |
| 566 | 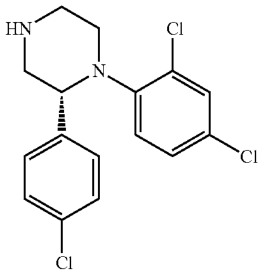 | 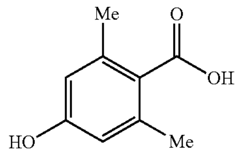 | 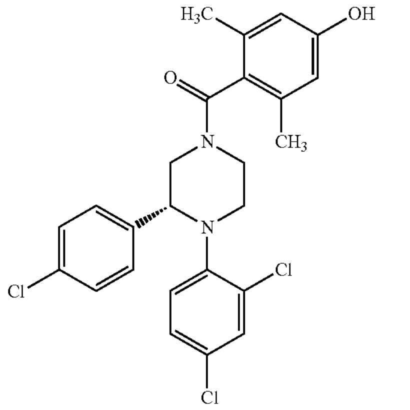 |
| 567 | 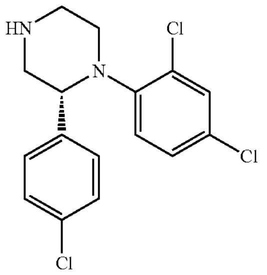 | 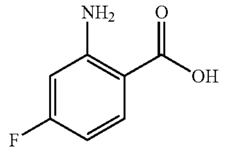 | 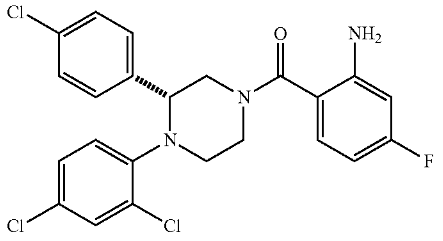 |
| 568 | 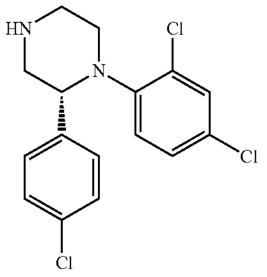 | 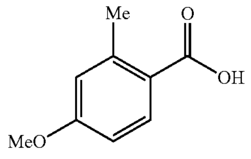 | 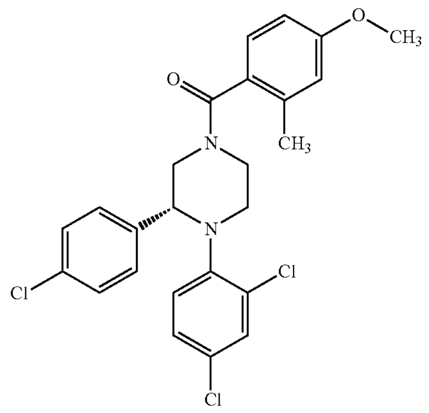 |

TABLE XIX-continued

| Example # | Piperazine | Carboxylic Acid | Example Structure |
|---|---|---|---|
| 569 | 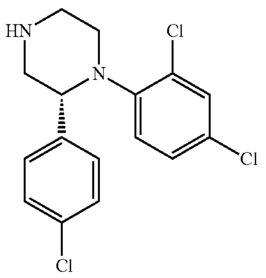 | 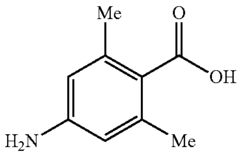 | 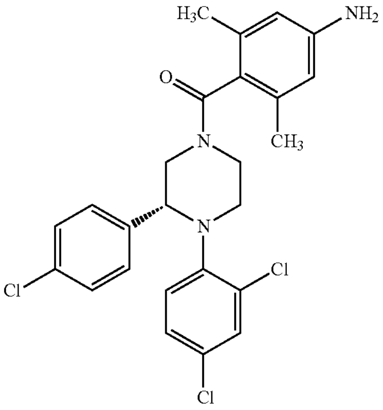 |
| 570 | 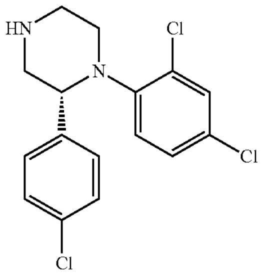 | 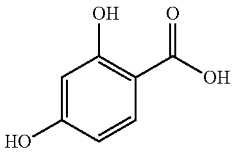 | 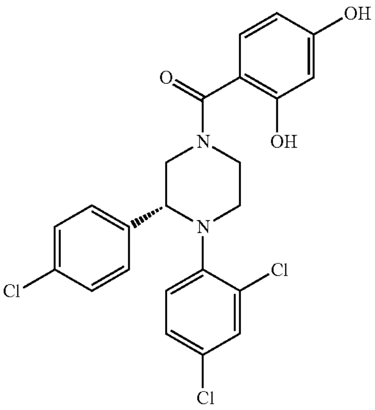 |

Preparation of Example 571

Example 571

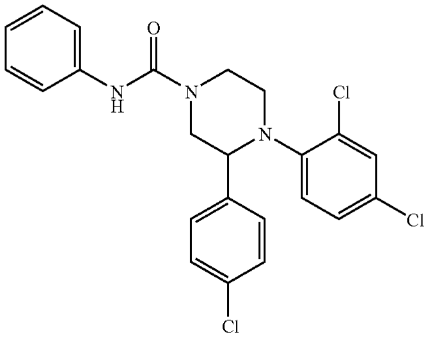

Example 571 was prepared by the reaction of phenyl isocyanate with Example 1 using procedures similar to those used to prepare Examples 7, Scheme 1.

Preparation of Examples 572-685

Examples 572-685 were prepared by the reaction of piperazine Example 1 and the carboxylic acid shown in Table XX, using the procedure of Scheme 5.

TABLE XX
| Example # | Carboxylic Acid | Example Structure |
|---|---|---|
| 572 | 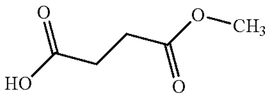 | 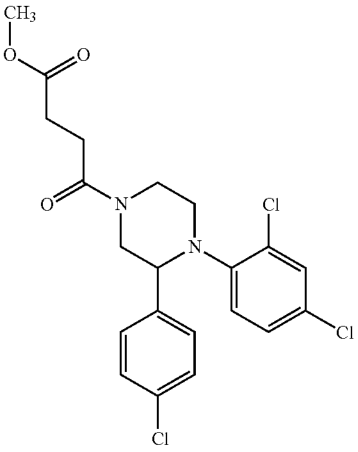 |
| 573 | 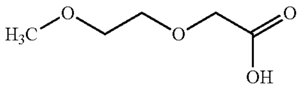 | 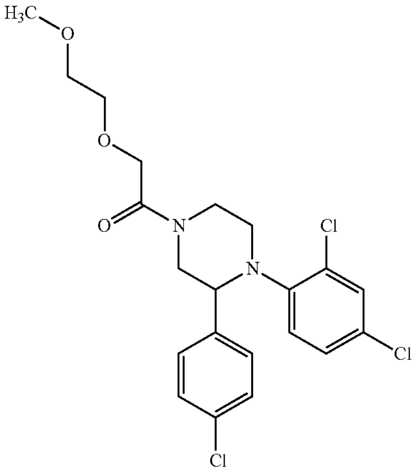 |
| 574 | 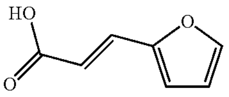 | 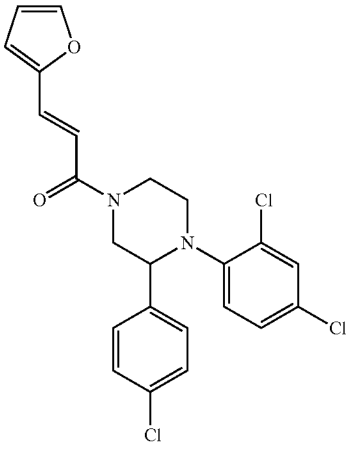 |

TABLE XX-continued
| Example # | Carboxylic Acid | Example Structure |
|---|---|---|
| 575 | 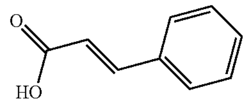 | 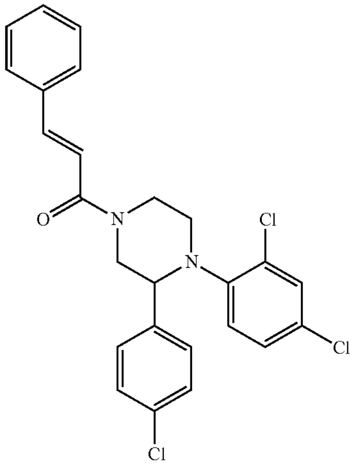 |
| 576 | 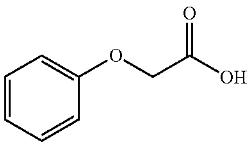 | 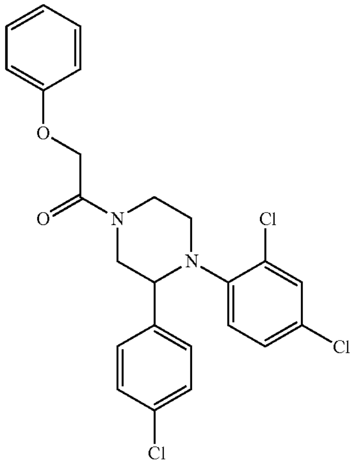 |
| 577 | 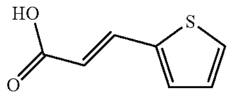 | 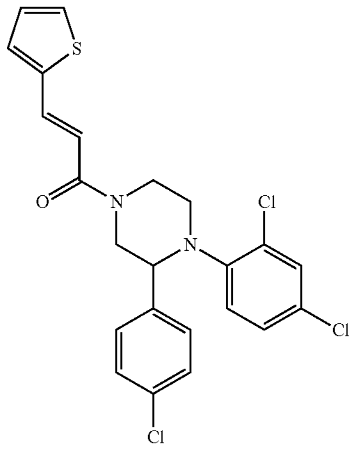 |

TABLE XX-continued
| Example # | Carboxylic Acid | Example Structure |
| --- | --- | --- |
| 578 | 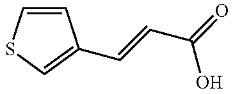 | 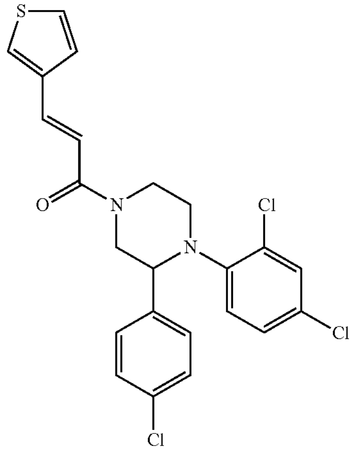 |
| 579 | 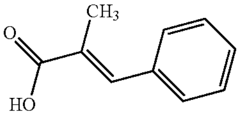 | 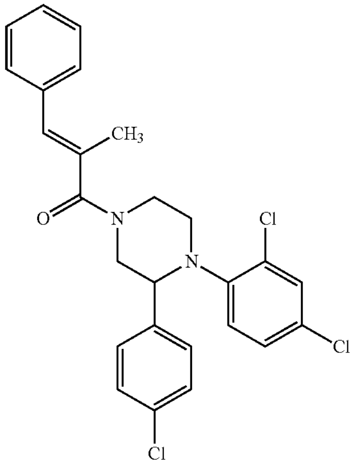 |
| 580 | 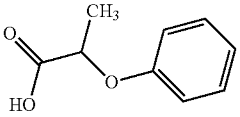 | 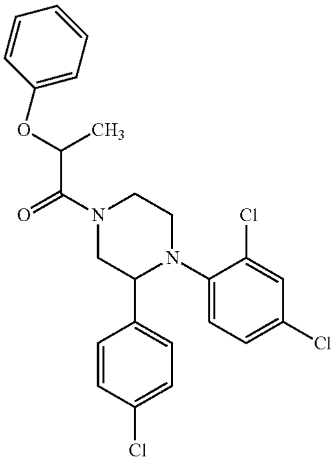 |

TABLE XX-continued
| Example # | Carboxylic Acid | Example Structure |
|---|---|---|
| 581 | 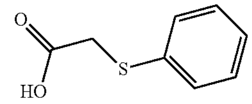 | 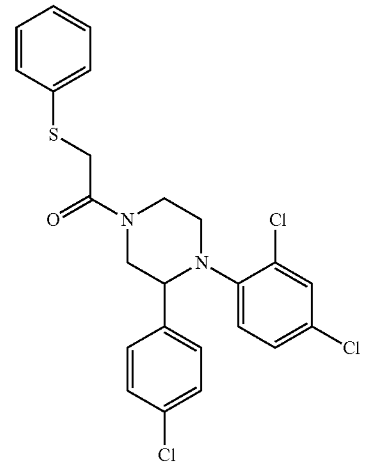 |
| 582 | 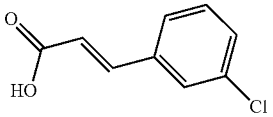 | 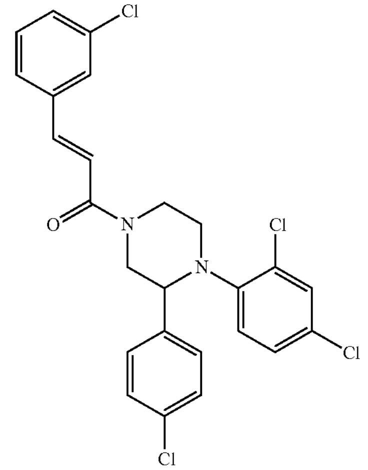 |
| 583 | 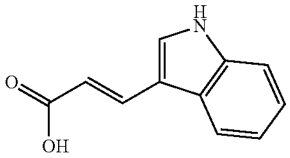 | 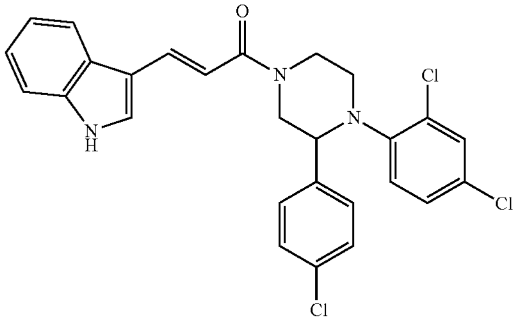 |
| 584 | 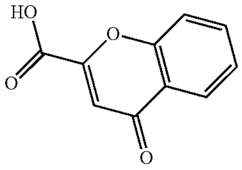 | 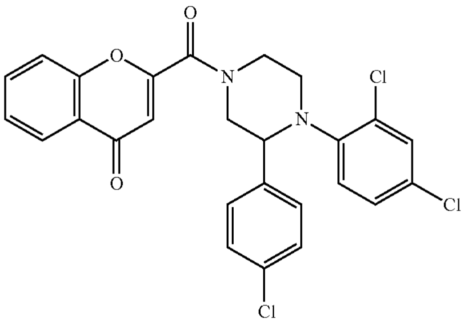 |

TABLE XX-continued
| Example # | Carboxylic Acid | Example Structure |
|---|---|---|
| 585 | 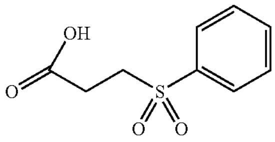 | 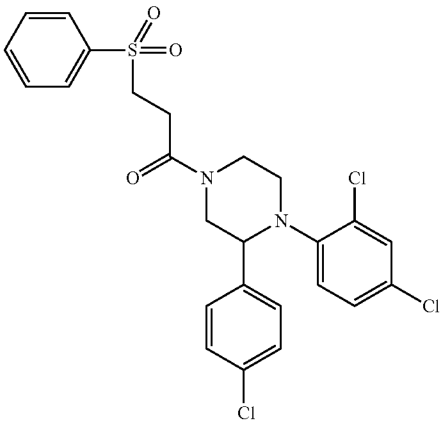 |
| 586 | 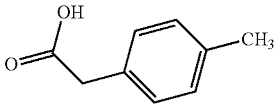 | 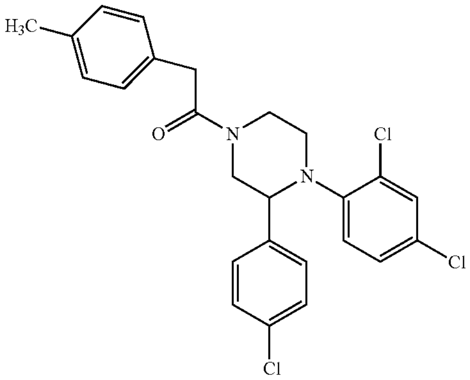 |
| 587 | 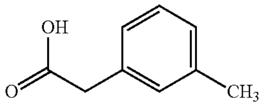 | 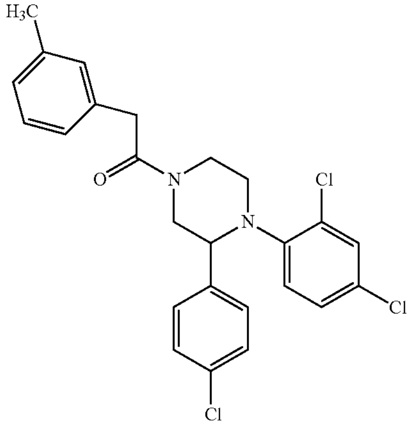 |

TABLE XX-continued
| Example # | Carboxylic Acid | Example Structure |
|---|---|---|
| 588 | 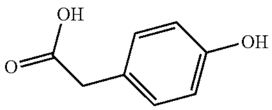 | 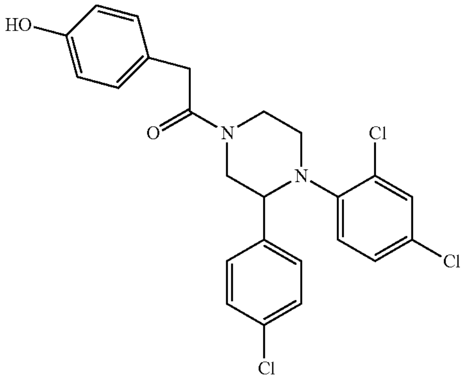 |
| 589 | 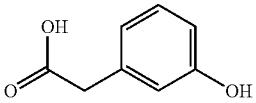 | 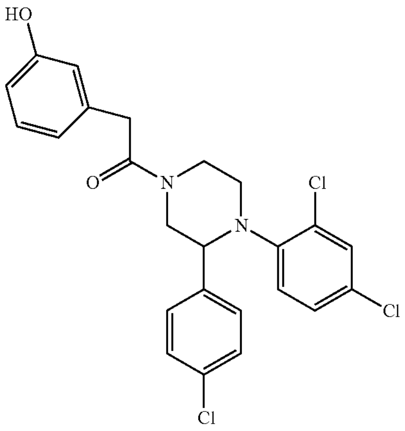 |
| 590 | 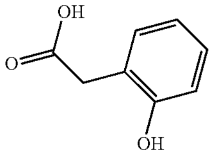 | 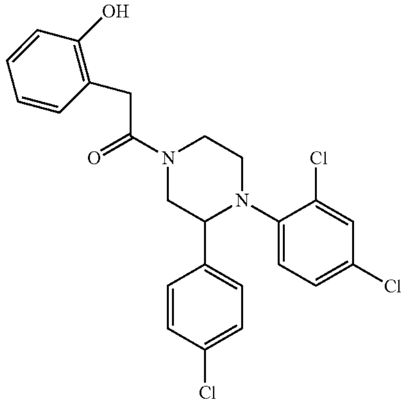 |

TABLE XX-continued
| Example # | Carboxylic Acid | Example Structure |
| --- | --- | --- |
| 591 | 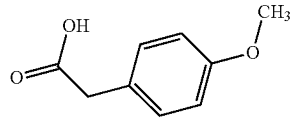 | 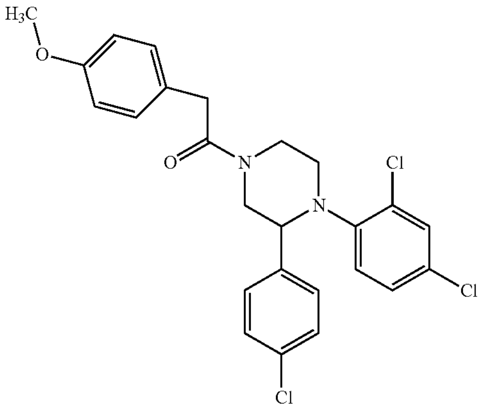 |
| 592 | 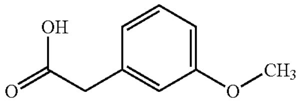 | 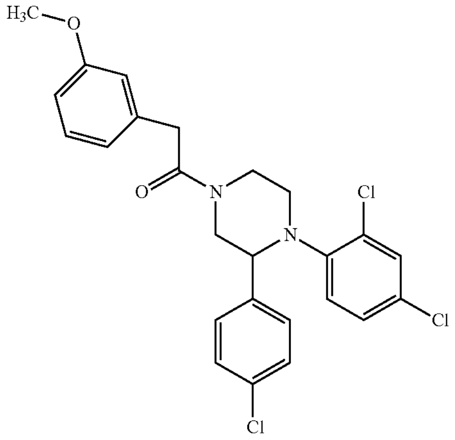 |
| 593 | 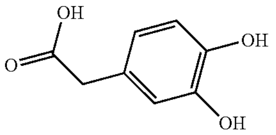 | 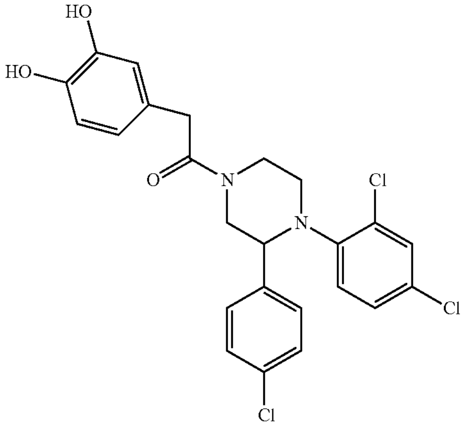 |

TABLE XX-continued
| Example # | Carboxylic Acid | Example Structure |
| --- | --- | --- |
| 594 | 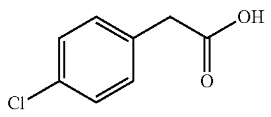 | 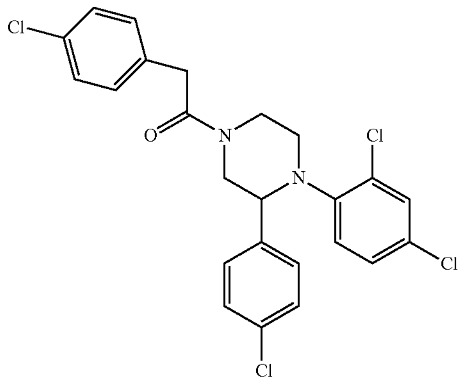 |
| 595 | 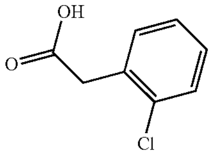 | 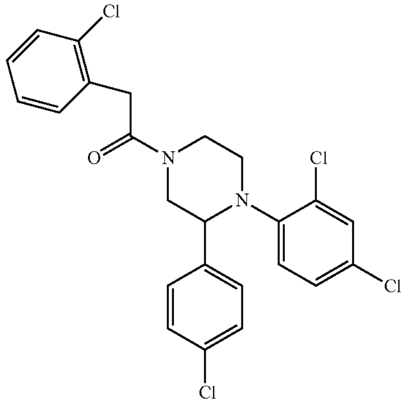 |
| 596 | 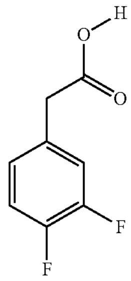 | 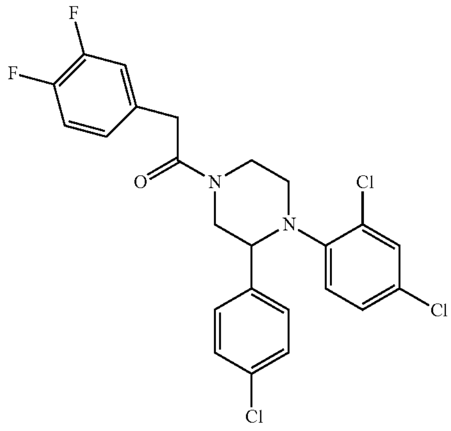 |

TABLE XX-continued
| Example # | Carboxylic Acid | Example Structure |
|---|---|---|
| 597 | 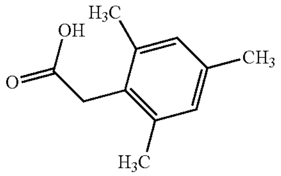 | 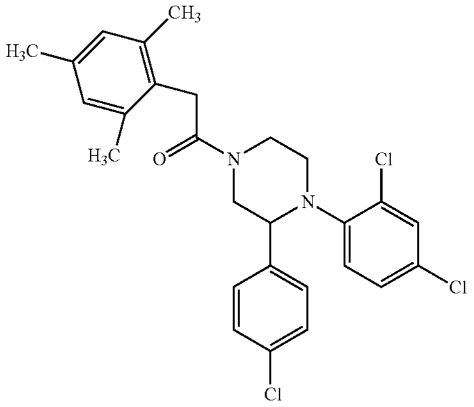 |
| 598 | 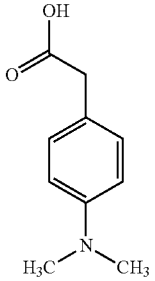 | 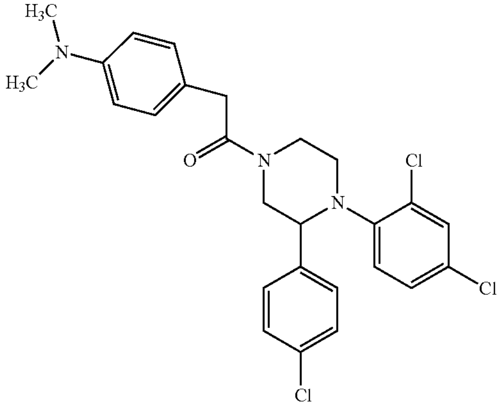 |
| 599 | 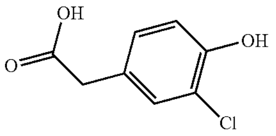 | 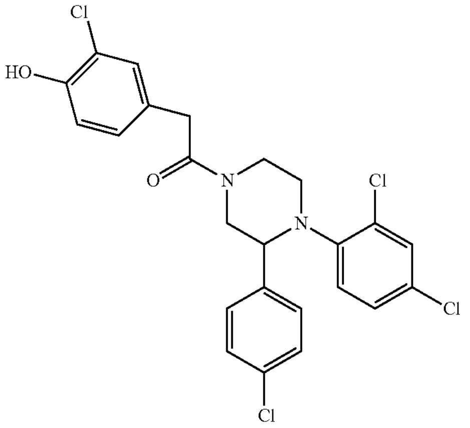 |

TABLE XX-continued
| Example # | Carboxylic Acid | Example Structure |
|---|---|---|
| 600 | 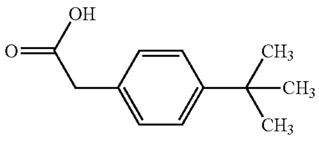 | 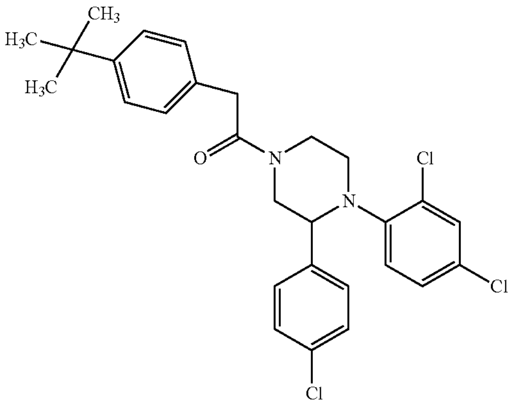 |
| 601 | 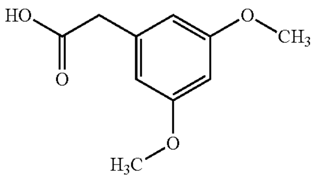 | 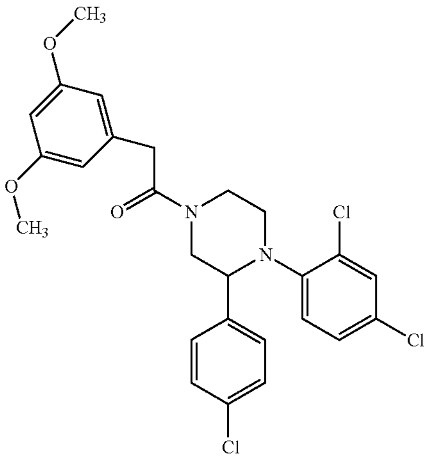 |
| 602 | 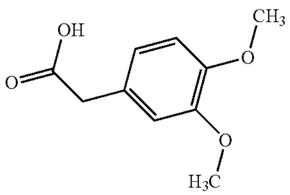 | 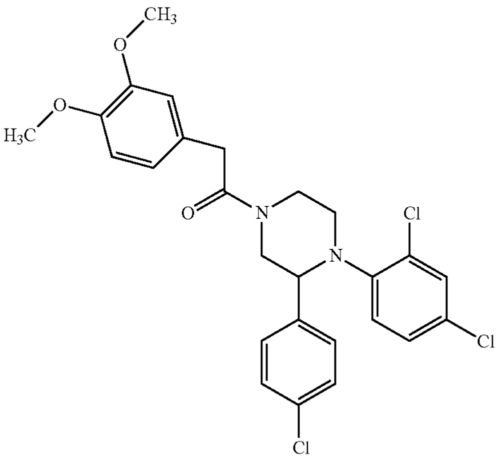 |

TABLE XX-continued
| Example # | Carboxylic Acid | Example Structure |
|---|---|---|
| 603 | 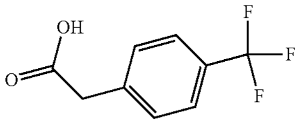 | 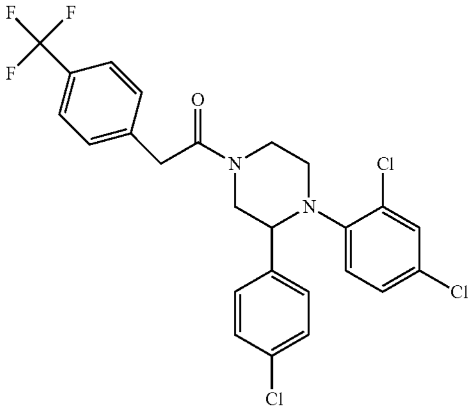 |
| 604 | 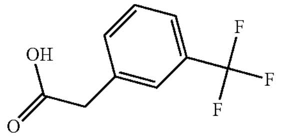 | 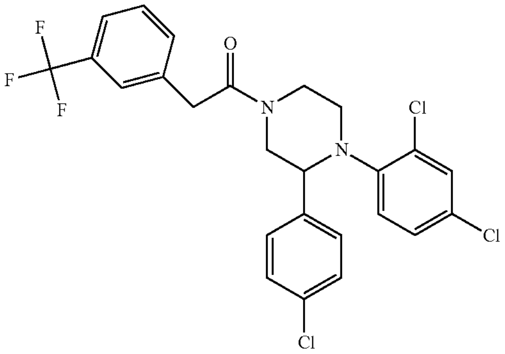 |
| 605 | 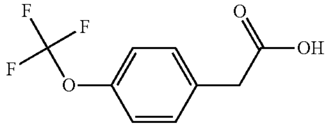 | 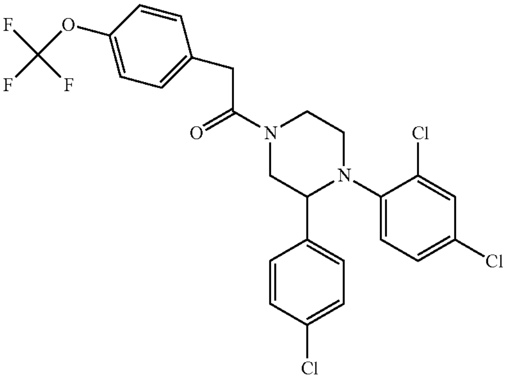 |

TABLE XX-continued
| Example # | Carboxylic Acid | Example Structure |
|---|---|---|
| 606 | 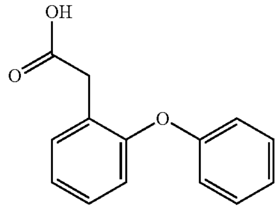 | 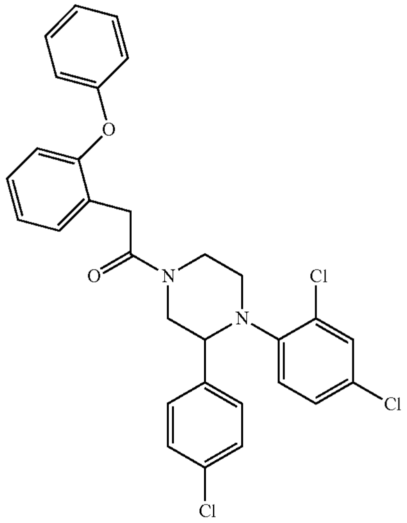 |
| 607 | 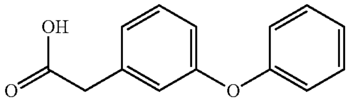 | 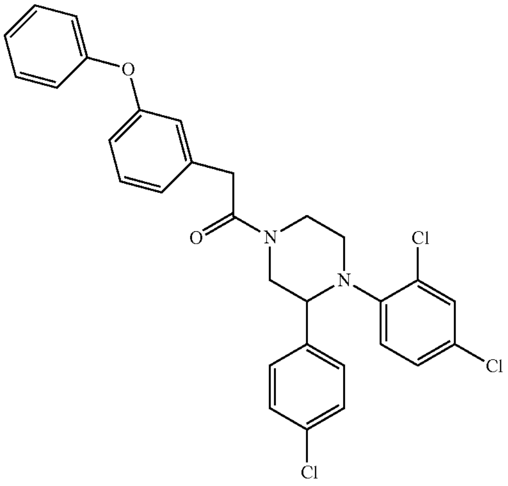 |
| 608 | 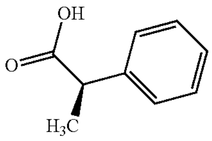 | 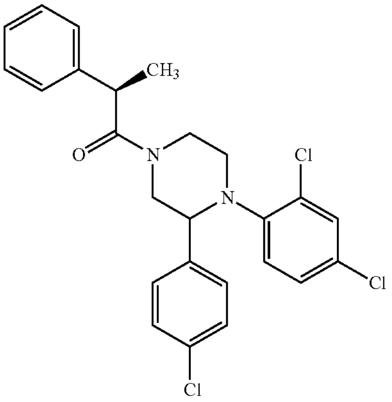 |

TABLE XX-continued
| Example # | Carboxylic Acid | Example Structure |
|---|---|---|
| 609 | 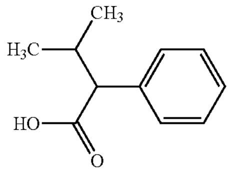 | 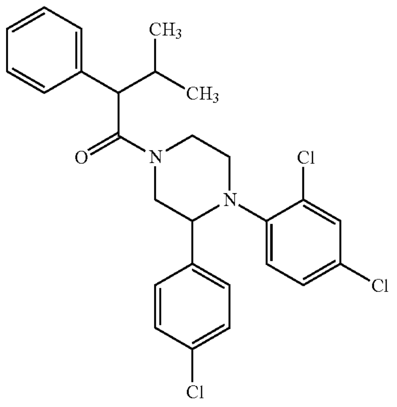 |
| 610 | 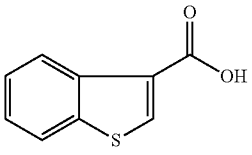 | 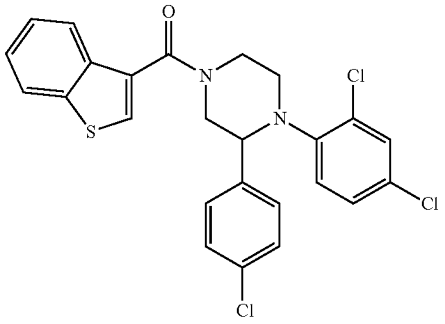 |
| 611 | 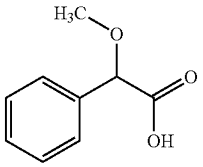 | 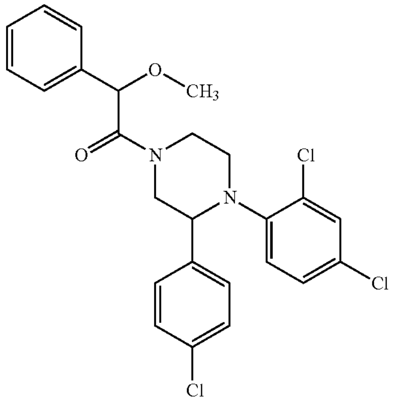 |
| 612 | 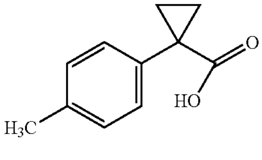 | 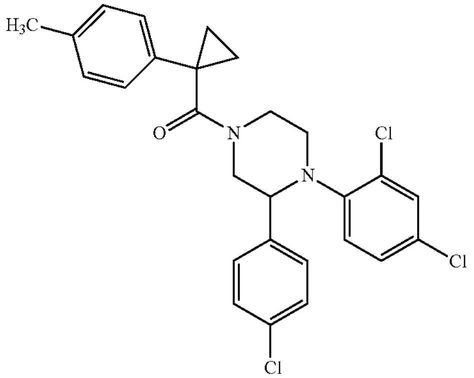 |

TABLE XX-continued
| Example # | Carboxylic Acid | Example Structure |
| --- | --- | --- |
| 613 | 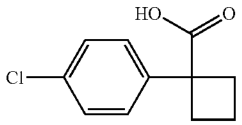 | 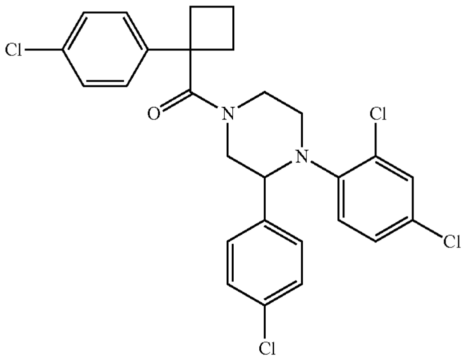 |
| 614 | 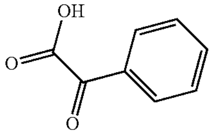 | 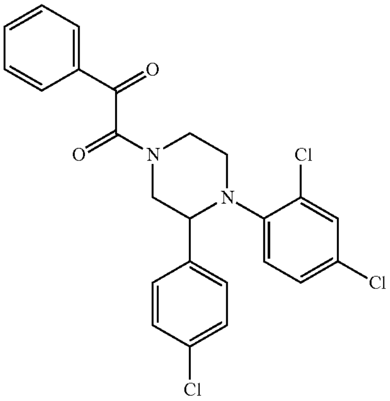 |
| 615 | 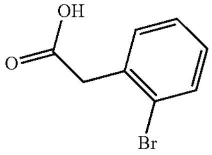 | 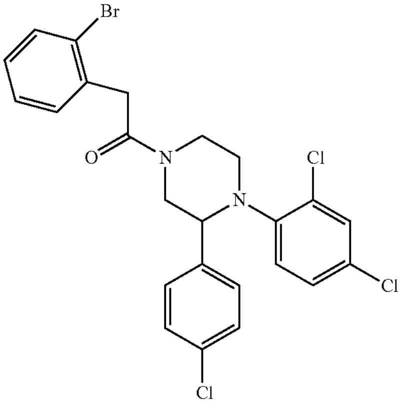 |
| 616 | 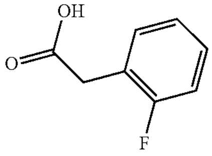 | 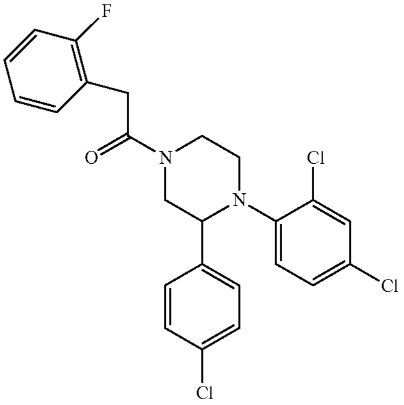 |

TABLE XX-continued
| Example # | Carboxylic Acid | Example Structure |
|---|---|---|
| 617 | 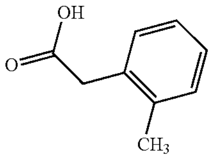 | 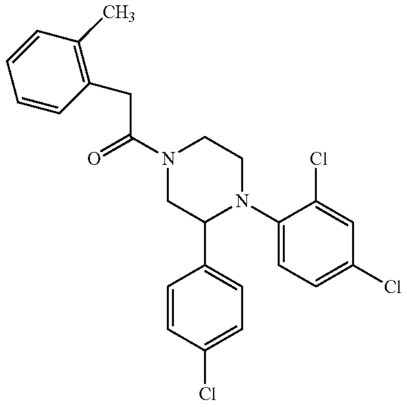 |
| 618 | 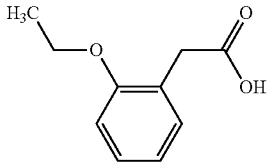 | 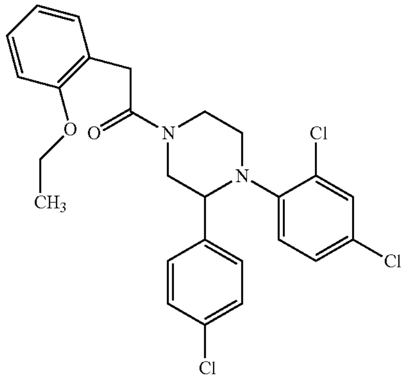 |
| 619 | 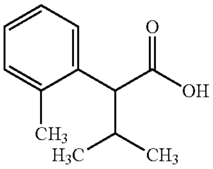 | 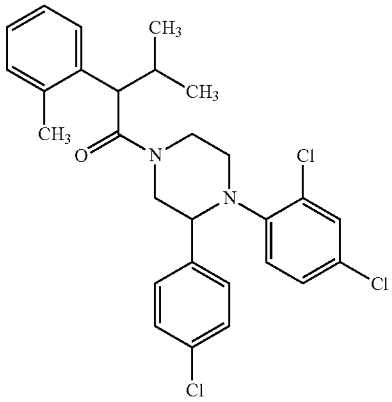 |

TABLE XX-continued
| Example # | Carboxylic Acid | Example Structure |
|---|---|---|
| 620 | 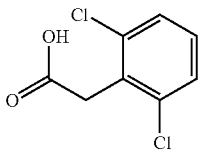 | 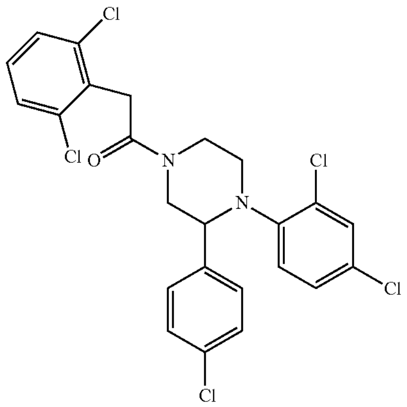 |
| 621 | 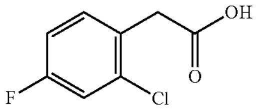 | 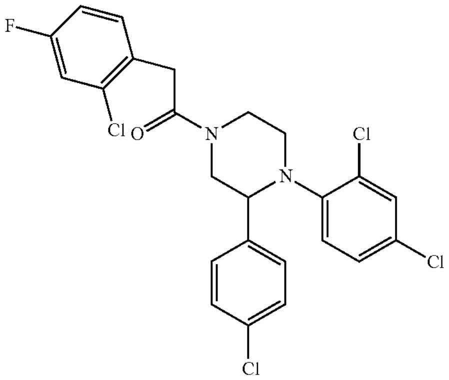 |
| 622 | 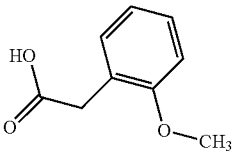 | 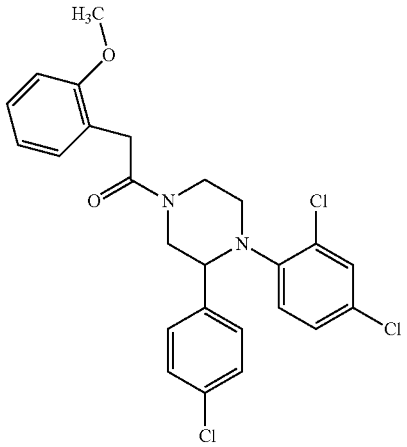 |

TABLE XX-continued
| Example # | Carboxylic Acid | Example Structure |
|---|---|---|
| 623 | 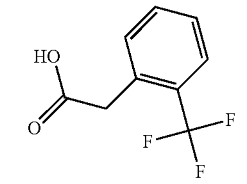 | 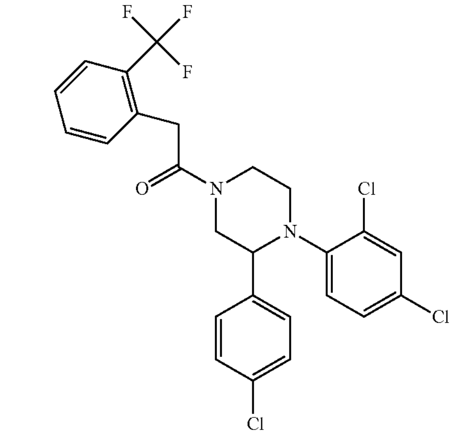 |
| 624 | 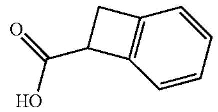 | 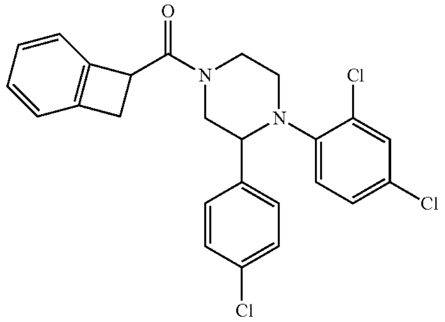 |
| 625 | 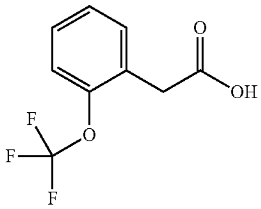 | 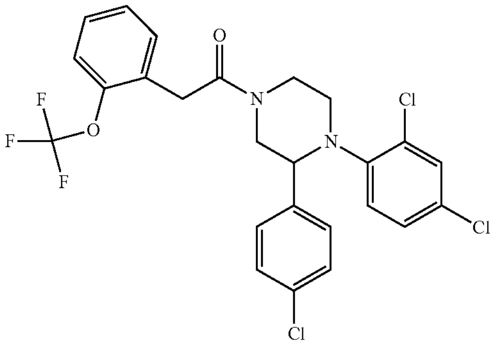 |
| 626 | 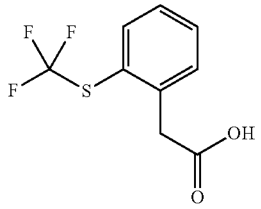 | 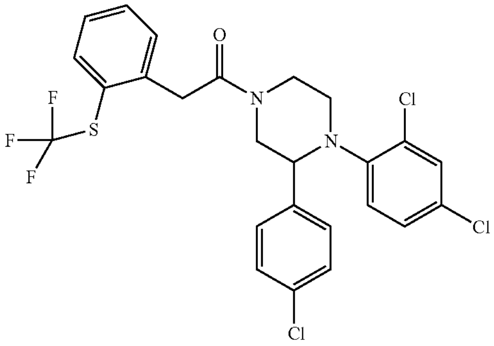 |

TABLE XX-continued
| Example # | Carboxylic Acid | Example Structure |
|---|---|---|
| 627 | 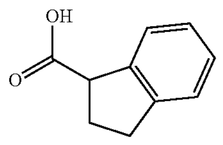 | 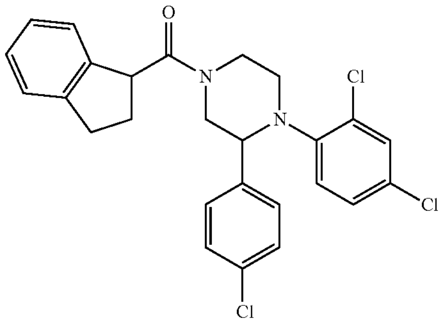 |
| 628 | 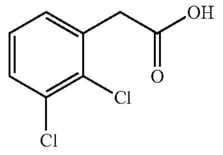 | 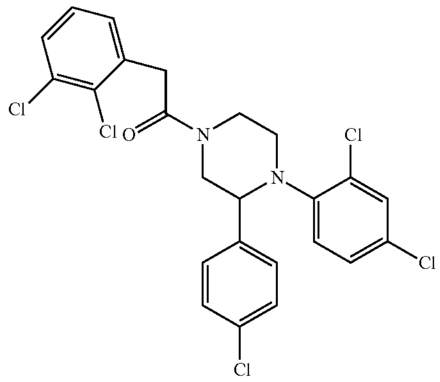 |
| 629 | 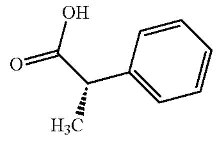 | 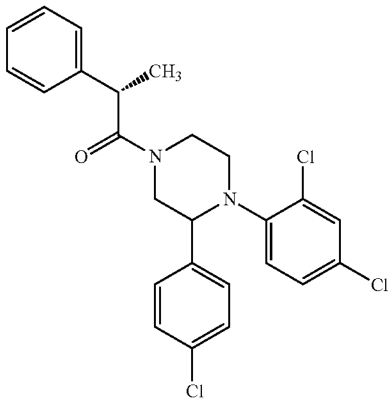 |
| 630 | 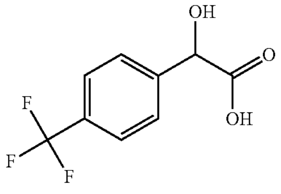 | 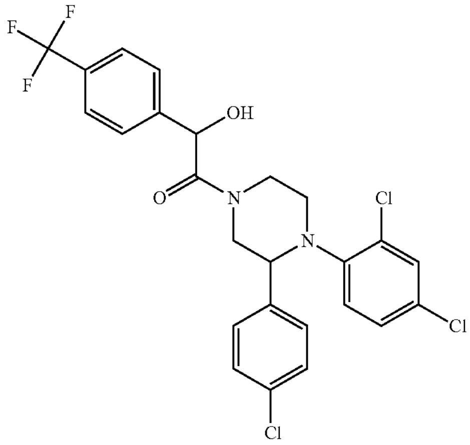 |

TABLE XX-continued
| Example # | Carboxylic Acid | Example Structure |
| --- | --- | --- |
| 631 | 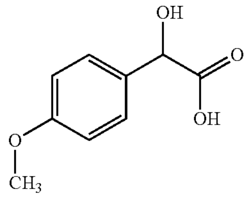 | 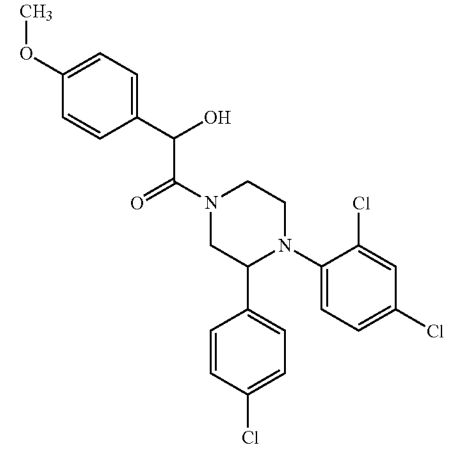 |
| 632 | 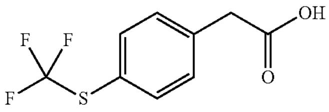 | 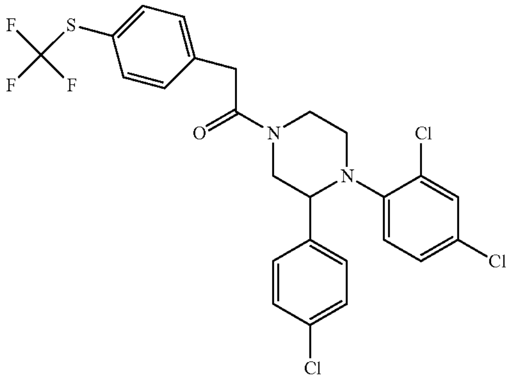 |
| 633 | 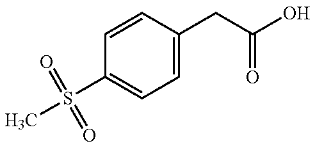 | 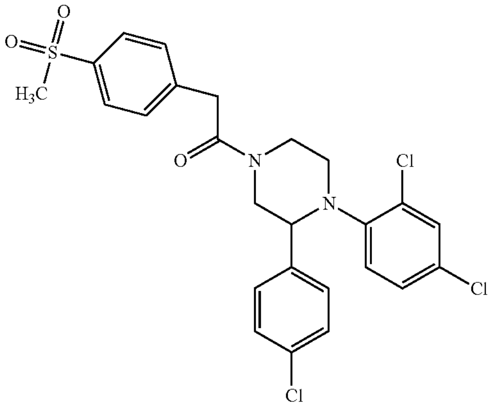 |

TABLE XX-continued
| Example # | Carboxylic Acid | Example Structure |
|---|---|---|
| 634 | 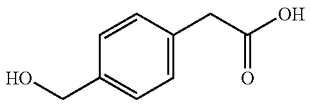 | 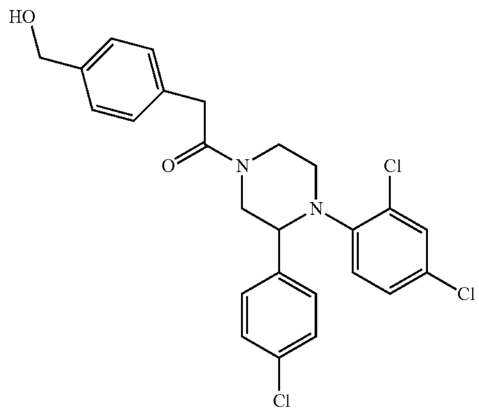 |
| 635 | 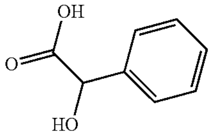 | 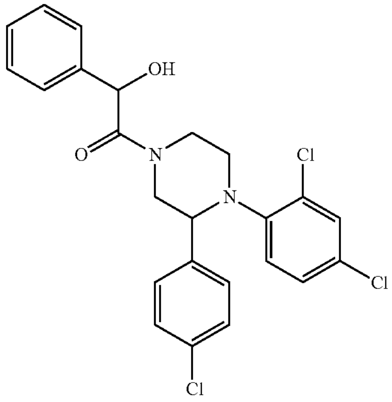 |
| 636 | 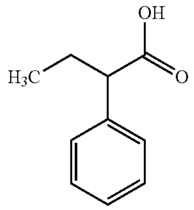 | 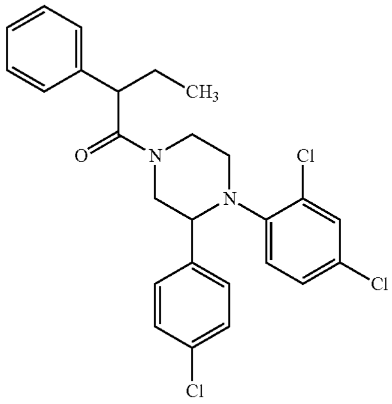 |

TABLE XX-continued
| Example # | Carboxylic Acid | Example Structure |
|---|---|---|
| 637 | 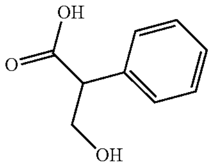 | 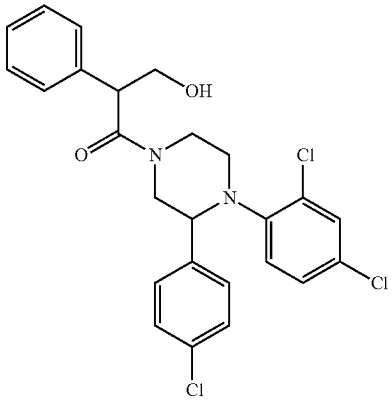 |
| 638 | 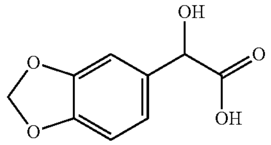 | 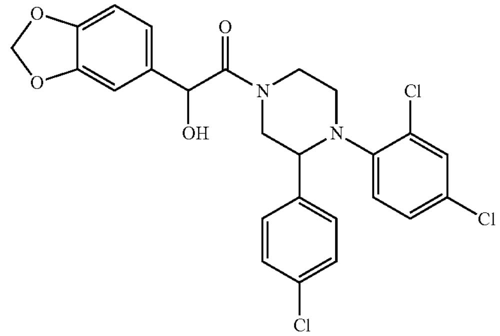 |
| 639 | 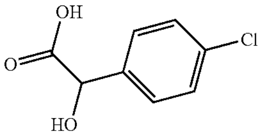 | 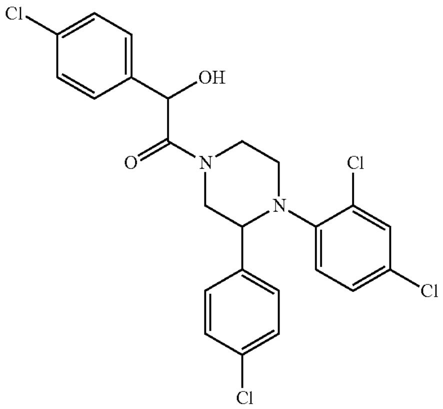 |
| 640 | 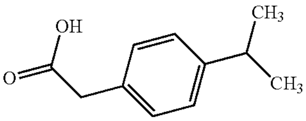 | 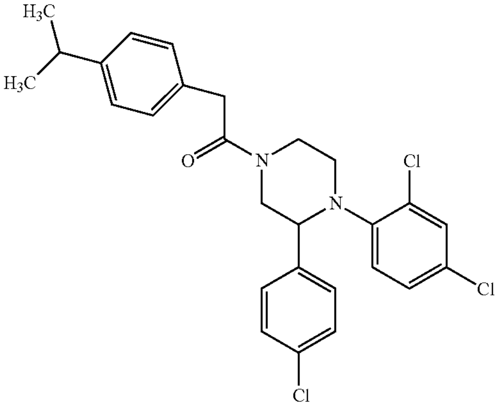 |

TABLE XX-continued
| Example # | Carboxylic Acid | Example Structure |
|---|---|---|
| 641 | 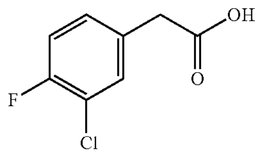 | 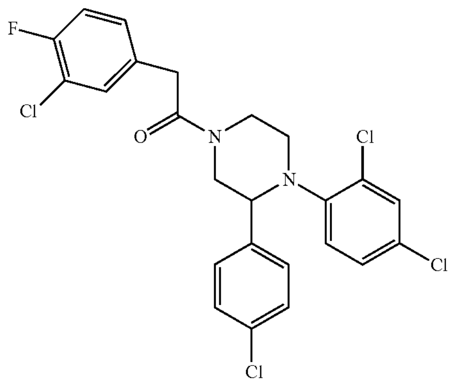 |
| 642 | 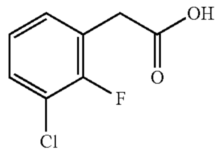 | 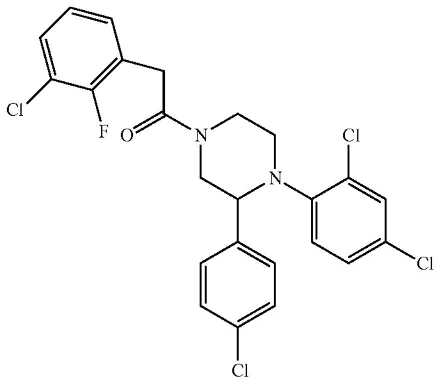 |
| 643 | 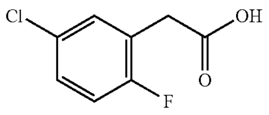 | 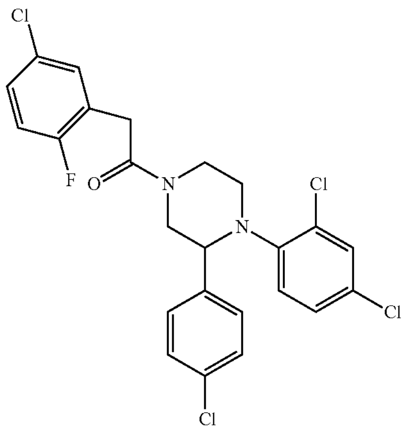 |

TABLE XX-continued
| Example # | Carboxylic Acid | Example Structure |
|---|---|---|
| 644 | 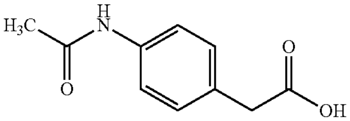 | 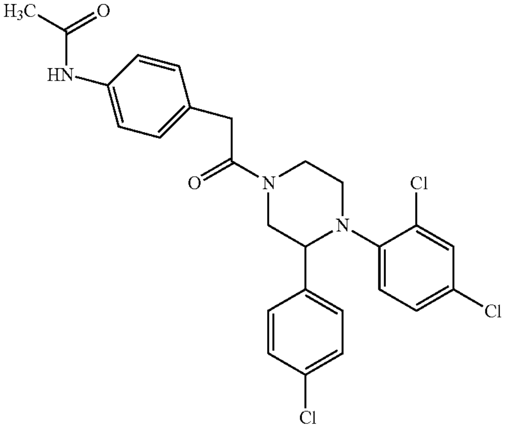 |
| 645 | 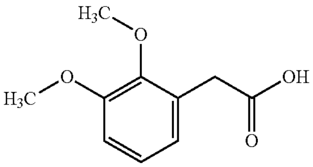 | 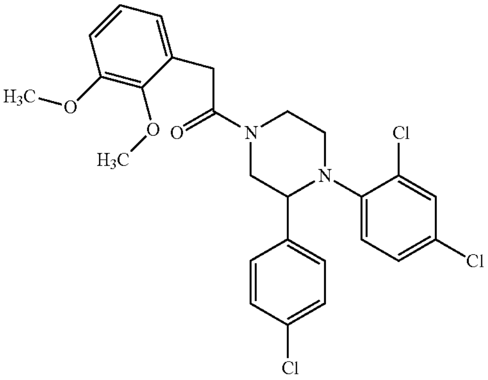 |
| 646 | 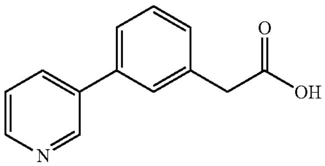 | 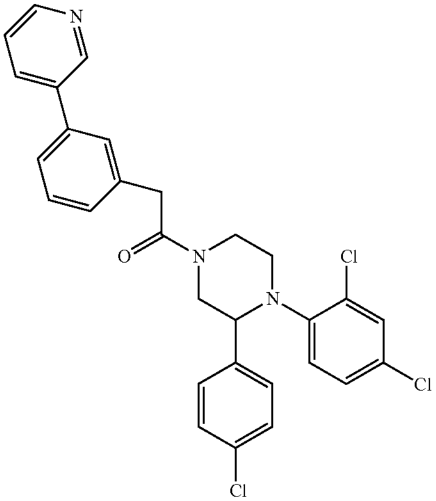 |

TABLE XX-continued
| Example # | Carboxylic Acid | Example Structure |
|---|---|---|
| 647 | 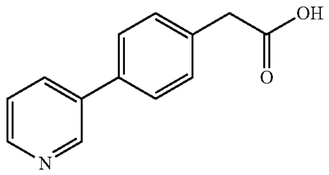 | 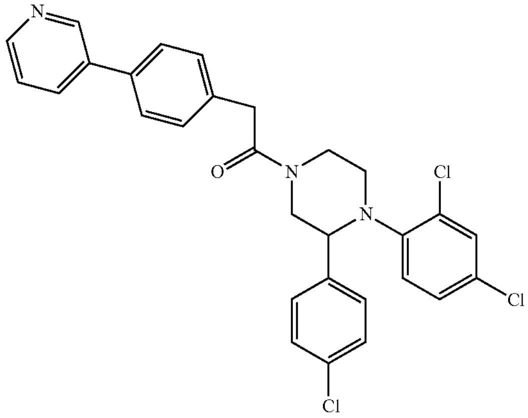 |
| 648 | 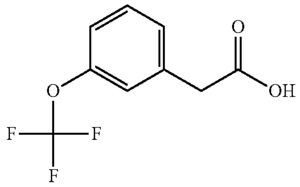 | 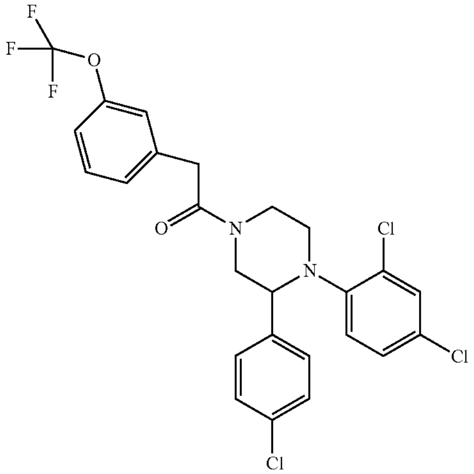 |
| 649 | 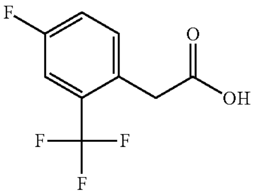 | 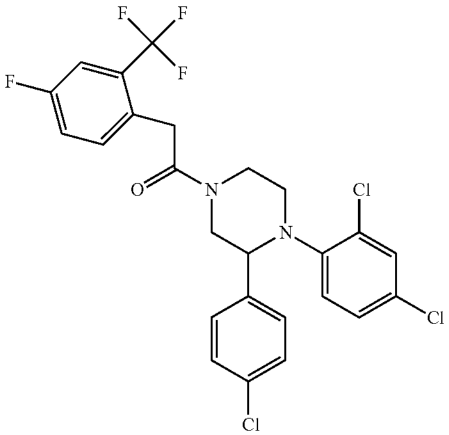 |

TABLE XX-continued
| Example # | Carboxylic Acid | Example Structure |
|---|---|---|
| 650 | 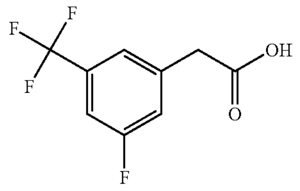 | 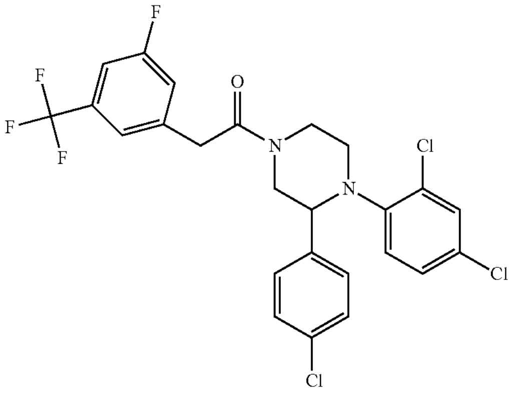 |
| 651 | 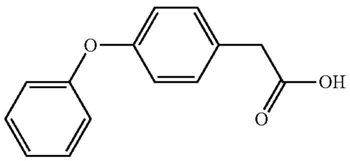 | 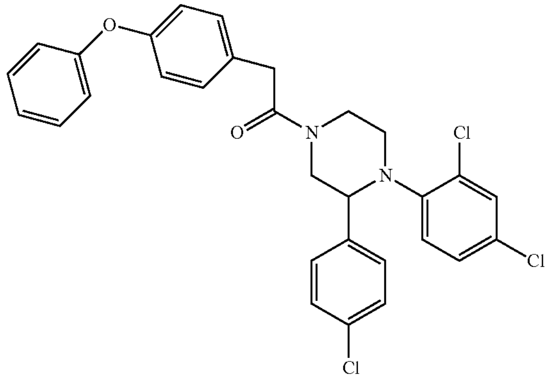 |
| 652 | 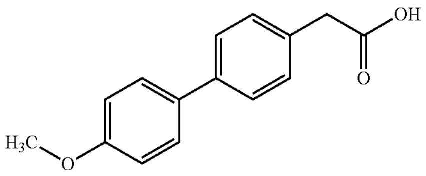 | 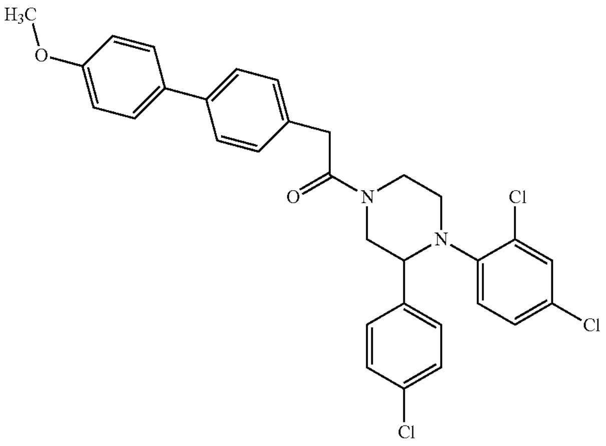 |

TABLE XX-continued
| Example # | Carboxylic Acid | Example Structure |
| --- | --- | --- |
| 653 | 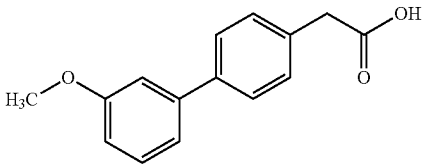 | 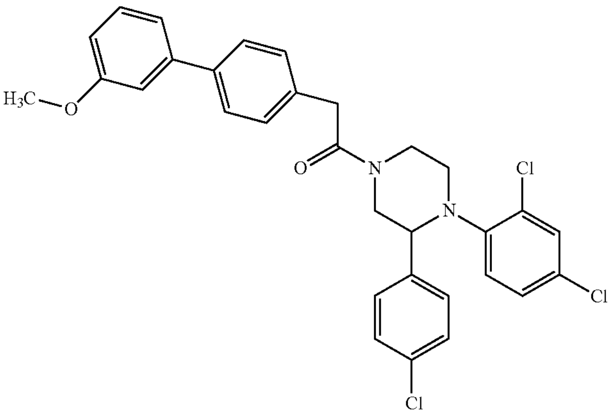 |
| 654 | 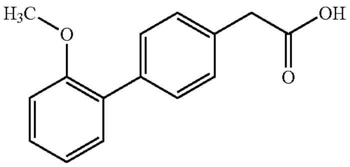 | 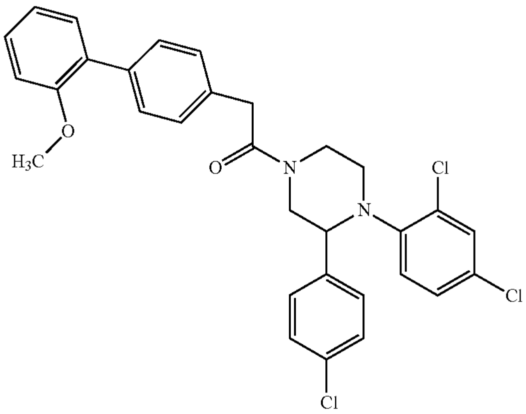 |
| 655 | 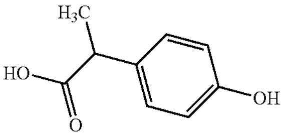 | 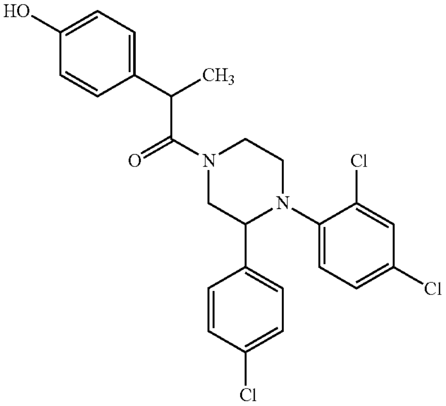 |

TABLE XX-continued
| Example # | Carboxylic Acid | Example Structure |
| --- | --- | --- |
| 656 | 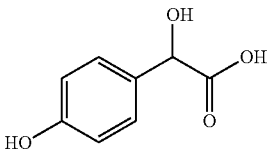 | 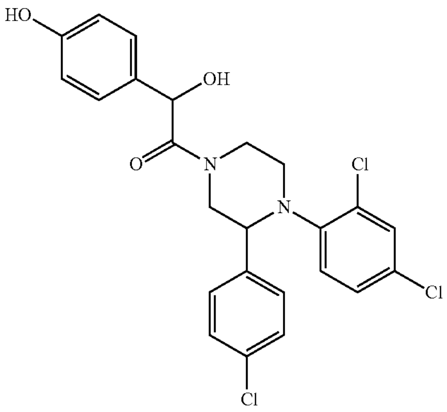 |
| 657 | 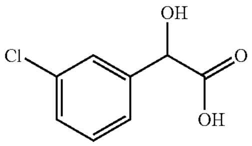 | 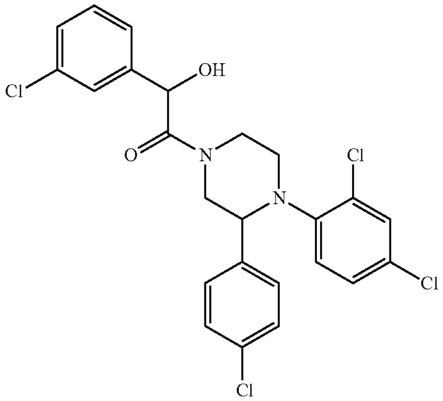 |
| 658 | 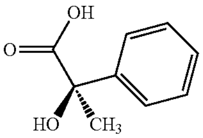 | 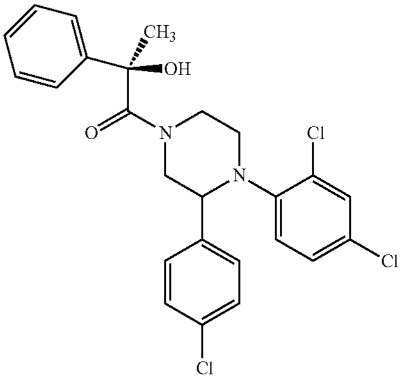 |
| 659 | 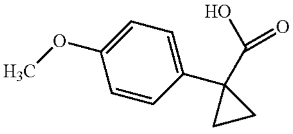 | 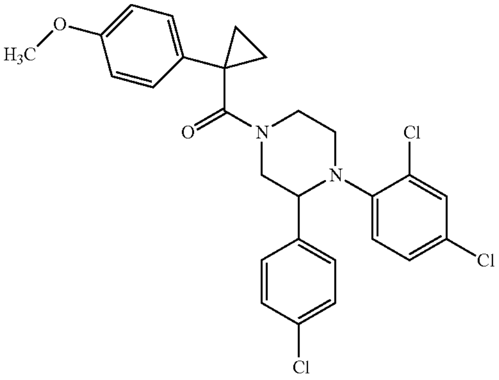 |

TABLE XX-continued
| Example # | Carboxylic Acid | Example Structure |
|---|---|---|
| 660 | 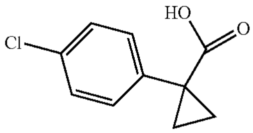 | 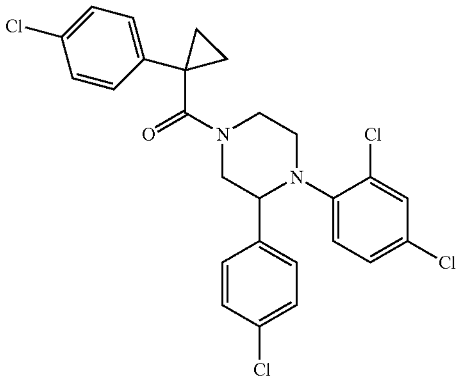 |
| 661 | 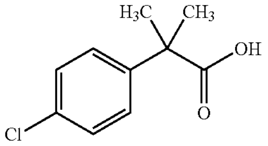 | 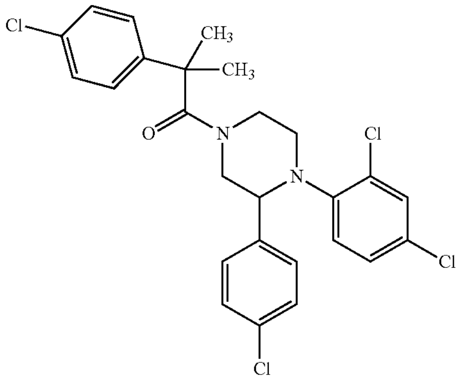 |
| 662 | 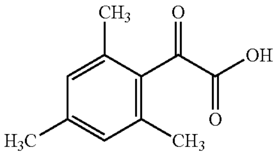 | 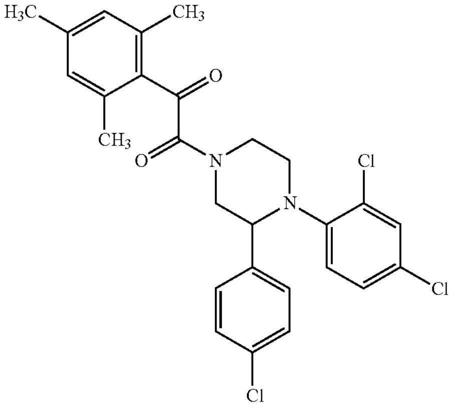 |
| 663 | 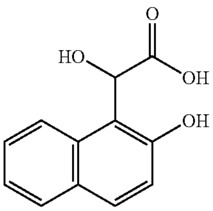 | 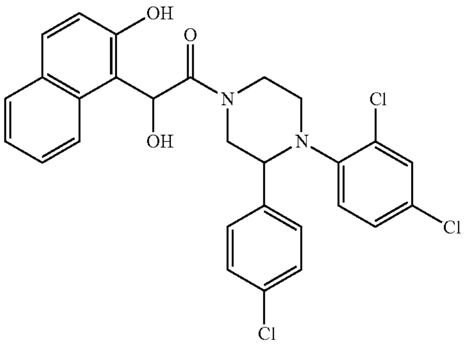 |

TABLE XX-continued
| Example # | Carboxylic Acid | Example Structure |
|---|---|---|
| 664 | 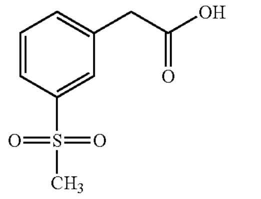 | 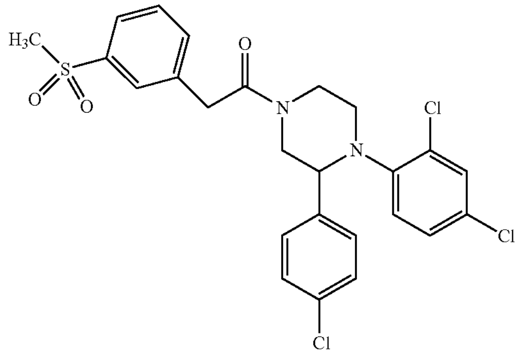 |
| 665 | 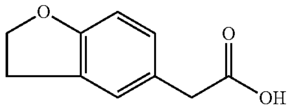 | 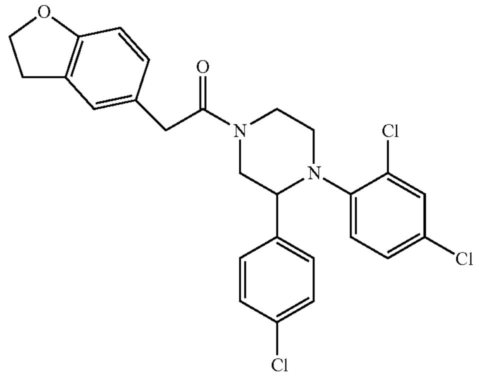 |
| 666 | 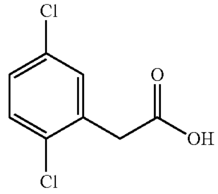 | 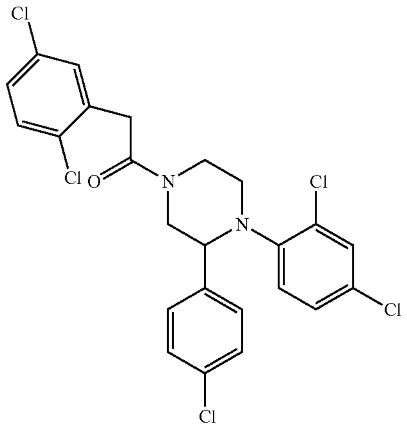 |
| 667 | 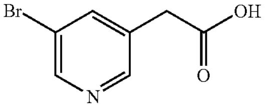 | 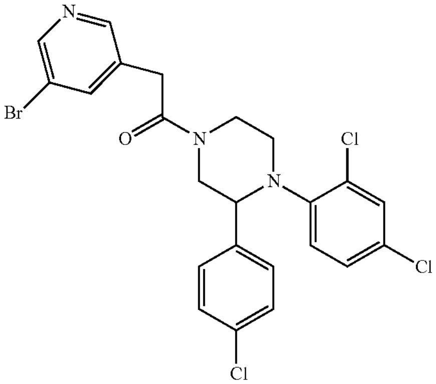 |

TABLE XX-continued
| Example # | Carboxylic Acid | Example Structure |
|---|---|---|
| 668 | 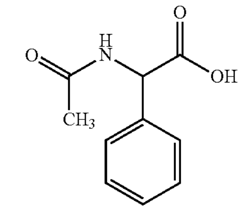 | 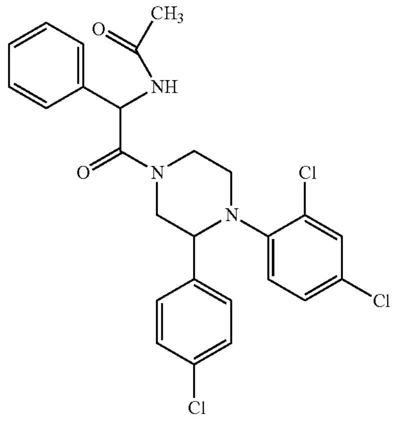 |
| 669 | 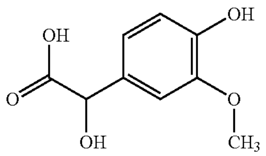 | 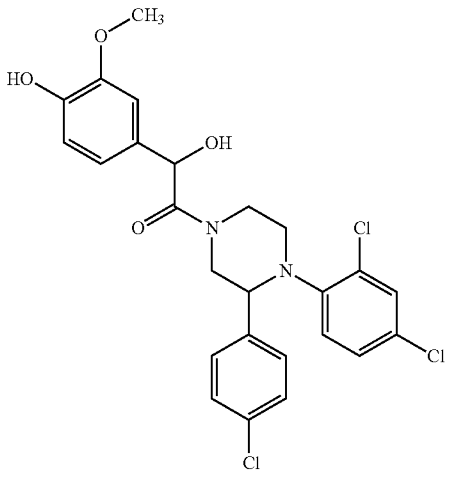 |
| 670 | 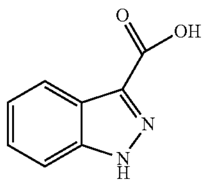 | 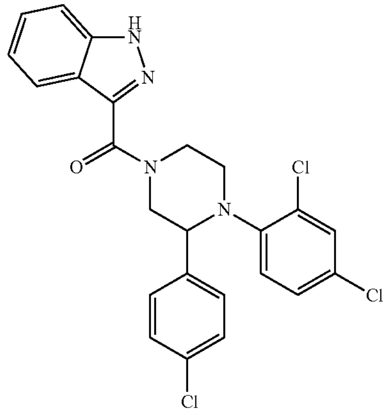 |

TABLE XX-continued
| Example # | Carboxylic Acid | Example Structure |
| --- | --- | --- |
| 671 | 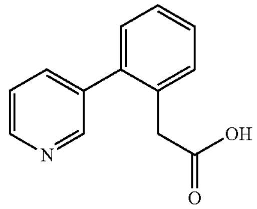 | 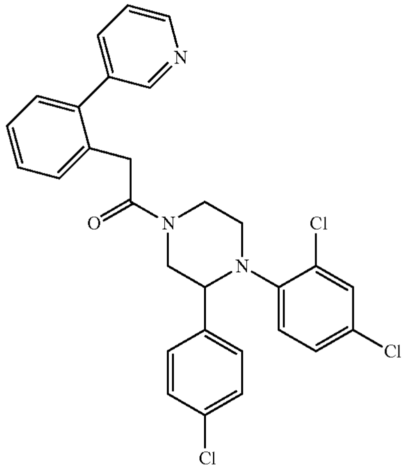 |
| 672 | 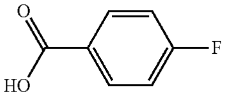 | 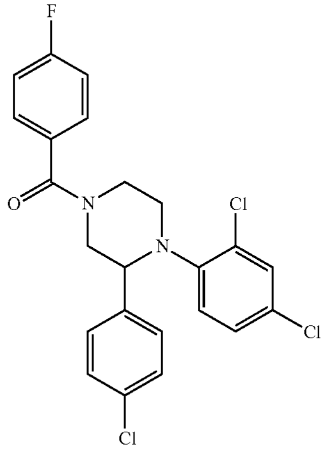 |
| 673 | 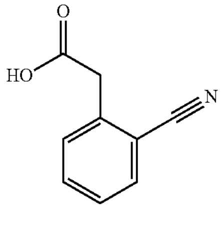 | 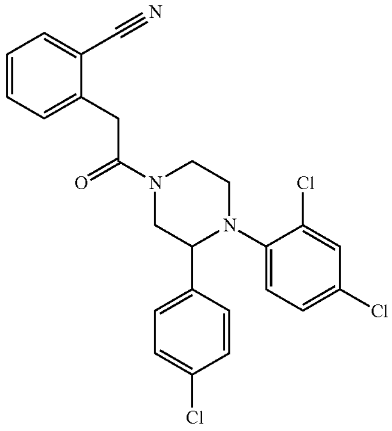 |

TABLE XX-continued
| Example # | Carboxylic Acid | Example Structure |
|---|---|---|
| 674 | 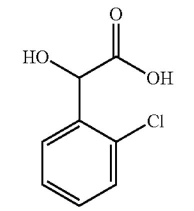 | 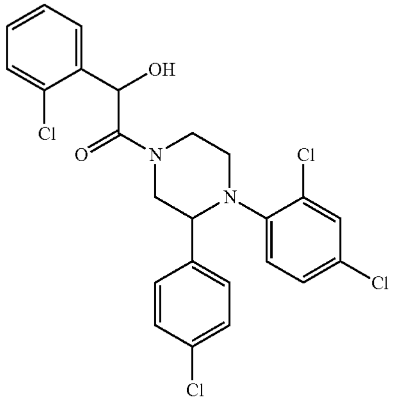 |
| 675 | 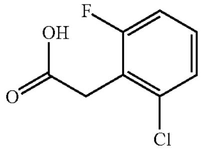 | 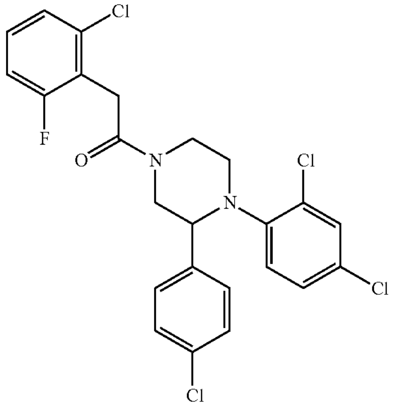 |
| 676 | 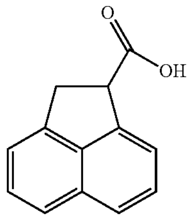 | 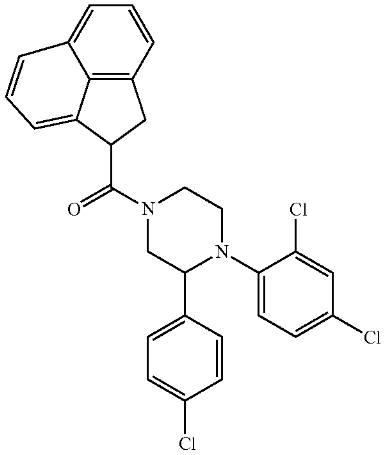 |

TABLE XX-continued
| Example # | Carboxylic Acid | Example Structure |
|---|---|---|
| 677 | 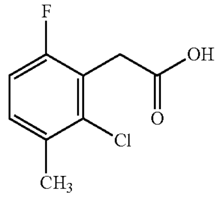 | 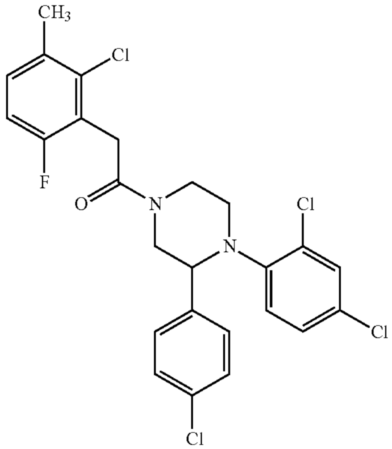 |
| 678 | 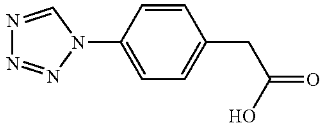 | 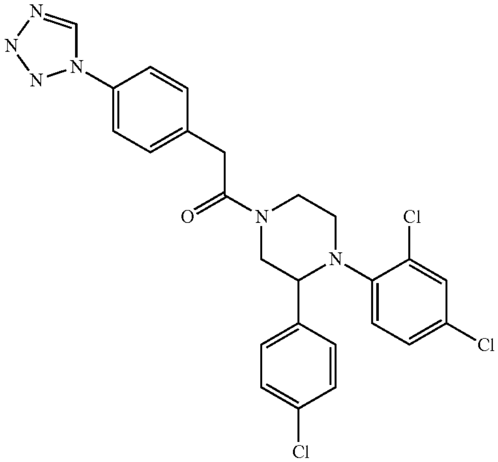 |
| 679 | 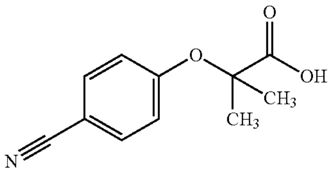 | 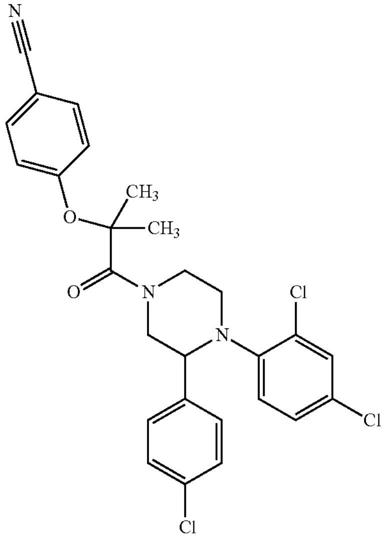 |

TABLE XX-continued
| Example # | Carboxylic Acid | Example Structure |
|---|---|---|
| 680 | 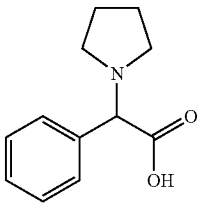 | 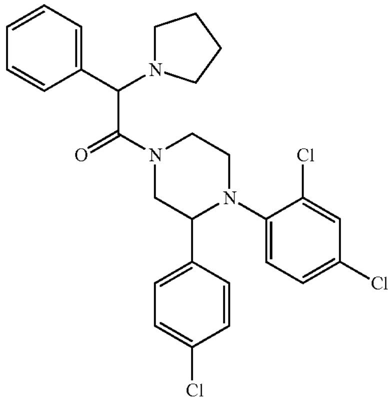 |
| 681 | 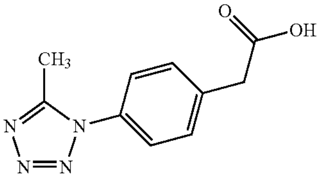 | 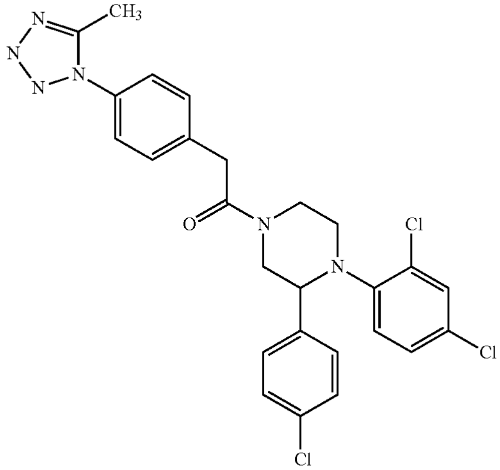 |
| 682 | 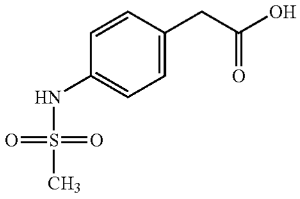 | 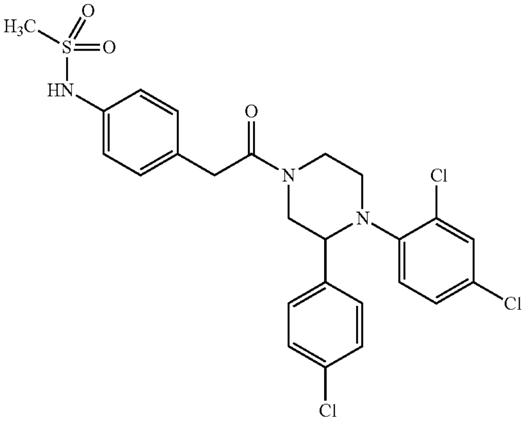 |

TABLE XX-continued

| Example # | Carboxylic Acid | Example Structure |
|---|---|---|
| 683 | 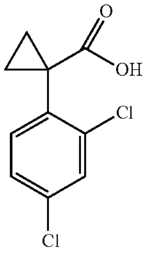 | 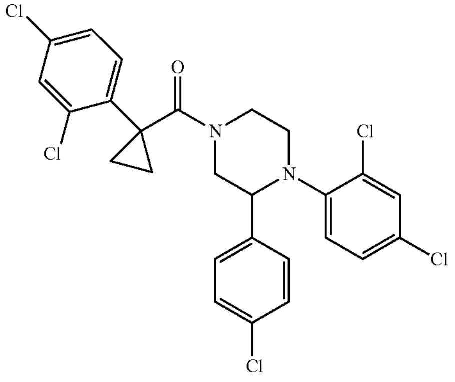 |
| 684 | 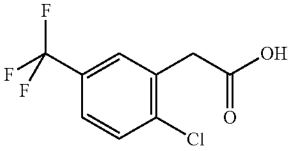 | 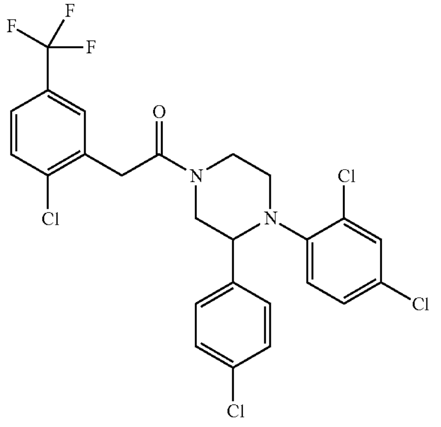 |
| 685 | 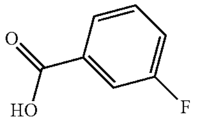 | 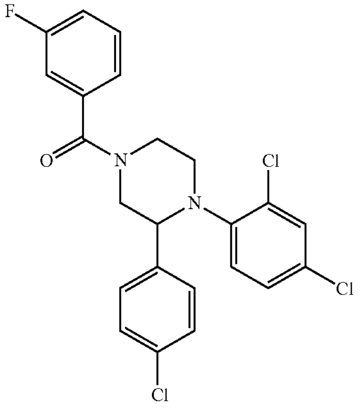 |

Preparation of Examples 686-766

Examples 686-766 were prepared by the reaction of piperazine Example 304 with the carboxylic acids shown in Table XXI, using the procedure of Scheme 5. Examples 735, 737, 739, 741, 743, 745, 747, 749, 751, 753, 755, 757, 759, 761, 763, and 765 prepared from the corresponding Boc carbamate by hydrolysis in 95% MeOH/5% (95% TFA/5% $H_2O$) solution in pre-weighed vials with shaking for 3 h. The solvent was removed in vacuo using a SpeedVac. Methanol and 2N HCl/ether was added and the samples shaken for 3 h. The solvent was removed in vacuo on a SpeedVac and the products were isolated as the HCl salt.

TABLE XXI
| Example # | Carboxylic Acid | Example Structure |
|---|---|---|
| 686 | 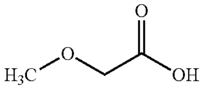 | 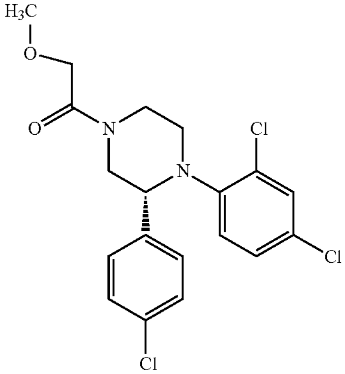 |
| 687 | 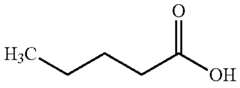 | 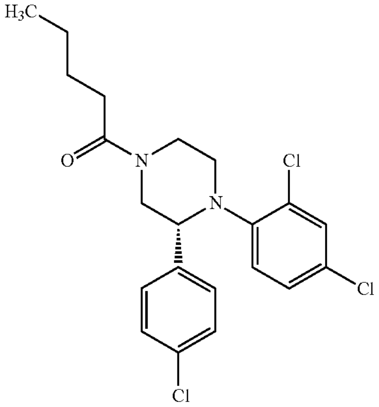 |
| 688 | 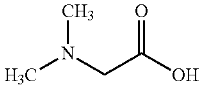 | 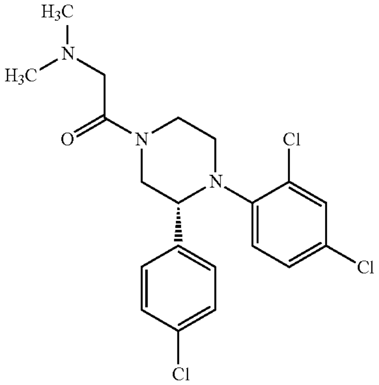 |
| 689 | 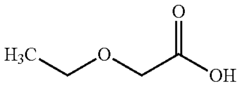 | 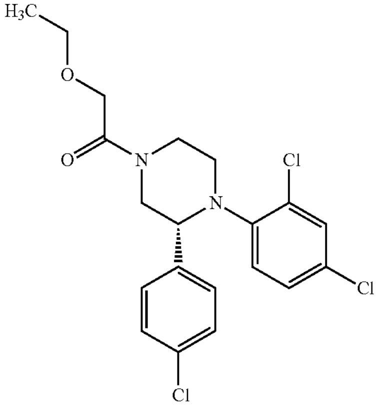 |

TABLE XXI-continued
| Example # | Carboxylic Acid | Example Structure |
|---|---|---|
| 690 | 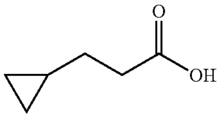 | 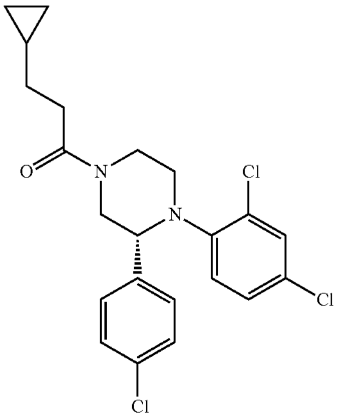 |
| 691 | 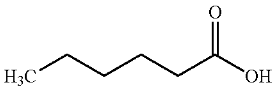 | 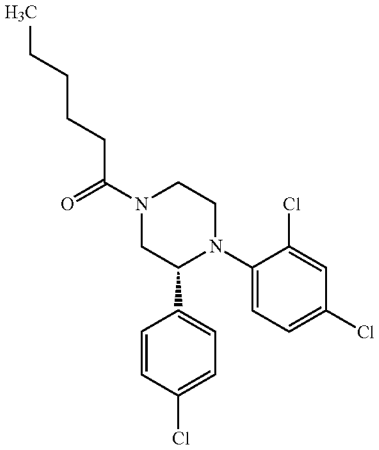 |
| 692 | 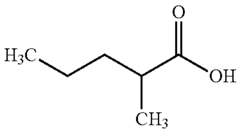 | 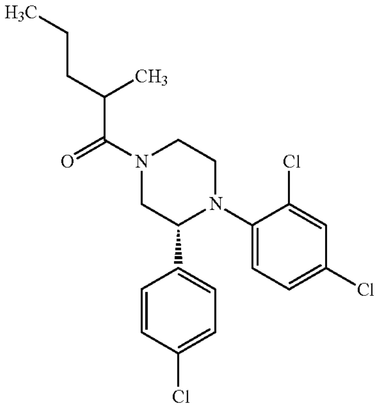 |

TABLE XXI-continued
| Example # | Carboxylic Acid | Example Structure |
|---|---|---|
| 693 | 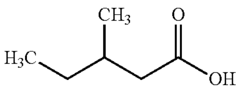 | 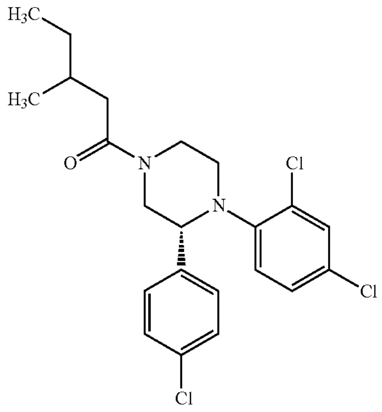 |
| 694 | 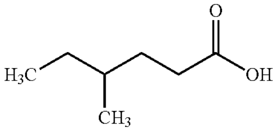 | 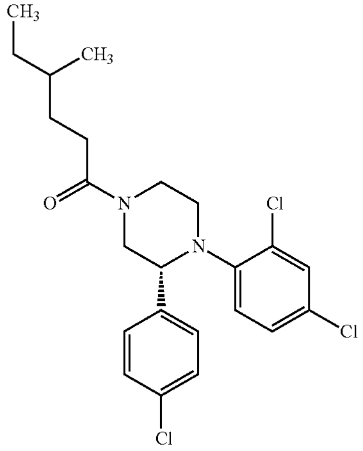 |
| 695 | 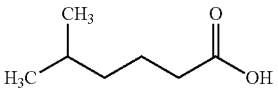 | 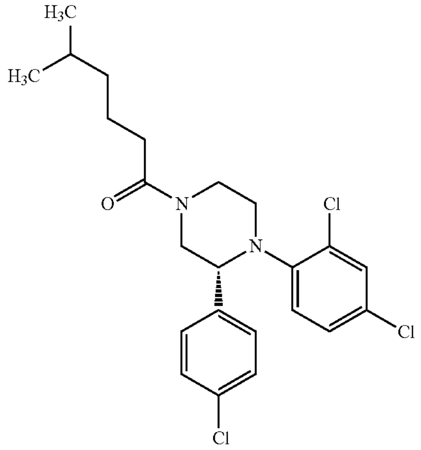 |

TABLE XXI-continued
| Example # | Carboxylic Acid | Example Structure |
|---|---|---|
| 696 | 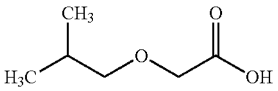 | 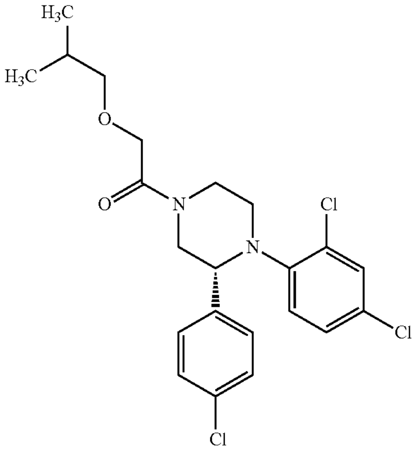 |
| 697 | 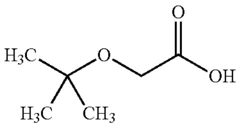 | 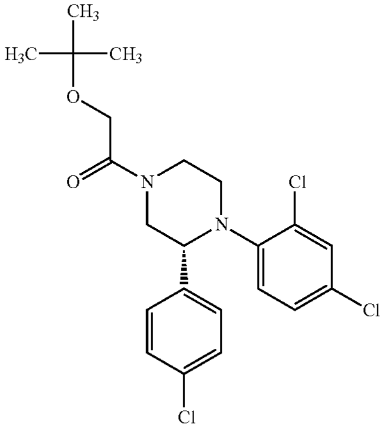 |
| 698 | 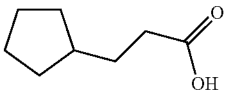 | 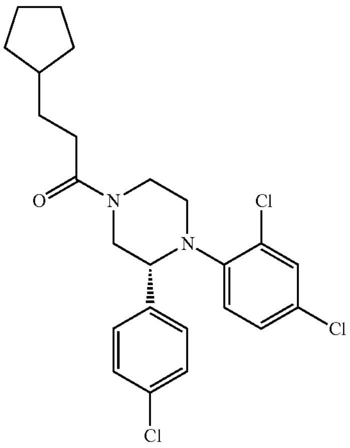 |

TABLE XXI-continued
| Example # | Carboxylic Acid | Example Structure |
|---|---|---|
| 699 | 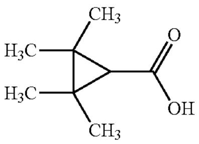 | 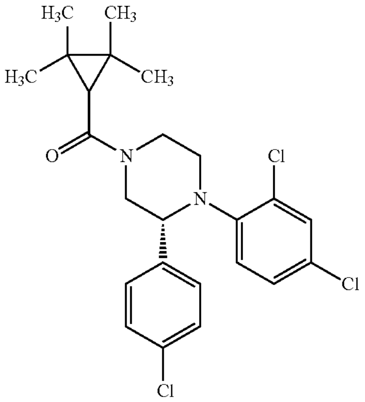 |
| 700 | 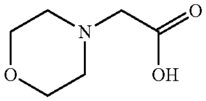 | 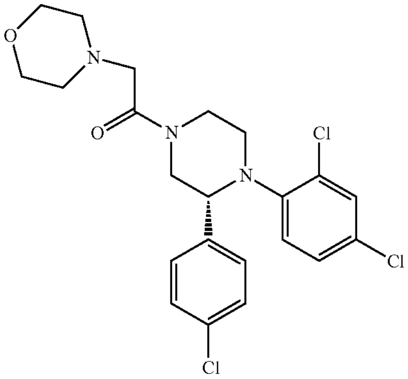 |
| 701 | 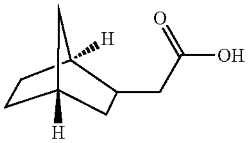 | 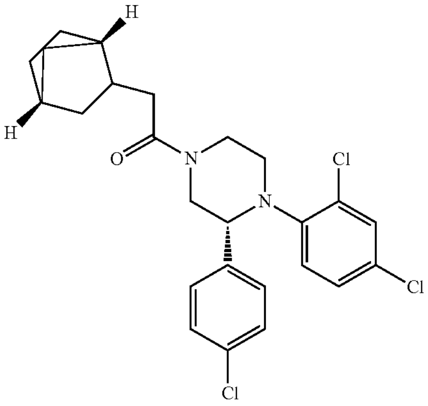 |

TABLE XXI-continued
| Example # | Carboxylic Acid | Example Structure |
|---|---|---|
| 702 | 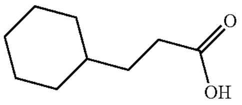 | 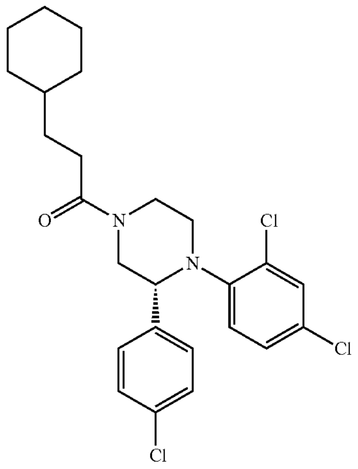 |
| 703 | 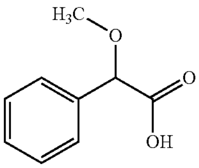 | 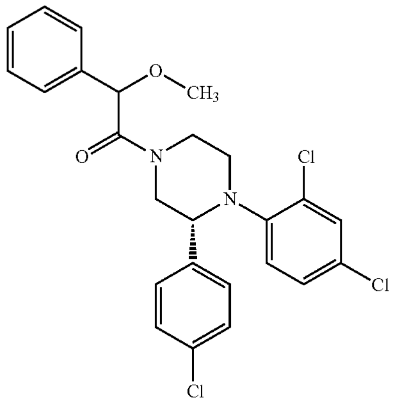 |
| 704 | 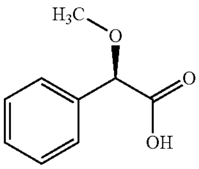 | 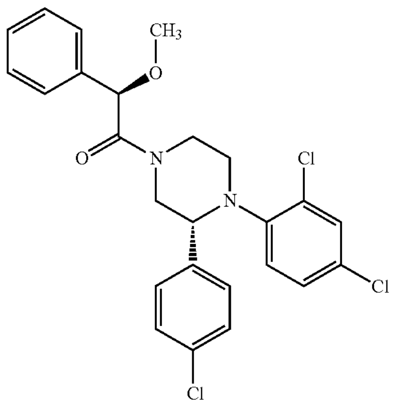 |

TABLE XXI-continued
| Example # | Carboxylic Acid | Example Structure |
|---|---|---|
| 705 | 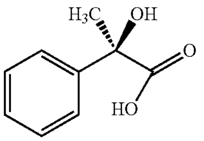 | 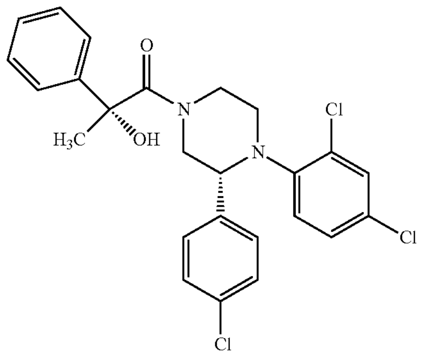 |
| 706 | 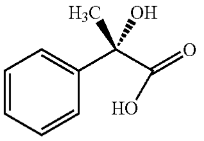 | 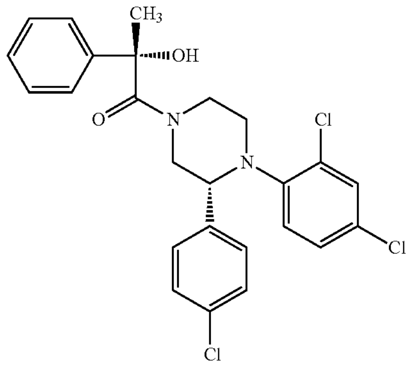 |
| 707 | 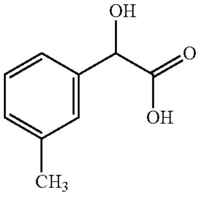 | 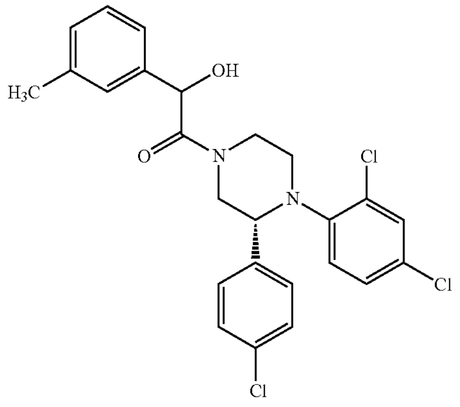 |
| 708 | 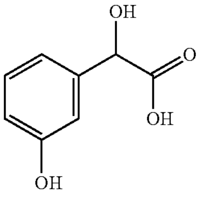 | 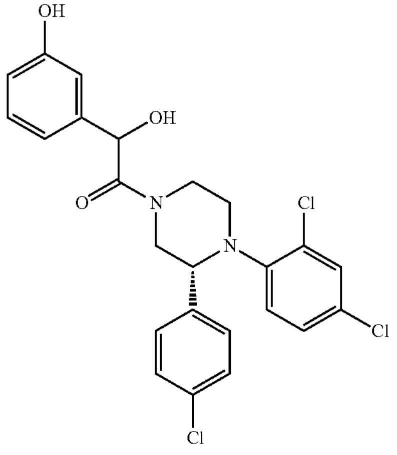 |

TABLE XXI-continued
| Example # | Carboxylic Acid | Example Structure |
|---|---|---|
| 709 | 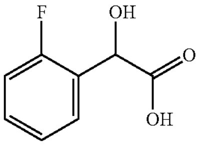 | 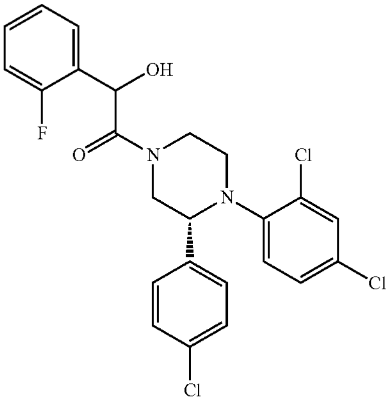 |
| 710 | 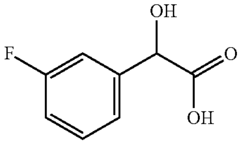 | 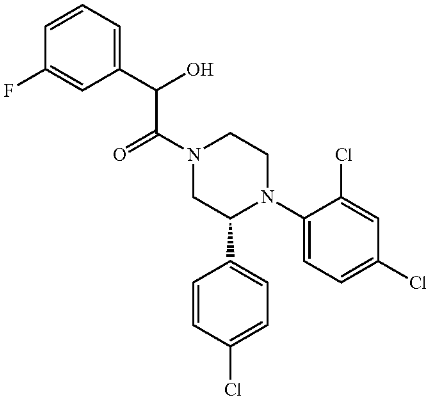 |
| 711 | 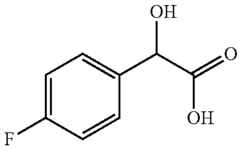 | 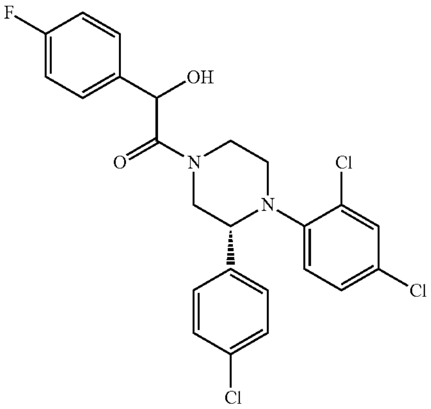 |
| 712 | 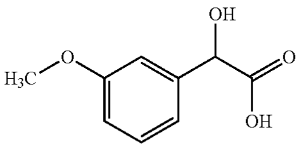 | 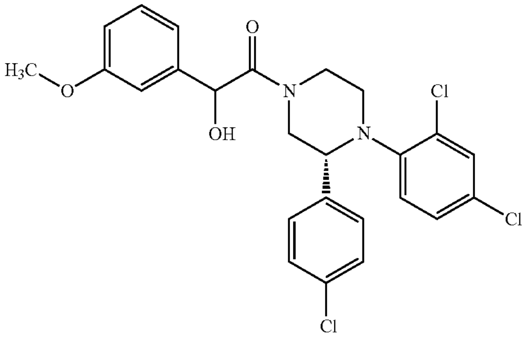 |

TABLE XXI-continued
| Example # | Carboxylic Acid | Example Structure |
|---|---|---|
| 713 | 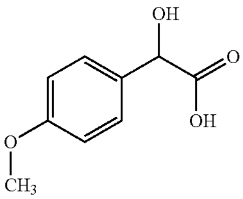 | 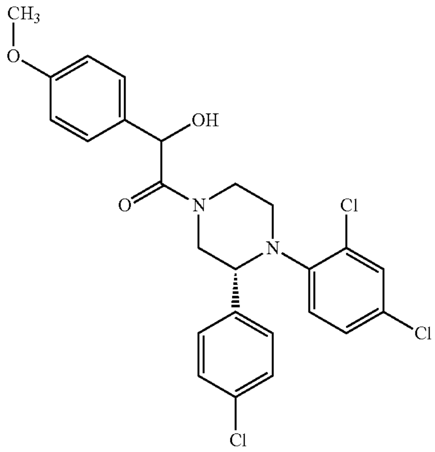 |
| 714 | 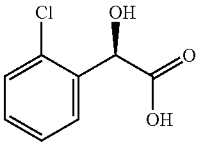 | 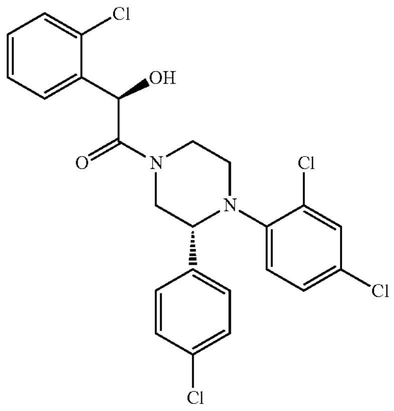 |
| 715 | 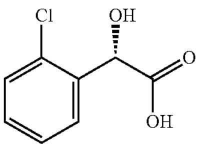 | 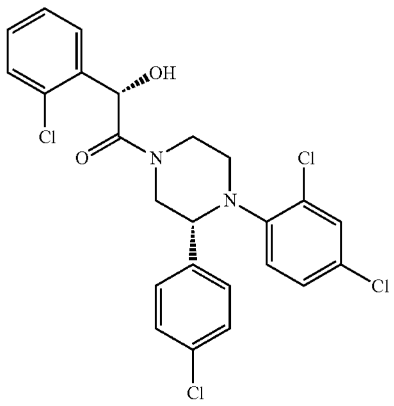 |

TABLE XXI-continued
| Example # | Carboxylic Acid | Example Structure |
|---|---|---|
| 716 | 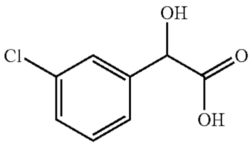 | 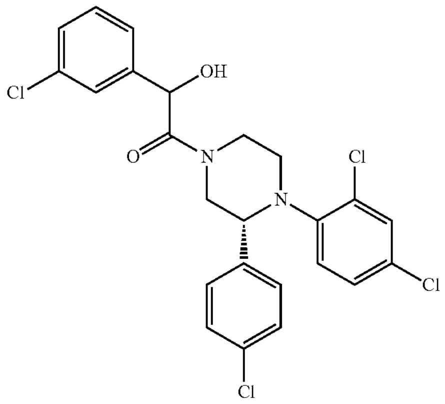 |
| 717 | 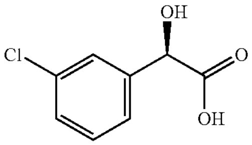 | 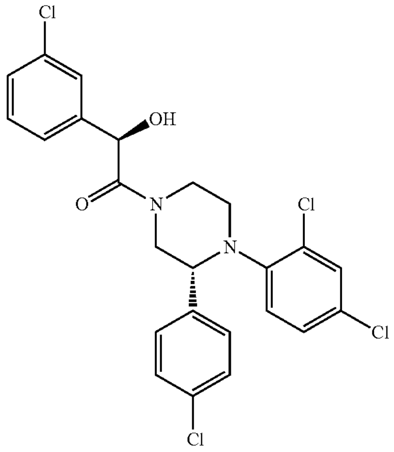 |
| 718 | 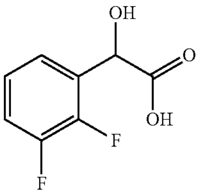 | 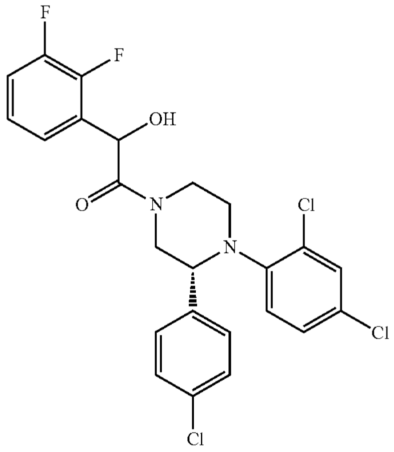 |

TABLE XXI-continued
| Example # | Carboxylic Acid | Example Structure |
| --- | --- | --- |
| 719 | 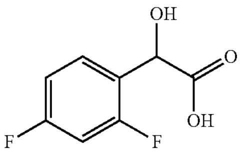 | 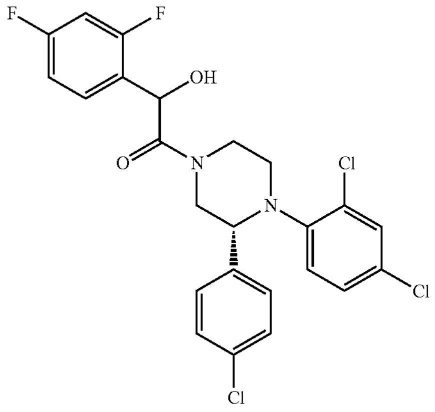 |
| 720 | 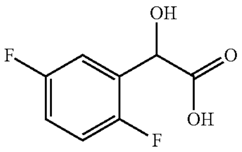 | 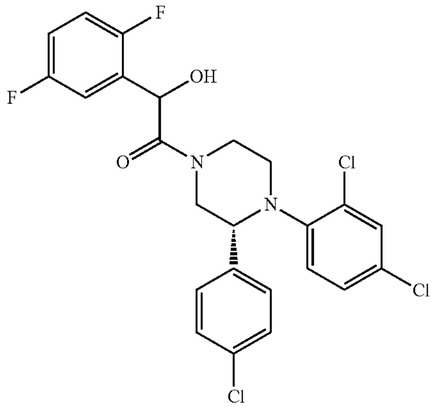 |
| 721 | 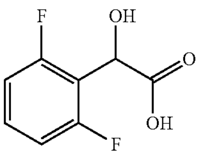 | 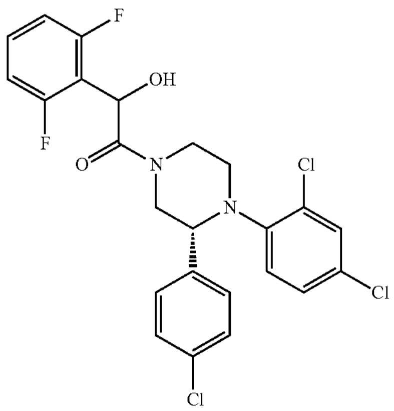 |

TABLE XXI-continued
| Example # | Carboxylic Acid | Example Structure |
|---|---|---|
| 722 | 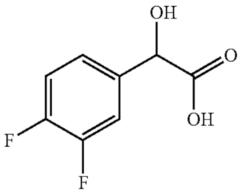 | 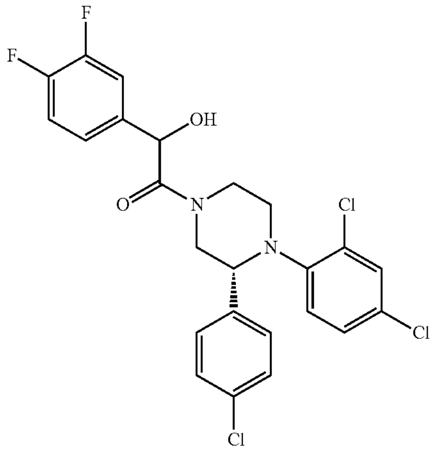 |
| 723 | 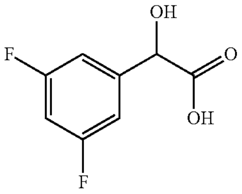 | 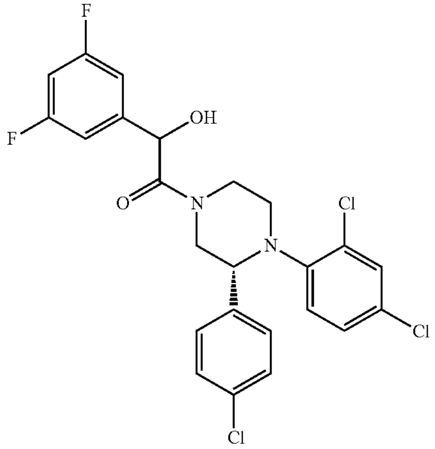 |
| 724 | 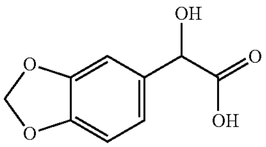 | 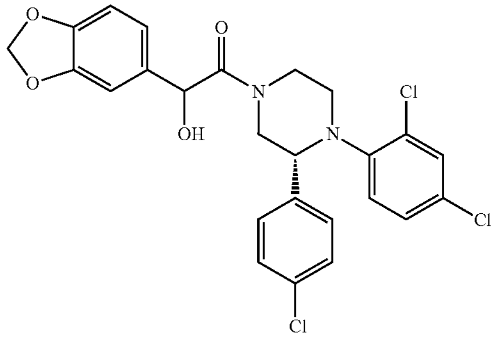 |

TABLE XXI-continued
| Example # | Carboxylic Acid | Example Structure |
|---|---|---|
| 725 | 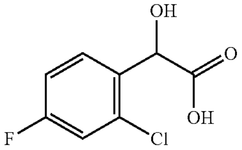 | 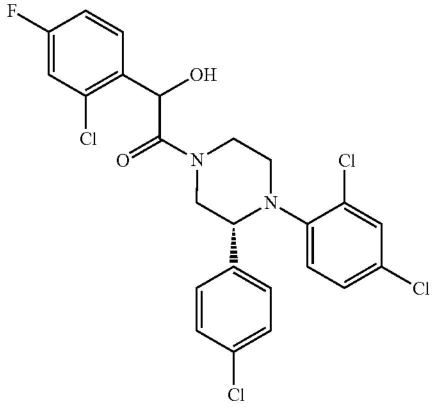 |
| 726 | 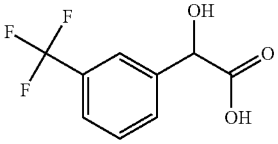 | 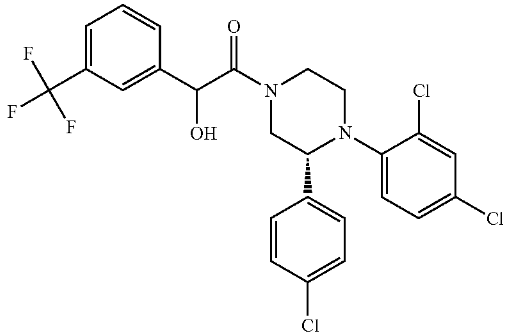 |
| 727 | 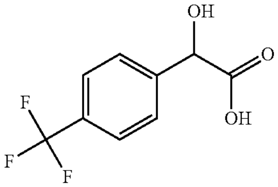 | 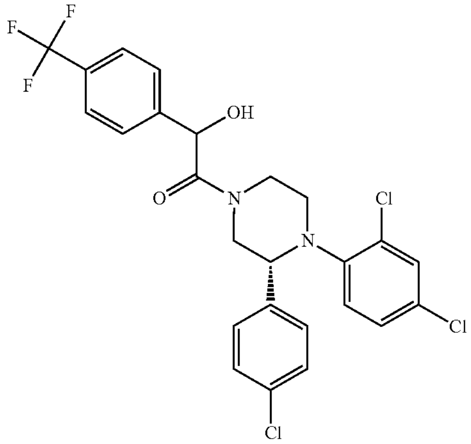 |
| 728 | 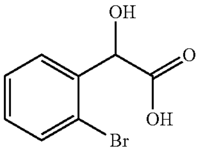 | 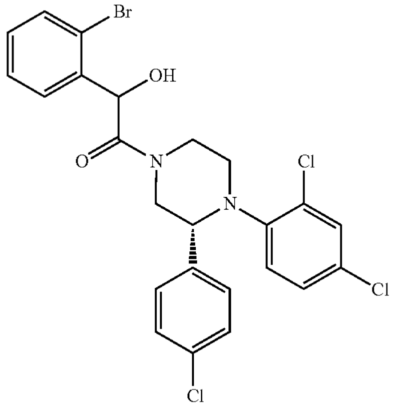 |

TABLE XXI-continued
| Example # | Carboxylic Acid | Example Structure |
|---|---|---|
| 729 | 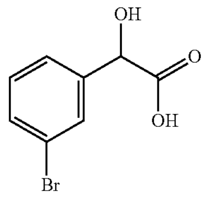 | 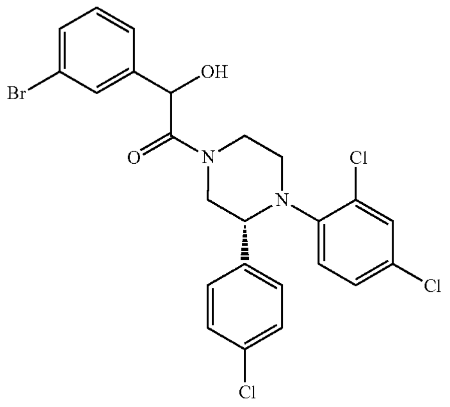 |
| 730 | 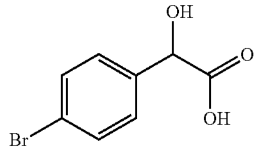 | 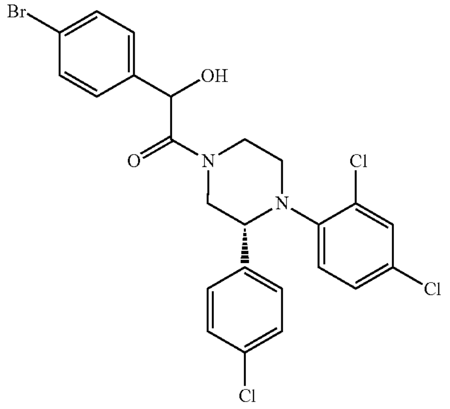 |
| 731 | 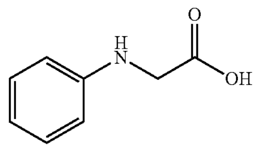 | 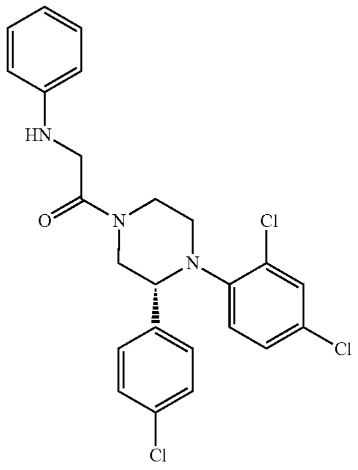 |

TABLE XXI-continued
| Example # | Carboxylic Acid | Example Structure |
| --- | --- | --- |
| 732 | 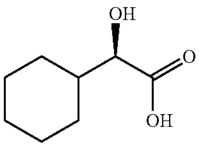 | 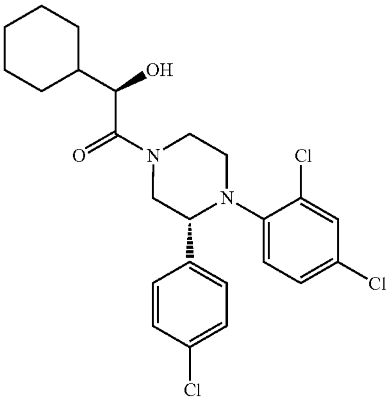 |
| 733 | 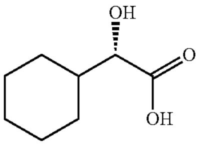 | 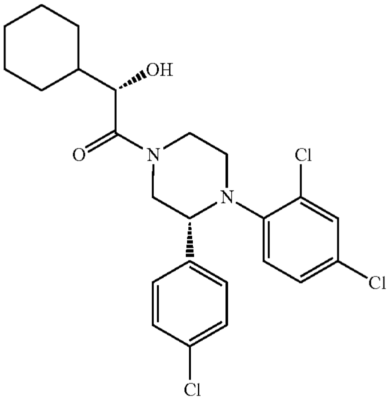 |
| 734 | 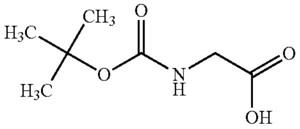 | 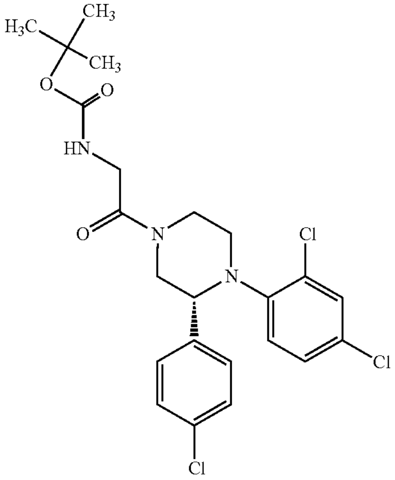 |

TABLE XXI-continued
| Example # | Carboxylic Acid | Example Structure |
|---|---|---|
| 735 | 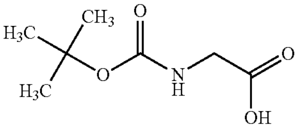 | 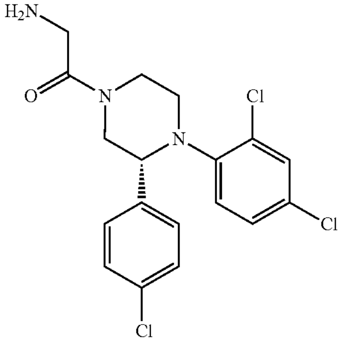 |
| 736 | 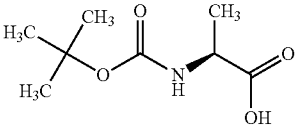 | 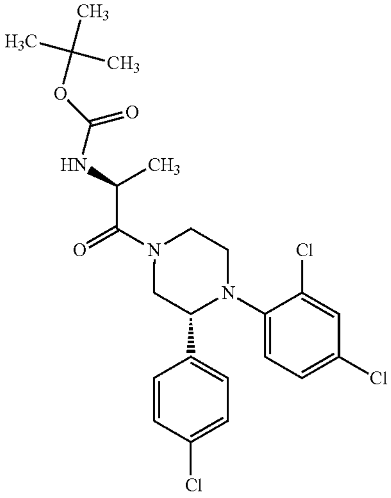 |
| 737 | 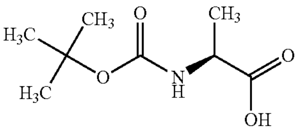 | 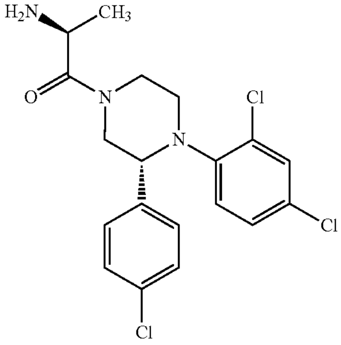 |

TABLE XXI-continued
| Example # | Carboxylic Acid | Example Structure |
| --- | --- | --- |
| 738 | 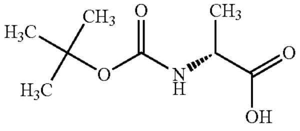 | 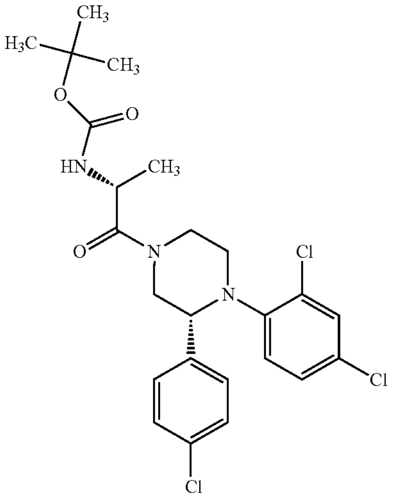 |
| 739 | 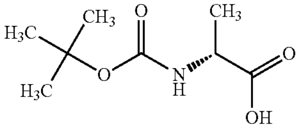 | 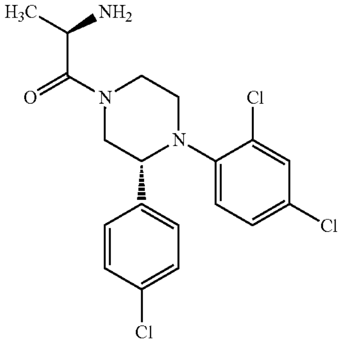 |
| 740 | 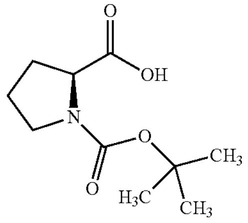 | 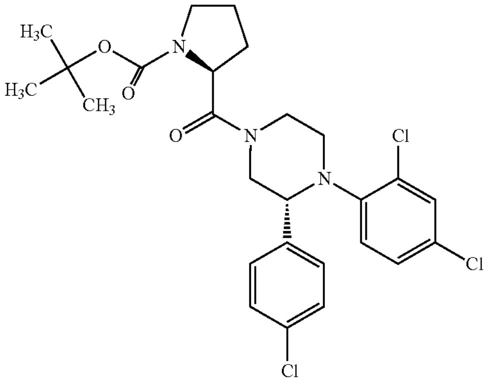 |
| 741 | 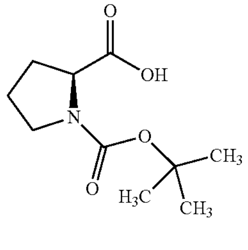 | 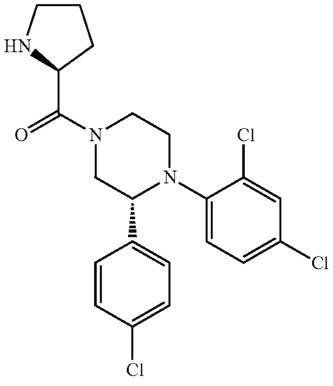 |

TABLE XXI-continued
| Example # | Carboxylic Acid | Example Structure |
|---|---|---|
| 742 | 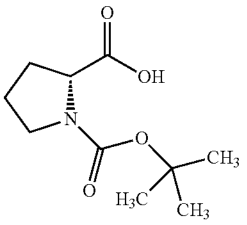 | 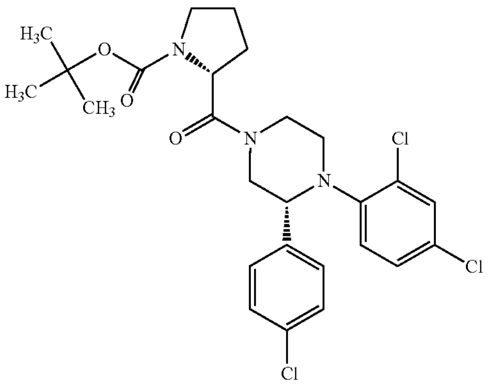 |
| 743 | 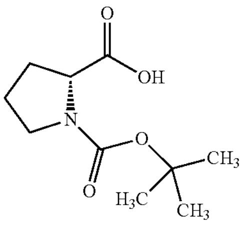 | 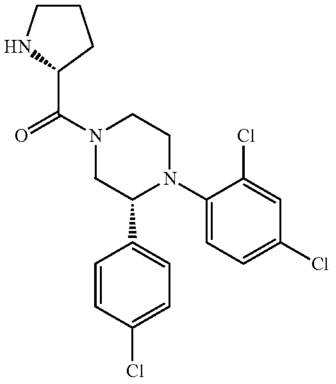 |
| 744 | 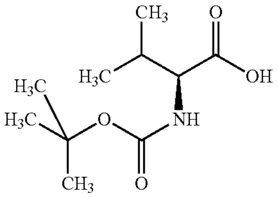 | 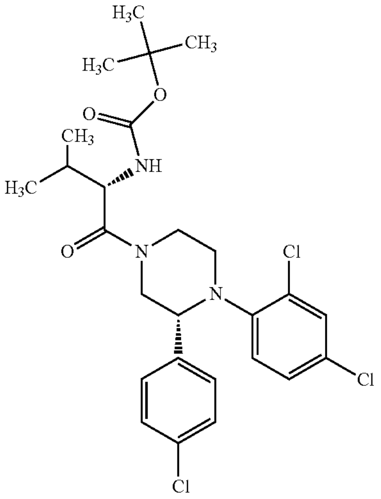 |

TABLE XXI-continued
| Example # | Carboxylic Acid | Example Structure |
|---|---|---|
| 745 | 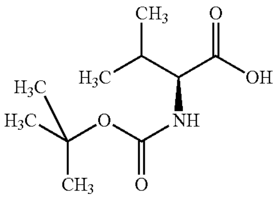 | 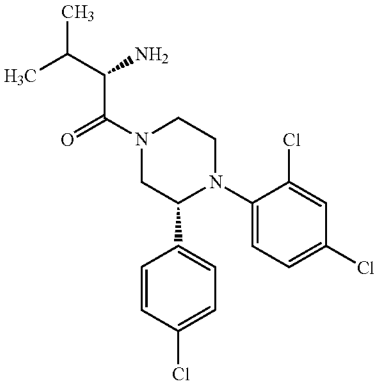 |
| 746 | 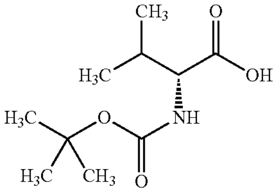 | 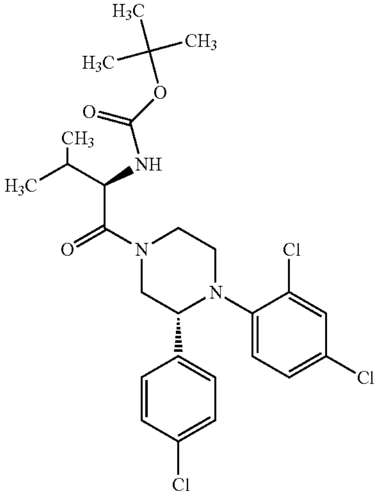 |
| 747 | 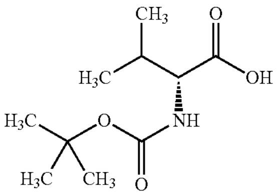 | 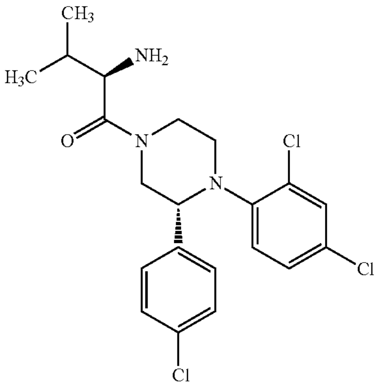 |

TABLE XXI-continued
| Example # | Carboxylic Acid | Example Structure |
|---|---|---|
| 748 | 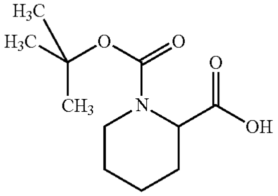 | 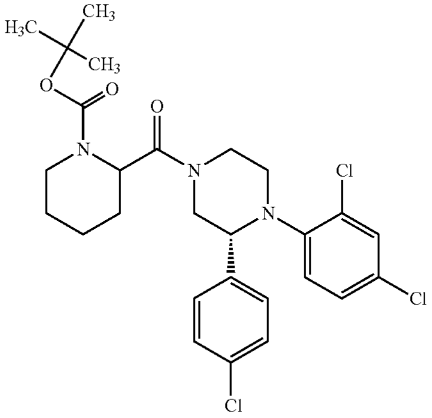 |
| 749 | 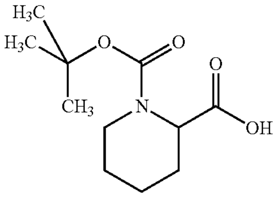 | 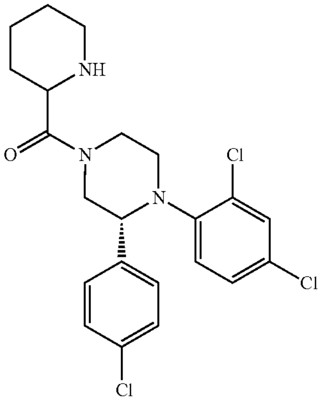 |
| 750 | 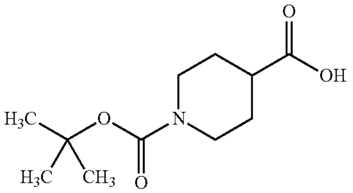 | 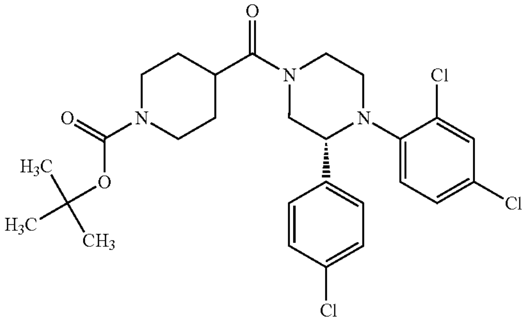 |
| 751 | 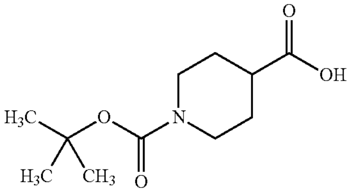 | 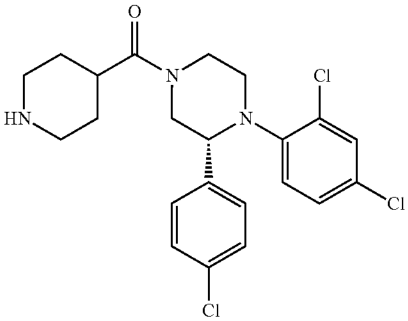 |

TABLE XXI-continued
| Example # | Carboxylic Acid | Example Structure |
| --- | --- | --- |
| 752 | 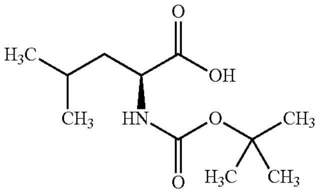 | 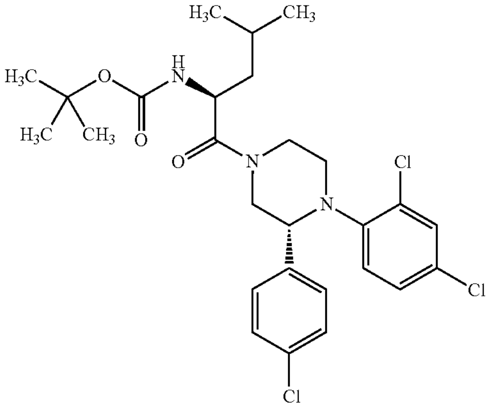 |
| 753 | 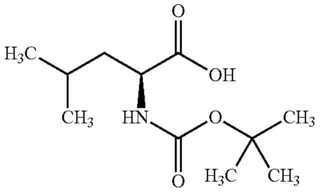 | 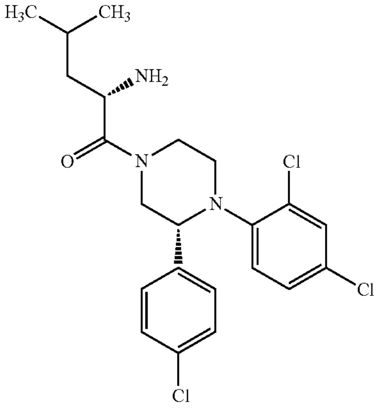 |
| 754 | 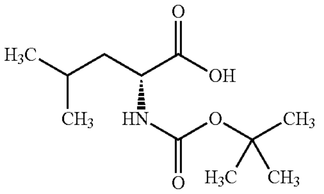 | 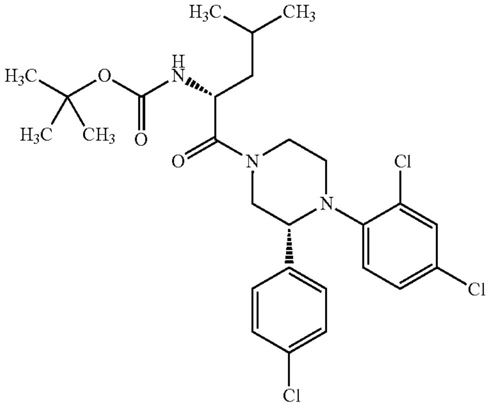 |

TABLE XXI-continued
| Example # | Carboxylic Acid | Example Structure |
|---|---|---|
| 755 | 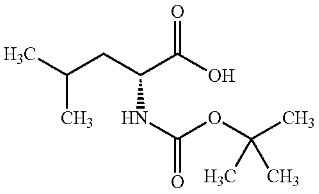 | 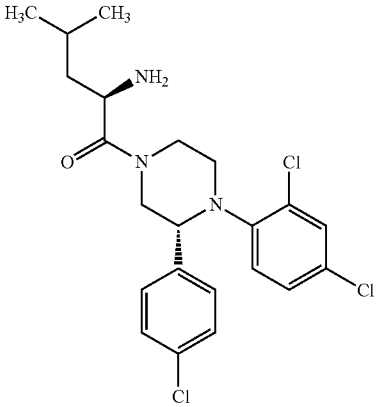 |
| 756 | 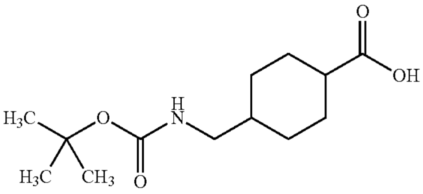 | 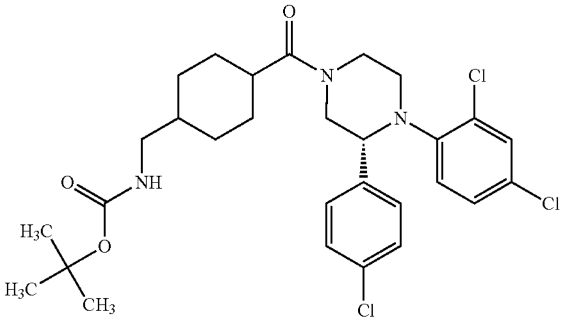 |
| 757 | 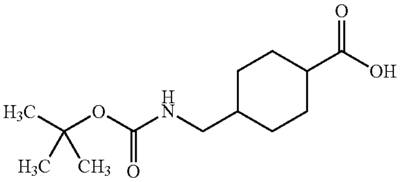 | 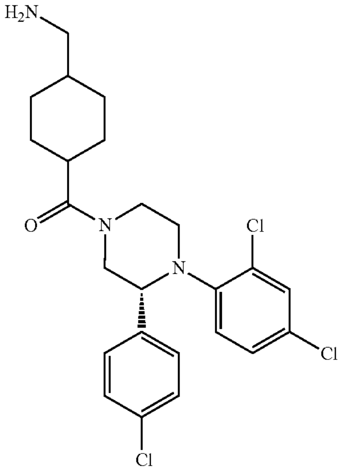 |

TABLE XXI-continued
| Example # | Carboxylic Acid | Example Structure |
|---|---|---|
| 758 | 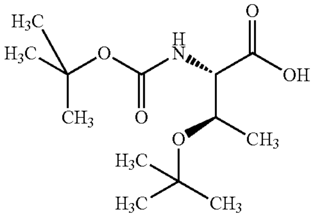 | 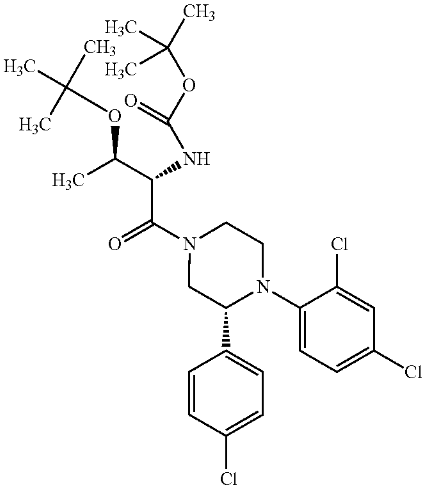 |
| 759 | 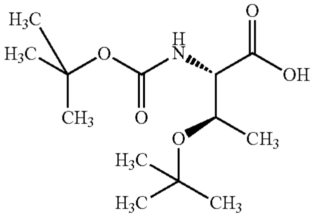 | 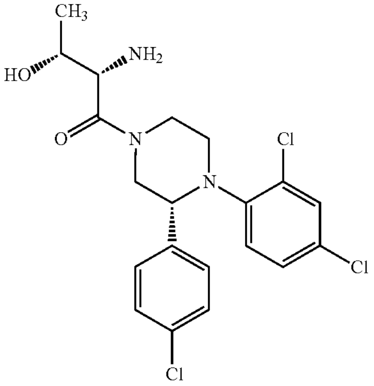 |
| 760 | 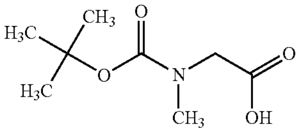 | 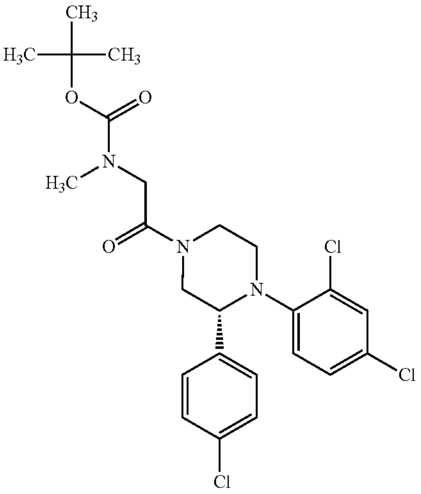 |

TABLE XXI-continued
| Example # | Carboxylic Acid | Example Structure |
|---|---|---|
| 761 | 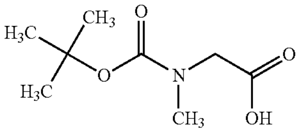 | 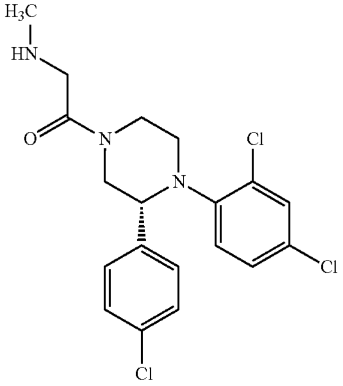 |
| 762 | 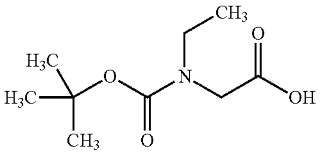 | 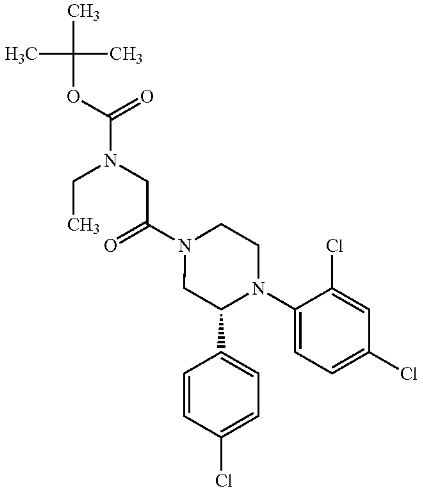 |
| 763 | 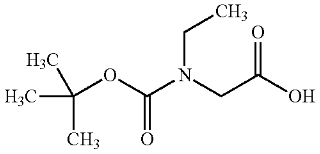 | 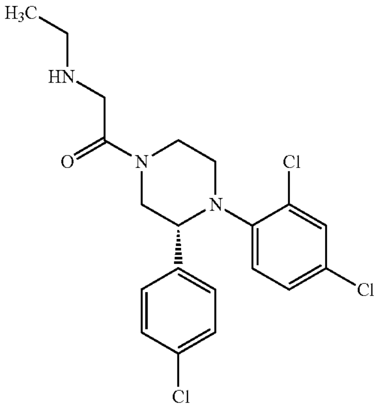 |
| 764 | 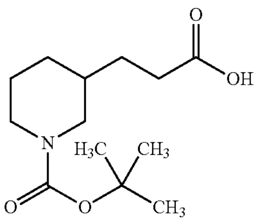 | 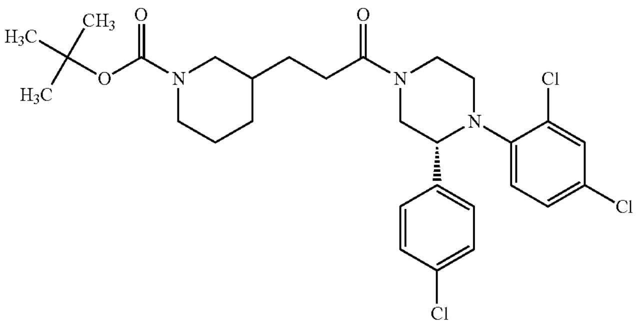 |

TABLE XXI-continued
| Example # | Carboxylic Acid | Example Structure |
| --- | --- | --- |
| 765 | 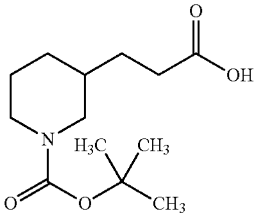 | 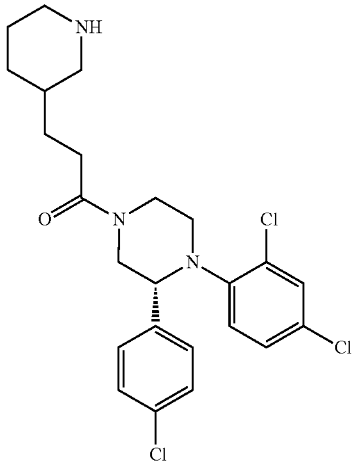 |
| 766 | 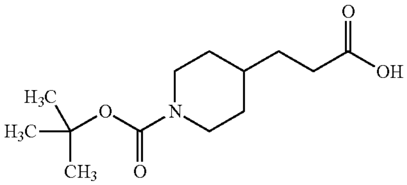 | 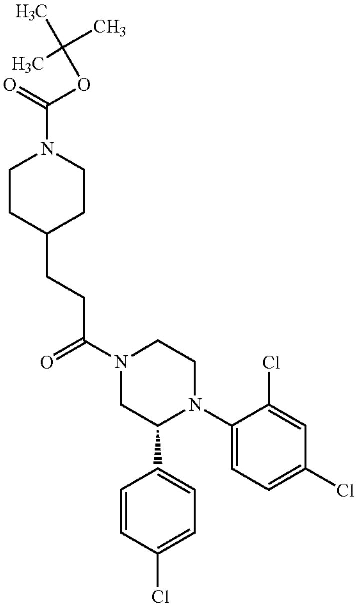 |
| 767 | 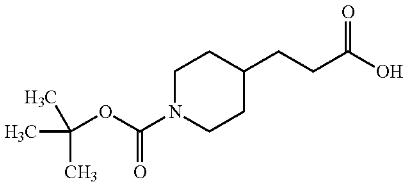 | 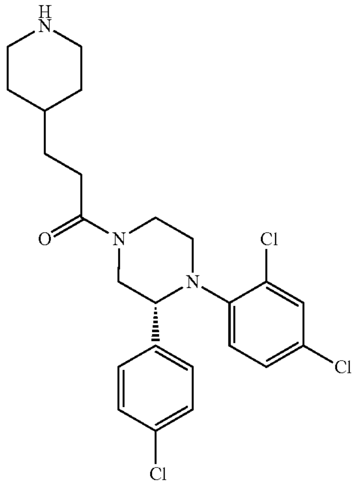 |

Preparation of Example 768

Example 768

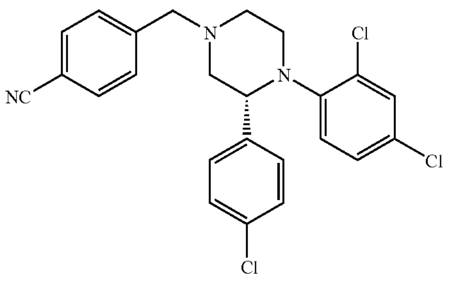

Example 768 was prepared by the method of Scheme 1, except that Example 304 was used instead of Example 1 and 4-cycanobenzaldehyde was used instead of benzaldehyde.

Preparation of Example 769

Scheme 74

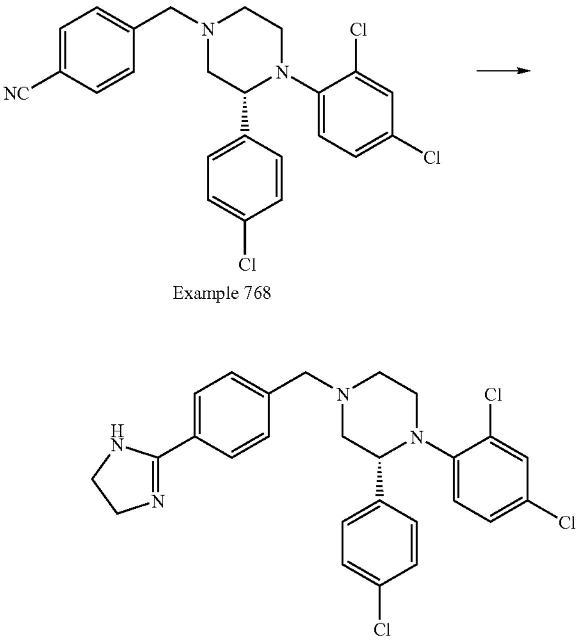

Example 768

Example 769

To the piperazine Example 768 (0.1 g, 0.22 mmol) in ethylenediamine (15 μL) was added Yttrium (III) trifluoromethane sulfonate (1.2 mg). The mixture was warmed to 100° C. and stirred for 20 h. An additional amount of ethylenediamine (0.2 mL) and Yttrium (III) trifluoromethane sulfonate (1 mg) was added, and the mixture was stirred at 10° C. for 4 days. Additional ethylenediamine (0.2 mL) and Yttrium (III) trifluoromethane sulfonate (1 mg) were then added, and the mixture stirred for an additional 24 h at 100° C. The reaction mixture was cooled to room temperature and purified by preparative TLC (25% EtOAc/hexane) to provide Example 769 (0.022 g).

Preparation of Example 770

Scheme 76

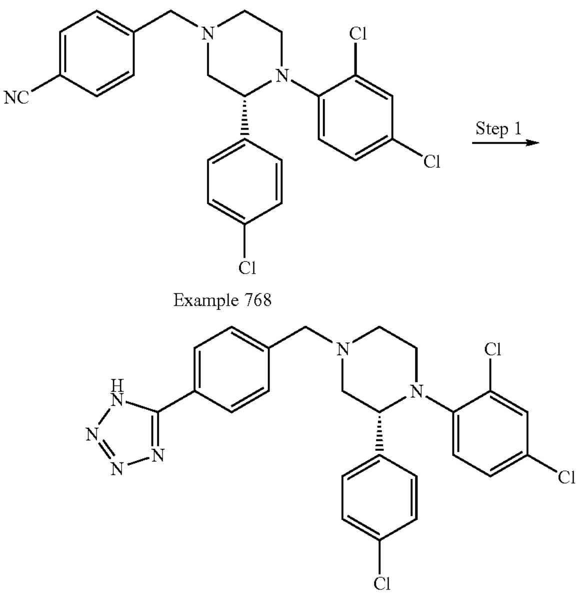

Example 768

Example 770

Step 1:

To the piperazine Example 768 (0.1 g, 0.22 mmol) in DMF (2.2 mL) in a microwave reactor vial was added $NaN_3$ (0.17 g, 2.6 mmol) and $NH_4Cl$ (0.14 g, 2.6 mmol). The reaction mixture was capped and irradiated in a microwave reactor at 20 W. The reaction temperature reached ~220° C. The reaction was irradiated for 25 minutes and cooled to room temperature. Saturated $NaHCO_3$ was added and the mixture was extracted with EtOAc. The organic layer was washed with water and brine. The organic layer was then dried ($MgSO_4$), filtered, and concentrated in vacuo. The residue was purified by silica gel preparative TLC (5% MeOH/$CH_2Cl_2$) to provide Example 770 (0.035 g).

Preparation of Examples 771-773

Scheme 77

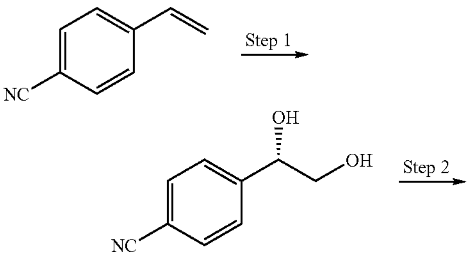

-continued

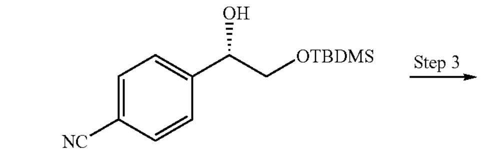

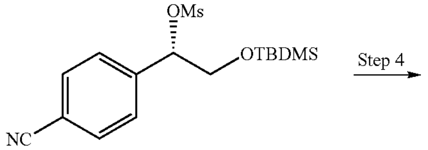

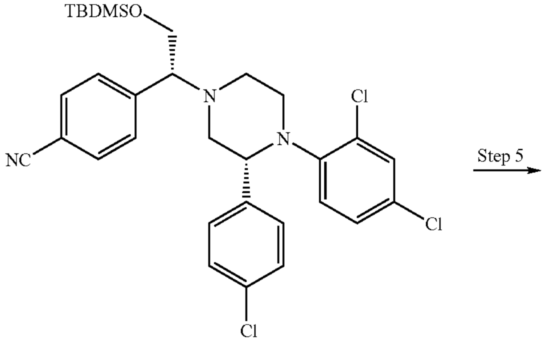

Example 771

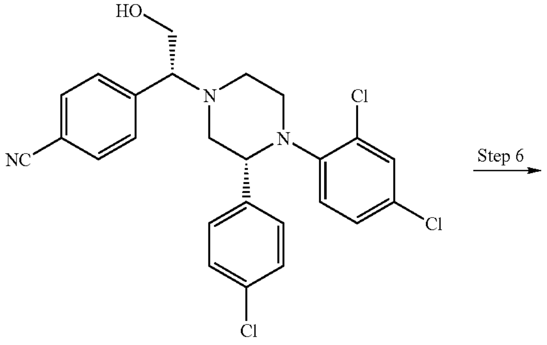

Example 772

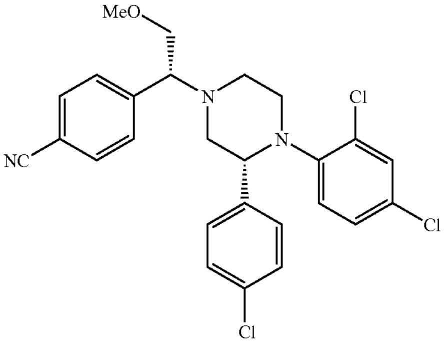

Example 773

Step 1

To AD mix α (available from Aldrich) (10.8 g) in tert-butyl alcohol/water (1:1) (78 mL) at 0° C. was added 4-cyanostyrene (1.0 g, 7.7 mmol). The reaction was stirred for 20 h, allowing the cold bath to expire. The reaction was cooled to 0° C. and solid sodium sulfite (10 g) was added. The mixture was allowed to warm to room temperature while stirring for 1 h. The mixture was then extracted with EtOAc. The organic layer was washed with water and brine, dried ($MgSO_4$), filtered, and concentrated in vacuo. The residue was purified by silica gel chromatography (5% $MeOH/CH_2Cl_2$) to provide the corresponding diol (1.24 g).

Step 2

To the diol prepared in step 1 (0.62 g, 3.8 mmol) in DMF (10 mL) at 0° C. was added imidazole (0.65 g, 9.5 mmol) followed by TBDMS-Cl (i.e., tert-butyldimethylsilyl chloride) (0.69 g, 4.6 mmol). The reaction mixture was stirred for 4 h while warming to room temperature. The reaction mixture was poured into brine and then extracted with EtOAc. The organic layer was washed with water, brine, dried ($MgSO_4$), filtered, and concentrated in vacuo. The residue was purified by silica gel chromatography (20% EtOAc/hexane) to provide a tert-butyldimethylsilyl ether (0.67 g).

Step 3

To the tert-butyldimethylsilyl ether prepared in step 2 (0.67 g, 2.4 mmol) in $CH_2Cl_2$ (8 mL) at 0° C. was added TEA (i.e., triethylamine) (0.5 mL, 3.6 mmol) followed by $MeSO_2Cl$ (0.22 mL, 2.9 mmol). The reaction mixture was stirred for 2 h and $CH_2Cl_2$ was added. The mixture was washed with saturated $NaHCO_{3(aq)}$, water, and brine. The organic layer was dried ($MgSO_4$), filtered, and concentrated in vacuo to provide a methylsulfonyl ester (0.87 g) that was used directly in step 4 without further purification.

Step 4

To the methylsulfonyl ester prepared in step 3 (0.34 g, 1 mmol) in acetonitrile (3 mL) was added piperazine Example 304 (0.44 g, 1.25 mmol) and potassium carbonate (0.35 g, 2.5 mmol). The reaction mixture was warmed to reflux and stirred for 24 h. The reaction was cooled to room temperature and EtOAc was added. The mixture was washed with water and brine. The organic layer was dried ($MgSO_4$), filtered, and concentrated in vacuo. The residue was purified by silica gel chromatography (20% EtOAc/hexane) to provide Example 771 (0.40 g).

Step 5

To Example 771 (0.40 g, 0.66 mmol) in THF (2 mL) at 0° C. was added tetrabutylammonium fluoride (1.0 M in THF, 0.74 mL). The reaction was stirred for 20 h while warming to room temperature. EtOAc was added and the mixture washed with water and brine. The organic layer was dried ($MgSO_4$), filtered, and concentrated in vacuo. The residue was purified by silica gel chromatography (60% EtOAc/hex) to provide Example 772 (0.31 g, 0.64 mmol).

Step 6

To Example 772 (0.15 g, 0.31 mmol) in THF at room temperature was added NaH (15 mg) (60% dispersion in mineral oil) followed by methyl iodide (0.024 mL, 0.38 mmoL). The reaction was stirred at room temperature for 20 h. Water was added slowly and the mixture was extracted with EtOAc. The organic layer was washed with water, brine, dried ($MgSO_4$), filtered, and concentrated in vacuo. The residue was purified by silica gel chromatography (30% EtOAc/hexane) to provide Example 773 (0.14 g).

Preparation of Example 774

Example 774

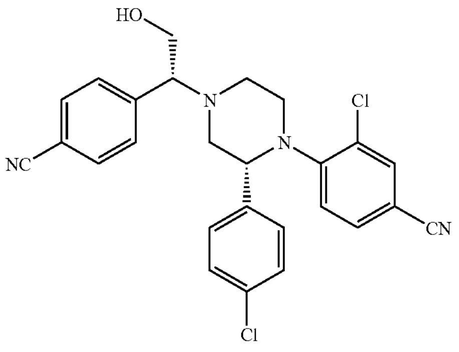

Example 774 was prepared using procedures similar to those used to prepare Example 772, except that the piperazine Example 305 was used instead of Example 304 in step 4 of Scheme 77.

Preparation of Example 775

Example 775

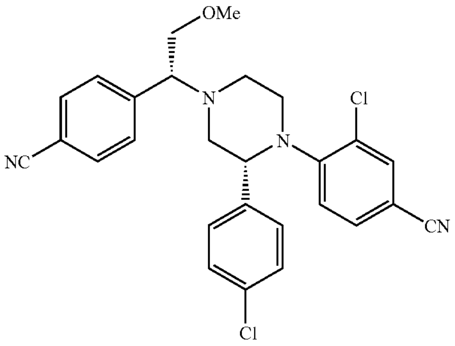

Example 775 was prepared using procedures similar to those used to prepare Example 773, except that the piperazine Example 305 was used instead of Example 304 in step 4 of Scheme 77.

Preparation of Example 776a and 776b

Scheme 78

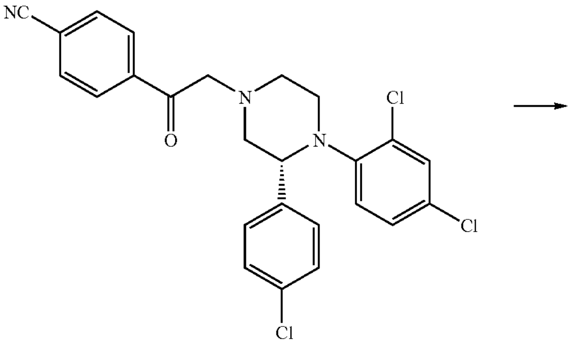

Example 399

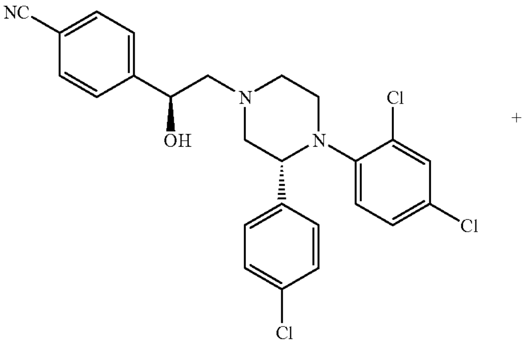

Example 776a

-continued

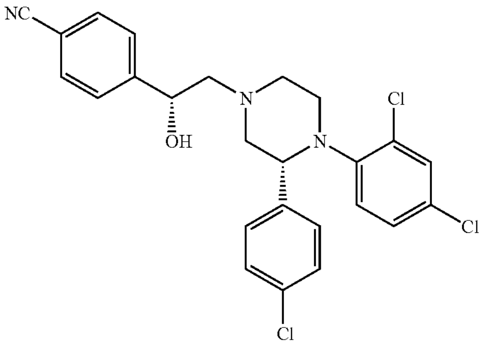

Example 776b

To Example 399 (0.16 g, 0.32 mmol) in MeOH (1.5 mL) at 0° C. was added $NaBH_4$ (0.012 g, 0.32 mmol) (with gas evolution). The cold bath was removed from the reaction vessel, and the reaction mixture was stirred for 45 minutes. The reaction mixture was concentrated in vacuo. Water was added and the reaction mixture was extracted with EtOAc. The organic layers were combined and washed with water, brine, dried ($MgSO_4$), filtered, and concentrated in vacuo. The residue was purified by silica gel chromatography (5-50% EtOAc/hexane) to provide the corresponding alcohol as a mixture of diastereomers (0.8 g, 0.16 mmol). The diastereomers were separated by chiral prep HPLC (Chiraicel OD, 85% hexane/IPA, 50 mL/min, 254 nm) to provide Examples 776a and 776b.

Alternatively, Example 776a was prepared by the following method:

Scheme 79

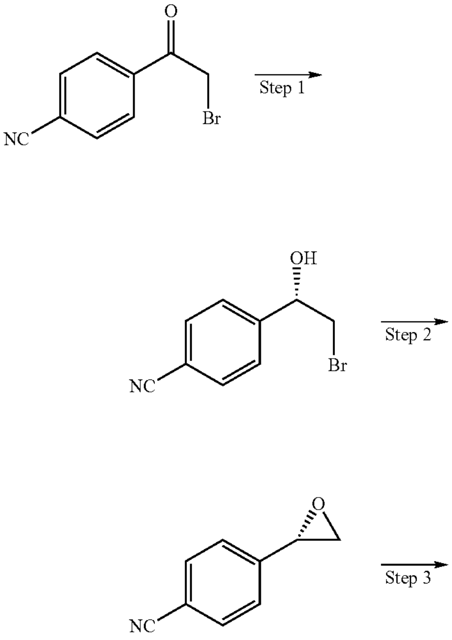

-continued

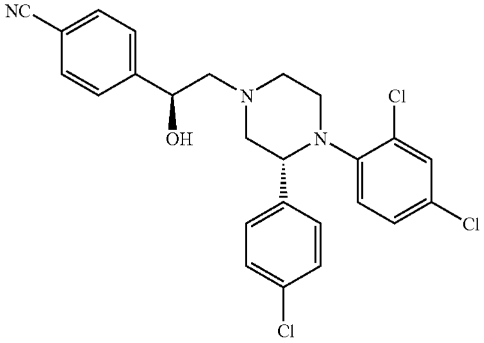

Example 776a

Step 1:

To 2-bromo-4'-cyanoacetophenone (1.0 g, 4.5 mmol) in THF (4.5 mL) at 0° C. was added (S)-2-methyl-CBS-oxazaborolidine (1M in toluene, 0.89 mL) followed by $BH_3.SMe_2$ (2.0M in THF, 1.3 mL). The mixture was stirred at 0° C. for 75 minutes. MeOH (~5 mL) was added (with gas evolution) and the mixture was stirred for 15 minutes. The reaction mixture was concentrated in vacuo. The residue was taken up into $CH_2Cl_2$ and washed with 1N HCL, water, and brine, dried ($MgSO_4$), filtered, and concentrated in vacuo to provide the corresponding alcohol which was used directly in the next step without further purification.

Step 2:

The alcohol prepared in step 1 was taken up into toluene (40 mL). 1N NaOH (40 mL) was added and the mixture was stirred at room temperature for 20 h. The organic layer was washed with water and brine, dried ($MgSO_4$), filtered, and concentrated in vacuo. The resulting residue was purified by silica gel chromatography (0-20% EtOAc/hexane) to provide the epoxide (0.52 g, 3.6 mmol).

Step 3:

To the piperazine Example 304 (0.15 g, 0.44 mmol) was added the epoxide (0.07 g, 0.48 mmol) prepared in step 2. The reaction mixture was heated neat (without solvent) at 100° C. for 18 h. The reaction was cooled to room temperature and the reaction mixture purified by silica gel chromatography (5-40% EtOAc/hexanes) to provide a residue (0.14 g) which was further purified by chiral preparative HPLC [Chiralcel OD 85% hexanes/IPA, 50 mL/min, 254 nm] to provide Example 776a (0.13 g, 0.29 mmol).

Preparation of Example 777

Example 777

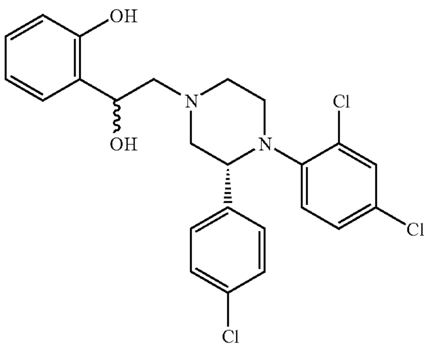

Example 777 was prepared from the ketone Example 780 by reduction with sodium borohydride as described above in Scheme 78.

Preparation of Example 778

Scheme 80

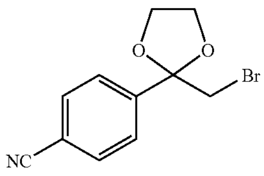

+

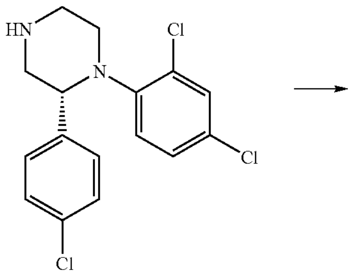

Example 304

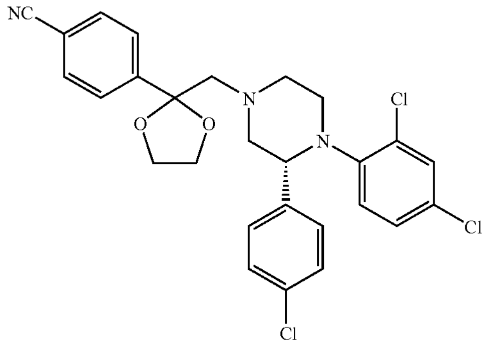

Example 778

To the piperazine Example 304 (0.15 g, 0.44 mmol) in DMF (1.5 mL) was added potassium carbonate (0.12 g, 0.88 mmol) and 4-[2-(bromomethyl)-1,3-dioxalane-2-yl]benzonitrile (0.15 g, 0.55 mmol) followed by sodium iodide (0.025 g, 0.16 mmol). The reaction mixture was warmed to 150° C. and stirred for 4 days. The reaction mixture was then cooled to room temperature and water was added. The resulting mixture was extracted with EtOAc. The combined organic layers were washed with water, brine, dried ($MgSO_4$), filtered, and concentrated in vacuo. The residue was purified by silica gel chromatography (0-25% EtOAc/hex) to provide the ketal Example 778 (0.10 g).

Preparation of Example 779

Example 779

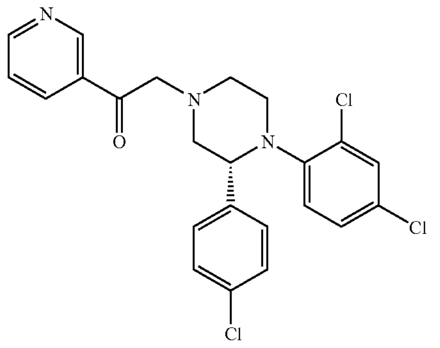

Example 779 was prepared in the same manner as Example 398 in scheme 69 except that 2-bromo-1-pyridin-3-ylethan-1-one hydrobromide was used instead of 2-bromoacetophenone.

Preparation of Example 780

Example 780

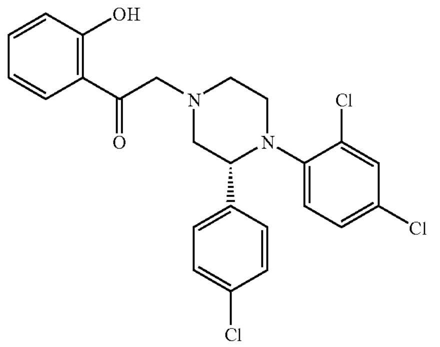

Example 780 was prepared in the same manner as Example 398 in scheme 69 except that 2-bromo-2'-hydroxyacetophenone was used instead of 2-bromoacetophenone.

Preparation of Example 781

Example 781

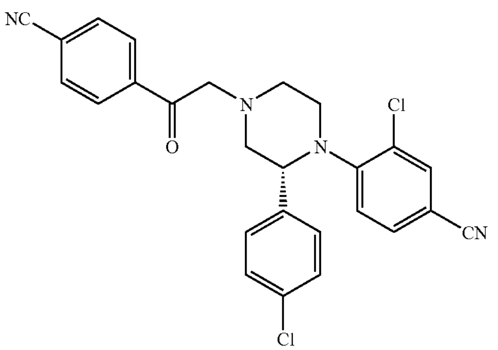

The ketone Example 781 was prepared in the same manner as Example 399, except that the piperazine Example 305 was used instead of Example 304.

Preparation of Examples

Scheme 81

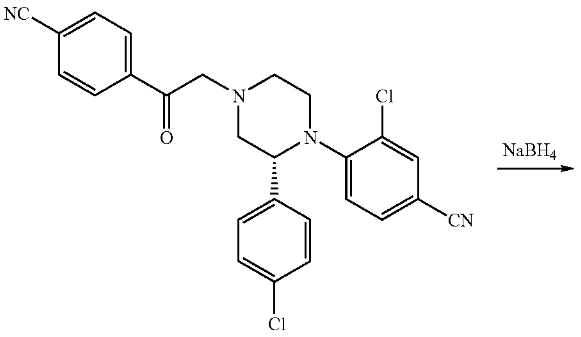

Example 781

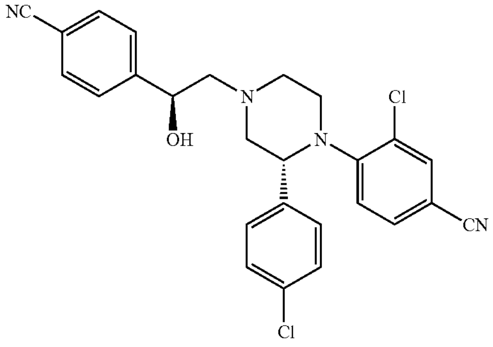

Example 781a

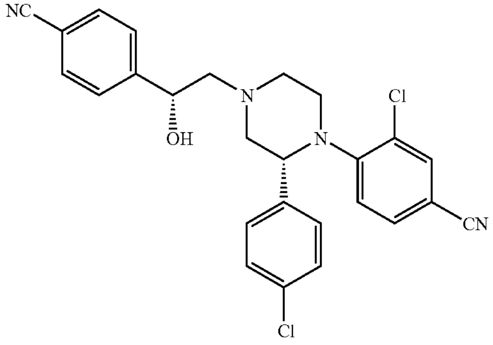

Example 781b

Example 781 was reduced with $NaBH_4$ using the procedure described for the reduction of Example 399 in Scheme 78 to provide a mixture of diasteromers (781a and 781b) that were separated by chiral preparative HPLC [Chiralcel OD, 25% IPA/hexane, 50 mL/min., 254 nm].

Preparation of Example 782-786

Examples 782-786 were prepared accoriding to the method of Scheme 38, using the appropriate piperazine and alcohol shown in Table XXII, below.

TABLE XXII
| Example # | Piperazine | Alcohol | Structure |
| --- | --- | --- | --- |
| 782 | 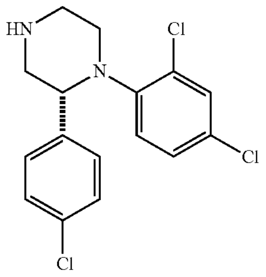 | 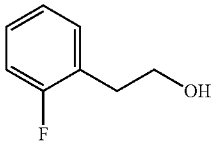 | 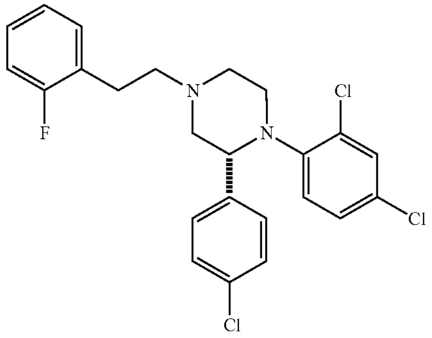 |
| 783 | 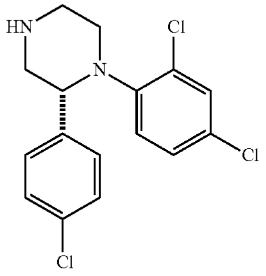 | 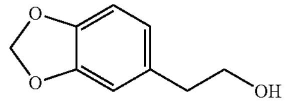 | 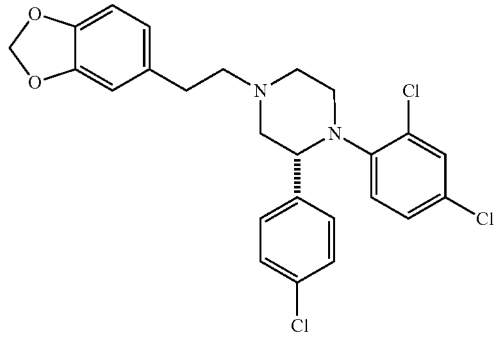 |
| 784 | 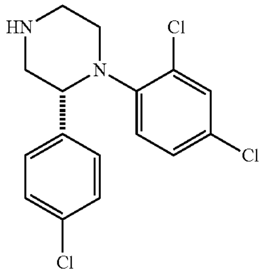 | 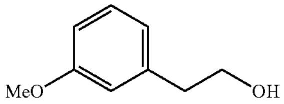 | 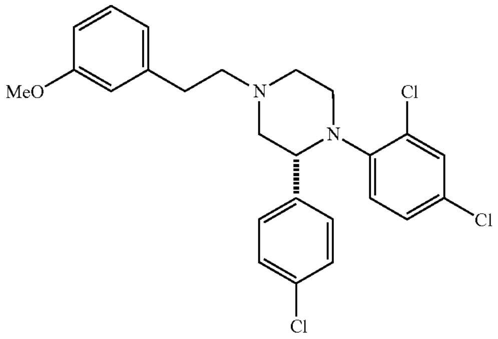 |
| 785 | 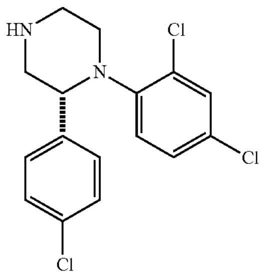 | 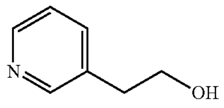 | 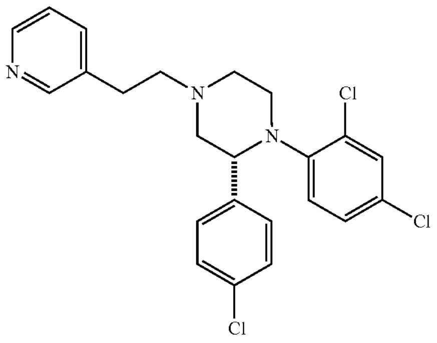 |

TABLE XXII-continued
| Example # | Piperazine | Alcohol | Structure |
| --- | --- | --- | --- |
| 786 | 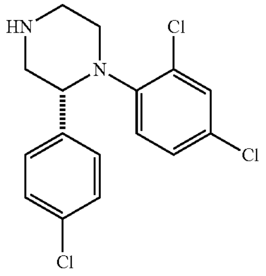 | 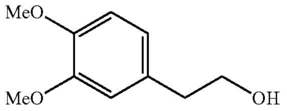 | 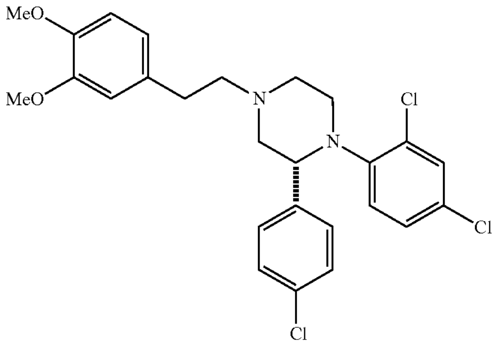 |
Preparation of Examples 787-792
Using the procedures outlined in Scheme 41, the Amide and Amine Examples 787-792 were prepared from the piperazine Example 304 and the carboxylic acid indicated in Table XXIII, below.
TABLE XXIII
| Acid | Amide | Amine |
| --- | --- | --- |
| 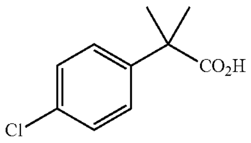 | 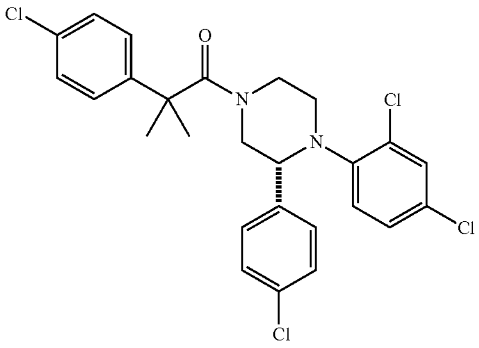<br>Example 787 | 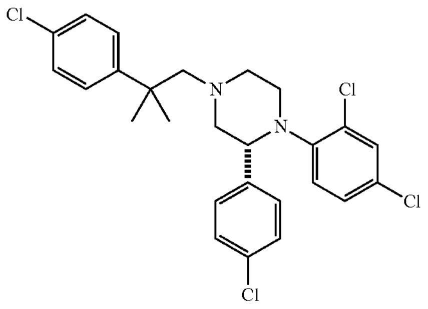<br>Example 788 |
| 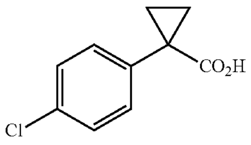 | 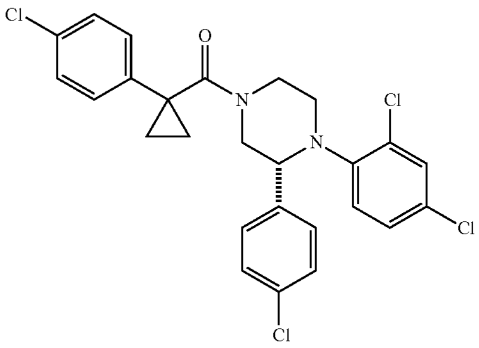<br>Example 789 | 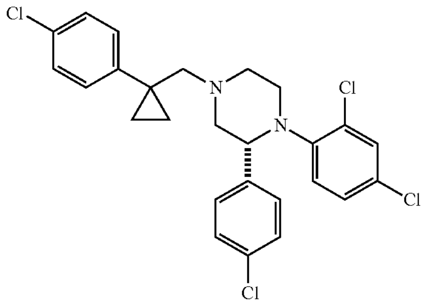<br>Example 790 |

TABLE XXIII-continued

| Acid | Amide | Amine |
| --- | --- | --- |
| 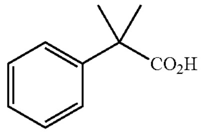 | 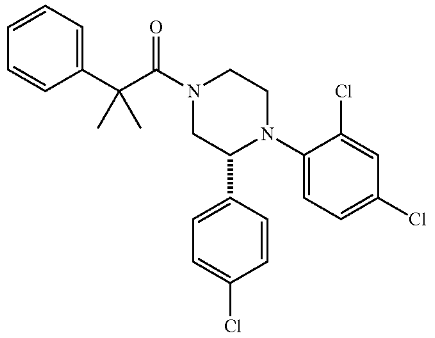 Example 791 | 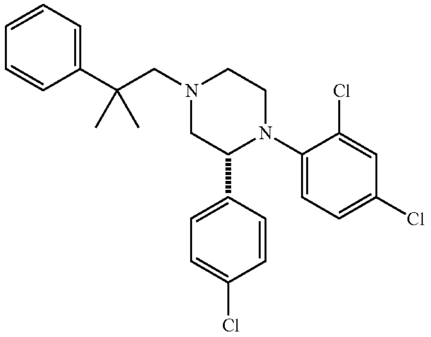 Example 792 |

Preparation of Example 793

Scheme 82

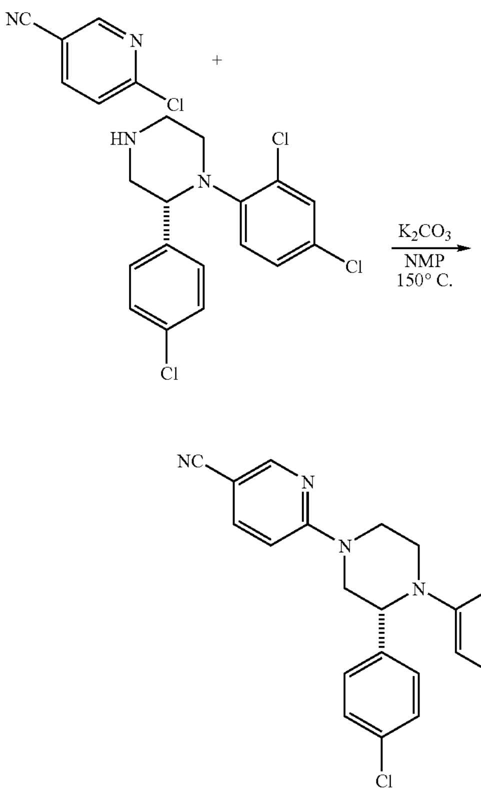

Example 793

2-Chloro-5-cyano-pyridine (56 mg), the piperazine Example 304 (125 mg), and $K_2CO_3$ (100 mg) were taken up in 1-methyl-2-pyrrolidinone (NMP) and heated at 120° C. for 18 hours. The reaction mixture was heated at 150° C. for 5 hours. The reaction mixture was cooled and partitioned between EtOAc and saturated $NaHCO_{3(aq.)}$. The aqueous layer was extracted with EtOAc. The combined organic layers were washed with brine and dried ($MgSO_4$). Filtration and concentration gave a yellow oil. Purification via thin-layer preparative chromatography (1.2/1 $CH_2Cl_2$/hexanes, $SiO_2$) furnished 110 mg (63%) of Example 793 as a colorless oil.

Preparation of Example 794

Scheme 83

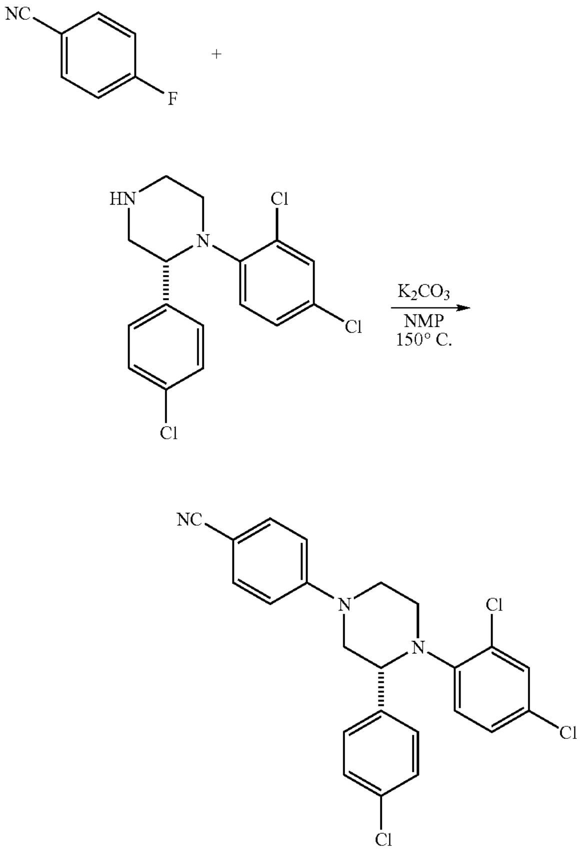

Example 794

Example 794 was prepared according to the procedure outlined above in Scheme 82 using 4-fluoro-benzonitrile in place of 2-chloro-5-cyano-pyridine.

Preparation of Examples 795-796

Scheme 84

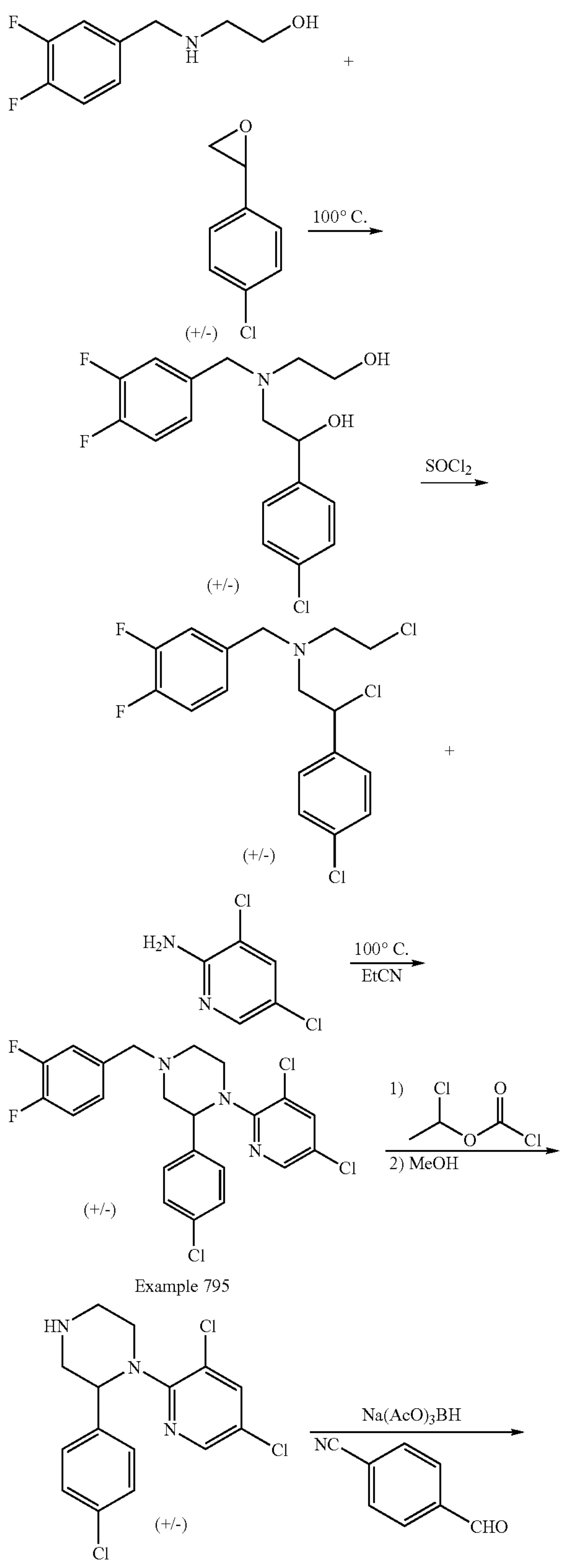

Example 795

-continued

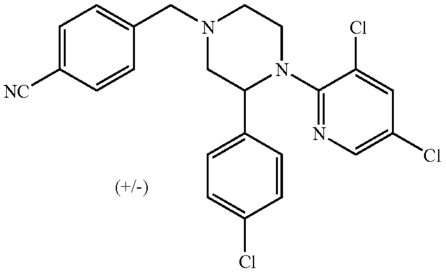

Example 796

Example 795 was prepared according to the procedures outlined in Steps 2, 3, and 4 of Scheme 7 using 2-(4-chlorophenyl)oxirane and 2-amino-3,5-dichloropyridine as indicated in Scheme 84, above. Example 796 was prepared from Example 795 using the procedures outlined in Steps 5 and 6 of Scheme 24.

Preparation of Examples 797, 797a, and 797b

Scheme 85

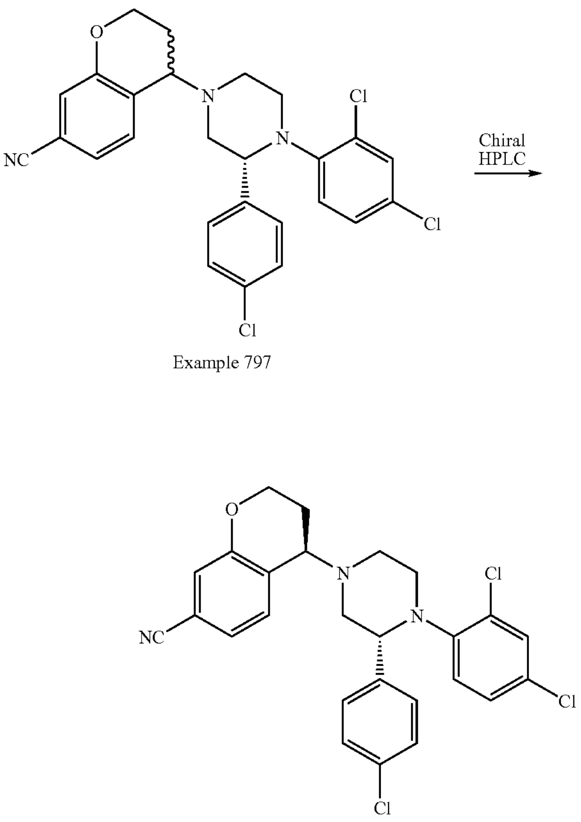

Example 797

Example 797a

-continued

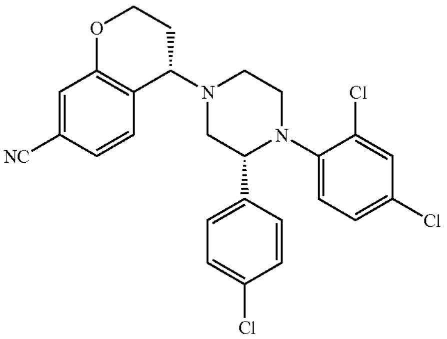

Example 797b

Example 797 was prepared in the same manner as Example 397 in Scheme 68 except that 7-cyano-4-chromanone was used instead of 4-chromanone. The 1:1 mixture of diastereomers of Example 797 was separated by chiral preparative HPLC [Chiralcel OD, 10% IPA/hexane, 40 mL/min, 254 nm] to provide a faster eluting and a slower eluting isomer.

Preparation of Examples 798, 798a, and 798b

Scheme 86

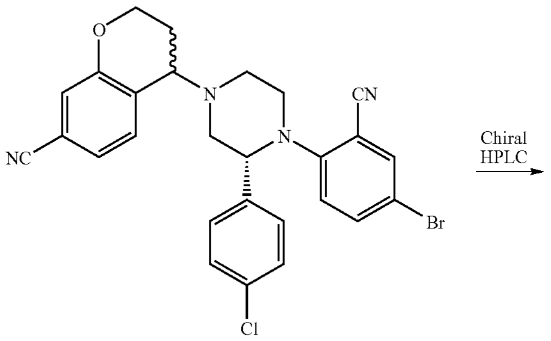

Example 798

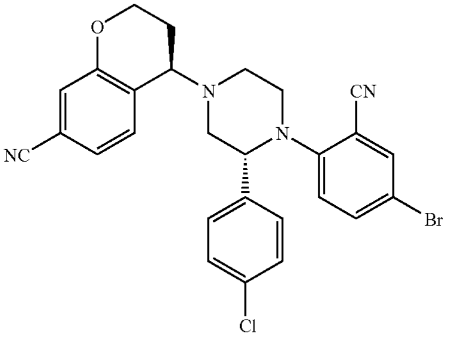

Example 798a

-continued

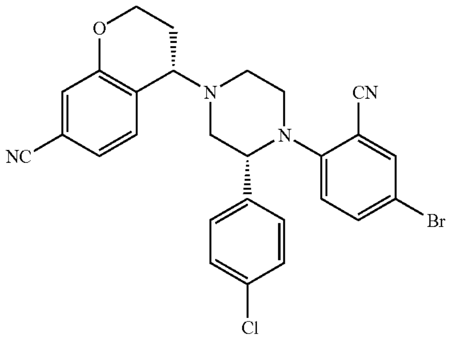

Example 798b

Example 798 was prepared in the same manner as Example 397 in scheme 68 except that 7-cyano-4-chromanone was used instead of 4-chromanone in step 1 and Example 309 was used instead of Example 304 in step 3. The 1:1 mixture of diastereomers of Example 798 was separated by chiral preparative HPLC [Chiralcel OD, 20% IPA/hexane, 45 ml/min, 254 nm] to provide a faster eluting and a slower eluting isomer.

Preparation of Examples 799, 799a, and 799b

Scheme 87

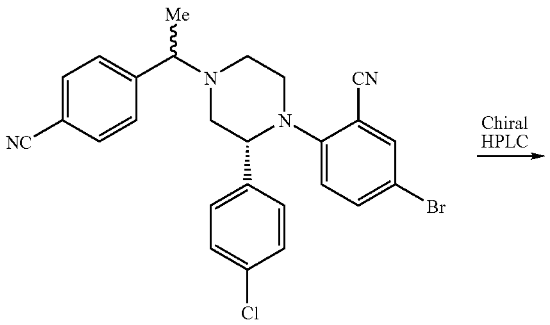

Example 799

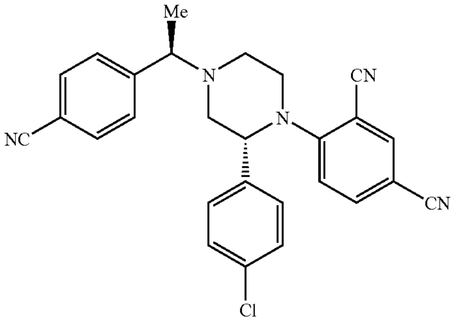

Example 799a

-continued

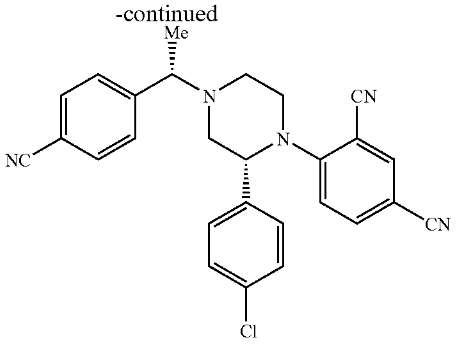

Example 799b

Example 799 was prepared in the same manner as Example 391 in scheme 65 except that Example 309 was used instead of Example 304 in step 3. The 1:1 mixture of diastereomers of Example 799 was separated by chiral preparative HPLC [Chiralcel OD, 25% IPA/hexane, 50 mL/min, 254 nm] to provide a faster eluting and a slower eluting isomer.

Preparation of Example 800

Scheme 88

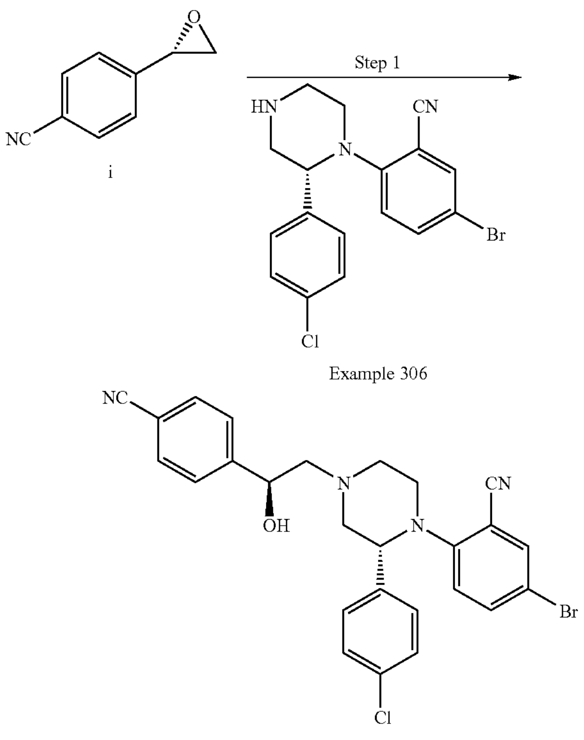

i

Example 306

Example 800

Step 1:

The epoxide i was prepared in the same manner as iii in Scheme 28 except that 2-bromo-4'-cyanoacetophenone was used instead of 2-bromo-4'-chloroacetophenone and (S)-CBS-oxazaborolidine was used instead of (R)-CBS-oxazaborolidine in step 1. The epoxide i (0.05 g, 0.36 mmol) was heated neat (without solvent) with the piperazine Example 306 (0.13 g, 0.33 mmol) at 100° C. for 18 h. The reaction mixture was cooled to room temperature and purified by silica gel chromatography (60% EtOAc/hexane). The residue, which contained a small amount of the minor diastereomer, was purified by chiral preparative HPLC [Chiralcel OD, 20% IPA/hexane, 50 mL/min, 254 nm] to provide Example 800 (0.11 g).

Preparation of Example 801

Example 801

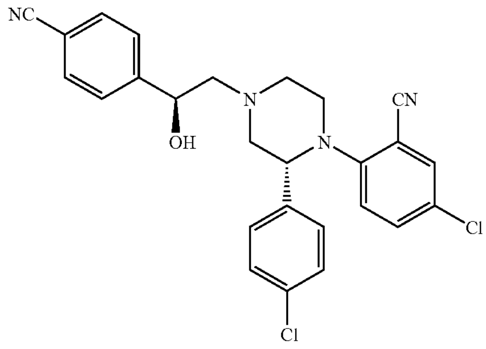

Example 801 was prepared in the same manner as Example 800 except that Example 305 was used instead of Example 306 in Scheme 88.

Preparation of Examples 802, 802a, and 802b

Scheme 89

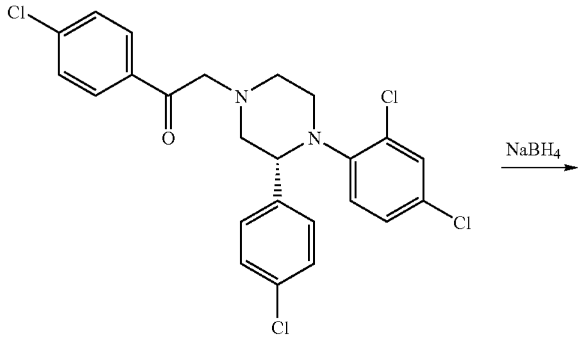

Example 802

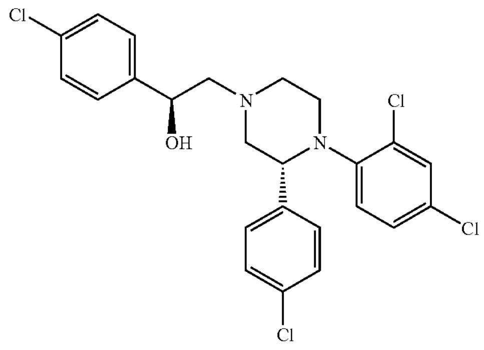

Example 802a

-continued

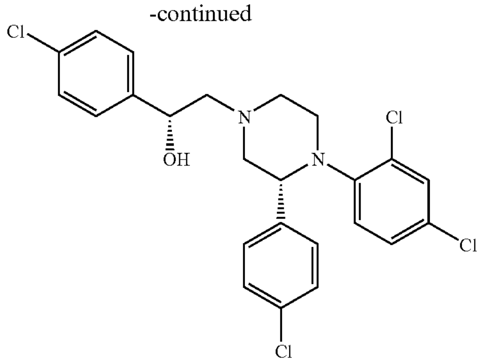

Example 802b

The ketone Example 802 was prepared in the same manner as Example 398 in Scheme 69 except that 2-bromo-4'-cyanoacetophenone was used instead of 2-bromoacetophenone. Example 802a and Example 802b were prepared in the same manner as Example 776a and Example 776b in Scheme 78 except that Example 802 was used instead of Example 399.

Method for Evaluating Cannabinoid $CB_1$ and $CB_2$ Affinity

Competition binding assays for cannabinoid $CB_1$ and $CB_2$ affinity were performed by incubating commercially purchased membranes prepared from cells expressing each receptor subtype (8 μg pro) with 0.5 nM $^3$H-CP55,940, a non-selective cannabinoid agonist, along with concentrations of drug ranging from 0.0001-3 μM in Buffer A (5 mM $MgCl_2$, 2.5 mM EDTA and 013% BSA). Non-specific binding was defined in the presence of 10 μM CP55,940. For saturation studies, concentrations of $^3$H-CP55,940 ranging from 0.1-5 nM were incubated with membranes in the presence and absence of 10 μM CP55,940. Assays were terminated after incubation for 1½ hours by rapid filtration onto 0.3% polyethylenamine treated GF/C filterplates using a BRANDEL cell harvester. The plates were dried and MICROSCINT scintillation cocktail was added, after which the bound radioactivity was quantified using a TOPCOUNT scintillation counter.

The dissociation constant ($K_d$) of $^3$H-CP55,940 at the $CB_1$ and $CB_2$ receptor were determined by plotting specific binding at each concentration of radioligand, and analysis by non-linear regression. For competition studies, the concentration of each drug that inhibited 50 percent of $^3$H-CP55,940 binding ($IC_{50}$) was determined by non-linear regression analysis of the radioligand displacement curves. Affinity constants ($K_i$) were calculated using the equation derived by Cheng and Prusoff (1973), defined as: $IC_{50}$/1+[conc. ligand/$K_d$]

GTPγS Binding Protocol

The functional efficacy of compounds to activate second messengers within the cell was determined utilizing the GTPγS binding assay. Guanine nucleotides are phosphorylated within the plasma membrane of the cell following binding and activation by agonists. A radiolabelled derivative of guanine triphosphate (GTP) is utilized in this assay as it cannot be dephosphorylated and therefore accumulates following agonist binding. The simultaneous presence of an antagonist into this system will shift the agonist concentration curve to the right, with increasing concentrations of antagonist producing a greater rightward shift in the dose-response curve of the agonist.

Commercially purchased membranes were incubated with 10 mM GDP to allow sufficient substrate for phosphorylation in the presence of agonist. The membranes were then pre-incubated with increasing concentrations of test compound for 30 minutes to determine if they were capable of stimulating phosphorylation alone. Increasing concentrations of the non-selective cannabinoid agonist WIN55,122 were then added in the presence or absence of each concentration of test compound. The assay was then incubated for 1 hour at room temperature. To complete the assay, $^{35}$S-GTPγS was added and the assay incubated for another 30 minutes. Assays were terminated by rapid filtration onto 10 mM sodium phosphate-treated GF/C filterplates using a Brandel cell harvester. The plates were dried and Microscint scintillation cocktail was added, after which the bound radioactivity was quantified using a Topcount scintillation counter.

The stimulation of $^{35}$S-GTPγS binding as a function of the concentration of the agonist WIN55,122, in the absence and presence of test compound, was plotted and the $EC_{50}$ determined by nonlinear regression analysis using GraphPad Prism software. A Schild analysis of the rightward shift in the dose response curve of WIN55,122 in the presence of test compound was determined by plotting the concentration of test compound against the negative log of the dose ratio [1−($EC_{50}$ agonist+test compound/EC50 of agonist alone)]. A linear regression analysis yields the Kb, defined as the X-intercept of the linear equation.

Preparation of Compound of Formula (II)

Step 1): To a solution of (S)-4-phenyl-2-oxazolidinone (41 g, 0.25 mol) in $CH_2Cl_2$ (200 mL), was added 4-dimethylaminopyridine (2.5 g, 0.02 mol) and triethylamine (84.7 mL, 0.61 mol) and the reaction mixture was cooled to 0° C. Methyl-4-(chloroformyl)butyrate (50 g, 0.3 mol) was added as a solution in $CH_2Cl_2$ (375 mL) dropwise over 1 h, and the reaction was allowed to warm to 22° C. After 17 h, water and $H_2SO_4$ (2N, 100 mL), was added the layers were separated, and the organic layer was washed sequentially with NaOH (10%), NaCl (sat'd) and water. The organic layer was dried over $MgSO_4$ and concentrated to obtain a semicrystalline product.

Step 2): To a solution of $TiCl_4$ (18.2 mL, 0.165 mol) in $CH_2Cl_2$ (600 mL) at 0° C., was added titanium isopropoxide (16.5 mL, 0.055 mol). After 15 min, the product of Step 1 (49.0 g, 0.17 mol) was added as a solution in $CH_2Cl_2$ (100 mL). After 5 min., diisopropylethylamine (DIPEA) (65.2 mL, 0.37 mol) was added and the reaction mixture was stirred at 0° C. for 1 h, the reaction mixture was cooled to −20° C., and 4-benzyloxybenzylidine(4-fluoro)aniline (114.3 g, 0.37 mol) was added as a solid. The reaction mixture was stirred vigorously for 4 h at −20° C., then acetic acid was added as a solution in $CH_2Cl_2$ dropwise over 15 min, the reaction mixture was allowed to warm to 0° C., and $H_2SO_4$ (2N) was added. The reaction mixture was stirred an additional 1 h, the layers were separated, washed with water, separated and the organic layer was dried. The crude product was crystallized from ethanol/water to obtain the pure intermediate.

Step 3): To a solution of the product of Step 2 (8.9 g, 14.9 mmol) in toluene (100 mL) at 50° C., was added N,O-bis(trimethylsilyl)acetamide (BSA) (7.50 mL, 30.3 mmol). After 0.5 h, solid TBAF (0.39 g, 1.5 mmol) was added and the reaction mixture stirred at 50° C. for an additional 3 h. The reaction mixture was cooled to 22° C., $CH_3OH$ (10 mL), was added. The reaction mixture was washed with HCl (1N), $NaHCO_3$ (1N) and NaCl (sat'd.), and the organic layer was dried over $MgSO_4$.

Step 4): To a solution of the product of Step 3 (0.94 g, 2.2 mmol) in $CH_3OH$ (3 mL), was added water (1 mL) and $LiOH.H_2O$ (102 mg, 2.4 mmole). The reaction mixture was stirred at 22° C. for 1 h and then additional $LiOH.H_2O$ (54 mg, 1.3 mmole) was added. After a total of 2 h, HCl (1N) and EtOAc was added, the layers were separated, the organic layer was dried and concentrated in vacuo. To a solution of the resultant product (0.91 g, 2.2 mmol) in $CH_2Cl_2$ at 22° C., was added ClC(O)C(O)Cl (0.29 mL, 3.3 mmol) and the mixture stirred for 16 h. The solvent was removed in vacuo.

Step 5): To an efficiently stirred suspension of 4-fluorophenylzinc chloride (4.4 mmol) prepared from 4-fluorophenylmagnesium bromide (1M in THF, 4.4 mL, 4.4 mmol) and $ZnCl_2$ (0.6 g, 4.4 mmol) at 4° C., was added tetrakis(triphenyl-phosphine)palladium (0.25 g, 0.21 mmol) followed by the product of Step 4 (0.94 g, 2.2 mmol) as a solution in THF (2 mL). The reaction was stirred for 1 h at 0° C. and then for 0.5 h at 22° C. HCl (1N, 5 mL) was added and the mixture was extracted with EtOAc. The organic layer was concentrated to an oil and purified by silica gel chromatography to obtain 1-(4-fluorophenyl)-4(S)-(4-hydroxyphenyl)-3(R)-(3-oxo-3-phenylpropyl)-2-azetidinone:

HRMS calc'd for $C_{24}H_{19}F_2NO_3$=408.1429, found 408.1411.

Step 6): To the product of Step 5 (0.95 g, 1.91 mmol) in THF (3 mL), was added (R)-tetrahydro-1-methyl-3,3-diphenyl-1H,3H-pyrrolo-[1,2-c][1,3,2]oxazaborole (120 mg, 0.43 mmol) and the mixture was cooled to −20° C. After 5 min, borohydride-dimethylsulfide complex (2M in THF, 0.85 mL, 1.7 mmol) was added dropwise over 0.5 h. After a total of 1.5 h, $CH_3OH$ was added followed by HCl (1 N) and the reaction mixture was extracted with EtOAc to obtain 1-(4-fluorophenyl)-3(R)-[3(S)-(4-fluorophenyl)-3-hydroxypropyl)]-4(S)-[4-(phenylmethoxy)phenyl]-2-azetidinone (compound 6A-1) as an oil. $^1H$ in $CDCl_3$ d H3=4.68. J=2.3 Hz. CI (M+H) 500.

Use of (S)-tetra-hydro-1-methyl-3,3-diphenyl-1H,3H-pyrrolo-[1,2-c][1,3,2]oxazaborole gives the corresponding 3(R)-hydroxypropyl azetidinone (compound 6B-1). $^1H$ in $CDCl_3$ d H3=4.69. J=2.3 Hz. CI (M+H) 500.

To a solution of compound 6A-1 (0.4 g, 0.8 mmol) in ethanol (2 mL), was added 10% Pd/C (0.03 g) and the reaction mixture was stirred under a pressure (60 psi) of $H_2$ gas for 16 h. The reaction mixture was filtered and the solvent was concentrated to obtain compound 6A. Mp 164-166° C.; CI (M+H) 410.

$[\alpha]_D^{25}$=−28.10 (c 3, $CH_3OH$). Elemental analysis calc'd for $C_{24}H_{21}F_2NO_3$: C, 70.41; H, 5.17; N, 3.42; found C, 70.25; H, 5.19; N, 3.54.

Similarly treat compound 6B-1 to obtain compound 6B. Mp 129.5-132.5° C.; CI (M+H) 410. Elemental analysis calc'd for $C_{24}H_{21}F_2NO_3$: C, 70.41; H, 5.17; N, 3.42; found C, 70.30; H, 5.14; N, 3.52.

Step 6' (Alternative): To a solution of the product of Step 5 (0.14 g, 0.3 mmol) in ethanol (2 mL), was added 10% Pd/C (0.03 g) and the reaction was stirred under a pressure (60 psi) of $H_2$ gas for 16 h. The reaction mixture was filtered and the solvent was concentrated to afford a 1:1 mixture of compounds 6A and 6B.

We claim:

1. A compound of Formula (I):

(I)

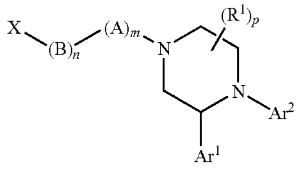

or a pharmaceutically acceptable salt or ester thereof, wherein:

$Ar^1$ and $Ar^2$ are each phenyl substituted with one or more groups $Y^1$ that are independently selected from the group consisting of $(C_2\text{-}C_6)$alkyl, cycloalkyl, heterocycloalkyl, heterocycloalkenyl, halo, haloalkyl, benzyl, aryl, heteroaryl, —O-aryl, —S-aryl, —$S(O)_2$-alkyl, —$S(O)_2$-cycloalkyl, —$(O)_2$-aryl, -alkylene-CN, —CN, —C(O)-alkyl, —C(O)-aryl, —C(O)-haloalkyl, —C(O)O-alkyl, —$N(R^2)$C(O)-alkyl, —$N(R^2)$C(O)—$N(R^2)_2$, —OH, —O-alkyl, —O-haloalkyl, —O-alkylene-C(O)OH, —S-alkyl, —S-haloalkyl, -alkylene-OH, -alkylene-C(O)—O-alkyl, —O-alkylene-aryl, and —$N(R^5)_2$ wherein said aryl, heteroaryl, the aryl portion of said —O-aryl, the aryl portion of said —S-aryl, the aryl portion of said —$S(O)_2$-aryl, the aryl portion of said benzyl, the aryl portion of said —C(O)-aryl, and the aryl portion of said —O-alkylene-aryl of $Y^1$ are unsubstituted or substituted with one or more groups Z; or two groups $Y^1$ form a —O—$CH_2$—O— group;

n and m are independently 0 or 1;

A is selected from the group consisting of —C(O)—, —$S(O)_2$—, —C(=N—$OR^2$)—, and —$(C(R^2)_2)_q$— wherein q is 1, 2, or 3;

B is selected from the group consisting of —$N(R^2)$—, —C(O)—, and —$(C(R^3)_2)_r$— wherein r is 1 or 2, with the proviso that when B is —C(O)—, then A is —C(O)— or —$(C(R^2)_2)_q$—;

X is selected from the group consisting of H, alkyl, —S-alkyl, —$S(O)_2$-alkyl, —$S(O)_2$-cycloalkyl, —$S(O)_2$-aryl, —$S(O)_2$-heteroaryl, cycloalkyl, benzo-fused cycloalkyl, benzo-fused heterocycloalkyl, benzo-fused heterocycloalkenyl, heterocycloalkyl, —$C(R^2)$=$C(R^2)$-aryl, —$C(R^2)$=$C(R^2)$-heteroaryl, —$OR^2$, —O-alkylene-O-alkyl, —S-aryl, —$N(R^4)_2$, —$(C(R^2)_2)$—S-heteroaryl, —C(O)—O-alkyl, —C(O)-aryl, —C(O)-heteroaryl, —N=O, —C(S-alkyl)=N—$S(O)_2$-aryl, —$C(N(R^2)_2)$=N—$S(O)_2$-aryl, and —$(C(R^2)_2)_s$-aryl wherein s is 0, 1, or 2, wherein the heteroaryl portion of said —$(C(R^2)_2)_s$-heteroaryl, the aryl portion of said —$C(R^2)$=$C(R^2)$-aryl, the heteroaryl portion of said —$C(R^2)$=$C(R^2)$-heteroaryl, the aryl portion of said —S-aryl, the aryl portion of said —$S(O)_2$-aryl, the heteroaryl portion of said —$S(O)_2$-heteroaryl, the aryl portion of said —C(O)-aryl, the heteroaryl portion of said —C(O)-heteroaryl, the aryl portion of said —$(C(R^2)_2)_s$-aryl, the aryl portion of said —C(S-alkyl)=N—$S(O)_2$-aryl, the aryl portion of said —$C(N(R^2)_2)$=N—$S(O)_2$-aryl, the benzo portion of said benzo-fused cycloalkyl, the benzo portion of said benzo-fused heterocycloalkyl, and the benzo portion of said benzo-fused heterocycloalkenyl of X are unsubstituted or substituted with one or more groups $Y^1$ that are independently selected from the group consisting of alkyl, cycloalkyl, heterocycloalkyl, heterocycloalkenyl, halo, haloalkyl, benzyl, aryl, heteroaryl, —O-aryl, —S-aryl, —$S(O)_2$-alkyl, —$S(O)_2$-cycloalkyl, —$S(O)_2$-aryl, -alkylene-CN, —C(O)-alkyl, —C(O)-aryl, —C(O)-haloalkyl, —C(O)O-alkyl, —$N(R^2)$C(O)-alkyl, —$N(R^2)$C(O)—$N(R^2)_2$, $R^2$—OH —O-alkyl, —O-haloalkyl, —O-alkylene-C(O)(OH), S-alkyl, —S-haloalkyl, -alkylene-OH, -alkylene-C(O)—O-alkyl, —O-alkylene-aryl, and —$N(R^5)$ wherein said aryl, heteroaryl, the aryl portion of said —O-aryl, the aryl portion of said —S-aryl, the aryl portion of said —$S(O)_2$aryl, the aryl portion of said benzyl, the aryl portion of said —C(O)-aryl, and the aryl portion of said —O-alkylene-aryl of $Y^1$ are unsubstituted or substituted with one or more groups Z; or two groups $Y^1$ form a —O—$CH_z$—O— group; and said cycloalkyl, the cycloalkyl portion of said —$S(O)_2$-cycloalkyl, said heterocycloalkyl, the cycloalkyl portion of said benzo-fused cycloalkyl, the heterocycloalkyl portion of said benzo-fused heterocycloalkyl, and the heterocycloalkenyl portion of said benzo-fused heterocycloalkenyl of X are unsubstituted or substituted with one or more groups $Y^2$;

with the proviso that the group X—$(B)_n$-$(A)_m$-, taken as a group, is not selected from the group consisting of —$C(R^2)$═$C(R^2)$-aryl and —$(C(R^2)_2)_s$-aryl wherein s is 0, 1, or 2, wherein the aryl portion of said —$C(R^2)$═$C(R^2)$-aryl and the aryl portion of said —$(C(R^2)_2)_s$-aryl of X are unsubstituted or substituted with one or more groups $Y^1$ independently selected from the group consisting of alkyl, cycloalkyl, halo, haloalkyl, benzyl, aryl, —O-aryl, —S-aryl, —$S(O)_2$-alkyl, —$S(O)_2$-cycloalkyl, —$S(O)_2$-aryl, -alkylene-CN, —CN, —C(O)-alkyl, —C(O)-aryl, —C(O)-haloalkyl, —C(O)O-alkyl, —$N(R^2)$C(O)-alkyl, —$N(R^2)$C(O)—$N(R^2)_2$, —OH, —O-alkyl, —O-haloalkyl, —O-alkylene-C(O)OH, —S-alkyl, —S-haloalkyl, -alkylene-OH, -alkylene-C(O)—O-alkyl, —O-alkylene-aryl, and —$N(R^5)_2$, wherein said aryl and the aryl portion of said —O-aryl, —S-aryl, —$S(O)_2$-aryl, benzyl, —C(O)-aryl, and —O-alkylene-aryl of $Y^1$ are unsubstituted or substituted with one or more groups Z;

each $R^1$ is independently selected from the group consisting of alkyl, haloalkyl, -alkylene-$N(R^5)_2$, -alkylene-$OR^2$, alkylene-$N_3$, -alkylene-CN, and alkylene-O—$S(O)_2$-alkyl; or two $R^1$ groups attached to the same ring carbon atom form a carbonyl group;

p is 0, 1, 2, 3, or 4;

each $R^2$ is independently H, alkyl, or aryl, wherein said aryl of $R^2$ is unsubstituted or substituted with one or more groups $Y^1$ that are independently selected from the group consisting of alkyl, cycloalkyl, heterocycloalkyl, heterocycloalkenyl, halo, haloalkyl, benzyl, a heteroaryl, —O-aryl, —S-aryl, —$(O)_2$-alkyl, —$S(O)_2$-cycloalkyl, —$S(O)_2$-aryl, -alkylene-CN, —CN, —C(O)-alkyl, —C(O)-aryl, —C(O)-haloalkyl, —C(O)O-alkyl, —$N(R^2)$C(O)-alkyl, —$N(R^2)$C(O)—$N(R^2)_2$, —OH, —O-alkyl, —O-haloalkyl, —O-alkylene-C(O)OH, —S-alkyl, —S-haloalkyl, -alkylene-OH, -alkylene-C(O)—O-alkyl, —O-alkylene-aryl, and —$N(R^5)$ wherein said aryl, heteroaryl, the aryl portion of said —O-aryl, the aryl portion of said —S-aryl the aryl portion of said —S(O)-aryl the aryl portion of said benzyl, the aryl portion of said —C(O)-aryl, and the aryl portion of said —O-alkylene-aryl of $Y^1$ are unsubstituted or substituted with one or more groups Z; or two groups $Y^1$ form a —O—$CH_2$—O— group;

each $R^3$ is independently selected from the group consisting of H, alkyl, unsubstituted aryl, —$OR^2$, -alkylene-O-alkyl, -alkylene-OH and aryl substituted with one or more $Y^1$ groups that are independently selected from the group consisting of alkyl, cycloalkyl, heterocycloalkyl, heterocycloalkenyl, halo, haloalkyl, benzyl, aryl, heteroaryl, —O-aryl, —S-aryl, —$S(O)_2$-alkyl, —$S(O)_2$-cycloalkyl, —$S(O)_2$-aryl, -alkylene-CN, —CN, —C(O)-alkyl, —C(O)-aryl, —C(O)-haloalkyl, —C(O)O-alkyl, —$N(R^2)$C(O)-alkyl, —$N(R^2)$C(O)—$N(R^2)_2$, —OH, —O-alkyl, —O-haloalkyl, —O-alkylene-C(O)OH, —S-alkyl, —S-haloalkyl, -alkylene-OH, -alkylene-C(O)—O-alkyl, —O-alkylene-aryl, and —$N(R^5)_2$ wherein said aryl, heteroaryl, the aryl portion of said —O-aryl, the aryl portion of said —S-aryl, the aryl portion of said —$S(O)_2$-aryl, the aryl portion of said benzyl, the aryl portion of said —C(O)-aryl, and the aryl portion of said —O-alkylene-aryl of $Y^1$ are unsubstituted or substituted with one or more groups Z; or two groups $Y^1$ form a —O—$CH_z$—O— group;

each $R^4$ is independently selected from the group consisting of H, alkyl, aryl, —C(O)—O-alkyl, —C(O)-alkyl, —C(O)-aryl, and —$S(O)_2$aryl, wherein said aryl, the aryl portion of said —C(O)-aryl, and the aryl portion of said —$S(O)_2$aryl of $R^4$ are unsubstituted or substituted with one or more $Y^1$ groups that are independently selected from the group consisting of alkyl, cycloalkyl, heterocycloalkyl, heterocycloalkenyl, halo, haloalkyl, benzyl, aryl, heteroaryl, —O-aryl, —S-aryl, —$S(O)_2$-alkyl, —$S(O)_2$-cycloalkyl, —$S(O)_2$-aryl, -alkylene-CN, —CN, —C(O)-alkyl, —C(O)-aryl, —C(O)-haloalkyl, —C(O)O-alkyl, —$N(R^2)$C(O)-alkyl, —$N(R^2)$C(O)—$N(R^2)$—OH, —O-alkyl, —O-haloalkyl, —O-alkylene-C(O)OH, —S-alkyl, —S-haloalkyl, -alkylene-OH, -alkylene-C(O)—O-alkyl, —O-alkylene-aryl, and —$N(R^5)_2$ wherein said aryl, heteroaryl, the aryl portion of said —O-aryl, the aryl portion of said —S-aryl, the aryl portion of said —$S(O)_2$-aryl, the aryl portion of said benzyl, the aryl portion of said —C(O)-aryl, and the aryl portion of said —O-alkylene-aryl of $Y^1$ are unsubstituted or substituted with one or more groups Z; or two groups $Y^1$ form a —O—$CH_2$— group;

each $R^5$ is independently selected from the group consisting of H, alkyl, aryl, —$S(O)_2$-alkyl, —$S(O)_2$-cycloalkyl, —$S(O)_2$-aryl, —C(O)—$N(R^2)_2$, —C(O)-alkyl, and -alkylene-OH, wherein said aryl and the aryl portion of said —$S(O)_2$-aryl of $R^5$ are unsubstituted or substituted with one or more Z groups;

each $Y^2$ is independently selected from the group consisting of alkyl, haloalkyl, aryl, -alkylene-aryl, —CN, —C(O)-alkyl, —$S(O)_2$-cycloalkyl, -alkylene-$N(R^4)_2$, —C(O)-alkylene-$N(R^4)_2$, —C(O)—O-alkyl, —C(O)-aryl, and —C(O)-haloalkyl, wherein said aryl and the aryl portion of said —C(O)-aryl of $Y^2$ are unsubstituted or substituted with one or more groups Z; or two groups $Y^2$ form a —O—$CH_2CH_2$—O— group; or two of said $Y^2$ substituents attached to the same ring carbon atom of a cycloalkyl, benzo-fused cycloalkyl, benzo-fused heterocycloalkyl, benzo-fused heterocycloalkenyl, or heterocycloalkyl ring, together with the ring carbon atom to which they are both attached, form a carbonyl group; and each Z is independently selected from the group consisting of alkyl, halo, haloalkyl, —OH, —O-alkyl, and —CN.

2. The compound of claim 1, or a pharmaceutically acceptable salt or ester thereof, wherein:

$Ar^1$ and $Ar^2$ are each phenyl substituted with one or more groups $Y^1$ that are independently selected from the group consisting of $(C_2$-$C_6)$alkyl, $(C_3$-$C_{10})$cycloalkyl, $(C_2$-$C_{10})$heterocycloalkyl, $(C_2$-$C_{10})$heterocycloalkenyl, halo, $(C_1$-$C_6)$haloalkyl, benzyl, $(C_6$-$C_{10})$aryl, $(C_2$-$C_{10})$heteroaryl, —O—$(C_6$-$C_{10})$aryl, —S—$(C_6$-$C_{10})$aryl, —$S(O)_2$—$(C_1$-$C_6)$alkyl, —$S(O)_2$—$(C_3$-$C_{10})$cycloalkyl, —$S(O)_2$—($C_6$-$C_{10}$)aryl, —($C_1$-$C_6$)alkylene-CN, —CN, —C(O)—($C_1$-$C_6$)alkyl, —C(O)—($C_6$-$C_{10}$)aryl, —C(O)—($C_1$-$C_6$)haloalkyl, —C(O)O—($C_1$-$C_6$)alkyl, —N($R^2$)C(O)—($C_1$-$C_6$)alkyl, —N($R^2$)C(O)—N($R^2$)$_2$, —OH, —O—($C_1$-$C_6$)alkyl, —O—($C_1$-$C_6$)haloalkyl, —O—($C_1$-$C_6$)alkylene-C(O)OH, —S—($C_1$-$C_6$)alkyl, —S—($C_1$-$C_6$)haloalkyl, —($C_1$-$C_6$)alkylene-OH, —($C_1$-$C_6$)alkylene-C(O)—O—($C_1$-$C_6$)alkyl, —O—($C_1$-$C_6$)alkylene-($C_6$-$C_{10}$)aryl, and —N($R^5$)$_2$, wherein said ($C_6$-$C_{10}$)aryl, said ($C_2$-$C_{10}$)heteroaryl, the ($C_6$-$C_{10}$)aryl portion of said —O—($C_6$-$C_{10}$)aryl, the ($C_6$-$C_{10}$)aryl portion of said —S—($C_6$-$C_{10}$)aryl, the ($C_6$-$C_{10}$)aryl portion of said —$S(O)_2$—($C_6$-$C_{10}$)aryl said benzyl, the ($C_6$-$C_{10}$)aryl portion of said —C(O)—($C_6$-$C_{10}$)aryl, and the ($C_6$-$C_{10}$)aryl portion of said —O—($C_1$-$C_6$)alkylene-($C_6$-$C_{10}$)aryl of $Y^1$ are unsubstituted or substituted with one or more groups Z; or two groups $Y^1$ form a —O—$CH_2$—O— group;

X is selected from the group consisting of H, ($C_1$-$C_6$)alkyl, —S—($C_1$-$C_6$)alkyl, —$S(O)_2$—($C_1$-$C_6$)alkyl, —$S(O)_2$—($C_3$-$C_{10}$)cycloalkyl, —$S(O)_2$—($C_6$-$C_{10}$)aryl, —$S(O)_2$—($C_2$-$C_{10}$)heteroaryl, ($C_3$-$C_{10}$)cycloalkyl, benzo-fused ($C_3$-$C_{10}$)cycloalkyl, benzo-fused ($C_2$-$C_{10}$)heterocycloalkyl, benzo-fused ($C_2$-$C_{10}$)heterocycloalkenyl, ($C_2$-$C_{10}$)heterocycloalkyl, —C($R^2$)═C($R^2$)—($C_6$-$C_{10}$)aryl, —C($R^2$)═C($R^2$)—($C_2$-$C_{10}$)heteroaryl, —O$R^2$, —O—($C_1$-$C_6$)alkylene-O—($C_1$-$C_6$)alkyl, —S—($C_6$-$C_{10}$)aryl, —N($R^4$)$_2$, —(C($R^2$)$_2$)$_s$—($C_2$-$C_{10}$)heteroaryl, —C(O)—O—($C_1$-$C_6$)alkyl, —C(O)—($C_6$-$C_{10}$)aryl, —C(O)—($C_2$-$C_{10}$)heteroaryl, —N═O, —C(S—($C_1$-$C_6$)alkyl)═N—$S(O)_2$—($C_6$-$C_{10}$)aryl, —C(N($R^2$)$_2$)═N—$S(O)_2$—($C_6$-$C_{10}$)aryl, and —(C($R^2$)$_2$)$_s$—($C_6$-$C_{10}$)aryl wherein s is 0, 1, or 2, wherein the ($C_2$-$C_{10}$)heteroaryl portion of said —(C($R^2$)$_2$)$_s$—($C_2$-$C_{10}$)heteroaryl, the ($C_6$-$C_{10}$)aryl portion of said —C($R^2$)═C($R^2$)—($C_6$-$C_{10}$)aryl, the ($C_2$-$C_{10}$)heteroaryl portion of said —C($R^2$)═C($R^2$)—($C_2$-$C_{10}$)heteroaryl, the ($C_6$-$C_{10}$)aryl portion of said —S—($C_6$-$C_{10}$)aryl, the ($C_6$-$C_{10}$)aryl portion of said —$S(O)_2$—($C_6$-$C_{10}$)aryl, the ($C_2$-$C_{10}$)heteroaryl portion of said —$S(O)_2$—($C_2$-$C_{10}$)heteroaryl, the ($C_6$-$C_{10}$)aryl portion of said —C(O)—($C_6$-$C_{10}$)aryl, the ($C_2$-$C_{10}$)heteroaryl portion of said —C(O)—($C_2$-$C_{10}$)heteroaryl, the ($C_6$-$C_{10}$)aryl portion of said —(C($R^3$)$_2$)$_s$—($C_6$-$C_{10}$)aryl, the ($C_6$-$C_{10}$)aryl portion of said —C(S—($C_1$-$C_6$)alkyl)═N—$S(O)_2$—($C_6$-$C_{10}$)aryl, the ($C_6$-$C_{10}$)aryl portion of said —C(N($R^2$)$_2$)═N—$S(O)_2$—($C_6$-$C_{10}$)aryl, the benzo portion of said benzo-fused ($C_3$-$C_{10}$)cycloalkyl, the benzo portion of said benzo-fused ($C_2$-$C_{10}$)heterocycloalkyl, and the benzo portion of said benzo-fused ($C_2$-$C_{10}$)heterocycloalkenyl of X are unsubstituted or substituted with one or more groups $Y^1$ that are independently selected from the group consisting of ($C_1$-$C_6$)alkyl, ($C_3$-$C_{10}$)cycloalkyl, ($C_2$-$C_{10}$)heterocycloalkyl, ($C_2$-$C_{10}$)heterocycloalkenyl, halo, ($C_1$-$C_6$)haloalkyl, benzyl, ($C_6$-$C_{10}$)aryl, ($C_2$-$C_{10}$)heteroaryl), —O—($C_6$-$C_{10}$)aryl, —S—($C_6$-$C_{10}$)aryl, —$S(O)_2$—($C_1$-$C_6$)alkyl, —$S(O)_2$—($C_3$-$C_{10}$)cycloalkyl, —$S(O)_2$—($C_6$-$C_{10}$)aryl, —($C_1$-$C_6$)alkylene-CN, —CN, —C(O)—($C_1$-$C_6$)alkyl, —C(O)—($C_6$-$C_{10}$)aryl, —C(O)—$C_1$-$C_6$)haloalkyl, —C(O)O—($C_1$-$C_6$)alkyl, —N($R^2$)C(O)—($C_1$-$C_6$)alkyl, —N($R^2$)C(O)—N($R^2$)$_2$, —OH, —O—($C_1$-$C_6$)alkyl, —O—($C_1$-$C_6$)haloalkyl, —O—($C_1$-$C_6$)alkylene-C(O)OH, —S—($C_1$-$C_6$)alkyl, —S—($C_1$-$C_6$)haloalkyl, —($C_1$-$C_6$)alkylene-OH, —($C_1$-$C_6$)alkylene-C(O)—O—($C_1$-$C_6$)alkyl, —O—($C_1$-$C_6$)alkylene-($C_6$-$C_{10}$)aryl, and —N($R^5$)$_2$, wherein said ($C_6$-$C_{10}$)aryl, said ($C_2$-$C_{10}$)heteroaryl, the ($C_6$-$C_{10}$)aryl portion of said —(O)—($C_6$-$C_{10}$)aryl, the ($C_6$-$C_{10}$)aryl portion of said —S—($C_6$-$C_{10}$)aryl, the ($C_6$-$C_{10}$)aryl portion of said —$S(O)_2$—($C_6$-$C_{10}$)aryl, said benzyl, the ($C_6$-$C_{10}$)aryl portion of said —C(O)—($C_6$-$C_{10}$)aryl, and the ($C_6$-$C_{10}$)aryl portion of —(O)—($C_1$-$C_{10}$)aryl of $Y^1$ are unsubstituted or substituted with one or more groups Z; or two groups $Y^1$ form a —O—$CH_2$—O— group; and said ($C_3$-$C_{10}$)cycloalkyl, the ($C_3$-$C_{10}$)cycloalkyl portion of said —$S(O)_2$—($C_3$-$C_{10}$)cycloalkyl, said ($C_2$-$C_{10}$)heterocycloalkyl, the ($C_3$-$C_{10}$)cycloalkyl portion of said benzo-fused ($C_3$-$C_{10}$)cycloalkyl, the ($C_2$-$C_{10}$)heterocycloalkyl portion of said benzo-fused ($C_2$-$C_{10}$)heterocycloalkyl, and the ($C_2$-$C_{10}$)heterocycloalkenyl portion of said benzo-fused ($C_2$-$C_{10}$)heterocycloalkenyl of X are unsubstituted or substituted with one or more groups $Y^2$;

with the proviso that the group X—$(B)_n$-$(A)_m$- is not alkyl nor is it selected from the group consisting of —C($R^2$)═C($R^2$)—($C_6$-$C_{10}$)aryl and —(C($R^2$)$_2$)$_s$—($C_6$-$C_{10}$)aryl wherein s is 0, 1, or 2, wherein the ($C_6$-$C_{10}$)aryl portion of said —C($R^2$)═C($R^2$)—($C_6$-$C_{10}$)aryl and the ($C_6$-$C_{10}$)aryl portion of said —(C($R^3$)$_2$)$_s$—($C_6$-$C_{10}$)aryl of X are unsubstituted or substituted with one or more groups $Y^1$ independently selected from the group consisting of ($C_1$-$C_6$)alkyl, ($C_3$-$C_{10}$)cycloalkyl, halo, ($C_1$-$C_6$)haloalkyl, benzyl, ($C_6$-$C_{10}$)aryl, ($C_2$-$C_{10}$)heteroaryl, —O—($C_6$-$C_{10}$)aryl, —S—($C_6$-$C_{10}$)aryl, —$S(O)_2$—($C_1$-$C_6$)alkyl, —$S(O)_2$—($C_3$-$C_{10}$)cycloalkyl, —$S(O)_2$—($C_6$-$C_{10}$)aryl, —($C_1$-$C_6$)alkylene-CN, —CN, —C(O)—($C_1$-$C_6$)alkyl, —C(O)—($C_6$-$C_{10}$)aryl, —C(O)—($C_1$-$C_6$)haloalkyl, —C(O)O—($C_1$-$C_6$)alkyl, —N($R^2$)C(O)—($C_1$-$C_6$)alkyl, —N($R^2$)C(O)—N($R^2$)$_2$, —OH, —O—($C_1$-$C_6$)alkyl, —O—($C_1$-$C_6$)haloalkyl, —O—($C_1$-$C_6$)alkylene-C(O)OH, —S—($C_1$-$C_6$)alkyl, —S—($C_1$-$C_6$)haloalkyl, —($C_1$-$C_6$)alkylene-OH, —($C_1$-$C_6$)alkylene-C(O)—O—($C_1$-$C_6$)alkyl, —O—($C_1$-$C_6$)alkylene-($C_6$-$C_{10}$)aryl, and —N($R^5$)$_2$, wherein said ($C_6$-$C_{10}$)aryl, the ($C_6$-$C_{10}$)aryl portion of —O—($C_6$-$C_{10}$)aryl, —S—($C_6$-$C_{10}$)aryl, —$S(O)_2$—($C_6$-$C_{10}$)aryl, benzyl, —C(O)—($C_6$-$C_{10}$)aryl, and the —O—($C_1$-$C_6$)alkylene-($C_6$-$C_{10}$)aryl of $Y^1$ are unsubstituted or substituted with one or more groups Z;

each $R^1$ is independently selected from the group consisting of ($C_1$-$C_6$)alkyl, ($C_1$-$C_6$)haloalkyl, —($C_1$-$C_6$)alkylene-N($R^5$)$_2$, —($C_1$-$C_6$)alkylene-O$R^2$, —($C_1$-$C_6$)alkylene-$N_3$, —($C_1$-$C_6$)alkylene-CN, and ($C_1$-$C_6$)alkylene-O—$S(O)_2$—($C_1$-$C_6$)alkyl, or two $R^1$ groups attached to the same ring carbon atom form a carbonyl group;

p is 0, 1, 2, 3, or 4;

each $R^2$ is independently H, ($C_1$-$C_6$)alkyl, or ($C_6$-$C_{10}$)aryl, wherein said ($C_6$-$C_{10}$)aryl of $R^2$ is unsubstituted or substituted with one or more groups $Y^1$ that are independently selected from the group consisting of ($C_1$-$C_6$)alkyl, ($C_3$-$C_{10}$)cycloalkyl, ($C_2$-$C_{10}$)heterocycloalkyl, ($C_2$-$C_{10}$)heterocycloalkenyl, halo, ($C_1$-$C_6$)haloalkyl, benzyl, ($C_6$-$C_{10}$)aryl, ($C_2$-$C_{10}$)heteroaryl, —O—($C_6$-$C_{10}$)aryl, —S—($C_6$-$C_{10}$)aryl, —$S(O)_2$—($C_1$-$C_6$)alkyl, —$S(O)_2$—($C_3$-$C_{10}$)cycloalkyl, —$S(O)_2$—($C_6$-$C_{10}$)aryl, —($C_1$-$C_6$)alkylene-CN, —CN, —C(O)—($C_1$-$C_6$)alkyl, —C(O)—($C_6$-$C_{10}$)aryl, —C(O)—($C_1$-$C_6$haloalkyl, —C(O)O—($C_1$-$C_6$)alkyl, —N($R^2$)C(O)—($C_1$-$C_6$)alkyl, —N($R^2$)C(O)—N($R^2$)$_2$, —OH, —O—($C_1$-$C_6$)alkyl, —O—($C_1$-$C_6$)haloalkyl, —O—

$(C_1-C_6)$alkylene-C(O)OH, —S—$(C_1-C_6)$alkyl, —S—$(C_1-C_6)$haloalkyl, —$(C_1-C_6)$alkylene-OH, —$(C_1-C_6)$alkylene-C(O)—O—$(C_1-C_6)$alkyl, —O—$(C_1-C_6)$alkylene-$(C_6-C_{10})$aryl, and —N($R^5$) wherein said $(C_6-C_{10})$aryl, said $(C_2-C_{10})$heteroaryl, the $(C_6-C_{10})$aryl portion of said —O—$(C_6-C_{10})$aryl, the $(C_6-C_{10})$aryl portion of said —S—$(C_6-C_{10})$aryl, the $(C_6-C_{10})$aryl portion of said —$S(O)_2$—$(C_6-C_{10})$aryl, said benzyl, the $(C_6-C_{10})$aryl portion of said —C(O)—$(C_6-C_{10})$aryl, and the $(C_6-C_{10})$aryl portion of said —O—$(C_1-C_6)$alkylene-$(C_6-C_{10})$aryl of $Y^1$ are unsubstituted or substituted with one or more groups Z; or two groups $Y^1$ form a —O—$CH_2$—O— group;

each $R^3$ is independently selected from the group consisting of H, $(C_1-C_6)$alkyl, unsubstituted $(C_6-C_{10})$aryl, —$OR^2$, —$(C_1-C_6)$alkylene-O—$(C_1-C_6)$alkyl, —$(C_1-C_6)$alkylene-OH and $(C_6-C_{10})$aryl substituted with one or more $Y^1$ groups that are independently selected from the group consisting of $(C_1-C_6)$alkyl, $(C_3-C_{10})$cycloalkyl, $(C_2-C_{10})$heterocycloalkyl, $(C_2-C_{10})$heterocycloalkenyl, halo, $(C_1-C_6)$haloalkyl, benzyl, $(C_6-C_{10})$aryl, $(C_2-C_{10})$heteroaryl, —O—$(C_6-C_{10})$aryl, —S—$(C_6-C_{10})$aryl, —$S(O)_2$—$(C_1-C_6)$alkyl, —$S(O)_2$—$(C_3-C_{10})$cycloalkyl, —$S(O)_2$—$(C_6-C_{10})$aryl, —$(C_1-C_6)$alkylene-CN, —CN, —C(O)—$(C_1-C_6)$alkyl, —C(O)—$(C_1-C_{10})$aryl, —C(O)—$(C_1-C_6)$haloalkyl, —C(O)O—$(C_1-C_6)$alkyl, —N($R^2$)C(O)—$(C_1-C_6)$alkyl, —N($R^2$)C(O)—N$(R^2)_2$, —OH, —O—$(C_1-C_6)$alkyl, —O—$(C_1-C_6)$haloalkyl, —O—$(C_1-C_6)$alkylene-C(O)OH, —S—$(C_1-C_6)$alkyl, —S—$(C_1-C_6)$haloalkyl, —$(C_1-C_6)$alkylene-OH, —$(C_1-C_6)$alkylene-C(O)—O—$(C_1-C_6)$alkyl, —O—$(C_1-C_6)$alkylene-$(C_6-C_{10})$aryl, and —N$(R^5)_2$, wherein $(C_1-C_{10})$aryl, said $(C_2-C_{10})$heteroaryl, the $(C_6-C_{10})$aryl portion of said —O—$(C_6-C_{10})$aryl, the $(C_6-C_{10})$aryl portion of said —S—$(C_6-C_{10})$aryl, the $(C_6-C_{10})$aryl portion of said —$S(O)_2$—$(C_6-C_{10})$aryl, said benzyl, the $(C_6-C_{10})$aryl portion of said —C(O)—$(C_6-C_{10})$aryl, and the $(C_6-C_{10})$aryl portion of said —O—$(C_1-C_6)$aryl of $Y^1$ are unsubstituted or substituted with one or more groups Z; or two groups $Y^1$ form a —O—$CH_2$—O— group;

each $R^4$ is independently selected from the group consisting of H, $(C_1-C_6)$alkyl, $(C_6-C_{10})$aryl, —C(O)—O—$(C_1-C_6)$alkyl, —C(O)—$(C_1-C_6)$alkyl, —C(O)—$(C_6-C_{10})$aryl, and —$S(O)_2$—$(C_6-C_{10})$aryl, wherein said $(C_6-C_{10})$aryl, the $(C_6-C_{10})$aryl portion of said —C(O)—$(C_6-C_{10})$aryl, and the $(C_6-C_{10})$aryl portion of said —$S(O)_2$—$(C_6-C_{10})$aryl of $R^4$ are unsubstituted or substituted with one or more $Y^1$ groups that are independently selected from the group consisting of $(C_1-C_6)$alkyl, $(C_3-C_{10})$cycloalkyl, $(C_2-C_{10})$heterocycloalkyl, $(C_2-C_{10})$heterocycloalkenyl, halo, $C_1-C_6$ haloalkyl, benzyl, $(C_6-C_{10})$aryl, $(C_2-C_{10})$heteroaryl, —O—$(C_6-C_{10})$aryl, —S—$(C_6-C_{10})$aryl, —$S(O)_2$—$(C_1-C_6)$alkyl, —$S(O)_2$—$(C_3-C_{10})$cycloalkyl, —$S(O)_2$—$(C_6-C_{10})$aryl, —$(C_1-C_6)$alkylene-CN, —CN, —C(O)—$(C_1-C_6)$alkyl, —C(O)—$(C_6-C_{10})$aryl, —C(O)—$(C_1-C_6)$haloalkyl, —C(O)O—$(C_1-C_6)$alkyl, —N($R^2$)C(O)—$(C_1-C_6)$alkyl, —N($R^2$)C(O)—N$(R^2)_2$, —OH, —O—$(C_1-C_6)$alkyl, —O—$(C_1-C_6)$haloalkyl, —O—$(C_1-C_6)$alkylene-C(O)OH, —S—$(C_1-C_6)$alkyl, —S—$(C_1-C_6)$haloalkyl, —$(C_1-C_6)$alkylene-OH, —$(C_1-C_6)$alkylene-C(O)—O—$(C_1-C_6)$alkyl, —O—$(C_1-C_6)$alkylene-$(C_6-C_{10})$aryl, and —N$(R^5)_2$, wherein said $(C_6-C_{10})$aryl, said $(C_2-C_{10})$heteroaryl, the $(C_6-C_{10})$aryl portion of said —O—$(C_6-C_{10})$aryl, the $(C_6-C_{10})$aryl portion of said —S—$(C_6-C_{10})$aryl, the $(C_6-C_{10})$aryl portion of said —$S(O)_2$—$(C_6-C_{10})$aryl, said benzyl, the $(C_6-C_{10})$aryl portion of said —C(O)—$(C_6-C_{10})$aryl, and the $(C_6-C_{10})$aryl portion of said —O—$(C_1-C_6)$alkylene-$(C_6-C_{10})$aryl of $Y^1$ are unsubstituted or substituted with one or more groups Z; or two groups $Y^1$ form a —O—$CH_2$—O— group;

each $R^5$ is independently selected from the group consisting of H, $(C_1-C_6)$alkyl, $(C_6-C_{10})$aryl, —$S(O)_2$—$(C_1-C_6)$alkyl, —$S(O)_2$—$(C_3-C_{10})$cycloalkyl, —$S(O)_2$-aryl, —C(O)—N$(R^2)_2$, —C(O)—$(C_1-C_6)$alkyl, and —$(C_1-C_6)$alkylene-OH, wherein said $(C_6-C_{10})$aryl and the $(C_6-C_{10})$aryl portion of said —$S(O)_2$—$(C_6-C_{10})$aryl of $R^5$ are unsubstituted or substituted with one or more Z groups;

each $Y^2$ is independently selected from the group consisting of $(C_1-C_6)$alkyl, $(C_1-C_6)$haloalkyl, $(C_6-C_{10})$aryl, —$(C_1-C_6)$alkylene-$(C_6-C_{10})$aryl, —CN, —C(O)—$(C_1-C_6)$alkyl, —$S(O)_2$—$(C_3-C_{10})$cycloalkyl, —$(C_1-C_6)$alkylene-N$(R^2)_2$, —C(O)—$(C_1-C_6)$alkylene-N$(R^4)_2$, —C(O)—O—$(C_1-C_6)$alkyl, —C(O)—$(C_6-C_{10})$aryl, and —C(O)—$(C_1-C_6)$haloalkyl, wherein said $(C_6-C_{10})$aryl and the $(C_6-C_{10})$aryl portion of said —C(O)—$(C_6-C_{10})$aryl of $Y^2$ are unsubstituted or substituted with one or more groups Z; or two groups $Y^2$ form a —O—$CH_2CH_2$—O— group; or two of said $Y^2$ substituents attached to the same ring carbon atom of a $(C_3-C_{10})$cycloalkyl, benzo-fused $(C_3-C_{10})$cycloalkyl, benzo-fused $(C_2-C_{10})$heterocycloalkyl, benzo-fused $(C_2-C_{10})$ heterocycloalkenyl, or $(C_2-C_{10})$heterocycloalkyl ring, together with the ring carbon atom to which they are both attached, form a carbonyl group; and each Z is independently selected from the group consisting of $(C_1-C_6)$alkyl, halo, $(C_1-C_6)$haloalkyl, —OH, —O—$(C_1-C_6)$alkyl, and —CN.

3. The compound of claim 1, or a pharmaceutically acceptable salt or ester thereof, wherein:

$Ar^2$ is a phenyl independently substituted with two $Y^1$ groups.

4. The compound of claim 3, or a pharmaceutically acceptable salt or ester thereof, wherein:

$Ar^2$ is a phenyl independently substituted with two $Y^1$ groups at the 2- and 4-position.

5. The compound of claim 1, or a pharmaceutically acceptable salt or ester thereof, wherein:

$Ar^1$ is a phenyl substituted with one $Y^1$ group at the 4-position.

6. The compound of claim 5, or a pharmaceutically acceptable salt or ester thereof, wherein:

$Ar^2$ is a phenyl independently substituted with two $Y^1$ groups at the 2- and 4-position.

7. The compound according to claim 1, or a pharmaceutically acceptable salt or ester thereof, wherein:

m is 1; and

A is —C(O)—.

8. The compound according to claim 7, or a pharmaceutically acceptable salt or ester thereof, wherein:

n is 0.

9. The compound according to claim 7, or a pharmaceutically acceptable salt or ester thereof, wherein:

n is 1; and B is —NH—.

10. The compound according to claim 7, or a pharmaceutically acceptable salt or ester thereof, wherein:

n is 1; and B is —$(C(R^2)_2)_r$— wherein r is 1 or 2.

11. The compound according to claim 7, or a pharmaceutically acceptable salt or ester thereof, wherein:

n is 1; and B is —$N(R^2)$—.

12. The compound according to claim 1, or a pharmaceutically acceptable salt or ester thereof, wherein:

m is 1; and A is —$S(O)_2$—.

13. The compound according to claim 12, or a pharmaceutically acceptable salt or ester thereof, wherein:

n is 0.

14. The compound according to claim 12, or a pharmaceutically acceptable salt or ester thereof, wherein:

n is 1; and B is —$N(R^2)$—.

15. The compound according to claim 1, or a pharmaceutically acceptable salt or ester thereof, wherein:

m is 1; A is —C(=N—$OR^2$)—; and n is 0.

16. The compound according to claim 1, or a pharmaceutically acceptable salt or ester thereof, wherein:

m is 1; A is —$(C(R^2)_2)_q$— wherein q is 1, 2, or 3; and n is 0.

17. The compound according to claim 16, wherein X is heteroaryl, and said heteroaryl of X is unsubstituted or substituted with one or more $Y^1$ groups.

18. The compound according to claim 17, wherein q is 1 or 2.

19. The compound according to claim 1, or a pharmaceutically acceptable salt or ester thereof, wherein:

m is 0; B is —$(C(R^3)_2)_r$— wherein r is 1, 2, or 3.

20. The compound according to claim 1, or a pharmaceutically acceptable salt or ester thereof, wherein:

m and n are both 1; and

B is —$(C(R^3)_2)_r$— wherein r is 1, 2, or 3.

21. The compound according to claim 1, or a pharmaceutically acceptable salt or ester thereof, wherein:

m and n are both 0.

22. The compound according to claim 1, or a pharmaceutically acceptable salt or ester thereof, wherein:

X is —$(C(R^2)_2)_s$-aryl wherein s is 0, 1, or 2.

23. The compound according to claim 1, or a pharmaceutically acceptable salt or ester thereof, wherein:

X is heteroaryl.

24. The compound according to claim 1, or a pharmaceutically acceptable salt or ester thereof, wherein:

X is cycloalkyl.

25. The compound according to claim 1, or a pharmaceutically acceptable salt or ester thereof, wherein:

X is heterocycloalkyl.

26. The compound according to claim 1, or a pharmaceutically acceptable salt or ester thereof, wherein:

X is alkyl.

27. The compound according to claim 1, or a pharmaceutically acceptable salt or ester thereof, wherein:

X is —$N(R^4)_2$.

28. The compound according to claim 20, or a pharmaceutically acceptable salt or ester thereof, wherein:

A is —C(O)—.

29. The compound according to claim 1, or a pharmaceutically acceptable salt or ester thereof, wherein:

m and n are both 1; A is —C(O)—; and B is —NH—.

30. The compound according to claim 1, or a pharmaceutically acceptable salt or ester thereof, having the following Formula (IA):

(IA)

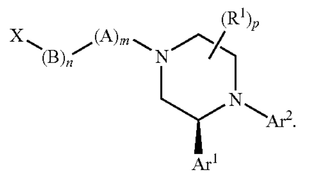

31. The compound according to claim 1, or a pharmaceutically acceptable salt or ester thereof, having the following Formula (IA):

(IB)

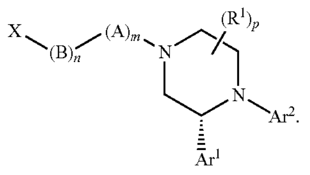

32. The compound according to claim 1, or a pharmaceutically acceptable salt or ester thereof, having the following Formula (IB):

(IC)

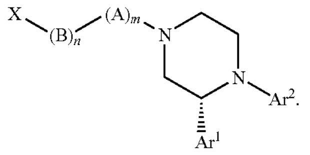

33. The compound according to claim 32, or a pharmaceutically acceptable salt or ester thereof, wherein:

m is 1; and A is —C(O)—.

34. The compound according to claim 33, or a pharmaceutically acceptable salt or ester thereof, wherein n is 0.

35. The compound according to claim 33, or a pharmaceutically acceptable salt or ester thereof, wherein:

n is 1; and B is —$N(R^2)$—.

36. The compound according to claim 32, or a pharmaceutically acceptable salt or ester thereof, wherein:

m is 1; A is —$S(O)_2$—.

37. The compound according to claim 36, or a pharmaceutically acceptable salt or ester thereof, wherein n is 0.

38. The compound according to claim 36, or a pharmaceutically acceptable salt or ester thereof, wherein:

n is 1; and B is —$N(R^2)$—.

39. A compound according to claim 1, or a pharmaceutically acceptable salt or ester thereof, selected from the group consisting of:

-continued
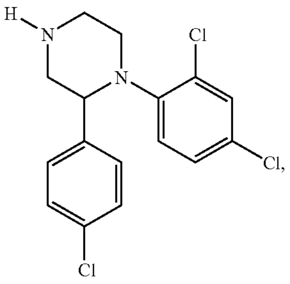
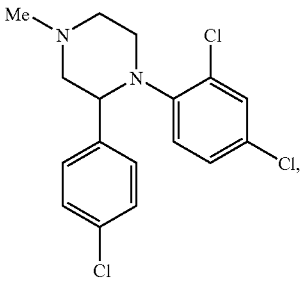
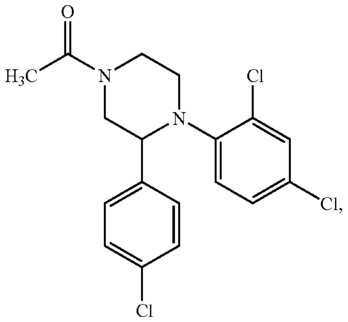
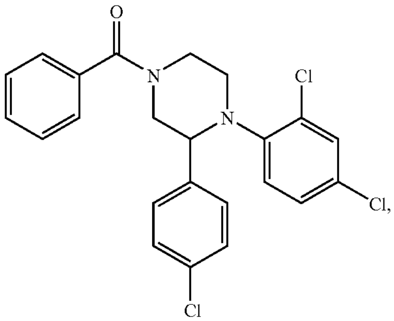
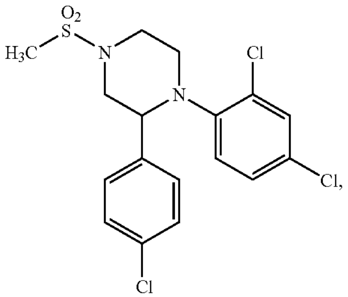
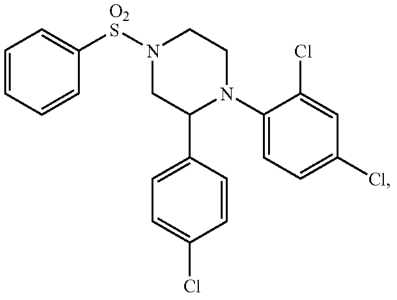
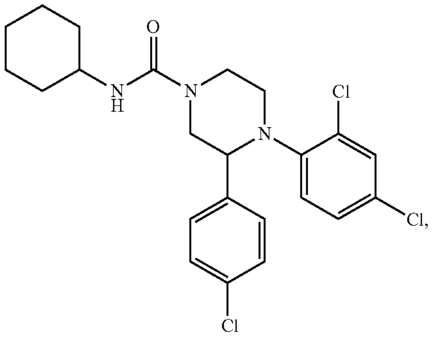
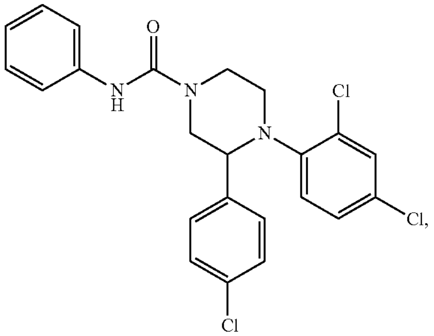
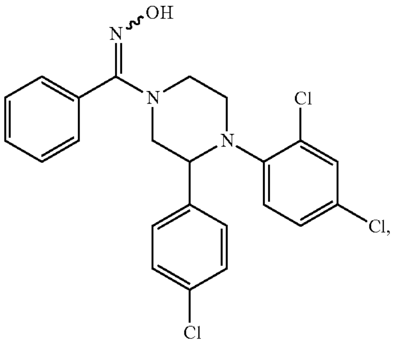
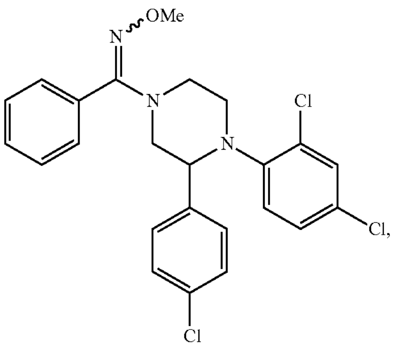

-continued
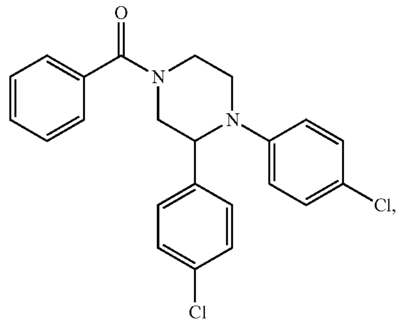
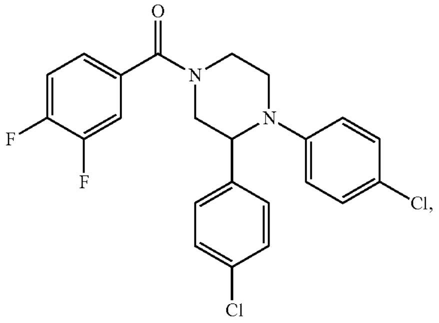
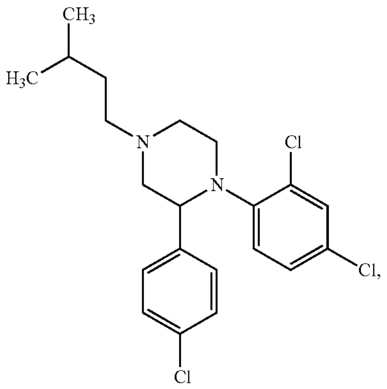
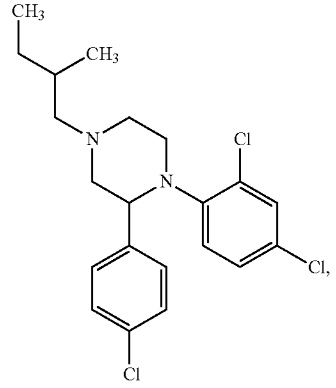
-continued
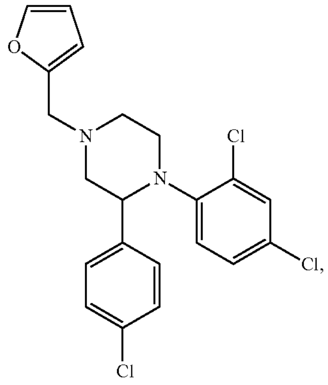
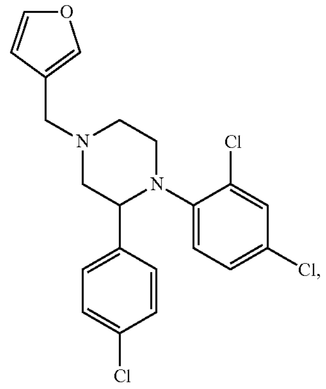
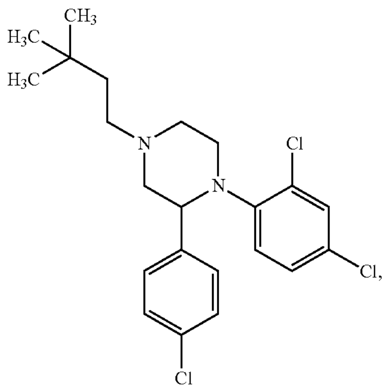
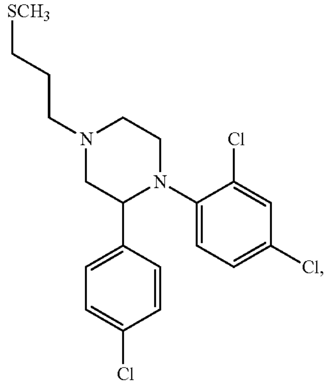

-continued
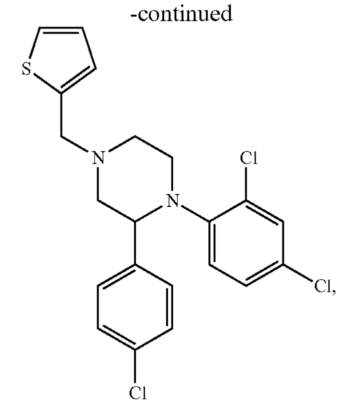
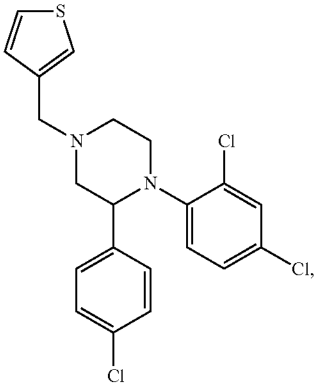
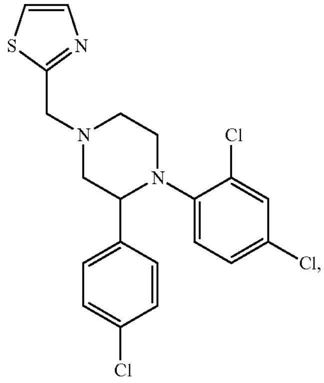
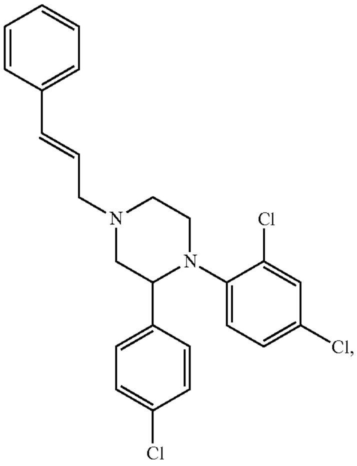
-continued
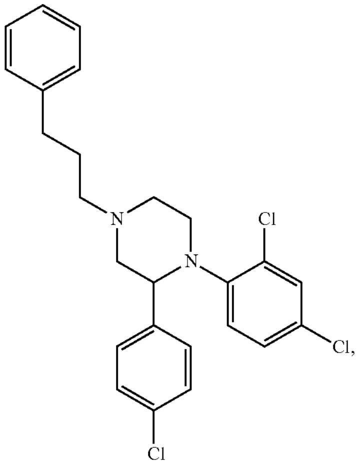
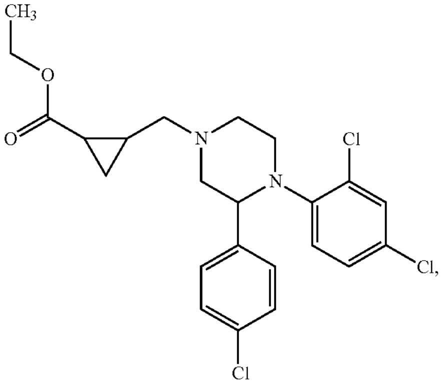
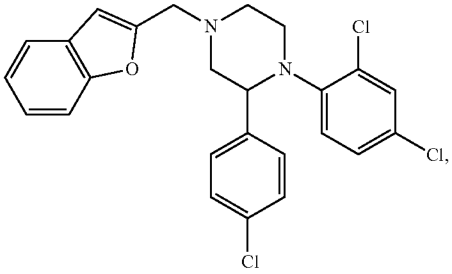
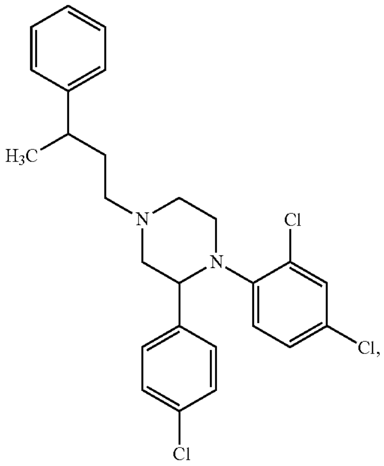

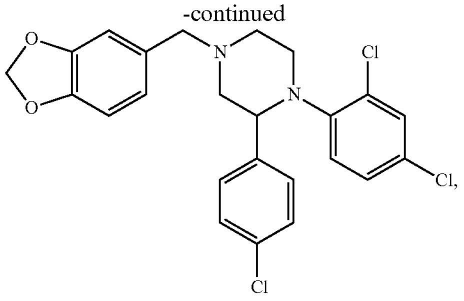
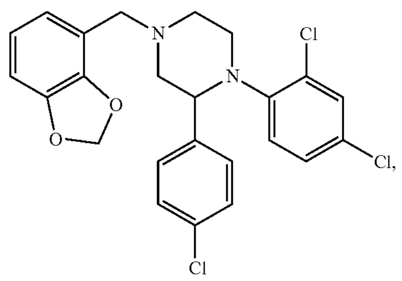
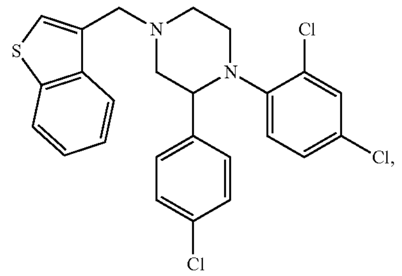
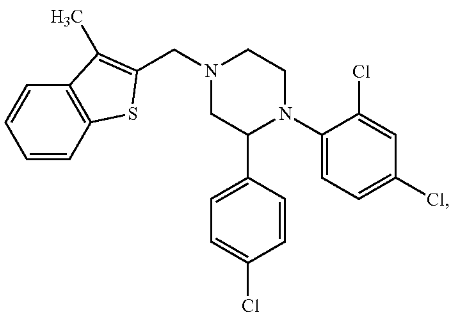
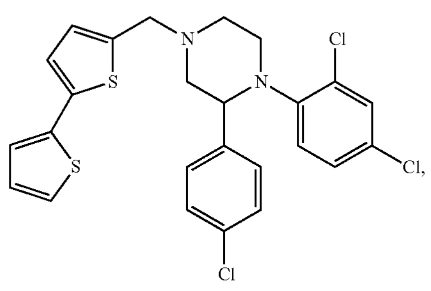
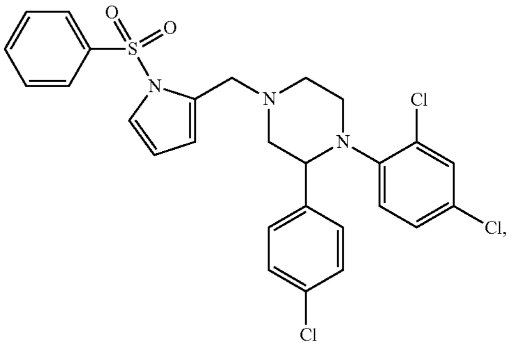
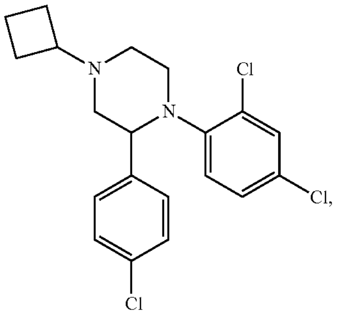
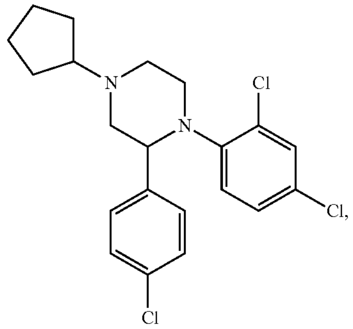
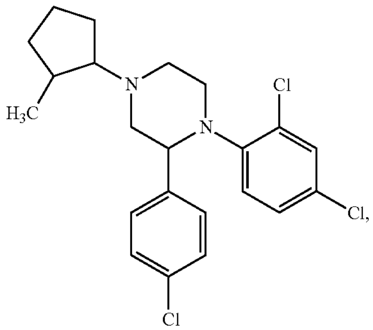
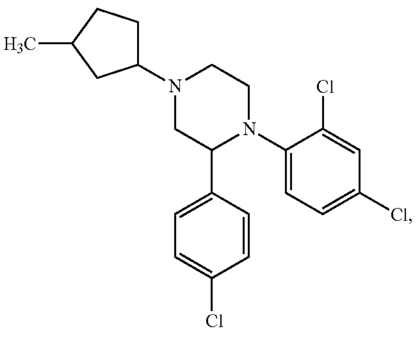

-continued
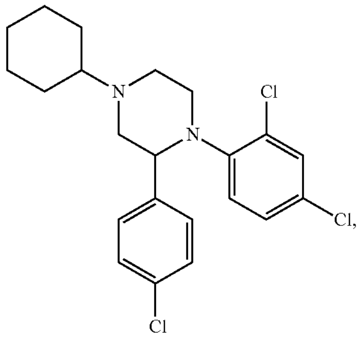
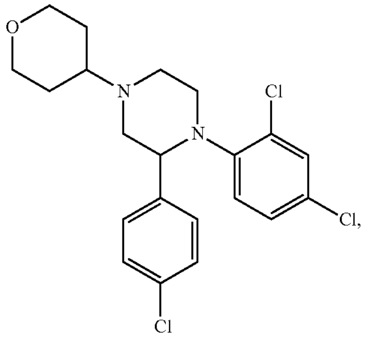
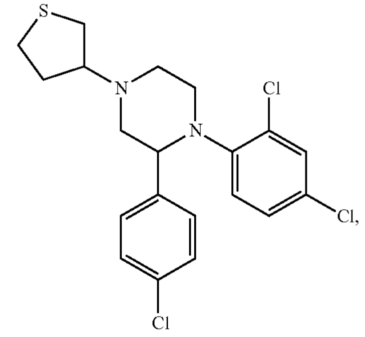
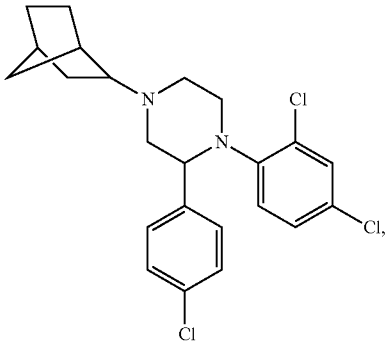
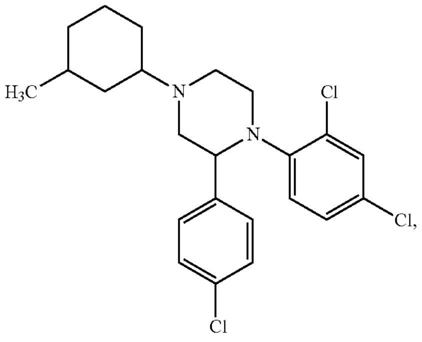
-continued
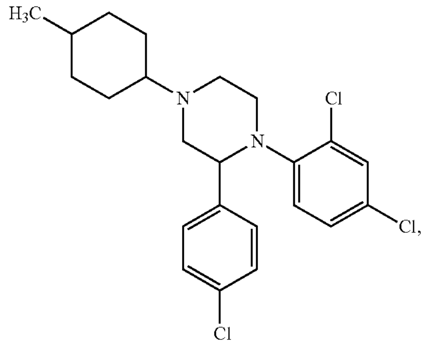
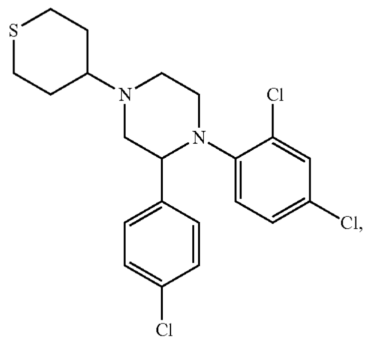
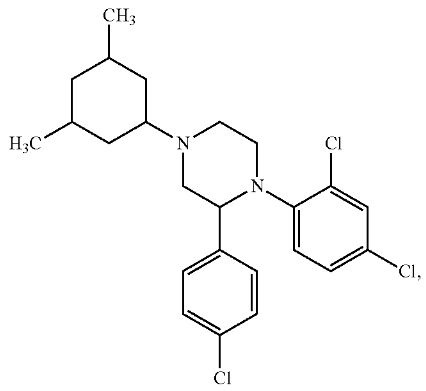
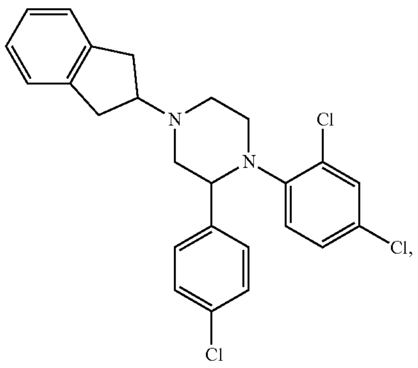

-continued
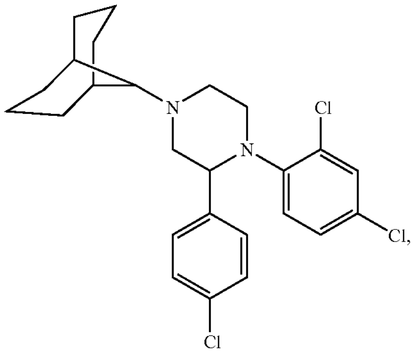
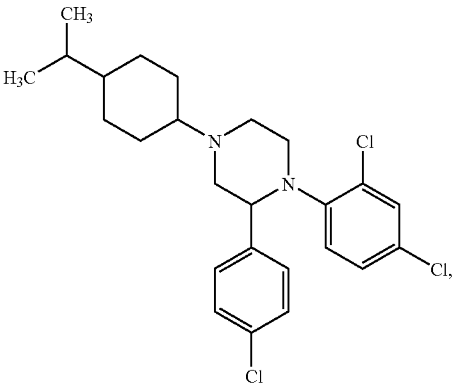
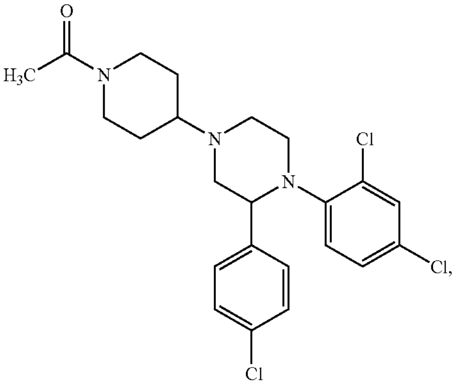
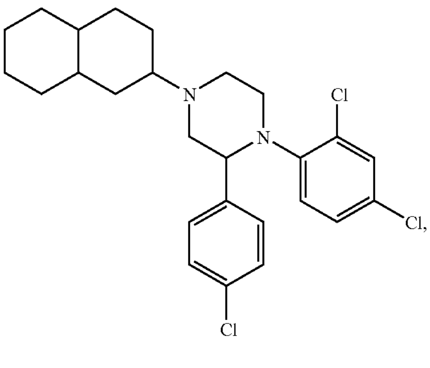
-continued
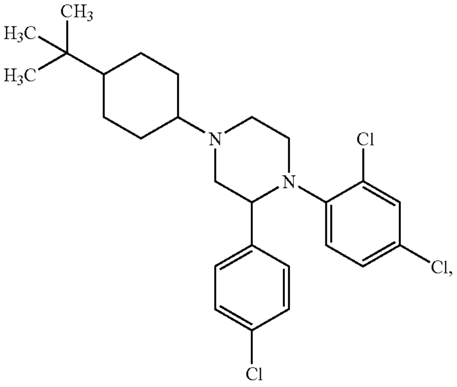
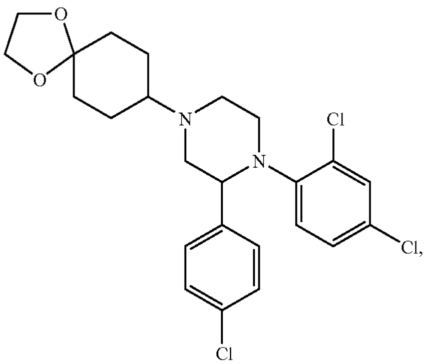
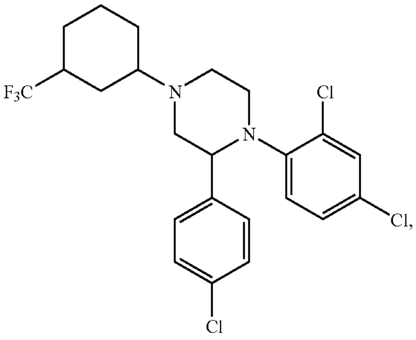
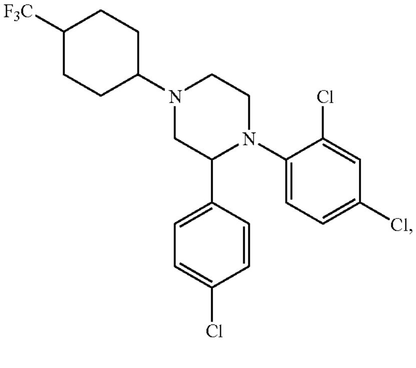

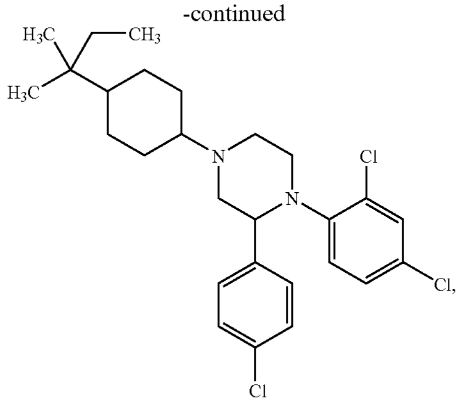
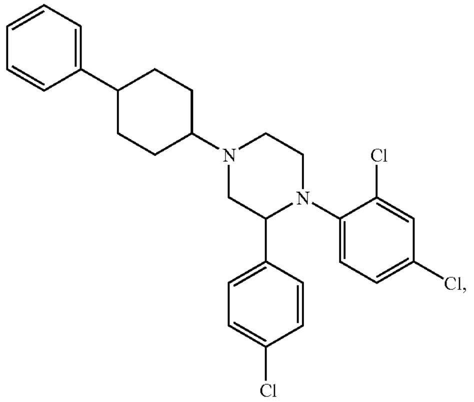
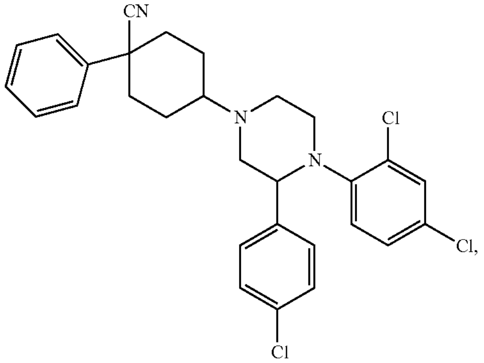
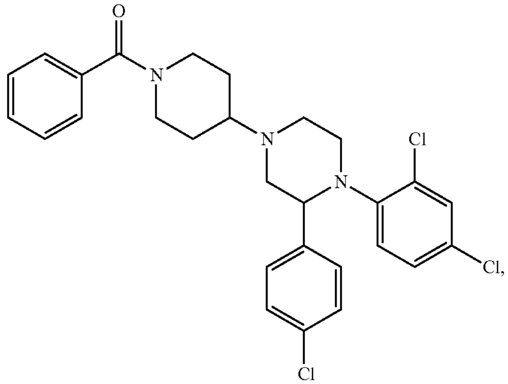
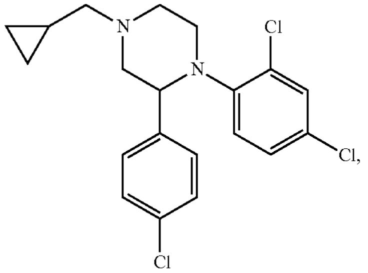
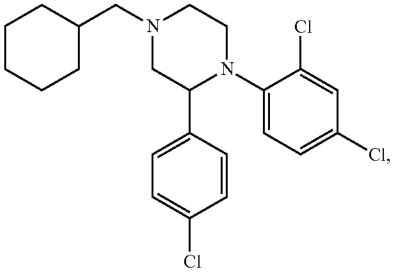
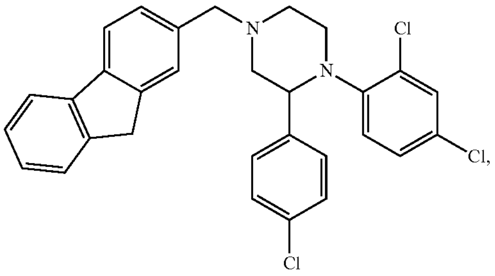
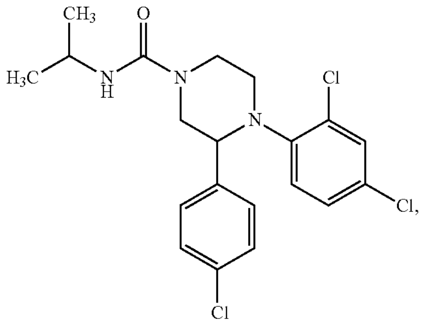
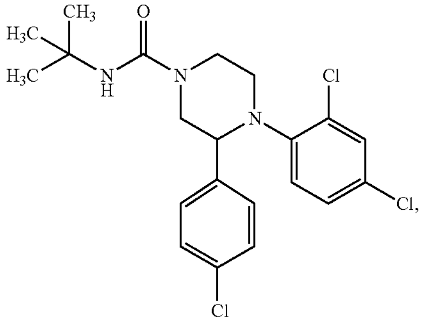

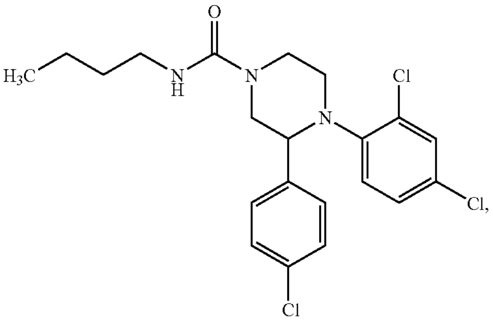
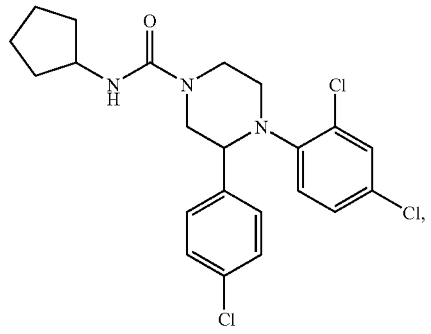
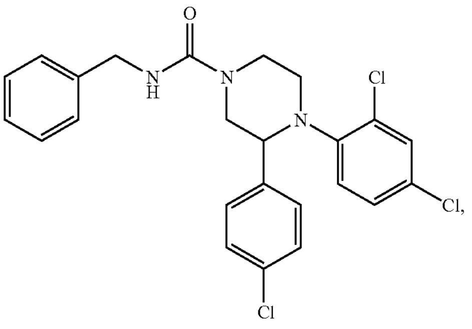
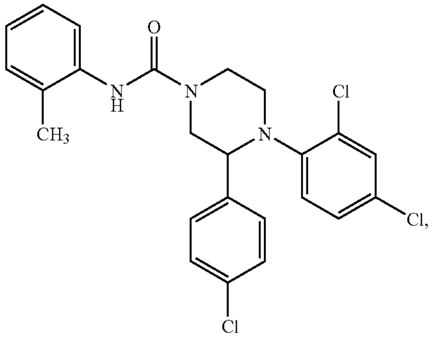
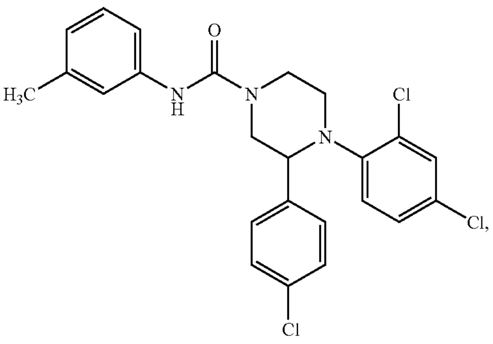
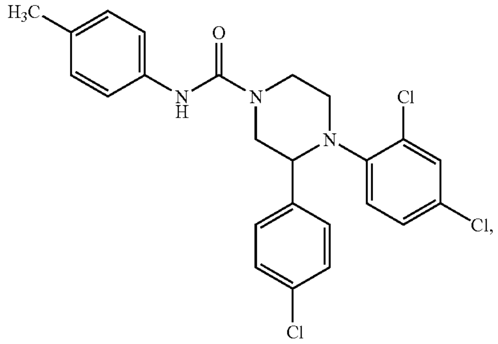
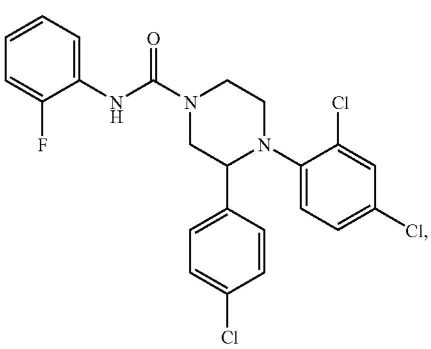
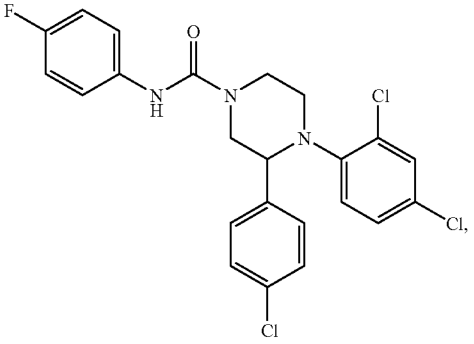
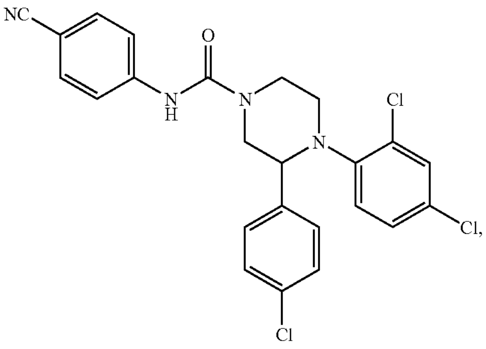
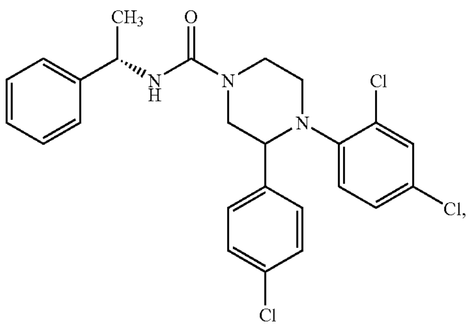

-continued
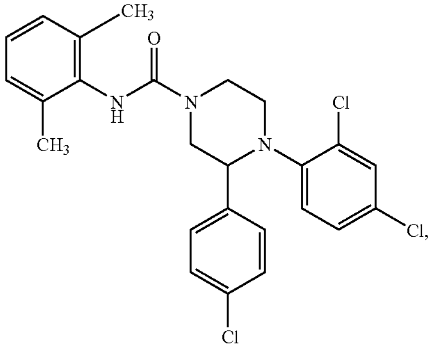
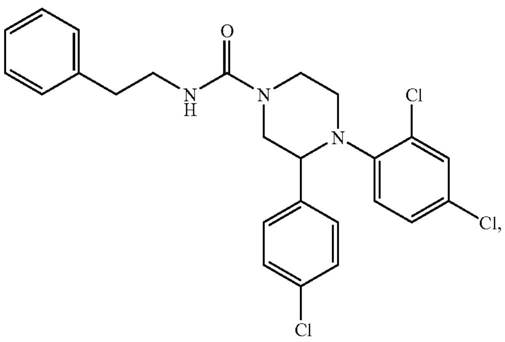
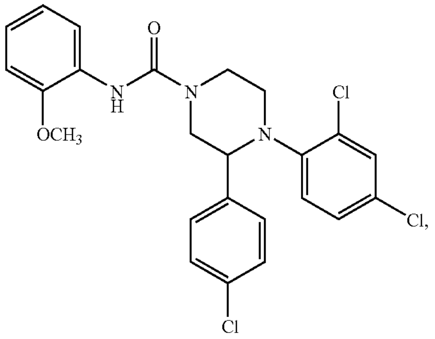
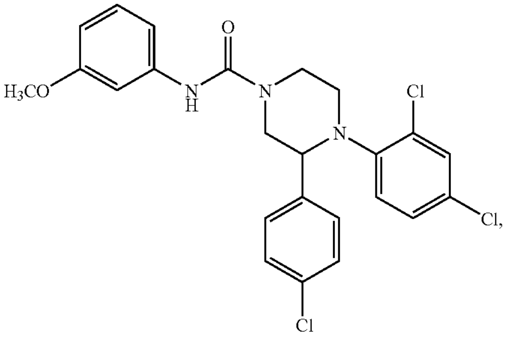
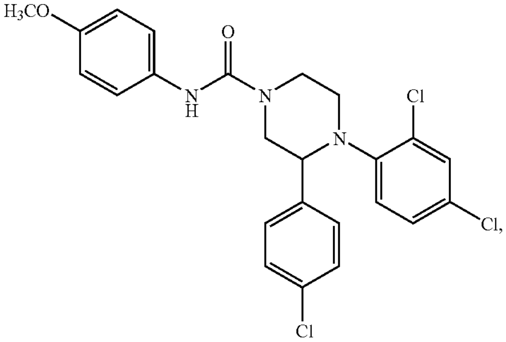
-continued
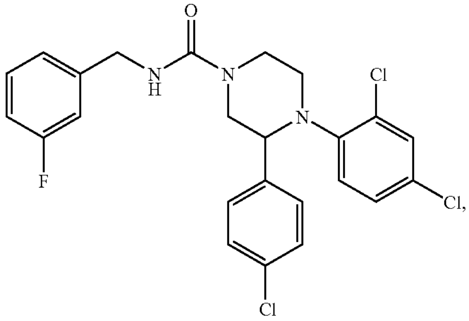
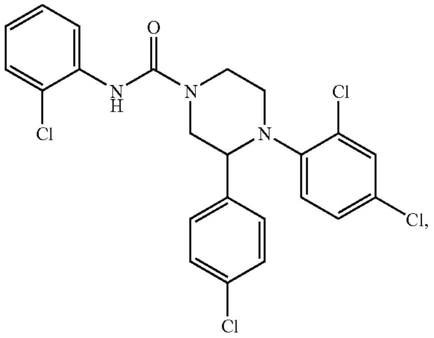
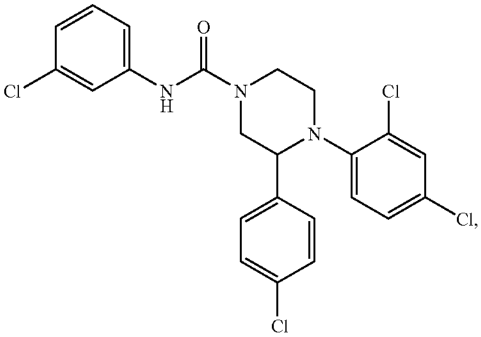
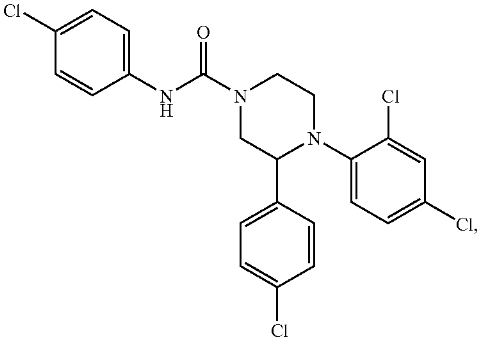
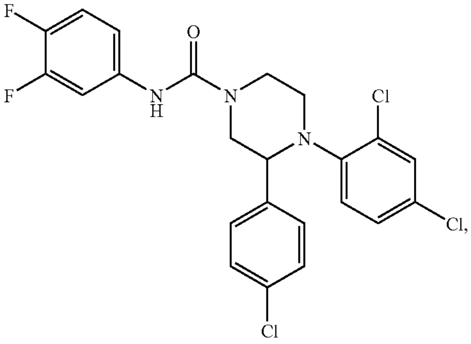

-continued
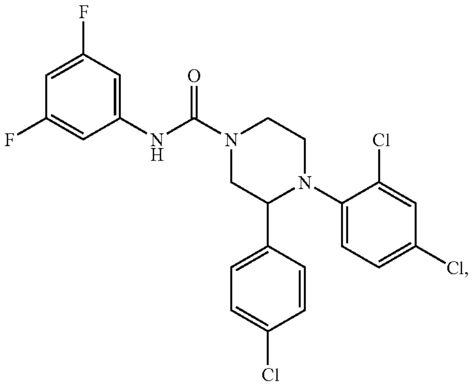
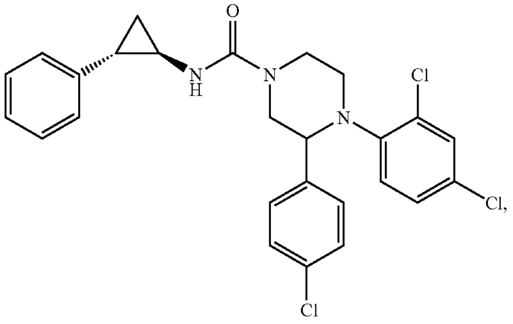
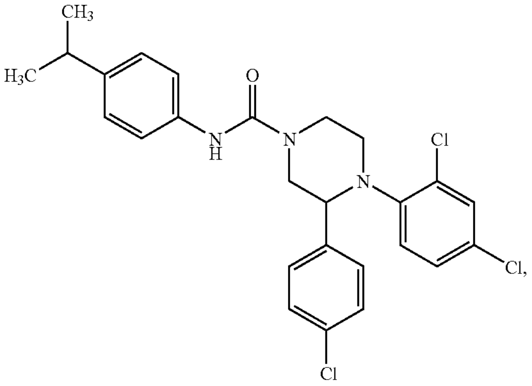
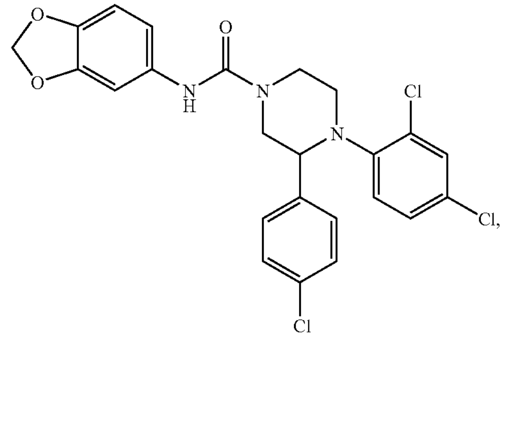
-continued
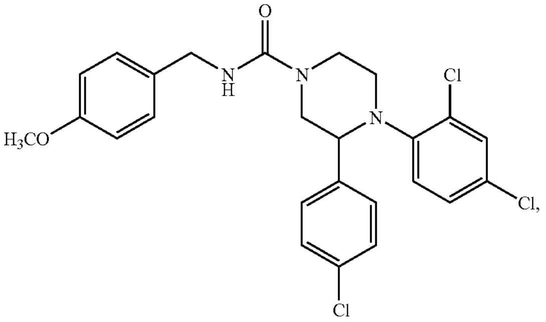
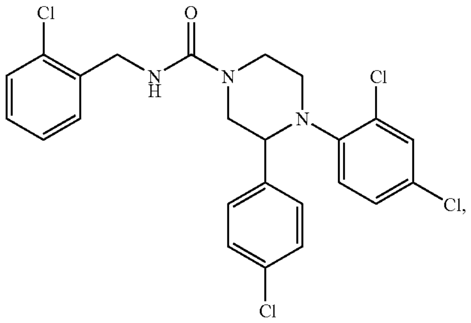
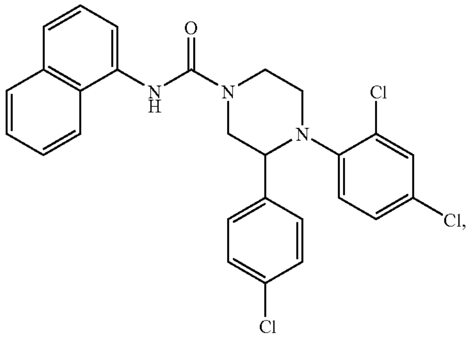
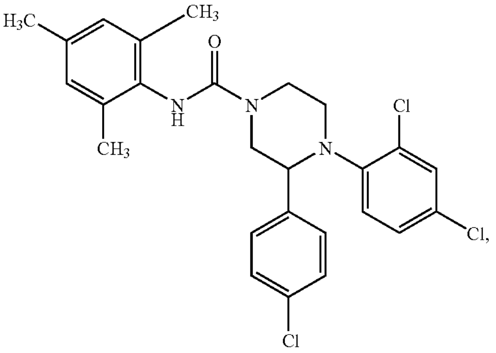
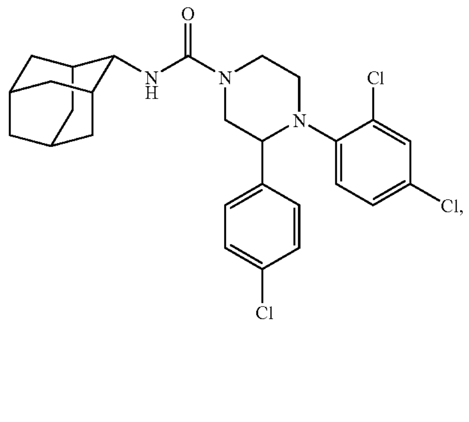

-continued
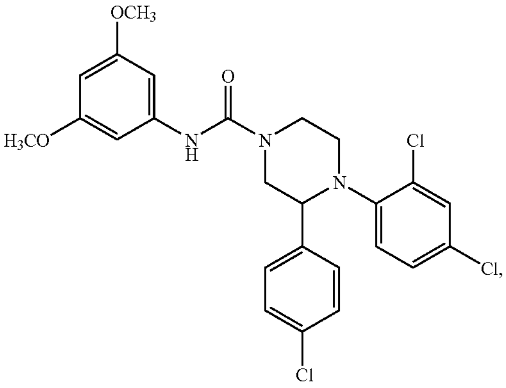
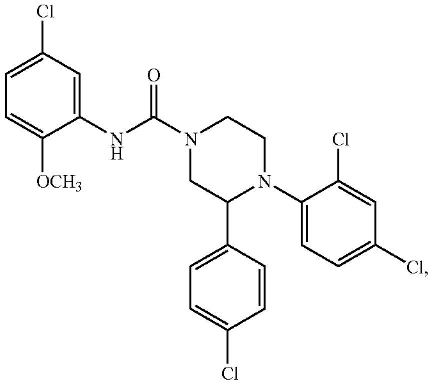
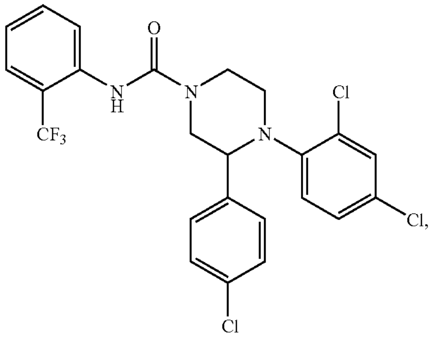
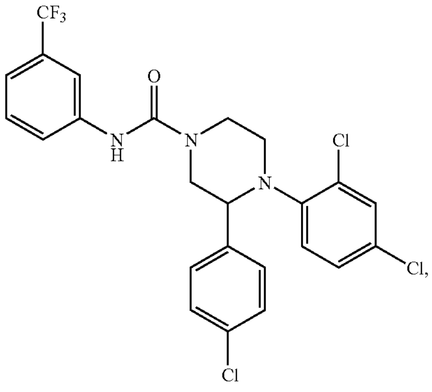
-continued
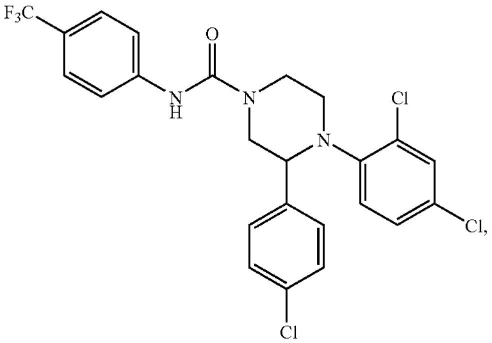
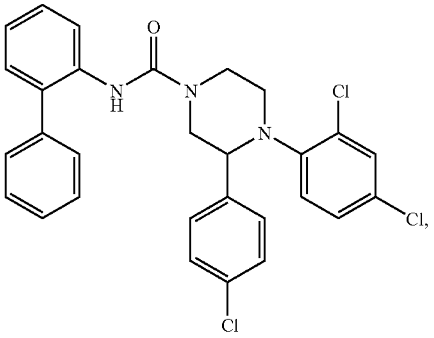
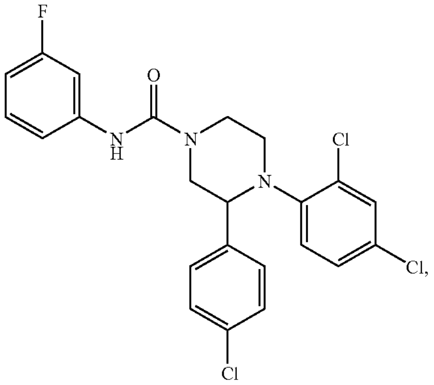
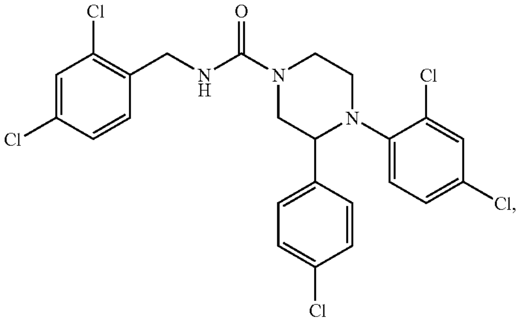
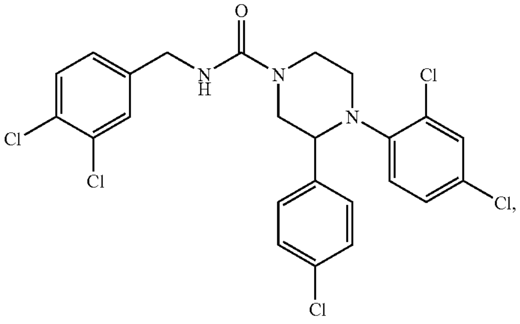

-continued
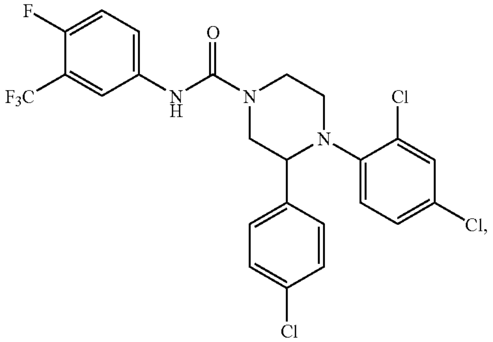
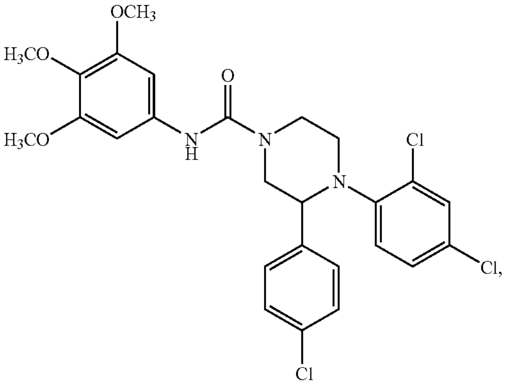
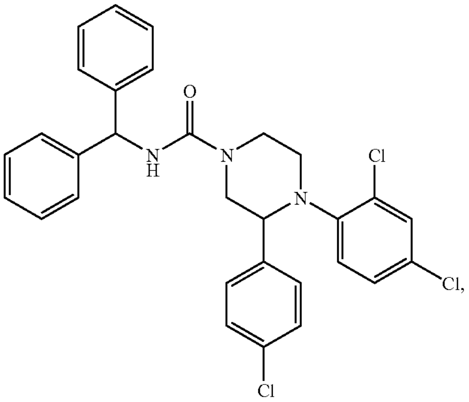
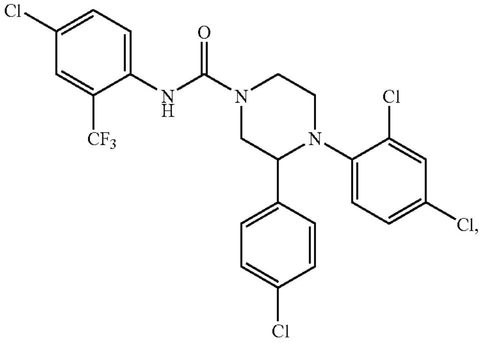
-continued
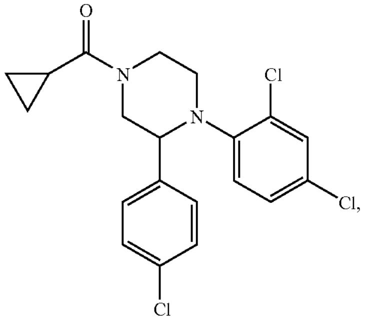
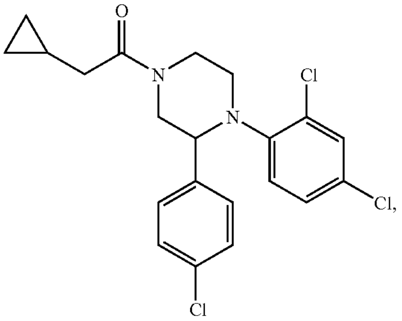
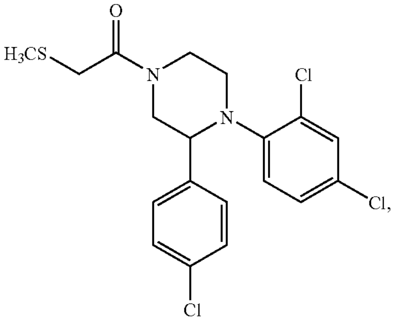
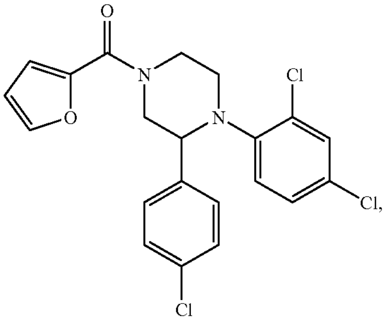
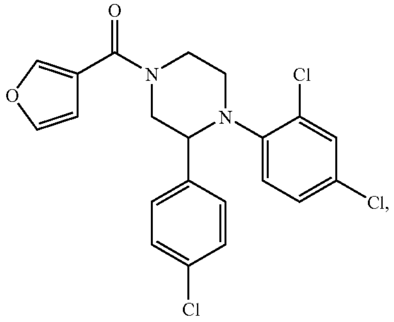

-continued
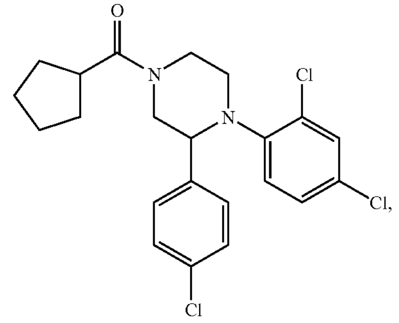
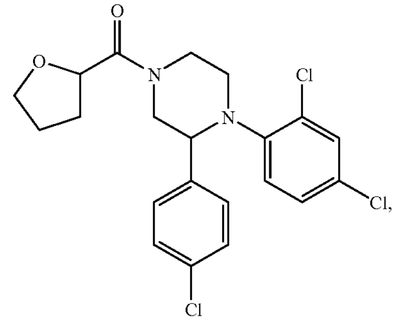
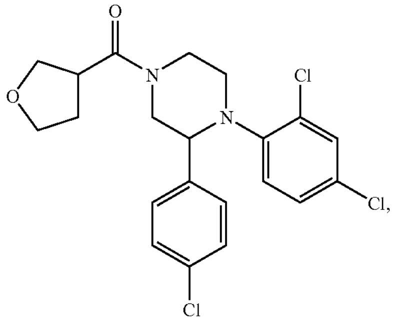
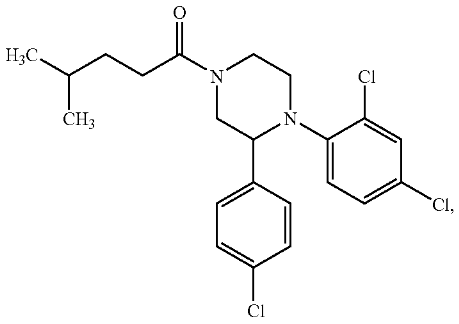
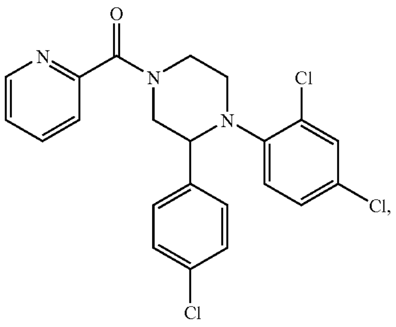
-continued
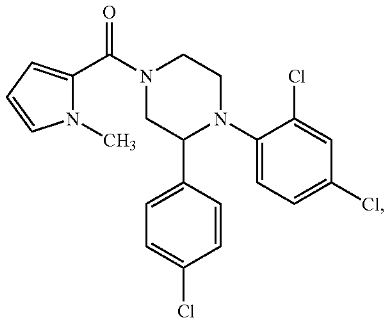
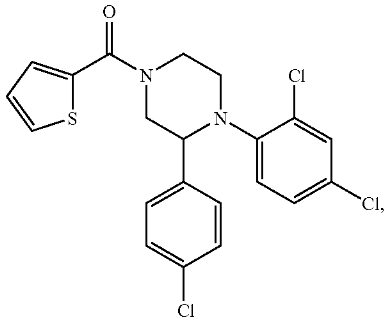
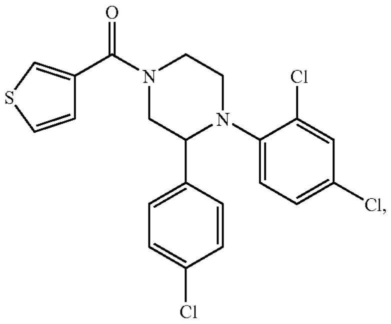
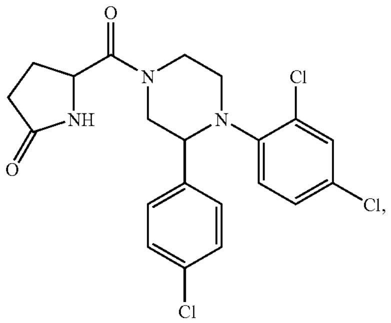
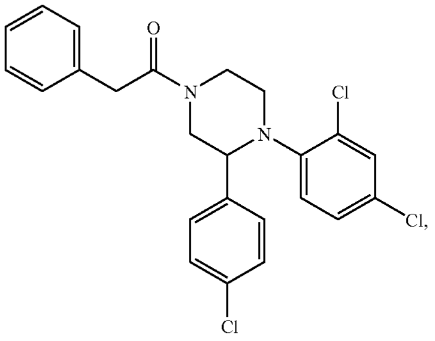

-continued
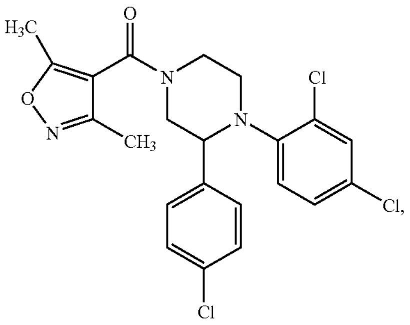
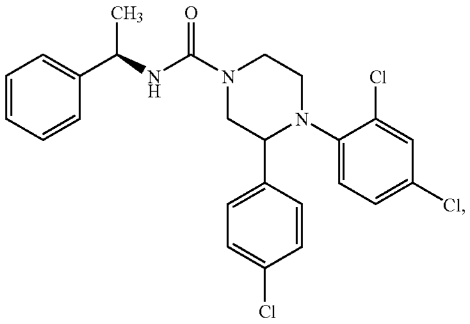
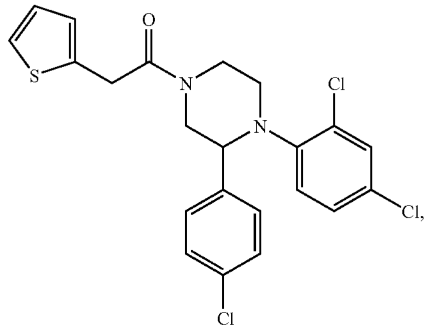
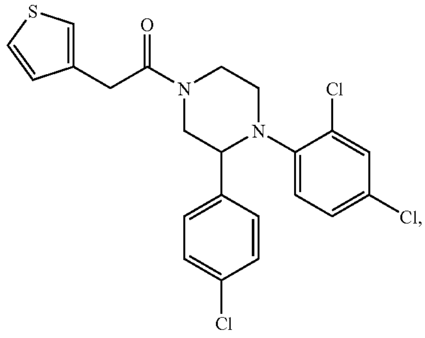
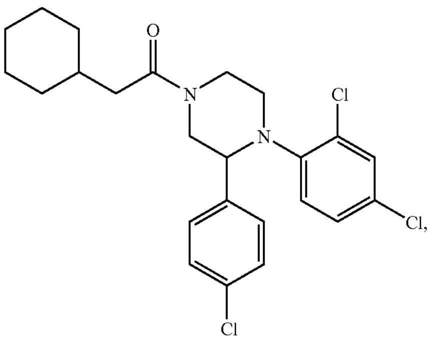
-continued
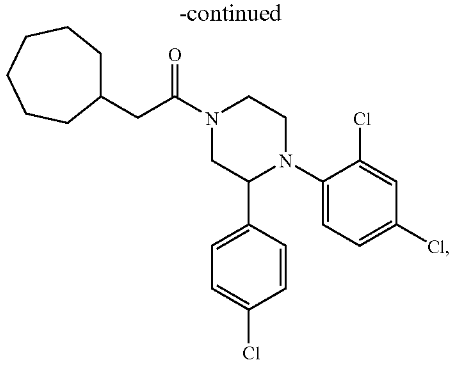
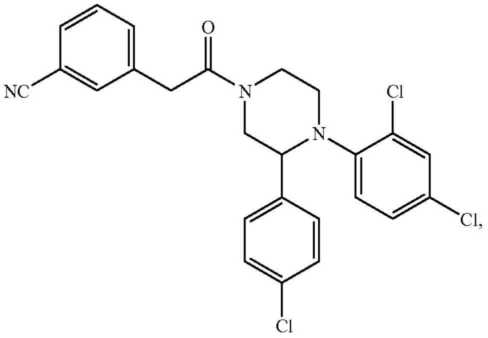
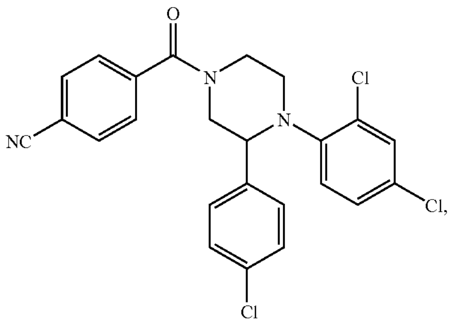
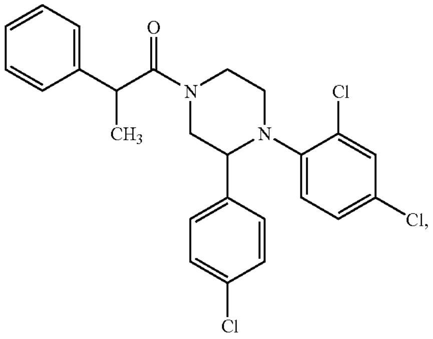
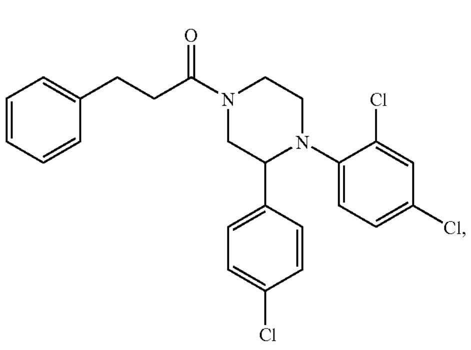

-continued
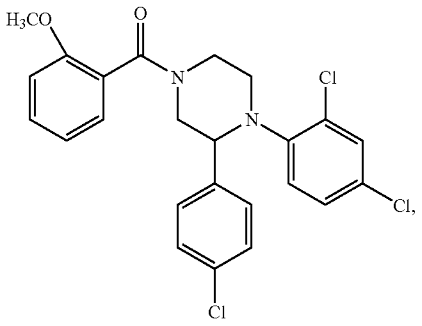
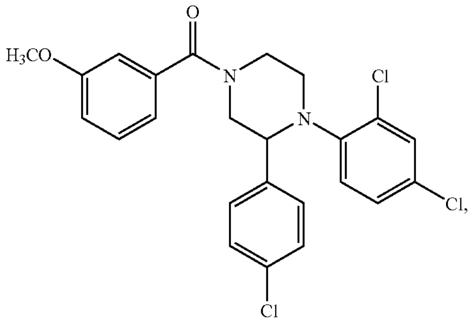
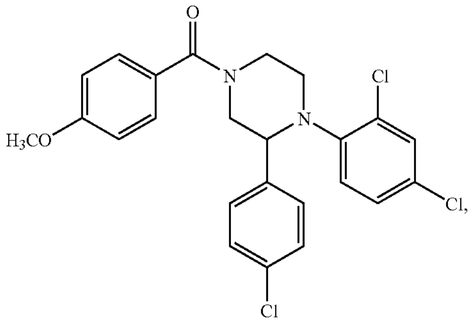
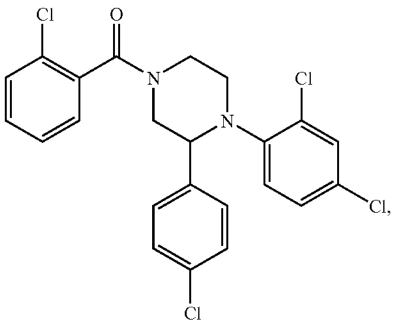
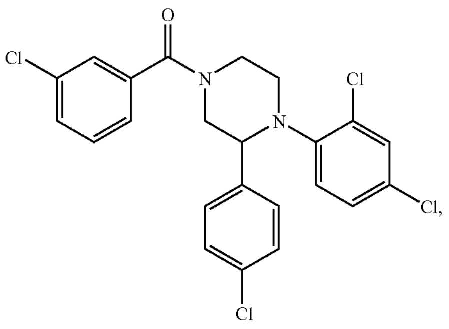
-continued
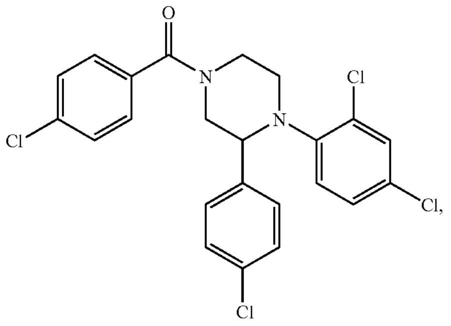
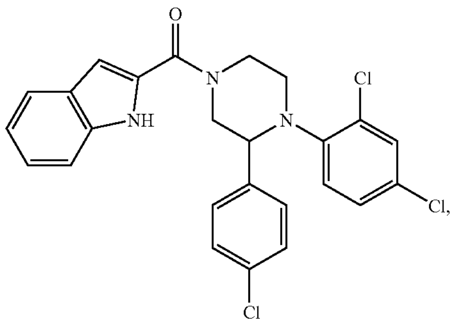
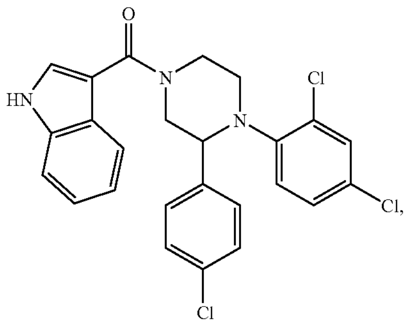
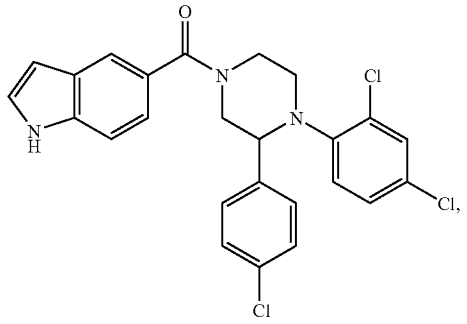
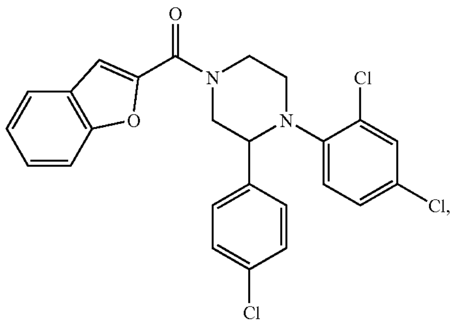

-continued
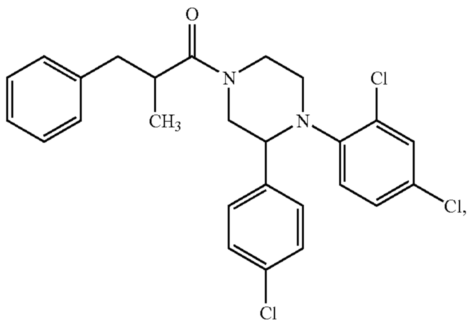
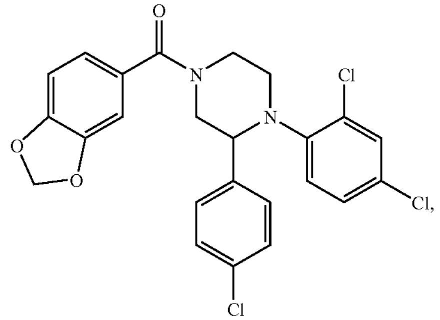
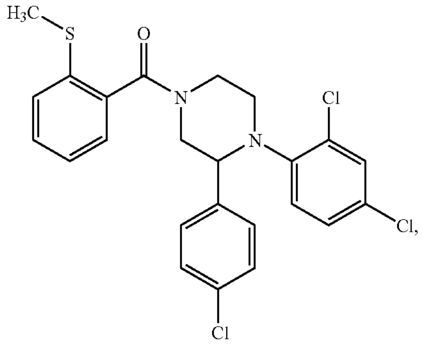
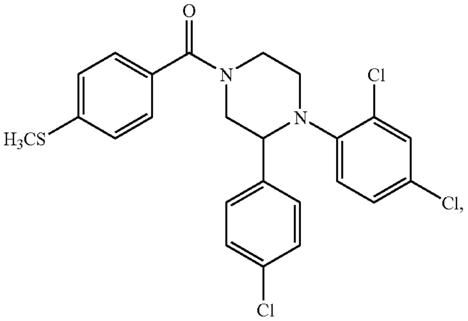
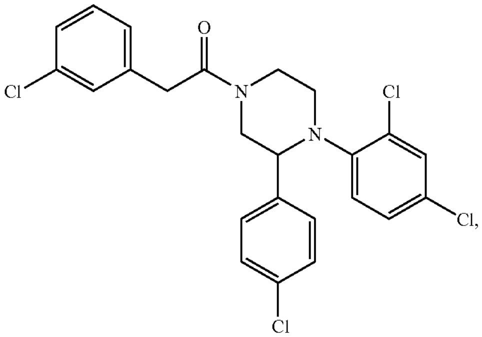
-continued
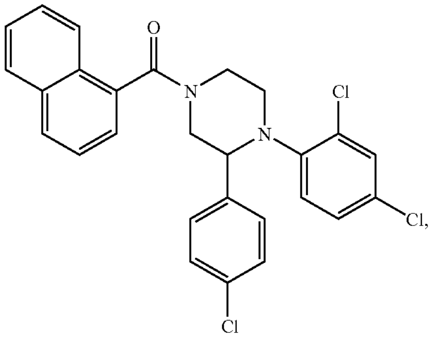
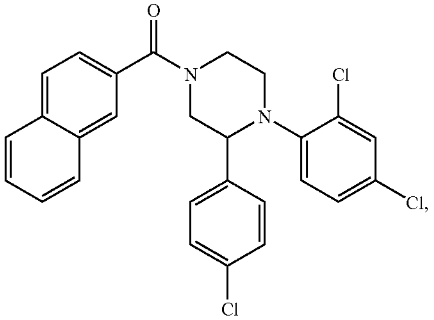
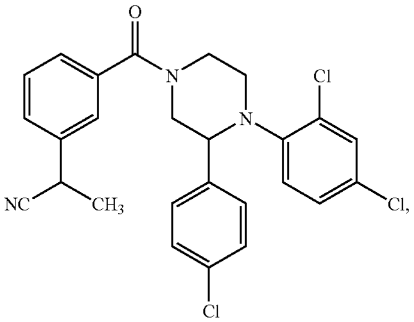
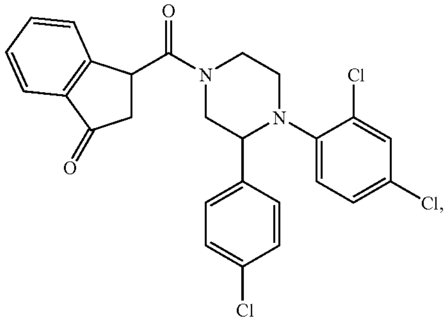
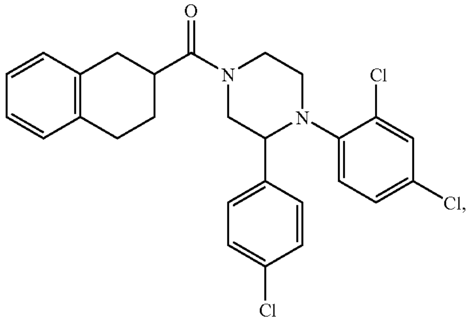

-continued
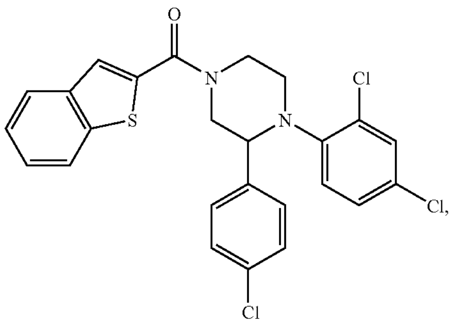
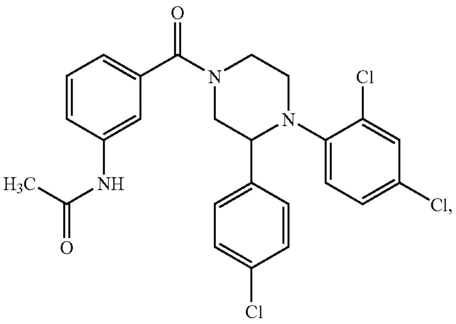
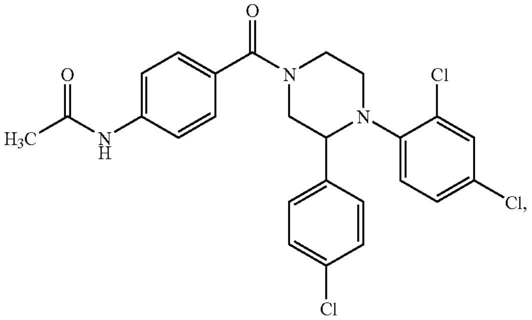
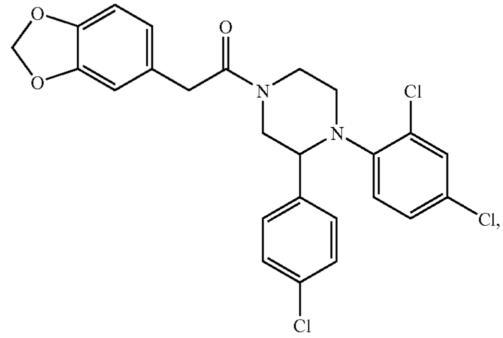
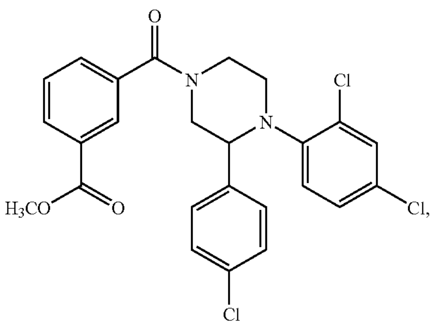
-continued
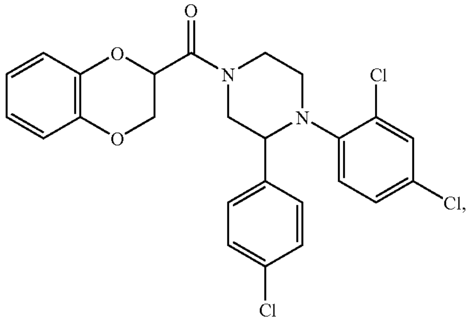
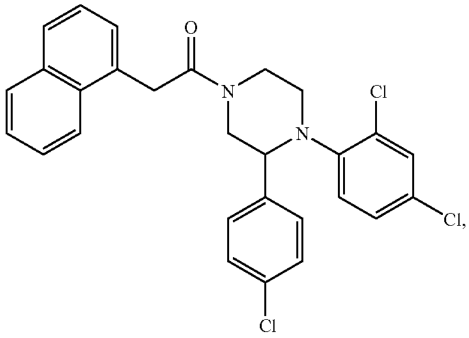
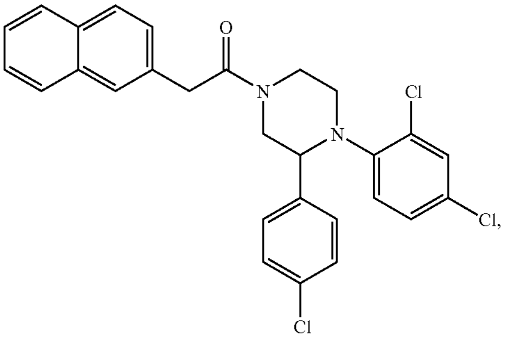
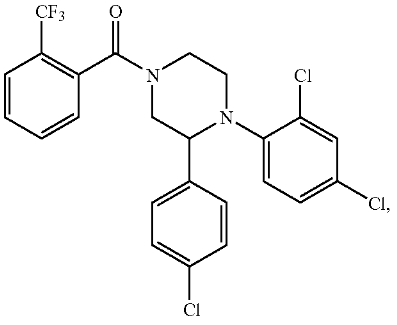
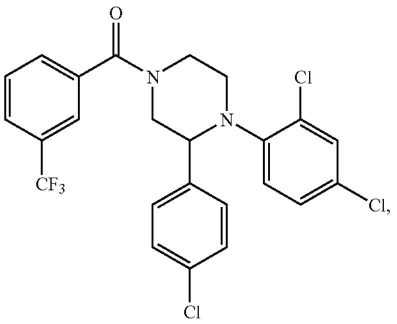

-continued
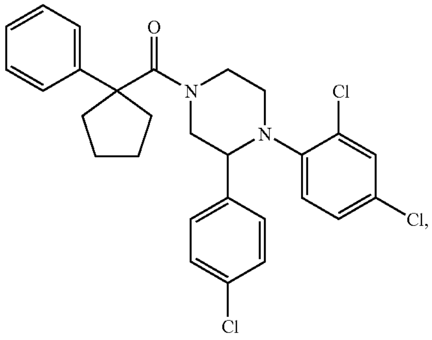
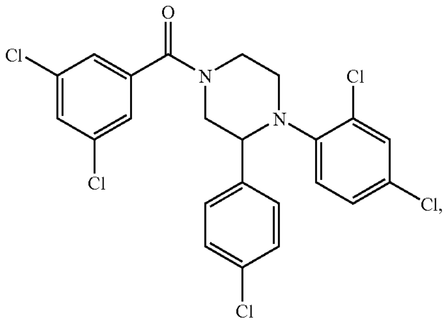
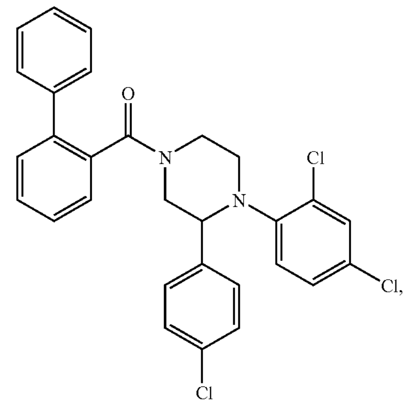
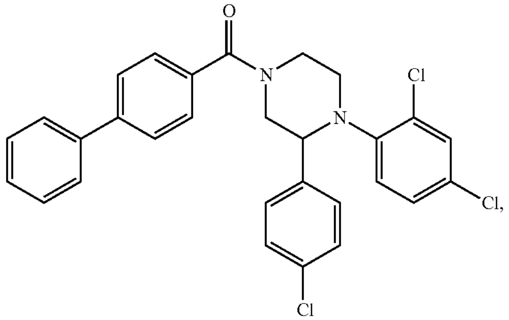
-continued
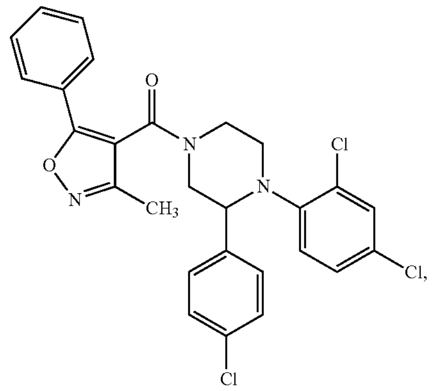
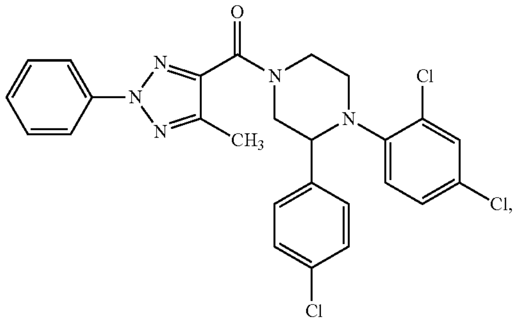
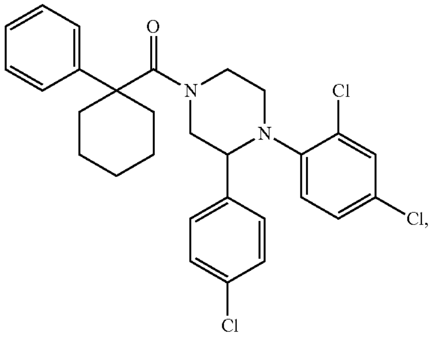
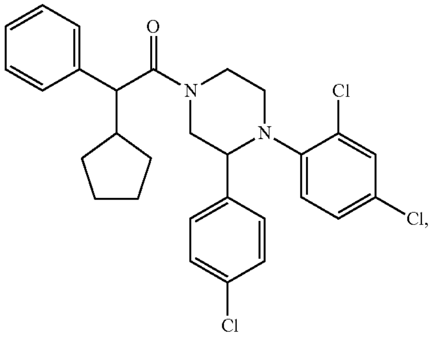
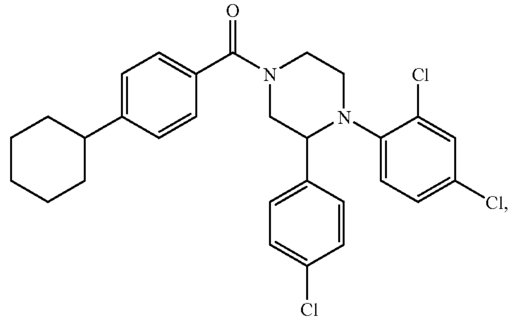

-continued
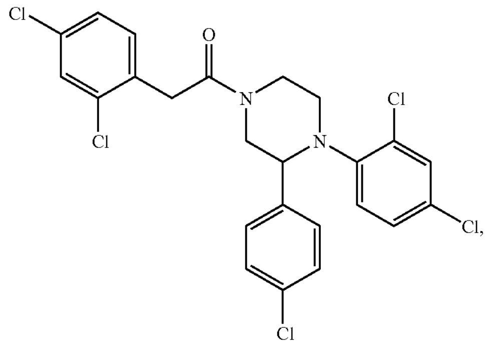
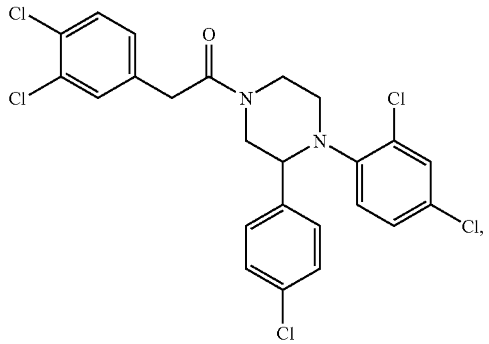
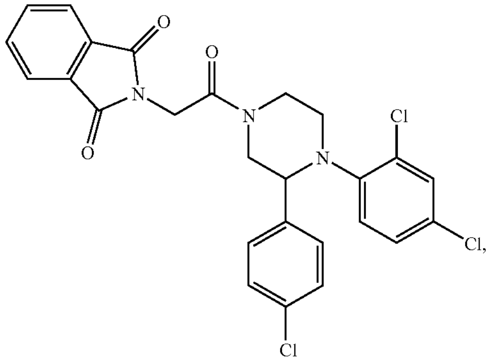
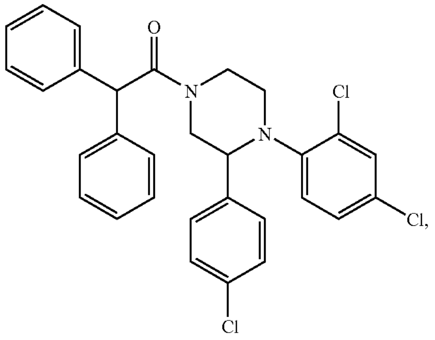
-continued
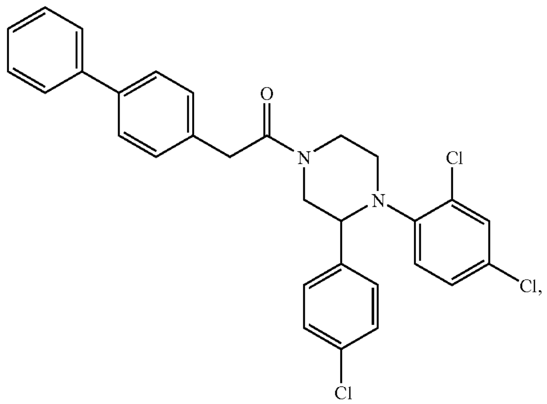
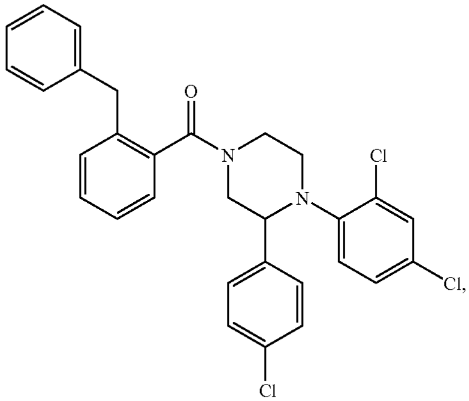
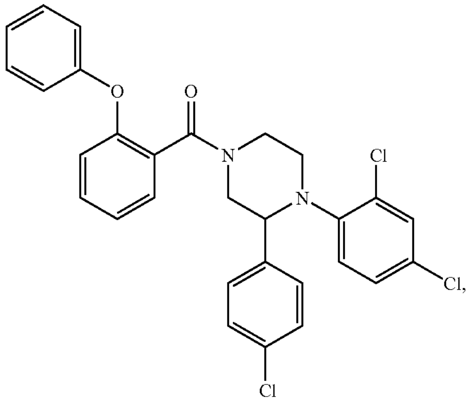
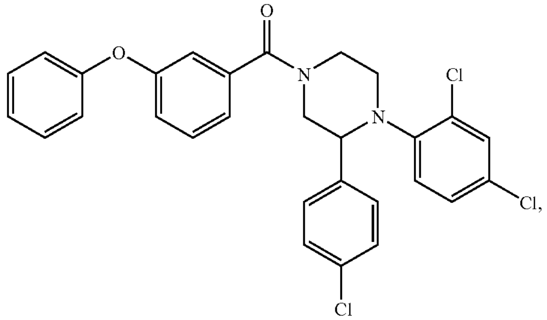

-continued
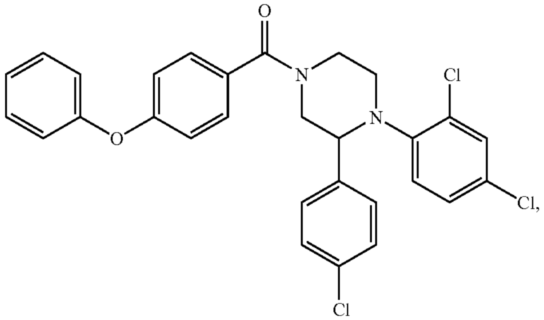
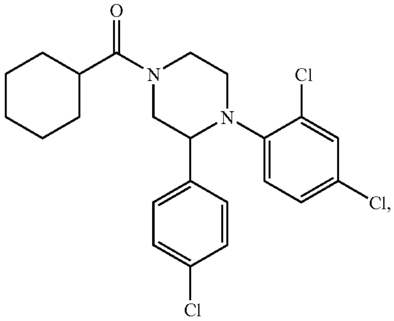
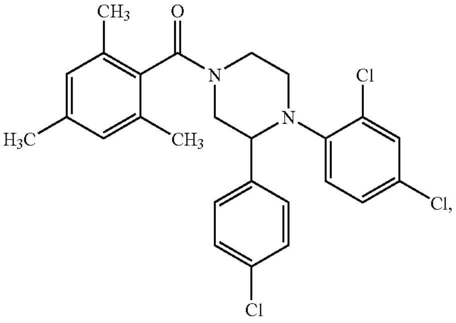
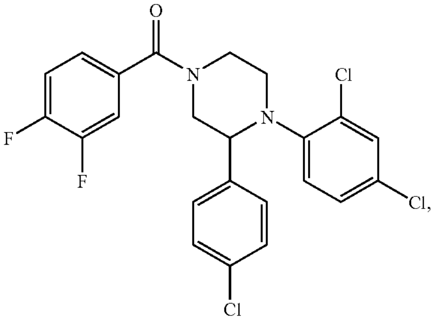
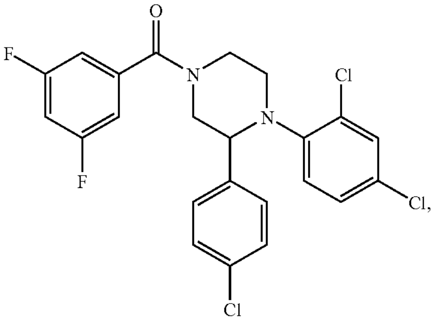
-continued
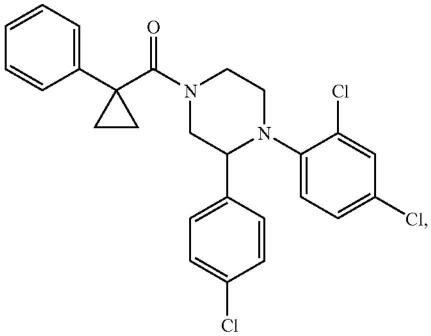
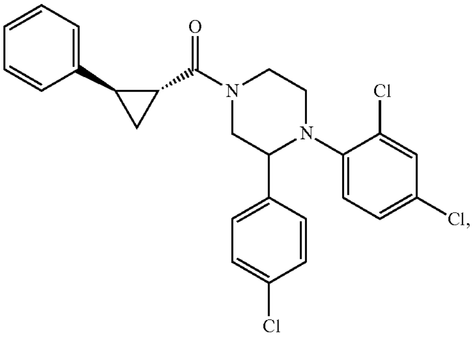
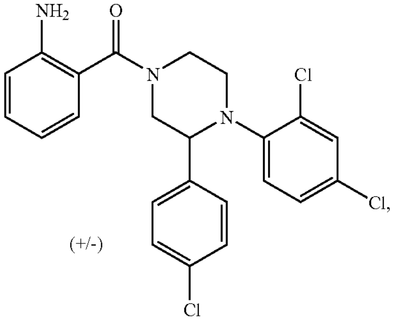
(+/-)
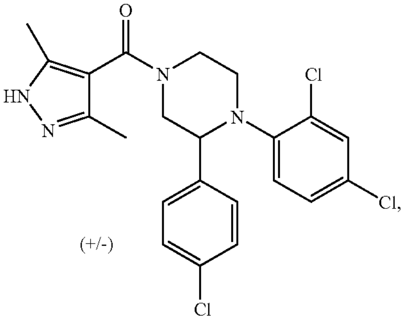
(+/-)
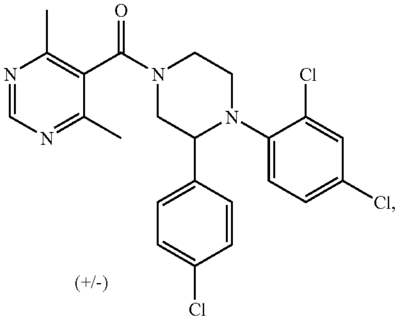
(+/-)

-continued
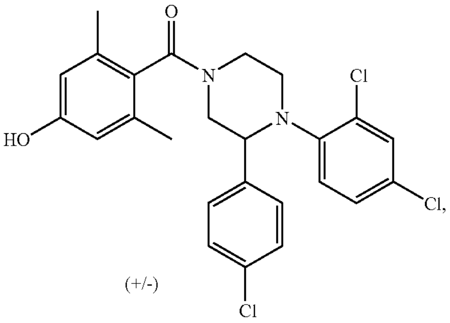
(+/-)
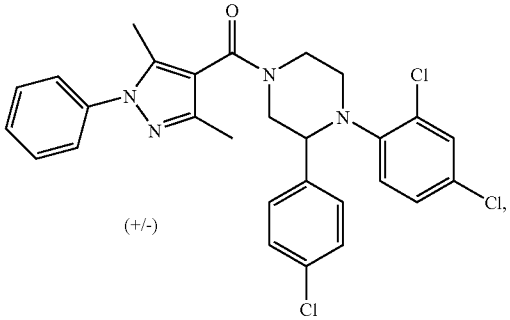
(+/-)
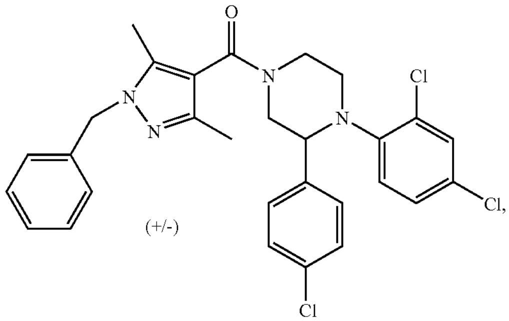
(+/-)
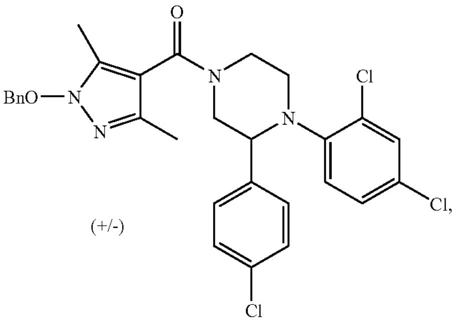
(+/-)
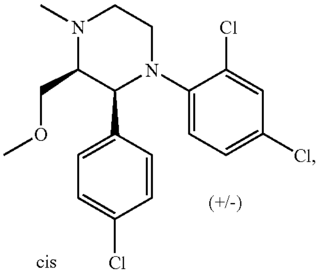
(+/-)
cis
-continued
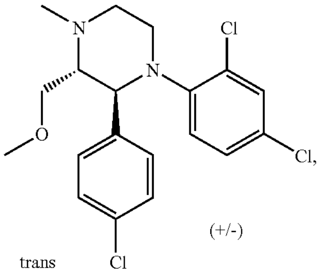
(+/-)
trans
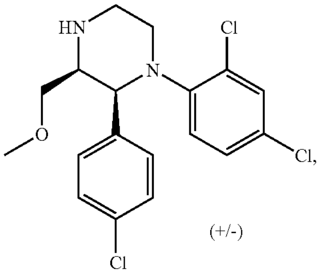
(+/-)
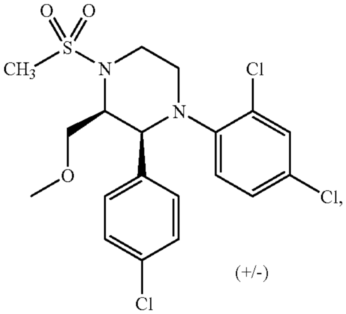
(+/-)
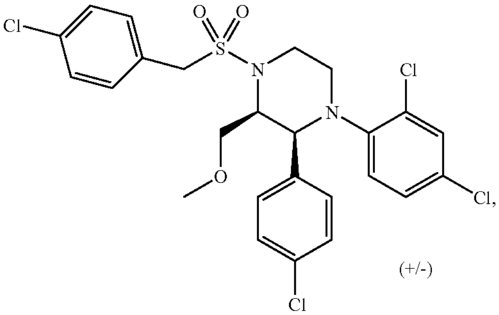
(+/-)
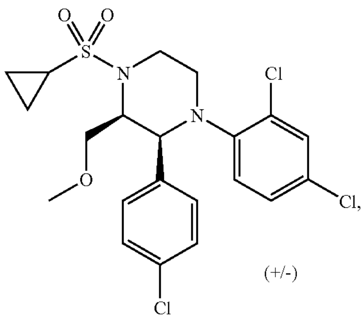
(+/-)

-continued
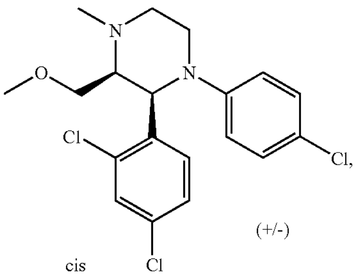
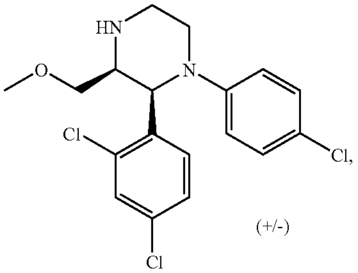
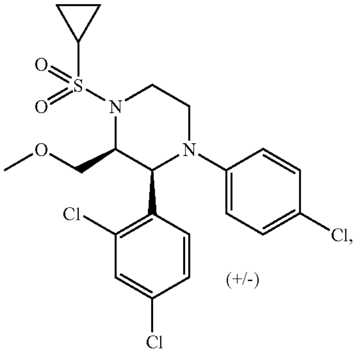
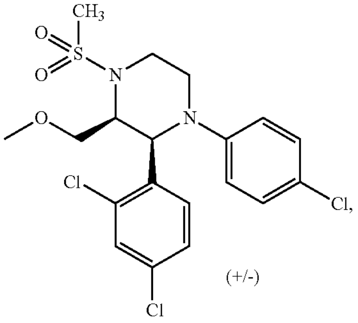
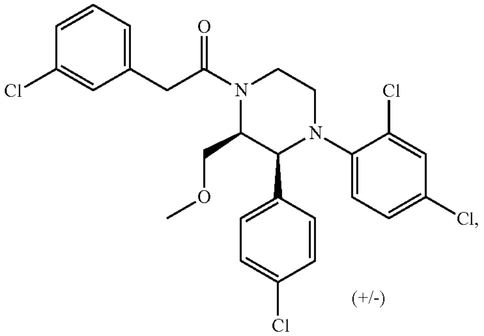
-continued
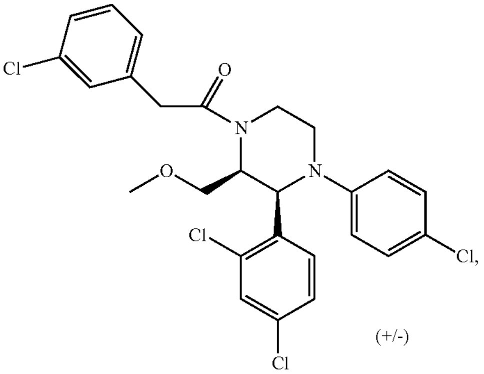
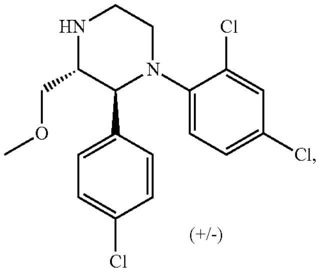
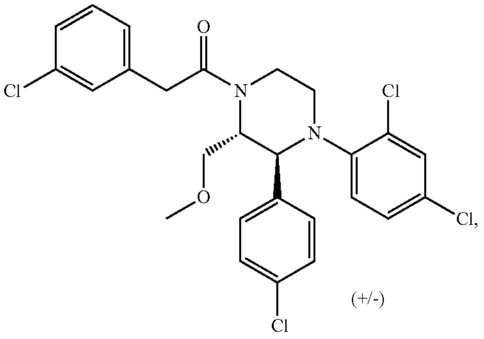
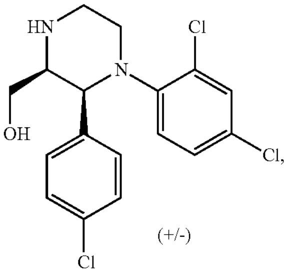
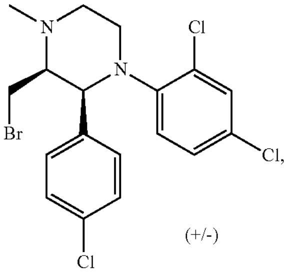

-continued
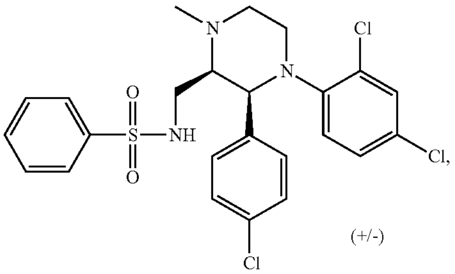
(+/-)
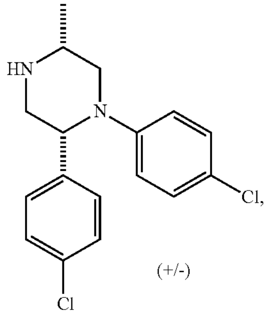
(+/-)
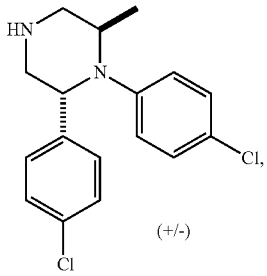
(+/-)
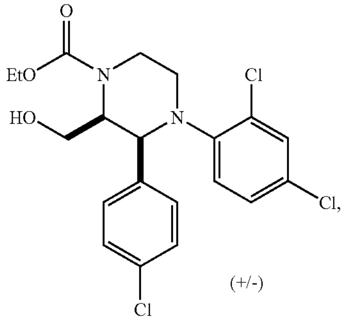
(+/-)
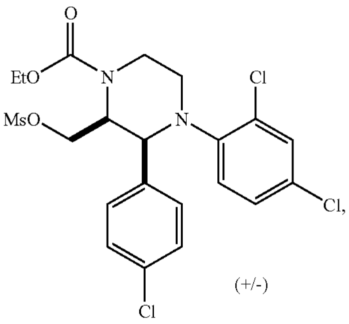
(+/-)
-continued
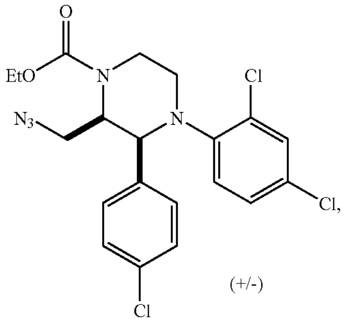
(+/-)
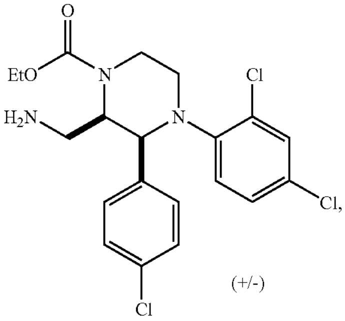
(+/-)
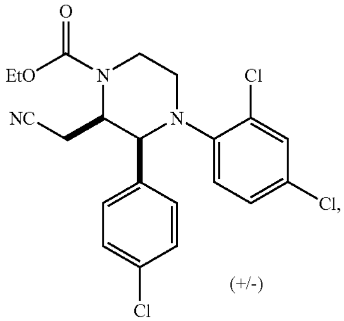
(+/-)
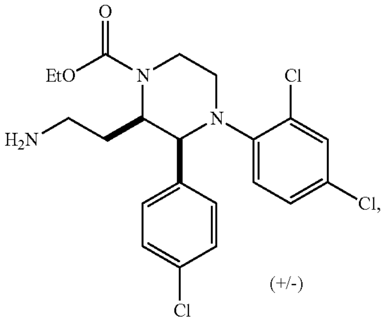
(+/-)
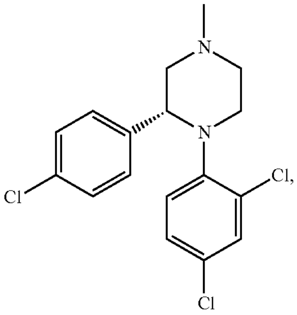

-continued
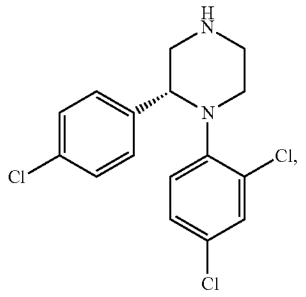
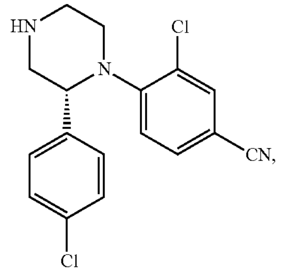
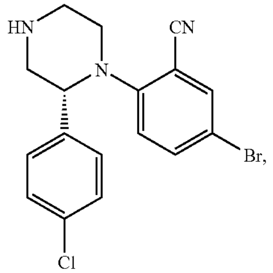
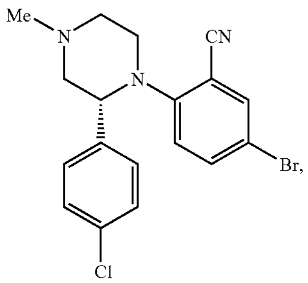
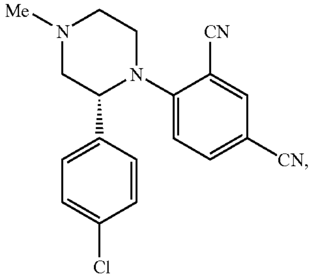
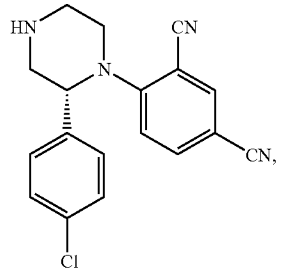
-continued
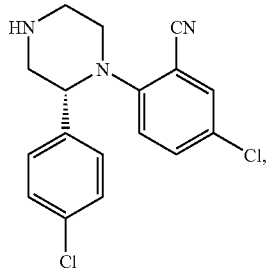
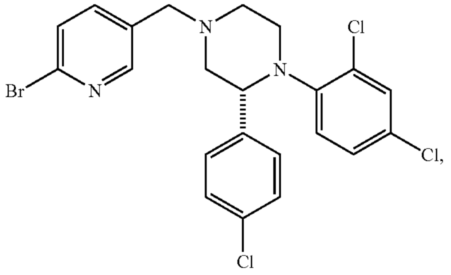
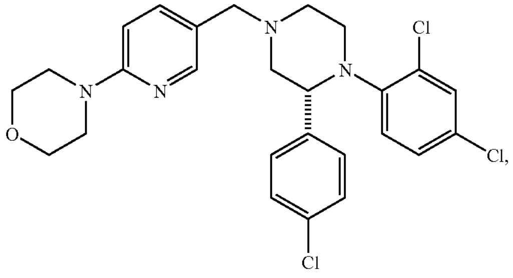
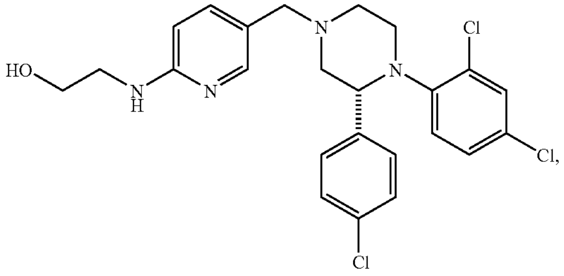
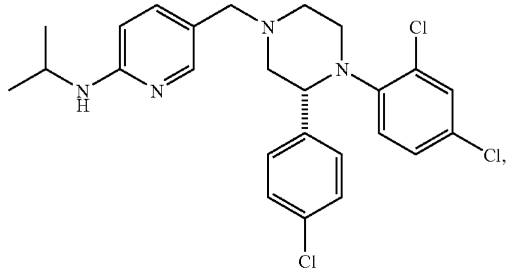
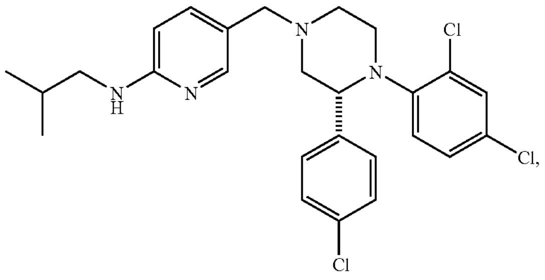

-continued
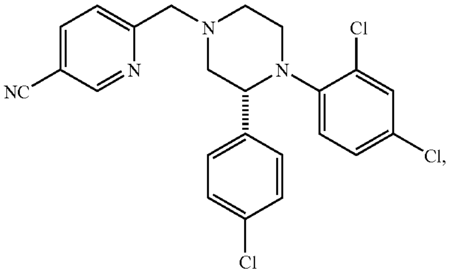
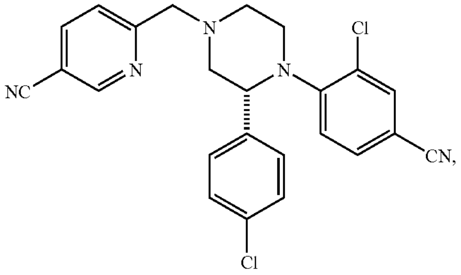
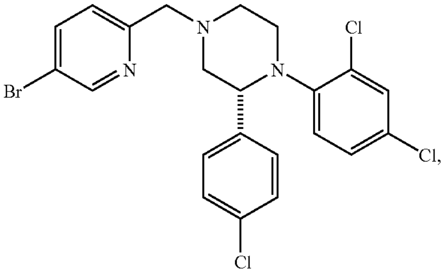
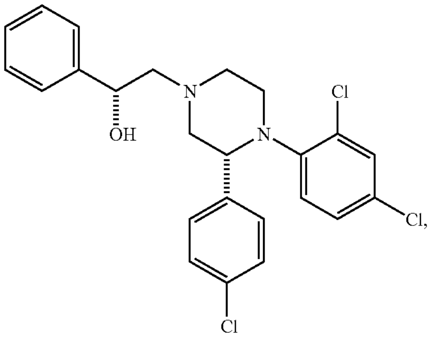
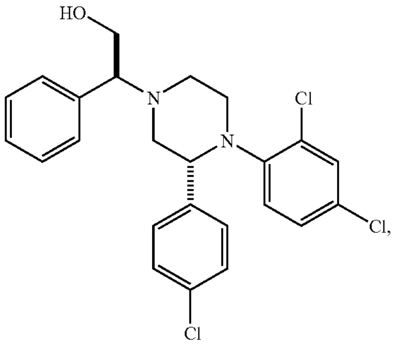
-continued
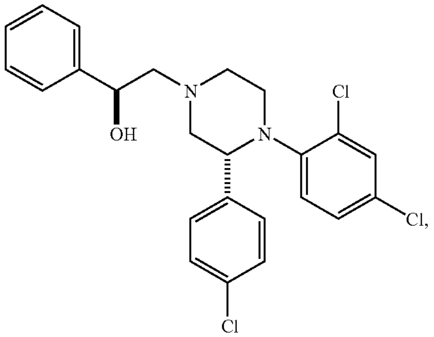
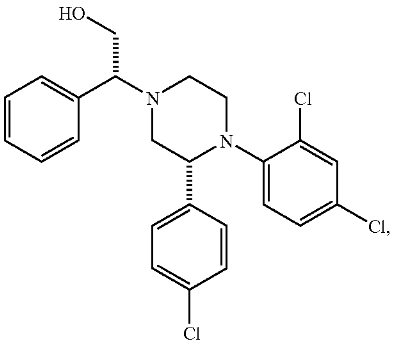
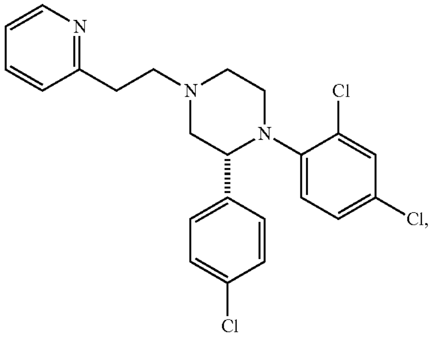
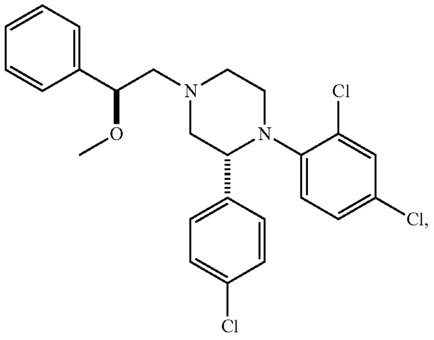
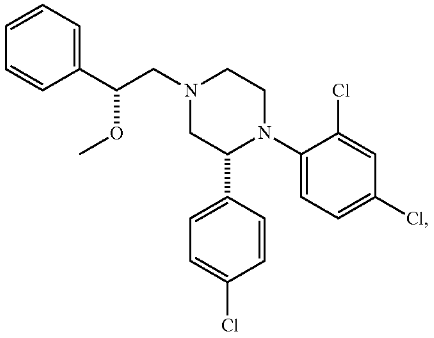

-continued
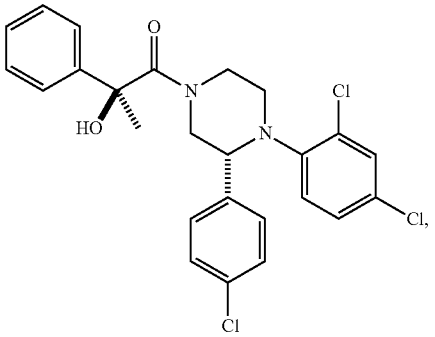
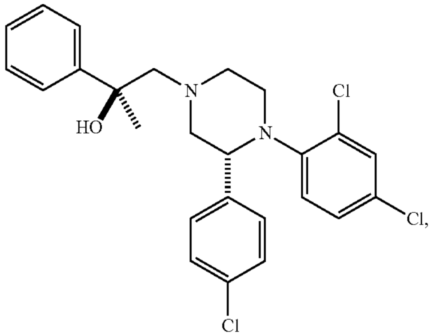
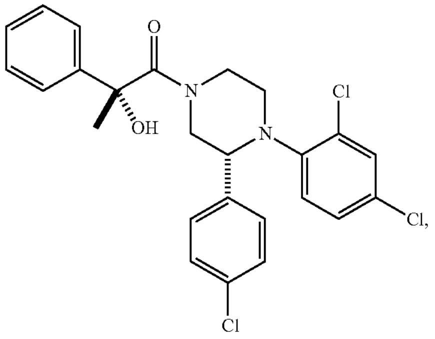
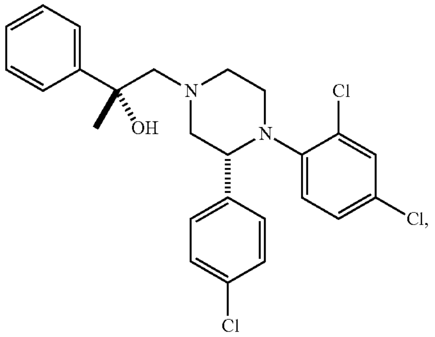
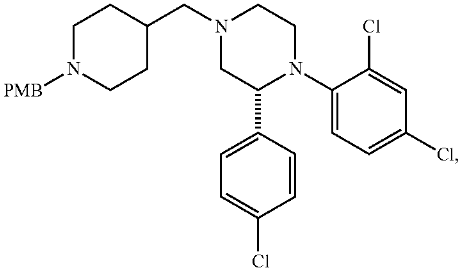
-continued
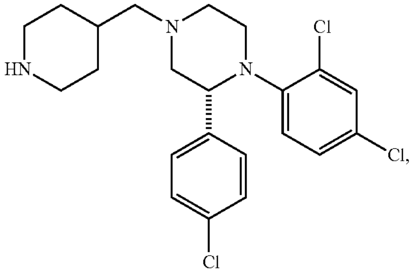
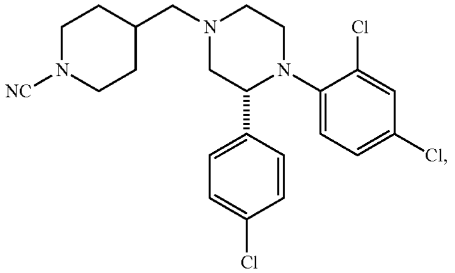
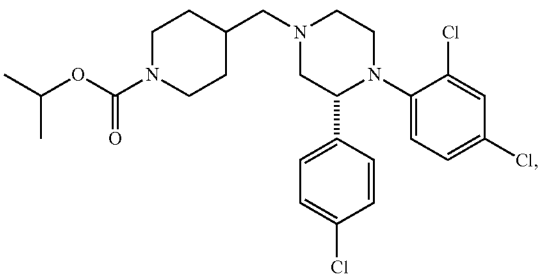
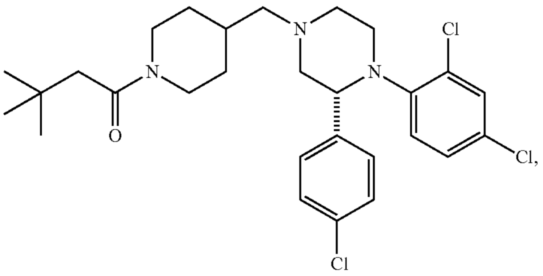
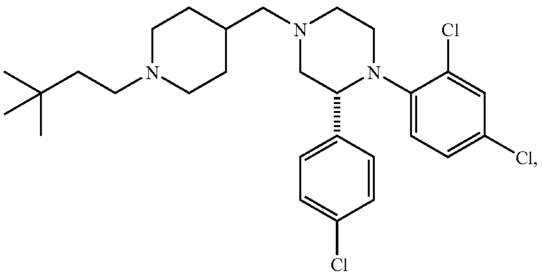
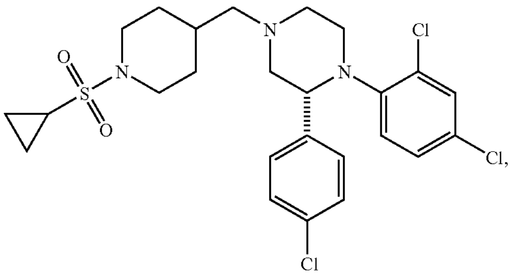

-continued
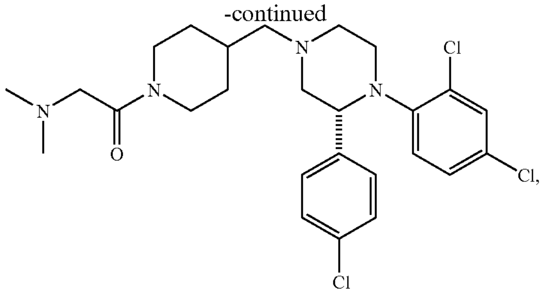
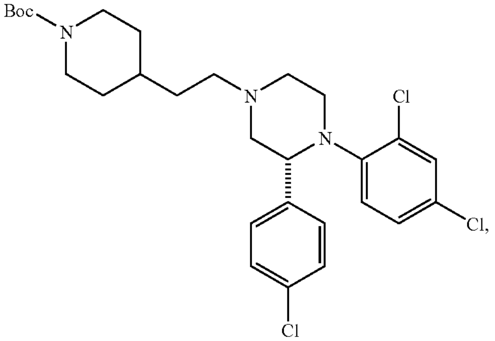
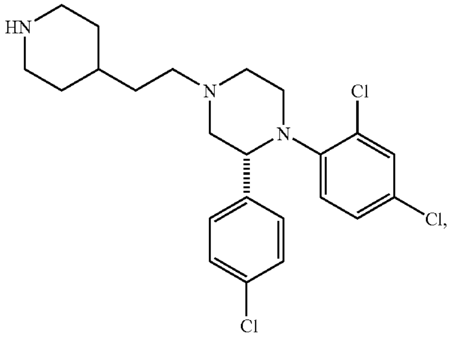
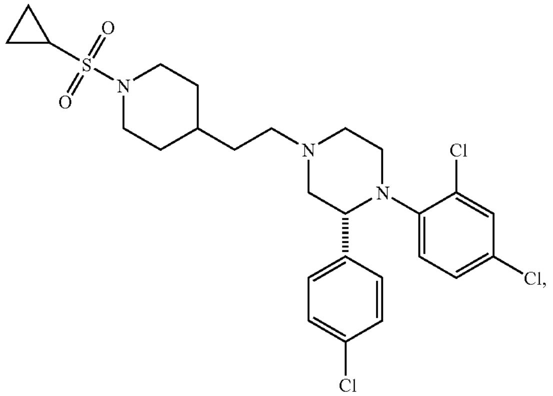
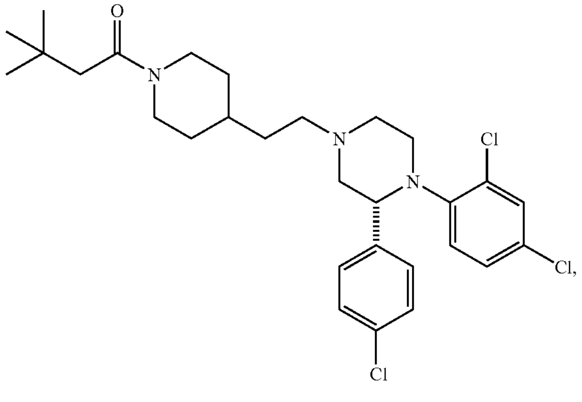
-continued
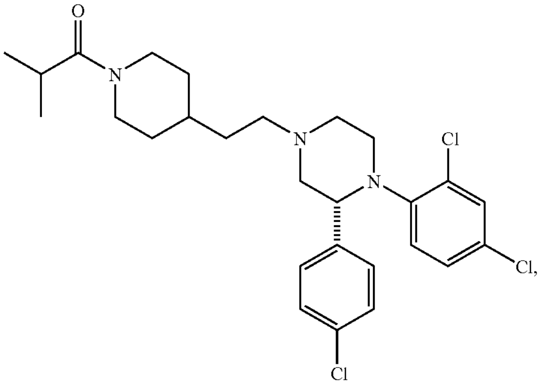
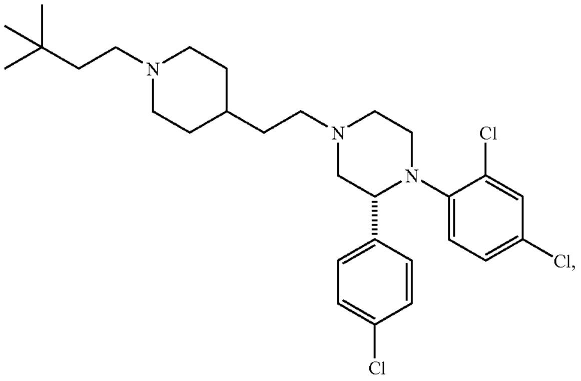
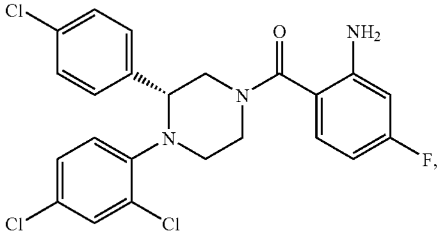
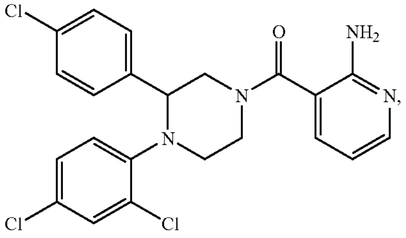
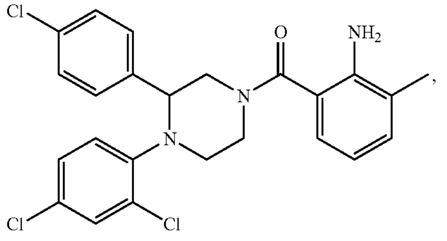
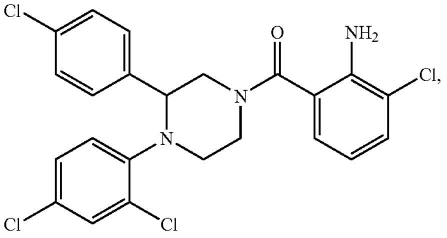

-continued
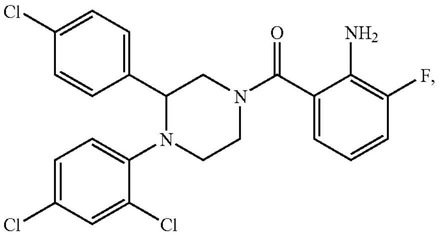
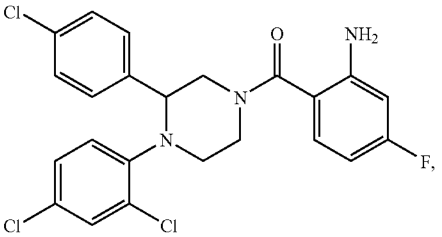
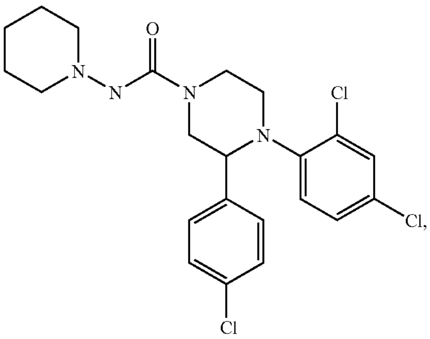
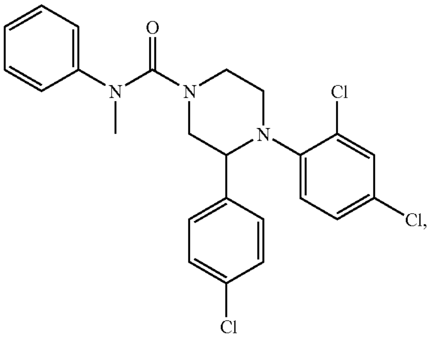
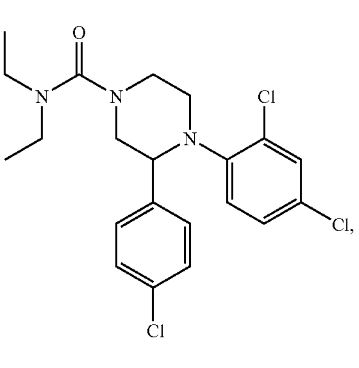
-continued
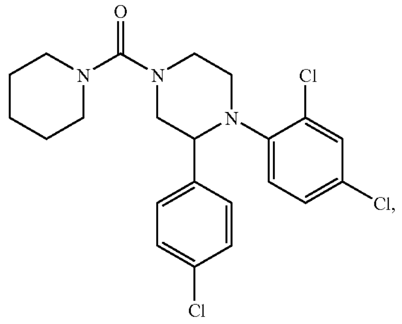
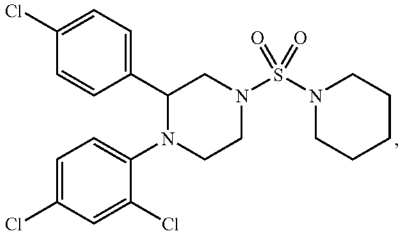
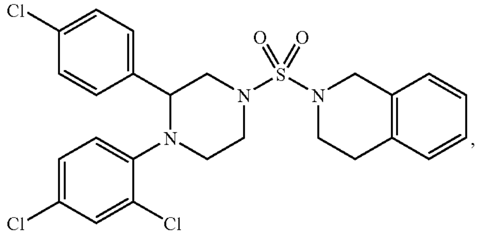
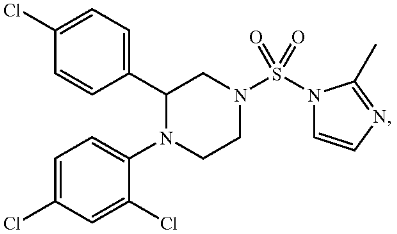
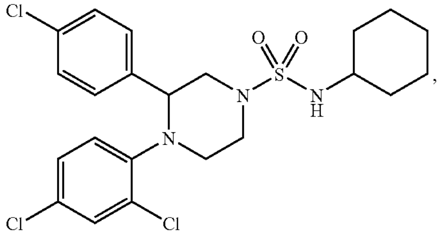
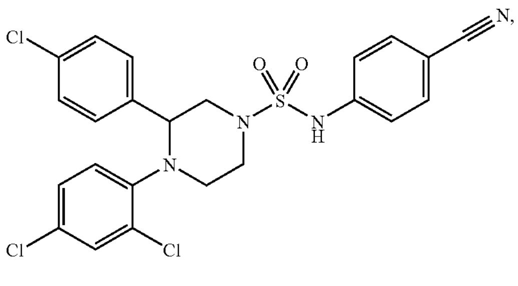

-continued
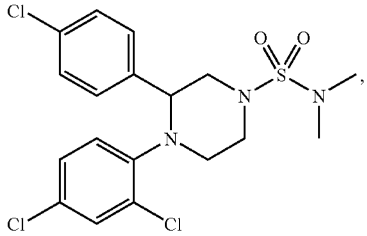
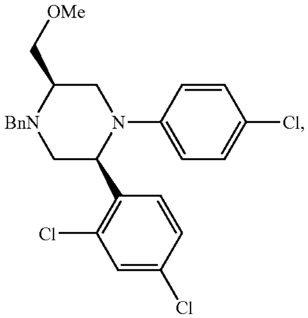
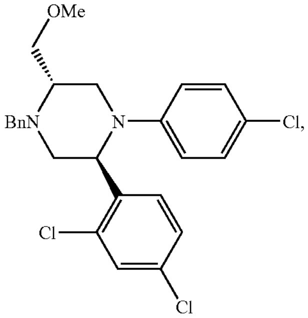
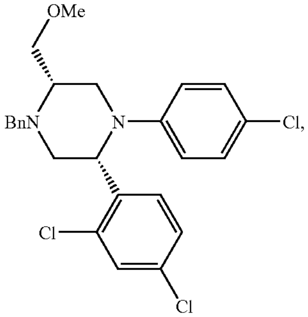
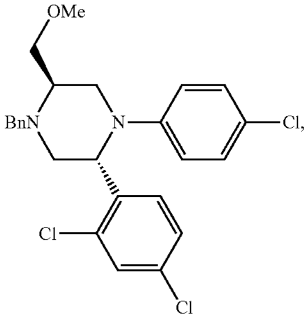
-continued
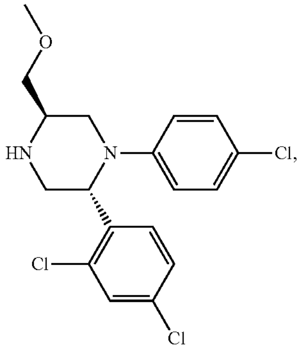
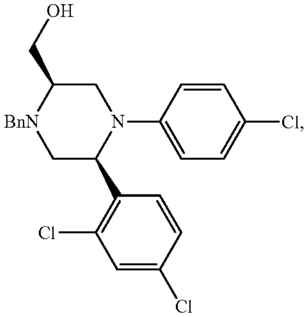
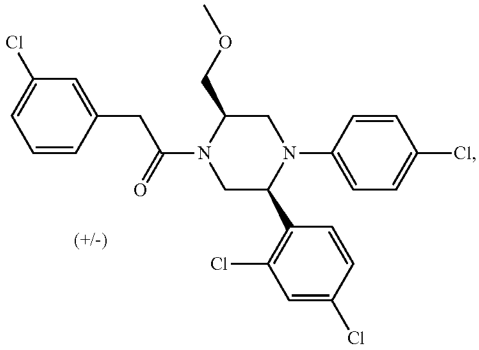
(+/-)
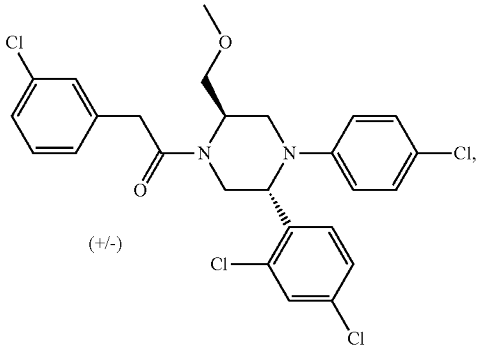
(+/-)
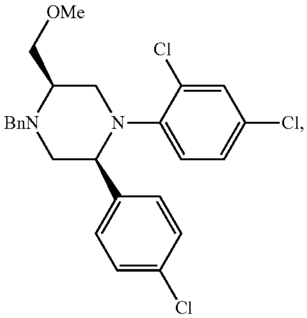

-continued
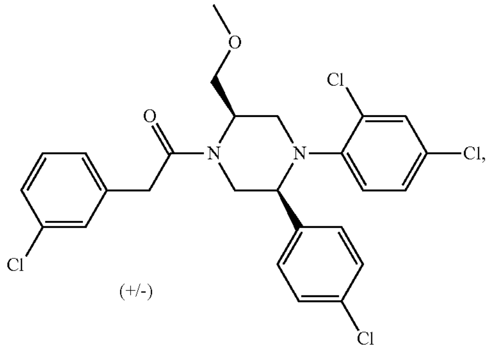
(+/-)
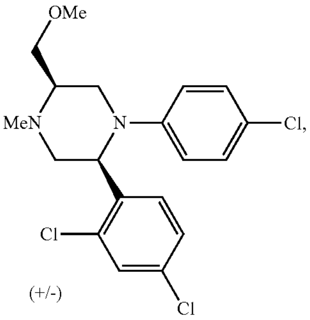
(+/-)
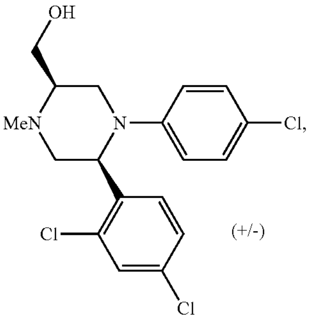
(+/-)
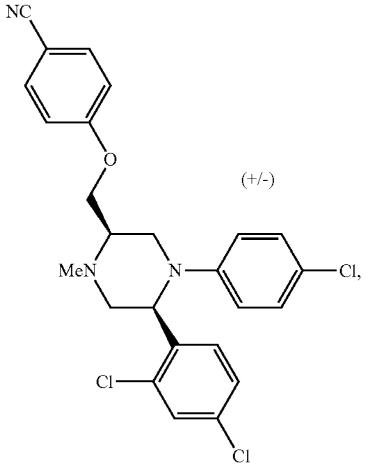
(+/-)
-continued
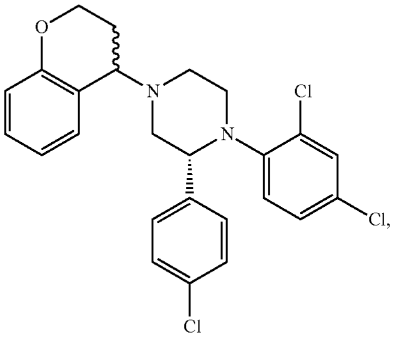
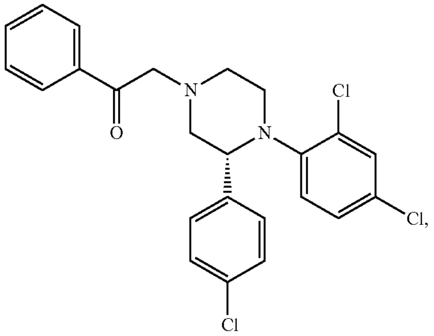
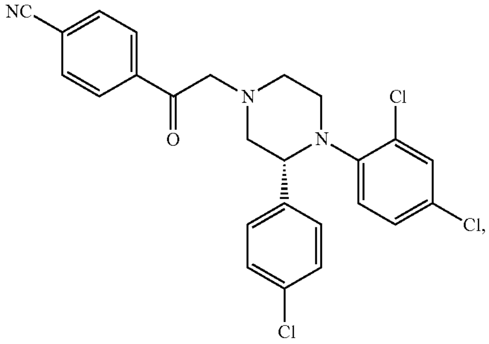
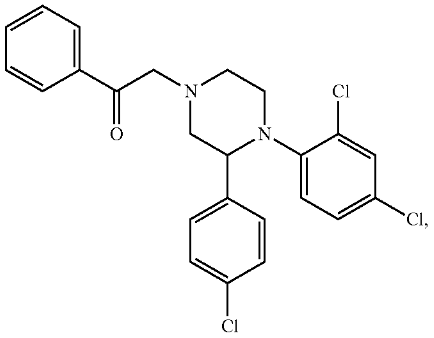
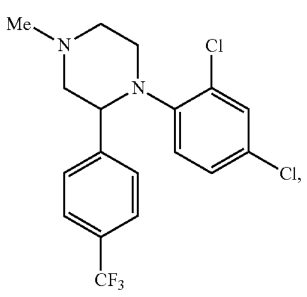

-continued
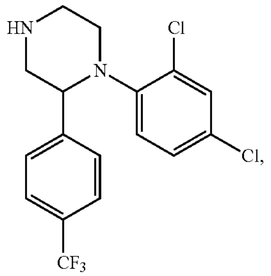
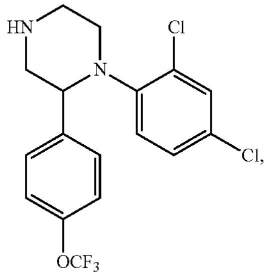
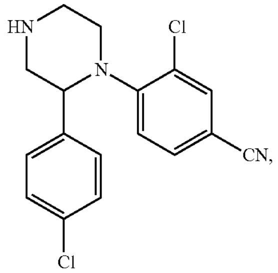
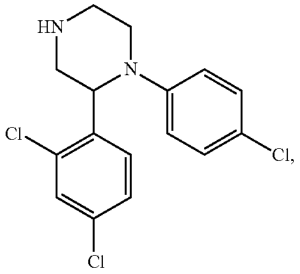
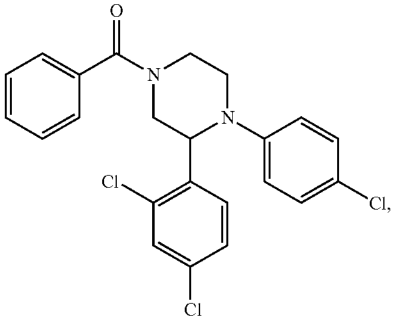
-continued
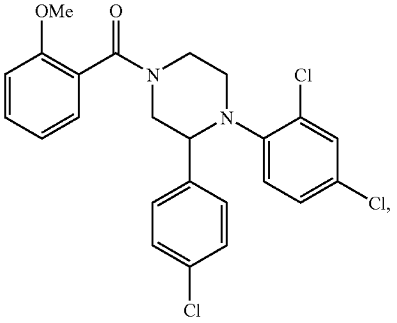
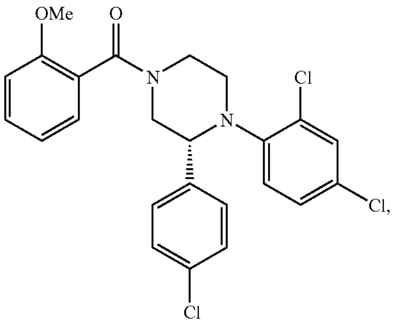
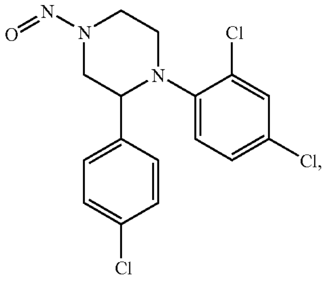
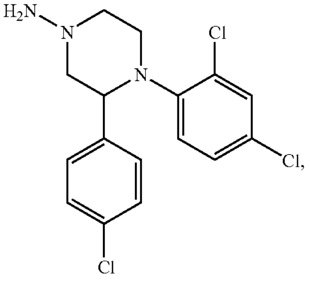
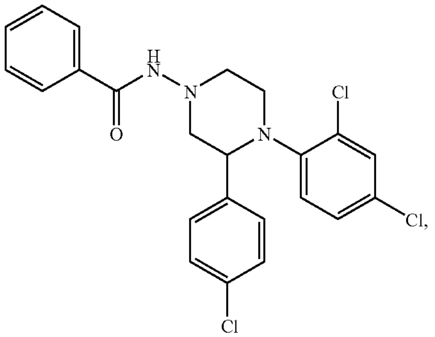

-continued
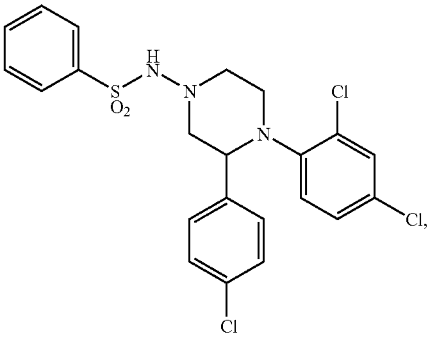
,
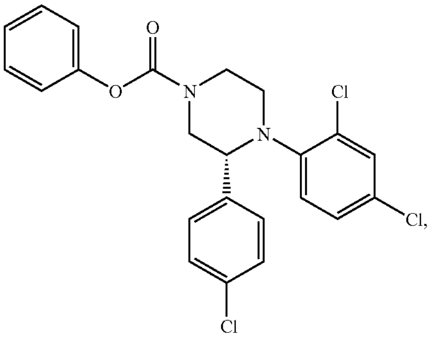
,
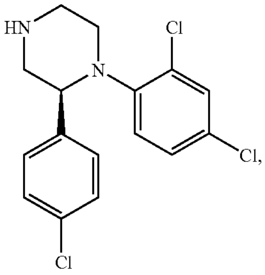
,
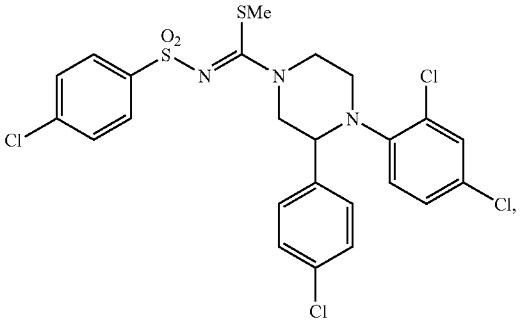
,
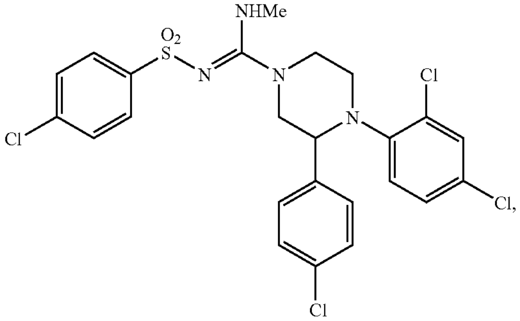
,
-continued
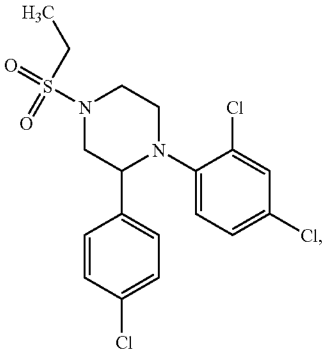
,
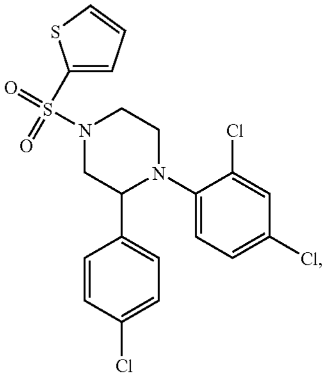
,
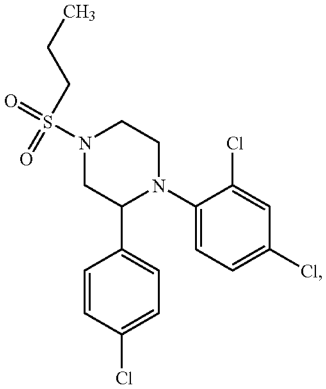
,
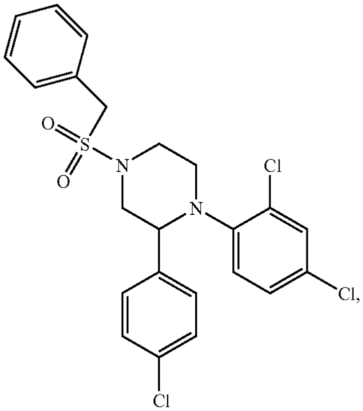
, -continued
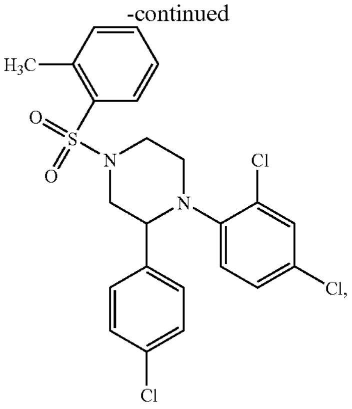
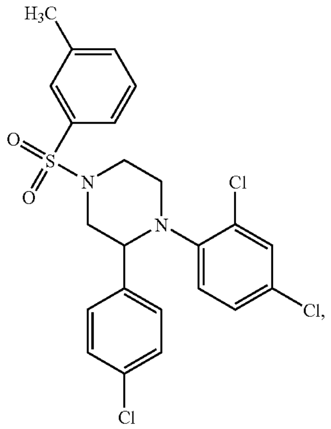
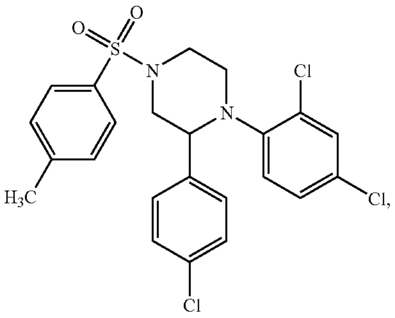
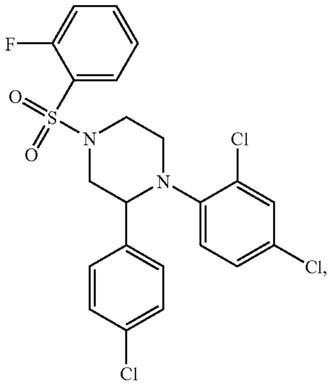
-continued
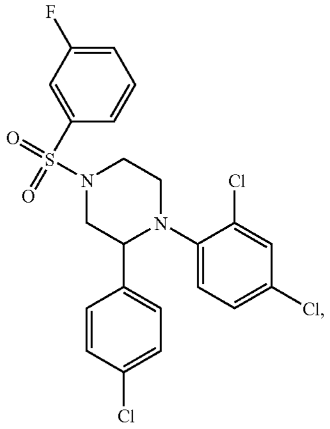
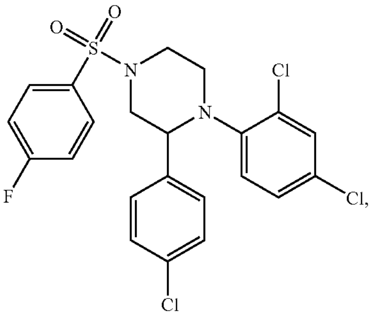
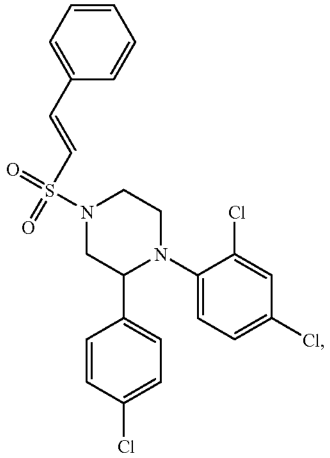
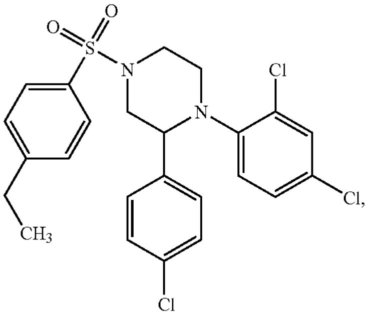

-continued
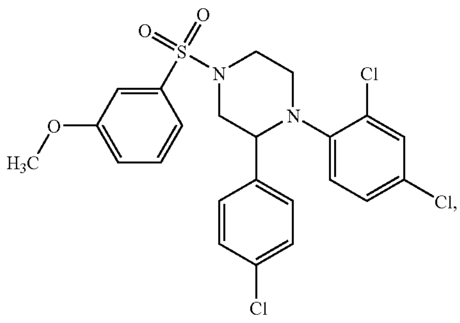
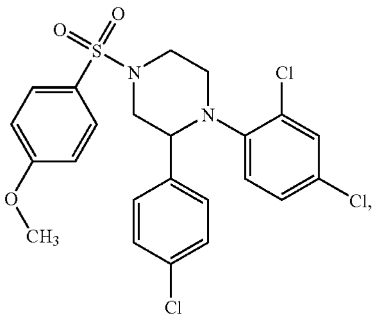
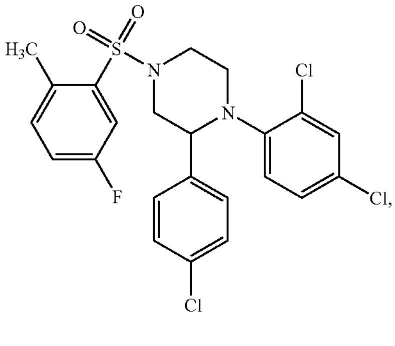
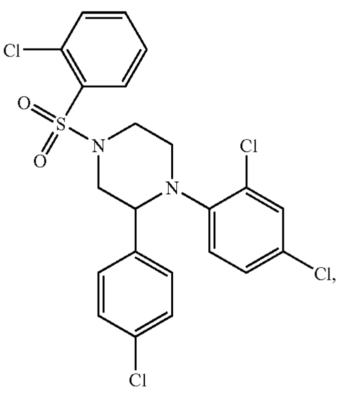
-continued
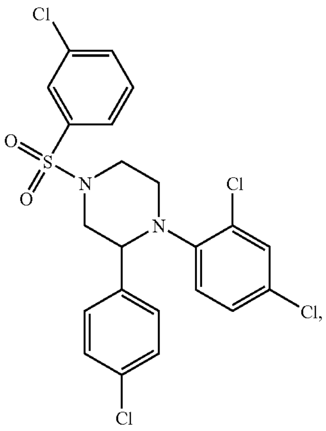
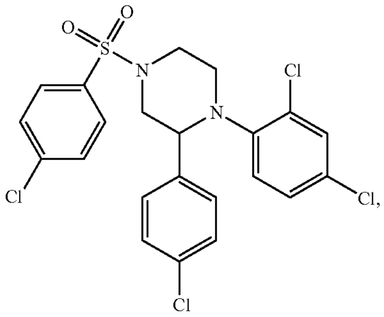
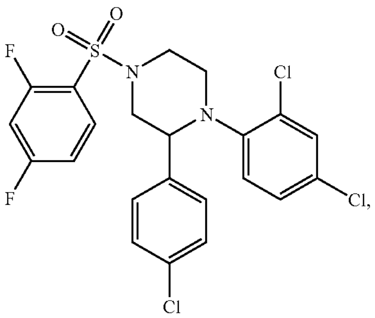
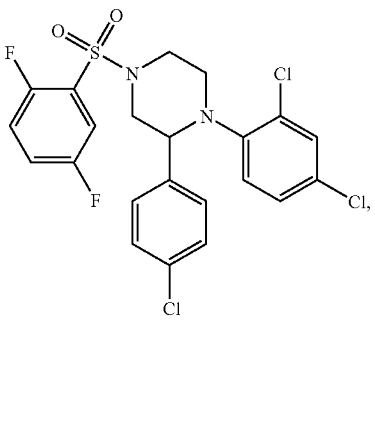

-continued
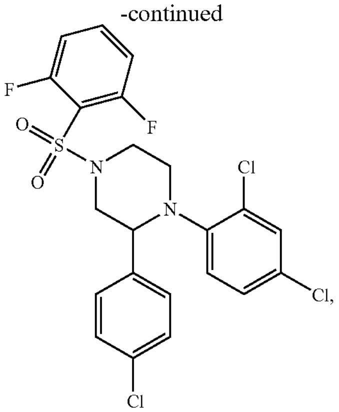
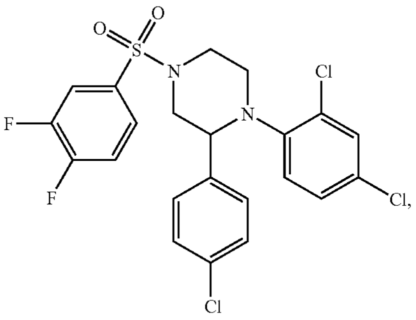
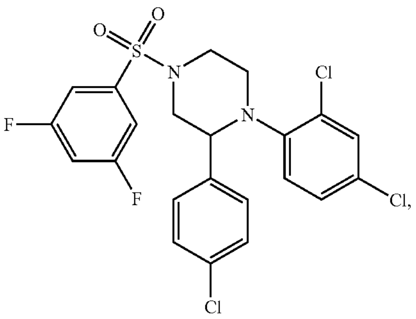
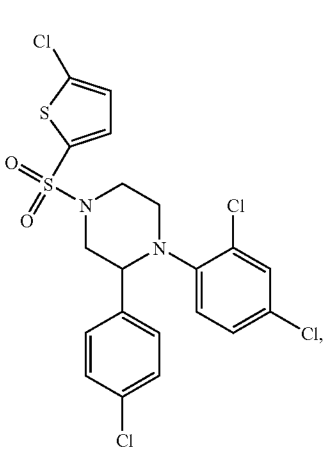
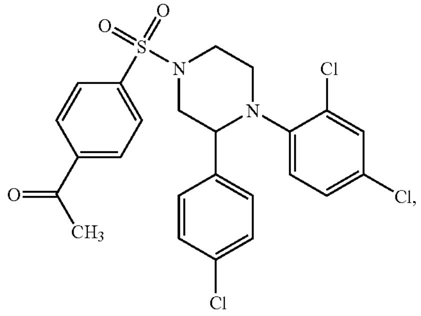
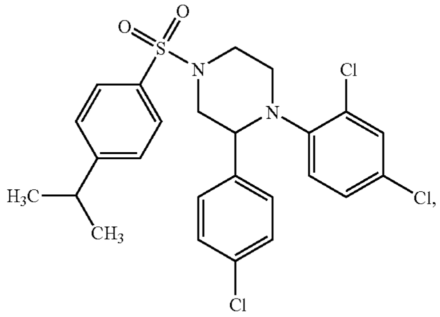
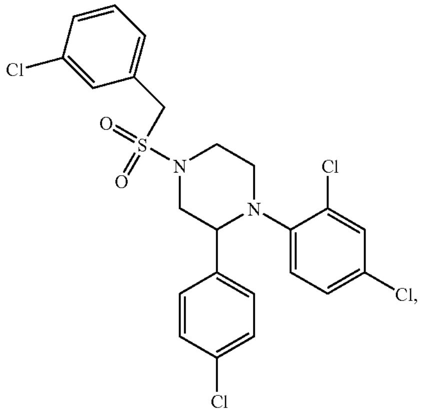
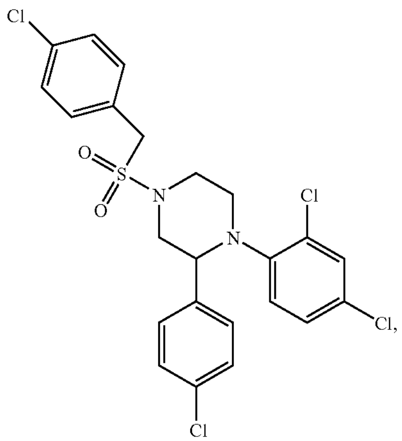

-continued
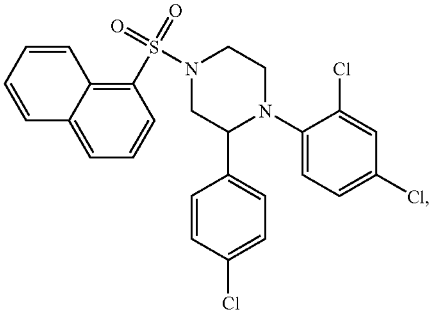
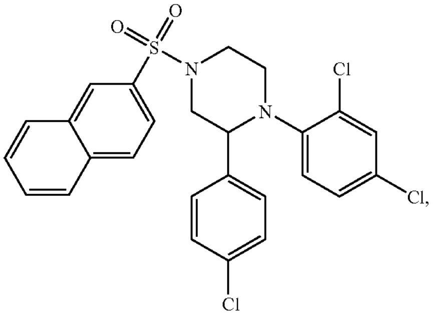
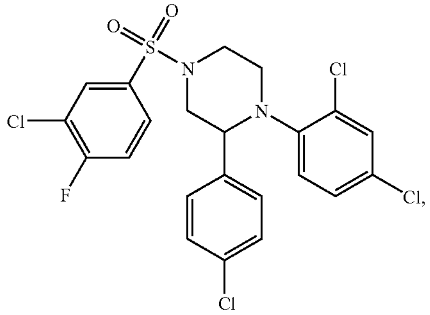
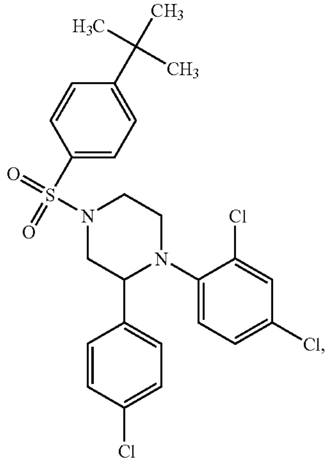
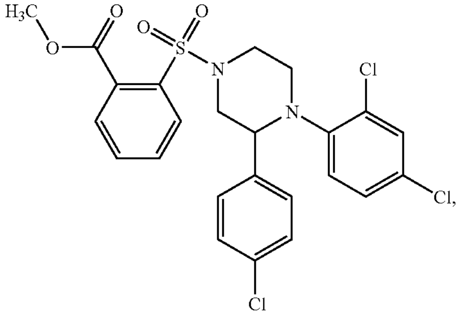
-continued
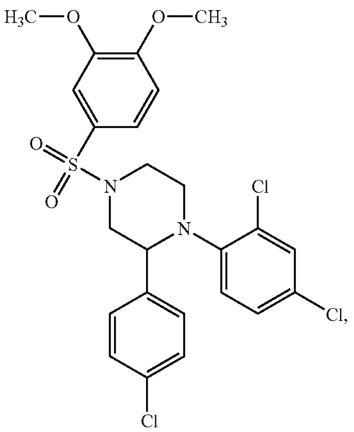
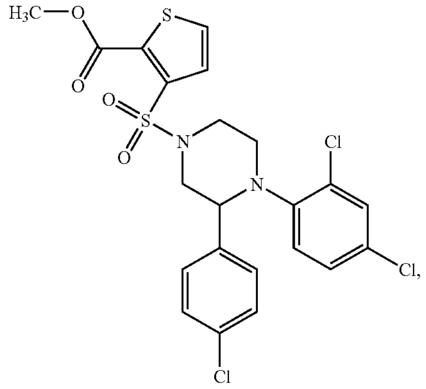
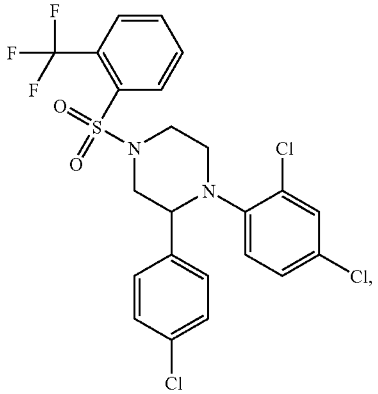
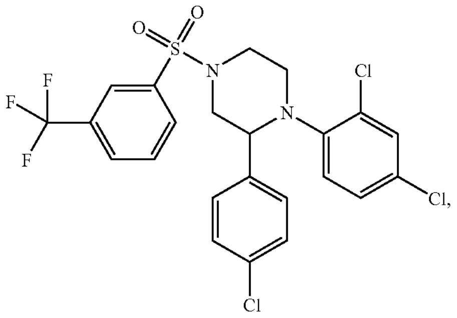

-continued
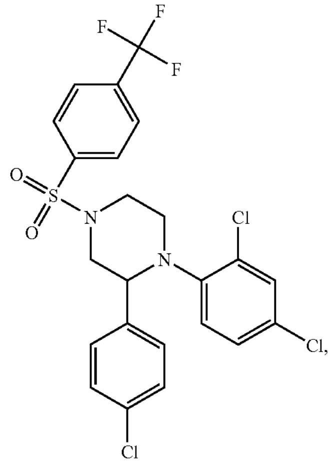
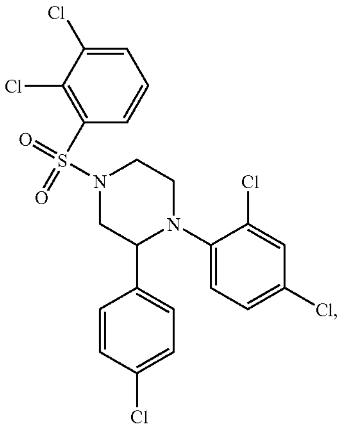
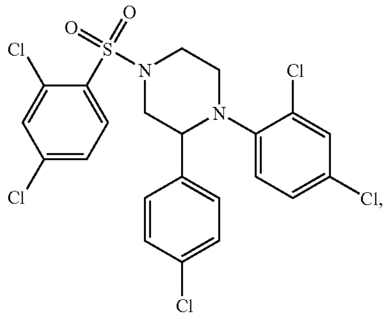
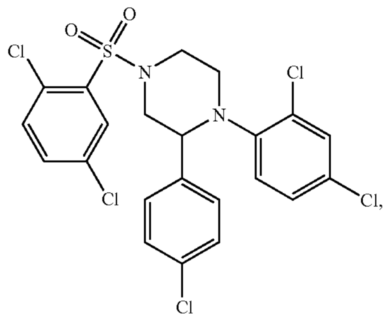
-continued
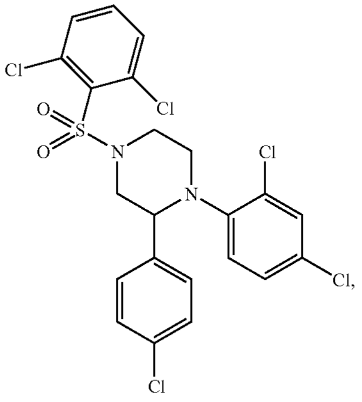
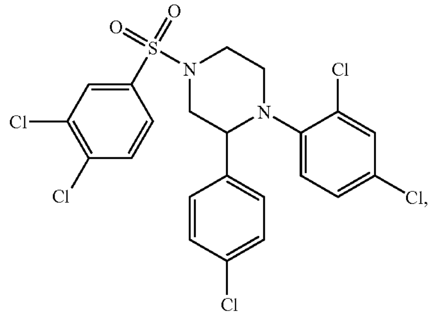
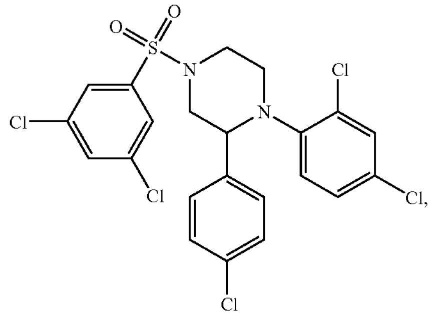
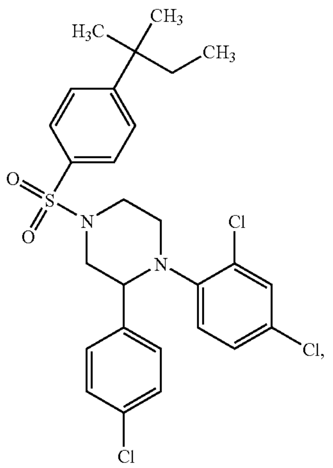

-continued
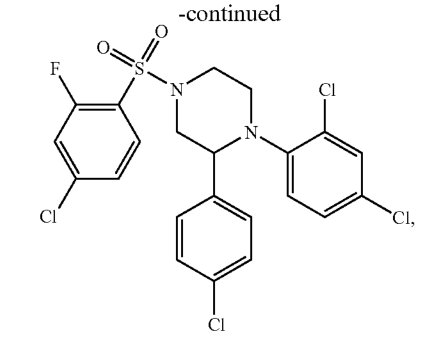
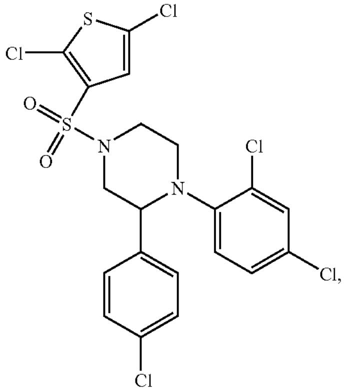
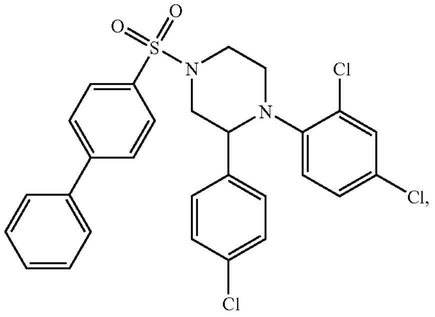
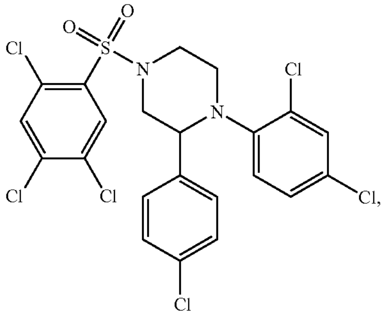
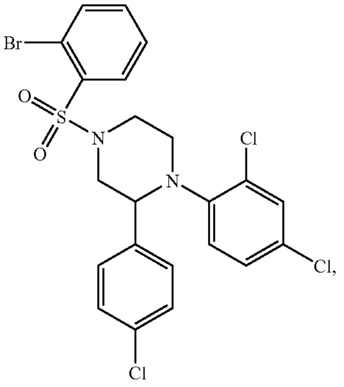
-continued
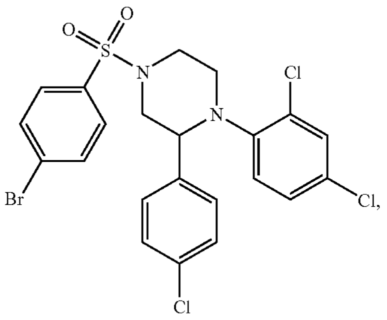
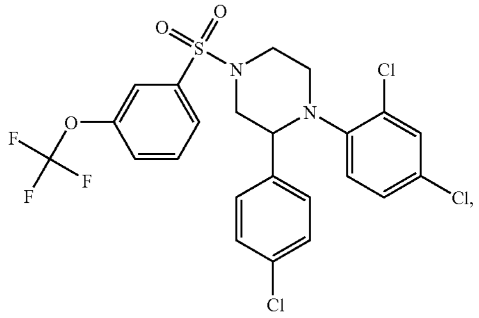
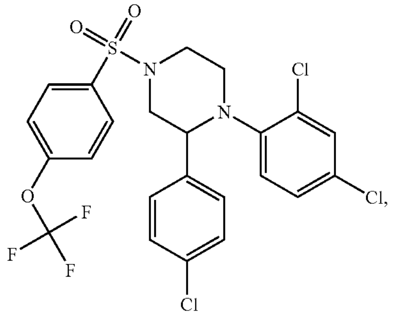
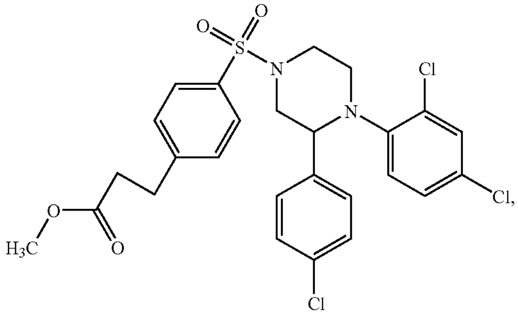
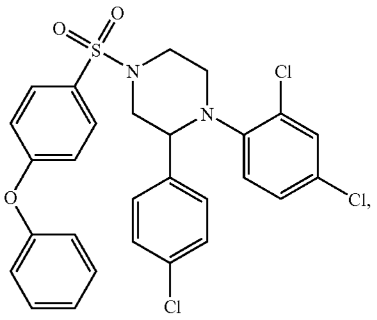

-continued
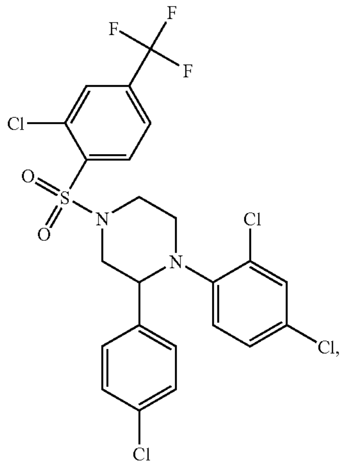
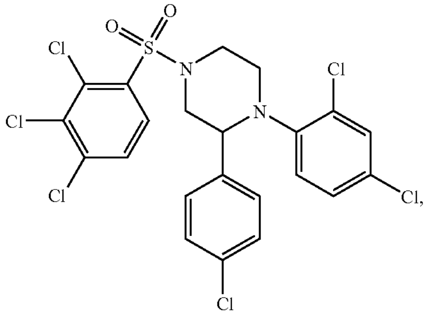
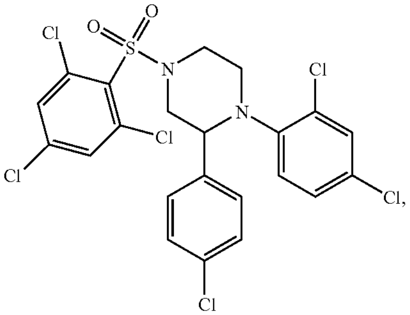
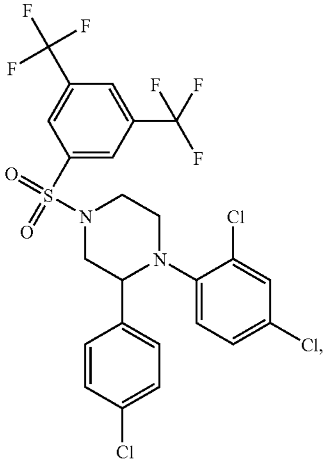
-continued
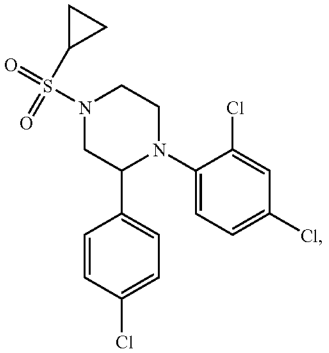
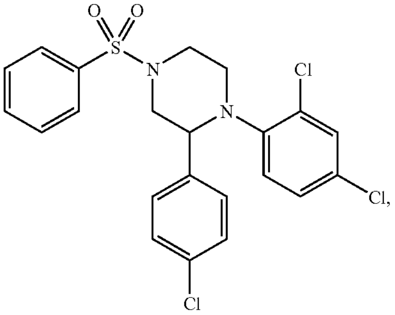
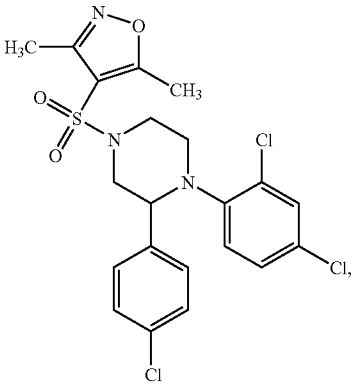
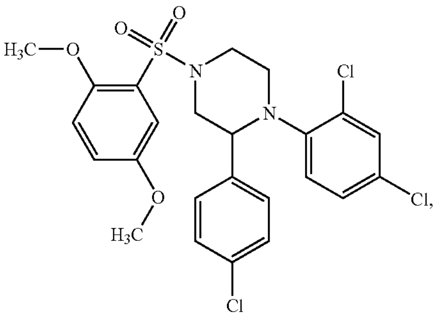

-continued
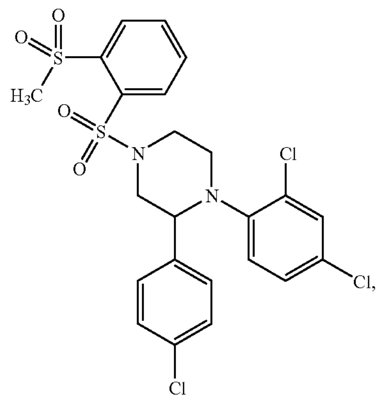
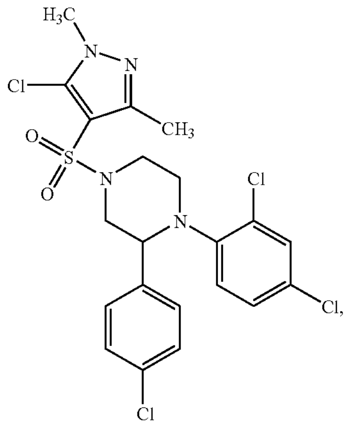
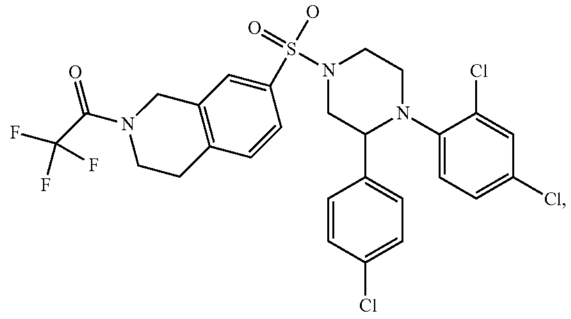
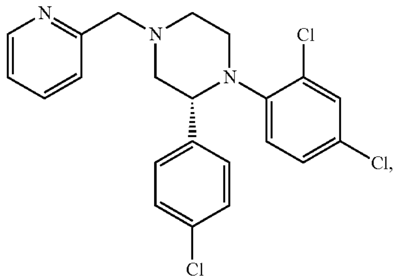
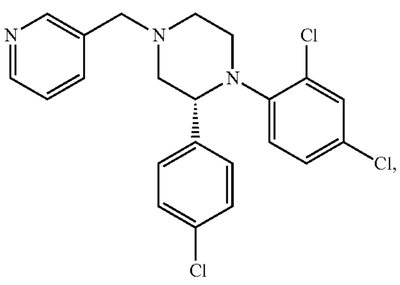
-continued
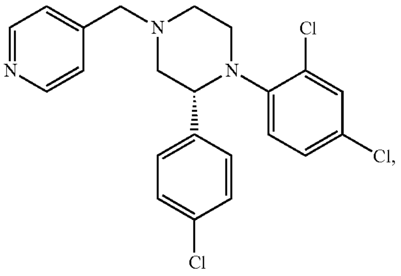
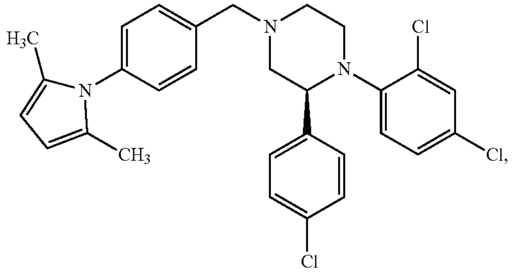
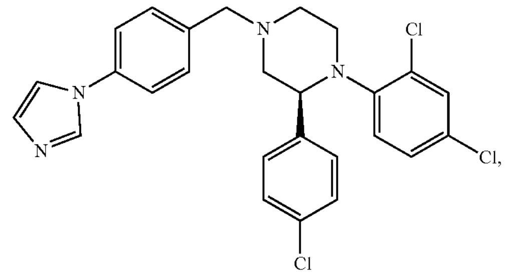
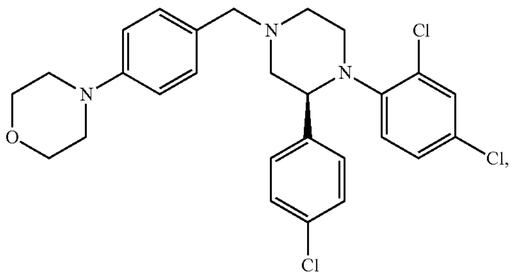
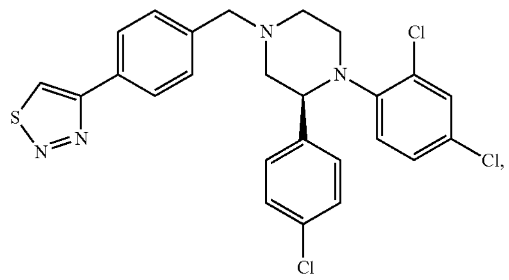
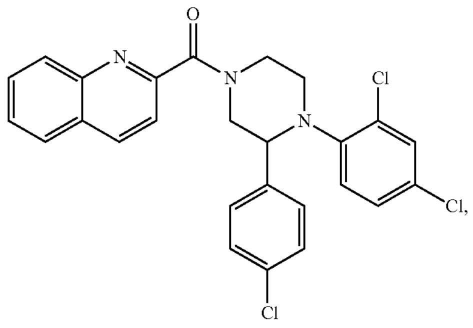

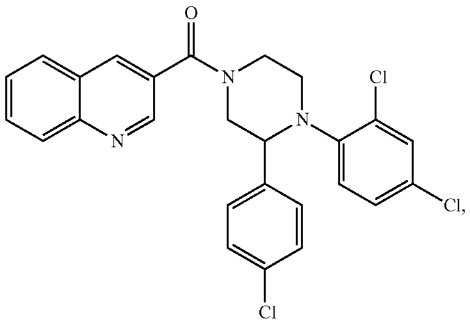
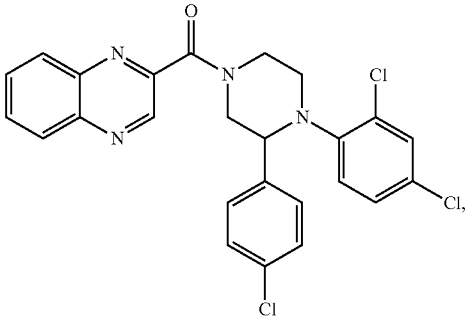
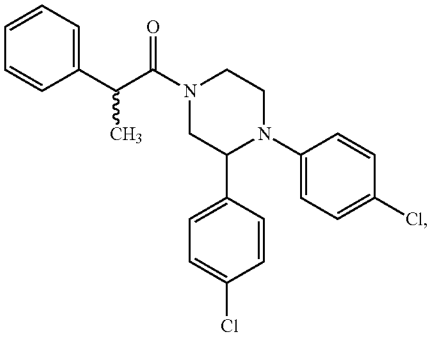
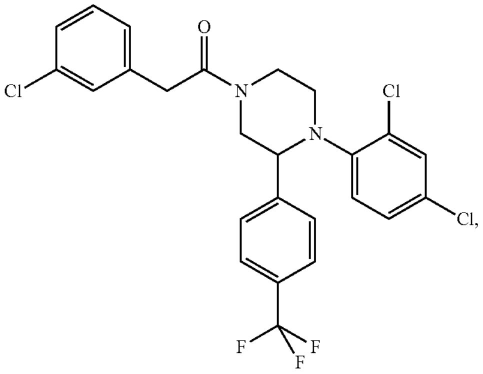
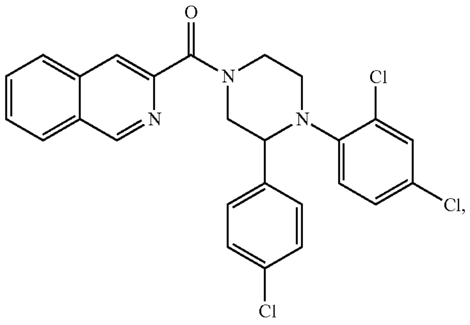
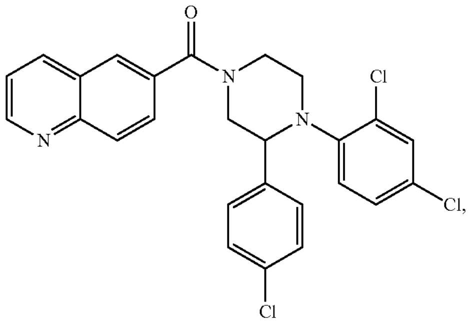
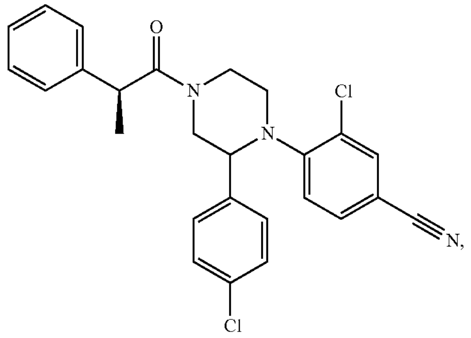
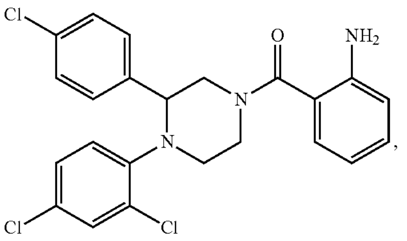
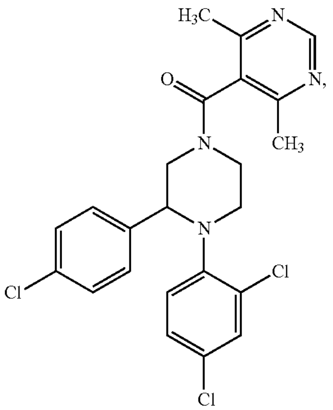
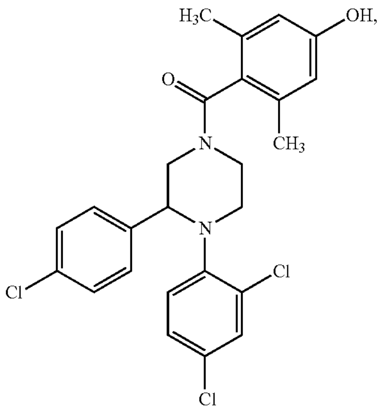

-continued
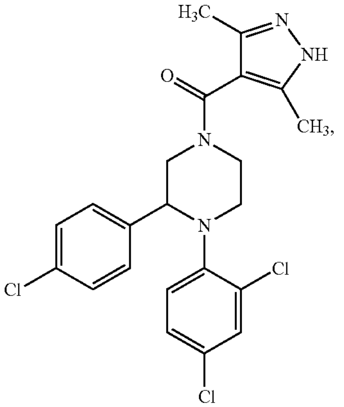
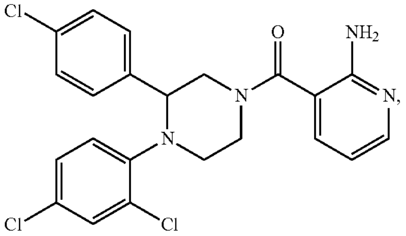
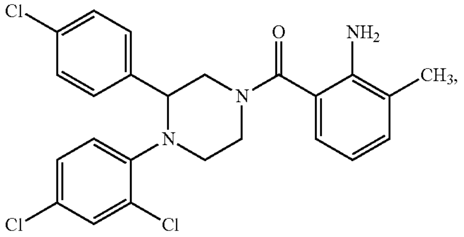
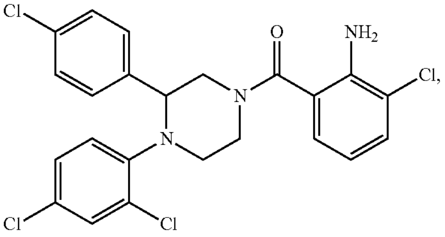
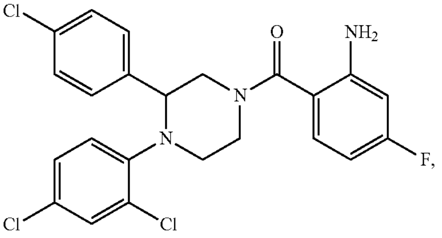
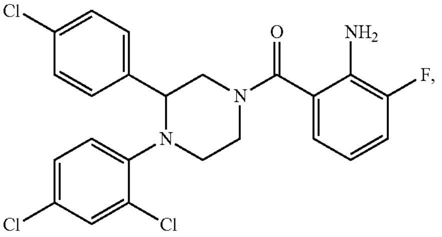
-continued
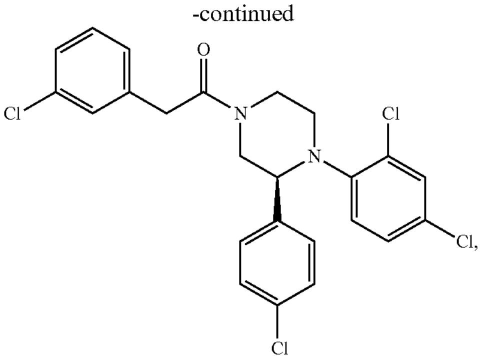
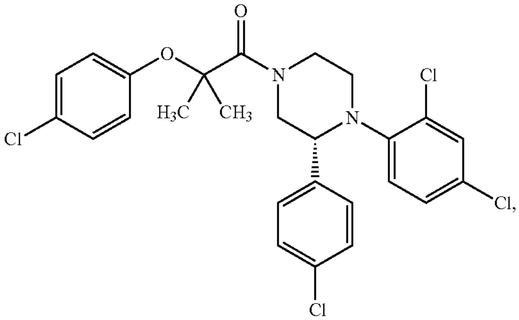
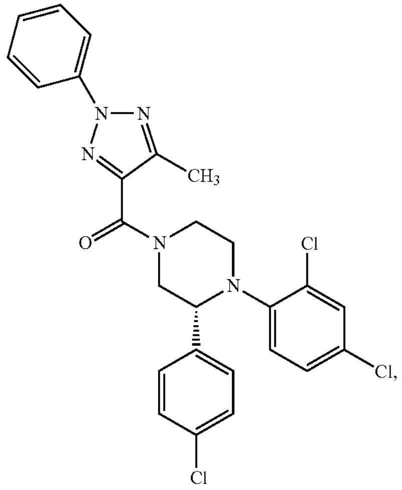
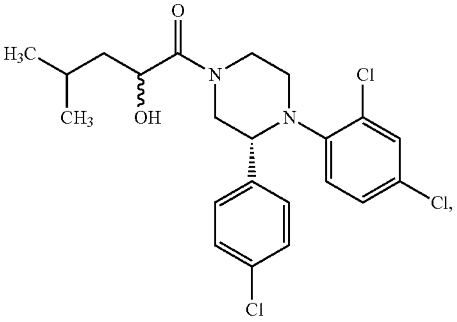

-continued
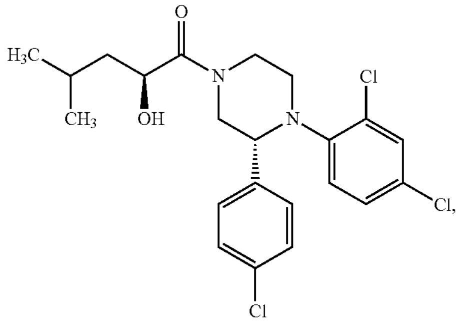
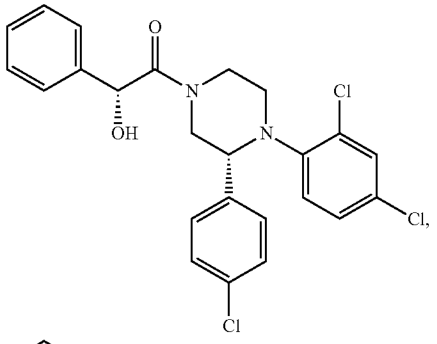
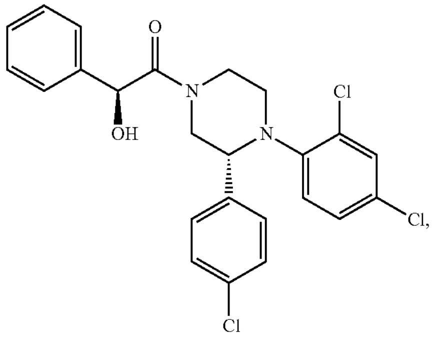
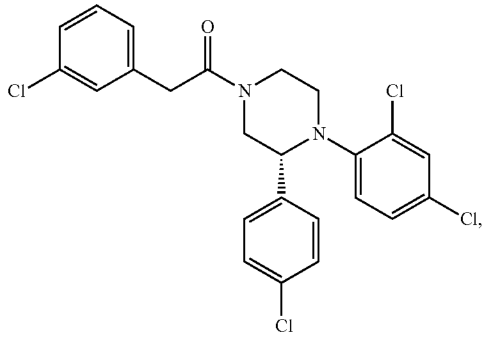
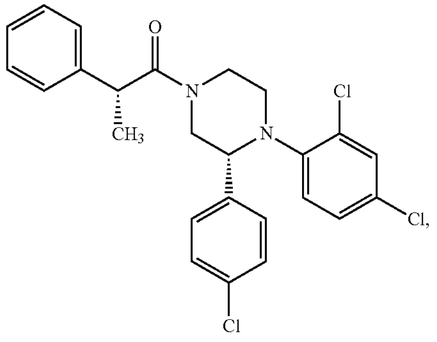
-continued
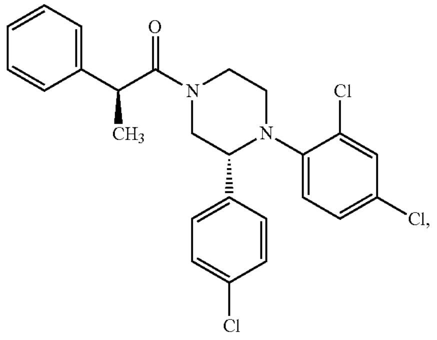
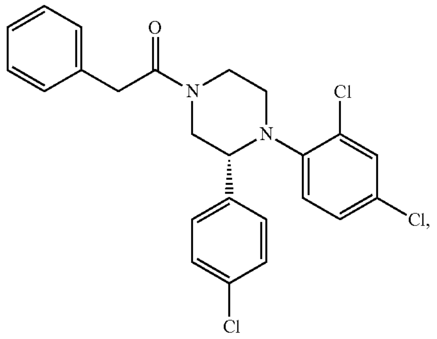
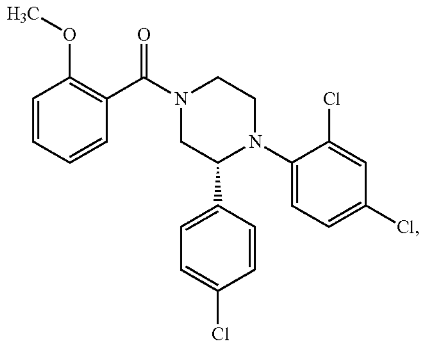
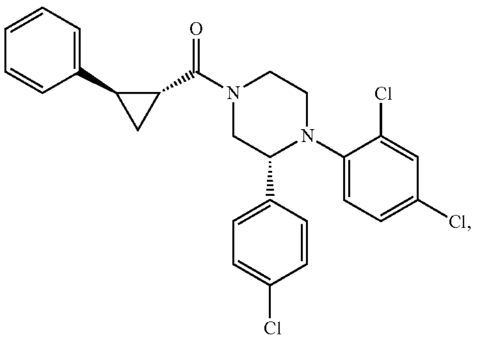
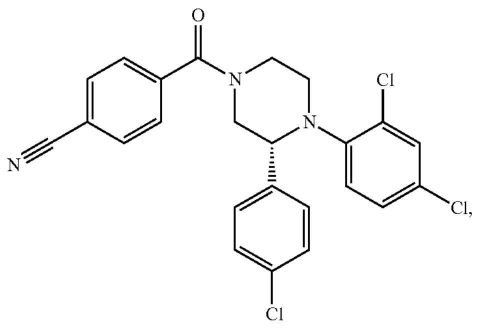

-continued
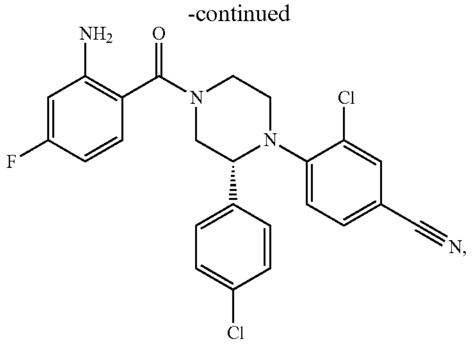,
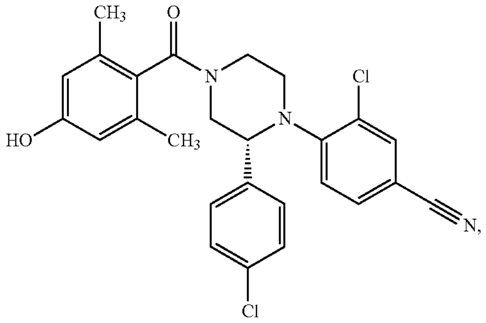,
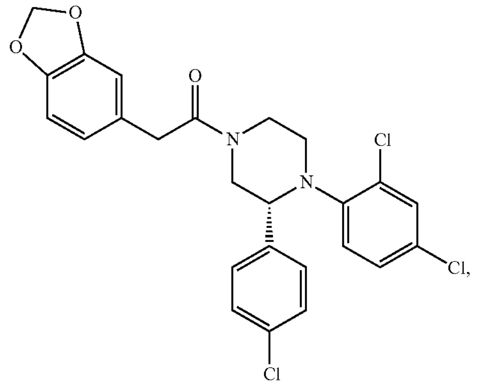,
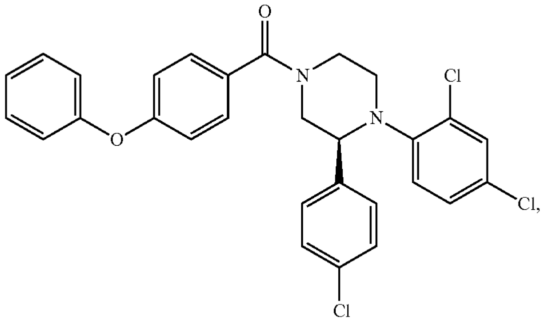,
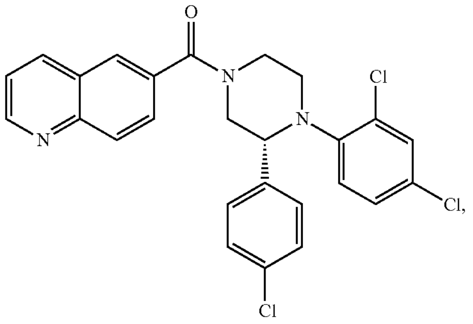,
-continued
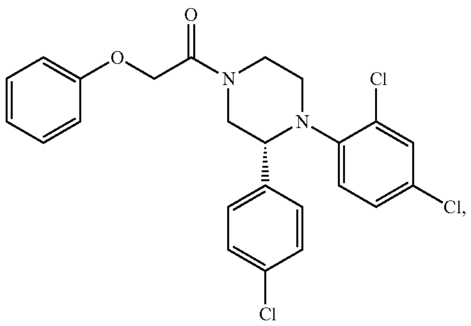,
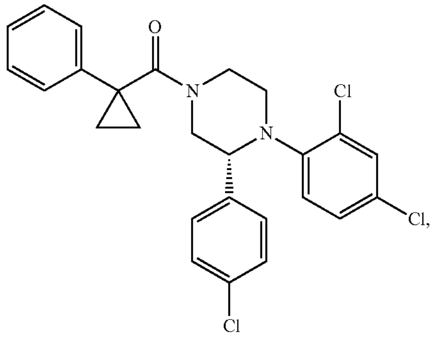,
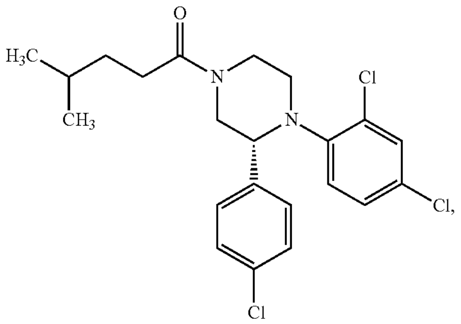,
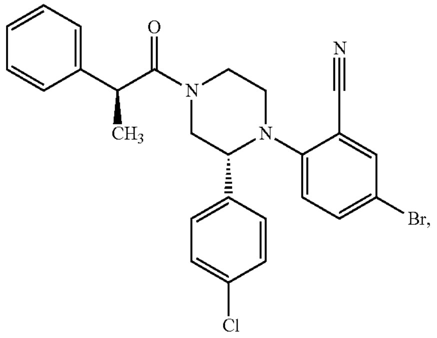,
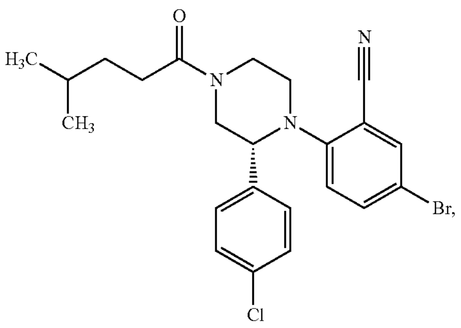, -continued
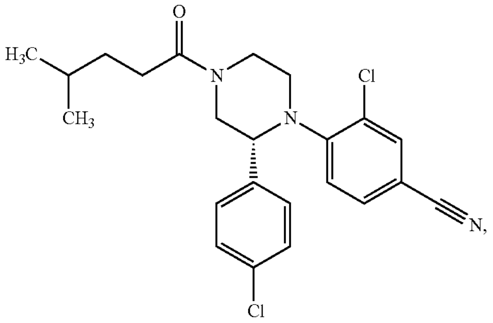
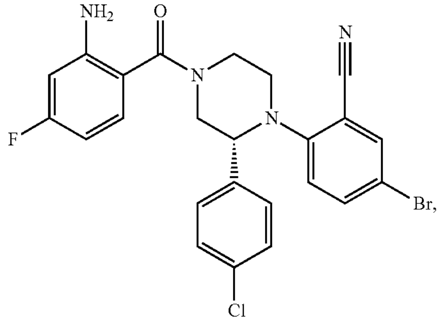
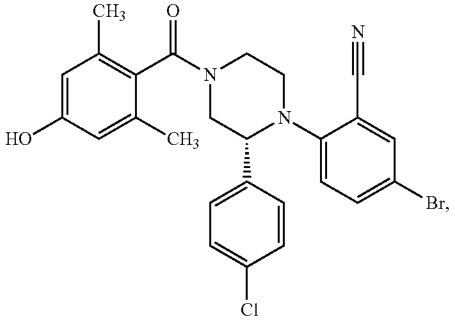
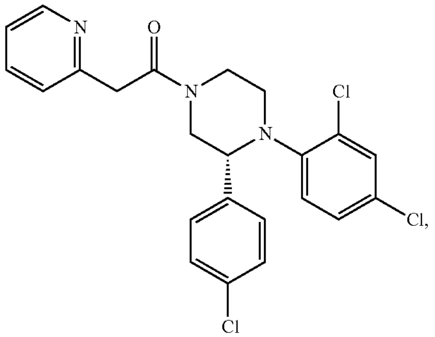
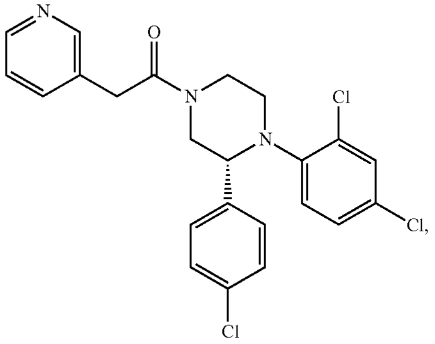
-continued
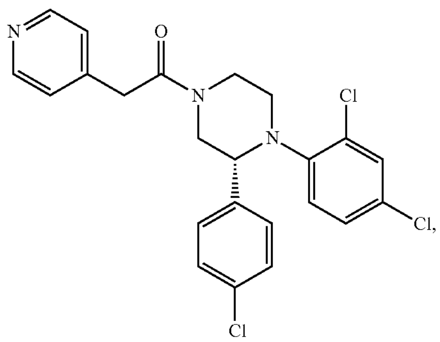
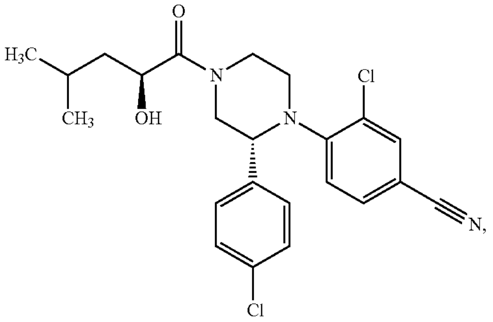
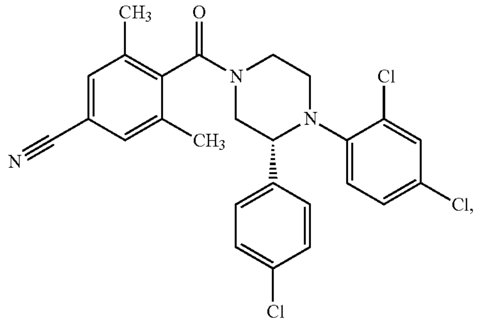
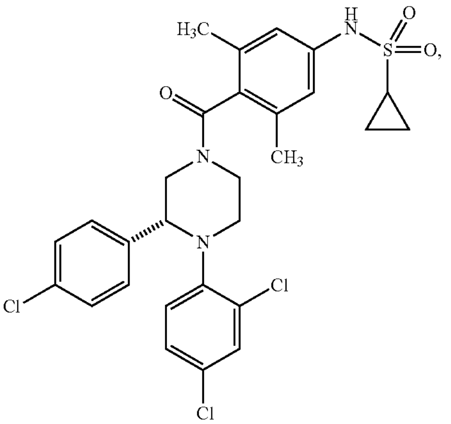

-continued
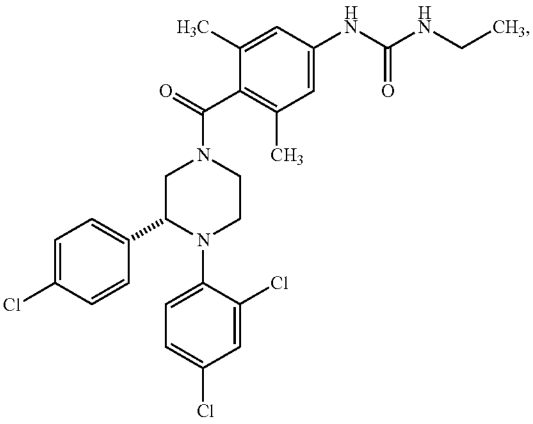
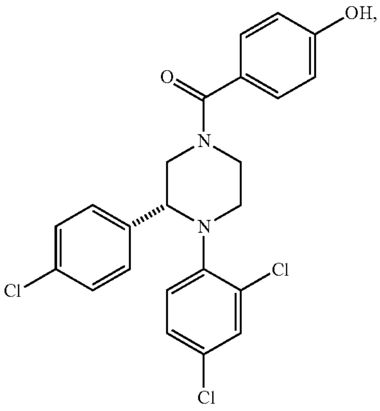
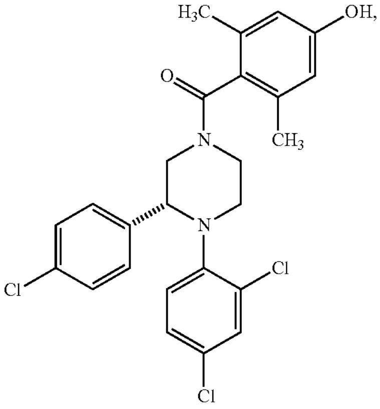
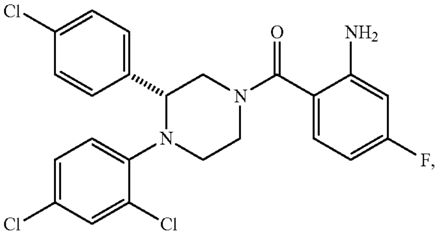
-continued
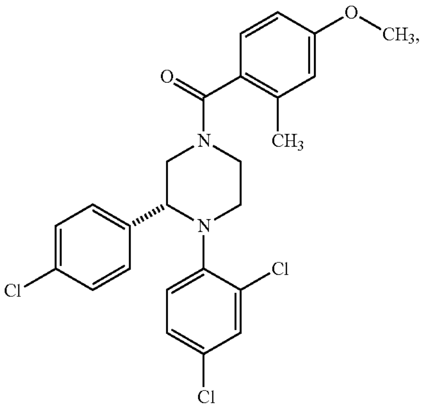
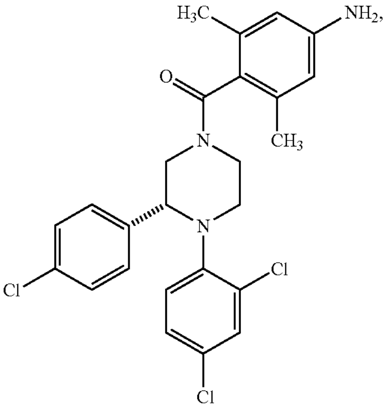
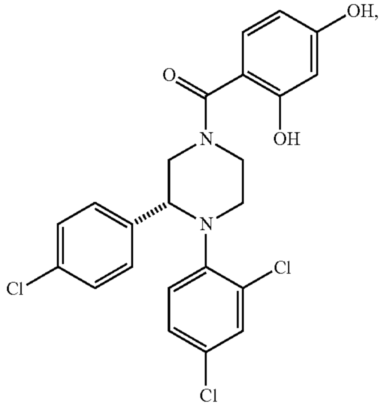
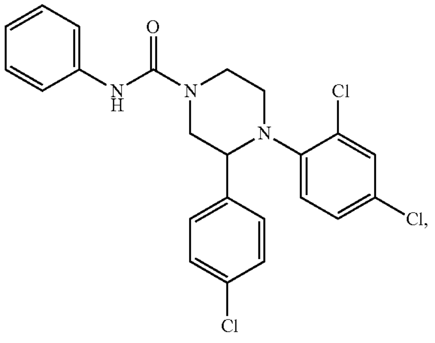

-continued
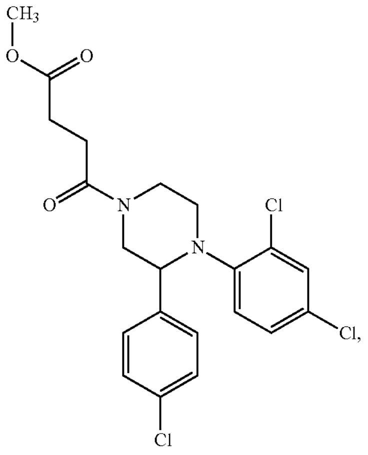
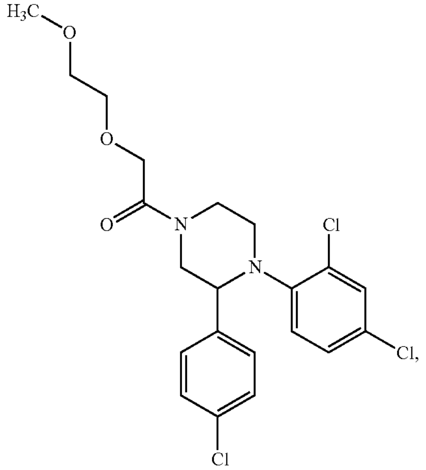
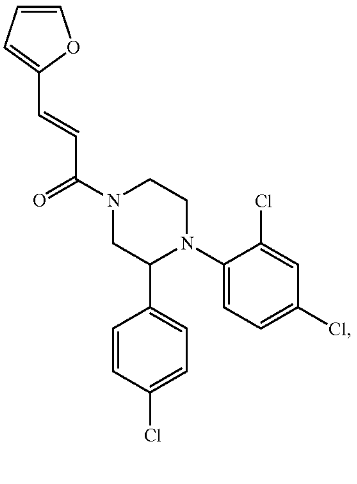
-continued
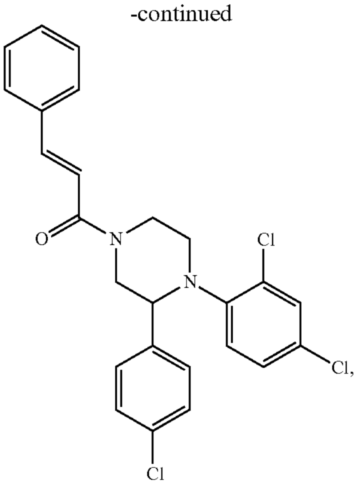
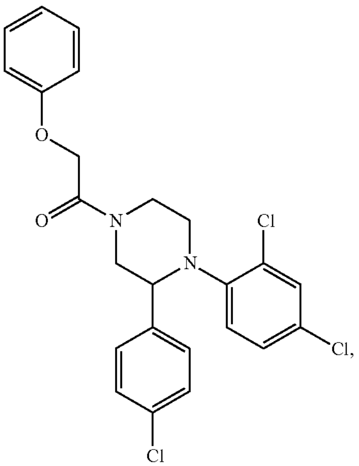
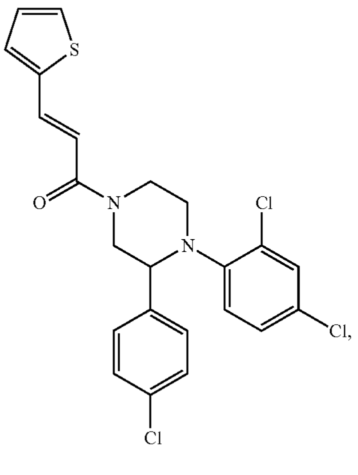

-continued
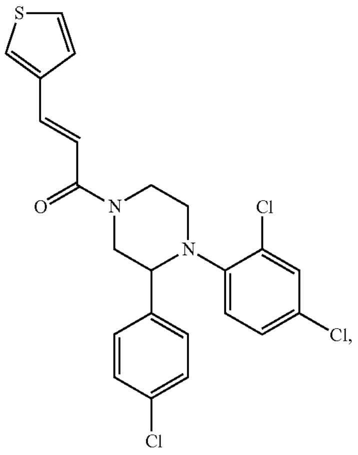
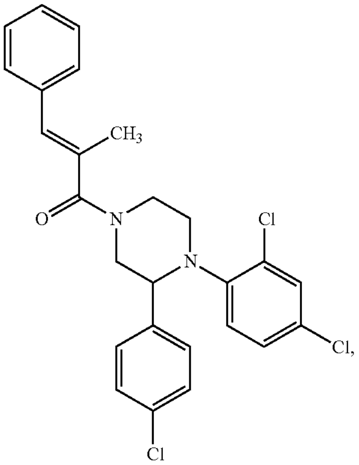
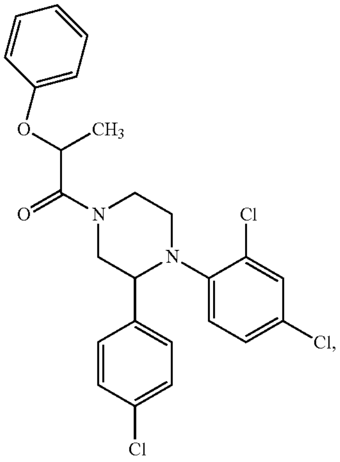
-continued
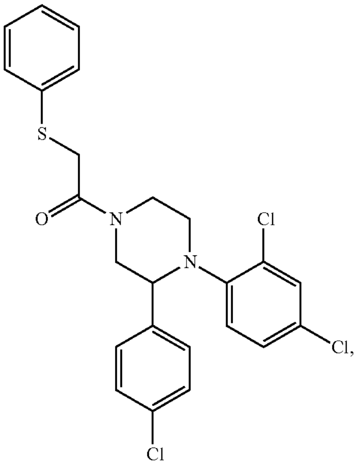
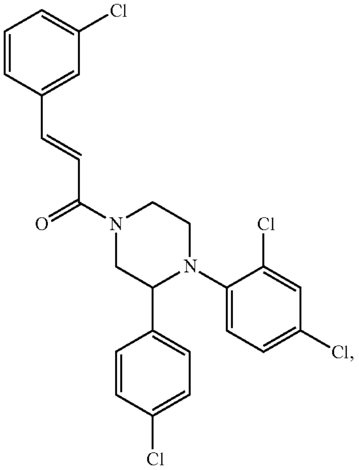
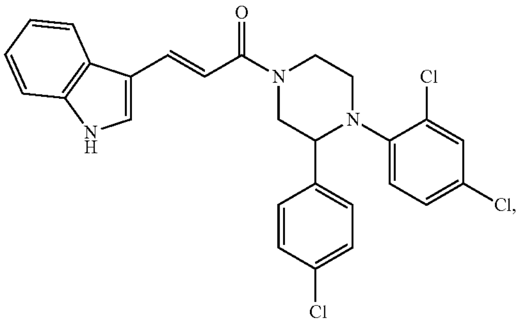
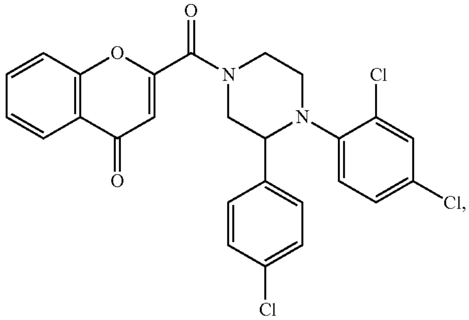

-continued
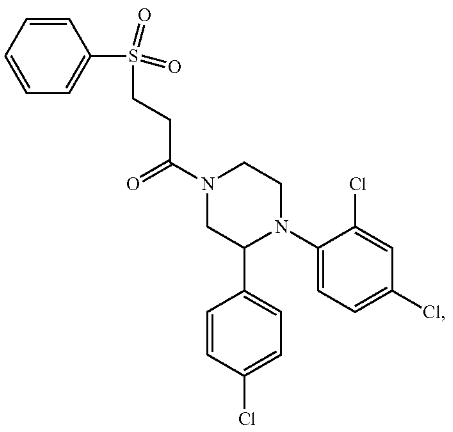
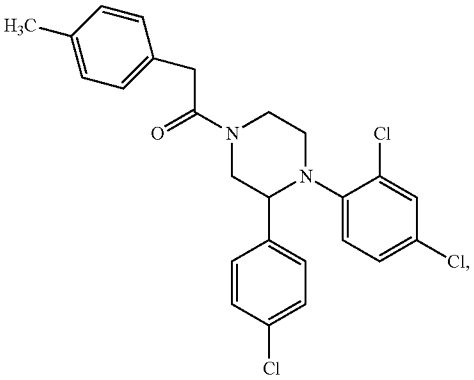
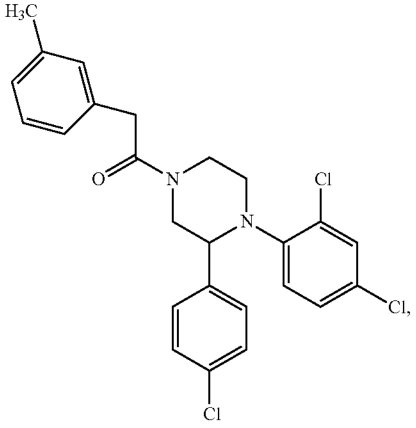
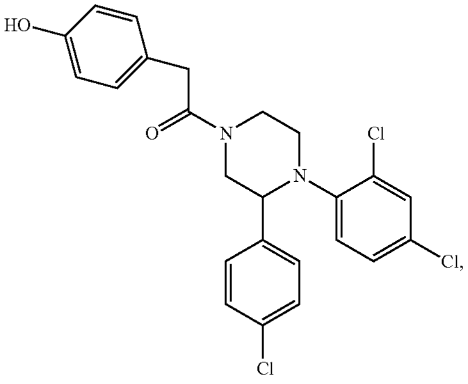
-continued
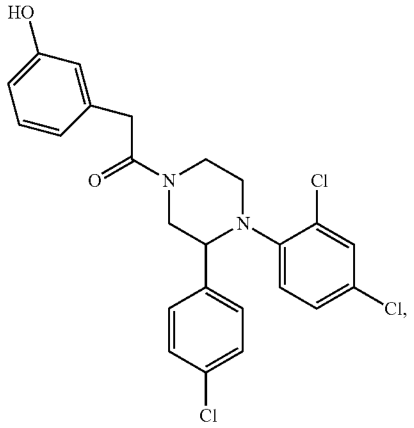
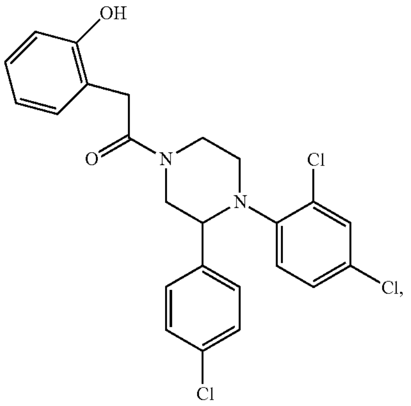
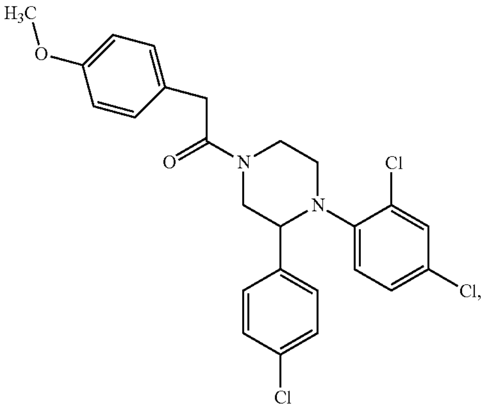
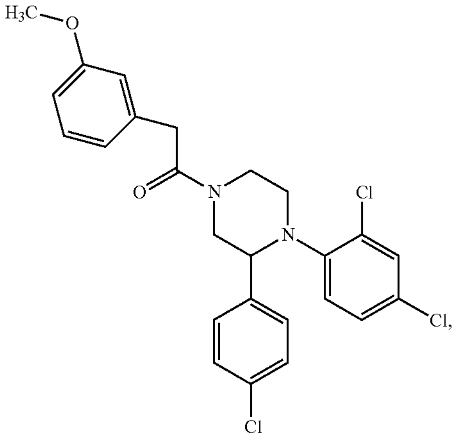

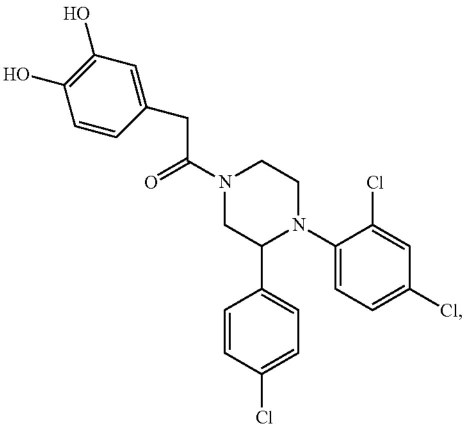
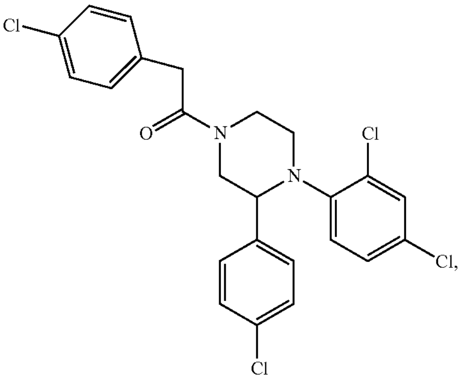
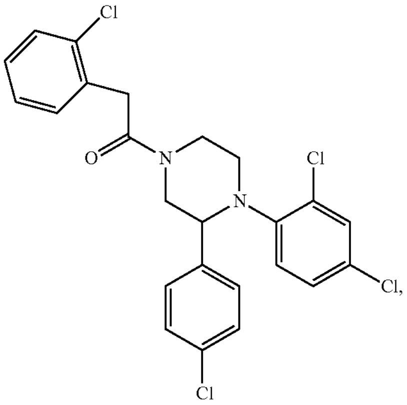
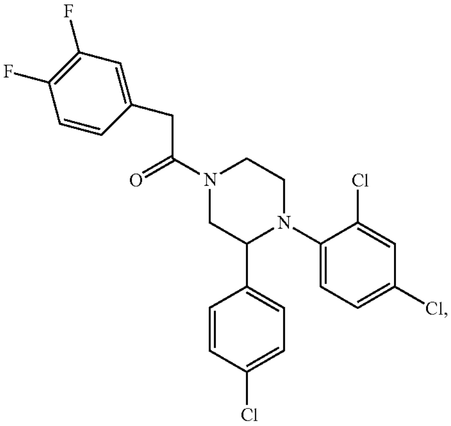
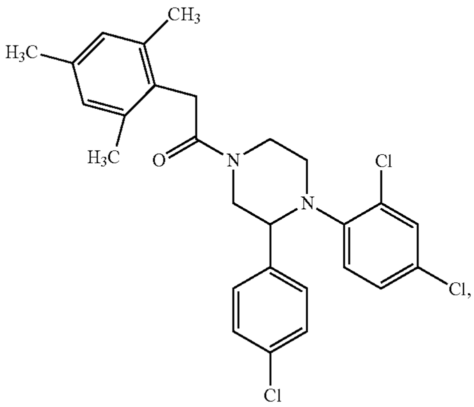
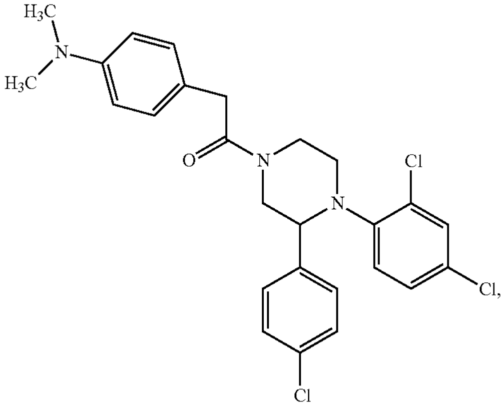
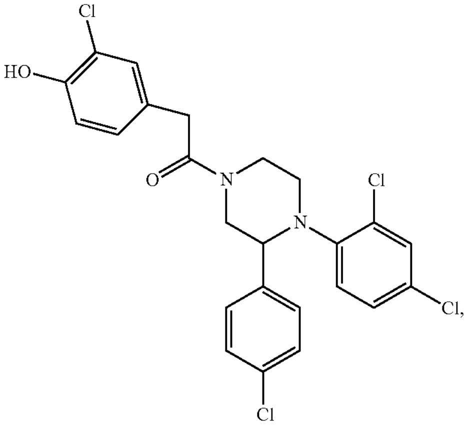
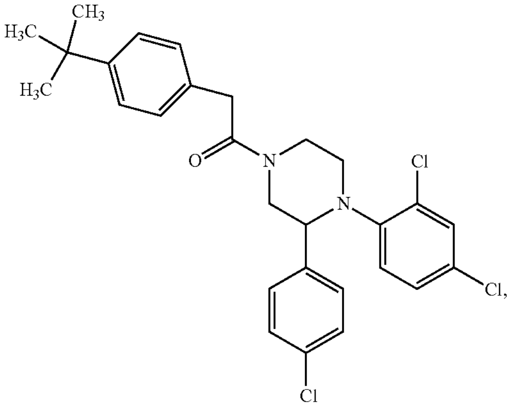

-continued
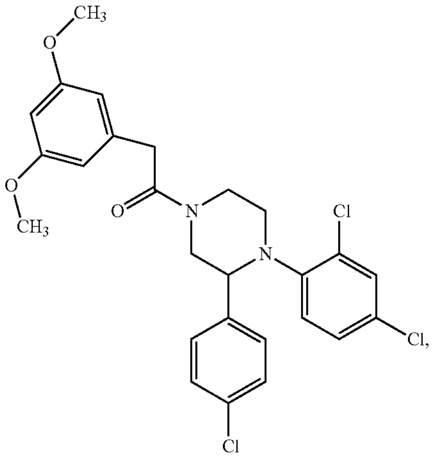
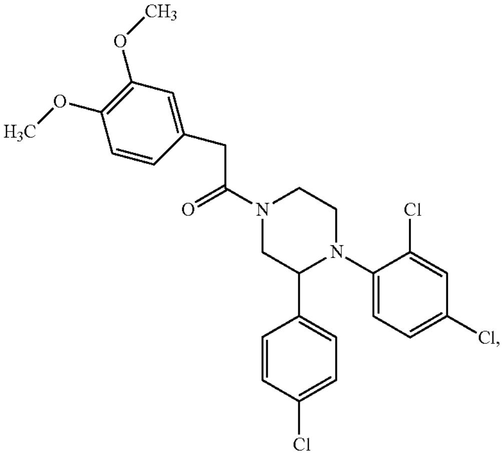
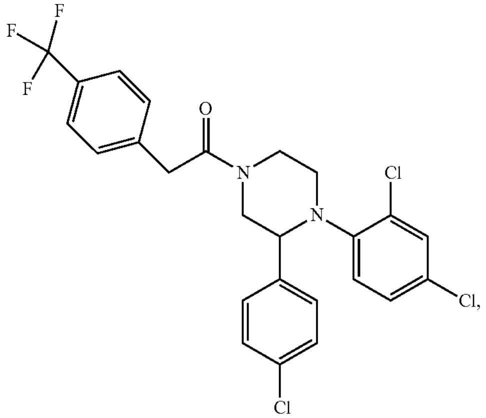
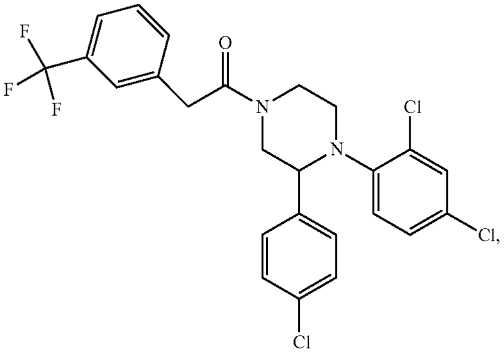
-continued
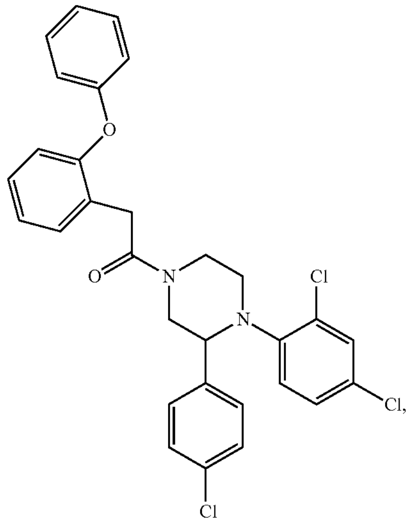
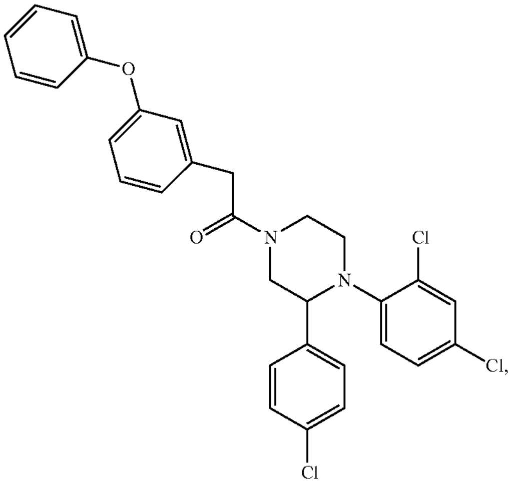
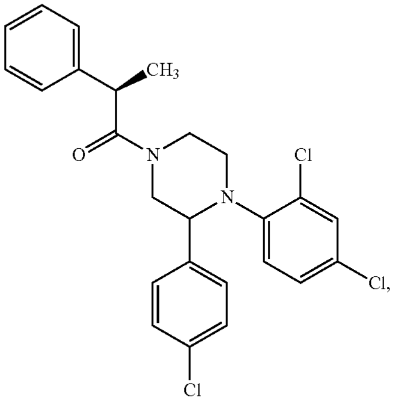

-continued
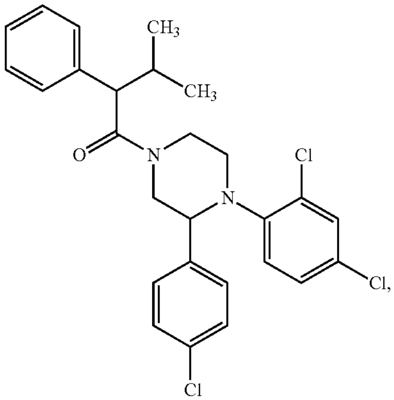
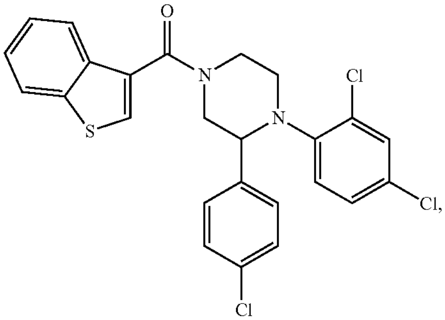
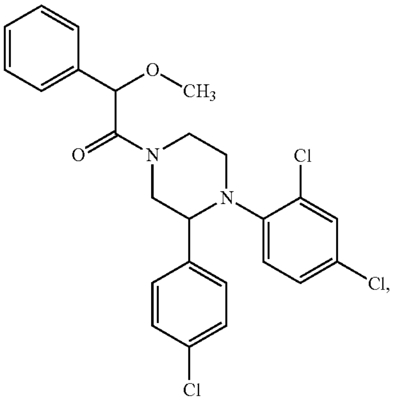
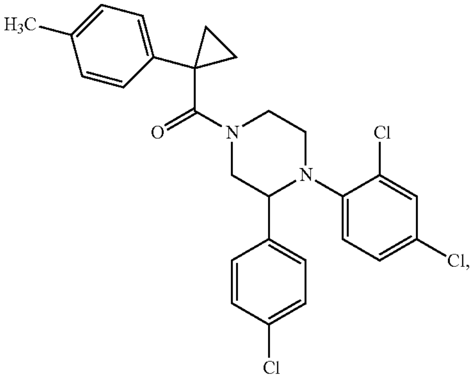
-continued
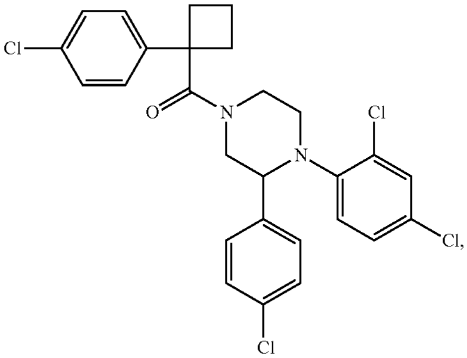
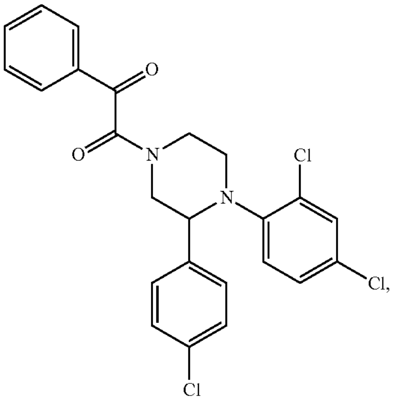
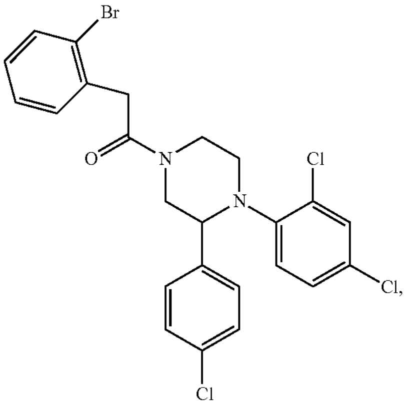
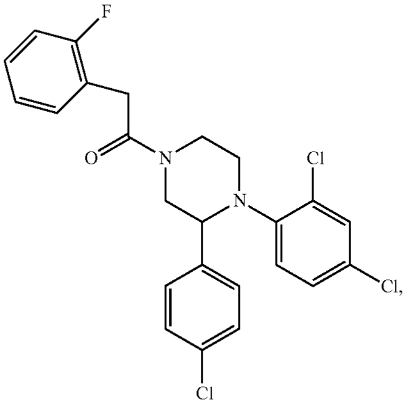

-continued
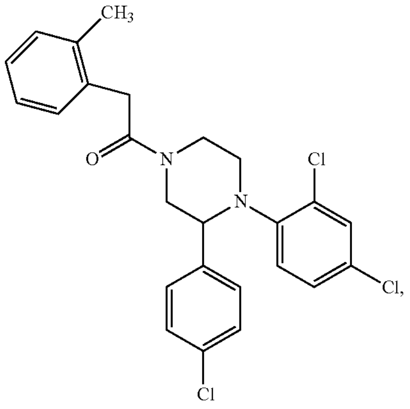
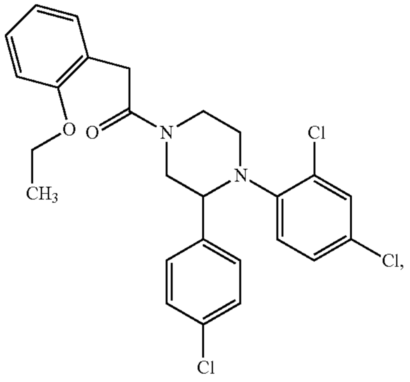
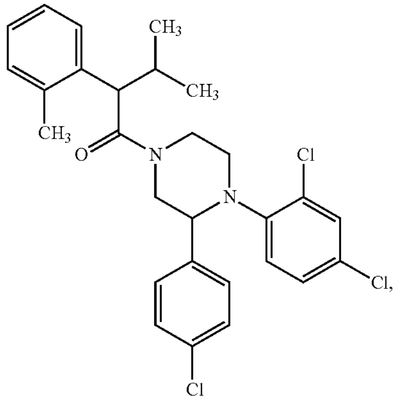
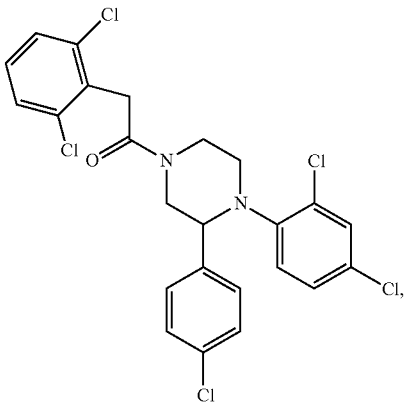
-continued
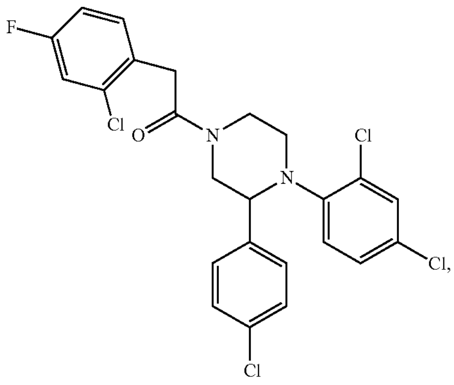
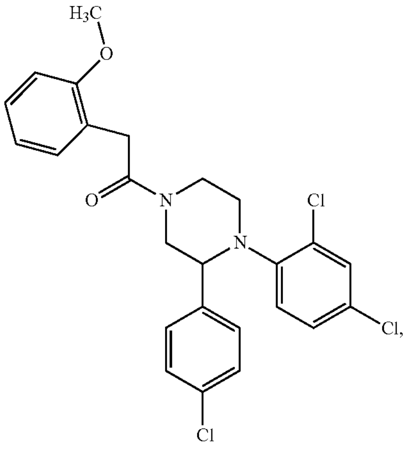
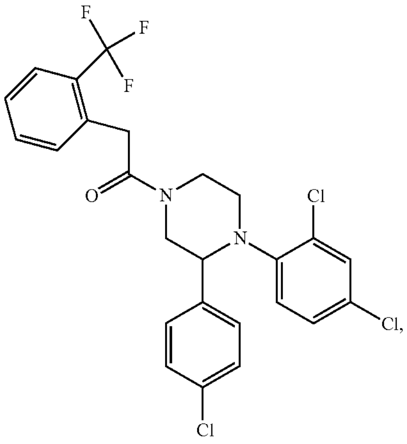
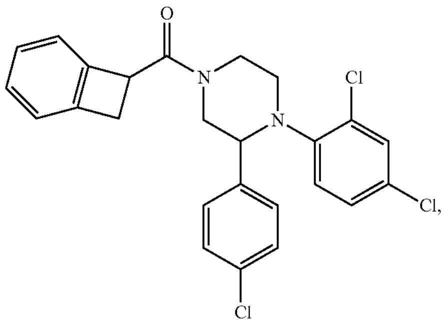

-continued
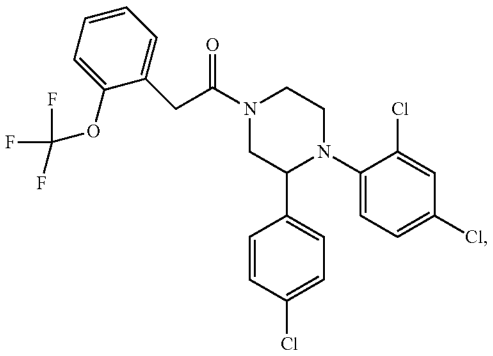
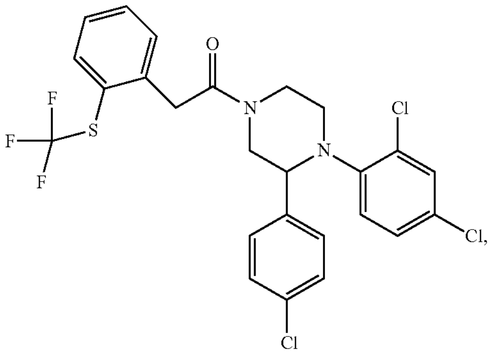
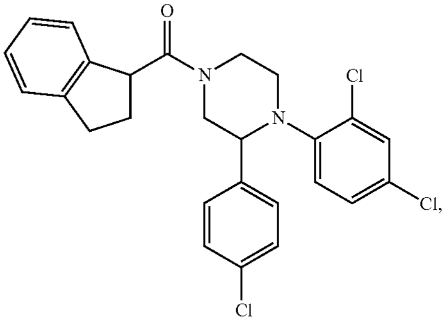
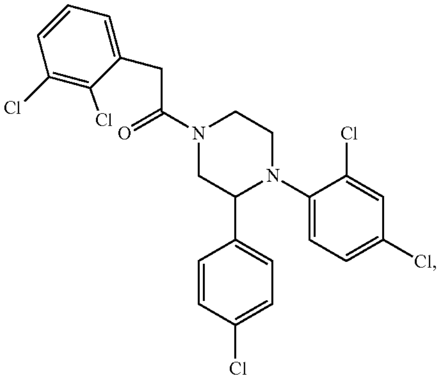
-continued
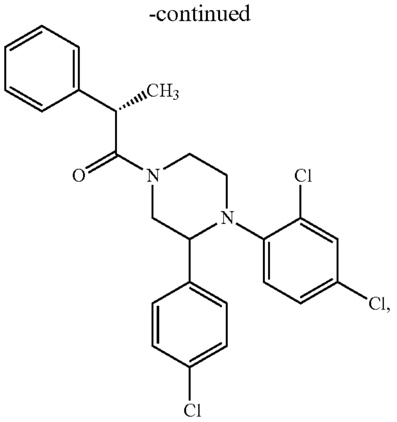
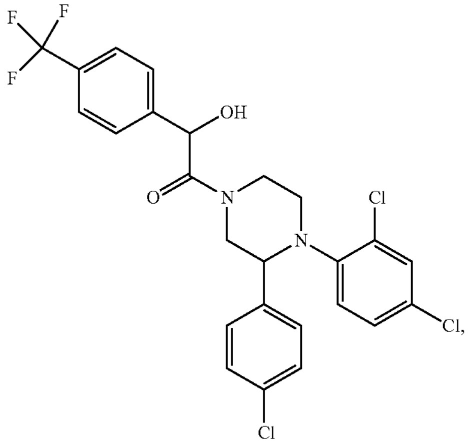
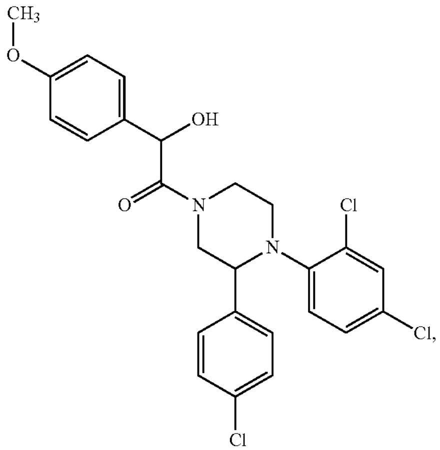
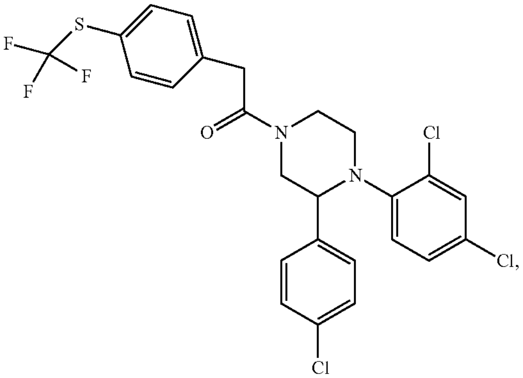

-continued
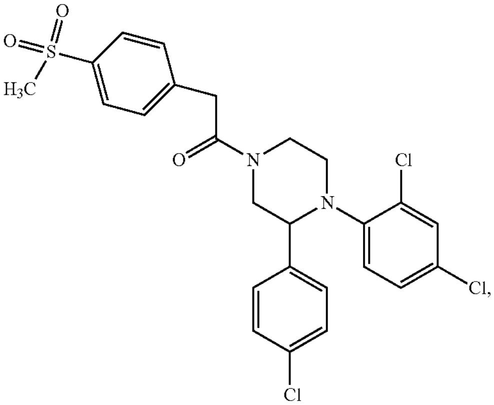
,
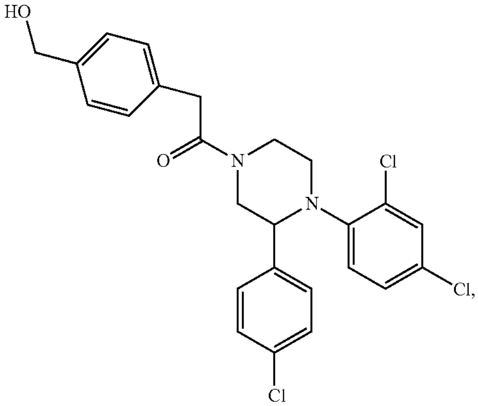
,
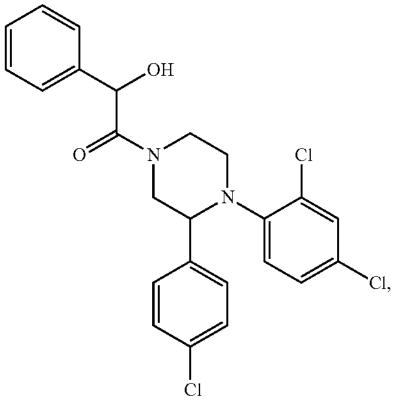
,
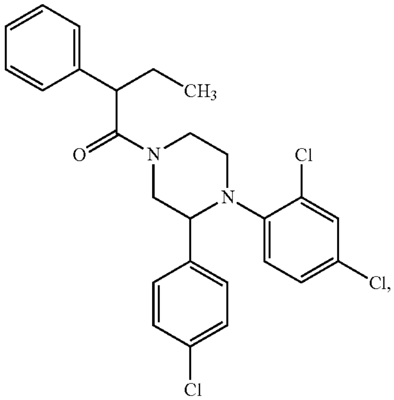
,
-continued
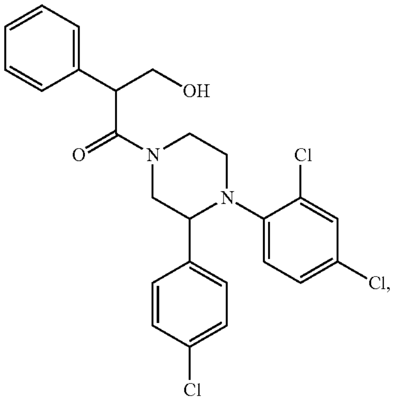
,
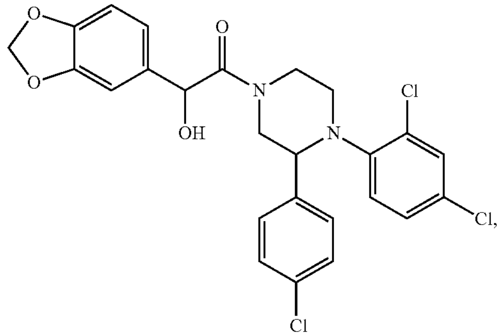
,
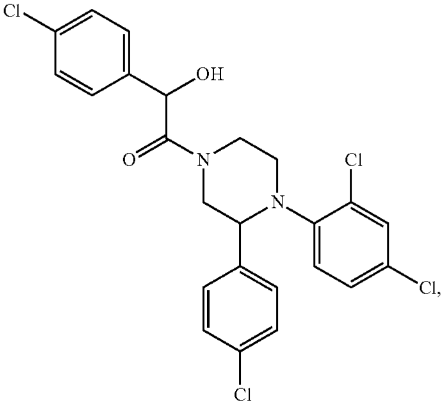
,
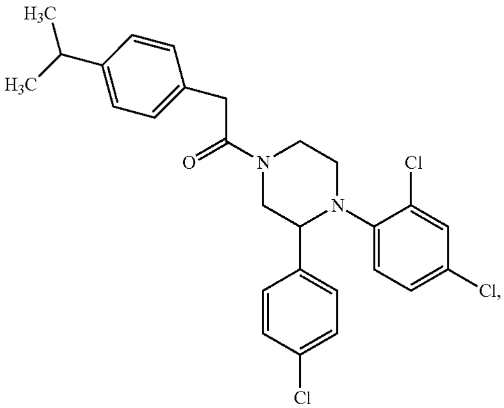
, -continued
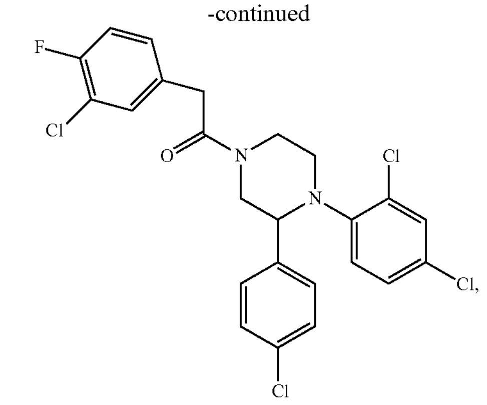
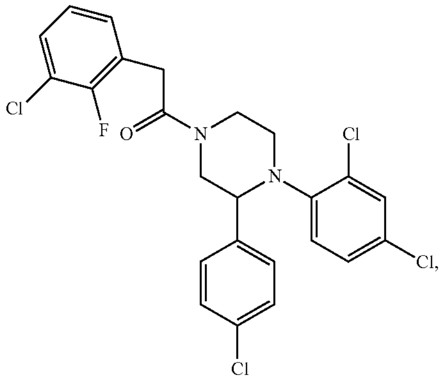
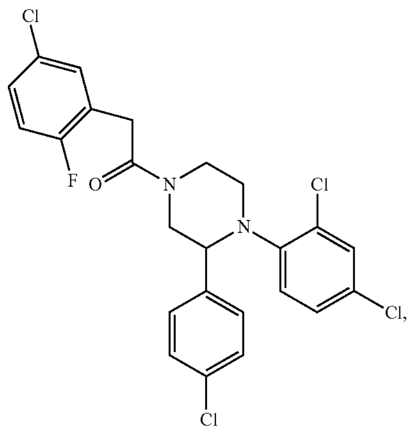
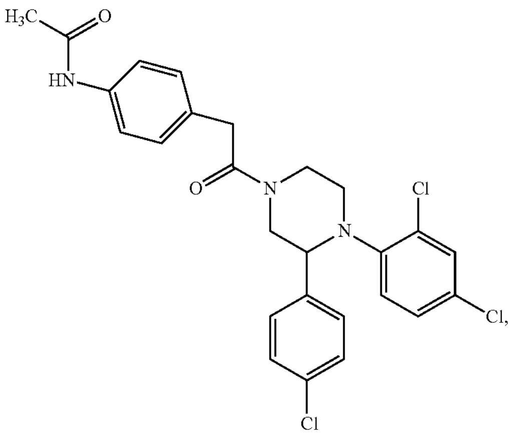
-continued
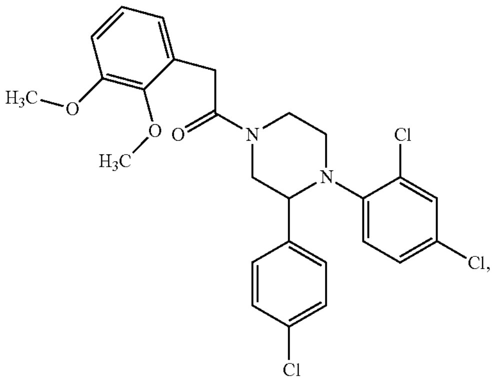
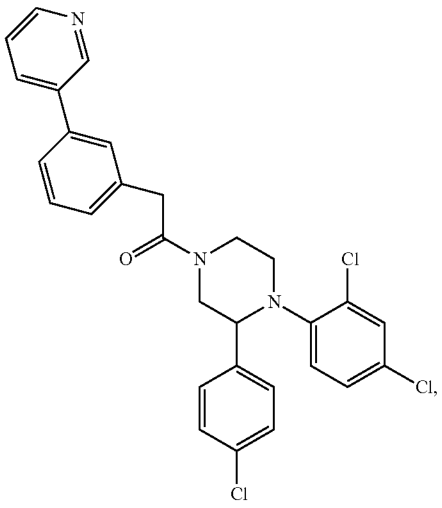
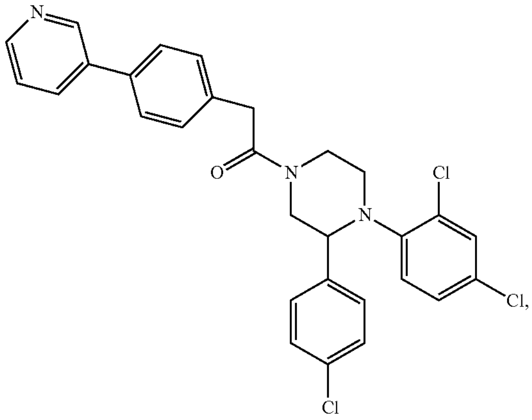

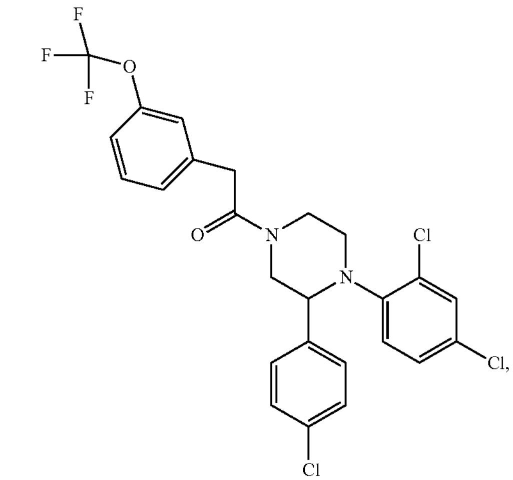
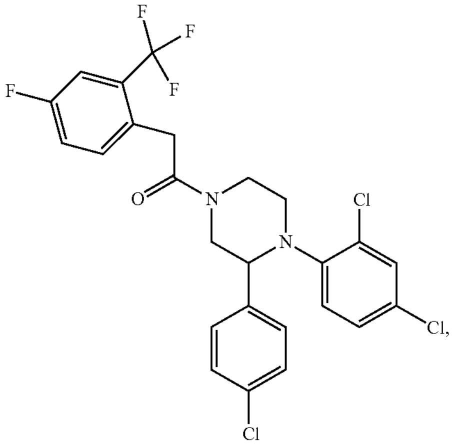
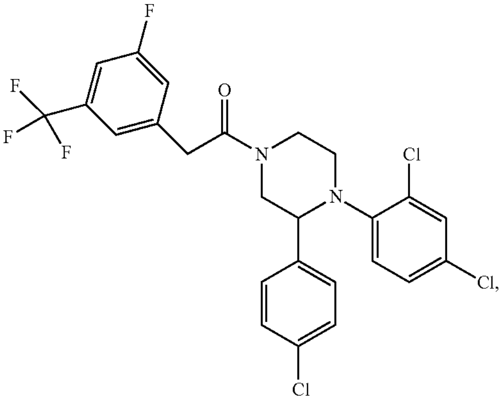
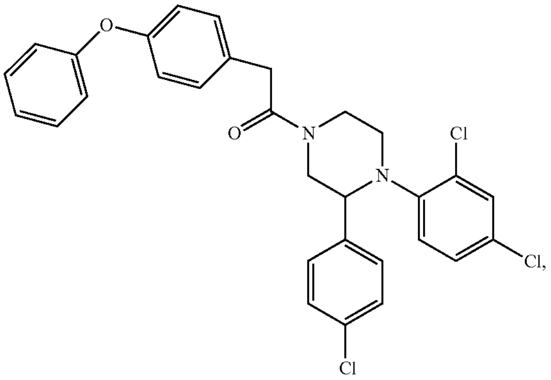
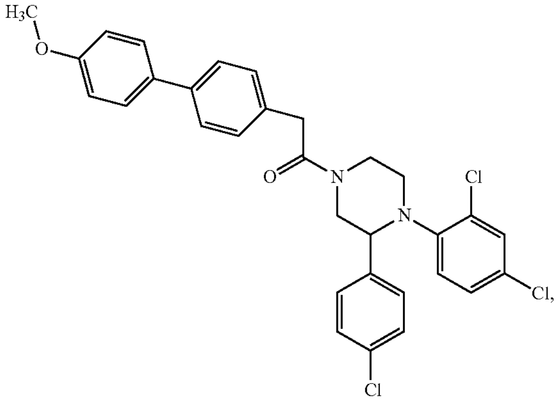
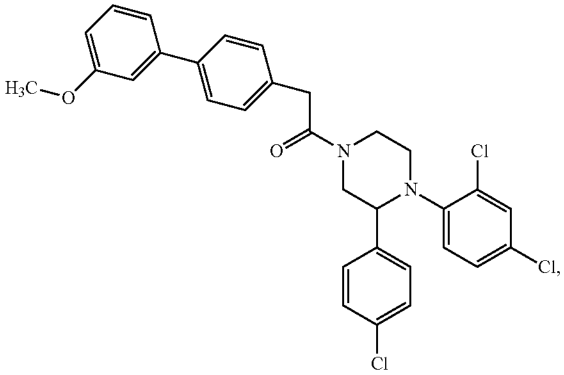
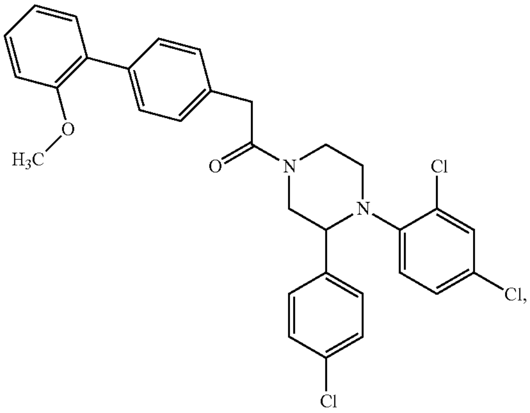
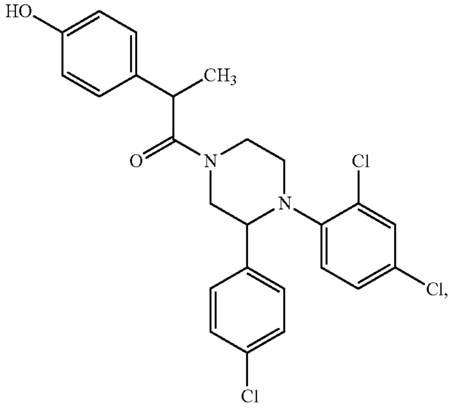

-continued
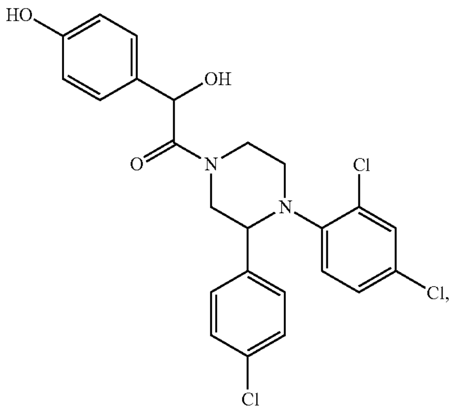
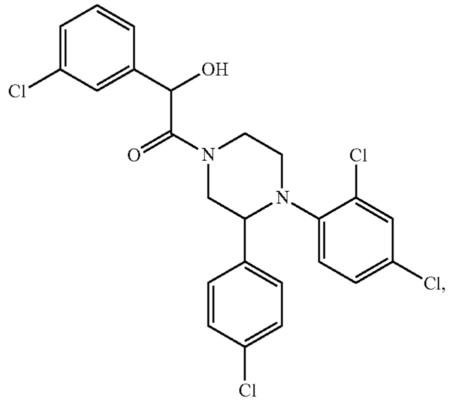
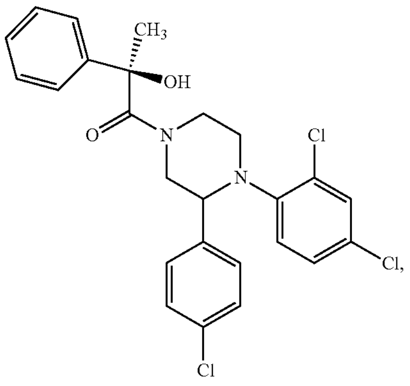
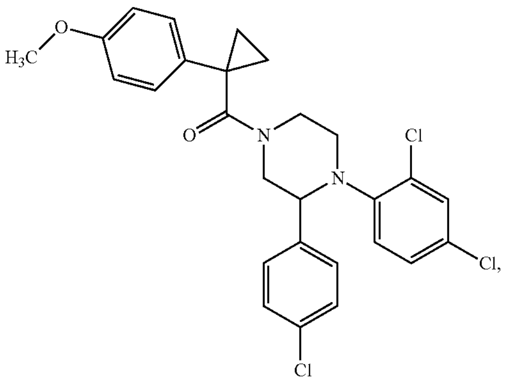
-continued
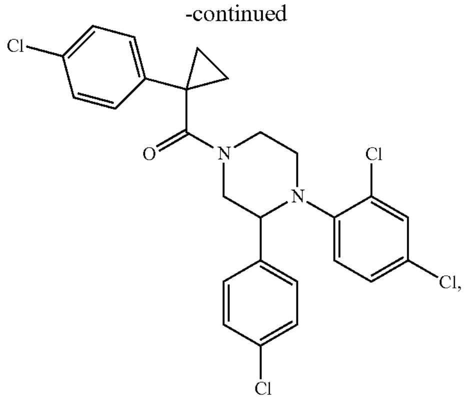
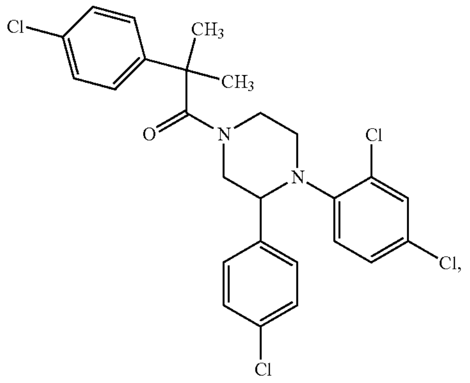
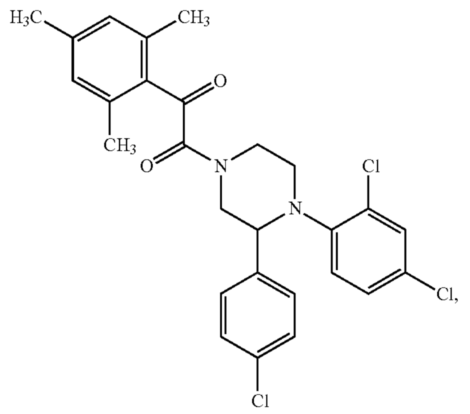
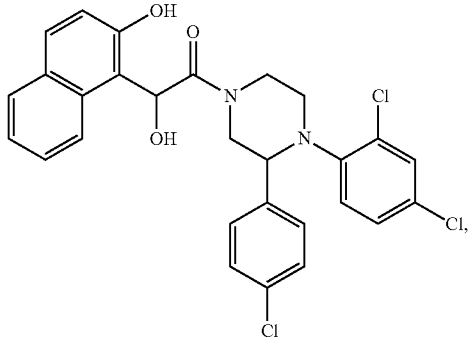

-continued
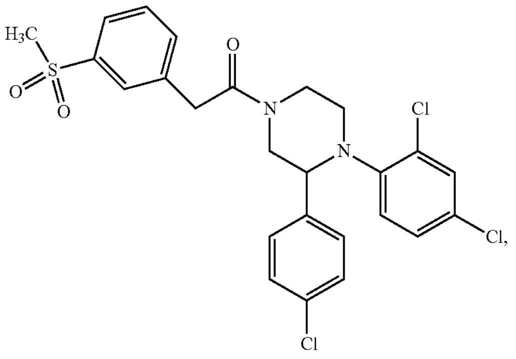
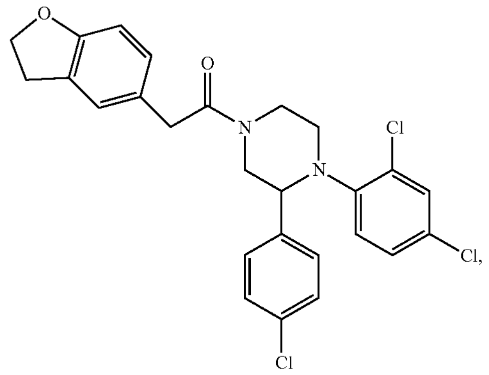
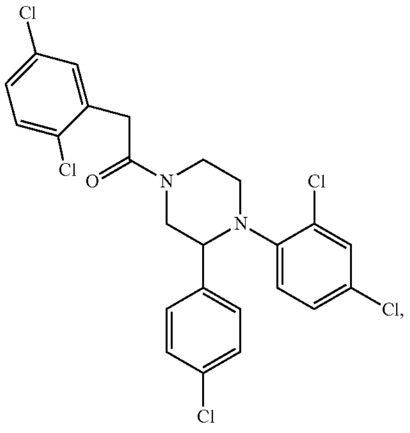
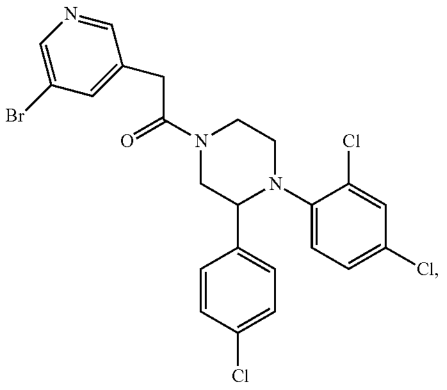
-continued
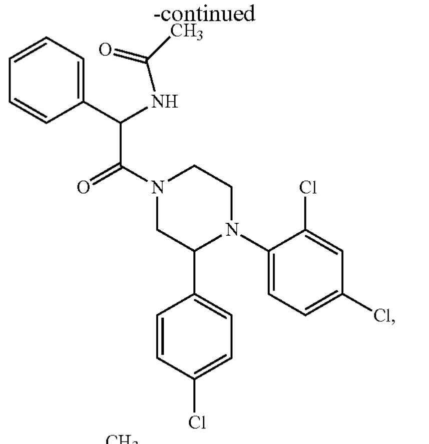
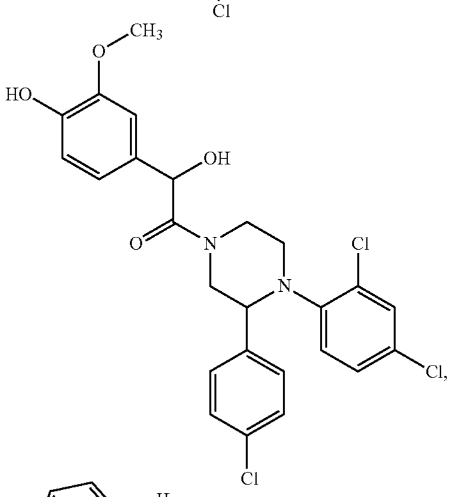
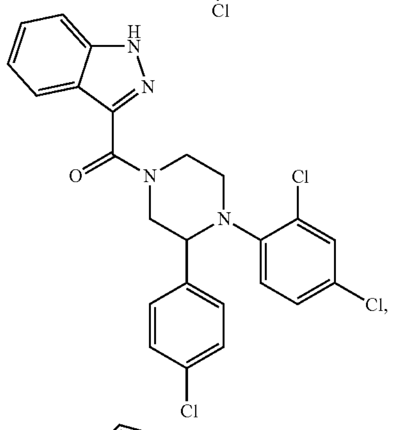
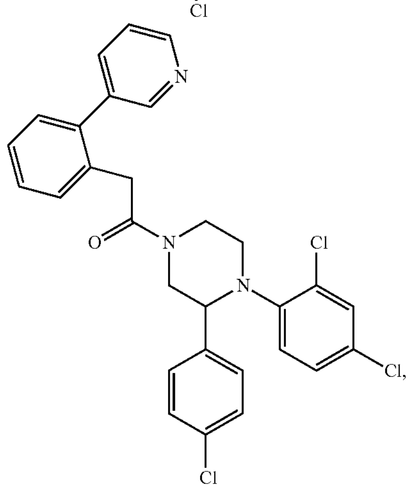

-continued
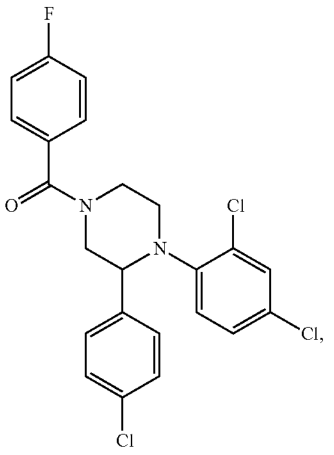
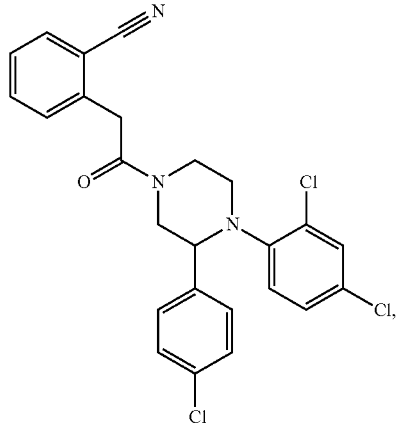
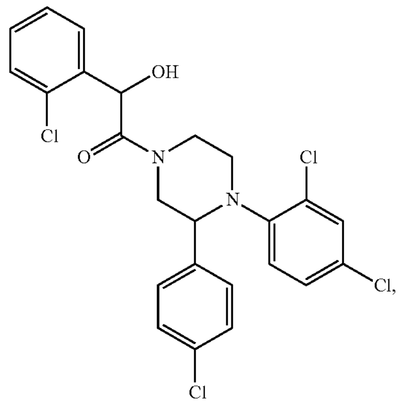
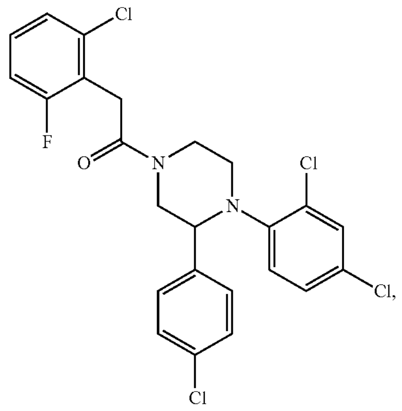
-continued
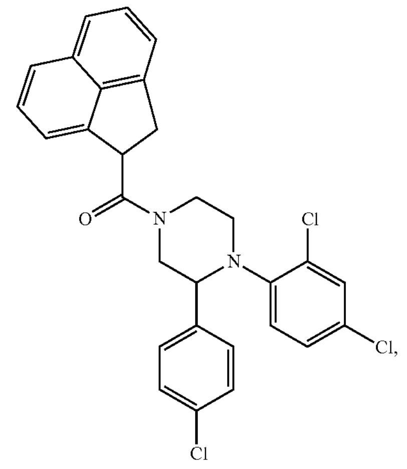
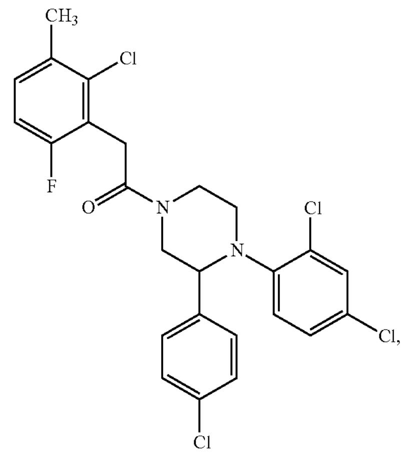
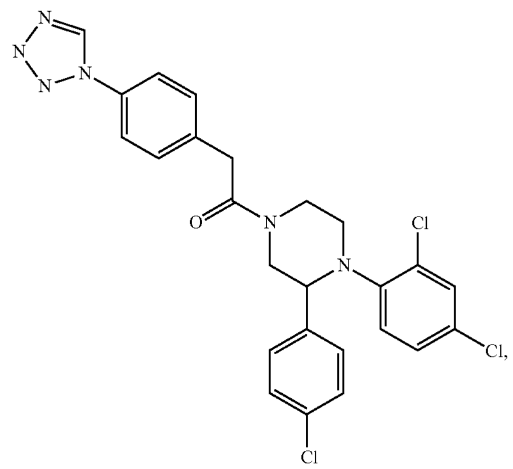

-continued
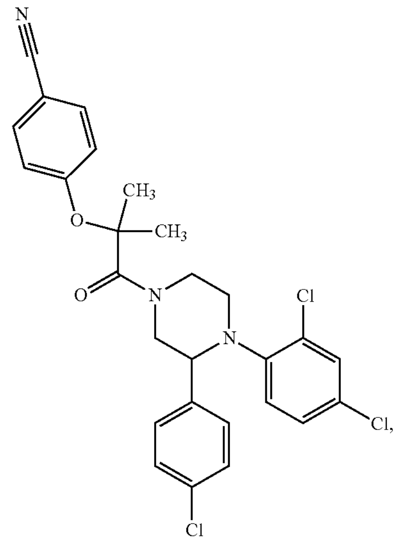
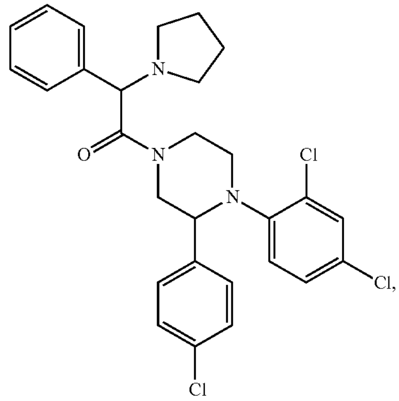
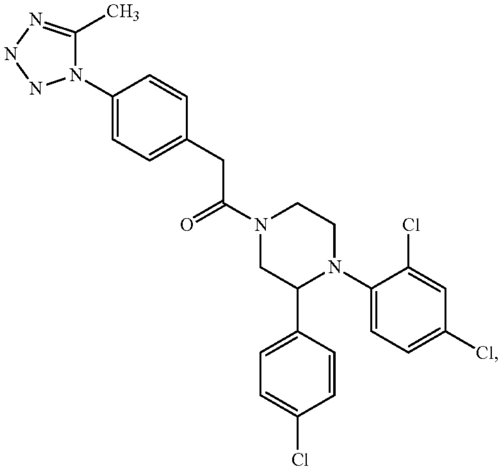
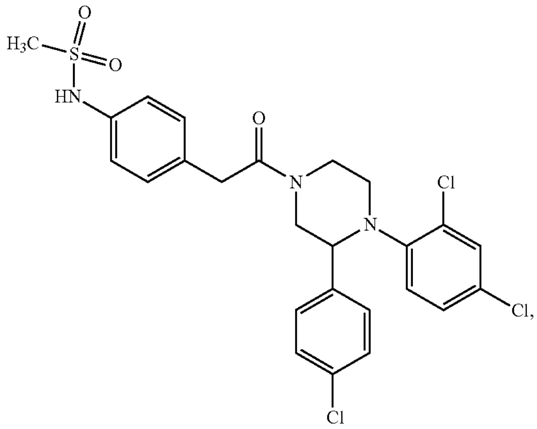
-continued
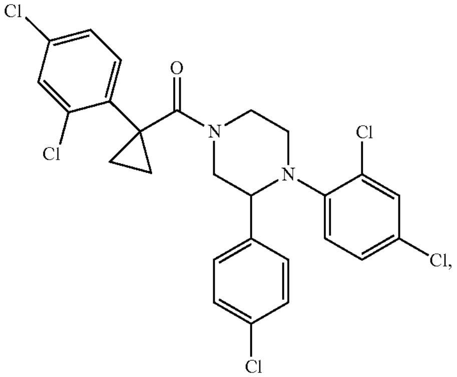
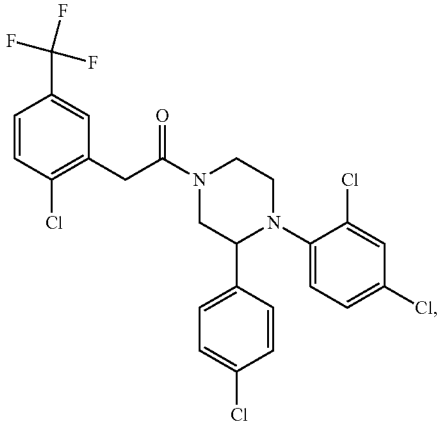
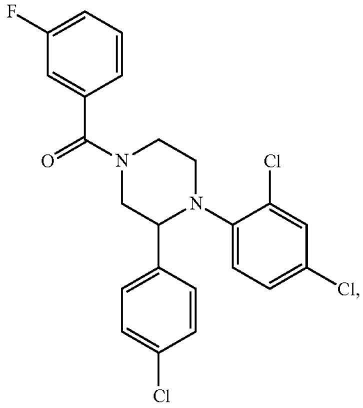

-continued
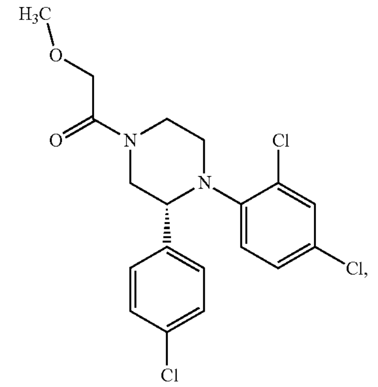
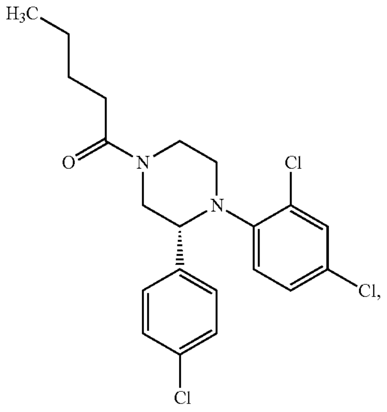
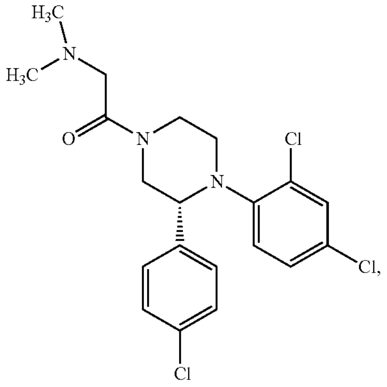
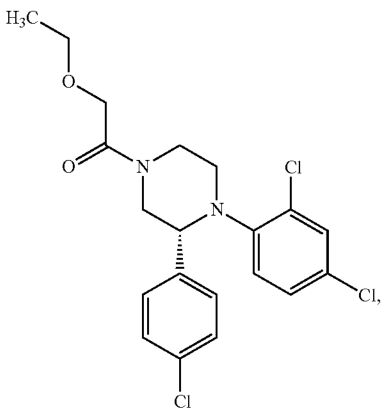
-continued
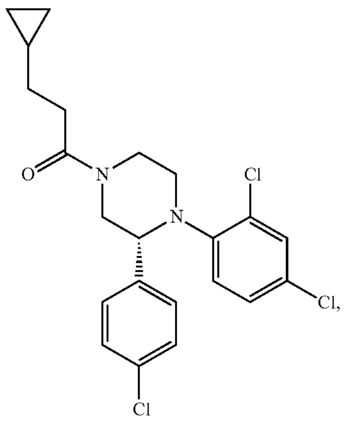
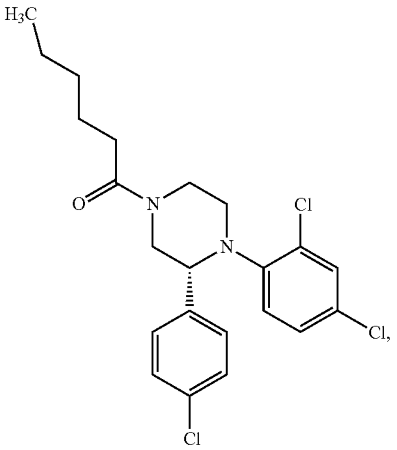
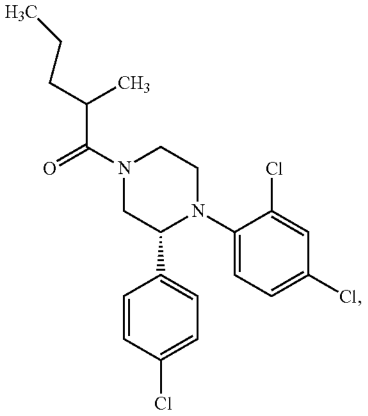
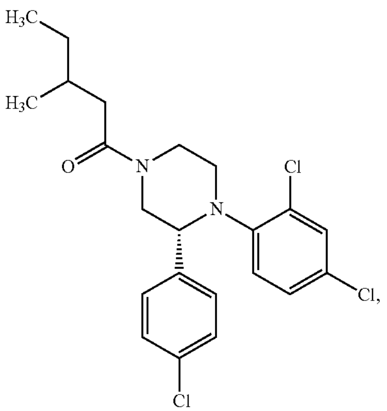

-continued
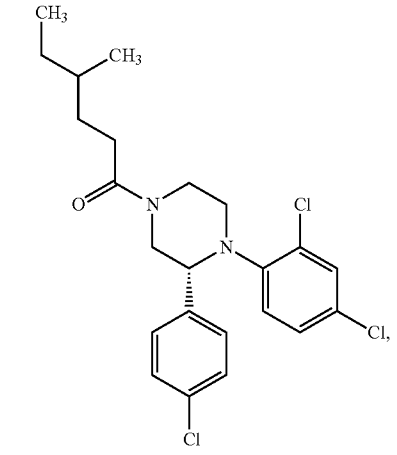
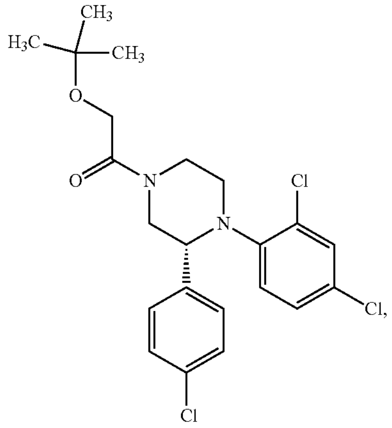
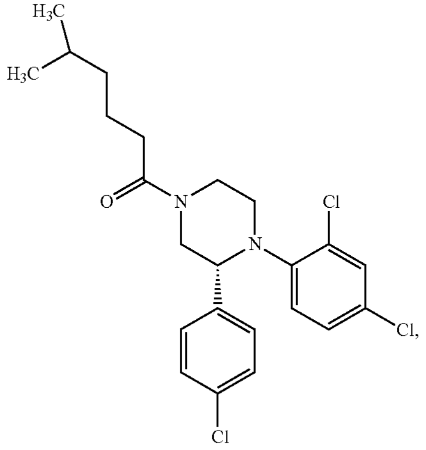
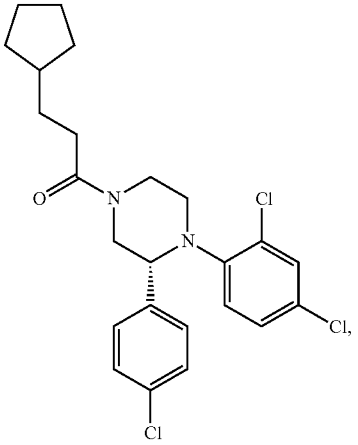
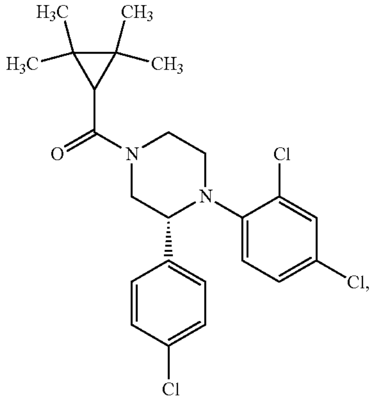
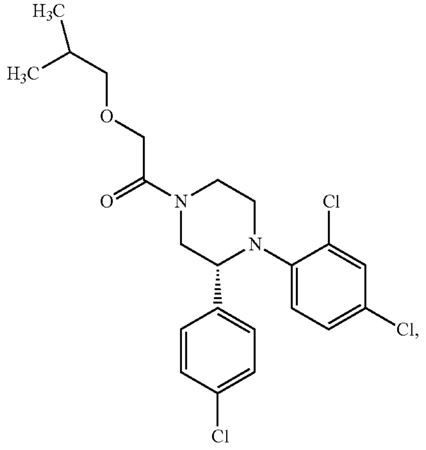
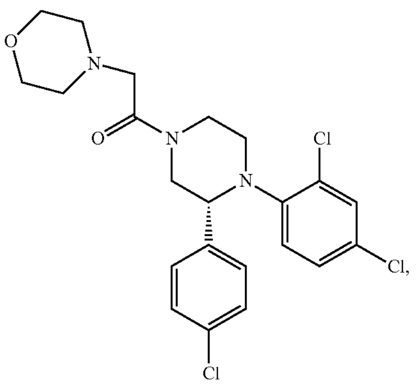

-continued
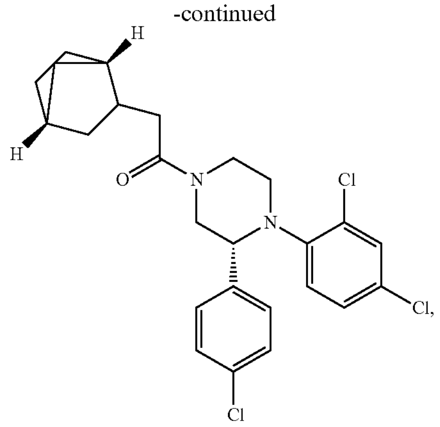
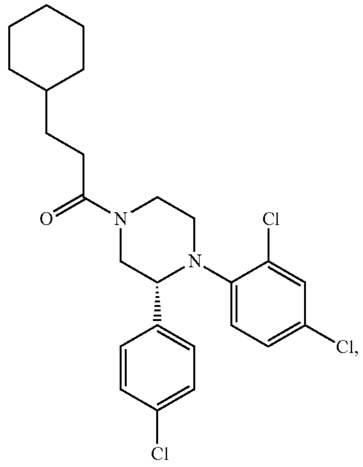
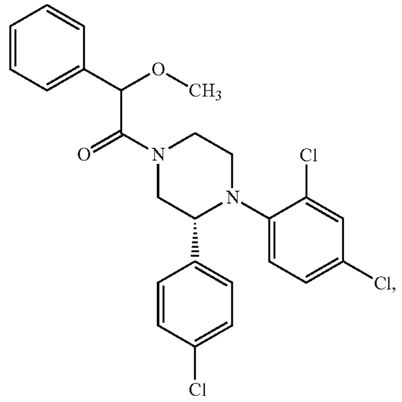
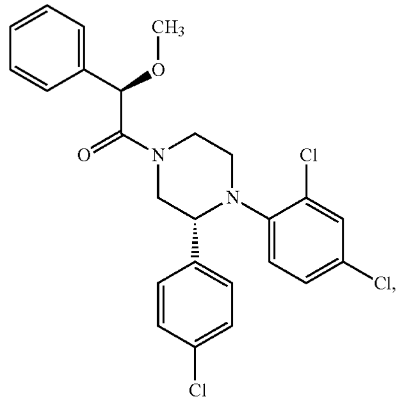
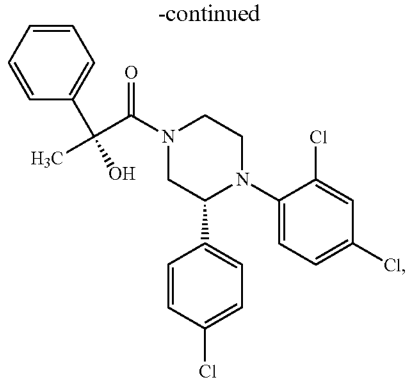
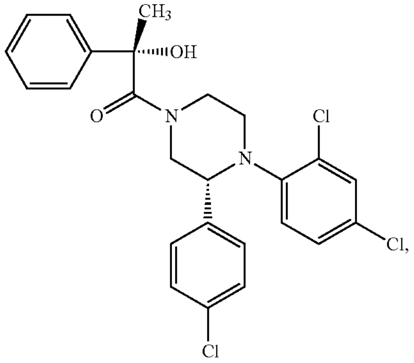
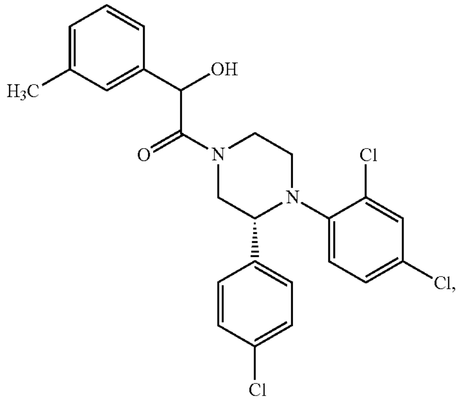
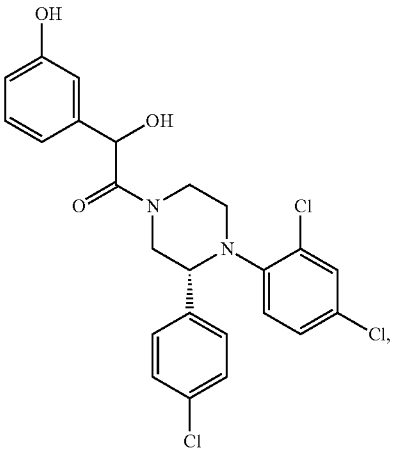
-continued -continued
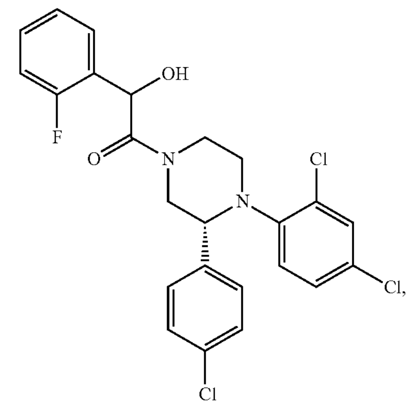
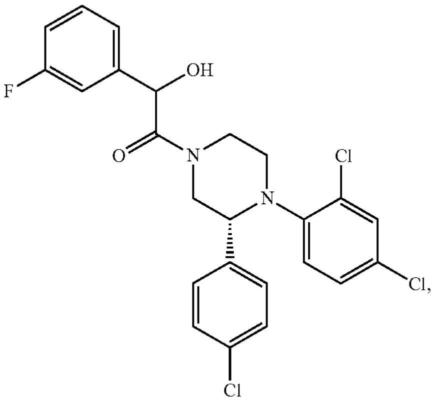
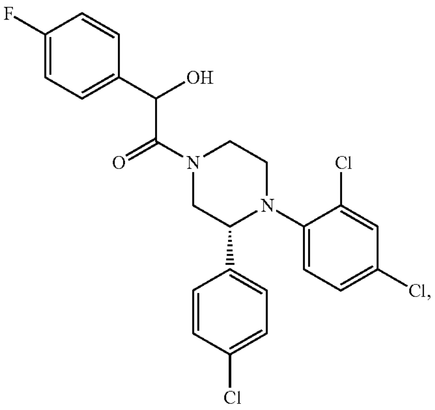
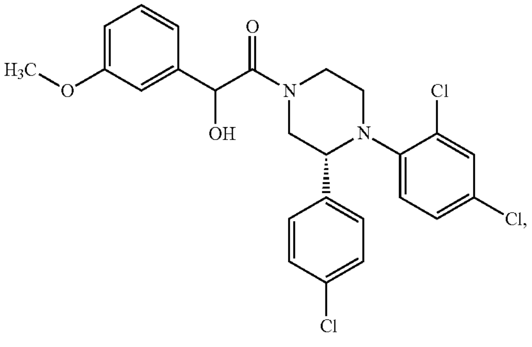
-continued
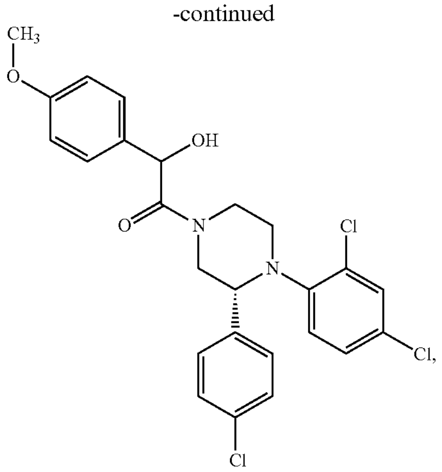
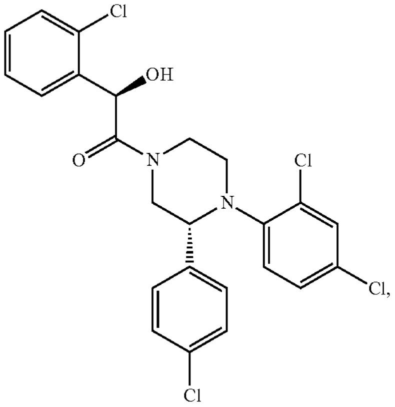
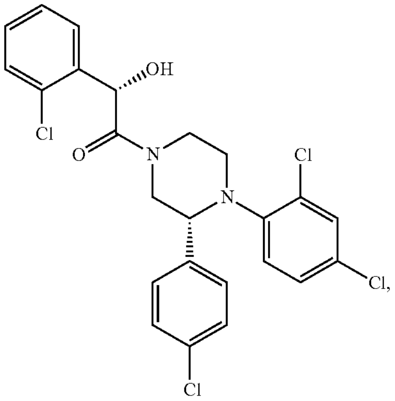
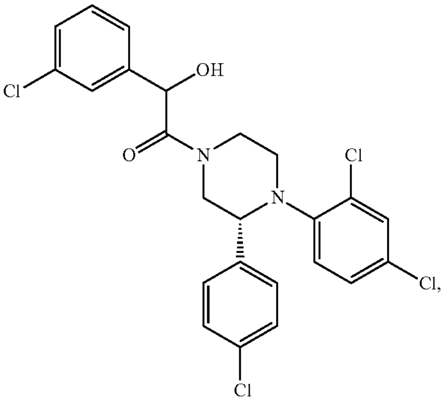

-continued
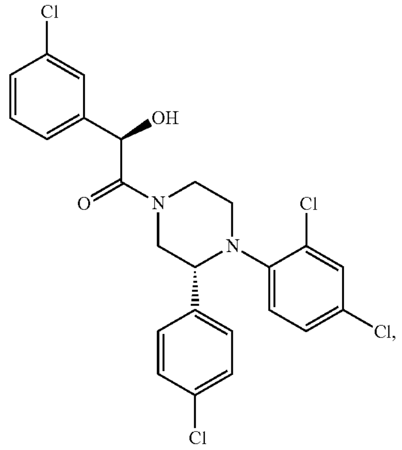
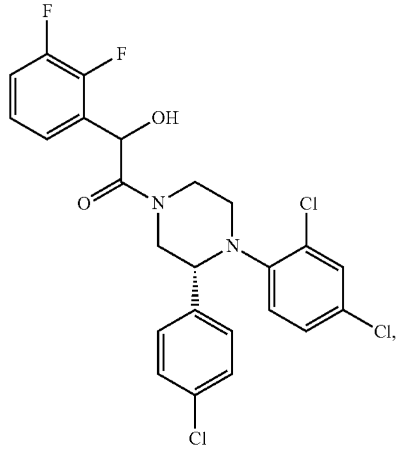
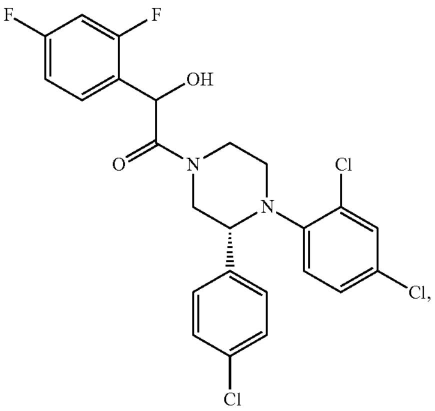
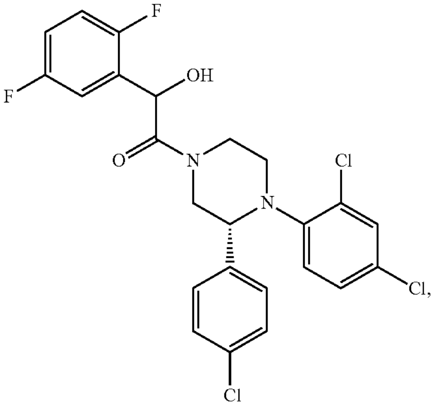
-continued
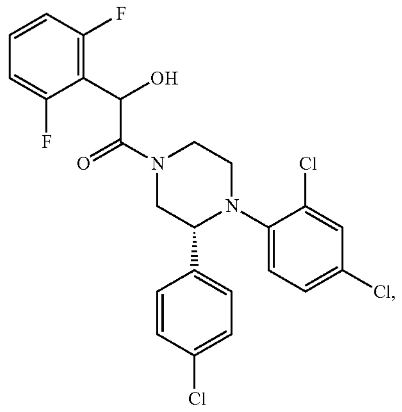
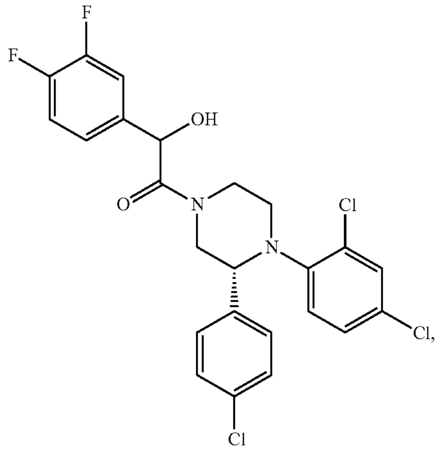
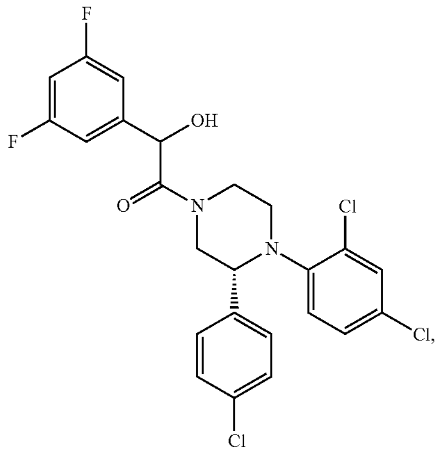
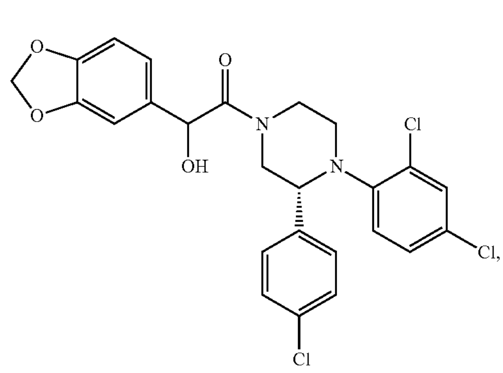

-continued
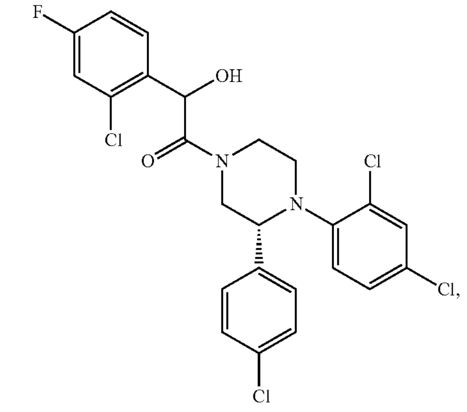
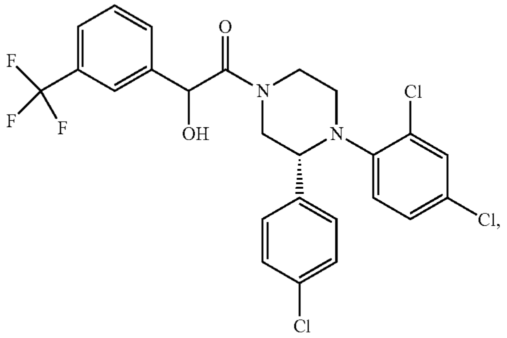
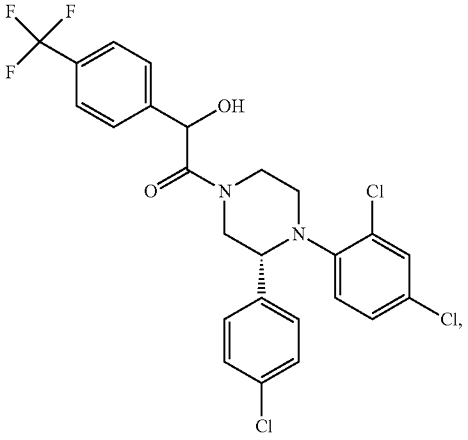
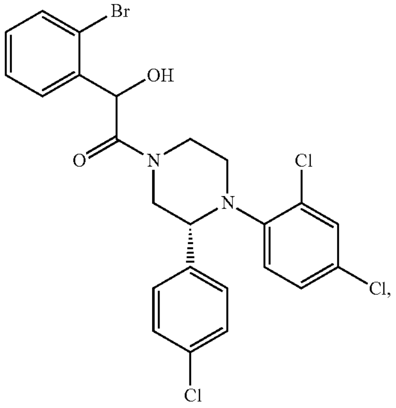
-continued
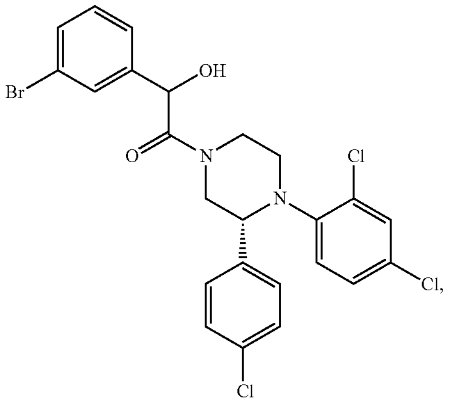
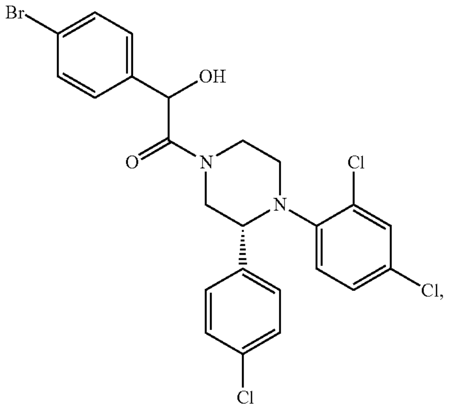
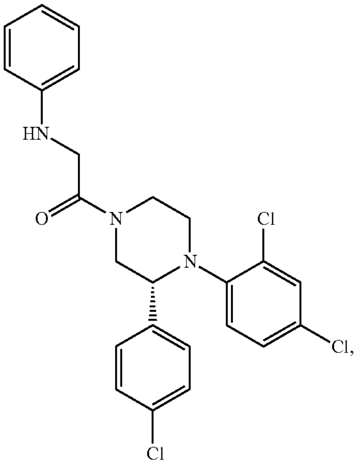
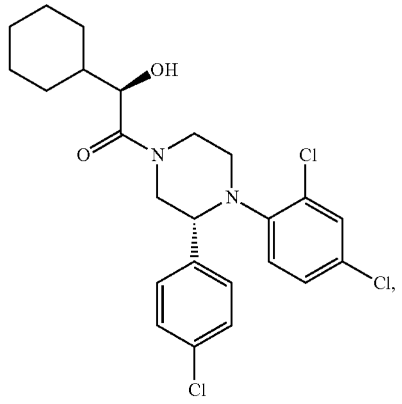

-continued
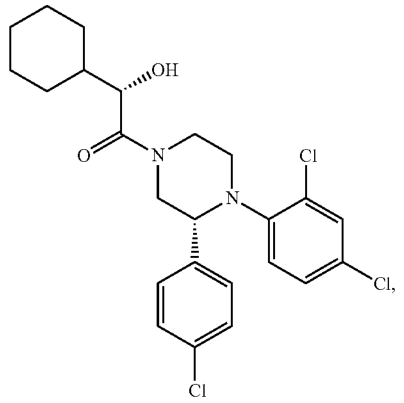
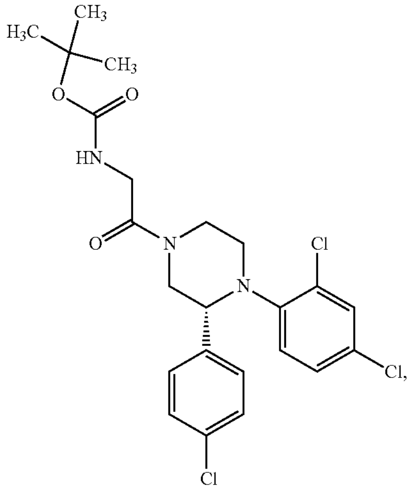
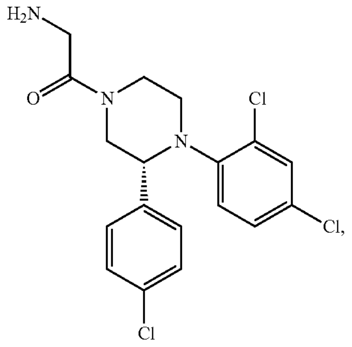
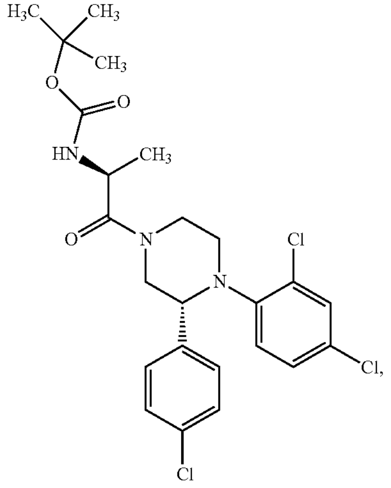
-continued
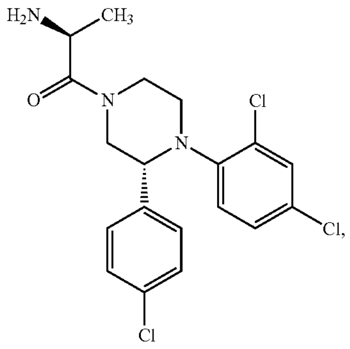
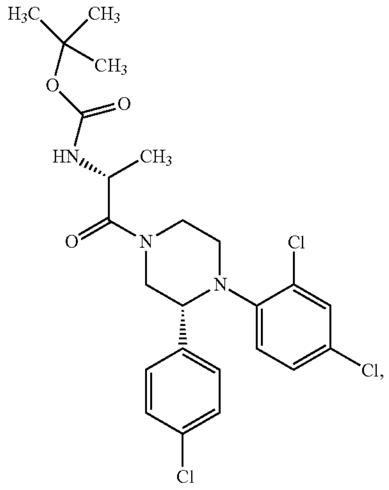
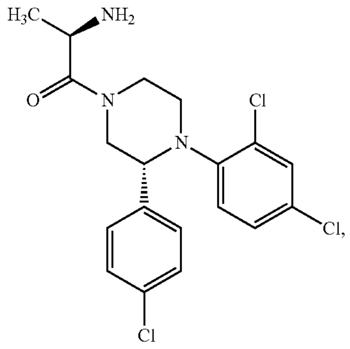
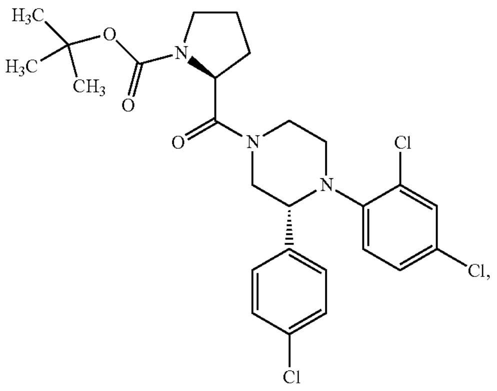

-continued
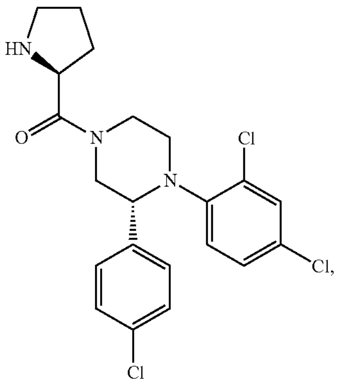
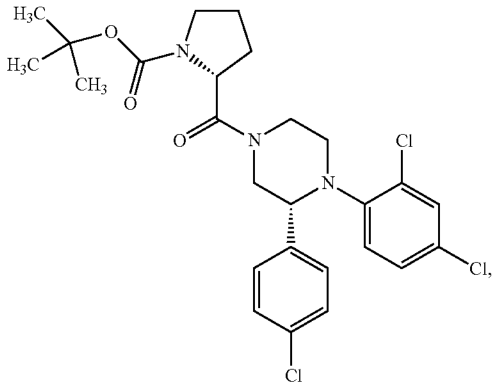
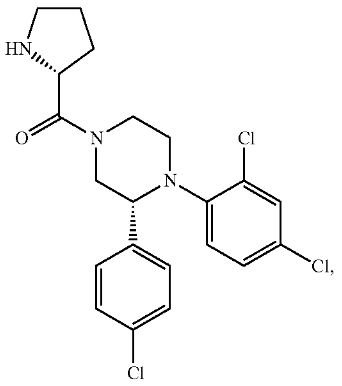
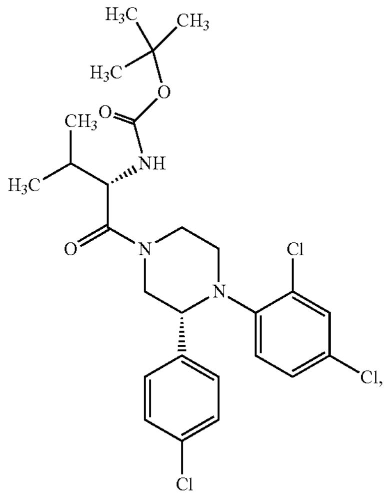
-continued
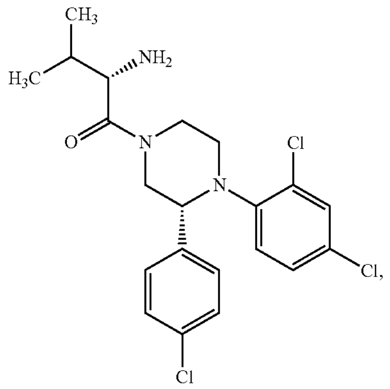
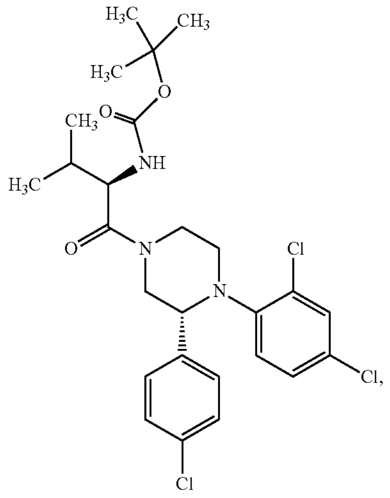
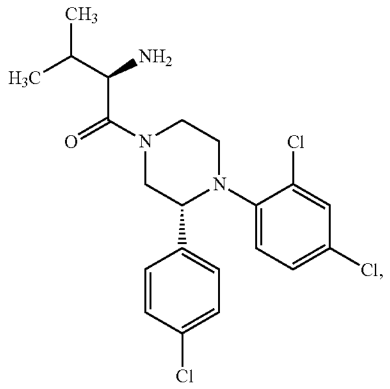
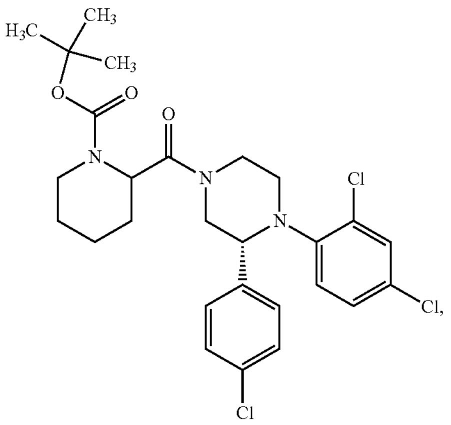

-continued
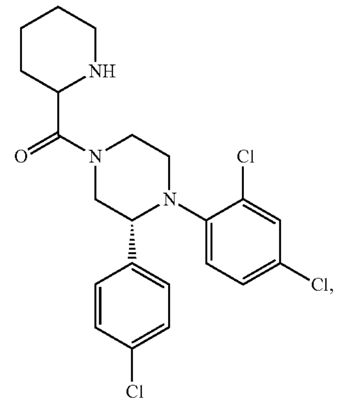
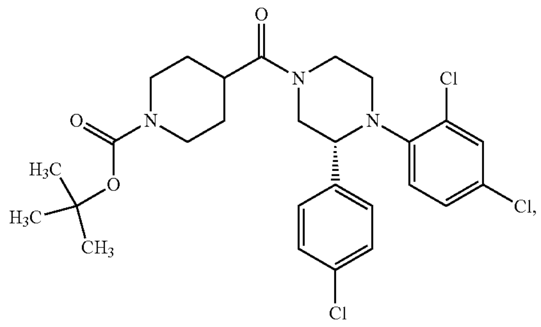
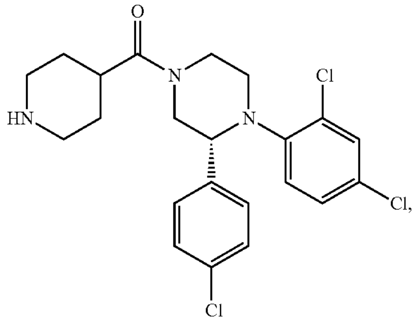
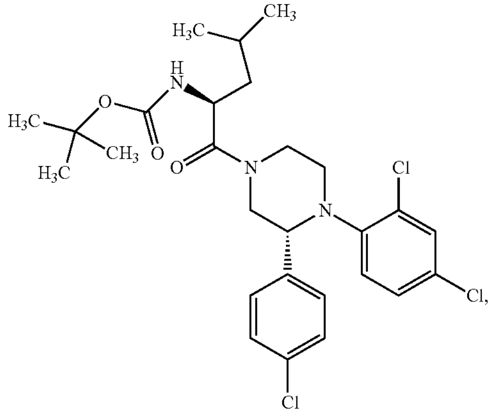
-continued
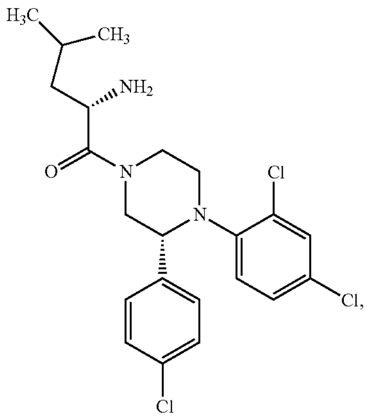
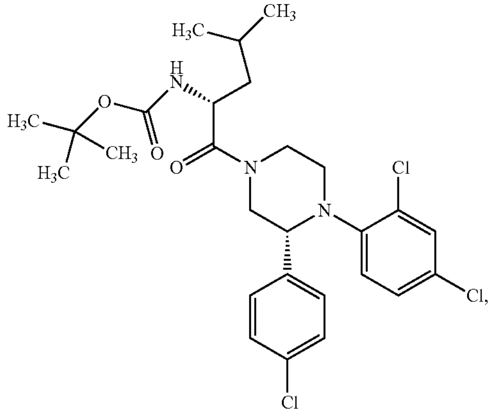
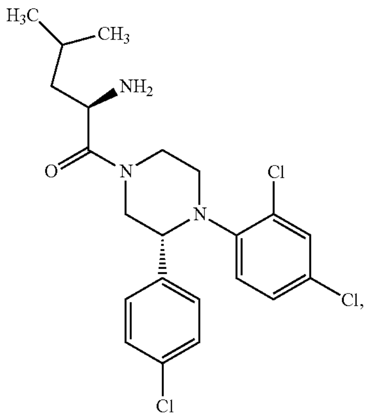
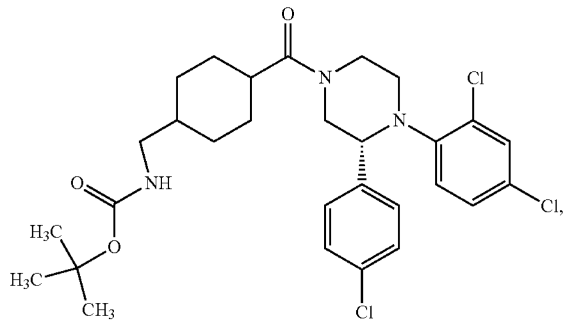

-continued
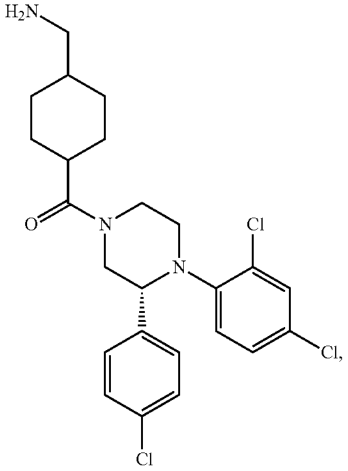
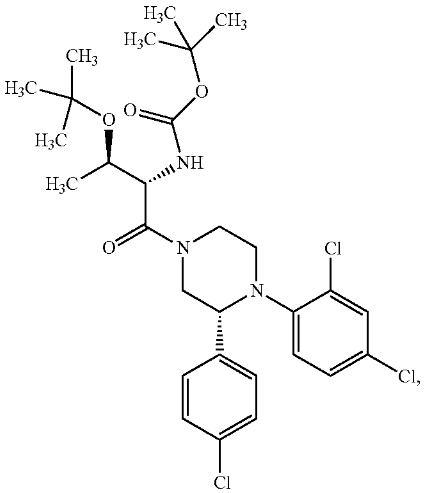
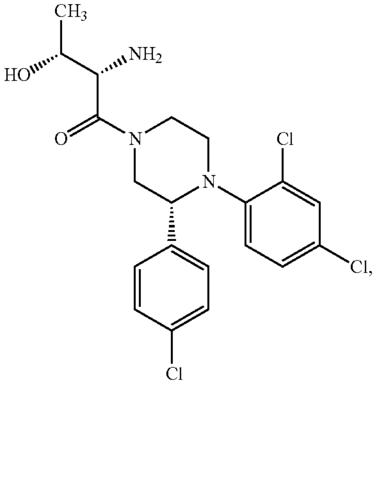
-continued
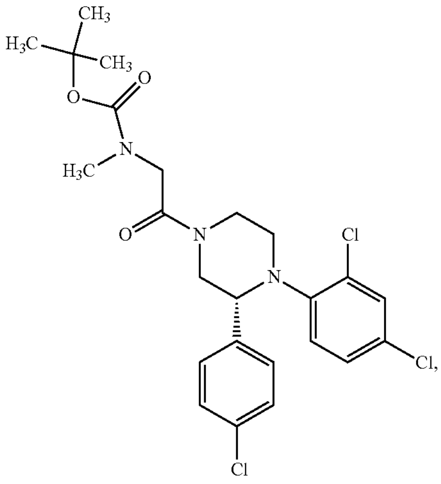
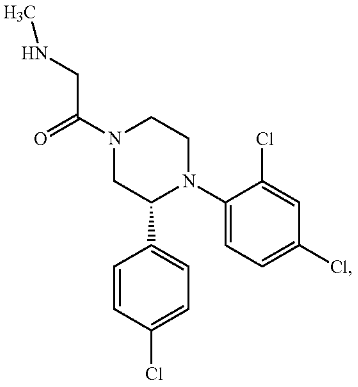
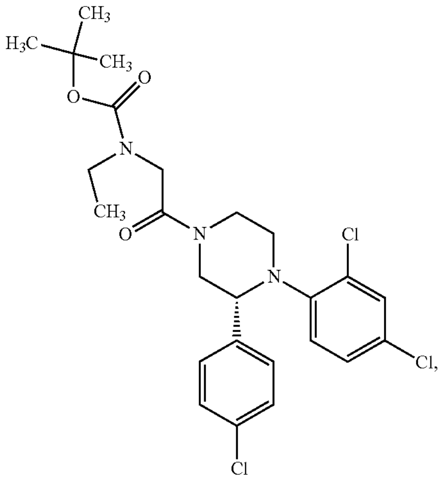

-continued
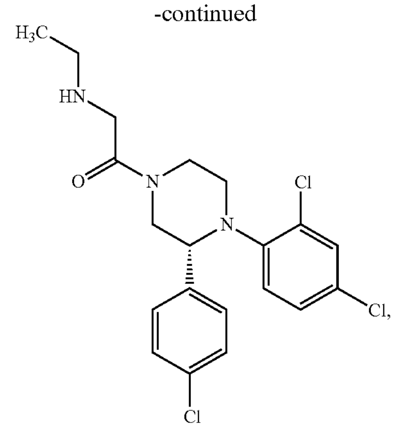
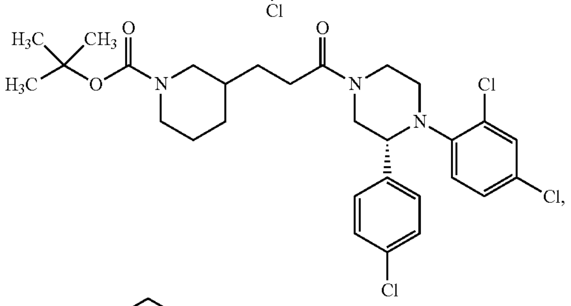
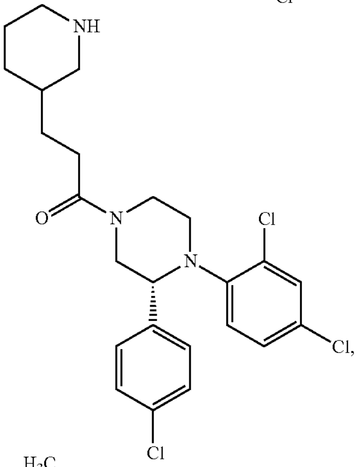
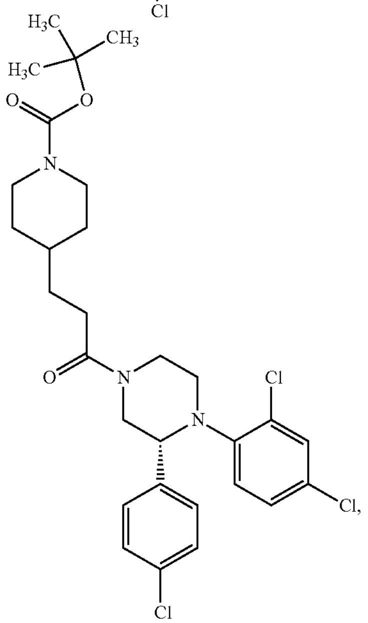
-continued
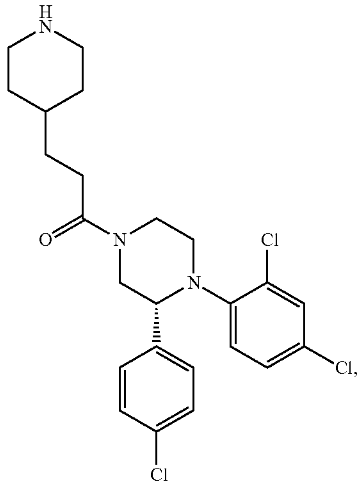
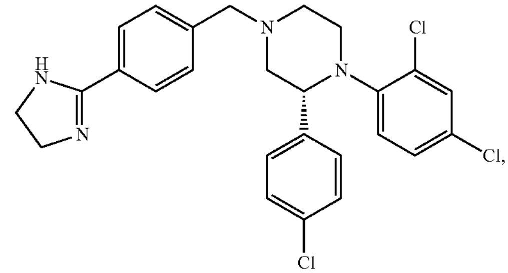
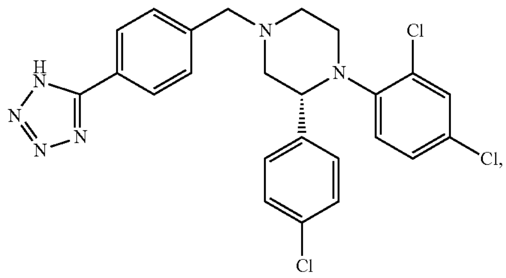
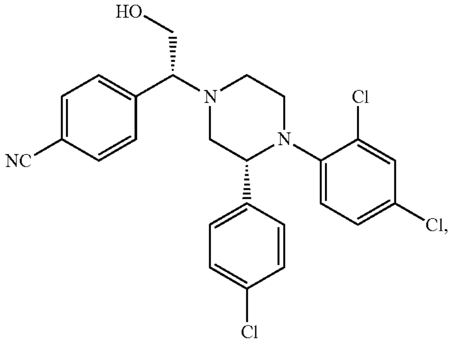
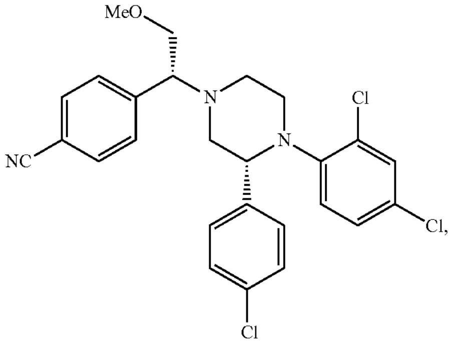

-continued
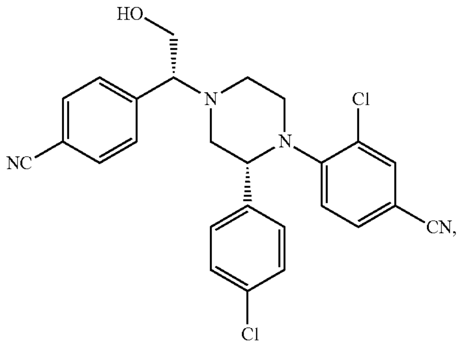
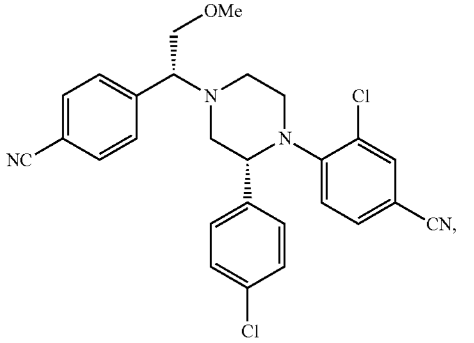
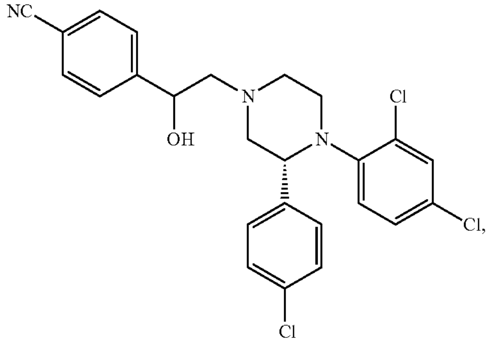
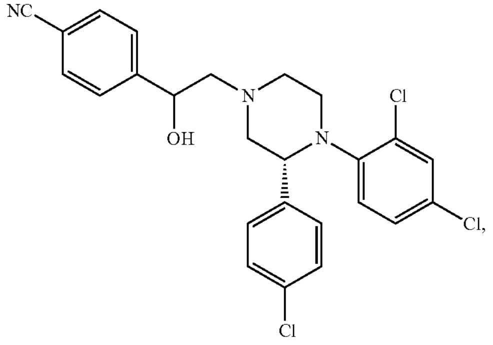
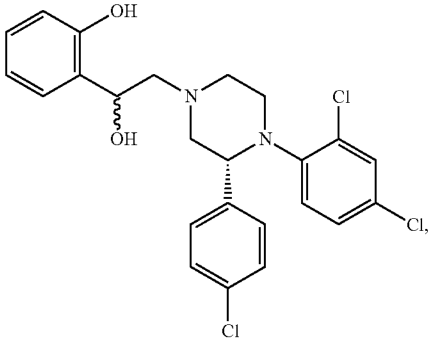
-continued
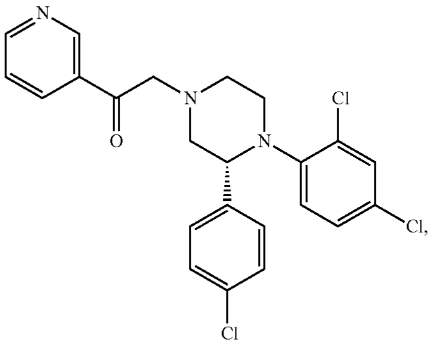
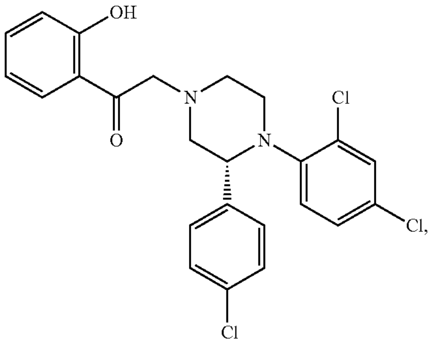
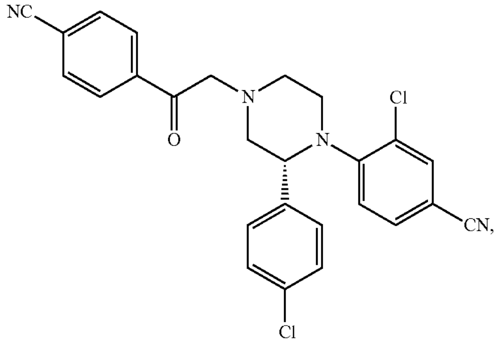
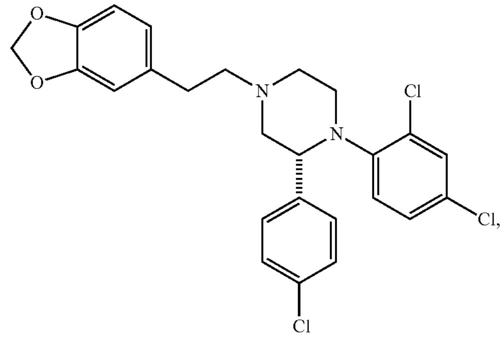
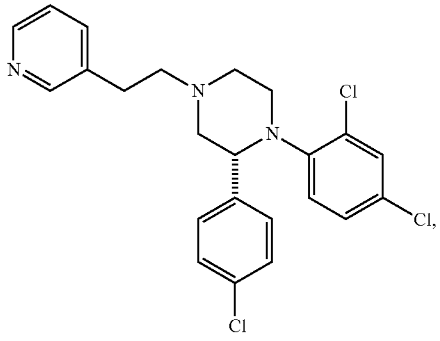

-continued
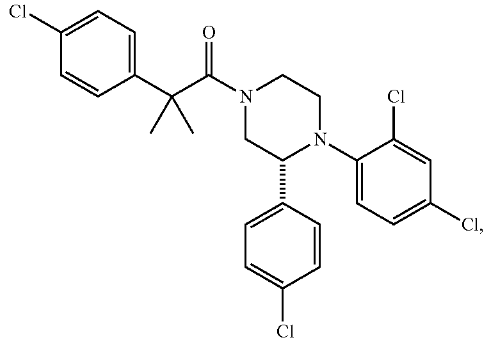
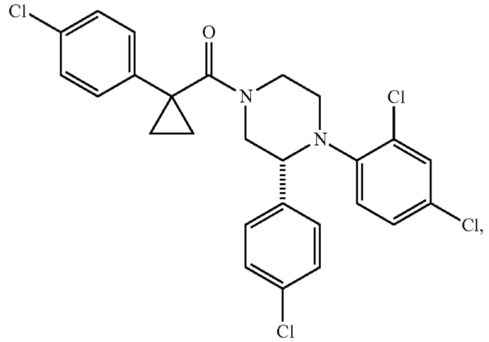
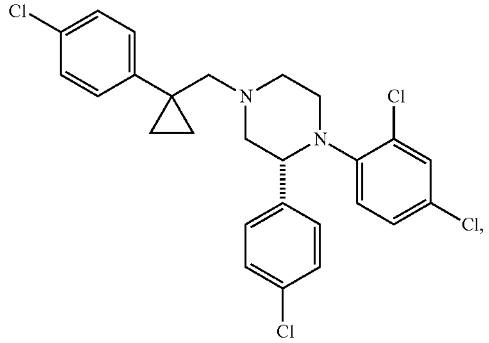
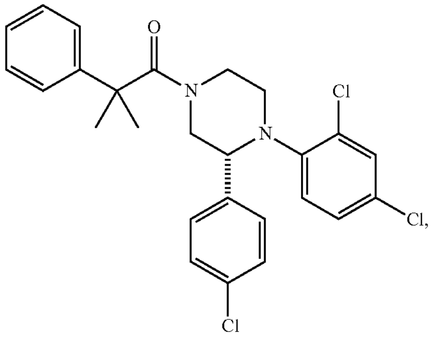
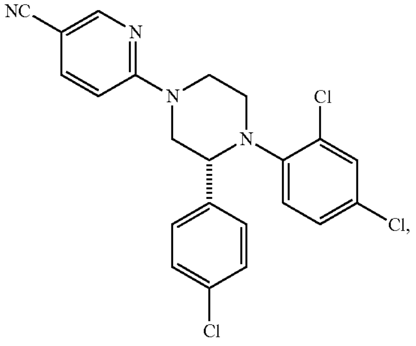
-continued
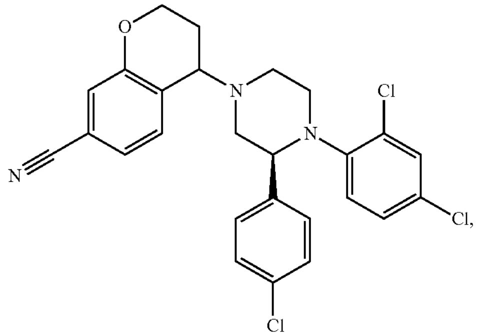
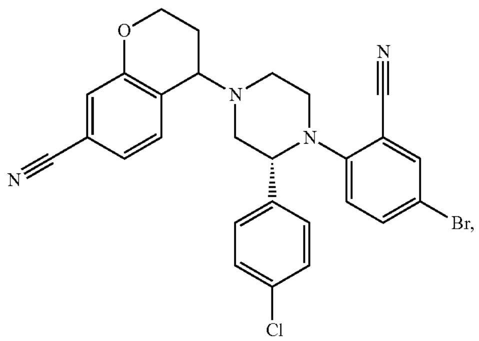
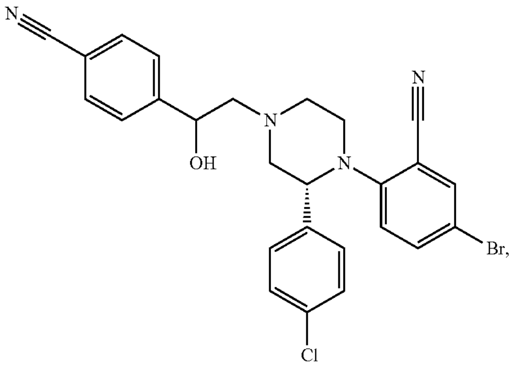
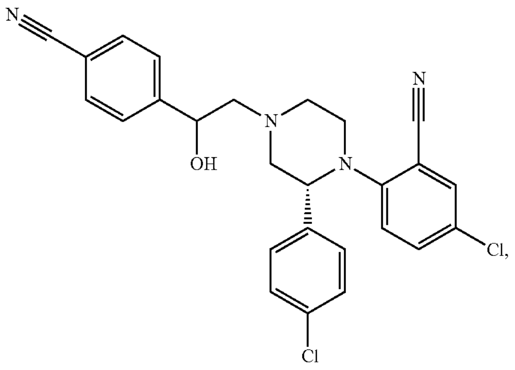

-continued
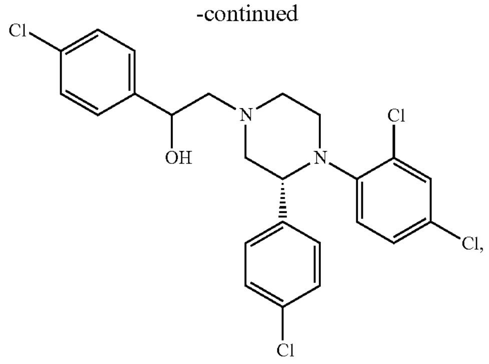
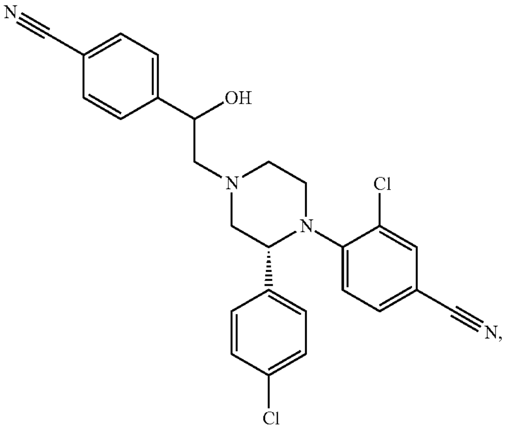
and
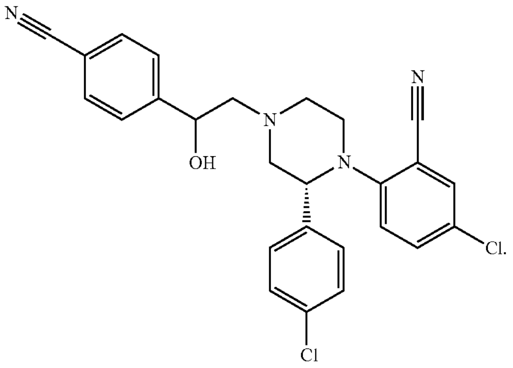
40. A compound of claim 1 selected from the group consisting of:
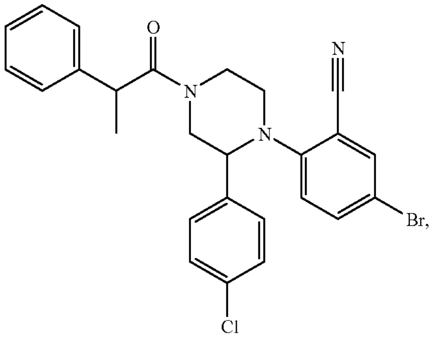
-continued
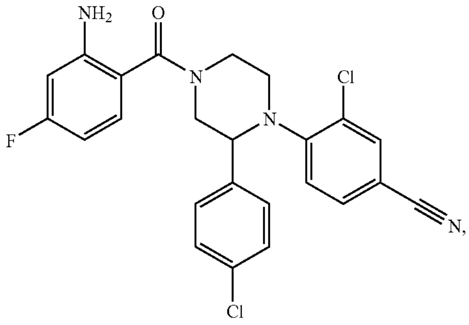
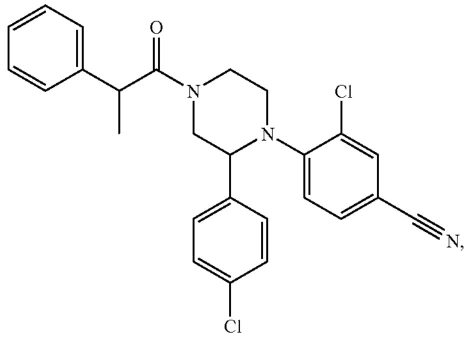
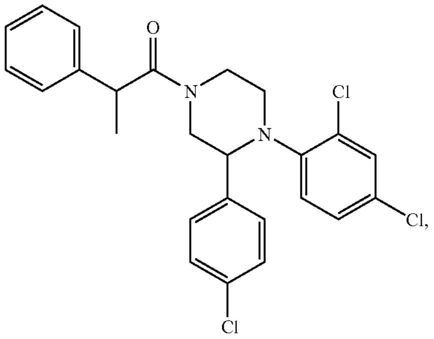
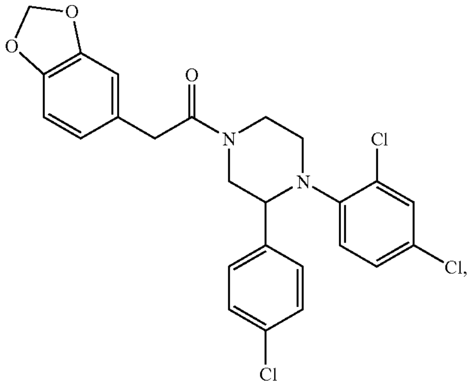
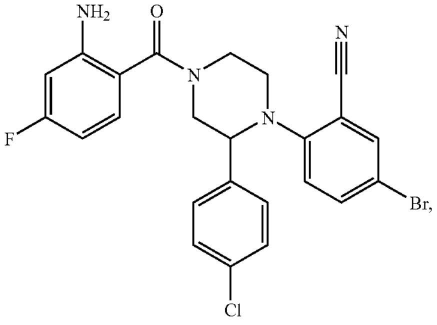

-continued
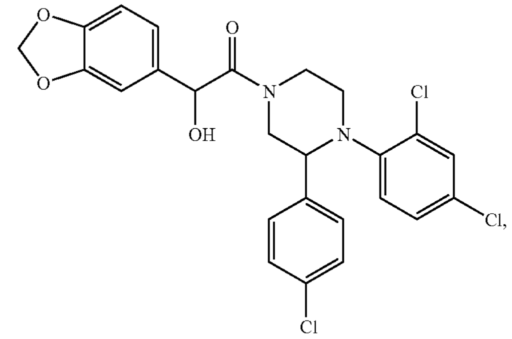
and
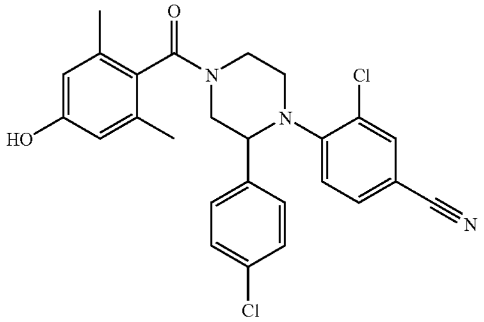
or a pharmaceutically acceptable salt or ester thereof.
41. A compound of the following formula:
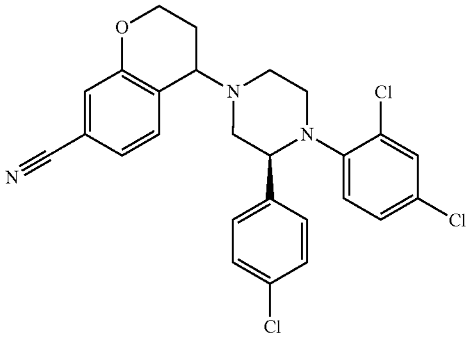
or a pharmaceutically acceptable salt or ester thereof.
42. A compound of the following formula:
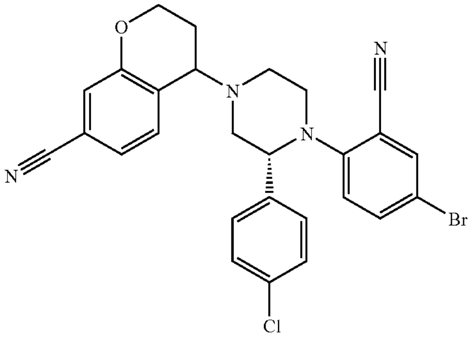
or a pharmaceutically acceptable salt or ester thereof.
43. A compound of claim 1 selected from the group consisting of:
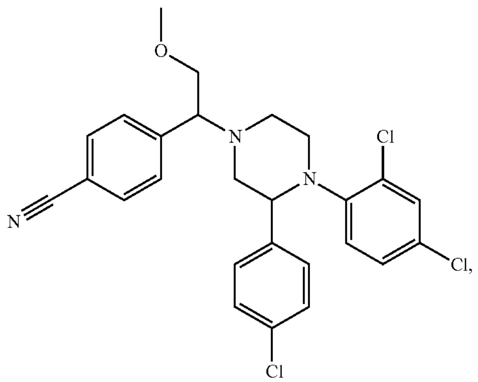
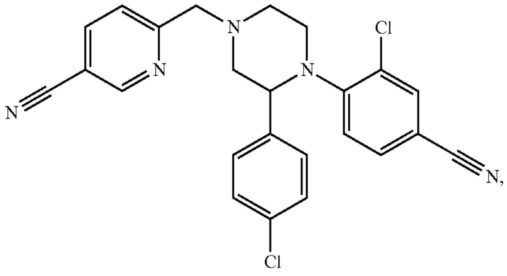
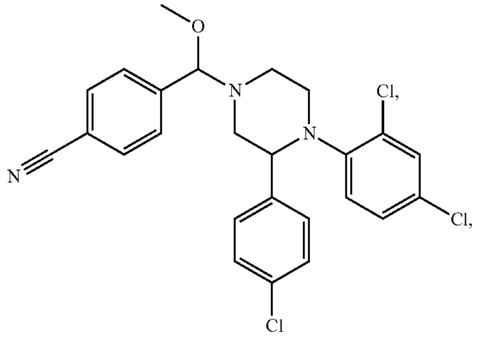
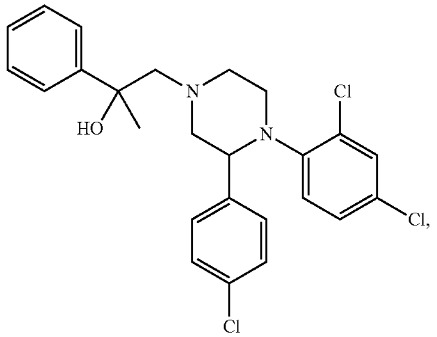
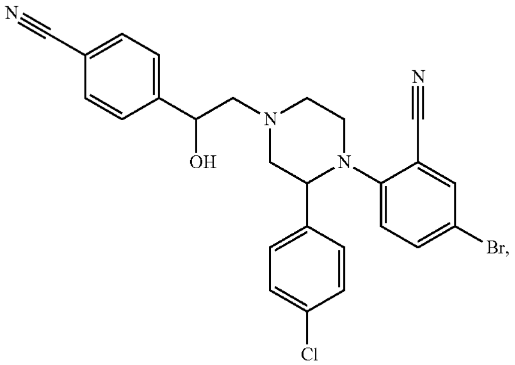

-continued

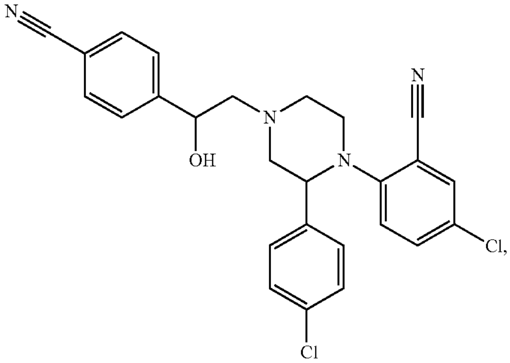

,

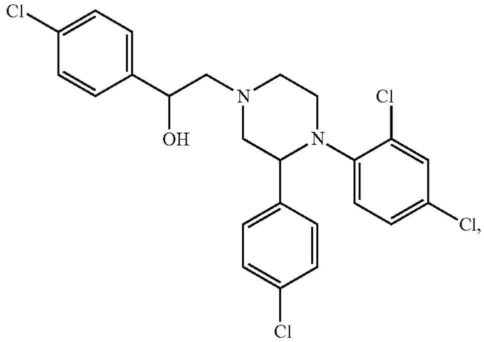

,

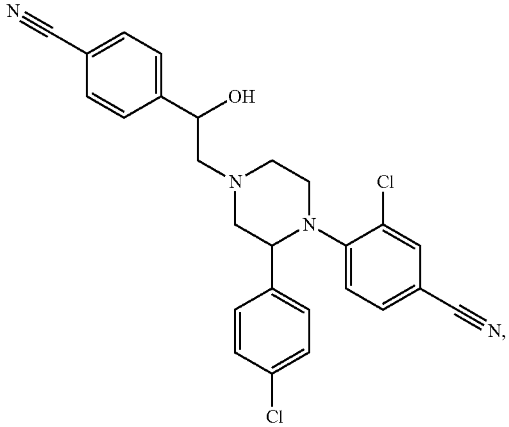

,

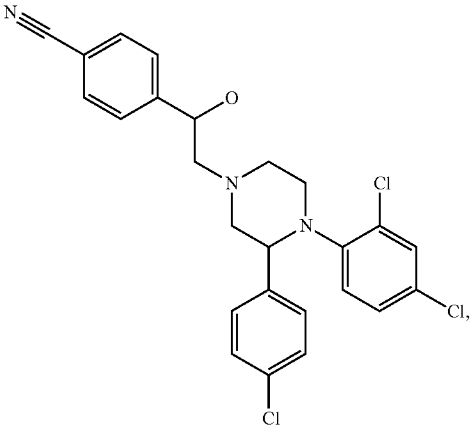

,

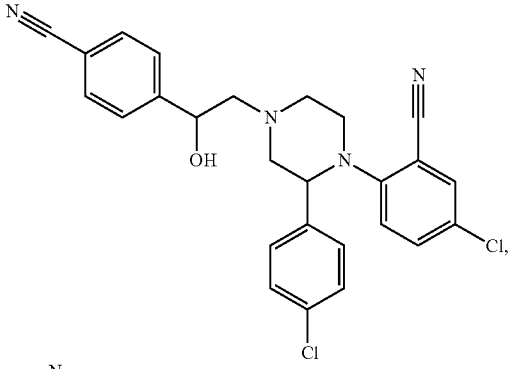

, and

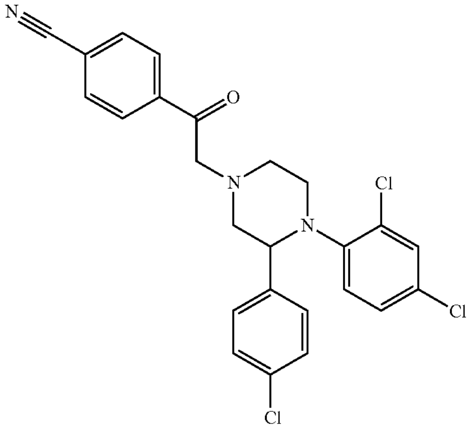

or a pharmaceutically acceptable salt or ester thereof.

44. The compound according to claim 1, or a pharmaceutically acceptable salt or ester thereof, in purified form.

45. A composition comprising:

at one compound according to claim 1, or a pharmaceutically acceptable salt or ester thereof; and a pharmaceutically acceptable carrier.

46. A method of treating, reducing, or ameliorating in a patient in need thereof, comprising:

administering to said patient an effective amount of at least one compound according to claim 1, or a pharmaceutically acceptable salt or ester thereof.

47. A method of treating, reducing, or ameliorating in a patient in need thereof, comprising:

administering to said patient an effective amount of a composition according to claim 45.

48. A composition comprising:

at one compound of Formula (I) according to claim 1, or a pharmaceutically acceptable salt or ester thereof; and at least one cholesterol lowering compound.

49. The composition of claim 48, wherein said at least one cholesterol lowering compound is at least one sterol absorption inhibitor or at least one 5α-stanol absorption inhibitor.

50. The composition of claim 48, wherein said at least one cholesterol lowering compound is at least one substituted azetidinone compound or substituted β-lactam compound or a pharmaceutically acceptable salt or ester thereof.

51. The composition of claim 50, wherein said at least one cholesterol lowering compound is ezetimibe.

* * * * *